United States Patent
Pace et al.

(10) Patent No.: US 11,331,010 B2
(45) Date of Patent: May 17, 2022

(54) FOCUSED STERILIZATION AND STERILIZED SUB-ASSEMBLIES FOR ANALYTE MONITORING SYSTEMS

(71) Applicant: ABBOTT DIABETES CARE INC., Alameda, CA (US)

(72) Inventors: Louis Pace, Alameda, CA (US); Vivek S. Rao, Alameda, CA (US); Steven T. Mitchell, Alameda, CA (US); Peter G. Robinson, Alameda, CA (US); Peter M. Voit, Alameda, CA (US); Matthew Simmons, Alameda, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 17/112,700

(22) Filed: Dec. 4, 2020

(65) Prior Publication Data
US 2021/0161437 A1    Jun. 3, 2021

Related U.S. Application Data

(63) Continuation of application No. PCT/US2019/035810, filed on Jun. 6, 2019.
(Continued)

(51) Int. Cl.
*A61B 5/145*   (2006.01)
*A61B 5/00*   (2006.01)
(Continued)

(52) U.S. Cl.
CPC .......... *A61B 5/14532* (2013.01); *A61B 5/68* (2013.01); *A61B 5/6833* (2013.01);
(Continued)

(58) Field of Classification Search
CPC ... A61B 5/1451; A61B 5/157; A61B 5/14503; A61B 5/150305; A61B 5/14532; A61B 5/1411; A61B 5/145; A61B 5/150335; A61B 5/150389; A61B 5/6849; A61B 5/150022; A61B 5/150748; A61B 5/0004;
(Continued)

(56) References Cited

U.S. PATENT DOCUMENTS 8,252,229 B2   8/2012  Thomas et al.
9,186,098 B2   11/2015  Lee et al.
(Continued)

FOREIGN PATENT DOCUMENTS

EP         3 202 324 A1    8/2017
WO     WO 2008/115409 A1   9/2008

OTHER PUBLICATIONS

International Search Report dated Aug. 6, 2019 in International Application No. PCT/US2019/035829.
(Continued)

*Primary Examiner* — Chu Chuan Liu
(74) *Attorney, Agent, or Firm* — Baker Botts L.L.P.

(57) ABSTRACT

A system includes a sensor applicator, a sensor control device arranged within the sensor applicator and including an electronics housing and a sensor extending from a bottom of the electronics housing, and a cap coupled to one of the sensor applicator and the sensor control device, wherein the cap is removable prior to deploying the sensor control device from the sensor applicator.

26 Claims, 109 Drawing Sheets

Related U.S. Application Data

(60) Provisional application No. 62/849,442, filed on May 17, 2019, provisional application No. 62/847,572, filed on May 14, 2019, provisional application No. 62/836,203, filed on Apr. 19, 2019, provisional application No. 62/836,193, filed on Apr. 19, 2019, provisional application No. 62/829,100, filed on Apr. 4, 2019, provisional application No. 62/798,703, filed on Jan. 30, 2019, provisional application No. 62/788,475, filed on Jan. 4, 2019, provisional application No. 62/784,074, filed on Dec. 21, 2018, provisional application No. 62/776,536, filed on Dec. 7, 2018, provisional application No. 62/681,906, filed on Jun. 7, 2018, provisional application No. 62/681,914, filed on Jun. 7, 2018.

(51) Int. Cl.
| | |
|---|---|
| *A61L 2/20* | (2006.01) |
| *G06F 1/16* | (2006.01) |
| *G06F 1/18* | (2006.01) |
| *G06F 9/06* | (2006.01) |
| *G06F 15/00* | (2006.01) |
| *A61B 17/34* | (2006.01) |
| *A61L 2/08* | (2006.01) |
| *A61B 5/1486* | (2006.01) |

(52) U.S. Cl.
CPC .............. *A61B 5/6849* (2013.01); *A61L 2/20* (2013.01); *A61L 2/208* (2013.01); *G06F 1/163* (2013.01); *G06F 1/1613* (2013.01); *G06F 1/183* (2013.01); *G06F 9/06* (2013.01); *G06F 15/00* (2013.01); *A61B 5/0004* (2013.01); *A61B 5/0022* (2013.01); *A61B 5/14865* (2013.01); *A61B 17/34* (2013.01); *A61B 17/3468* (2013.01); *A61B 17/3496* (2013.01); *A61B 2560/0214* (2013.01); *A61B 2560/04* (2013.01); *A61B 2560/0406* (2013.01); *A61B 2560/0425* (2013.01); *A61B 2560/063* (2013.01); *A61B 2562/02* (2013.01); *A61B 2562/12* (2013.01); *A61B 2562/125* (2013.01); *A61B 2562/16* (2013.01); *A61B 2562/18* (2013.01); *A61B 2562/182* (2013.01); *A61B 2562/242* (2013.01); *A61L 2/087* (2013.01); *A61L 2/206* (2013.01); *A61L 2202/18* (2013.01); *A61L 2202/24* (2013.01); *A61M 2205/195* (2013.01); *A61M 2205/8206* (2013.01)

(58) Field of Classification Search
CPC ............ A61B 5/15087; A61B 5/15144; A61B 5/150877; A61B 5/150503; A61B 5/15105; A61B 5/150358; A61B 2560/063; A61B 2560/0406; A61B 2560/0443; A61B 2562/16; A61B 2562/242
See application file for complete search history.

(56) References Cited

U.S. PATENT DOCUMENTS

| | | |
|---|---|---|
| 9,215,992 B2 | 12/2015 | Donnay et al. |
| 9,265,453 B2 | 2/2016 | Curry et al. |
| 9,402,544 B2 | 8/2016 | Yee et al. |
| 9,931,066 B2 | 4/2018 | Pace et al. |
| 2006/0193375 A1* | 8/2006 | Lee .................... H04L 27/0008 375/219 |
| 2008/0027296 A1 | 1/2008 | Hadvary et al. |
| 2008/0255440 A1 | 10/2008 | Eilersen et al. |
| 2011/0213225 A1* | 9/2011 | Bernstein ............ A61B 5/0017 600/309 |
| 2011/0319729 A1 | 12/2011 | Donnay et al. |
| 2012/0197222 A1 | 8/2012 | Donnay |
| 2012/0303043 A1* | 11/2012 | Donnay ............ A61B 5/14532 606/129 |
| 2013/0137950 A1 | 5/2013 | Harttig et al. |
| 2013/0150691 A1 | 6/2013 | Pace et al. |
| 2014/0066730 A1 | 3/2014 | Roesicke et al. |
| 2015/0018639 A1 | 1/2015 | Stafford |
| 2016/0183854 A1 | 6/2016 | Lee |
| 2016/0331283 A1 | 11/2016 | Rao et al. |
| 2017/0188912 A1* | 7/2017 | Halac ................. A61B 5/14503 |
| 2017/0290535 A1 | 10/2017 | Rao et al. |
| 2017/0290546 A1 | 10/2017 | Antonio et al. |
| 2018/0325433 A1 | 11/2018 | Prais et al. |
| 2018/0368772 A1 | 12/2018 | Gray et al. |
| 2019/0076073 A1 | 3/2019 | Donnay et al. |
| 2019/0117131 A1 | 4/2019 | Halac et al. |
| 2020/0100712 A1 | 4/2020 | Stafford |

OTHER PUBLICATIONS

International Search Report dated Aug. 6, 2019 in International Application No. PCT/US2019/035810.
U.S. Appl. No. 17/112,698, filed Dec. 4, 2020.
U.S. Appl. No. 17/112,747, filed Dec. 4, 2020.
International Search Report dated Aug. 6, 2019 in International Application No. PCT/US2019/035797.
U.S. Appl. No. 17/112,698, filed Sep. 9, 2021, Final Office Action.

* cited by examiner

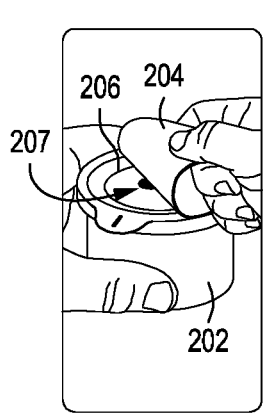 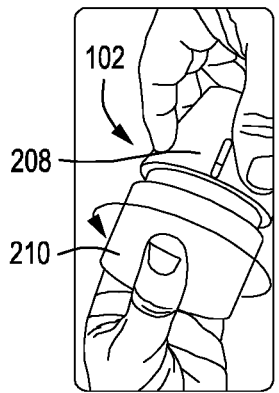 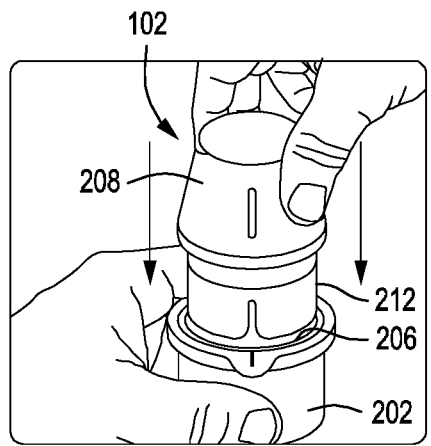
FIG. 2A  FIG. 2B  FIG. 2C
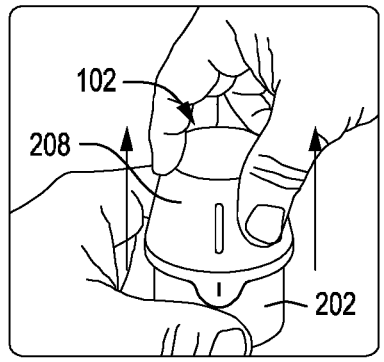 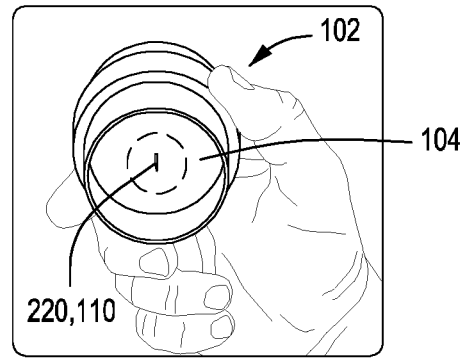
FIG. 2D  FIG. 2E
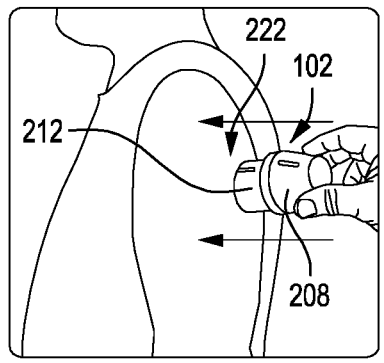 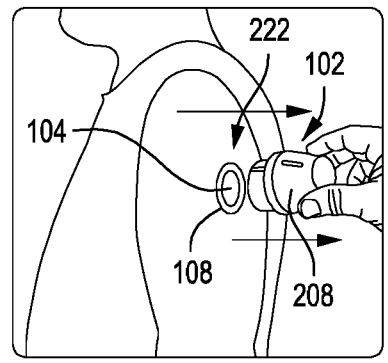
FIG. 2F  FIG. 2G

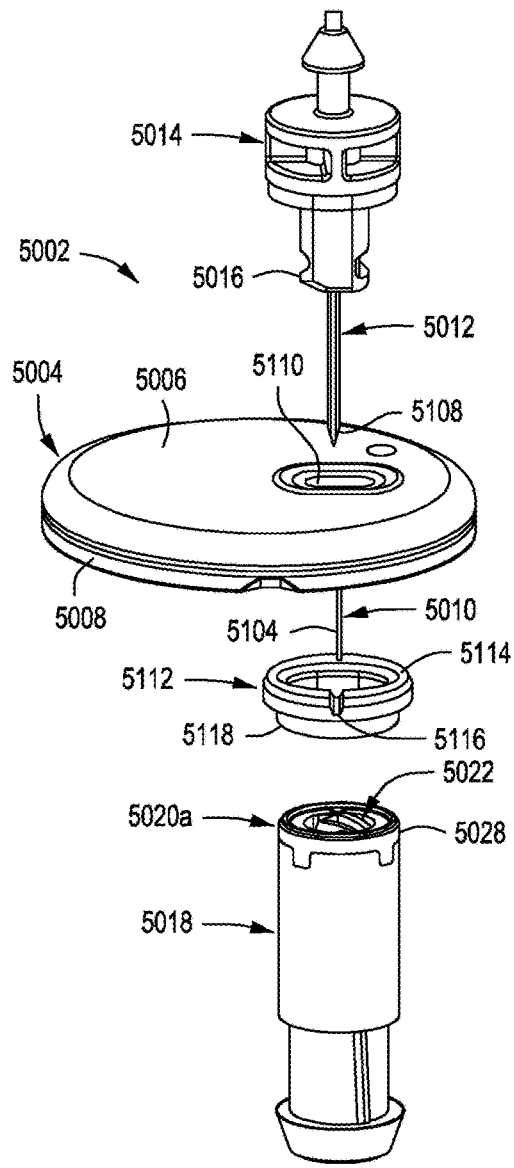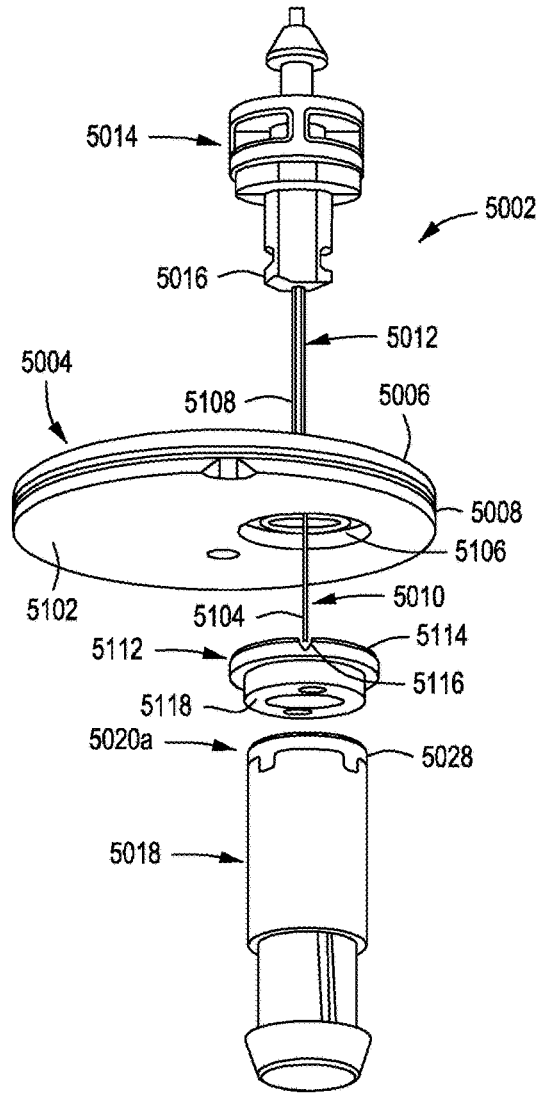
FIG. 51A
FIG. 51B

FOCUSED STERILIZATION AND STERILIZED SUB-ASSEMBLIES FOR ANALYTE MONITORING SYSTEMS

CROSS REFERENCE TO RELATED APPLICATIONS

This application is a continuation of International Patent Application No. PCT/US2019/035810, filed Jun. 6, 2019, which claims the benefit of U.S. Provisional Patent Application No. 62/681,906 filed Jun. 7, 2018, U.S. Provisional Patent Application No. 62/681,914 filed Jun. 7, 2018, U.S. Provisional Patent Application No. 62/776,536 filed Dec. 7, 2018, U.S. Provisional Patent Application No. 62/784,074 filed Dec. 21, 2018, U.S. Provisional Patent Application No. 62/788,475 filed Jan. 4, 2019, U.S. Provisional Patent Application No. 62/798,703 filed Jan. 30, 2019, U.S. Provisional Patent Application No. 62/829,100 filed Apr. 4, 2019, U.S. Provisional Patent Application No. 62/836,203 filed Apr. 19, 2019, U.S. Provisional Patent Application No. 62/836,193 filed Apr. 19, 2019, U.S. Provisional Patent Application No. 62/847,572 filed May 14, 2019, and U.S. Provisional Patent Application No. 62/849,442 filed May 17, 2019 which are hereby incorporated by reference in their entireties.

BACKGROUND

Diabetes is an incurable chronic disease in which the body does not produce or properly utilize insulin, a hormone produced by the pancreas that regulates blood glucose. When blood glucose levels rise, e.g., after a meal, insulin lowers the blood glucose levels by moving the blood glucose from the blood and into the body cells. When the pancreas does not produce sufficient insulin (a condition known as Type I Diabetes) or the body does not properly utilize insulin (a condition known as Type II Diabetes), the blood glucose remains in the blood, which could result in hyperglycemia or abnormally high blood sugar levels.

If symptoms of diabetes are not carefully monitored and treated, numerous complications can arise, including diabetic ketoacidosis, nonketotic hyperosmolar coma, cardiovascular disease, stroke, kidney failure, foot ulcers, eye damage, and nerve damage. Traditionally, monitoring has involved an individual pricking a finger to draw blood and testing the blood for glucose levels. Advancements that are more recent have allowed for continuous and long-term monitoring of blood glucose using biological sensors that are maintained in contact with bodily fluids for periods of days, weeks, or longer.

Analyte monitoring systems, for example, have been developed to facilitate long-term monitoring of bodily fluid analytes, such as glucose. Analyte monitoring systems typically include a sensor applicator configured to place a biological sensor into contact with a bodily fluid. More specifically, during delivery of the sensor to the skin of a user, at least a portion of the sensor is positioned below the skin surface, e.g., in the subcutaneous or dermal tissue.

It is important for devices implanted in the body or positioned below the skin to be sterile upon insertion. Sterilization can include any number of processes that effectively eliminate or kill transmissible agents, such as bacteria, fungi, and viruses. These transmittable agents, if not eliminated from the device, may be substantially detrimental to the health and safety of the user.

Some but not all analyte monitoring systems might require separate sterilization processes to sterilize the sensor and the electronic components. Electron beam sterilization, for example, is one example of radiation sterilization that can be used to terminally sterilize the sensor. Radiation sterilization, however, can harm the electronic components associated with the sensor. Consequently, the electronic components are commonly sterilized via gaseous chemical sterilization using, for example, ethylene oxide. Ethylene oxide, however, can damage the chemistry provided on the sensor. As such, integrating electronics and the sensor into one unit can complicate the sterilization process.

These issues can be worked around by separating the components into a sensor unit (e.g., a biological analyte sensor) and an adaptor unit (containing the data transmission electronics), so that each component can be packaged and sterilized separately using the appropriate sterilization method. This approach, however, requires additional components, additional packaging, additional process steps, and final user assembly of the two components, introducing a possibility of user error. Thus, a need exists for analyte monitoring systems that may be sterilized without separating the components.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 2A-2G are progressive views of the assembly and application of the system of FIG. 1 incorporating a two-piece architecture.

FIGS. 51A and 51B are exploded isometric top and bottom views, respectively of the sensor control device of FIGS. 50A-50B.

FIG. 111A is a top view of the sensor control device of FIG. 109 in preparation for pressure testing and/or vacuum sealing, according to one or more embodiments.

FIG. 111B is a cross-sectional side view of the sensor control device of FIG. 109 with a compressor.

FIG. 112 is a partial cross-sectional side view of an example sensor control device, according to one or more embodiments.

FIG. 113 is a cross-sectional side view of an example sensor applicator, according to one or more embodiments.

FIGS. 114A and 114B are top and bottom perspective views, respectively, of an example embodiment of the plug of FIGS. 27A-27B.

FIGS. 115A and 115B are perspective views depicting an example embodiment of the connector of FIGS. 27A-27B in open and closed states, respectively.

FIG. 116 is a perspective view of an example embodiment of the sensor of FIGS. 27A-27B.

FIGS. 117A and 117B are bottom and top perspective views, respectively, depicting an example embodiment of a sensor module assembly.

FIGS. 118A and 118B are close-up partial views of an example embodiment of the sensor plug of FIGS. 114A-114B having certain axial stiffening features.

FIG. 119 is a side view of an example sensor, according to one or more embodiments of the disclosure.

FIGS. 120A and 120B are isometric and partially exploded isometric views of an example connector assembly, according to one or more embodiments.

FIG. 120C is an isometric bottom view of the connector of FIGS. 120A-120B.

Figure 121A:
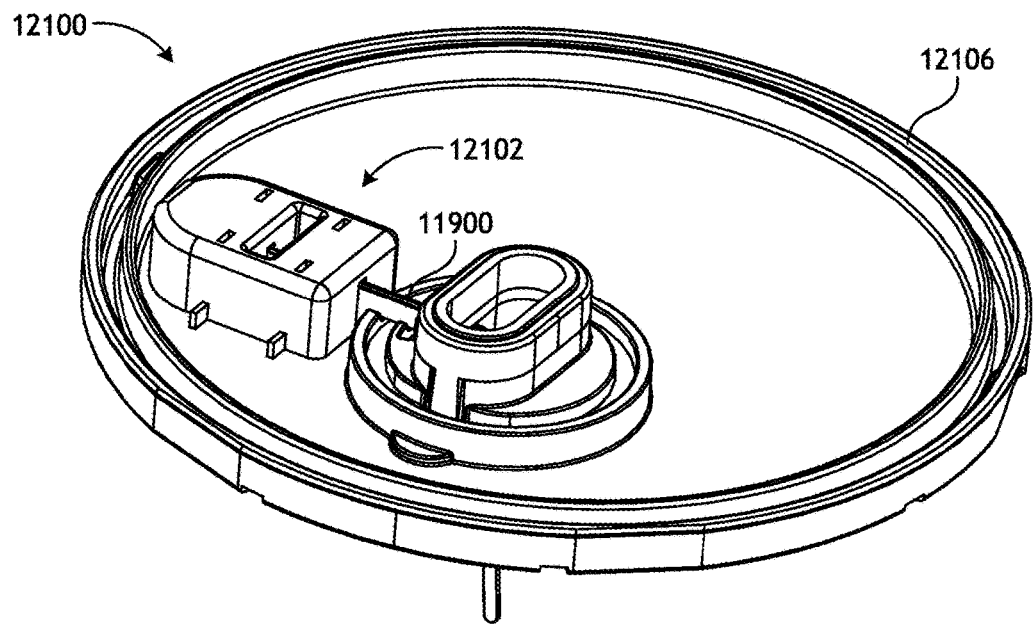
Figure 121B:
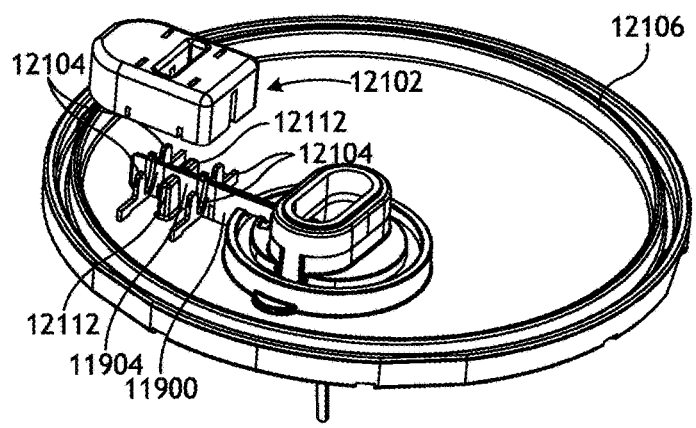

FIGS. 121A and 121B are isometric and partially exploded isometric views of another example connector assembly, according to one or more embodiments.

Figure 121C:
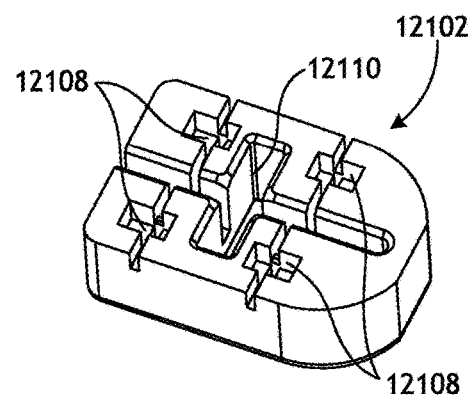

FIG. 121C is an isometric bottom view of the connector of FIGS. 121A-121B.

DETAILED DESCRIPTION

The present application is generally related to systems, devices, and methods for assembling an applicator and sensor control device for use in an in vivo analyte monitoring system.

Figure 1:
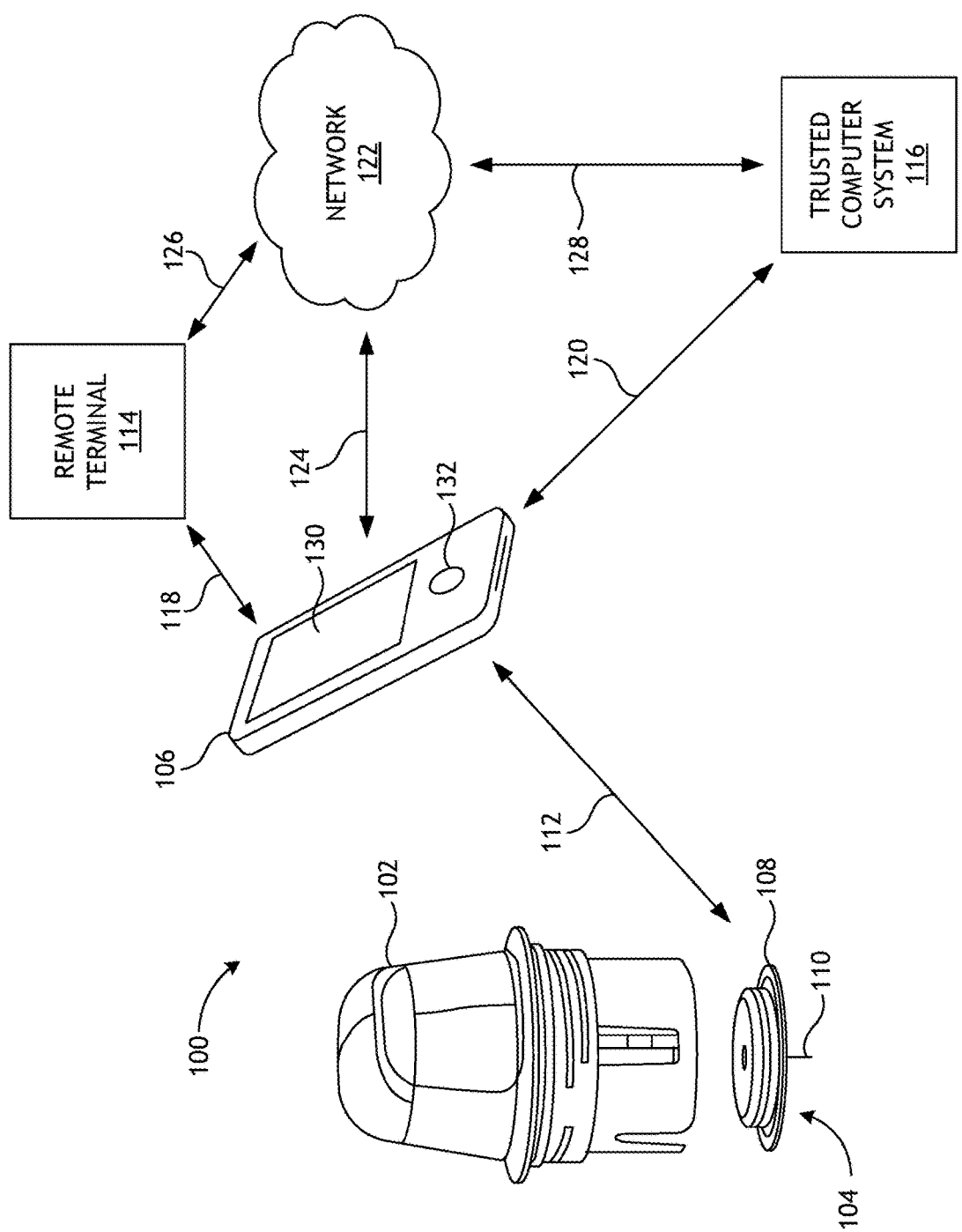
FIG. 1 is a conceptual diagram depicting an example analyte monitoring system that may incorporate one or more embodiments of the present disclosure.

FIG. 1 is a conceptual diagram depicting an example analyte monitoring system 100 that may incorporate one or more embodiments of the present disclosure. A variety of analytes can be detected and quantified using the system 100 (hereafter "the system 100") including, but not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, but not limited to, antibiotics (e.g., gentamicin, vancomycin, and the like), digitoxin, digoxin, drugs of abuse, theophylline, and warfarin, may also be determined.

As illustrated, the system 100 includes a sensor applicator 102 (alternately referred to as an "inserter"), a sensor control device 104 (also referred to as an "in vivo analyte sensor control device"), and a reader device 106. The sensor applicator 102 is used to deliver the sensor control device 104 to a target monitoring location on a user's skin (e.g., the arm of the user). Once delivered, the sensor control device 104 is maintained in position on the skin with an adhesive patch 108 coupled to the bottom of the sensor control device 104. A portion of a sensor 110 extends from the sensor control device 104 and is positioned such that it can be transcutaneously positioned and otherwise retained under the surface of the user's skin during the monitoring period.

An introducer may be included to promote introduction of the sensor 110 into tissue. The introducer may comprise, for example, a needle often referred to as a "sharp." Alternatively, the introducer may comprise other types of devices, such as a sheath or a blade. The introducer may transiently reside in proximity to the sensor 110 prior to tissue insertion and then be withdrawn afterward. While present, the introducer may facilitate insertion of the sensor 110 into tissue by opening an access pathway for the sensor 110 to follow. For example, the introducer may penetrate the epidermis to provide an access pathway to the dermis to allow subcutaneous implantation of the sensor 110. After opening the access pathway, the introducer may be withdrawn (retracted) so that it does not represent a hazard while the sensor 110 remains in place. In illustrative embodiments, the introducer may be solid or hollow, beveled or non-beveled, and/or circular or non-circular in cross-section. In more particular embodiments, suitable introducers may be comparable in cross-sectional diameter and/or tip design to an acupuncture needle, which may have a cross-sectional diameter of about 250 microns. It is to be recognized, however, that suitable introducers may have a larger or smaller cross-sectional diameter if needed for particular applications.

In some embodiments, a tip of the introducer (while present) may be angled over the terminus of the sensor 110, such that the introducer penetrates a tissue first and opens an access pathway for the sensor 110. In other illustrative embodiments, the sensor 110 may reside within a lumen or groove of the introducer, with the introducer similarly opening an access pathway for the sensor 110. In either case, the introducer is subsequently withdrawn after facilitating sensor 110 insertion. Moreover, the introducer (sharp) can be made of a variety of materials, such as various types of metals and plastics.

When the sensor control device 104 is properly assembled, the sensor 110 is placed in communication (e.g., electrical, mechanical, etc.) with one or more electrical components or sensor electronics included within the sensor control device 104. In some applications, for example, the sensor control device 104 may include a printed circuit board (PCB) having a data processor (e.g., an application specific integrated circuit or ASIC) mounted thereto, and the sensor 110 may be operatively coupled to the data processor which, in turn, may be coupled with an antenna and a power source.

The sensor control device 104 and the reader device 106 are configured to communicate with one another over a local communication path or link 112, which may be wired or wireless, uni- or bi-directional, and encrypted or non-encrypted. The reader device 106 may constitute an output medium for viewing analyte concentrations and alerts or notifications determined by the sensor 110 or a processor associated therewith, as well as allowing for one or more user inputs, according to some embodiments. The reader device 106 may be a multi-purpose smartphone or a dedicated electronic reader instrument. While only one reader device 106 is shown, multiple reader devices 106 may be present in certain instances.

The reader device 106 may also be in communication with a remote terminal 114 and/or a trusted computer system 116 via communication path(s)/link(s) 118 and/or 120, respectively, which also may be wired or wireless, uni- or bi-directional, and encrypted or non-encrypted. The reader device 106 may also or alternately be in communication with a network 122 (e.g., a mobile telephone network, the internet, or a cloud server) via communication path/link 124. The network 122 may be further communicatively coupled to remote terminal 114 via communication path/link 126 and/or the trusted computer system 116 via communication path/link 128.

Alternately, the sensor control device 104 may communicate directly with the remote terminal 114 and/or the trusted computer system 116 without an intervening reader device 106 being present. For example, the sensor 110 may communicate with the remote terminal 114 and/or the trusted computer system 116 through a direct communication link to the network 122, according to some embodiments, as described in U.S. Pat. No. 10,136,816, incorporated herein by reference in its entirety.

Any suitable electronic communication protocol may be used for each of the communication paths or links, such as near field communication (NFC), radio frequency identification (RFID), BLUETOOTH® or BLUETOOTH® low energy protocols, WiFi, or the like. The remote terminal 114 and/or the trusted computer system 116 may be accessible, according to some embodiments, by individuals other than a primary user who have an interest in the user's analyte levels. The reader device 106 may include a display 130 and an optional input component 132. The display 130 may comprise a touch-screen interface, according to some embodiments.

In some embodiments, the sensor control device 104 may automatically forward data to the reader device 106. For example, analyte concentration data may be communicated automatically and periodically, such as at a certain frequency as data is obtained or after a certain time period has passed, with the data being stored in a memory until transmittal (e.g., every minute, five minutes, or other predetermined time period). In other embodiments, the sensor control device 104 may communicate with the reader device 106 in a non-automatic manner and not according to a set schedule. For example, data may be communicated from the sensor control device 104 using RFID technology when the sensor electronics are brought into communication range of the reader device 106. Until communicated to the reader device 106, data may remain stored in a memory of the sensor control device 104. Thus, a patient does not have to maintain close proximity to the reader device 106 at all times, and can instead upload data when convenient. In yet other embodiments, a combination of automatic and non-automatic data transfer may be implemented. For example, data transfer may continue on an automatic basis until the reader device 106 is no longer in communication range of the sensor control device 104.

The sensor control device 104 is often included with the sensor applicator 104 in what is known as a "two-piece" architecture that requires final assembly by a user before the sensor 110 can be properly delivered to the target monitoring location. More specifically, the sensor 110 and the associated electrical components included in the sensor control device 104 are provided to the user in multiple (two) packages, and the user must open the packaging and follow instructions to manually assemble the components before delivering the sensor 110 to the target monitoring location with the sensor applicator 102.

More recently, however, advanced designs of sensor control devices and sensor applicators have resulted in a one-piece architecture that allows the system to be shipped to the user in a single, sealed package that does not require any final user assembly steps. Rather, the user need only open one package and subsequently deliver the sensor control device to the target monitoring location. The one-piece system architecture may prove advantageous in eliminating component parts, various fabrication process steps, and user assembly steps. As a result, packaging and waste are reduced, and the potential for user error or contamination to the system is mitigated.

In the illustrated embodiment, the system 100 may comprise what is known as a "two-piece" architecture that requires final assembly by a user before the sensor 110 can be properly delivered to the target monitoring location. More specifically, the sensor 110 and the associated electrical components included in the sensor control device 104 are provided to the user in multiple (two) packages, where each may or may not be sealed with a sterile barrier but are at least enclosed in packaging. The user must open the packaging and follow instructions to manually assemble the components and subsequently deliver the sensor 110 to the target monitoring location with the sensor applicator 102.

FIGS. 2A-2G are progressive views of the assembly and application of the system 100 incorporating a two-piece architecture. FIGS. 2A and 2B depict the first and second packages, respectively, provided to the user for final assembly. More specifically, FIG. 2A depicts a sensor container or tray 202 that has a removable lid 204. The user prepares the sensor tray 202 by removing the lid 204, which acts as a sterile barrier to protect the internal contents of the sensor tray 202 and otherwise maintain a sterile internal environment. Removing the lid 204 exposes a platform 206 positioned within the sensor tray 202, and a plug assembly 207 (partially visible) is arranged within and otherwise strategically embedded within the platform 206. The plug assembly 207 includes a sensor module (not shown) and a sharp module (not shown). The sensor module carries the sensor 110 (FIG. 1), and the sharp module carries an associated sharp used to help deliver the sensor 110 transcutaneously under the user's skin during application of the sensor control device 104 (FIG. 1).

FIG. 2B depicts the sensor applicator 102 and the user preparing the sensor applicator 102 for final assembly. The sensor applicator 102 includes a housing 208 sealed at one end with an applicator cap 210. In some embodiments, for example, an O-ring or another type of sealing gasket may seal an interface between the housing 208 and the applicator cap 210. In at least one embodiment, the O-ring or sealing gasket may be molded onto one of the housing 208 and the applicator cap 210. The applicator cap 210 provides a barrier that protects the internal contents of the sensor applicator 102. In particular, the sensor applicator 102 contains an electronics housing (not shown) that retains the electrical components for the sensor control device 104 (FIG. 1), and the applicator cap 210 may or may not maintain a sterile environment for the electrical components. Preparation of the sensor applicator 102 includes uncoupling the housing 208 from the applicator cap 210, which can be accomplished by unscrewing the applicator cap 210 from the housing 208. The applicator cap 210 can then be discarded or otherwise placed aside.

FIG. 2C depicts the user inserting the sensor applicator 102 into the sensor tray 202. The sensor applicator 102 includes a sheath 212 configured to be received by the platform 206 to temporarily unlock the sheath 212 relative to the housing 208, and also temporarily unlock the platform 206 relative to the sensor tray 202. Advancing the housing 208 into the sensor tray 202 results in the plug assembly 207 (FIG. 2A) arranged within the sensor tray 202, including the sensor and sharp modules, being coupled to the electronics housing arranged within the sensor applicator 102.

In FIG. 2D, the user removes the sensor applicator 102 from the sensor tray 202 by proximally retracting the housing 208 with respect to the sensor tray 202.

FIG. 2E depicts the bottom or interior of the sensor applicator 102 following removal from the sensor tray 202 (FIG. 2). The sensor applicator 102 is removed from the sensor tray 202 with the sensor control device 104 fully assembled therein and positioned for delivery to the target monitoring location. As illustrated, a sharp 220 extends from the bottom of the sensor control device 104 and carries a portion of the sensor 110 within a hollow or recessed portion thereof. The sharp 220 is configured to penetrate the skin of a user and thereby place the sensor 110 into contact with bodily fluid.

FIGS. 2F and 2G depict example delivery of the sensor control device 104 to a target monitoring location 222, such as the back of an arm of the user. FIG. 2F shows the user advancing the sensor applicator 102 toward the target monitoring location 222. Upon engaging the skin at the target monitoring location 222, the sheath 212 collapses into the housing 208, which allows the sensor control device 104 (FIGS. 2E and 2G) to advance into engagement with the skin. With the help of the sharp 220 (FIG. 2E), the sensor 110 (FIG. 2E) is advanced transcutaneously into the patient's skin at the target monitoring location 222.

FIG. 2G shows the user retracting the sensor applicator 102 from the target monitoring location, with the sensor control device 104 successfully attached to the user's skin. The adhesive patch 108 (FIG. 1) applied to the bottom of sensor control device 104 adheres to the skin to secure the sensor control device 104 in place. The sharp 220 (FIG. 2E) is automatically retracted when the housing 208 is fully advanced at the target monitoring location 222, while the sensor 110 (FIG. 2E) is left in position to measure analyte levels.

For the two-piece architecture system, the sensor tray 202 (FIG. 2A) and the sensor applicator 102 (FIG. 2B) are provided to the user as separate packages, thus requiring the user to open each package and finally assemble the system. In some applications, the discrete, sealed packages allow the sensor tray 202 and the sensor applicator 102 to be sterilized in separate sterilization processes unique to the contents of each package and otherwise incompatible with the contents of the other.

More specifically, the sensor tray 202, which includes the plug assembly 207 (FIG. 2A), including the sensor 110 (FIGS. 1 and 2E) and the sharp 220 (FIG. 2E), may be sterilized using radiation sterilization, such as electron beam (or "e-beam") irradiation. Radiation sterilization, however, can damage the electrical components arranged within the electronics housing of the sensor control device 104. Consequently, if the sensor applicator 102, which contains the electronics housing of the sensor control device 104, needs to be sterilized, it may be sterilized via another method, such as gaseous chemical sterilization using, for example, ethylene oxide. Gaseous chemical sterilization, however, can damage the enzymes or other chemistry and biologics included on the sensor 110. Because of this sterilization incompatibility, the sensor tray 202 and the sensor applicator 102 may be sterilized in separate sterilization processes and subsequently packaged separately, and thereby requiring the user to finally assemble the components upon receipt.

According to embodiments of the present disclosure, the system 100 (FIG. 1) may comprise a one-piece architecture that incorporates sterilization techniques specifically designed for a one-piece architecture. The one-piece architecture allows the system 100 to be shipped to the user in a single, sealed package that does not require any final user assembly steps. Rather, the user need only open one package and subsequently deliver the sensor control device to the target monitoring location, as generally described above with reference to FIGS. 2E-2G. The one-piece system architecture described herein may prove advantageous in eliminating component parts, various fabrication process steps, and user assembly steps. As a result, packaging and waste are reduced, and the potential for user error or contamination to the system is mitigated.

Focused Electron Beam Sterilization with Collimator

Figure 3A:
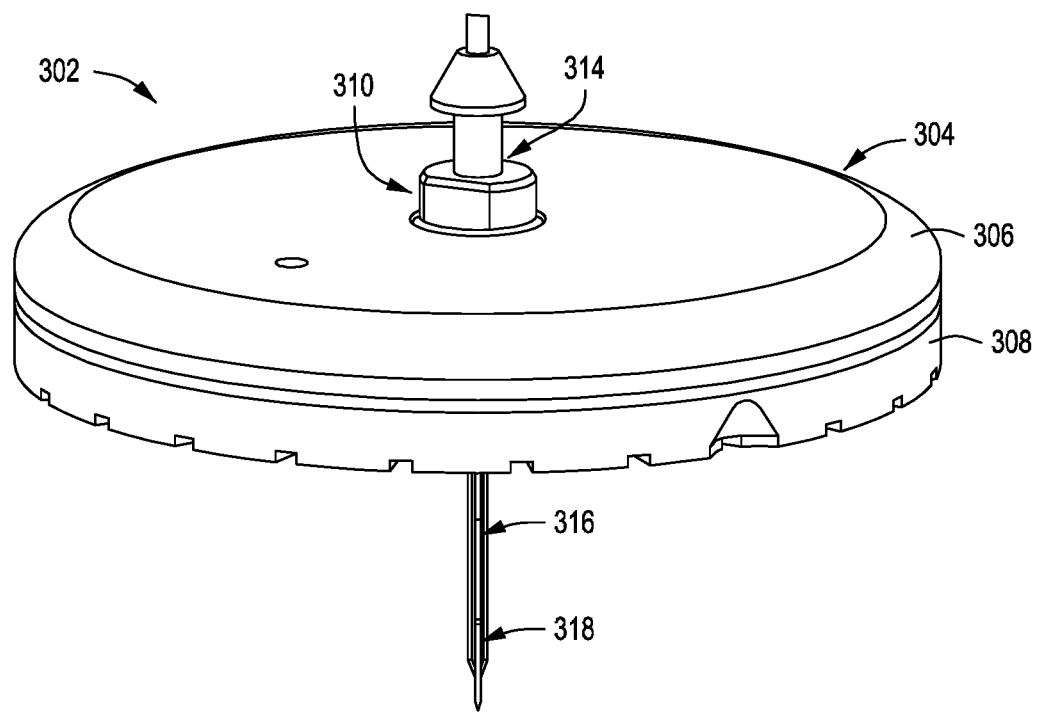
FIGS. 3A and 3B are isometric and side views, respectively, of an example sensor control device.
Figure 3B:
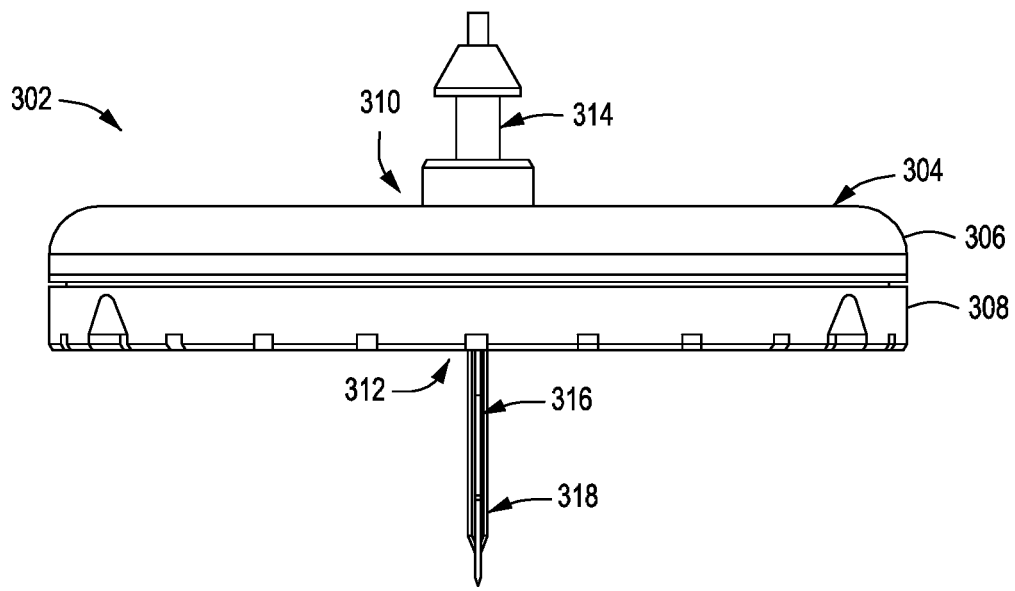

FIGS. 3A and 3B are isometric and side views, respectively, of an example sensor control device 302, according to one or more embodiments of the present disclosure. The sensor control device 302 (alternately referred to as a "puck") may be similar in some respects to the sensor control device 104 of FIG. 1 and therefore may be best understood with reference thereto. The sensor control device 302 may replace the sensor control device 104 of FIG. 1 and, therefore, may be used in conjunction with the sensor applicator 102 (FIG. 1), which delivers the sensor control device 302 to a target monitoring location on a user's skin.

The sensor control device 302, however, may be incorporated into a one-piece system architecture. Unlike the two-piece architecture system, for example, a user is not required to open multiple packages and finally assemble the sensor control device 302. Rather, upon receipt by the user, the sensor control device 302 is already fully assembled and properly positioned within the sensor applicator 102. To use the sensor control device 302, the user need only break one barrier (e.g., the applicator cap 210 of FIG. 2B) before promptly delivering the sensor control device 302 to the target monitoring location.

As illustrated, the sensor control device 302 includes an electronics housing 304 that is generally disc-shaped and may have a circular cross-section. In other embodiments, however, the electronics housing 304 may exhibit other cross-sectional shapes, such as ovoid (e.g., pill-shaped), a squircle, or polygonal, without departing from the scope of the disclosure. The electronics housing 304 may be configured to house or otherwise contain various electrical components used to operate the sensor control device 302.

The electronics housing 304 may include a shell 306 and a mount 308 that is matable with the shell 306. The shell 306 may be secured to the mount 308 via a variety of ways, such as a snap fit engagement, an interference fit, sonic welding, or one or more mechanical fasteners (e.g., screws). In some cases, the shell 306 may be secured to the mount 308 such that a sealed interface therebetween is generated. In such embodiments, a gasket or other type of seal material may be positioned at or near the outer diameter (periphery) of the shell 306 and the mount 308, and securing the two components together may compress the gasket and thereby generate a sealed interface. In other embodiments, an adhesive may be applied to the outer diameter (periphery) of one or both of the shell 306 and the mount 308. The adhesive secures the shell 306 to the mount 308 and provides structural integrity, but may also seal the interface between the two components and thereby isolate the interior of the electronics housing 304 from outside contamination. If the sensor control device 302 is assembled in a controlled environment, there may be no need to terminally sterilize the internal electrical components. Rather, the adhesive coupling may provide a sufficient sterile barrier for the assembled electronics housing 304.

The sensor control device 302 may further include a plug assembly 310 that may be coupled to the electronics housing 304. The plug assembly 310 may be similar in some respects to the plug assembly 207 of FIG. 2A. For example, the plug assembly 310 may include a sensor module 312 (partially visible) interconnectable with a sharp module 314 (partially visible). The sensor module 312 may be configured to carry and otherwise include a sensor 316 (partially visible), and the sharp module 314 may be configured to carry and otherwise include a sharp 318 (partially visible) used to help deliver the sensor 316 transcutaneously under a user's skin during application of the sensor control device 302. As illustrated, corresponding portions of the sensor 316 and the sharp 318 extend from the electronics housing 304 and, more particularly, from the bottom of the mount 308. The exposed portion of the sensor 316 may be received within a hollow or recessed portion of the sharp 318. The remaining portion of the sensor 316 is positioned within the interior of the electronics housing 304.

Figure 4A:
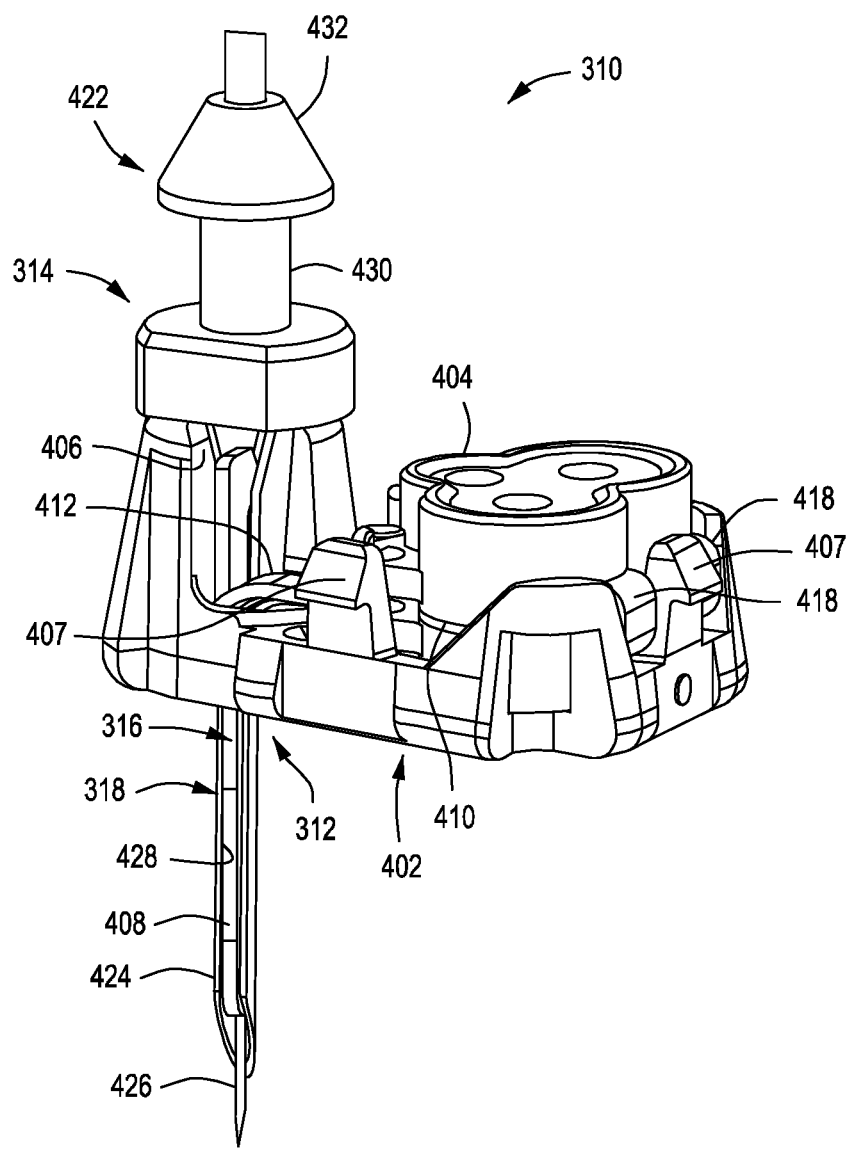
FIGS. 4A and 4B are isometric and exploded views, respectively, of the plug assembly of FIGS. 3A-3B.
Figure 4B:
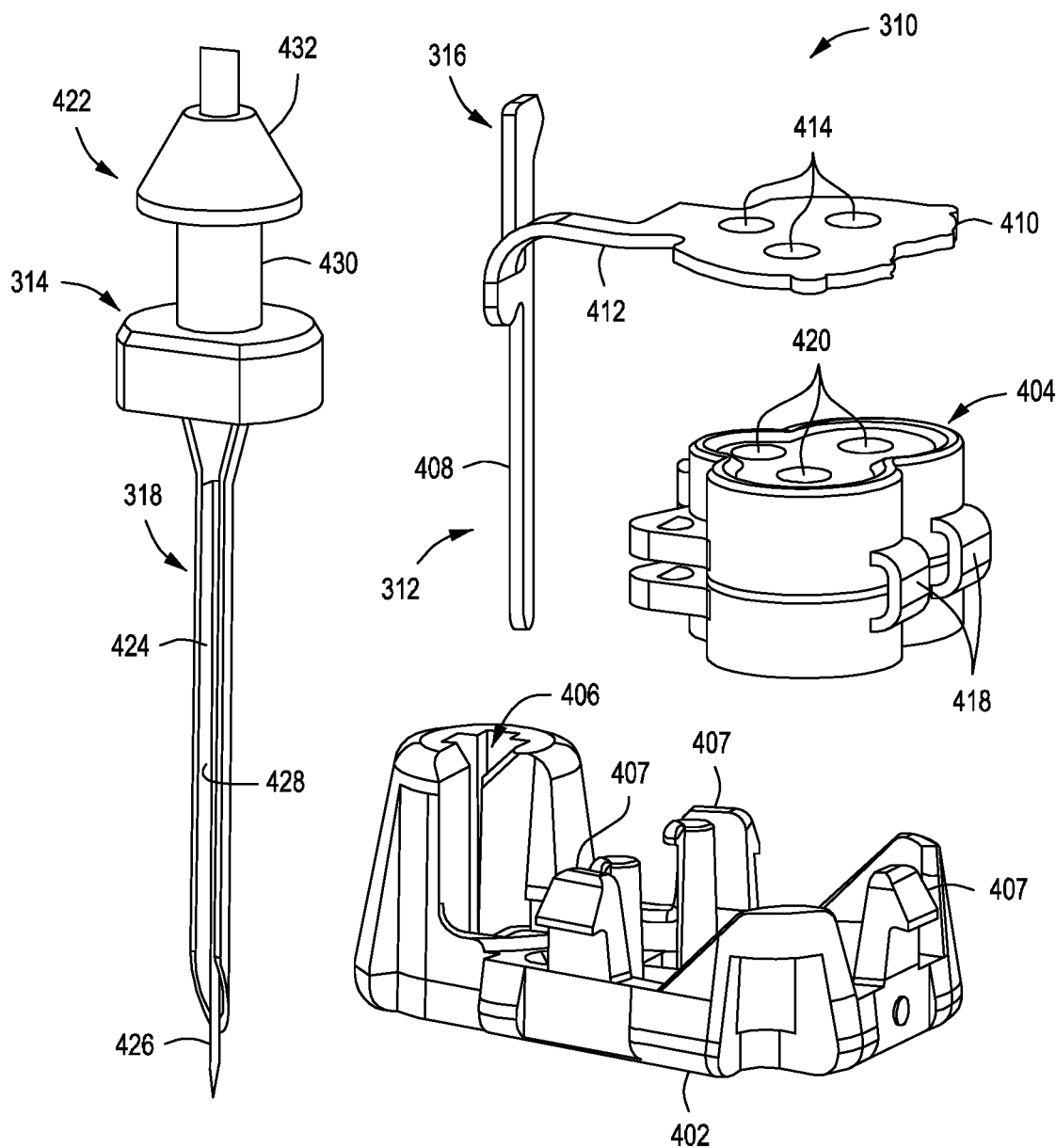

FIGS. 4A and 4B are isometric and exploded views, respectively, of the plug assembly 310, according to one or more embodiments. The sensor module 312 may include the sensor 316, a plug 402, and a connector 404. The plug 402 may be designed to receive and support both the sensor 316 and the connector 404. As illustrated, a channel 406 may be defined through the plug 402 to receive a portion of the sensor 316. Moreover, the plug 402 may provide one or more deflectable arms 407 configured to snap into corresponding features provided on the bottom of the electronics housing 304 (FIGS. 3A-3B).

The sensor 316 includes a tail 408, a flag 410, and a neck 412 that interconnects the tail 408 and the flag 410. The tail 408 may be configured to extend at least partially through the channel 406 and extend distally from the plug 402. The tail 408 includes an enzyme or other chemistry or biologic and, in some embodiments, a membrane may cover the chemistry. In use, the tail 408 is transcutaneously received beneath a user's skin, and the chemistry included thereon helps facilitate analyte monitoring in the presence of bodily fluids.

The flag 410 may comprise a generally planar surface having one or more sensor contacts 414 (three shown in FIG. 4B) arranged thereon. The sensor contact(s) 414 may be configured to align with a corresponding number of compliant carbon impregnated polymer modules (not shown) encapsulated within the connector 404.

The connector 404 includes one or more hinges 418 that enables the connector 404 to move between open and closed states. The connector 404 is depicted in FIGS. 4A-4B in the closed state, but can pivot to the open state to receive the flag 410 and the compliant carbon impregnated polymer module(s) therein. The compliant carbon impregnated polymer module(s) provide electrical contacts 420 (three shown) configured to provide conductive communication between the sensor 316 and corresponding circuitry contacts provided within the electronics housing 304 (FIGS. 3A-3B). The connector 404 can be made of silicone rubber and may serve as a moisture barrier for the sensor 316 when assembled in a compressed state and after application to a user's skin.

The sharp module 314 includes the sharp 318 and a sharp hub 422 that carries the sharp 318. The sharp 318 includes an elongate shaft 424 and a sharp tip 426 at the distal end of the shaft 424. The shaft 424 may be configured to extend through the channel 406 and extend distally from the plug 402. Moreover, the shaft 424 may include a hollow or recessed portion 428 that at least partially circumscribes the tail 408 of the sensor 316. The sharp tip 426 may be configured to penetrate the skin while carrying the tail 408 to put the active chemistry present on the tail 408 into contact with bodily fluids.

The sharp hub 422 may include a hub small cylinder 430 and a hub snap pawl 432, each of which may be configured to help couple the plug assembly 310 (and the entire sensor control device 302) to the sensor applicator 102 (FIG. 1).

Figure 5A:
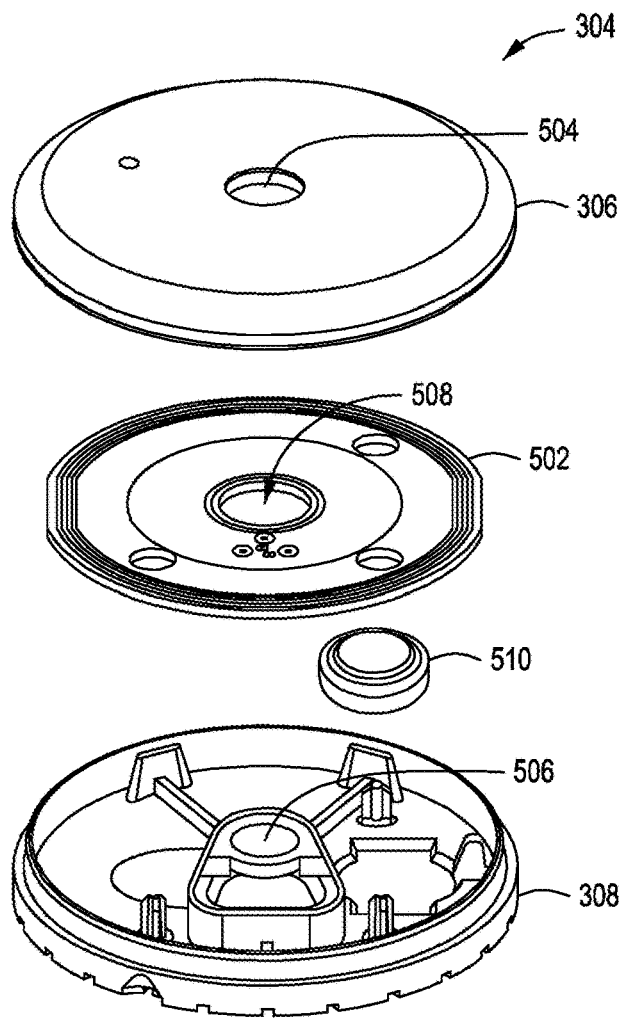
FIGS. 5A and 5B are exploded and bottom isometric views, respectively, of the electronics housing of FIGS. 3A-3B.
Figure 5B:
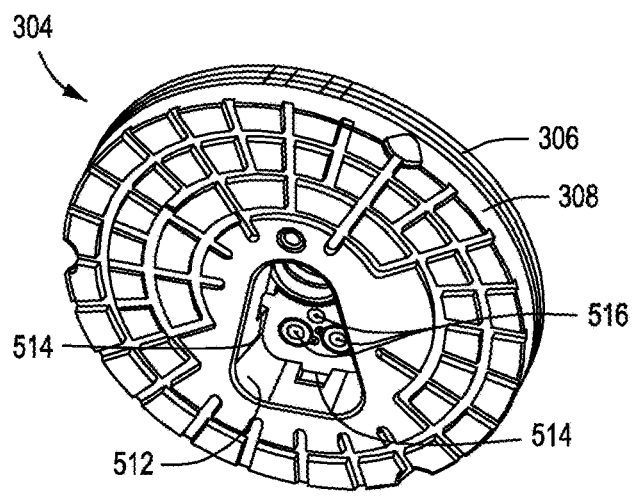

FIGS. 5A and 5B are exploded and bottom isometric views, respectively, of the electronics housing 304, according to one or more embodiments. The shell 306 and the mount 308 operate as opposing clamshell halves that enclose or otherwise substantially encapsulate the various electronic components of the sensor control device 302 (FIGS. 3A-3B).

A printed circuit board (PCB) 502 may be positioned within the electronics housing 304. A plurality of electronic modules (not shown) may be mounted to the PCB 502 including, but not limited to, a data processing unit, resistors, transistors, capacitors, inductors, diodes, and switches. The data processing unit may comprise, for example, an application specific integrated circuit (ASIC) configured to implement one or more functions or routines associated with operation of the sensor control device 302. More specifically, the data processing unit may be configured to perform data processing functions, where such functions may include but are not limited to, filtering and encoding of data signals, each of which corresponds to a sampled analyte level of the user. The data processing unit may also include or otherwise communicate with an antenna for communicating with the reader device 106 (FIG. 1).

As illustrated, the shell 306, the mount 308, and the PCB 502 each define corresponding central apertures 504, 506, and 508, respectively. When the electronics housing 304 is assembled, the central apertures 504, 506, and 508 coaxially align to receive the plug assembly 310 (FIGS. 4A-4B) therethrough. A battery 510 may also be housed within the electronics housing 304 and configured to power the sensor control device 302.

In FIG. 5B, a plug receptacle 512 may be defined in the bottom of the mount 308 and provide a location where the plug assembly 310 (FIGS. 4A-4B) may be received and coupled to the electronics housing 304, and thereby fully assemble the sensor control device 302 (FIG. 3A-3B). The profile of the plug 402 (FIGS. 4A-4B) may match or be shaped in complementary fashion to the plug receptacle 512, and the plug receptacle 512 may provide one or more snap ledges 514 (two shown) configured to interface with and receive the deflectable arms 407 (FIGS. 4A-4B) of the plug 402. The plug assembly 310 is coupled to the electronics housing 304 by advancing the plug 402 into the plug receptacle 512 and allowing the deflectable arms 407 to lock into the corresponding snap ledges 514. When the plug assembly 310 (FIGS. 4A-4B) is properly coupled to the electronics housing 304, one or more circuitry contacts 516 (three shown) defined on the underside of the PCB 502 may make conductive communication with the electrical contacts 420 (FIGS. 4A-4B) of the connector 404 (FIGS. 4A-4B).

Figure 6B:
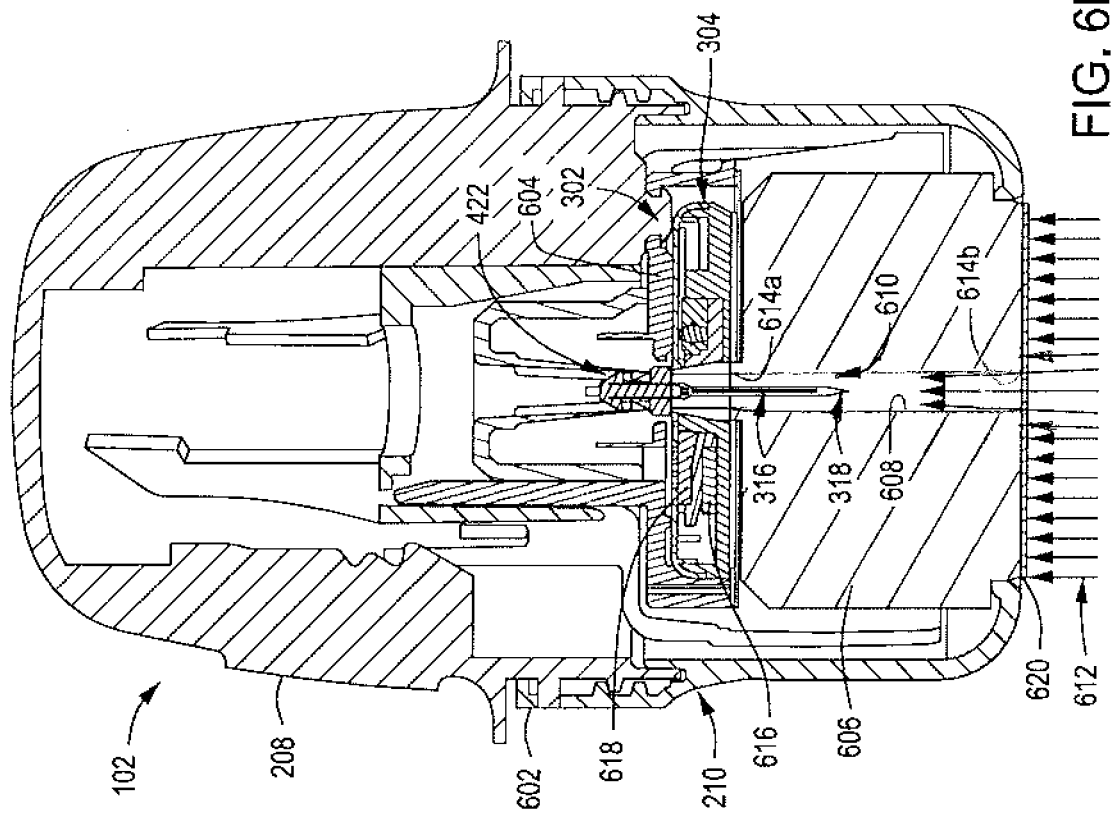
FIGS. 6A and 6B are side and cross-sectional side views, respectively, of the sensor applicator of FIG. 1 with the cap of FIG. 2B coupled thereto.
Figure 6A:
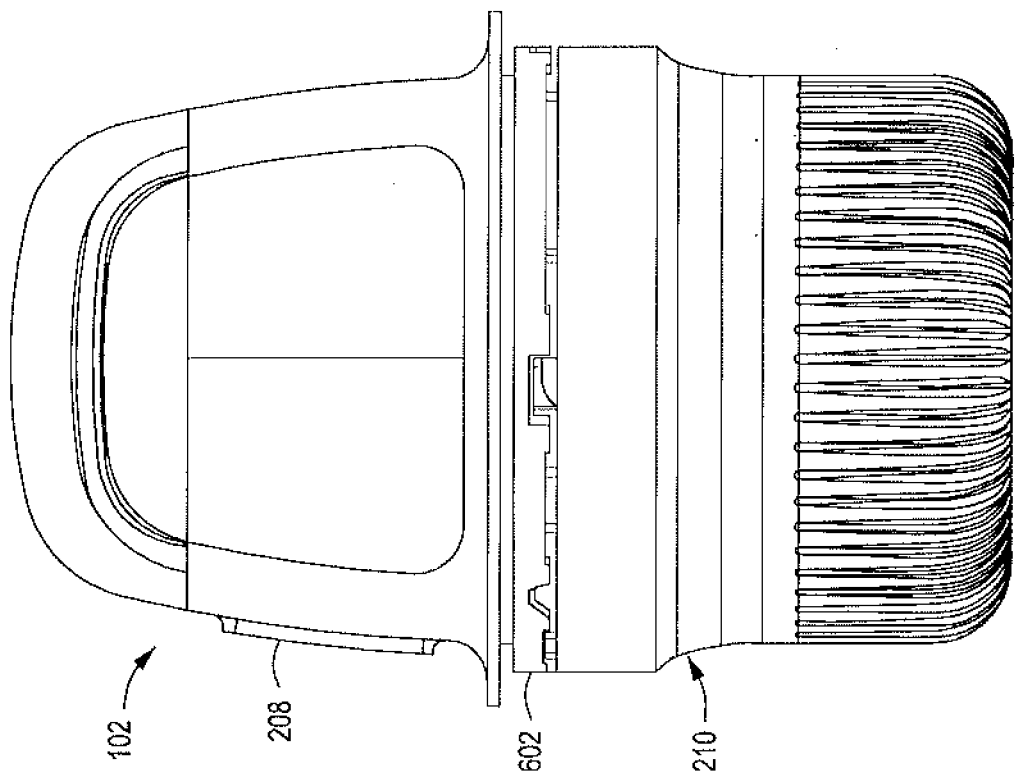

FIGS. 6A and 6B are side and cross-sectional side views, respectively, of the sensor applicator 102 with the applicator cap 210 coupled thereto. More specifically, FIGS. 6A-6B depict how the sensor applicator 102 might be shipped to and received by a user, according to at least one embodiment. In some embodiments, however, the sensor applicator 102 might further be sealed within a bag (not shown) and delivered to the user within the bag. The bag may be made of a variety of materials that help prevent the ingress of humidity into the sensor applicator 102, which might adversely affect the sensor 316. In at least one embodiment, for example, the sealed back might be made of foil. Any and all of the sensor applicators described or discussed herein may be sealed within and delivered to the user within the bag.

According to the present disclosure, and as seen in FIG. 6B, the sensor control device 302 is already assembled and installed within the sensor applicator 102 prior to being delivered to the user. The applicator cap 210 may be threaded to the housing 208 and include a tamper ring 602. Upon rotating (e.g., unscrewing) the applicator cap 210 relative to the housing 208, the tamper ring 602 may shear and thereby free the applicator cap 210 from the sensor applicator 102. Following which, the user may deliver the sensor control device 302 to the target monitoring location, as generally described above with reference to FIGS. 2E-2G.

In some embodiments, as mentioned above, the applicator cap 210 may be secured to the housing 208 via a sealed engagement to protect the internal components of the sensor applicator 102. In at least one embodiment, for example, an O-ring or another type of sealing gasket may seal an interface between the housing 208 and the applicator cap 210. The O-ring or sealing gasket may be a separate component part or alternatively molded onto one of the housing 208 and the applicator cap 210.

The housing 208 may be made of a variety of rigid materials. In some embodiments, for example, the housing 208 may be made of a thermoplastic polymer, such as polyketone. In other embodiments, the housing 208 may be made of cyclic olefin copolymer (COC), which can help prevent moisture ingress into the interior of the sensor applicator 102. As will be appreciated, any and all of the housings described or discussed herein may be made of polyketone or COC.

With specific reference to FIG. 6B, the sensor control device 302 may be loaded into the sensor applicator 102 by mating the sharp hub 422 with a sensor carrier 604 included within the sensor applicator 102. Once the sensor control device 302 is mated with the sensor carrier 604, the applicator cap 210 may then be secured to the sensor applicator 102.

In the illustrated embodiment, a collimator 606 is positioned within the applicator cap 210 and may generally help support the sensor control device 302 while contained within the sensor applicator 102. In some embodiments, the collimator 606 may form an integral part or extension of the applicator cap 210, such as being molded with or overmolded onto the applicator cap 210. In other embodiments, the collimator 606 may comprise a separate structure fitted within or attached to the applicator cap 210, without departing from the scope of the disclosure. In yet other embodiments, as discussed below, the collimator 606 may be omitted in the package received by the user, but otherwise used while sterilizing and preparing the sensor applicator 102 for delivery.

The collimator 606 may be designed to receive and help protect parts of the sensor control device 302 that need to be sterile, and isolate the sterile components of the sensor applicator 102 from microbial contamination from other locations within the sensor control device 302. To accomplish this, the collimator 606 may define or otherwise provide a sterilization zone 608 (alternately referred to as a "sterile barrier enclosure" or a "sterile sensor path") configured to receive the sensor 316 and the sharp 318 as extending from the bottom of the electronics housing 304. The sterilization zone 608 may generally comprise a hole or passageway extending at least partially through the body of the collimator 606. In the illustrated embodiment, the sterilization zone 608 extends through the entire body of the collimator 606, but may alternatively extend only partially therethrough, without departing from the scope of the disclosure.

When the sensor control device 302 is loaded into the sensor applicator 102 and the applicator cap 210 with the collimator 606 is secured thereto, the sensor 316 and the sharp 318 may be positioned within a sealed region 610 at least partially defined by the sterilization zone 608. The sealed region 610 is configured to isolate the sensor 316 and the sharp 318 from external contamination and may include (encompass) select portions of the interior of the electronics housing 304 and the sterilization zone 608 of the collimator 606.

While positioned within the sensor applicator 102, the fully assembled sensor control device 302 may be subjected to radiation sterilization 612. The radiation sterilization 612 may comprise, for example, e-beam irradiation, but other methods of sterilization may alternatively be used including, but not limited to, low energy X-ray irradiation. In some embodiments, the radiation sterilization 612 may be delivered either through continuous processing irradiation or through pulsed beam irradiation. In pulsed beam irradiation, the beam of radiation sterilization 612 is focused at a target location and the component part or device to be sterilized is moved to the target location at which point the radiation sterilization 612 is activated to provide a directed pulse of radiation. The radiation sterilization 612 is then turned off, and another component part or device to be sterilized is moved to the target location and the process is repeated.

The collimator 606 may be configured to focus the radiation (e.g., beams, waves, energy, etc.) from the radiation sterilization 612 toward the components that are required to be sterile, such as the sensor 316 and the sharp 318. More specifically, the hole or passageway of the sterilization zone 608 allows transmission of the radiation to impinge upon and sterilize the sensor 316 and the sharp 318, while the remaining portions of the collimator 606 prevent (impede) the propagating radiation from disrupting or damaging the electronic components within the electronics housing 304.

The sterilization zone 608 can exhibit any suitable cross-sectional shape necessary to properly focus the radiation on the sensor 316 and the sharp 318 for sterilization. In the illustrated embodiment, for example, the sterilization zone 608 is circular cylindrical, but could alternatively exhibit a polygonal cross-sectional shape, such as cubic or rectangular (e.g., including parallelogram), without departing from the scope of the disclosure.

In the illustrated embodiment, the sterilization zone 608 provides a first aperture 614a at a first end and a second aperture 614b at a second end opposite the first end. The first aperture 614a may be configured to receive the sensor 316 and the sharp 318 into the sterilization zone 608, and the second aperture 614b may allow the radiation (e.g., beams, waves, etc.) from the radiation sterilization 612 to enter the sterilization zone 608 and impinge upon the sensor 316 and the sharp 318. In the illustrated embodiment, the first and second apertures 614a,b exhibit identical diameters.

The body of the collimator 606 reduces or eliminates the radiation sterilization 612 from penetrating through the body material and thereby damaging the electronic components within the electronics housing 304. To accomplish this, in some embodiments, the collimator 606 may be made of a material that has a mass density greater than 0.9 grams per cubic centimeter (g/cc). One example material for the collimator 606 is polyethylene, but could alternatively comprise any material having a mass density similar to or greater than polyethylene. In some embodiments, for example, the material for the collimator 606 may comprise, but is not limited to, a metal (e.g., lead, stainless steel) or a high-density polymer.

In at least one embodiment, the design of the collimator 606 may be altered so that the collimator 606 may be made of a material that has a mass density less than 0.9 grams per cubic centimeter (g/cc) but still operate to reduce or eliminate the radiation sterilization 612 from impinging upon the electronic components within the electronics housing 304. To accomplish this, in some embodiments, the size (e.g., length) of the collimator 606 may be increased such that the propagating electrons from the radiation sterilization 612 are required to pass through a larger amount of material before potentially impinging upon sensitive electronics. The larger amount of material may help absorb or dissipate the dose strength of the radiation sterilization 612 such that it becomes harmless to the sensitive electronics. In other embodiments, however, the converse may equally be true. More specifically, the size (e.g., length) of the collimator 606 may be decreased as long as the material for the collimator 606 exhibits a large enough mass density.

In addition to the radiation blocking characteristics of the body of the collimator 606, in some embodiments, one or more shields 616 (one shown) may be positioned within the sensor housing 304 to protect sensitive electronic components from radiation while the sensor control device 302 is subjected to the radiation sterilization 612. The shield 616, for example, may be positioned to interpose a data processing unit 618 and the radiation source (e.g., an e-beam electron accelerator). In such embodiments, the shield 616 may be positioned adjacent to and otherwise aligned with the data processing unit 618 and the radiation source to block or mitigate radiation exposure (e.g., e-beam radiation or energy) that might otherwise damage the sensitive electronic circuitry of the data processing unit 618.

The shield 616 may be made of any material capable of blocking (or substantially blocking) the transmission of radiation. Suitable materials for the shield 616 include, but are not limited to, lead, tungsten, iron-based metals (e.g., stainless steel), copper, tantalum, tungsten, osmium, or any combination thereof. Suitable metals may be corrosion-resistant, austenitic, and any non-magnetic metal with a density ranging between about 5 grams per cubic centimeter (g/cc) and about 15 g/cc. The shield 616 may be fabricated via a variety of manufacturing techniques including, but not limited to, stamping, casting, injection molding, sintering, two-shot molding, or any combination thereof.

In other embodiments, however, the shield 616 may comprise a metal-filled thermoplastic polymer such as, but not limited to, polyamide, polycarbonate, or polystyrene. In such embodiments, the shield 616 may be fabricated by mixing the shielding material in an adhesive matrix and dispensing the combination onto shaped components or otherwise directly onto the data processing unit 618. Moreover, in such embodiments, the shield 616 may comprise an enclosure that encapsulates (or substantially encapsulates) the data processing unit 618.

In some embodiments, a collimator seal 620 may be applied to the end of the collimator 606 to seal off the sterilization zone 608 and, thus, the sealed region 610. As illustrated, the collimator seal 620 may seal the second aperture 614b. The collimator seal 620 may be applied before or after the radiation sterilization 612. In embodiments where the collimator seal 620 is applied before undertaking the radiation sterilization 612, the collimator seal 620 may be made of a radiation permeable microbial barrier material that allows radiation to propagate therethrough. With the collimator seal 620 in place, the sealed region 610 is able to maintain a sterile environment for the assembled sensor control device 302 until the user removes (unthreads) the applicator cap 210.

In some embodiments, the collimator seal 620 may comprise two or more layers of different materials. The first layer may be made of a synthetic material (e.g., a flash-spun high-density polyethylene fiber), such as Tyvek® available from DuPont®. Tyvek® is highly durable and puncture resistant and allows the permeation of vapors. The Tyvek® layer can be applied before or after the radiation sterilization 612, and following the radiation sterilization 612, a foil or other vapor and moisture resistant material layer may be sealed (e.g., heat sealed) over the Tyvek® layer to prevent the ingress of contaminants and moisture into the sterilization zone 608 and the sealed region 610. In other embodiments, the collimator seal 620 may comprise only a single protective layer applied to the end of the collimator 606. In such embodiments, the single layer is gas permeable for the sterilization process, but is also capable of protection against moisture and other harmful elements once the sterilization process is complete. Accordingly, the collimator seal 620 may operate as a moisture and contaminant layer, without departing from the scope of the disclosure.

It is noted that, while the sensor 316 and the sharp 318 extend from the bottom of the electronics housing 304 and into the sterilization zone 608 generally concentric with a centerline of the sensor applicator 102 and the applicator cap 210, it is contemplated herein to have an eccentric arrangement. More specifically, in at least one embodiment, the sensor 316 and the sharp 318 may extend from the bottom of the electronics housing 304 eccentric to the centerline of the sensor applicator 102 and the applicator cap 210. In such embodiments, the collimator 606 may be re-designed and otherwise configured such that the sterilization zone 608 is also eccentrically positioned to receive the sensor 316 and the sharp 318, without departing from the scope of the disclosure.

In some embodiments, the collimator 606 may comprise a first or "internal" collimator capable of being housed within the applicator cap 210 or otherwise within the sensor applicator 102, as generally described above. A second or "external" collimator (not shown) may also be included or otherwise used in the assembly (manufacturing) process to help sterilize the sensor applicator 102. In such embodiments, the external collimator may be positioned external to the sensor applicator 102 and the applicator cap 210 and used simultaneously with the internal collimator 606 to help focus the radiation sterilization 612 on the sensor 316 and the sharp 318.

In one embodiment, for example, the external collimator may initially receive the radiation sterilization 612. Similar to the internal collimator 606, the external collimator may provide or define a hole or passageway extending through the external collimator. The beams of the radiation sterilization 612 passing through the passageway of the external collimator may be focused and received into the sterilization zone 608 of the internal collimator 606 via the second aperture 614b. Accordingly, the external collimator may operate to pre-focus the radiation energy, and the internal collimator 606 may fully focus the radiation energy on the sensor 316 and the sharp 318.

In some embodiments, the internal collimator 606 may be omitted if the external collimator is capable of properly and fully focusing the radiation sterilization 612 to properly sterilize the sensor 316 and the sharp 318. In such embodiments, the sensor applicator may be positioned adjacent the external collimator and subsequently subjected to the radiation sterilization 612, and the external collimator may prevent radiation energy from damaging the sensitive electronics within the electronics housing 304. Moreover, in such embodiments, the sensor applicator 102 may be delivered to the user without the internal collimator 606 positioned within the applicator cap 210, thus eliminating complexity in manufacturing and use.

Figure 7A:
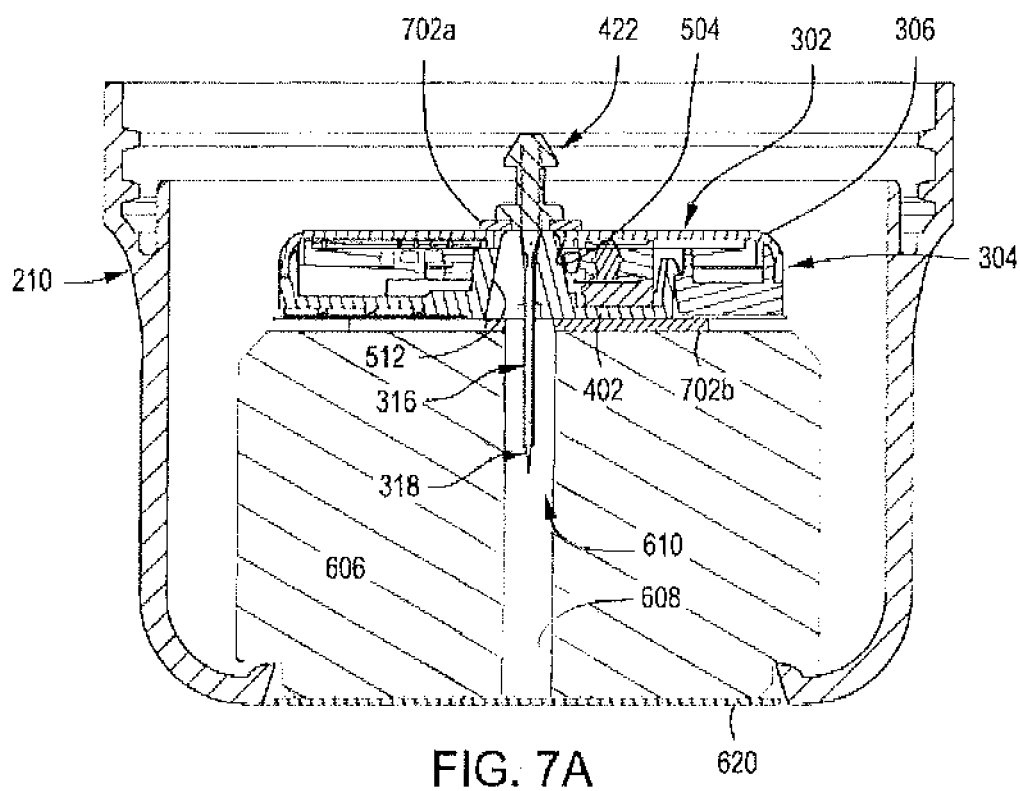
FIG. 7A is an enlarged cross-sectional side view of the sensor control device of FIG. 6B mounted within the cap of FIG. 6B.

FIG. 7A is an enlarged cross-sectional side view of the sensor control device 302 mounted within the applicator cap 210, according to one or more embodiments. As indicated above, portions of the sensor 316 and the sharp 318 may be arranged within the sealed region 610 and thereby isolated from external contamination. The sealed region 610 may include (encompass) select portions of the interior of the electronics housing 304 and the sterilization zone 608 of the collimator 606. In one or more embodiments, the sealed region 610 may be defined and otherwise formed by at least a first seal 702a, a second seal 702b, and the collimator seal 620.

The first seal 702a may be arranged to seal the interface between the sharp hub 422 and the top of the electronics housing 304. More particularly, the first seal 702a may seal the interface between the sharp hub 422 and the shell 306. Moreover, the first seal 702a may circumscribe the first central aperture 504 defined in the shell 306 such that contaminants are prevented from migrating into the interior of the electronics housing 304 via the first central aperture 504. In some embodiments, the first seal 702a may form part of the sharp hub 422. For example, the first seal 702a may be overmolded onto the sharp hub 422. In other embodiments, the first seal 702a may be overmolded onto the top surface of the shell 306. In yet other embodiments, the first seal 702a may comprise a separate structure, such as an O-ring or the like, that interposes the sharp hub 422 and the top surface of the shell 306, without departing from the scope of the disclosure.

The second seal 702b may be arranged to seal the interface between the collimator 606 and the bottom of electronics housing 304. More particularly, the second seal 702b may be arranged to seal the interface between the mount 308 and the collimator 606 or, alternatively, between the collimator 606 and the bottom of the plug 402 as received within the bottom of the mount 308. In applications including the plug 402, as illustrated, the second seal 702b may be configured to seal about and otherwise circumscribe the plug receptacle 512. In embodiments that omit the plug 402, the second seal 702b may alternatively circumscribe the second central aperture 506 (FIG. 5A) defined in the mount 308. Consequently, the second seal 702b may prevent contaminants from migrating into the sterilization zone 608 of the collimator 606 and also from migrating into the interior of the electronics housing 304 via the plug receptacle 512 (or alternatively the second central aperture 506).

In some embodiments, the second seal 702b may form part of the collimator 606. For example, the second seal 702b may be overmolded onto the top of the collimator 606. In other embodiments, the second seal 702b may be overmolded onto the plug 402 or the bottom of the mount 308. In yet other embodiments, the second seal 702b may comprise a separate structure, such as an O-ring or the like, that interposes the collimator 606 and the plug 402 or the bottom of the mount 308, without departing from the scope of the disclosure.

Upon loading the sensor control device 302 into the sensor applicator 102 (FIG. 6B) and securing the applicator cap 210 to the sensor applicator 102, the first and second seals 702a,b become compressed and generate corresponding sealed interfaces. The first and second seals 702a,b may be made of a variety of materials capable of generating a sealed interface between opposing structures. Suitable materials include, but are not limited to, silicone, a thermoplastic elastomer (TPE), polytetrafluoroethylene (PTFE or Teflon®), or any combination thereof.

As discussed above, the collimator seal 620 may be configured to seal off the bottom of the sterilization zone 608 and, thus, the bottom of the sealed region 610. Accordingly, the first and second seals 702a,b and the collimator seal 620 each create corresponding barriers at their respective sealing locations. The combination of these seals 702a,b and 620 allows the sealed region 610 containing the sensor 316 and the sharp 318 to be terminally sterilized.

Figure 7B:
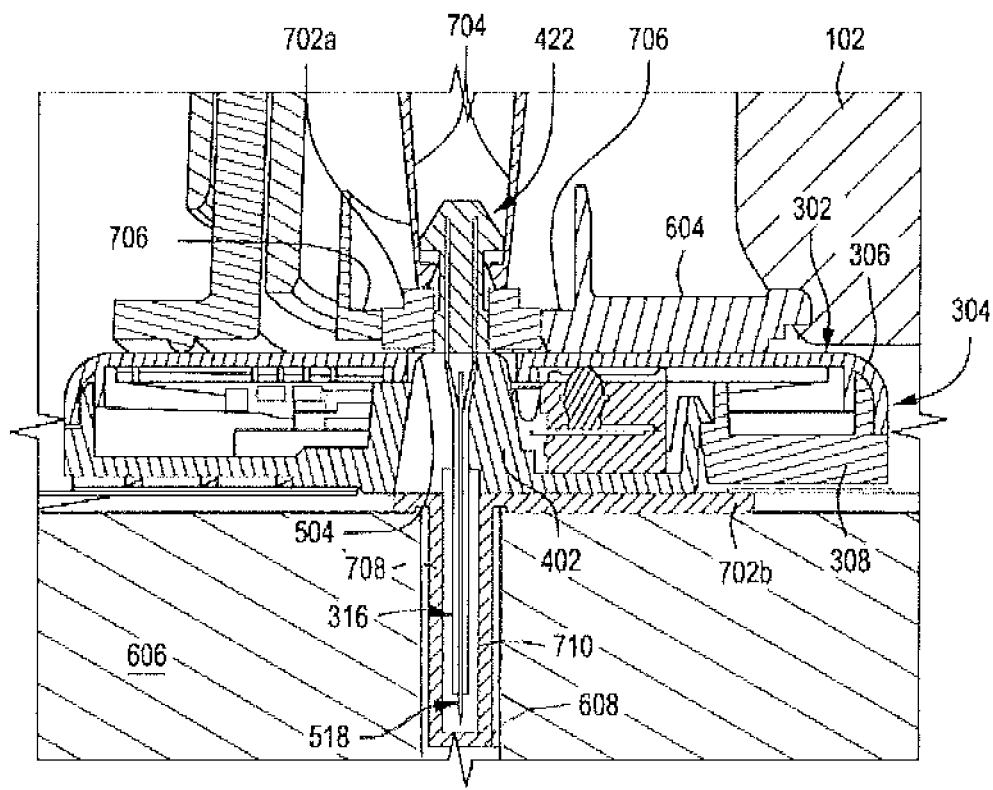
FIG. 7B is an enlarged cross-sectional side view of another embodiment of the sensor control device of FIG. 6B mounted within the sensor applicator of FIG. 6B.

FIG. 7B is an enlarged cross-sectional side view of another embodiment of the sensor control device 302 mounted within the sensor applicator 102, according to one or more embodiments. More specifically, FIG. 7B depicts alternative embodiments of the first and second seals 702a,b. The first seal 702a is again arranged to seal the interface between the sharp hub 422 and the top of the electronics housing 304 and, more particularly, seal off the first central aperture 504 defined in the shell 306. In the illustrated embodiment, however, the first seal 702a may be configured to seal both axially and radially. More particularly, when the sensor control device 302 is introduced into the sensor applicator 102, the sharp hub 422 is received by the sensor carrier 604. The first seal 702*a* may be configured to simultaneously bias against one or more axially extending members 704 of the sensor carrier 604 and one or more radially extending members 706 of the sensor carrier 604. Such dual biased engagement compresses the first seal 702*a* both axially and radially and thereby allows the first seal 702*a* to seal against the top of the electronics housing 304 in both the radial and axial directions.

The second seal 702*b* is again arranged to seal the interface between the collimator 606 and the bottom of electronics housing 304 and, more particularly, between the mount 308 and the collimator 606 or, alternatively, between the collimator 606 and the bottom of the plug 402 as received within the bottom of the mount 308. In the illustrated embodiment, however, the second seal 702*b* may extend into the sterilization zone 608 and define or otherwise provide a cylindrical well 708 sized to receive the sensor 316 and the sharp 1408 as extending from the bottom of the mount 308. In some embodiments, a desiccant 710 may be positioned within the cylindrical well to aid maintenance of a low humidity environment for biological components sensitive to moisture.

In some embodiments, the second seal 702*b* may be omitted and the collimator 606 may be directly coupled to the electronics housing 304. More specifically, in at least one embodiment, the collimator 606 may be threadably coupled to the underside of the mount 308. In such embodiments, the collimator 606 may provide or otherwise define a threaded extension configured to mate with a threaded aperture defined in the bottom of the mount 308. Threadably coupling the collimator 606 to the mount 308 may seal the interface between the collimator 606 and the bottom of electronics housing 304, and thus operate to isolate sealed region 610. Moreover, in such embodiments, the pitch and gauge of the threads defined on the collimator 606 and the mount 308 may match those of the threaded engagement between the applicator cap 210 and the sensor applicator 102. As a result, as the applicator cap 210 is threaded to or unthreaded from the sensor applicator 102, the collimator 606 may correspondingly be threaded to or unthreaded from the electronics housing 404.

Embodiments disclosed herein include:

A. An analyte monitoring system that includes a sensor applicator, a sensor control device positioned within the sensor applicator and including an electronics housing, a sensor extending from a bottom of the electronics housing, a sharp hub positioned adjacent a top of the electronics housing, and a sharp carried by the sharp hub and extending through the electronics housing and from the bottom of the electronics housing. The analyte monitoring system further including a cap coupled to the sensor applicator, and a collimator positioned within the cap and defining a sterilization zone that receives the sensor and the sharp extending from the bottom of the electronics housing.

B. A method of preparing an analyte monitoring system includes loading a sensor control device into a sensor applicator, the sensor control device including an electronics housing, a sensor extending from a bottom of the electronics housing, a sharp hub positioned adjacent a top of the electronics housing, and a sharp carried by the sharp hub and extending through the electronics housing and from the bottom of the electronics housing. The method further including securing a cap to the sensor applicator, wherein a collimator is arranged within the cap and defines a sterilization zone that receives the sensor and the sharp extending from the bottom of the electronics housing, sterilizing the sensor and the sharp with radiation sterilization while positioned within the sterilization zone, and preventing radiation from the radiation sterilization from damaging electronic components within the electronics housing with the collimator.

C. A method of preparing an analyte monitoring system includes loading a sensor control device into a sensor applicator, the sensor control device including an electronics housing, a sensor extending from a bottom of the electronics housing, a sharp hub positioned adjacent a top of the electronics housing, and a sharp carried by the sharp hub and extending through the electronics housing and from the bottom of the electronics housing. The method further including positioning the sensor applicator adjacent a collimator, subjecting the sensor and the sharp to radiation sterilization, and preventing radiation from the radiation sterilization from damaging the electronic components within the electronics housing with the collimator.

Each of embodiments A, B, and C may have one or more of the following additional elements in any combination: Element 1: wherein the sterilization zone comprises a passageway extending at least partially through the collimator. Element 2: wherein the sterilization zone comprises a cross-sectional shape selected from the group consisting of cubic, rectangular, and any combination thereof. Element 3: wherein the sterilization zone defines a first aperture at a first end and a second aperture at a second end, and wherein the first aperture receives the sensor and the sharp extending from the bottom of the electronics housing and a seal is arranged at the second aperture. Element 4: further comprising a sealed region encompassing the sterilization zone and a portion of an interior of the electronics housing, wherein the sealed region is defined by a first seal that seals an interface between the sharp hub and the top of the electronics housing, a second seal that seals an interface between the collimator and the bottom of the electronics housing, and a third seal that seals an end of the sterilization zone. Element 5: wherein the first seal circumscribes a central aperture defined in the top of the electronics housing and prevents contaminants from migrating into the portion of the interior of the electronics housing via the central aperture, and wherein the second seal circumscribes an aperture defined in the bottom of the electronics housing and prevents contaminants from migrating into the portion of the interior of the electronics housing via the aperture. Element 6: wherein the first seal provides one or both of an axial and a radial seal. Element 7: wherein the second seal extends into the sterilization zone and defines a cylindrical well that receives the sensor and the sharp. Element 8: further comprising a printed circuit board arranged within the electronics housing, a data processing unit mounted to the printed circuit board, and a shield positioned within the electronics housing to protect the data processing unit from radiation from a radiation sterilization process. Element 9: wherein the shield is made of a non-magnetic metal selected from the group consisting of lead, tungsten, iron, stainless steel, copper, tantalum, osmium, a thermoplastic polymer mixed with a non-magnetic metal, and any combination thereof.

Element 10: further comprising creating a sealed region as the cap is secured to the sensor applicator, the sealed region encompassing the sterilization zone and a portion of an interior of the electronics housing. Element 11: wherein creating the sealed region comprises sealing an interface between the sharp hub and the top of the electronics housing with a first seal, sealing an interface between the collimator and the bottom of the electronics housing with a second seal, and sealing an end of the sterilization zone with a third seal. Element 12: wherein sealing the interface between the sharp hub and the top of the electronics housing with the first seal comprises providing one or both of an axial seal and a radial seal with the first seal. Element 13: wherein the collimator comprises an internal collimator and sterilizing the sensor and the sharp with the radiation sterilization further comprises positioning the sensor applicator adjacent an external collimator arranged external to the sensor applicator, focusing the radiation with the external collimator to be received by the internal collimator, and preventing the radiation from damaging the electronic components within the electronics housing with the external and internal collimators. Element 14: wherein the sterilization zone defines a first aperture at a first end of the collimator and a second aperture at a second end of the collimator, and wherein sterilizing the sensor and the sharp comprises introducing radiation into the sterilization zone via the second aperture. Element 15: wherein preventing the radiation from the radiation sterilization from damaging the electronic components comprises blocking the radiation with the material of the collimator. Element 16: wherein a printed circuit board is arranged within the electronics housing and a data processing unit is mounted to the printed circuit board, the method further comprising protecting the data processing unit from radiation from the radiation sterilization process with a shield positioned within the electronics housing.

Element 17: wherein positioning the sensor applicator adjacent the collimator comprises arranging the collimator such that it resides external to the sensor applicator during the radiation sterilization.

By way of non-limiting example, exemplary combinations applicable to A, B, and C include: Element 2 with Element 3; Element 4 with Element 5; Element 4 with Element 6; Element 4 with Element 7; Element 8 with Element 9; Element 10 with Element 11; and Element 11 with Element 12.

External Sterilization Assemblies

Referring again briefly to FIG. 1, prior to being delivered to an end user, the sensor control device 104 must be sterilized to render the product free from viable microorganisms. The sensor 110 is commonly sterilized using radiation sterilization, such as electron beam ("e-beam") irradiation. Radiation sterilization, however, can damage the electronic components within the sensor control device 104, which are commonly sterilized via gaseous chemical sterilization (e.g., using ethylene oxide). Gaseous chemical sterilization, however, can damage the enzymes or other chemistry and biologics included on the sensor 110.

In the past, this sterilization incompatibility has been circumvented by separating the sensor 110 and the electronic components and sterilizing each individually. This approach, however, requires additional parts, packaging, process steps, and final assembly by the user, which introduces a possibility of user error. According to the present disclosure, the sensor control device 104, or any device requiring terminal sterilization, may be properly sterilized using an external sterilization assembly designed to focus sterilizing radiation (e.g., beams, waves, energy, etc.) toward component parts requiring sterilization, while simultaneously preventing the propagating radiation from disrupting or damaging sensitive electronic components.

Figure 8:
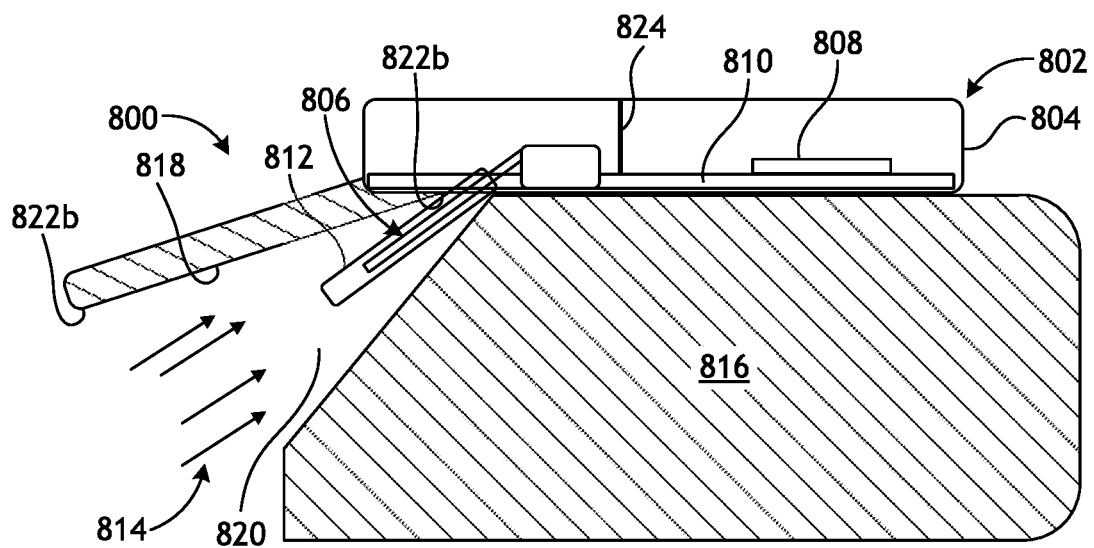
FIGS. 8-12 are schematic diagrams of example external sterilization assemblies, according to one or more embodiments of the present disclosure.

FIG. 8 is a schematic diagram of an example external sterilization assembly 800, according to one or more embodiments of the present disclosure. The external sterilization assembly 800 (hereafter the "assembly 800") may be designed and otherwise configured to help sterilize a medical device 802. The medical device 802 may comprise, for example, a sensor control device similar in some respects to the sensor control device 104 of FIG. 1, but could alternatively comprise other types of medical devices, health care products, or systems requiring terminal sterilization of specific component parts. Example medical devices or health care products that may incorporate the principles of the present disclosure include, but are not limited to, ingestible products, cardiac rhythm management (CRM) devices, under-skin sensing devices, externally mounted medical devices, or any combination thereof.

The medical device 802 may include a housing 804, a part 806 requiring sterilization, and one or more radiation sensitive components 808. In the illustrated embodiment, the radiation sensitive component 808 may be mounted to a printed circuit board (PCB) 810 positioned within the housing 804, and the housing 804 may comprise an electronics housing for a sensor control device. The radiation sensitive component 808 may include one or more electronic modules such as, but not limited to, a data processing unit (e.g., an application specific integrated circuit or ASIC), a resistor, a transistor, a capacitor, an inductor, a diode, and a switch. In other embodiments, however, the radiation sensitive component 808 may comprise a radiation sensitive chemical solution or analyte, as described herein with reference to FIG. 12.

In some embodiments, the part 806 may comprise a sensor (e.g., the sensor 110 of FIG. 1) that extends from the housing 804. As illustrated, the part 806 may extend at an angle from the bottom of the housing 804, but could alternatively extend perpendicular to the bottom or from another surface of the housing 804. In at least one embodiment, the part 806 may further include a sharp that may also require sterilization and may help implant the sensor beneath the skin of a user. In some embodiments, as illustrated, the part 806 may be encapsulated with a cap 812 that provides a sealed barrier that protects exposed portions of the part 806 (e.g., the sensor and associated sharp) until the part 806 is needed for use.

The medical device 802 may be subjected to radiation sterilization 814 to properly sterilize the part 806 for use. Suitable radiation sterilization 814 processes include, but are not limited to, electron beam (e-beam) irradiation, gamma ray irradiation, X-ray irradiation, or any combination thereof. In embodiments that include the cap 812, the cap 812 may be made of a material that permits propagation of the radiation 814 therethrough to facilitate radiation sterilization of the part 806. Suitable materials for the cap 812 include, but are not limited to, a non-magnetic metal (e.g., aluminum, copper, gold, silver, etc.), a thermoplastic, ceramic, rubber (e.g., ebonite), a composite material (e.g., fiberglass, carbon fiber reinforced polymer, etc.), an epoxy, or any combination thereof. In some embodiments, the cap 812 may be transparent or translucent, but can otherwise be opaque, without departing from the scope of the disclosure.

The assembly 800 may include a radiation shield 816 positioned external to the medical device 802 and configured to help sterilize the part 806 while preventing (impeding) propagating radiation 814 from disrupting or damaging the radiation sensitive component(s) 808. To accomplish this, the radiation shield 816 may provide a collimator 818 that generally comprises a hole or passageway extending at least partially through the body of the radiation shield 816. The collimator 818 defines a sterilization zone 820 configured to focus the radiation 814 toward the part 806. In the illustrated embodiment, the part 806 may also be received within the sterilization zone 820 for sterilization.

While focusing the radiation 814 (e.g., beams, waves, energy, etc.) toward the part 806, the radiation shield 816 may be made of a material that reduces or eliminates the radiation 814 from penetrating therethrough and thereby damaging the radiation sensitive component(s) 808 within the housing 804. In other words, the radiation shield 816 may be made of a material having a density sufficient to absorb the dose of the beam energy being delivered. In some embodiments, for example, the radiation shield 816 may be made of any material that has a mass density greater than 0.9 grams per cubic centimeter (g/cc). In other embodiments, however, the mass density of a suitable material may be less than 0.9 g/cc, without departing from the scope of the disclosure. Suitable materials for the radiation shield 816 include, but are not limited to, a high-density polymer, (e.g., polyethylene, polypropylene, polystyrene, polytetrafluoroethylene, etc.), a metal (e.g., lead, stainless steel, aluminum, etc.), any combination thereof, or any material having a mass density greater than 0.9 g/cc.

The collimator 818 can exhibit any suitable cross-sectional shape necessary to focus the radiation on the part 806 for sterilization. In the illustrated embodiment, for example, the collimator 818 is conical or frustoconical in shape. In other embodiments, however, the collimator 818 may exhibit a polygonal cross-sectional shape, such as cubic, rectangular (e.g., including parallelogram), or pyramidal, without departing from the scope of the disclosure. In yet other embodiments, the collimator 818 may exhibit a circular cross-sectional shape with parallel sides.

In the illustrated embodiment, the collimator 818 provides a first aperture 822a and a second aperture 822b where the first and second apertures 822a,b are defined at opposing ends of the sterilization zone 820. The first aperture 822a may allow the radiation 814 to enter the sterilization zone 820 and impinge upon the part 806, and the second aperture 822b may be configured to receive the part 806 into the sterilization zone 820. In embodiments where the collimator 818 is conical or frustoconcial in shape, the second aperture 822b may have a diameter that is smaller than the diameter of the first aperture 822a. In such embodiments, for example, the size of the second aperture 822b may range between about 0.5 mm and about 3.0 mm, and the size of the first aperture 822a may range between about 5.0 mm and about 16.0 mm. As will be appreciated, however, the respective diameters of the first and second apertures 822a,b may be greater or less than the ranges provided herein, without departing from the scope of the disclosure. Indeed, the diameters of the first and second apertures 822a,b may be scaled to the device size and need only be large enough to allow a sufficient dose of radiation to impinge upon the part 806. Moreover, in at least one embodiment, the collimator 818 may be cylindrical in shape where the first and second apertures 822a,b exhibit identical diameters.

In some embodiments, the assembly 800 may further include a barrier shield 824 positioned within the housing 804. The barrier shield 824 may be configured to help block radiation 814 (e.g., electrons) from propagating within the housing 804 toward the radiation sensitive component(s) 808. The barrier shield 824 may be made of any of the materials mentioned above for the radiation shield 816. In the illustrated embodiment, the barrier shield 824 is positioned vertically within the housing 804, but may alternatively be positioned at any other angular configuration suitable for protecting the radiation sensitive component(s) 808.

Figure 9:
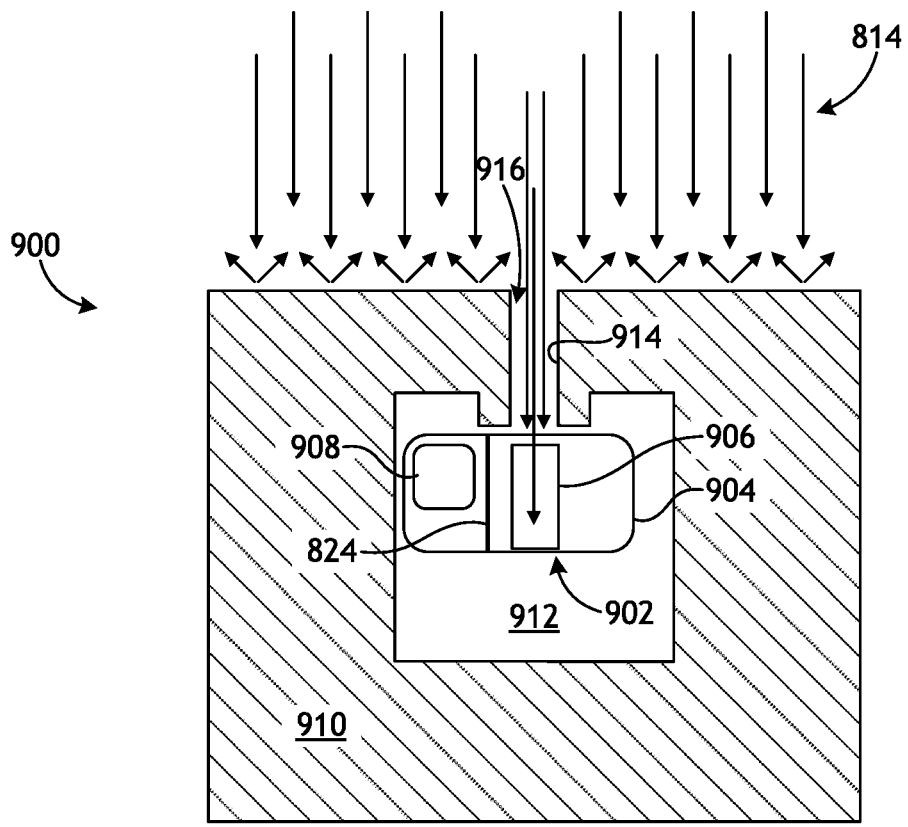

FIG. 9 is a schematic diagram of another example external sterilization assembly 900, according to one or more additional embodiments of the present disclosure. The external sterilization assembly 900 (hereafter the "assembly 900") may be similar in some respects to the assembly 800 of FIG. 8 and therefore may be best understood with reference thereto, where like numerals will refer to similar components not described again. Similar to the assembly 800, the assembly 900 may be designed and otherwise configured to help sterilize a medical device 902. In the illustrated embodiment, the medical device 902 may comprise a two-piece sensor control device, but could alternatively comprise any of the medical devices mentioned herein with respect to the medical device 802.

As illustrated, the medical device 902 includes a housing 904, a part 906 requiring sterilization, and one or more radiation sensitive components 908 positioned within the housing 904. The housing 904 may comprise packaging or an enclosure that contains the part 906 and the radiation sensitive component(s) 908. The radiation sensitive component(s) 908 may comprise any of the electronic modules mentioned herein with respect to the radiation sensitive component(s) 808 of FIG. 8. The part 906 may comprise, for example a needle/sensor subassembly, and may be subjected to radiation sterilization 814 to properly sterilize the part 906 for use.

The assembly 900 may include a radiation shield 910 positioned external to the medical device 902 and configured to help sterilize the part 906 while preventing (impeding) propagating radiation 814 from damaging the radiation sensitive component(s) 908. In the illustrated embodiment, the radiation shield 910 may define or otherwise provide an internal cavity 912 into which the medical device 902 may be positioned. Similar to the radiation shield 816 of FIG. 8, the radiation shield 910 may provide a collimator 914 that generally comprises a hole or passageway extending at least partially through the body of the radiation shield 910 and providing access into the cavity 912. The collimator 914 may define a sterilization zone 916 that helps focus the radiation 814 toward the part 906. The radiation shield 910 may be made of any of the materials mentioned above with respect to the radiation shield 816 to reduce or eliminate the radiation 814 from penetrating therethrough, except for at the collimator 914, and thereby damaging the radiation sensitive component(s) 908 within the housing 904.

To properly sterilize the part 906, the radiation sterilization 814 may be directed at the medical device 902. The collimator 914 and sterilization zone 916 may be configured to concentrate and/or focus the radiation sterilization 814 toward the part 906, while the remaining portions of the radiation shield 910 prevent (impede) the propagating radiation 814 from damaging the radiation sensitive component(s) 908 within the housing 904. In the illustrated embodiment, the collimator 914 and sterilization zone 916 exhibit a circular cross-sectional shape with parallel sides, but could alternatively exhibit other cross-sectional shapes including, but not limited to, conical, frustoconical, pyramidal, polygonal, or any combination thereof.

In some embodiments, the assembly 900 may further include the barrier shield 824 positioned within the housing 904 to help block radiation 814 (e.g., electrons) from propagating within the housing 904 toward the radiation sensitive component(s) 908.

Figure 10:
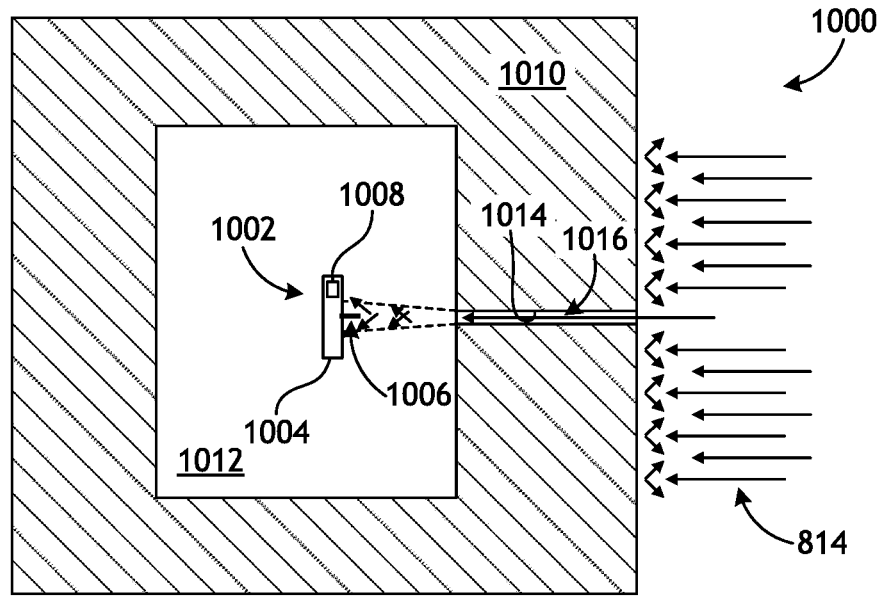

FIG. 10 is a schematic diagram of another example external sterilization assembly 1000, according to one or more additional embodiments of the present disclosure. The external sterilization assembly 1000 (hereafter the "assembly 1000") may be similar in some respects to the assembly 900 of FIG. 15 and therefore may be best understood with reference thereto, where like numerals will refer to similar components not described again. Similar to the assembly 900, the assembly 1000 may be designed and otherwise configured to help sterilize a medical device 1002. In the illustrated embodiment, the medical device 1002 may comprise a sensor control device similar to the sensor control device 104 of FIG. 1, but could alternatively comprise any of the medical devices mentioned herein with respect to the medical device 802 of FIG. 8.

As illustrated, the medical device 1002 includes a housing 1004, a part 1006 requiring sterilization, and one or more radiation sensitive components 1008 positioned within the housing 1004. In the illustrated embodiment, the housing 1004 may comprise an electronics housing for a sensor control device (e.g., the sensor control device 104 of FIG. 1) and the radiation sensitive component(s) 1008 may comprise any of the electronic modules mentioned herein with respect to the radiation sensitive component(s) 808 of FIG. 8. In some embodiments, the part 1006 may comprise a sensor (e.g., the sensor 110 of FIG. 1) that extends from the housing 1004, and may further include a sharp also requiring sterilization and used to help implant the sensor beneath the skin of a user.

The assembly 1000 may include a radiation shield 1010 positioned external to the medical device 1002 and configured to help sterilize the part 1006 while preventing (impeding) propagating radiation 814 from disrupting or damaging the radiation sensitive component(s) 1008. The radiation shield 1010 may be made of any of the materials mentioned above with respect to the radiation shield 816 of FIG. 8 to reduce or eliminate the radiation 814 from penetrating therethrough and thereby damaging the radiation sensitive component(s) 1008 within the housing 1004.

In the illustrated embodiment, the radiation shield 1010 may define or otherwise provide an internal cavity 1012 into which the medical device 1002 may be positioned for sterilization. In some embodiments, the radiation shield 1010 may comprise a box and the internal cavity 1012 may be formed within the interior of the box. The radiation shield 1010 may also provide a collimator 1014 that extends at least partially through the body of the radiation shield 1010 and provides access into the cavity 1012. The collimator 1014 may define a sterilization zone 1016 that focuses the radiation 814 toward the part 1006 for sterilization.

To properly sterilize the part 1006, the radiation sterilization 814 may be directed at the medical device 1002. The collimator 1014 and the sterilization zone 1016 may concentrate and/or focus the radiation sterilization 814 toward the part 1006, while the remaining portions of the radiation shield 1010 prevent (impede) the propagating radiation 814 from damaging the radiation sensitive component(s) 1008 within the housing 1004. In the illustrated embodiment, the collimator 1014 exhibits a circular cross-sectional shape with parallel sides, but could alternatively exhibit other cross-sectional shapes including, but not limited to, conical, frustoconical, pyramidal, polygonal, or any combination thereof.

Figure 11:
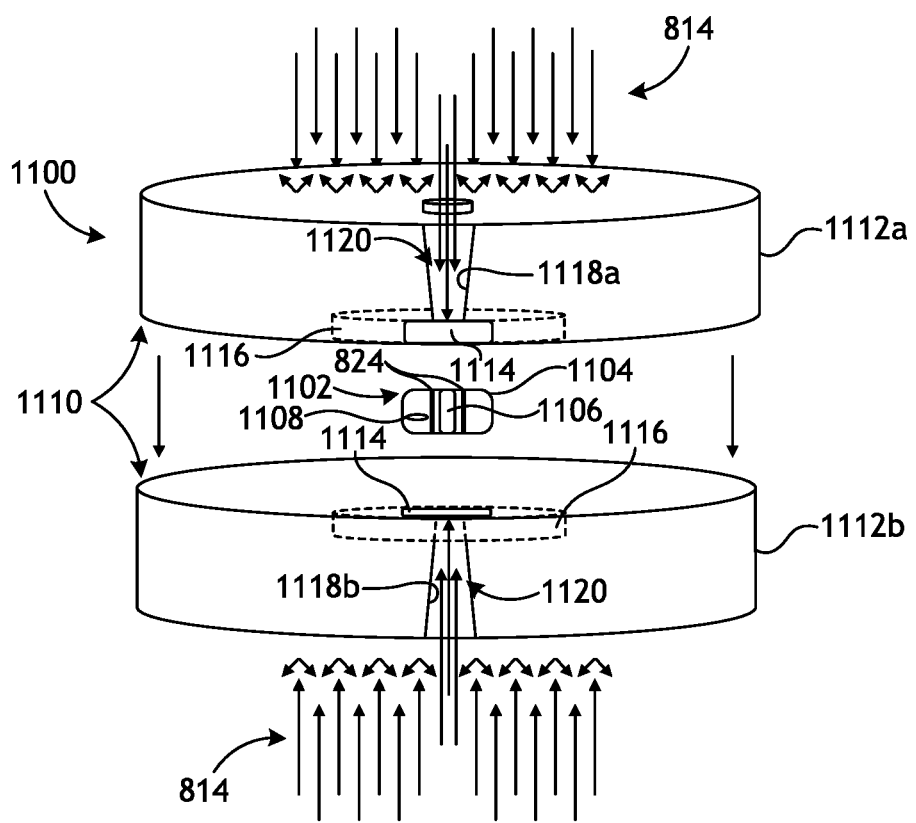

FIG. 11 is a schematic diagram of another example external sterilization assembly 1100, according to one or more additional embodiments of the present disclosure. The external sterilization assembly 1100 (hereafter the "assembly 1100") may be similar in some respects to the assemblies 800, 900, and 1000 of FIGS. 8, 9, and 10, respectively, and therefore may be best understood with reference thereto. Similar to the assemblies 800-1000, the assembly 1100 may be designed and otherwise configured to help sterilize a medical device 1102. In the illustrated embodiment, the medical device 1102 may comprise a two piece sensor control device, but could alternatively comprise any of the medical devices mentioned herein with respect to the medical device 802.

As illustrated, the medical device 1102 includes a housing 1104, a part 1106 requiring sterilization, and one or more radiation sensitive components 1108 positioned within the housing 1104. The radiation sensitive component(s) 1108 may comprise any of the electronic modules mentioned herein with respect to the radiation sensitive component(s) 808 of FIG. 8. In the illustrated embodiment, the part 1106 may comprise, for example, a needle/sensor subassembly, and may be subjected to radiation sterilization 814 to properly sterilize the part 1106 for use.

The assembly 1100 may include a radiation shield 1110 positioned external to the medical device 1102 and configured to help sterilize the part 1106 while preventing (impeding) propagating radiation 814 from damaging the radiation sensitive component(s) 1108. The radiation shield 1110 may be made of any of the materials mentioned above with respect to the radiation shield 816 of FIG. 8 to reduce or eliminate the radiation 814 from penetrating therethrough and thereby damaging the radiation sensitive component(s) 1108.

In the illustrated embodiment, the radiation shield 1110 may comprise a clamshell structure including a first portion 1112a and a second portion 1112b matable (or engageable) with the first portion 1112a. The radiation shield 1110 may also provide or otherwise define an internal cavity 1114 into which the medical device 1102 may be positioned for sterilization. In some embodiments, as illustrated, the first and second portions 1112a,b may cooperatively define a portion of the internal cavity 1114 such that when the first and second portions 1112a,b are properly mated, the internal cavity 1114 is formed. In other embodiments, however, the internal cavity 1114 may be defined wholly within the first portion 1112a or wholly within the second portion 1112b.

In some embodiments, the assembly 1100 may further include an absorber 1116 configured to protect the medical device 1102. In at least one embodiment, as illustrated, portions of the absorber 1116 may be provided by or otherwise form part of each of the first and second portions 1112a,b. In such embodiments, the internal cavity 1114 may be defined, at least in part by the absorber 1116. The absorber 1116 may be made of a material that absorbs stray radiation without causing Bremsstrahlung protons being generated. The material for the absorber 1116 may comprise, for example, any of the high-density polymers mentioned herein for the radiation shield 816 of FIG. 8.

Similar to the radiation shield 816 of FIG. 8, the radiation shield 1110 may provide a collimator. In the illustrated embodiment, however, the radiation shield 1110 provides or otherwise defines a first collimator 1118a and a second collimator 1118b, but could alternatively include only one of the collimators 1118a,b, without departing from the scope of the disclosure. The first collimator 1118a generally comprises a hole or passageway extending at least partially through the first portion 1112a of the radiation shield 1110, and the second collimator 1118b generally comprises a hole or passageway extending at least partially through the second portion 1112b. Each collimator 1118a,b provides access into the internal cavity 1114 and the collimators 1118a,b cooperatively define a sterilization zone 1120 that includes the internal cavity 1114 and helps focus the radiation 814 toward the part 1106 for sterilization.

To properly sterilize the part 1106, the medical device 1102 may be positioned within the internal cavity 1114 and the opposing portions 1112a,b may be mated to encapsulate the medical device 1102. The medical device 1102 may be situated within the sterilization zone 1120 once properly positioned within the cavity 1114. The radiation sterilization 814 may then be directed at the medical device 1102 on opposing sides of the radiation shield 1110, and the collimators 1118a,b may concentrate and/or focus the radiation sterilization 814 toward the part 1106 on opposing sides of the part 1106. The remaining portions of the radiation shield 1110 prevent (impede) the propagating radiation 814 from damaging the radiation sensitive component(s) 1108 within the housing 1104. In the illustrated embodiment, each collimator 1118a,b exhibits a conical or frustoconical cross-sectional shape, but could alternatively exhibit other cross-sectional shapes including, but not limited to, circular, pyramidal, polygonal, or any combination thereof.

In some embodiments, the assembly 1100 may further include one or more barrier shields 824 (two shown) positioned within the housing 1104 to help block radiation 814 (e.g., electrons) from propagating within the housing 1104 toward the radiation sensitive component(s) 1108.

Figure 12:
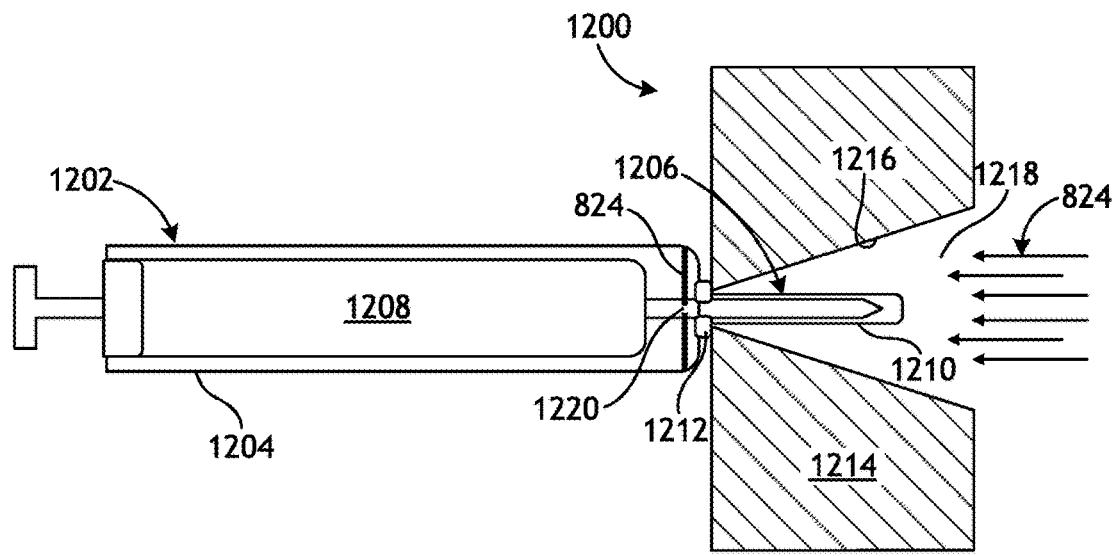

FIG. 12 is a schematic diagram of another example external sterilization assembly 1200, according to one or more additional embodiments of the present disclosure. The external sterilization assembly 1200 (hereafter the "assembly 1200") may be designed and otherwise configured to help sterilize a medical device 1202, which, in the illustrated embodiment, comprises a hypodermic needle or syringe. As illustrated, the medical device 1202 includes a housing 1204 (e.g., a barrel or vial), a part 1206 requiring sterilization, and one or more radiation sensitive components 1208 positioned within the housing 1204. In the illustrated embodiment, the radiation sensitive component 1208 may comprise a chemical solution or an analyte (e.g., an active agent, pharmaceutical, biologic, etc.) that may be sensitive to irradiation, and the part 1206 may comprise a needle designed to deliver the chemical solution.

In some embodiments, as illustrated, the part 1206 may be encased or otherwise surrounded by a cap 1210 (e.g., a needle cap) that encapsulates the part 1206. Moreover, in at least one embodiment, the cap 1210 may be sealed against the housing 1204 with a sealing element 1212, such as an O-ring or the like. The cap 1210 and the sealing element 1212 may cooperatively provide a sterile barrier system that surrounds and protects exposed portions of the part 1206 until required to be used. The part 1206 may be subjected to radiation sterilization 814 to properly sterilize the part 1206 for use.

The assembly 1200 may include a radiation shield 1214 positioned external to the medical device 1202 and configured to help sterilize the part 1206 while preventing (impeding) propagating radiation 814 from damaging the radiation sensitive component 1208. As illustrated, the radiation shield 1214 may provide a collimator 1216 that generally comprises a hole or passageway extending at least partially through the body of the radiation shield 1214 and defines a sterilization zone 1218 configured to focus the radiation 814 toward the part 1206 for sterilization. In the illustrated embodiment, the part 1206 may also be received within the sterilization zone 1218. The collimator 1216 allows transmission of the radiation 814 to impinge upon and sterilize the part 1206, while the remaining portions of the radiation shield 1214 prevent (impede) the propagating radiation 814 from damaging the radiation sensitive component(s) 1208 within the housing 1204. In the illustrated embodiment, the collimator 1216 is conical or frustoconical in shape, but may alternatively exhibit other cross-sectional shapes, such as polygonal, pyramidal, circular, or any combination thereof.

In embodiments including the cap 1210, the body of the cap 1210 may comprise a material that permits propagation of radiation 814 therethrough to facilitate radiation sterilization of the part 1206. Suitable materials for the cap 1210 may be the same as mentioned herein for the cap 812 of FIG. 8.

In some embodiments, the assembly 1200 may further include the barrier shield 824 positioned to help block radiation 814 (e.g., electrons) from propagating within the housing 1204 toward the radiation sensitive component 1208 (e.g., the chemical solution). In the illustrated embodiment, the barrier shield 824 may define or otherwise provide a central aperture 1220 configured to allow the radiation sensitive component 1208 to exit the housing 1204 via the part 1206 (e.g., the needle). In other embodiments, the barrier shield 824 may provide a tortuous pathway that allows the radiation sensitive component 1208 to exit the housing 1204 via the part 1206.

Figure 13:
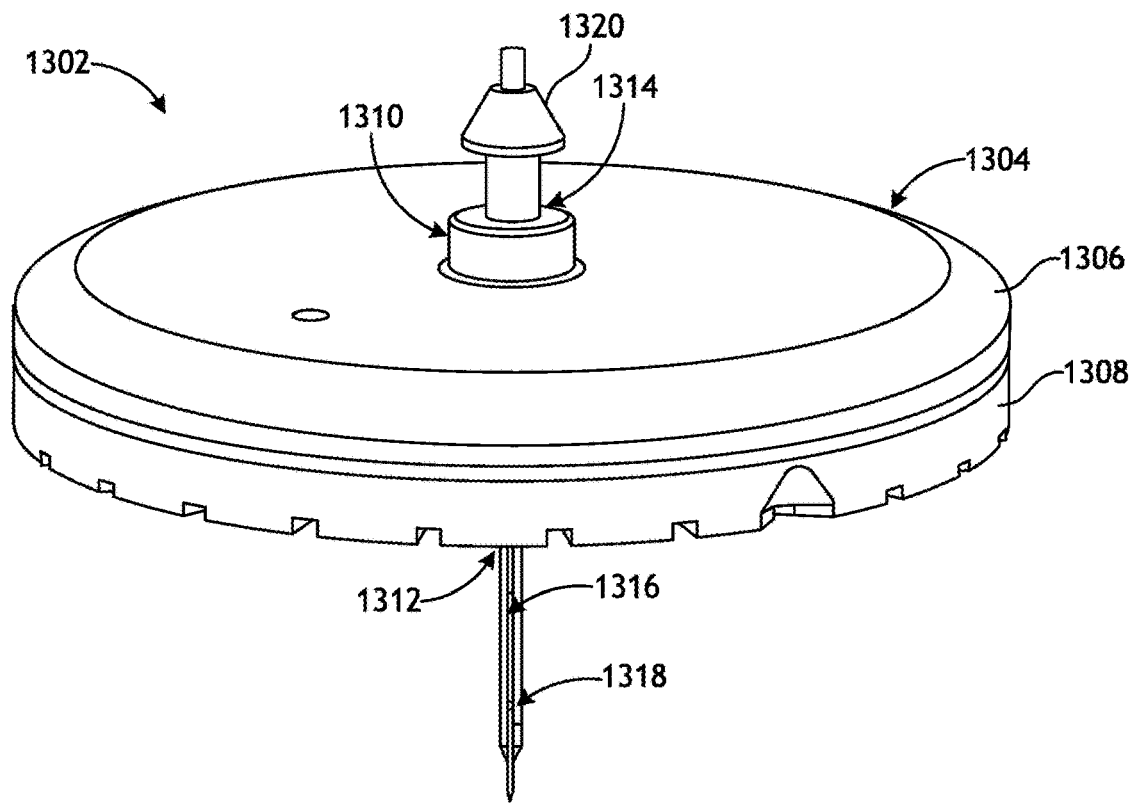
FIG. 13 is an isometric view of an example sensor control device.

FIG. 13 is an isometric view of an example sensor control device 1302, according to one or more additional embodiments of the present disclosure. The sensor control device 1302 may be the same as or similar to the sensor control device 104 of FIG. 1 and, therefore, may be used in conjunction with the sensor applicator 102 (FIG. 1), which delivers the sensor control device 1302 to a target monitoring location on a user's skin. Moreover, the sensor control device 1302 may be alternately characterized as a medical device, similar to one or more of the medical devices 1402-1202 of FIGS. 8-12 described herein. Accordingly, the sensor control device 1302 may also require proper sterilization prior to being used.

As illustrated, the sensor control device 1302 includes an electronics housing 1304 that is generally disc-shaped and may have a circular cross-section. In other embodiments, however, the electronics housing 1304 may exhibit other cross-sectional shapes, such as ovoid (e.g., pill-shaped), a squircle, or polygonal, without departing from the scope of the disclosure. The electronics housing 1304 may be configured to house or otherwise contain various electronic components used to operate the sensor control device 1302.

The electronics housing 1304 may include a shell 1306 and a mount 1308 that is matable with the shell 1306. The shell 1306 may be secured to the mount 1308 via a variety of ways, such as a snap fit engagement, an interference fit, sonic welding, one or more mechanical fasteners (e.g., screws), or any combination thereof. In some cases, the shell 1306 may be secured to the mount 1308 such that a sealed interface therebetween is generated. In such embodiments, a gasket or other type of seal material may be positioned at or near the outer diameter (periphery) of the shell 1306 and the mount 1308, and securing the two components together may compress the gasket and thereby generate a sealed interface. In other embodiments, an adhesive may be applied to the outer diameter (periphery) of one or both of the shell 1306 and the mount 1308. The adhesive secures the shell 1306 to the mount 1308 and provides structural integrity, but may also seal the interface between the two components and thereby isolate the interior of the electronics housing 1304 from outside contamination.

In the illustrated embodiment, the sensor control device 1302 may further include a plug assembly 1310 that may be coupled to the electronics housing 1304. The plug assembly 1310 may include a sensor module 1312 (partially visible) interconnectable with a sharp module 1314 (partially visible). The sensor module 1312 may be configured to carry and otherwise include a sensor 1316 (partially visible), and the sharp module 1314 may be configured to carry and otherwise include a sharp 1318 (partially visible) used to help deliver the sensor 1316 transcutaneously under a user's skin during application of the sensor control device 1302. The sharp module 1314 may include a sharp hub 1320 that carries the sharp 1318.

As illustrated, corresponding portions of the sensor 1316 and the sharp 1318 extend from the electronics housing 1304 and, more particularly, from the bottom of the mount 1308. The exposed portion of the sensor 1316 (alternately referred to as the "tail") may be received within a hollow or recessed portion of the sharp 1318. The remaining portions of the sensor 1316 are positioned within the interior of the electronics housing 1304.

Figure 14B:
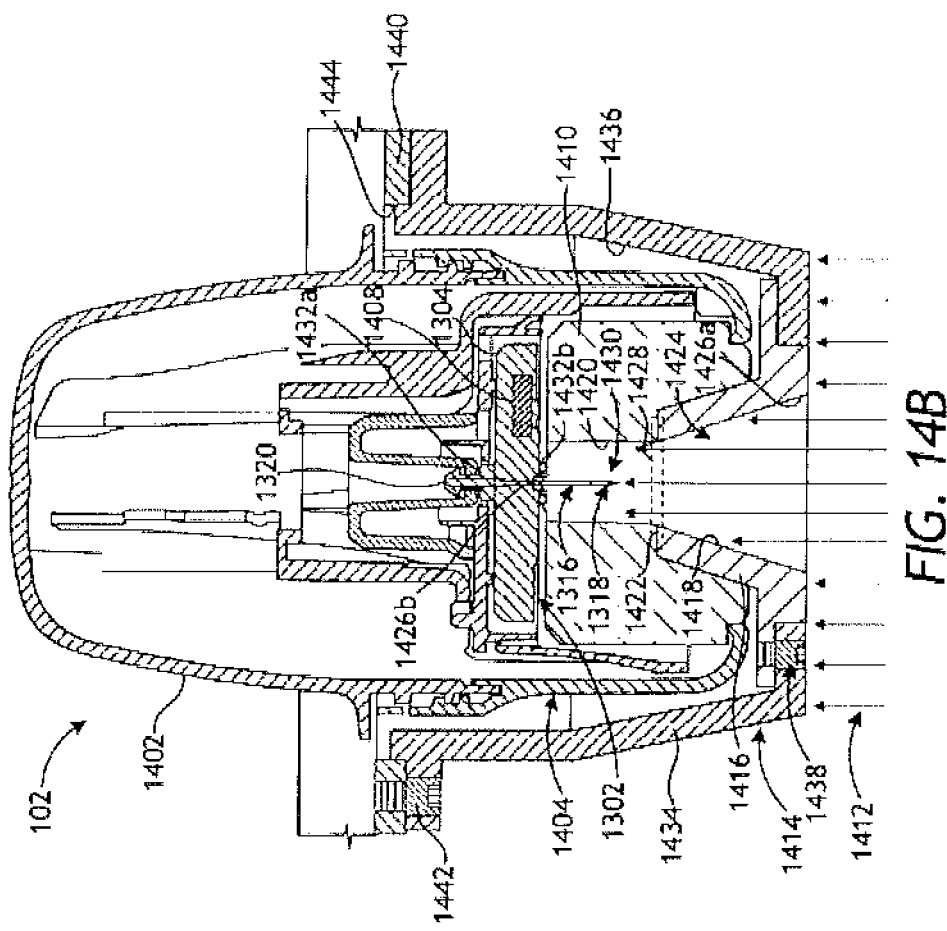
FIG. 14B is a cross-sectional side view of the sensor applicator of FIG. 14A.
Figure 14A:
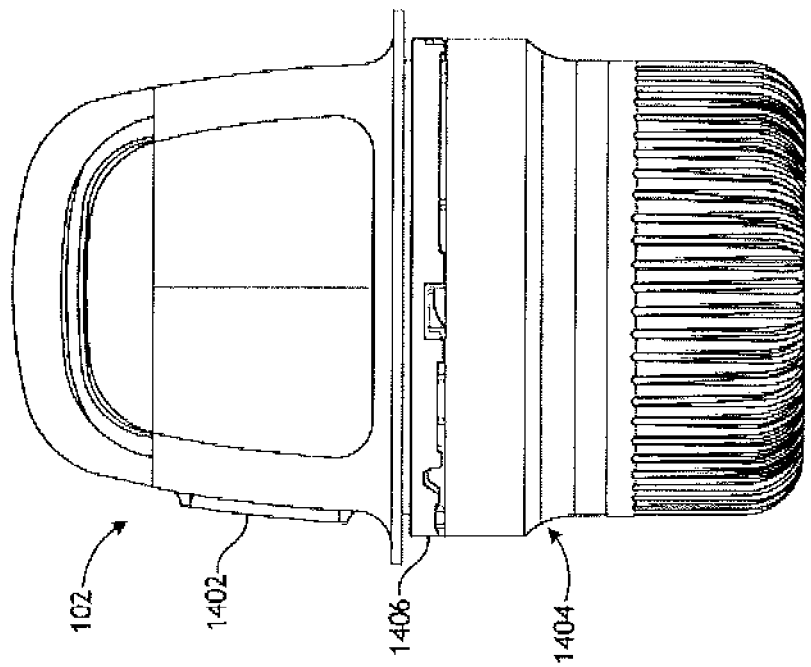
FIG. 14A is a side view of the sensor applicator of FIG. 1.

FIG. 14A is a side view of the sensor applicator 102 of FIG. 1. As illustrated, the sensor applicator 102 includes a housing 1402 and an applicator cap 1404 that may be removably coupled to the housing 1402. In some embodiments, the applicator cap 1404 may be threaded to the housing 1402 and include a tamper ring 1406. Upon rotating (e.g., unscrewing) the applicator cap 1404 relative to the housing 1402, the tamper ring 1406 may shear and thereby free the applicator cap 1404 from the sensor applicator 102. Once the applicator cap 1404 is removed, a user may then use the sensor applicator 102 to position the sensor control device 1302 (FIGS. 13 and 14B) at a target monitoring location on the user's body.

In some embodiments, the applicator cap 1404 may be secured to the housing 1402 via a sealed engagement to protect the internal components of the sensor applicator 102. In at least one embodiment, for example, an O-ring or another type of sealing gasket may seal an interface between the housing 1402 and the applicator cap 1404. The O-ring or sealing gasket may be a separate component part or alternatively molded onto one of the housing 1402 and the applicator cap 1404.

FIG. 14B is a cross-sectional side view of the sensor applicator 102. As illustrated, the sensor control device 1302 may be received within the sensor applicator 102 and the applicator cap 1404 may be coupled to the sensor applicator 102 to secure the sensor control device 1302 therein. The sensor control device 1302 may include one or more radiation sensitive components 1408 arranged within the electronics housing 1304. The radiation sensitive component 1408 can include an electronic component or module such as, but not limited to, a data processing unit, a resistor, a transistor, a capacitor, an inductor, a diode, a switch, or any combination thereof. The data processing unit may comprise, for example, an application specific integrated circuit (ASIC) configured to implement one or more functions or routines associated with operation of the sensor control device 1302. In operation, the data processing unit may perform data processing functions, such as filtering and encoding of data signals corresponding to a sampled analyte level of the user. The data processing unit may also include or otherwise communicate with an antenna for communicating with the reader device 106 (FIG. 1).

In the illustrated embodiment, a cap fill 1410 may be positioned within the applicator cap 1404 and may generally help support the sensor control device 1302 within the sensor applicator 102. In one or more embodiments, the cap fill 1410 may comprise an integral part or extension of the applicator cap 1404, such as being molded with or overmolded onto the applicator cap 1404. In other embodiments, the cap fill 1410 may comprise a separate structure fitted within or otherwise attached to the applicator cap 1404, without departing from the scope of the disclosure.

The sensor control device 1302 and, more particularly, the distal ends of the sensor 1316 and the sharp 1318 extending from the bottom of the electronics housing 1304, may be sterilized while positioned within the sensor applicator 102. More specifically, the fully assembled sensor control device 1302 may be subjected to radiation sterilization 1412, which may be similar to the radiation sterilization 814 of FIGS. 8-12. The radiation sterilization 1412 may be delivered either through continuous processing irradiation or through pulsed beam irradiation. In pulsed beam irradiation, the beam of radiation sterilization 1412 is focused at a target location and the component part or device to be sterilized is moved to the target location at which point the irradiation is activated to provide a directed pulse of radiation. The radiation sterilization 1412 is then turned off, and another component part or device to be sterilized is moved to the target location and the process is repeated.

According to the present disclosure, an external sterilization assembly 1414 may be used to help focus the radiation 1412 in sterilizing the distal ends of the sensor 1316 and the sharp 1318, while simultaneously preventing (impeding) propagating radiation 1412 from damaging the radiation sensitive component 1408. As illustrated, the external sterilization assembly 1414 (hereafter the "assembly 1414") may include a radiation shield 1416 positioned at least partially external to the sensor applicator 102. The radiation shield 1416 may provide or define an external collimator 1418 configured to help focus the radiation 1412 (e.g., beams, waves, energy, etc.) toward the components to be sterilized. More specifically, the external collimator 1418 allows transmission of the radiation 1412 to impinge upon and sterilize the sensor 1316 and the sharp 1318, but prevent the radiation 1412 from damaging the radiation sensitive component 1408 within the electronics housing 1304.

In the illustrated embodiment, the external collimator 1418 is designed to align with an internal collimator 1420 defined by the cap fill 1410. Similar to the external collimator 1418, the internal collimator 1420 may help focus the radiation 1412 toward the components to be sterilized. As illustrated, the cap fill 1410 may define a radial shoulder 1422 sized to receive and otherwise mate with an end of the radiation shield 1416, and the external collimator 1418 transitions to the internal collimator 1420 at the radial shoulder 1422. In some embodiments, the transition between the external and internal collimators 1418, 1420 may be continuous, flush, or smooth. In other embodiments, however, the transition may be discontinuous or stepped, without departing from the scope of the disclosure.

The external and internal collimators 1418, 1420 may cooperatively define a sterilization zone 1424 that focuses the radiation 1412 and into which the distal ends of the sensor 1316 and the sharp 1318 may be positioned. The propagating radiation 1412 may traverse the sterilization zone 1424 to impinge upon and sterilize the sensor 1316 and the sharp 1318. However, the cap fill 1410 and the radiation shield 1416 may each be made of materials that substantially prevent the radiation 1412 from penetrating the inner wall(s) of the sterilization zone 1424 and thereby damaging the radiation sensitive component 1408 within the housing 1304. In other words, the cap fill 1410 and the radiation shield 1416 may each be made of materials having a density sufficient to absorb the dose of the beam energy being delivered. In some embodiments, for example, one or both of the cap fill 1410 and the radiation shield 1416 may be made of a material that has a mass density greater than 0.9 grams per cubic centimeter (g/cc). In other embodiments, however, the mass density of a suitable material may be less than 0.9 g/cc, without departing from the scope of the disclosure. Suitable materials for the cap fill 1410 and the radiation shield 1416 include, but are not limited to, a high-density polymer, (e.g., polyethylene, polypropylene, polystyrene, polytetrafluoroethylene, etc.), a metal (e.g., lead, stainless steel, aluminum, etc.), any combination thereof, or any material having a mass density greater than 0.9 g/cc. In at least one embodiment, the cap fill 1410 may be made of machined or 3D printed polypropylene and the radiation shield 1416 may be made of stainless steel.

In some embodiments, the design of the sterilization zone 1424 may be altered so that one or both of the cap fill 1410 and the radiation shield 1416 may be made of a material that has a mass density less than 0.9 g/cc but may still operate to prevent the radiation sterilization 1412 from damaging the radiation sensitive component 1408. In such embodiments, the size (e.g., length) of the sterilization zone 1424 may be increased such that the propagating electrons from the radiation sterilization 1412 are required to pass through a larger amount of material before potentially impinging upon the radiation sensitive component 1408. The larger amount of material may help absorb or dissipate the dose strength of the radiation 1412 such that it becomes harmless to the sensitive electronics. In other embodiments, however, the converse may equally be true. More specifically, the size (e.g., length) of the sterilization zone 1424 may be decreased as long as the material for the cap fill 1410 and/or the radiation shield 1416 exhibits a large enough mass density.

The sterilization zone 1424 defined by the external and internal collimators 1418, 1420 can exhibit any suitable cross-sectional shape necessary to properly focus the radiation 1412 on the sensor 1316 and the sharp 1318 for sterilization. In the illustrated embodiment, for example, the external collimator 1418 is conical or frustoconical in shape, but the internal collimator 1420 exhibits a circular cross-sectional shape with parallel sides. In other embodiments, however, one or both of the external and internal collimators 1418, 1420 may exhibit a polygonal cross-sectional shape, such as cubic or rectangular (e.g., including parallelogram), without departing from the scope of the disclosure.

In the illustrated embodiment, the sterilization zone 1424 provides a first aperture 1426a defined by the external collimator 1418 and a second aperture 1426b defined by the internal collimator 1420, where the first and second apertures 1426a,b are located at opposing ends of the sterilization zone 1424. The first aperture 1426a permits the radiation 1412 to enter the sterilization zone 1424, and the second aperture 1426b provides a location where radiation 1412 can impact the sensor 1316 and the sharp 1318. In the illustrated embodiment, the second aperture 1426b also provides a location where the sensor 1316 and the sharp 1318 may be received into the sterilization zone 1424.

The diameter of the first aperture 1426a may be larger than the diameter of the second aperture 1426b. In such embodiments, for example, the size of the first aperture 1426a may range between about 5.0 mm and about 16.0 mm, and the size of the second aperture 1426b may range between about 0.5 mm and about 3.0 mm. The respective diameters of the first and second apertures 1426a,b, however, may be greater or less than the ranges provided herein, without departing from the scope of the disclosure, and depending on the application. Indeed, the diameters of the first and second apertures 1426a,b need only be large enough to allow a sufficient dose of radiation to impinge upon the sensor 1316 and the sharp 1318. In some embodiments, the sterilization zone 1424 defined by the external and internal collimators 1418 may be substantially cylindrical and otherwise exhibit a circular or polygonal cross-section. In such embodiments, the first and second apertures 1426a,b may exhibit identical diameters and the walls of the sterilization zone 1424 may be substantially parallel between the first and second ends of the sterilization zone 1424.

In some embodiments, a cap seal 1428 (shown in dashed lines) may be arranged at the interface between the cap fill 1410 and the radiation shield 1416. The cap seal 1428 may comprise a radiation permeable microbial barrier. In some embodiments, for example, the cap seal 1428 may be made of a synthetic material (e.g., a flash-spun high-density polyethylene fiber), such as TYVEK® available from DuPont®. The cap seal 1428 may seal off a portion of the sterilization zone 1424 to help form part of a sealed region 1430 configured to isolate the sensor 1316 and the sharp 1318 from external contamination.

The sealed region 1430 may include (encompass) select portions of the interior of the electronics housing 1304 and the sterilization zone 1424. In one or more embodiments, the sealed region 1430 may be defined and otherwise formed by at least the cap seal 1428, a first or "top" seal 1432a, and a second or "bottom" seal 1432b. The cap seal 1428 and the top and bottom seals 1432a,b may each create corresponding barriers at their respective sealing locations, thereby allowing the sterilization zone 1424 containing the sensor 1316 and the sharp 1318 to be terminally sterilized.

The top seal 1432a may be arranged to seal the interface between the sharp hub 1320 and the top of the electronics housing 1304 (i.e., the shell 1306 of FIG. 13) and thereby prevent contaminants from migrating into the interior of the electronics housing 1304. In some embodiments, the top seal 1432a may form part of the sharp hub 1320, such as being overmolded onto the sharp hub 1320. In other embodiments, however, the top seal 1432a may form part of or be overmolded onto the top surface of the shell 1306. In yet other embodiments, the top seal 1432a may comprise a separate structure, such as an O-ring or the like, that interposes the sharp hub 1320 and the top surface of the shell 1306, without departing from the scope of the disclosure.

The bottom seal 1432b may be arranged to seal the interface between the cap fill 1410 and the bottom of electronics housing 1304 (i.e., the mount 1308 of FIG. 13). The bottom seal 1432b may prevent contaminants from migrating into the sterilization zone 1424 and from migrating into the interior of the electronics housing 1304. In some embodiments, the bottom seal 1432b may form part of the cap fill 1410, such as being overmolded onto the top of the cap fill 1410. In other embodiments, the bottom seal 1432b may form part of or be overmolded onto the bottom of the mount 1308. In yet other embodiments, the bottom seal 1432b may comprise a separate structure, such as an O-ring or the like, that interposes the cap fill 1410 and the bottom of the mount 1308, without departing from the scope of the disclosure.

Upon loading the sensor control device 1302 into the sensor applicator 102 and securing the applicator cap 1404 to the sensor applicator 102, the top and bottom seals 1432a,b may compress and generate corresponding sealed interfaces. The top and bottom seals 1432a,b may be made of a variety of materials capable of generating a sealed interface between opposing structures. Suitable materials include, but are not limited to, silicone, a thermoplastic elastomer (TPE), polytetrafluoroethylene (e.g., TEFLON®), or any combination thereof.

It is noted that, while the sensor 1316 and the sharp 1318 extend from the bottom of the electronics housing 1304 and into the sterilization zone 1424 generally concentric with a centerline of the sensor applicator 102 and the applicator cap 1404, it is contemplated herein to have an eccentric arrangement. More specifically, in at least one embodiment, the sensor 1316 and the sharp 1318 may extend from the bottom of the electronics housing 1304 eccentric to the centerline of the sensor applicator 102 and the applicator cap 1404. In such embodiments, the external and internal collimators 1418, 1420 may be re-designed and otherwise configured such that the sterilization zone 1424 is also eccentrically positioned to receive the sensor 1316 and the sharp 1318, without departing from the scope of the disclosure.

In some embodiments, the external sterilization assembly 1414 may further include a sterilization housing or "pod" 1434 coupled to or forming part of the radiation shield 1416. The sterilization pod 1434 provides and otherwise defines a chamber 1436 sized to receive all or a portion of the sensor applicator 102. Once properly seated (received) within the sterilization pod 1434, the sensor applicator 102 may be subjected to the radiation sterilization 1412 to sterilize the sensor 1316 and the sharp 1318. The sterilization pod 1434 may be made of any of the materials mentioned herein for the radiation shield 1416 to help prevent the radiation 1412 from propagating through the walls of the sterilization pod 1434.

In some embodiments, the radiation shield 1416 may be removably coupled to the sterilization pod 1434 using one or more mechanical fasteners 1438 (one shown), but could alternatively be removably coupled via an interference fit, a snap fit engagement, etc. Removably coupling the radiation shield 1416 to the sterilization pod 1434 enables the radiation shield 1416 to be interchangeable with differently designed (sized) shields to fit particular sterilization applications for varying types and designs of the sensor applicator 102. Accordingly, the sterilization pod 1434 may comprise a universal mount that allows the radiation shield 1416 to be interchanged with other shield designs having different parameters for the external collimator 1418, as needed.

In some embodiments, the external sterilization assembly 1414 may further include a mounting tray 1440 coupled to or forming part of the sterilization pod 1434. The sterilization pod 1434 may be removably coupled to the mounting tray 1440 using, for example, one or more mechanical fasteners 1442 (one shown). The mounting tray 1440 may provide or define a central aperture 1444 sized to receive the sensor applicator 102 and alignable with the chamber 1436 to enable the sensor applicator 102 to enter the chamber 1436. As described below, in some embodiments, the mounting tray 1440 may define a plurality of central apertures 1444 for receiving a corresponding plurality of sensor applicators for sterilization.

Figure 15:
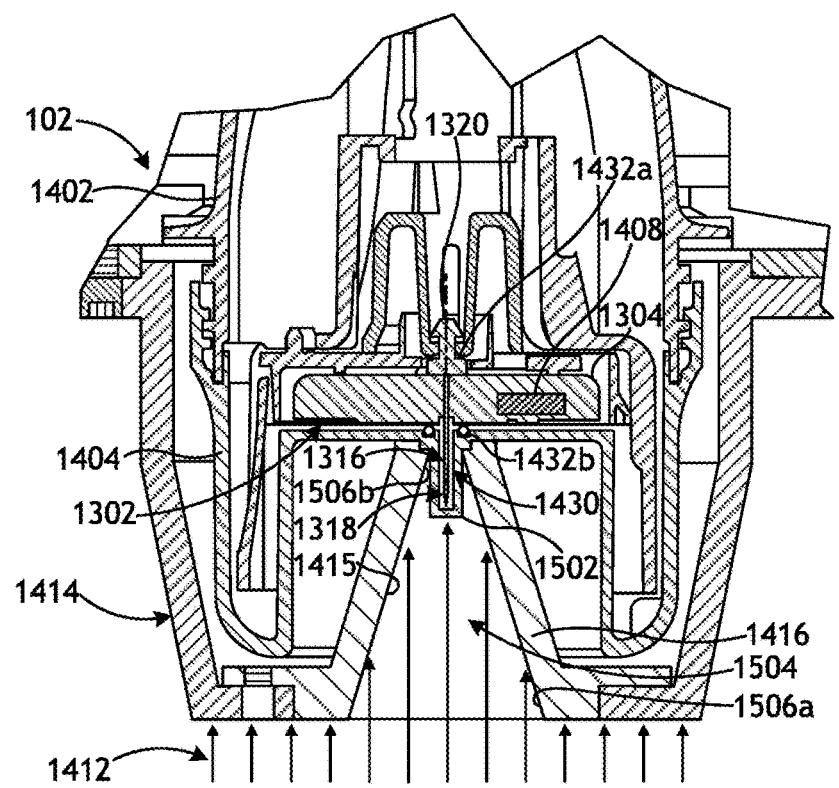
FIG. 15 is a cross-sectional side view of the sensor applicator of FIG. 14A and another example embodiment of the external sterilization assembly of FIG. 14B, according to one or additional more embodiments.

FIG. 15 is a cross-sectional side view of the sensor applicator 102 and another example embodiment of the external sterilization assembly 1414, according to one or more additional embodiments. As illustrated, the sensor control device 1302 is again received within the sensor applicator 102 and the applicator cap 1404 is coupled to the housing 1402 to secure the sensor control device 1302 therein.

In the illustrated embodiment, the applicator cap 1404 may be inverted and may define or otherwise provide a cap post 1502 sized to receive the distal ends of the sensor 1316 and the sharp 1318 extending from the bottom of the electronics housing 1304. The cap post 1502 helps provide a portion of the sealed region 1430 configured to isolate the sensor 1316 and the sharp 1318 from external contamination. In the illustrated embodiment, the sealed region 1430 may be defined and otherwise formed by the cap post 1502 and the top and bottom seals 1432a,b, which create corresponding barriers at their respective sealing locations. The top seal 1432a may again be arranged to seal the interface between the sharp hub 1320 and the top of the electronics housing 1304 (i.e., the shell 1306 of FIG. 13), and the bottom seal 1432b may be arranged to seal an interface between the applicator cap 1404 and the bottom of electronics housing 1304 (i.e., the mount 1308 of FIG. 13). In some embodiments, the bottom seal 1432b may interpose the cap post 1502 and the bottom of electronics housing 1304.

In the illustrated embodiment, the radiation shield 1416 may be positioned external to the sensor applicator 102 and may extend into the inverted portion of the applicator cap 1404. The external collimator 1418 provided by the radiation shield 1416 defines a sterilization zone 1504 configured to focus the radiation 1412 toward the sensor 1316 and the sharp 1318. In the illustrated embodiment, the cap post 1502 and portions of the sensor 1316 and the sharp 1318 positioned within the cap post 1502 extend into the sterilization zone 1504. Propagating radiation 1412 may traverse the sterilization zone 1504 to sterilize the sensor 1316 and the sharp 1318 positioned within the cap post 1502. As indicated above, however, the radiation shield 1416 may be made of a material that substantially prevents the radiation 1412 from penetrating the wall(s) of the sterilization zone 1504 and thereby damaging the radiation sensitive component 1408 within the housing 1304.

In the illustrated embodiment, the external collimator 1418 defines a first aperture 1506a at a first end of the sterilization zone 1504 and a second aperture 1506b at the second end of the sterilization zone 1504. The first aperture 1506a permits the radiation 1412 to enter the sterilization zone 1504, and the second aperture 1506b provides a location where radiation 1412 is focused toward the sensor 1316 and the sharp 1318. The second aperture 1506b may also provide a location where the sensor 1316 and the sharp 1318 positioned within the cap post 1502 may be received into the sterilization zone 1504.

As illustrated, the external collimator 1418 and associated sterilization zone 1504 are conical or frustoconical in shape, and the diameter of the first aperture 1506a is larger than the diameter of the second aperture 1506b. The size of the first aperture 1506a may range between about 5.0 mm and about 16.0 mm, and the size of the second aperture 1506b may range between about 0.5 mm and about 3.0 mm, but could alternatively be greater or less than the provided ranges, without departing from the scope of the disclosure. Indeed, the sizes of the apertures 1506a,b may vary depending on the scale of the device. In other embodiments, however, the external collimator 1418 and associated sterilization zone 1504 may be substantially cylindrical and otherwise exhibit a circular or polygonal cross-section where the first and second apertures 1506a,b exhibit substantially identical diameters and the walls of the sterilization zone 1504 are substantially parallel.

Figure 16:
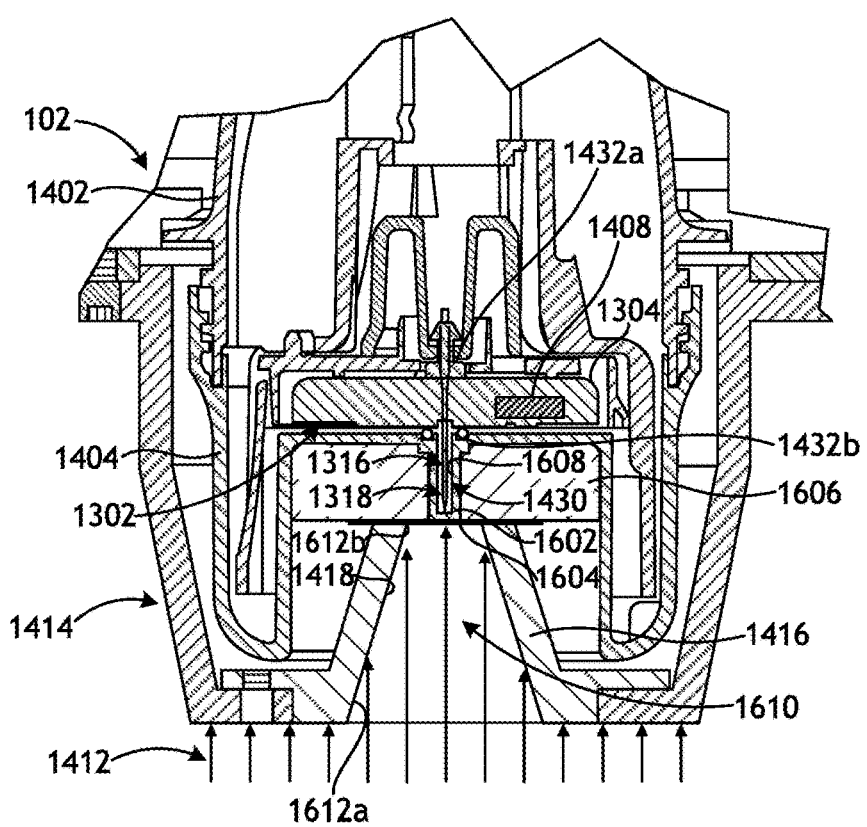
FIG. 16 is a cross-sectional side view of the sensor applicator of FIG. 14A and another example embodiment of the external sterilization assembly of FIG. 14B, according to one or more additional embodiments.

FIG. 16 is a cross-sectional side view of the sensor applicator 102 and another example embodiment of the external sterilization assembly 1414, according to one or more additional embodiments. As illustrated, the sensor control device 1302 is again received within the sensor applicator 102 and the applicator cap 1404 is coupled to the housing 1402 to secure the sensor control device 1302 therein.

In the illustrated embodiment, the applicator cap 1404 may again be inverted and may define or otherwise provide a cap post 1602 sized to receive the distal ends of the sensor 1316 and the sharp 1318 extending from the bottom of the electronics housing 1304. Moreover, the radiation shield 1416 may be positioned external to the sensor applicator 102 and may extend into the inverted portion of the applicator cap 1404. More specifically, the radiation shield 1416 may extend into the inverted portion of the applicator cap 1404 and to the bottom of the cap post 1602. Unlike the cap post 1502 of FIG. 15, however, the bottom of the cap post 1602 may be open ended. In some embodiments, a cap seal 1604 may be arranged at the interface between the cap post 1602 and the radiation shield 1416 to seal off the open end of the cap post 1602. The cap seal 1604 may be similar to the cap seal 1428 of FIG. 14B, and therefore will not be described again.

In some embodiments, a cap fill 1606 may be positioned within the applicator cap 1404. In one or more embodiments, the cap fill 1606 may comprise an integral part or extension of the applicator cap 1404, such as being molded with or overmolded onto the applicator cap 1404. In other embodiments, the cap fill 1606 may comprise a separate structure fitted within or otherwise attached to the applicator cap 1404, without departing from the scope of the disclosure. The cap fill 1606 may also provide or otherwise define an internal collimator 1608 that may help focus the radiation 1412 toward the components to be sterilized. In at least one embodiment, as illustrated, the cap post 1602 may be received within the internal collimator 1608.

The external and internal collimators 1418, 1608 may cooperatively define a sterilization zone 1610 that focuses the radiation 1412 toward the sensor 1316 and the sharp 1318. The propagating radiation 1412 may traverse the sterilization zone 1610 to impinge upon and sterilize the sensor 1316 and the sharp 1318. However, the cap fill 1606 and the radiation shield 1416 may each be made of any of the materials mentioned herein that substantially prevent the radiation 1412 from penetrating the inner wall(s) of the sterilization zone 1610 and thereby damaging the radiation sensitive component 1408 within the housing 1304. In at least one embodiment, the cap fill 1606 may be made of machined or 3D printed polypropylene and the radiation shield 1416 may be made of stainless steel.

The external and internal collimators 1418, 1608 can exhibit any suitable cross-sectional shape necessary to properly focus the radiation 1412 toward the sensor 1316 and the sharp 1318 for sterilization. In the illustrated embodiment, for example, the external collimator 1418 is conical or frustoconical in shape, and the internal collimator 1608 is substantially cylindrical with internal walls that are substantially parallel. In other embodiments, however, the external and internal collimators 1418, 1608 may exhibit other cross-sectional shapes, without departing from the scope of the disclosure.

In the illustrated embodiment, the external collimator 1418 defines a first aperture 1612*a* that permits the radiation 1412 to enter the sterilization zone 1610 and a second aperture 1612*b* positioned at or near the bottom opening to the cap post 1602 to focus the radiation 1412 at the sensor 1316 and the sharp 1318 positioned within the cap post 1602. The diameter of the first aperture 1612*a* is larger than the diameter of the second aperture 1612*b* and, as with prior embodiments, the size of the first aperture 1612*a* may range between about 5.0 mm and about 16.0 mm, and the size of the second aperture 1612*b* may range between about 0.5 mm and about 3.0 mm. In the illustrated embodiment, the external collimator 1418 funnels the electrons of the radiation 1412 toward the bottom opening to the cap post 1602 and amplifies the electrons at the sensor 1316 and the sharp 1318.

The cap seal 1604 may be arranged at the interface between the radiation shield 1416 and the cap post 1602 and/or the cap fill 1606. The cap seal 1604 may seal off a portion of the sterilization zone 1610 to help form part of the sealed region 1430 configured to isolate the sensor 1316 and the sharp 1318 from external contamination. The sealed region 1430 may include (encompass) select portions of the interior of the electronics housing 1304 and the sterilization zone 1610. In the illustrated embodiment, the sealed region 1430 may be defined and otherwise formed by the cap post 1602 and the top and bottom seals 1432*a,b*, which create corresponding barriers at their respective sealing locations. The bottom seal 1432*b* may be arranged to seal an interface between the applicator cap 1404 and the bottom of electronics housing 1304 (i.e., the mount 1308 of FIG. 13).

Figure 17A:
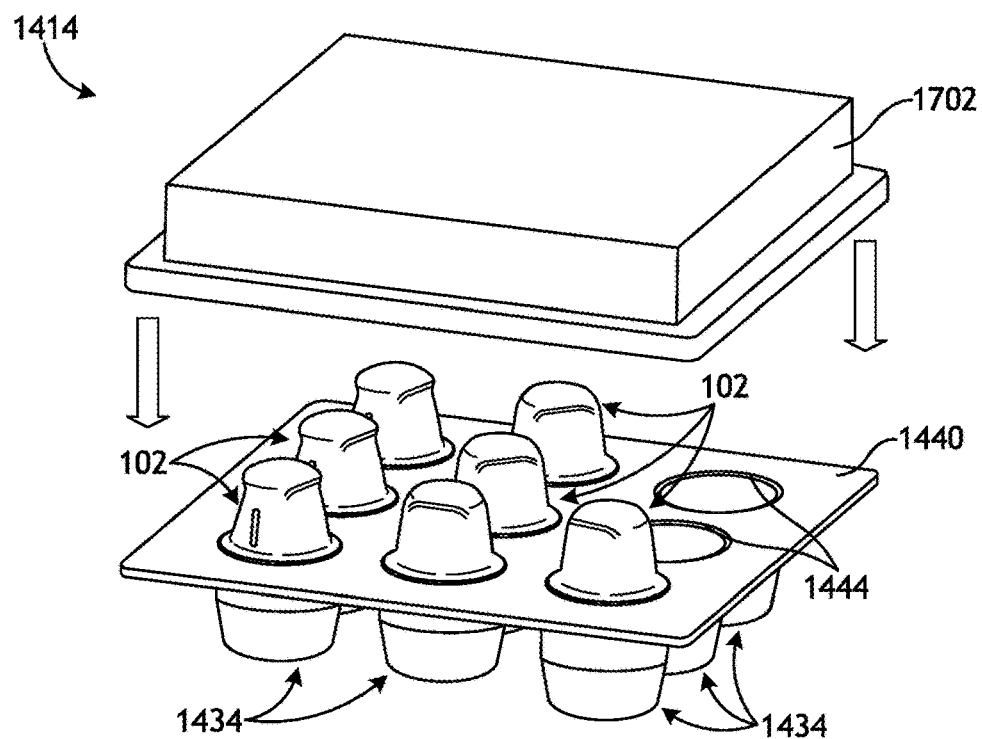
FIGS. 17A and 17B are isometric top and bottom views, respectively, of one example of the external sterilization assembly of FIG. 14B, according to one or more embodiments.
Figure 17B:
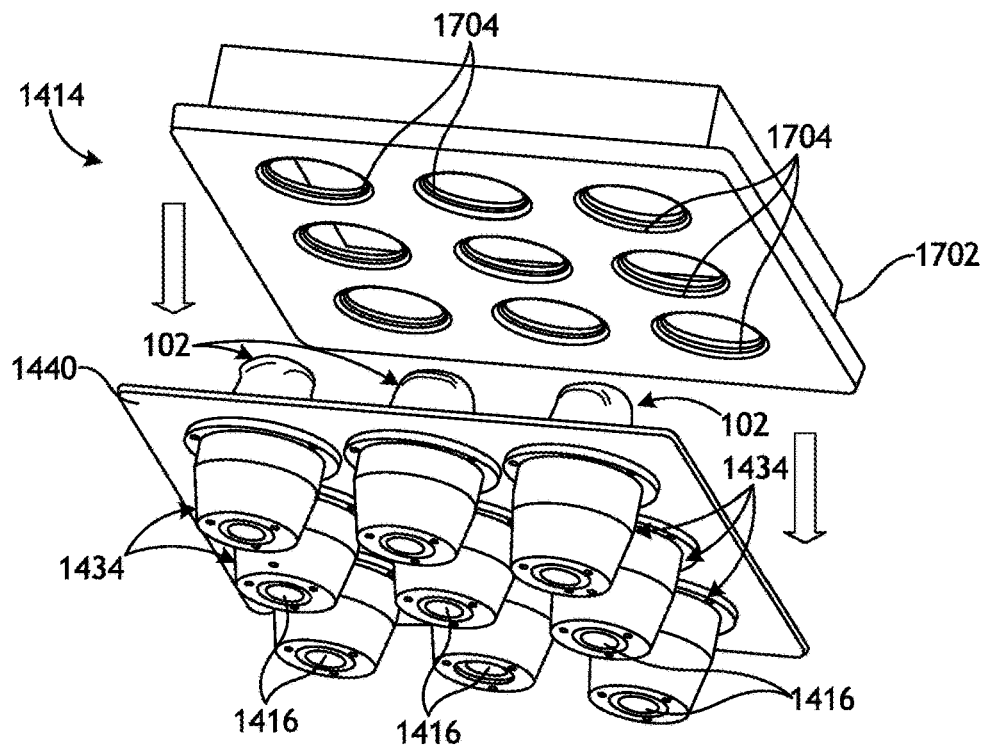

FIGS. 17A and 17B are partially exploded isometric top and bottom views, respectively, of one example of the external sterilization assembly 1414, according to one or more embodiments. In at least one embodiment, the assembly 1414 may be designed and otherwise configured to accommodate and help sterilize a plurality of sensor applicators 102 (i.e., with the sensor control devices positioned therein). In the illustrated embodiment, the mounting tray 1440 defines a plurality of central apertures 1444 (FIG. 17A), and a plurality of sterilization pods 1434 may be aligned with the central apertures 1444 and coupled to the mounting tray 1440. The sensor applicators 102 may be received within the sterilization pods 1434 via the central apertures 1444, and each sterilization pod 1434 may have a corresponding shield 1416 (FIG. 17B) coupled thereto or otherwise forming part thereof.

In some embodiments, the assembly 1414 may further include a cover 1702 matable with the mounting tray 1440. The cover 1702 may include or define a plurality of apertures 1106 (FIG. 17B) sized to receive the tops of the sensor applicators 102 when the cover 1702 is placed on top of the mounting tray 1440. In some embodiments, the cover 1702 may be made of any of the materials mentioned herein for the radiation shield 1416 to help prevent the radiation sterilization from propagating through the walls of the assembly 1414. With the cover 1702 mated with the mounting tray 1414, the sensor applicators 102 may be encapsulated or otherwise encased within the assembly 1414.

Embodiments disclosed herein include:

D. An external sterilization assembly that includes a radiation shield positionable external to a medical device having a part requiring sterilization and a radiation sensitive component, and a collimator defined by the radiation shield and alignable with the part requiring sterilization, wherein the collimator focuses radiation from a radiation sterilization process toward the part requiring sterilization and the radiation shield prevents the radiation from damaging the radiation sensitive component.

E. An external sterilization assembly that includes a radiation shield positionable external to a sensor applicator that includes a housing, a cap coupled to the housing, and a sensor control device positioned within the housing, wherein the sensor control device includes an electronics housing, a radiation sensitive component arranged within the electronics housing, and a sensor and a sharp extending from the electronics housing. The external sterilization assembly further including an external collimator defined by the radiation shield and alignable with the sensor and the sharp, wherein the external collimator focuses radiation from a radiation sterilization process toward the sensor and the sharp and the radiation shield prevents the radiation from damaging the radiation sensitive component.

F. A method including arranging a radiation shield external to a sensor applicator having a housing, a cap coupled to the housing, and a sensor control device positioned within the housing, wherein the sensor control device includes an electronics housing, a radiation sensitive component arranged within the electronics housing, and a sensor and a sharp extending from the electronics housing. The method further including focusing radiation from a radiation sterilization process toward the sensor and the sharp with an external collimator defined by the radiation shield, and preventing the radiation from damaging the radiation sensitive component with the radiation shield.

Each of embodiments D, E, and F may have one or more of the following additional elements in any combination: Element 1: wherein the radiation shield is made of a material selected from the group consisting of a high-density polymer, a metal, and any combination thereof. Element 2: wherein the radiation sensitive component is selected from the group consisting of an electronic module, a chemical solution, and any combination thereof. Element 3: wherein the collimator comprises a cross-sectional shape selected from the group consisting of conical, frustoconical, pyramidal, circular, cubic, rectangular, and any combination thereof. Element 4: further comprising a cap that encapsulates the part requiring sterilization and provides a sealed barrier. Element 5: wherein the radiation shield defines an internal cavity that receives the medical device, and the collimator focuses the radiation into the internal cavity.

Element 6: wherein the radiation shield is made of a material selected from the group consisting of a high-density polymer, a metal, and any combination thereof. Element 7: wherein the external collimator comprises a cross-sectional shape selected from the group consisting of conical, frustoconical, pyramidal, circular, cubic, rectangular, and any combination thereof. Element 8: further comprising a sterilization pod defining a chamber that receives at least a portion of the sensor applicator, wherein the radiation shield is removably coupled to the sterilization pod. Element 9: further comprising a mounting tray that defines a central aperture alignable with the chamber and sized to receive the sensor applicator, and a cover matable with the mounting tray to encase the sensor applicator. Element 10: wherein the external collimator is alignable with an internal collimator defined by a cap fill positioned within the cap, and wherein the external and internal collimators cooperatively define a sterilization zone into which the sensor and the sharp are received. Element 11: wherein the external collimator comprises a cross-sectional shape selected from the group consisting of conical, frustoconical, pyramidal, circular, cubic, rectangular, and any combination thereof. Element 12: further comprising a cap seal arranged at an interface between the external and internal collimators. Element 13: wherein the cap is inverted and provides a cap post that receives the sensor and the sharp. Element 14: wherein the external collimator and the cap post cooperatively define a sterilization zone and the sensor and the sharp positioned within the cap post extend into the sterilization zone.

Element 15: wherein arranging the radiation shield external to the sensor applicator comprises positioning the sensor applicator within a chamber defined by a sterilization pod, the radiation shield being removably coupled to the sterilization pod. Element 16: wherein positioning the sensor applicator within the chamber defined by the sterilization pod further comprise extending the sensor applicator through a central aperture defined by a mounting tray and aligned with the chamber, positioning a cover on the mounting tray and thereby encasing the sensor applicator, and undertaking the radiation sterilization process while the sensor applicator is encased by the cover. Element 17: wherein the external collimator comprises a cross-sectional shape selected from the group consisting of conical, frustoconical, pyramidal, circular, cubic, rectangular, and any combination thereof.

By way of non-limiting example, exemplary combinations applicable to D, E, and F include: Element 8 with Element 9; Element 10 with Element 11; Element 10 with Element 12; Element 13 with Element 14; and Element 15 with Element 16.

Hybrid Sterilization Assemblies

Referring again briefly, to FIG. 1, prior to being delivered to an end user, the sensor control device 104 must be sterilized to render the product free from viable microorganisms. The sensor 110 is commonly sterilized using radiation sterilization, such as electron beam ("e-beam") irradiation. Radiation sterilization, however, can damage the electronic components within the sensor control device 104, which are commonly sterilized via gaseous chemical sterilization (e.g., using ethylene oxide). Gaseous chemical sterilization, however, can damage the enzymes or other chemistry and biologics included on the sensor 110.

In the past, this sterilization incompatibility has been circumvented by separating the sensor 110 and the electronic components and sterilizing each individually. This approach, however, requires additional parts, packaging, process steps, and final assembly by the user, which introduces a possibility of user error. According to the present disclosure, the sensor control device 104, or any device requiring terminal sterilization, may be properly sterilized using external sterilization assemblies designed to focus sterilizing radiation (e.g., beams, waves, energy, etc.) toward component parts requiring sterilization, while simultaneously preventing the propagating radiation from disrupting or damaging sensitive electronic components.

Figure 18:
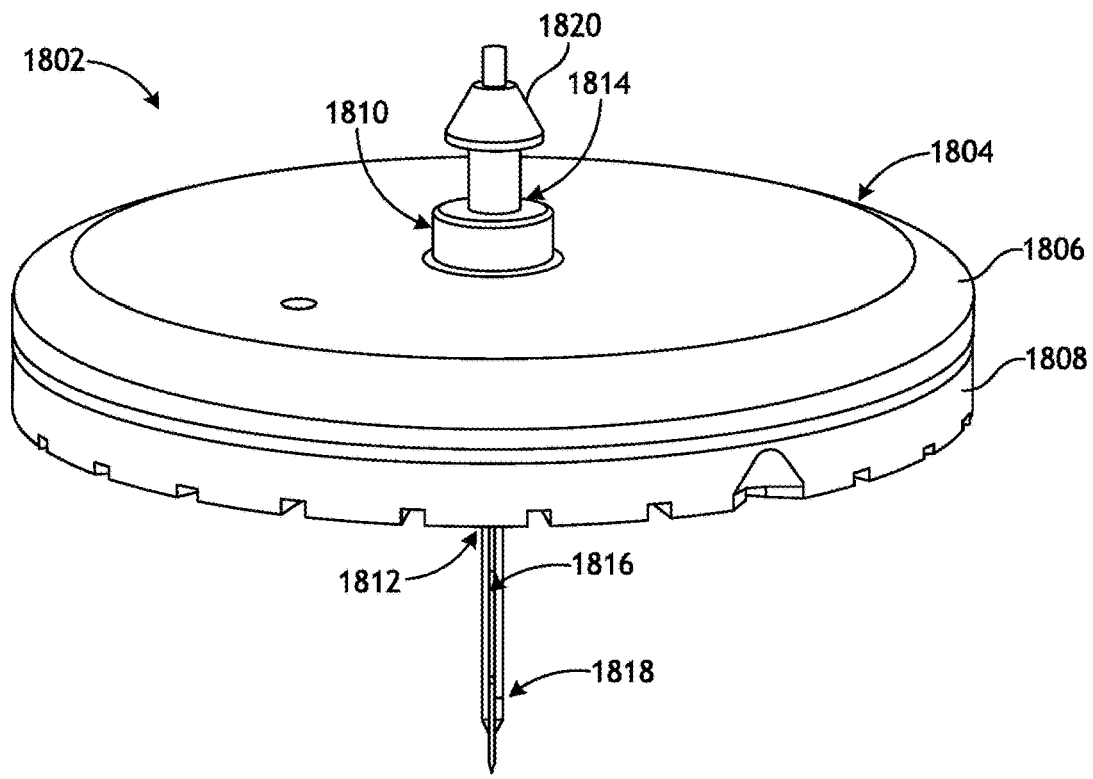
FIG. 18 is an isometric view of an example sensor control device.

FIG. 18 is an isometric view of an example sensor control device 1802, according to one or more embodiments of the present disclosure. The sensor control device 1802 may be the same as or similar to the sensor control device 104 of FIG. 1 and, therefore, may be used in conjunction with the sensor applicator 102 (FIG. 1), which delivers the sensor control device 1802 to a target monitoring location on a user's skin. Accordingly, the sensor control device 1802 also requires proper sterilization prior to being used.

As illustrated, the sensor control device 1802 includes an electronics housing 1804 that is generally disc-shaped and may have a circular cross-section. In other embodiments, however, the electronics housing 1804 may exhibit other cross-sectional shapes, such as ovoid (e.g., pill- or egg-shaped), a squircle, polygonal, or any combination thereof, without departing from the scope of the disclosure. The electronics housing 1804 may be configured to house or otherwise contain various electronic components used to operate the sensor control device 1802.

The electronics housing 1804 may include a shell 1806 and a mount 1808 that is matable with the shell 1806. The shell 1806 may be secured to the mount 1808 via a variety of ways, such as a snap fit engagement, an interference fit, sonic or laser welding, one or more mechanical fasteners (e.g., screws), or any combination thereof. In some cases, the shell 1806 may be secured to the mount 1808 such that a sealed interface is generated therebetween. In such embodiments, a gasket or other type of seal material may be positioned at or near the outer diameter (periphery) of the shell 1806 and the mount 1808, and securing the two components together may compress the gasket and thereby generate a sealed interface. In other embodiments, an adhesive may be applied to the outer diameter (periphery) of one or both of the shell 1806 and the mount 1808. The adhesive secures the shell 1806 to the mount 1808 and provides structural integrity, but may also seal the interface between the two components and thereby isolate the interior of the electronics housing 1804 from outside contamination.

In the illustrated embodiment, the sensor control device 1802 may optionally include a plug assembly 1810 that may be coupled to the electronics housing 1804. The plug assembly 1810 may include a sensor module 1812 (partially visible) interconnectable with a sharp module 1814 (partially visible). The sensor module 1812 may be configured to carry and otherwise include a sensor 1816 (partially visible), and the sharp module 1814 may be configured to carry and otherwise include an introducer or sharp 1818 (partially visible) used to help deliver the sensor 1816 transcutaneously under a user's skin during application of the sensor control device 1802. In the illustrated embodiment, the sharp module 1814 includes a sharp hub 1820 that carries the sharp 1818.

As illustrated, corresponding portions of the sensor 1816 and the sharp 1818 extend distally from the electronics housing 1804 and, more particularly, from the bottom of the mount 1808. In at least one embodiment, the exposed portion of the sensor 1816 (alternately referred to as the "tail") may be received within a hollow or recessed portion of the sharp 1818. The remaining portions of the sensor 1816 are positioned within the interior of the electronics housing 1804.

Figure 19A:
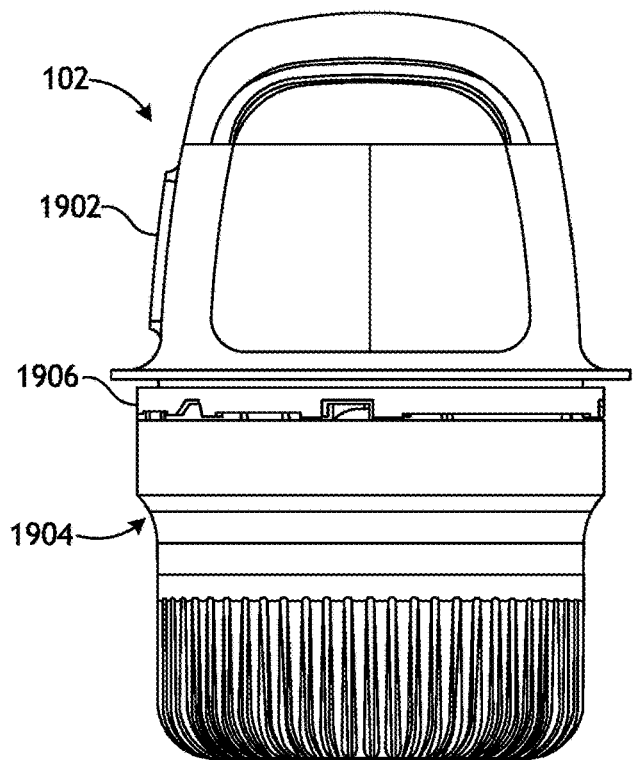
FIG. 19A is a side view of the sensor applicator of FIG. 1.

FIG. 19A is a side view of the sensor applicator 102 of FIG. 1. As illustrated, the sensor applicator 102 includes a housing 1902 and an applicator cap 1904 that may be removably coupled to the housing 1902. In some embodiments, the applicator cap 1904 may be threaded to the housing 1902 and include a tamper ring 1906. Upon rotating (e.g., unscrewing) the applicator cap 1904 relative to the housing 1902, the tamper ring 1906 may shear and thereby free the applicator cap 1904 from the sensor applicator 102. Once the applicator cap 1904 is removed, a user may then use the sensor applicator 102 to position the sensor control device 1802 (FIG. 18) at a target monitoring location on the user's body.

Figure 19B:
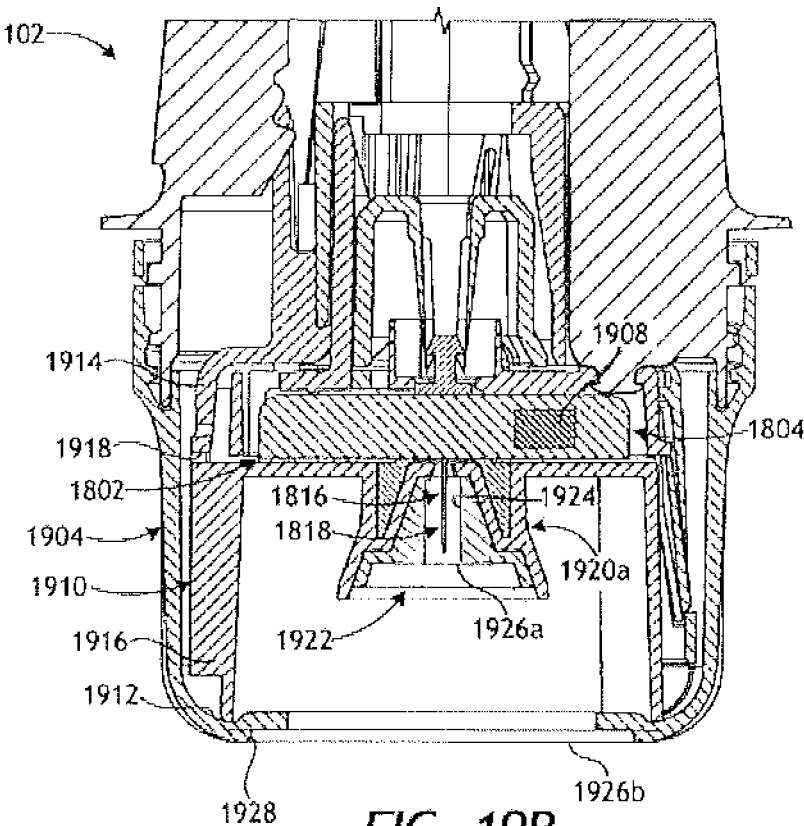
FIG. 19B is a partial cross-sectional side view of the sensor applicator of FIG. 3A.

FIG. 19B is a partial cross-sectional side view of the sensor applicator 102. As illustrated, the sensor control device 1802 may be received within the sensor applicator 102 and the applicator cap 1904 may be coupled to the housing 1902 to secure the sensor control device 1802 within. The sensor control device 1802 may include one or more radiation sensitive components 1908 arranged within the electronics housing 1804. The radiation sensitive component 1908 can include an electronic component or module such as, but not limited to, a data processing unit, a resistor, a transistor, a capacitor, an inductor, a diode, a switch, or any combination thereof. The data processing unit may comprise, for example, an application specific integrated circuit (ASIC) configured to implement one or more functions or routines associated with operation of the sensor control device 1802. In operation, the data processing unit may perform data processing functions, such as filtering and encoding of data signals corresponding to a sampled analyte level of the user. The data processing unit may also include or otherwise communicate with an antenna for communicating with the reader device 106 (FIG. 1).

In the illustrated embodiment, an applicator insert 1910 may be positioned within the applicator cap 1904 and may generally help support the sensor control device 1802 within the sensor applicator 102. In one embodiment, the applicator insert 1910 may comprise an integral part or extension of the applicator cap 1904, such as being molded with or overmolded onto the applicator cap 1904. In other embodiments, the applicator insert 1910 may comprise a separate structure fitted within or otherwise attached to the applicator cap 1904, without departing from the scope of the disclosure. In such embodiments, for example, screwing the applicator cap 1904 onto the housing 1908 may progressively advance an inner surface 1912 of the applicator insert 1910 into axial and/or radial engagement with a bottom edge, surface or portion of the applicator insert 1910 to thereby axially secure the applicator insert 1910 within the applicator cap 1904.

The sensor applicator 102 may further include a sheath 1914 and, in some embodiments, the applicator insert 1910 may engage the sheath 1914 to rotationally fix the applicator insert 1910 within the applicator cap 1904. More specifically, the applicator insert 1910 may provide or otherwise define one or more radial alignment features 1916 (one shown) matable with a corresponding groove or slot 1918 defined in the sheath 1914. The radial alignment feature 1916 may comprise, for example, a rail, a flag, a tab, a protrusion, or the like extending from the main body of the applicator insert 1910 and may mate with the slot 1918 by sliding the radial alignment feature 1916 longitudinally into the slot 1918, for example. Mating engagement between the radial alignment feature 1916 and the slot 1918 may also help angularly (rotationally) orient the applicator insert 1910 relative to the sensor control device 1802. As will be appreciated, however, the matable structures may alternatively be reversed, where the radial alignment feature 1916 is instead provided on the sheath 1914 and the slot 1918 is provided on the applicator insert 1910.

The applicator insert 1910 may provide and otherwise define an internal collimator 1920*a*, which forms part of a hybrid sterilization assembly described in more detail below. The internal collimator 1920*a* may help define a portion of a sterilization zone 1922 and, more particularly, an upper portion 1924 of the sterilization zone 1922. When the sensor control device 1802 is installed in the sensor applicator 102, the distal ends of the sensor 1816 and the sharp 1818 may extend from the bottom of the electronics housing 1804 and reside within the upper portion 1924.

In some embodiments, a microbial barrier 1926*a* may be positioned at an opening to the upper portion 1924 of the sterilization zone 1922. The microbial barrier 1926*a* may help seal at least some of the upper portion 1924 of the sterilization zone 1922 to thereby isolate the distal ends of the sensor 1816 and the sharp 1818 from external contamination. The microbial barrier 1926*a* may be made of a radiation permeable material, such as a synthetic material (e.g., a flash-spun high-density polyethylene fiber). One example synthetic material comprises TYVEK®, available from DuPont®. In other embodiments, however, the microbial barrier 1926*a* may comprise, but is not limited to, tape, paper, film, foil, or any combination thereof. In at least one embodiment, the microbial barrier 1926*a* may comprise or otherwise be formed by a thinned portion of the applicator insert 1910, without departing from the scope of the disclosure.

In some embodiments, a moisture barrier 1926b may be positioned or otherwise arranged at an opening 1928 to the applicator cap 1904. Similar to the microbial barrier 1926a, the moisture barrier 1926b may be configured to help isolate portions of the sensor applicator 102 from external contamination. The moisture barrier 1926b may be made of any of the materials mentioned above with reference to the microbial barrier 1926a. In at least one embodiment, however, the moisture barrier 1926b may comprise a thinned portion of the applicator cap 1904, without departing from the scope of the disclosure. In such embodiments, the opening 1928 would not be necessary.

Figure 20A:
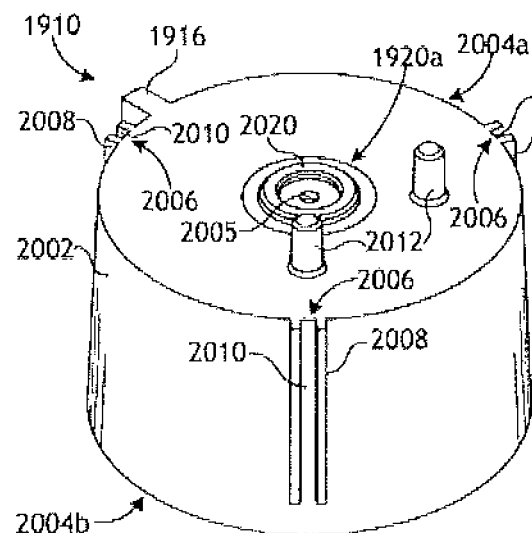
FIGS. 20A-20C are various views of the applicator insert of FIG. 19B, according to one or more embodiments of the disclosure.
Figure 20B:
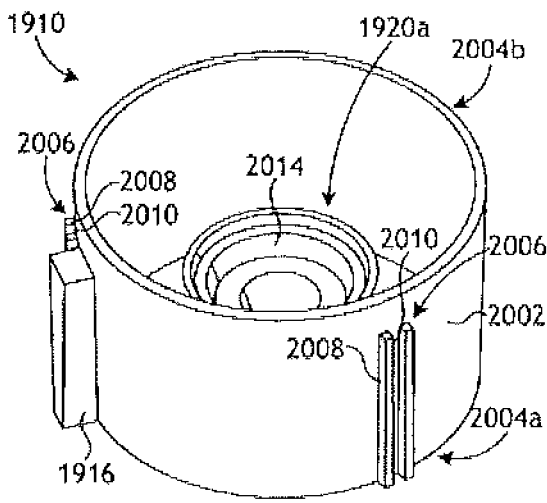
Figure 20C:
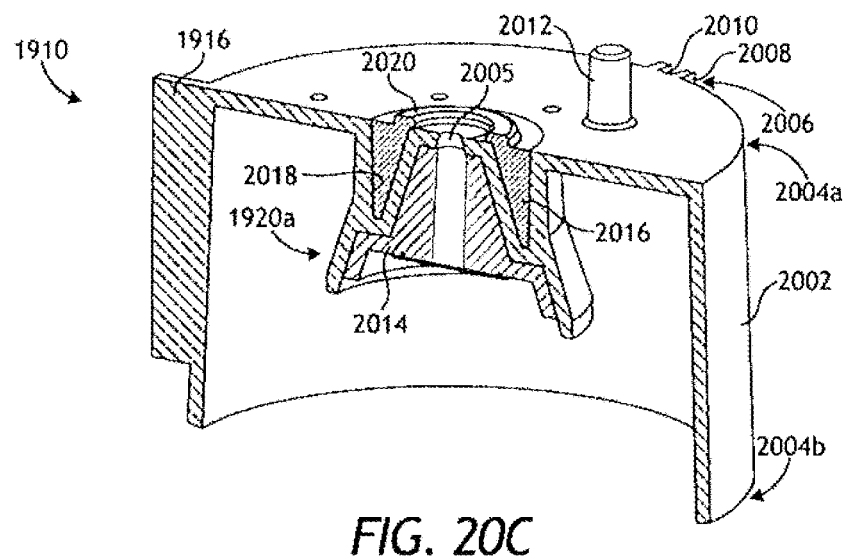

FIGS. 20A-20C are various views of the applicator insert 1910, according to one or more embodiments of the disclosure. More specifically, FIG. 20A is an isometric top view, FIG. 20B is an isometric bottom view, and FIG. 20C is an isometric cross-sectional view of the applicator insert 1910. As illustrated, the applicator insert 1910 includes a generally cylindrical body 2002 having a first or top end 2004a and a second or bottom end 2004b opposite the top end 2004a. The top end 2004a is generally closed except for an aperture 2005 sized to receive the sensor 1816 (FIG. 19B) and the sharp 1918 (FIG. 19B) therethrough, and the bottom end 2004b is generally open.

The radial alignment feature 1916 described above is provided on a sidewall of the body 2002. In some embodiments, additional radial alignment features 2006 (three shown) may be provided or otherwise defined on the sidewall of the body 2002. In the illustrated embodiment, the additional radial alignment features 2006 each comprise a pair of longitudinally-extending tabs or projections 2008 angularly offset from each other on the sidewall to cooperatively define a slot 2010 therebetween. The slot 2010 may be size to receive a projection or tab provided on the sheath 1914 (FIG. 19B) to help angularly (rotationally) orient the applicator insert 1910 relative to the sensor control device 1802 (FIG. 19B). Moreover, similar to the arrangement of the radial alignment feature 1916, the matable structures of the additional radial alignment features 2006 may alternatively be reversed, where the additional radial alignment features 2006 are instead provided on the sheath 1914 and the corresponding projection or tab is provided on the applicator insert 1910.

As best seen in FIGS. 20A and 20C, the applicator insert 1910 may further include one or more sensor locating features 2012 that may be used to also help properly orient the applicator insert 1910 relative to the sensor control device 1802 (FIG. 19B) within the sensor applicator 102 (FIG. 19B). As illustrated, the sensor locating features 2012 may be defined on and extend axially from the top end 2004a of the body 2002. The sensor locating features 2012 may be sized to be received within corresponding apertures defined in the bottom of the sensor control device 1802. In the illustrated embodiment, the sensor locating features 2012 comprise cylindrical projections, but could alternatively comprise other types of structural features suitable for mating with the corresponding features on the bottom of the sensor control device 1802. The sensor locating features 2012, in conjunction with the radial alignment feature 1916 and the additional radial alignment features 2006, may prove especially advantageous in embodiments where the sensor control device 1802 comprises an eccentric orientation, where the sensor 1916 and the sharp 1918 are not concentric with the centerline of the sensor control device.

The internal collimator 1920a may be formed or otherwise provided at the top end 2004a of the applicator insert 1910. As best seen in FIG. 20C, the internal collimator 1920a may be defined by the applicator insert 1910 and may include a collimating insert 2014 and a gasket 2016. The internal collimator 1920a may be fabricated by first fabricating or otherwise producing the collimating insert 2014. The applicator insert 1910 may then be overmolded onto the collimating insert 2014. Also, the collimating insert 2014 could be insert molded into the applicator insert 1910. Accordingly, the applicator insert 1910 may be made of a hard plastic. The gasket 2016 may then be molded onto the applicator insert 1910 in a second shot molding (overmolding) process.

The collimating insert 2014 may be made of a material that reduces or prevents sterilizing radiation from penetrating therethrough. Suitable materials for the collimating insert 2014 include, but are not limited to, a high-density polymer, (e.g., polyethylene, polypropylene, polystyrene, polytetrafluoroethylene, polyamide, etc.), a metal (e.g., lead, tungsten, stainless steel, aluminum, etc.), a composite material, or any combination thereof. In some embodiments, the collimating insert 2014 may be made of any material that has a mass density greater than 0.9 grams per cubic centimeter (g/cc).

The gasket 2016 may be made of any material that helps form a sealed interface with the bottom of the electronics housing 1804 (FIG. 19B) when the applicator insert 1910 is installed in the sensor applicator 102 (FIG. 19B). Suitable materials for the gasket 2016 include, but are not limited to, silicone, a thermoplastic elastomer (TPE), polytetrafluoroethylene (e.g., TEFLON®), or any combination thereof. As illustrated, the gasket 2016 may fill a void 2018 defined by the applicator insert 1910 and may provide an annular projection 2020 that protrudes past and/or from the upper surface of the top end 2004a of the body 2002. The annular projection 2020 may prove advantageous in not only facilitating a sealed interface, but also in helping to take up tolerances as the applicator insert 1910 is installed in the sensor applicator 102. Moreover, the mass of the gasket 2016 may also help absorb radiation during the sterilization processes described below, thus providing another layer of protection against radiation propagation. In at least one embodiment, the gasket 2016 may be large enough or of a material that absorbs sufficient radiation that the collimating insert 2014 may be omitted from the internal collimator 1920a.

Figure 21:
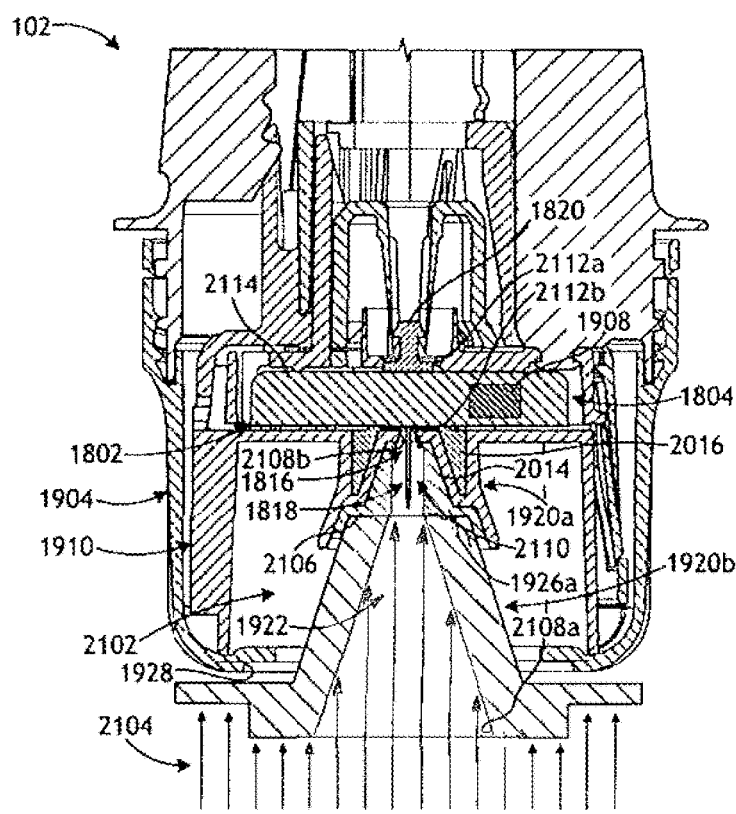
FIG. 21 is another cross-sectional side view of the sensor applicator of FIG. 19A showing a hybrid sterilization assembly, according to one or more embodiments of the disclosure.

FIG. 21 is another cross-sectional side view of the sensor applicator 102 of FIG. 19A showing a hybrid sterilization assembly 2102, according to one or more embodiments of the disclosure. The hybrid sterilization assembly 2102, alternately referred to as a "split collimation assembly" or "cooperative collimation assembly," may be used to help sterilize the sensor control device 1802 and, more particularly, the distal ends of the sensor 1816 and the sharp 1818 extending from the bottom of the electronics housing 1804 while positioned within the sensor applicator 102. More specifically, the fully assembled sensor control device 1802 may be subjected to radiation sterilization 2104 to sterilize the exposed portions of the sensor 1816 and the sharp 1818. Suitable radiation sterilization 2104 processes include, but are not limited to, electron beam (e-beam) irradiation, gamma ray irradiation, X-ray irradiation, or any combination thereof.

The radiation sterilization 2104 may be delivered either through continuous processing irradiation or through pulsed beam irradiation. In pulsed beam irradiation, the beam of radiation sterilization 2104 is focused at a target location and the component part or device to be sterilized is moved to the target location at which point the irradiation is activated to provide a directed pulse of radiation. The radiation sterilization 2104 is then turned off, and another component part or device to be sterilized is moved to the target location and the process is repeated.

According to the present disclosure, the hybrid sterilization assembly 2102 may be used to help focus the radiation 2104 in sterilizing the distal ends of the sensor 1816 and the sharp 1818, while simultaneously preventing (impeding) propagating radiation 2104 from damaging the radiation sensitive component 1908. As illustrated, the hybrid sterilization assembly 2102 (hereafter the "assembly 2102") may include the internal collimator 1920*a* previously described above and an external collimator 1920*b*. As illustrated, the internal collimator 1920*a* may be arranged within the sensor applicator 102, and the external collimator 1920*b* may extend into the sensor applicator 102 (i.e., the applicator cap 1904) by penetrating the opening 1928 to the applicator cap 1904. The internal and external collimators 1920*a,b* may cooperatively define the sterilization zone 1922 that focuses the radiation 2104 (e.g., beams, waves, energy, etc.) to impinge upon and sterilize the sensor 1816 and the sharp 1818.

In the illustrated embodiment, the external collimator 1920*b* is designed to align with the internal collimator 1920*a* and, more particularly, with the collimating insert 2014. In at least one embodiment, for example, the collimating insert 2014, may define a radial shoulder 2106 sized to receive and otherwise mate with an end of the external collimator 1920*b* extended into the applicator cap 1904. The external collimator 1920*b* may transition to the internal collimator 1920*a* at the radial shoulder 2106. In some embodiments, the transition between the internal and external collimators 1920*a,b* may be continuous, flush, or smooth. In other embodiments, however, the transition may be discontinuous or stepped, without departing from the scope of the disclosure.

Similar to the collimating insert 2014 of the internal collimator 1920*a*, the external collimator 1920*b* may be made of a material that substantially prevents the radiation 2104 from penetrating the inner wall(s) of the sterilization zone 1922 and thereby damaging the radiation sensitive component 1908 within the electronics housing 1804. Accordingly, the external collimator 1920*b* may be made of any of the materials mentioned herein as being suitable for the collimating insert 2014. In at least one embodiment, the collimating insert 2014 and the external collimator 1920*b* may each be made of stainless steel. Moreover, however, as mentioned above the gasket 2016 may also provide a degree of shielding or protection against the radiation from damaging the radiation sensitive component 1908.

The sterilization zone 1922 defined by the internal and external collimators 1920*a,b* can exhibit any suitable cross-sectional shape necessary to properly focus the radiation 2104 on the sensor 1816 and the sharp 1818 for sterilization. In the illustrated embodiment, for example, the external collimator 1920*b* is conical or frustoconical in shape, and the internal collimator 1920*a* exhibits a circular cross-sectional shape with parallel sides. In other embodiments, however, one or both of the internal and external collimators 1920*a,b* may exhibit a polygonal cross-sectional shape, such as cubic or rectangular (e.g., including parallelogram), without departing from the scope of the disclosure.

In the illustrated embodiment, the sterilization zone 1922 provides a first aperture 2108*a* defined by the external collimator 1920*b* and a second aperture 2108*b* defined by the internal collimator 1920*a*, where the first and second apertures 2108*a,b* are located at opposing ends of the sterilization zone 1922. The first aperture 2108*a* permits the radiation 2104 to enter the sterilization zone 1922, and the second aperture 2108*b* provides a location where the sensor 1816 and the sharp 1818 may be received into the sterilization zone 1922.

The diameter of the first aperture 2108*a* may be larger than the diameter of the second aperture 2108*b*. For example, the size of the first aperture 2108*a* may range between about 5.0 mm and about 16.0 mm, and the size of the second aperture 2108*b* may range between about 0.5 mm and about 5.0 mm. The respective diameters of the first and second apertures 2108*a,b*, however, may be greater or less than the ranges provided herein, without departing from the scope of the disclosure, and depending on the application. Indeed, the diameters of the first and second apertures 2108*a,b* need only be large enough to allow a sufficient dose of radiation to impinge upon the sensor 1816 and the sharp 1818. In embodiments where the sterilization zone 1922 is substantially cylindrical and otherwise exhibit a circular or polygonal cross-section, the first and second apertures 2108*a,b* may exhibit identical diameters. In such embodiments, the walls of the sterilization zone 1922 may or may not be substantially parallel between the first and second ends of the sterilization zone 1922.

The microbial barrier 1926*a* may be installed at the interface between the internal and external collimators 1920*a,b* and otherwise positioned at or near the radial shoulder 2106. The microbial barrier 1926*a* may be present during the radiation sterilization process. As indicated above, the microbial barrier 1926*a* may help seal at least a portion of the sterilization zone 1922. More particularly, the microbial barrier 1926*a* may seal off a portion of the sterilization zone 1922 to help form part of a sealed region 2110 configured to isolate the sensor 1816 and the sharp 1818 from external contamination. The sealed region 2110 may include (encompass) select portions of the interior of the electronics housing 1804 and the sterilization zone 1922. In one or more embodiments, the sealed region 2110 may be defined and otherwise formed by at least the microbial barrier 1926*a*, a first or "top" seal 2112*a*, and a second or "bottom" seal 2112*b*. The microbial barrier 1926*a* and the top and bottom seals 2112*a,b* may each create corresponding barriers at their respective sealing locations, thereby allowing the sterilization zone 1922 containing the sensor 1816 and the sharp 1818 to be terminally sterilized.

The top seal 2112*a* may be arranged to seal the interface between the sharp hub 1820 and the top of the electronics housing 1804 (i.e., the shell 1806 of FIG. 18) and thereby prevent contaminants from migrating into the interior of the electronics housing 1804. In some embodiments, the top seal 2112*a* may form part of the sharp hub 1820, such as being overmolded onto the sharp hub 1820. In other embodiments, however, the top seal 2112*a* may form part of or be overmolded onto the top surface of the shell 1806. In yet other embodiments, the top seal 2112*a* may comprise a separate structure, such as an O-ring or the like, that interposes the sharp hub 1820 and the top surface of the shell 1806, without departing from the scope of the disclosure.

The bottom seal 2112*b* may comprise the gasket 2016 (FIG. 20C) and, more particularly, the annular projection 2020 (FIGS. 20A and 20C) overmolded onto the applicator insert 1910. In operation, the bottom seal 2112*b* may be arranged to seal the interface between the applicator insert 1910 and the bottom of electronics housing 1804 (i.e., the mount 1808 of FIG. 18). The bottom seal 2112*b* may prevent contaminants from migrating into the sterilization zone 1922 and from migrating into the interior of the electronics housing 1804.

Upon loading the sensor control device 1802 into the sensor applicator 102 and securing the applicator cap 1904 to the sensor applicator 102, the top and bottom seals 2112a,b may become progressively compressed and thereby generate corresponding sealed interfaces. The top and bottom seals 2112a,b may be made of a variety of materials capable of generating a sealed interface between opposing structures. Suitable materials include, but are not limited to, silicone, a thermoplastic elastomer (TPE), polytetrafluoroethylene (e.g., TEFLON®), or any combination thereof.

Once the radiation sterilization process is finished, the external collimator 1920b may be removed from the applicator cap 1904, and the moisture barrier 1926b may be placed to occlude the opening 1928 in the applicator cap 1904. Upon delivery, a user may simply remove the applicator cap 1904 in preparation for delivering the sensor control device 1802. In at least one embodiment, removing the applicator cap 1904 will simultaneously remove the applicator insert 1910, which may be received into the applicator cap 1904 in a manner that allows the applicator insert 1910 to be secured to the applicator cap 1904 for disassembly. In such embodiments, for example, the applicator insert 1910 may be coupled to the applicator cap 1904 using a snap fit engagement or the like.

In some embodiments, the electronics housing 1804 may be filled with a potting material 2114 that fills in voids within the sensor control device 1802. The potting material 2114 may comprise a biocompatible material that meets the requirements of ISO 10993. In some embodiments, for example, the potting material 2114 may comprise a urethane material, such as Resinaid® 3672, or silicone materials, such as SI 5055 or SI 5240 available from Henkel®. In other embodiments, the potting material 2114 may comprise an acrylate adhesive material, such as GE4949 available from Delo®.

The potting material 2114 may also serve as an additional safety barrier for absorbing or deflecting propagating radiation 2104. In at least one embodiment, for example, the potting material 2114 may exhibit an e-beam resistance of at least 85 kGy. Accordingly, instead of passing through air typically present within the electronics housing 1804, the radiation 2104 may be required to pass through the potting material 2114 before impinging upon the radiation sensitive component(s) 1908. Although the potting material 2114 may not comprise a high density material, it may nonetheless serve as another level of radiation shielding. Moreover, the potting material 2114 may also increase the robustness of the sensor control device 1802 and the electronics housing 1804. Consequently, using the potting material 2114 may allow the electronics hosing 1804 to be made out of thinner materials, if desired.

It is noted that, while the sensor 1816 and the sharp 1818 extend from the bottom of the electronics housing 1804 and into the sterilization zone 1922 generally concentric with a centerline of the sensor applicator 102 and the applicator cap 1904, it is contemplated herein to have an eccentric arrangement. More specifically, in at least one embodiment, the sensor 1816 and the sharp 1818 may extend from the bottom of the electronics housing 1804 eccentric to the centerline of the sensor applicator 102 and the applicator cap 1904. In such embodiments, the internal and external collimators 1920a,b may be re-designed and otherwise configured such that the sterilization zone 1922 is also eccentrically positioned to receive the sensor 1816 and the sharp 1818, without departing from the scope of the disclosure.

Figure 22A:
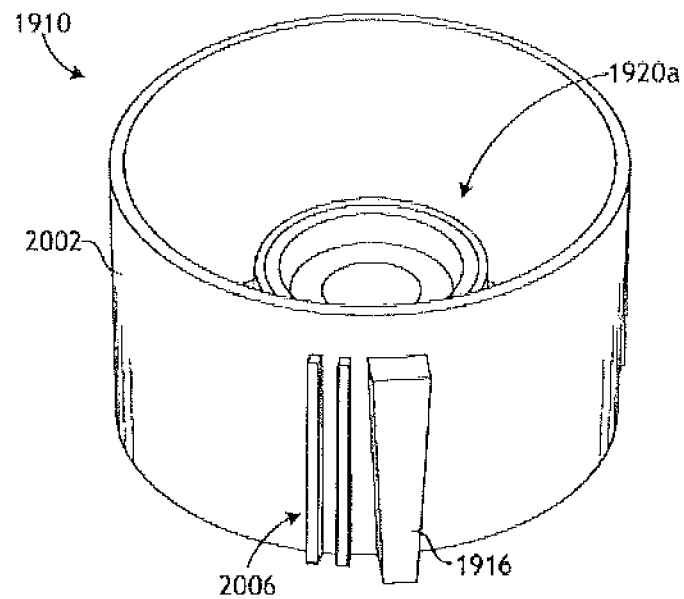
FIGS. 22A and 22B are isometric and cross-sectional side views, respectively, of another embodiment of the applicator insert of FIGS. 20A-20C.
Figure 22B:
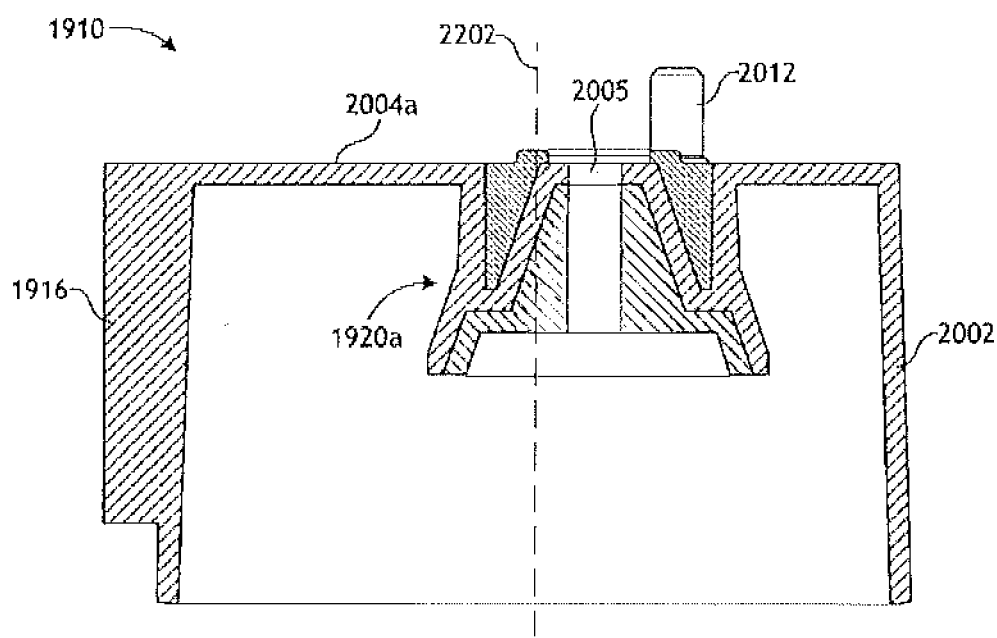

FIGS. 22A and 22B are isometric and cross-sectional side views of another embodiment of the applicator insert 1910. The applicator insert 1910 depicted in FIGS. 22A-22B may be similar in most respects to the applicator insert 1910 of FIGS. 20A-20C. Unlike the applicator insert 1910 of FIGS. 20A-20C, however, the applicator insert 1910 of FIGS. 22A-22B exhibits an eccentric orientation where the internal collimator 1920a is located eccentric to a centerline 2202 (FIG. 22B) of the body 2002. In such embodiments, the sensor control device 1802 (FIGS. 19B and 21) may also exhibit an eccentric orientation such that the sensor 1816 (FIGS. 19B and 21) and the sharp 1818 (FIGS. 19B and 21) are able to extend into the aperture 2005 defined in the top end 2004a of the applicator insert 1910. Moreover, in such embodiments, the radial alignment feature 1916, the additional radial alignment features 2006, and the sensor locating features 2012 may prove particularly advantageous in helping to properly orient the applicator insert 1910 relative to the sensor control device 1802 within the sensor applicator 102 (FIGS. 19B and 21).

Embodiments disclosed herein include:

H. A sensor applicator that includes a housing having a sensor control device arranged therein, the sensor control device including a sensor, a sharp, and a radiation sensitive component, an applicator cap removably coupled to the housing, an applicator insert positionable within the applicator cap and defining an internal collimator that receives a distal end of the sensor and the sharp, and an external collimator extendable into the applicator cap, wherein the internal and external collimators cooperatively focus radiation from a radiation sterilization process toward the sensor and the sharp and simultaneously prevent the radiation from damaging the radiation sensitive component.

I. A method of sterilizing a sensor control device that includes positioning the sensor control device within a housing of a sensor applicator, the sensor control device including a sensor, a sharp, and a radiation sensitive component, receiving a distal end of the sensor and the sharp within an internal collimator defined by an applicator insert, removably coupling an applicator cap to the housing and thereby securing the applicator insert within the applicator cap, extending an external collimator into the applicator cap and aligning the external collimator with the internal collimator, and cooperatively focusing radiation from a radiation sterilization process toward the sensor and the sharp with the internal and external collimators while simultaneously preventing the radiation from damaging the radiation sensitive component.

J. A hybrid sterilization assembly that includes an applicator insert positionable within an applicator cap of a sensor applicator, an internal collimator defined by the applicator insert to receive a distal end of a sensor and a sharp of a sensor control device arranged within a housing of the sensor applicator, and an external collimator extendable into the applicator cap and alignable with the internal collimator, wherein the internal and external collimators cooperatively focus radiation from a radiation sterilization process toward the sensor and the sharp and simultaneously prevent the radiation from damaging the radiation sensitive component.

Each of embodiments H, I, and J may have one or more of the following additional elements in any combination: Element 1: wherein the applicator insert engages an inner surface of the applicator cap to axially secure the applicator insert within the applicator cap. Element 2: further comprising a sheath extending from the housing and into the applicator cap when the applicator cap is coupled to the housing, and one or more radial alignment features provided on the applicator insert and matable with one or more corresponding features provided on the sheath to rotationally orient the applicator insert relative to the sensor control device. Element 3: further comprising one or more sensor locating features provided on the applicator insert and matable with one or more corresponding features on the sensor control device to rotationally orient the applicator insert relative to the sensor control device. Element 4: wherein the internal collimator includes a collimating insert and the external collimator is alignable with the collimating insert. Element 5: wherein the collimating insert and the external collimator are each made of a material selected from the group consisting of a high-density polymer, a metal, a composite material, and any combination thereof. Element 6: wherein the internal collimator further includes a gasket engageable with a bottom of the sensor control device to generate a sealed interface. Element 7: wherein the external collimator comprises a cross-sectional shape selected from the group consisting of conical, frustoconical, pyramidal, circular, cubic, rectangular, and any combination thereof. Element 8: further comprising a potting material arranged within the sensor control device.

Element 9: further comprising engaging an inner surface of the applicator cap against the applicator insert and thereby axially securing the applicator insert within the applicator cap. Element 10: wherein the internal collimator includes a gasket, the method further comprising engaging the gasket against a bottom of the sensor control device as the applicator insert is axially secured within the applicator cap, and generating a sealed interface with the gasket against the bottom of the sensor control device. Element 11: wherein the internal and external collimators cooperatively define a sterilization zone that receives the sensor and the sharp, the method further comprising sealing at least a portion of the sterilization zone with a microbial barrier positioned at an interface between the internal and external collimators. Element 12: wherein the internal collimator includes a collimating insert and wherein aligning the external collimator with the internal collimator comprises aligning the external collimator with the collimating insert. Element 13: wherein the external collimator comprises a cross-sectional shape selected from the group consisting of conical, frustoconical, pyramidal, circular, cubic, rectangular, and any combination thereof.

Element 14: further comprising a microbial barrier positioned at an interface between the internal and external collimators. Element 15: wherein the internal collimator includes a collimating insert and wherein the collimating insert and the external collimator are each made of a material selected from the group consisting of a high-density polymer, a metal, a composite material, and any combination thereof. Element 16: wherein the internal collimator further includes a gasket engageable with a bottom of the sensor control device to generate a sealed interface. Element 17: wherein the external collimator comprises a cross-sectional shape selected from the group consisting of conical, frustoconical, pyramidal, circular, cubic, rectangular, and any combination thereof.

By way of non-limiting example, exemplary combinations applicable to H, I, and J include: Element 4 with Element 5; Element 4 with Element 6; Element 9 with Element 10; and Element 15 with Element 16.

Internal Sterilization Assemblies

Prior to being delivered to an end user, some medical devices must be sterilized to render the product free from viable microorganisms. Some medical devices, however, include under-skin sensing devices or sensors that must be sterilized using radiation sterilization, such as electron beam ("e-beam") irradiation. Radiation sterilization, however, can damage electronic components associated with the medical device, which are commonly sterilized via gaseous chemical sterilization (e.g., using ethylene oxide). Gaseous chemical sterilization, however, can damage the enzymes or other chemistry and biologics included on the under-skin sensing devices.

In the past, this sterilization incompatibility has been circumvented by separating the under-skin sensing devices and the electronic components and sterilizing each individually. This approach, however, requires additional parts, packaging, process steps, and final assembly by the user, which introduces a possibility of user error. According to the present disclosure, any device requiring terminal sterilization, may be properly sterilized using an internal sterilization assembly designed to focus sterilizing radiation (e.g., beams, waves, energy, etc.) toward component parts requiring sterilization, while simultaneously preventing the propagating radiation from disrupting or damaging sensitive electronic components.

Figure 23:
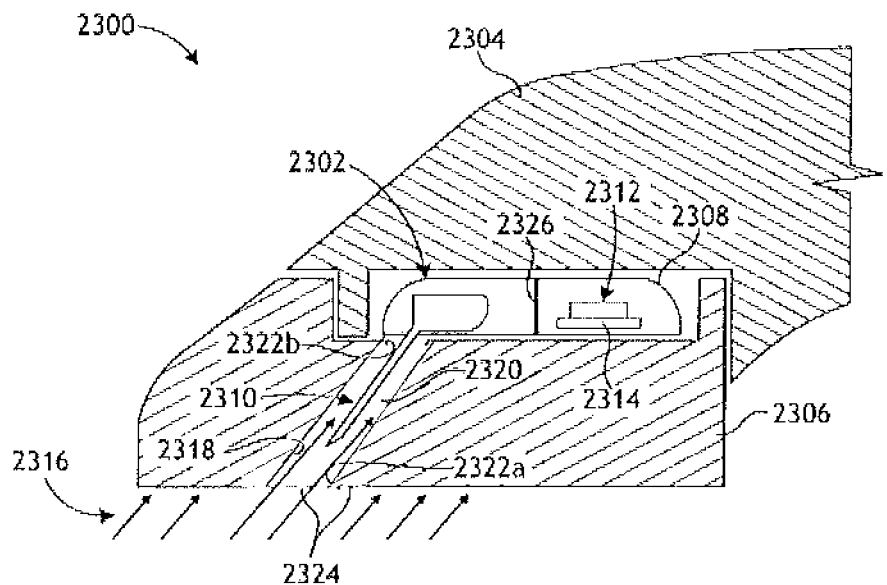
FIG. 23 is a diagram of an example analyte monitoring system that may incorporate one or more embodiments of the present disclosure.

FIG. 23 is a schematic diagram of an example internal sterilization assembly 2300, according to one or more embodiments of the present disclosure. The internal sterilization assembly 2300 (hereafter the "assembly 2300") may be designed and otherwise configured to help sterilize a medical device 2302. The medical device 2302 may comprise a type of a health care product including any device, mechanism, assembly, or system requiring terminal sterilization of one or more component parts. Suitable examples of the medical device 2302 include, but are not limited to, ingestible products, cardiac rhythm management (CRM) devices, under-skin sensing devices, externally mounted medical devices, medication delivery devices, or any combination thereof.

In the illustrated embodiment, the medical device 2302 comprises an under-skin sensing device or "sensor control device," also referred to as an "in vivo analyte sensor control device". As illustrated, the medical device 2302 may be housed within a sensor applicator 2304 (alternately referred to as an "inserter") and a cap 2306 may be removably coupled to the sensor applicator 2304. The medical device 2302 includes a housing 2308, a part 2310 requiring sterilization, and one or more radiation sensitive components 2312. In some embodiments, the part 2310 may comprise a sensor that extends from the housing 2308. In at least one embodiment, the part 2310 may further include a sharp that may also require sterilization and may help implant the sensor beneath the skin of a user. As illustrated, the part 2310 may extend at an angle from the bottom of the housing 2308, but could alternatively extend perpendicularly from the bottom or from another surface of the housing 2308. Moreover, as illustrated, the part 2310 may extend from one end of the housing 2308 or otherwise offset from a centerline of the housing 2308, but may alternatively extend concentric with the housing, without departing from the scope of the disclosure.

The sensor applicator 2304 is used to deliver the medical device 2302 to a target monitoring location on a user's skin (e.g., the arm of the user). In some embodiments, the cap 2306 may be threaded to the sensor applicator 2304 and removed from the sensor applicator 2304 by unscrewing the cap 2306 from engagement with the sensor applicator 2304. Once the cap 2306 is removed, a user may then use the sensor applicator 2304 to position the medical device 2302 at a target monitoring location on the user's body. The part 2310 is positioned such that it can be transcutaneously positioned and otherwise retained under the surface of the user's skin. In some embodiments, the medical device 2302 may be spring loaded for ejection from the sensor applicator 2304. Once delivered, the medical device 2302 may be maintained in position on the skin with an adhesive patch (not shown) coupled to the bottom of the medical device 2302.

In the illustrated embodiment, the radiation sensitive component 2312 may be mounted to a printed circuit board (PCB) 2314 positioned within the housing 2308. The radiation sensitive component 2312 may include one or more electronic modules such as, but not limited to, a data processing unit (e.g., an application specific integrated circuit or "ASIC"), a resistor, a transistor, a capacitor, an inductor, a diode, a switch, or any combination thereof. In other embodiments, however, the radiation sensitive component 2312 may comprise a radiation sensitive chemical solution or analyte (e.g., an active agent, pharmaceutical, biologic, etc.). In such embodiments, the medical device 2302 may alternatively comprise a hypodermic needle or syringe and the chemical solution or analyte may be positioned within an ampoule of the medical device 2302.

The medical device 2302 may be subjected to radiation sterilization 2316 to properly sterilize the part 2310 for use. Suitable radiation sterilization 2316 processes include, but are not limited to, electron beam (e-beam) irradiation, gamma ray irradiation, X-ray irradiation, or any combination thereof. The cap 2306 may define a collimator 2318 that allows the radiation 2316 to impinge upon and sterilize the part 2310. The cap 2306, however, may also act as a radiation shield that helps prevent (impede) propagating radiation 2316 from disrupting or damaging the radiation sensitive component(s) 2312. To accomplish this, the cap 2306 may be made of a material that reduces or prevents the radiation 2316 from penetrating therethrough.

More specifically, the cap 2306 may be made of a material having a density sufficient to absorb the dose of the radiation 2316 beam energy being delivered. In some embodiments, for example, the cap 2306 may be made of any material that has a mass density greater than 0.9 grams per cubic centimeter (g/cc). In other embodiments, however, the mass density of a suitable material may be less than 0.9 g/cc, without departing from the scope of the disclosure. Suitable materials for the cap 2306 include, but are not limited to, a high-density polymer, (e.g., polyethylene, polypropylene, polystyrene, polytetrafluoroethylene, etc.), a metal (e.g., lead, stainless steel, aluminum, etc.), any combination thereof, or any material having a mass density greater than 0.9 g/cc.

As illustrated, the collimator 2318 generally comprises a hole or passageway extending at least partially through the cap 2306. The collimator 2318 defines a sterilization zone 2320 configured to focus the radiation 2316 toward the part 2310. In the illustrated embodiment, the part 2310 may be received within the sterilization zone 2320 for sterilization. The collimator 2318 can exhibit any suitable cross-sectional shape necessary to focus the radiation 2316 on the part 2310 for sterilization. In the illustrated embodiment, for example, the collimator 2318 exhibits a circular cross-sectional shape with parallel sides. In other embodiments, however, the collimator 2318 may exhibit a polygonal cross-sectional shape, such as cubic or rectangular (e.g., including parallelogram), without departing from the scope of the disclosure.

In the illustrated embodiment, the collimator 2318 provides a first aperture 2322*a* and a second aperture 2322*b* where the first and second apertures 2322*a,b* are defined at opposing ends of the sterilization zone 2320. The first aperture 2322*a* may allow the radiation 2316 to enter the sterilization zone 2320 and impinge upon the part 2310, and the second aperture 2322*b* may be configured to receive the part 2310 into the sterilization zone 2320. In embodiments where the collimator 2318 is cylindrical in shape, the first and second apertures 2322*a,b* exhibit identical diameters.

In some embodiments, a cap seal 2324 (shown in dashed lines) may be positioned at the opening of the collimator 2318 and otherwise at the first aperture 2322*a*. The cap seal 2324 may comprise a radiation permeable, microbial barrier. In some embodiments, for example, the cap seal 2324 may be made of a synthetic material (e.g., a flash-spun high-density polyethylene fiber), such as TYVEK® available from DuPont®. In other embodiments, however, the cap seal 2324 may comprise, but it no limited to, tape, paper, foil, or any combination thereof. In yet other embodiments, the cap seal 2324 may comprise a thinned portion of the cap 2306, without departing from the scope of the disclosure. In such embodiments, the first aperture 2322*a* would be omitted.

The cap seal 2324 may seal off a portion of the sterilization zone 2320 to isolate the part 2310 from external contamination, while simultaneously allowing the radiation 2316 to pass therethrough to sterilize the part 2310. In some embodiments, a desiccant (not shown) may be arranged within the sterilization zone 2320.

In some embodiments, the assembly 2300 may further include a barrier shield 2326 positioned within the housing 2308. The barrier shield 2326 may be configured to help block radiation 2316 (e.g., electrons) from propagating within the housing 2308 toward the radiation sensitive component(s) 2312. The barrier shield 2326 may be made of any of the materials mentioned above for the cap 2306. In the illustrated embodiment, the barrier shield 2326 is positioned vertically within the housing 2308, but may alternatively be positioned at any other angular configuration suitable for protecting the radiation sensitive component(s) 2312.

Figure 24:
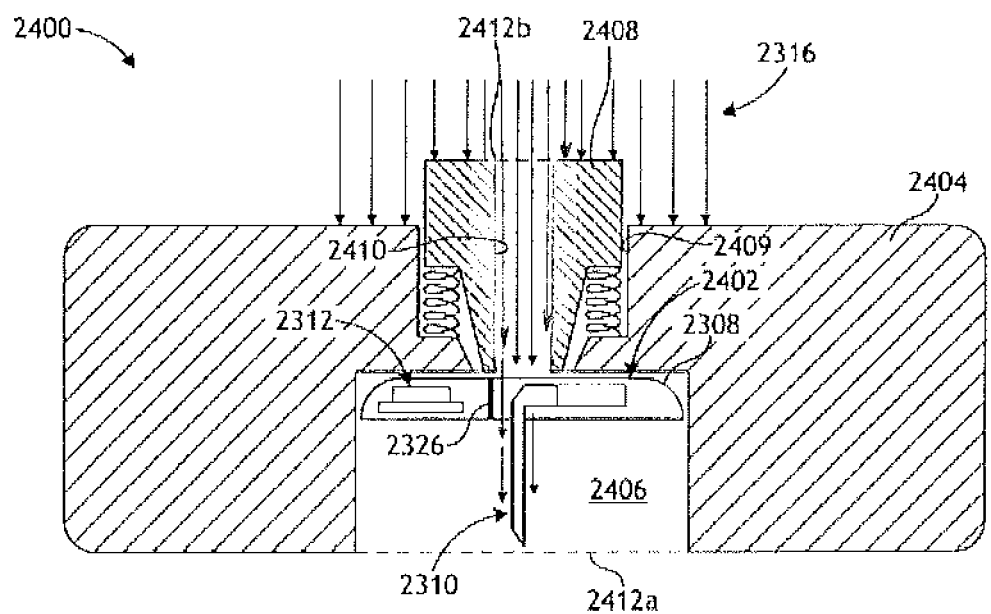
FIG. 24 is a schematic diagram of an example internal sterilization assembly, according to one or more additional embodiments of the present disclosure.

FIG. 24 is a schematic diagram of another example internal sterilization assembly 2400, according to one or more additional embodiments of the present disclosure. The internal sterilization assembly 2400 (hereafter the "assembly 2400") may be similar in some respects to the assembly 2300 of FIG. 23 and therefore may be best understood with reference thereto, where like numeral represent like components not described again in detail. Similar to the assembly 2300 of FIG. 23, for example, the assembly 2400 may be designed and otherwise configured to help sterilize a medical device 2402, which may be similar to the medical device 2302 of FIG. 23. The medical device 2402 may comprise a sensor control device similar to the medical device 2302 of FIG. 23, but may alternatively comprise any of the health care products mentioned herein.

As illustrated, the medical device 2402 may be housed within a sensor applicator 2404 and, more specifically, within a pocket 2406 defined in the sensor applicator 2404. In some embodiments, a desiccant (not shown) may be arranged within the pocket 2406. Similar to the medical device 2302 of FIG. 23, the medical device 2402 may include the housing 2308, the part 2310 requiring sterilization, and the radiation sensitive component(s) 2312. In some embodiments, the assembly 2400 may further include the barrier shield 2326, as generally described above. As illustrated, the part 2310 may extend perpendicularly from the bottom of the housing 2308, but could alternatively extend at an angle or from another surface. Moreover, as illustrated, the part 2310 may extend along a centerline of the housing 2308, but may alternatively extend eccentric to the centerline, without departing from the scope of the disclosure.

The sensor applicator 2404 is used to deliver the medical device 2402 to a target monitoring location on a user's skin (e.g., the arm of the user). As illustrated, the sensor applicator 2404 may include a spring-loaded button 2408 at least partially received within the sensor applicator 2404. The button 2408 extends within a channel 2409 defined in the sensor applicator 2404 and is engageable with the top of the housing 2308 at its bottom end. In at least one embodiment, a sealed interface is created where the bottom of the button 2406 engages the housing 2308. The medical device 2402 may be deployed for use from the pocket 2406 by pressing down on the button 2408, which acts on the housing 2308 and thereby pushes the medical device 2402 distally and out of the pocket 2406 and away from the sensor applicator 2404. The part 2310 is positioned such that it can be transcutaneously positioned and otherwise retained under the surface of the user's skin. Once delivered, the medical device 2402 may be maintained in position on the skin with an adhesive patch (not shown) coupled to the bottom of the medical device 2402.

The medical device 2402 may be subjected to radiation sterilization 2316 to properly sterilize the part 2310 prior to use. In the illustrated embodiment, the radiation sterilization 2316 is directed to the top of the sensor applicator 2404 and the button 2408 defines a collimator 2410 that allows the radiation 2316 to impinge upon and sterilize the part 2310. As illustrated, the collimator 2410 generally comprises a hole or passageway extending at least partially through the button 2408. The collimator 2410 focuses the radiation 2316 toward the part 2310 and can exhibit any suitable cross-sectional shape necessary to focus the radiation 2316 on the part 2310 for sterilization. In the illustrated embodiment, for example, the collimator 2410 exhibits a circular cross-section with parallel sides. In other embodiments, however, the collimator 2410 may exhibit a polygonal cross-sectional shape, such as cubic or rectangular (e.g., including parallelogram), without departing from the scope of the disclosure.

Portions of the sensor applicator 2404 and the button 2408, however, may also act as a radiation shield that helps prevent (impede) propagating radiation 2316 from disrupting or damaging the radiation sensitive component(s) 2312, except through the collimator 2410. To accomplish this, the sensor applicator 2404 and the button 2408 may be made of a material similar to the material of the cap 2306 of FIG. 23. In at least one embodiment, the radiation sterilization 2316 may be emitted from a device or machine configured to focus and/or aim the radiation 2316 directly into the collimator 2410, and thereby mitigating radiation 2316 exposure to adjacent portions of the sensor applicator 2404.

In some embodiments, a first seal 2412a (shown in dashed lines) may be positioned at the opening of the pocket 2406, and a second seal 2412b may be arranged at the opening to the collimator 2410 at the top of the button 2406. The seals 2412a,b may comprise radiation permeable, microbial barriers, similar to the cap seal 2324 of FIG. 23. The first seal 2412a may seal off the pocket 2406 on the bottom of the sensor applicator 2404 to isolate the part 2310 from external contamination, and the second seal 2412b may seal off the collimator 2410, while simultaneously allowing the radiation 2316 to pass therethrough to sterilize the part 2310.

Figure 25:
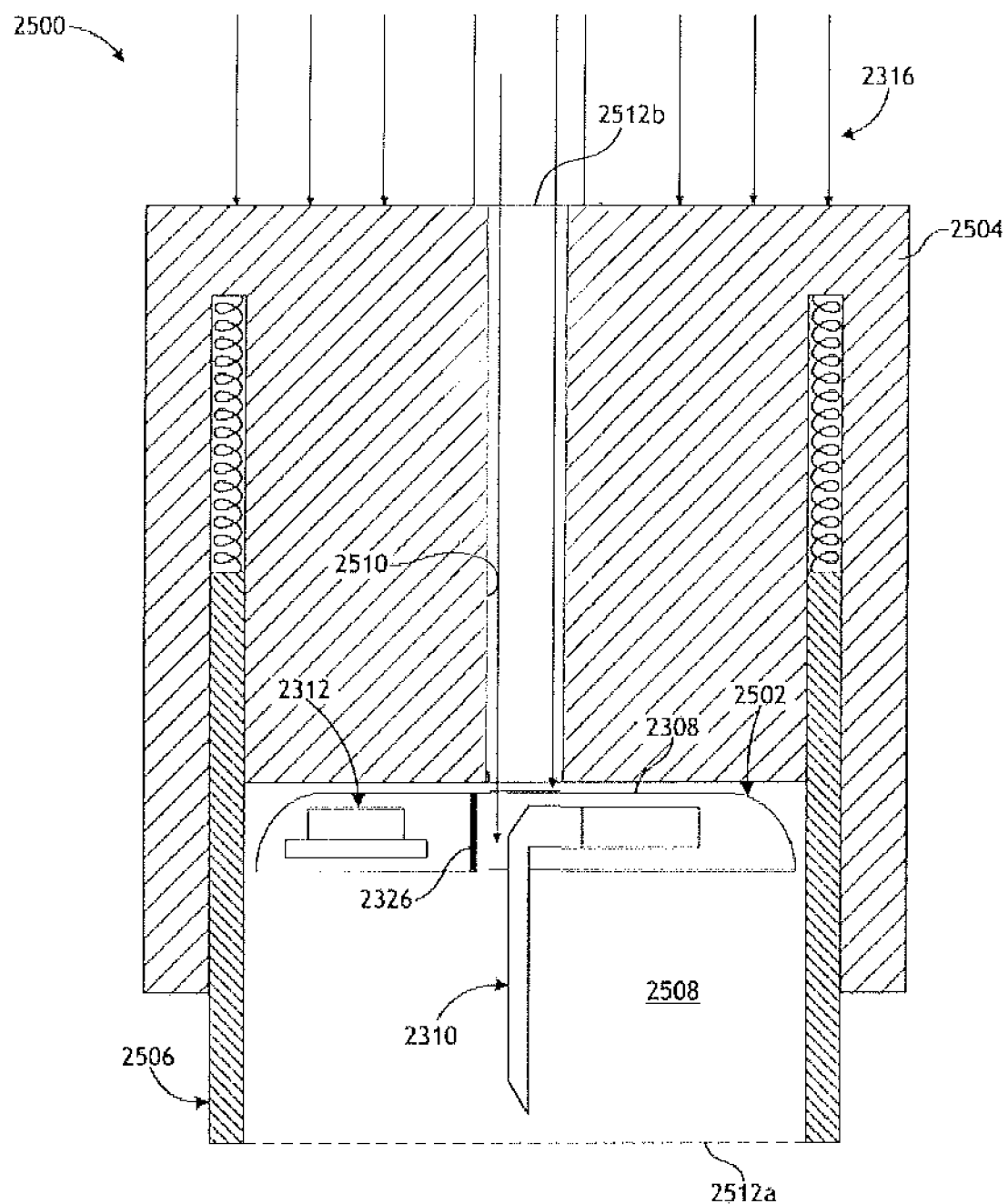
FIG. 25 is a schematic diagram of another example internal sterilization assembly, according to one or more additional embodiments of the present disclosure.

FIG. 25 is a schematic diagram of another example internal sterilization assembly 2500, according to one or more additional embodiments of the present disclosure. The internal sterilization assembly 2500 (hereafter the "assembly 2500") may be similar in some respects to the assemblies 2300 and 2400 of FIGS. 23 and 24 and therefore may be best understood with reference thereto, where like numeral represent like components not described again in detail. Similar to the assemblies 2300 and 2400 of FIGS. 23 and 24, for example, the assembly 2500 may be designed and otherwise configured to help sterilize a medical device 2502, which may be similar to the medical devices 2302 and 2402 of FIGS. 23 and 24. The medical device 2502 may comprise a sensor control device similar to the medical devices 2302 and 2402 of FIGS. 23 and 24, but may alternatively comprise any of the health care products mentioned herein.

As illustrated, the medical device 2502 may be housed within a sensor applicator 2504, which may include a spring-loaded sheath 2506. The medical device 2502 may be positioned within a pocket 2508 defined at least partially by the sheath 2506. In some embodiments, a desiccant (not shown) may be arranged within the pocket 2508. Similar to the medical devices 2302 and 2402 of FIGS. 23 and 24, the medical device 2502 may include the housing 2308, the part 2310 requiring sterilization, and the radiation sensitive component(s) 2312. In some embodiments, the assembly 2500 may further include the barrier shield 2326, as generally described above.

As illustrated, the part 2310 may extend perpendicularly from the bottom of the housing 2308, but could alternatively extend at an angle or from another surface. Moreover, as illustrated, the part 2310 may extend along a centerline of the housing 2308, but may alternatively extend eccentric to the centerline, without departing from the scope of the disclosure.

The sensor applicator 2504 is used to deliver the medical device 2502 to a target monitoring location on a user's skin (e.g., the arm of the user). The medical device 2502 may be deployed for use from the pocket 2508 by forcing the sheath 2506 against the user's skin and thereby causing the sheath 2506 to collapse into the body of the sensor applicator 2504. Once the sheath 2506 collapses past the housing 2308, the medical device 2502 may be discharged from the sensor applicator 2504. The part 2310 is positioned such that it can be transcutaneously positioned and otherwise retained under the surface of the user's skin. Once delivered, the medical device 2502 may be maintained in position on the skin with an adhesive patch (not shown) coupled to the bottom of the medical device 2502. \

The medical device 2502 may be subjected to radiation sterilization 2316 to properly sterilize the part 2310 prior to use. In the illustrated embodiment, the radiation sterilization 2316 is directed to the top of the sensor applicator 2504, which defines a collimator 2510 that allows the radiation 2316 to impinge upon and sterilize the part 2310. As illustrated, the collimator 2510 generally comprises a hole or passageway extending through the body of the sensor applicator 2504. The collimator 2510 focuses the radiation 2316 toward the part 2310 and can exhibit any suitable cross-sectional shape necessary to focus the radiation 2316 on the part 2310 for sterilization. In the illustrated embodiment, for example, the collimator 2510 exhibits a circular cross-sectional shape with parallel sides. In other embodiments, however, the collimator 2510 may exhibit a polygonal cross-sectional shape, such as cubic or rectangular (e.g., including parallelogram), without departing from the scope of the disclosure.

The sensor applicator 2504, however, may also act as a radiation shield that helps prevent (impede) propagating radiation 2316 from disrupting or damaging the radiation sensitive component(s) 2312, except through the collimator 2510. To accomplish this, the sensor applicator 2504 may be made of a material similar to the material of the cap 2306 of FIG. 23. In at least one embodiment, however, the radiation sterilization 2316 may be emitted from a device or machine configured to focus and/or aim the radiation 2316 directly into the collimator 2510, and thereby mitigating radiation 2316 exposure to adjacent portions of the sensor applicator 2504.

In some embodiments, a first seal 2512a (shown in dashed lines) may be positioned at the opening of the pocket 2508, and a second seal 2512b may be arranged at the opening to the collimator 2510 at the top of the sensor applicator 2504. The seals 2512a,b may comprise radiation permeable, microbial barriers, similar to the cap seal 2324 of FIG. 23. The first seal 2512a may seal off the pocket 2508 on the bottom of the sensor applicator 2504 to isolate the part 2310 from external contamination, and the second seal 2512b may seal off the collimator 2510, while simultaneously allowing the radiation 2316 to pass therethrough to sterilize the part 2310.

Embodiments disclosed herein include:

K. An internal sterilization assembly that includes a sensor applicator, a medical device at least partially housed within the sensor applicator and having a part requiring sterilization and a radiation sensitive component, and a cap removably coupled to the sensor applicator and providing a collimator alignable with the part requiring sterilization, wherein the collimator focuses radiation from a radiation sterilization process toward the part requiring sterilization and the radiation is prevented from damaging the radiation sensitive component.

Embodiment K may have one or more of the following additional elements in any combination: Element 1: wherein the radiation sensitive component is selected from the group consisting of an electronic module, a chemical solution, and any combination thereof. Element 2: wherein the collimator comprises a cross-sectional shape selected from the group consisting of circular, cubic, rectangular, and any combination thereof. Element 3: wherein the medical device comprises an in vivo analyte sensor control device and the part requiring sterilization comprises at least one of a sensor and a sharp extending from the housing of the in vivo analyte sensor control device. Element 4: wherein the at least one of the sensor and the sharp extends at an angle from the bottom of the housing. Element 5: wherein the at least one of the sensor and the sharp extends perpendicularly from the bottom of the housing. Element 6: wherein the at least one of the sensor and the sharp extends from the bottom of the housing along a centerline of the housing. Element 7: wherein the at least one of the sensor and the sharp extends from the bottom of the housing offset from a centerline of the housing. Element 8: wherein the cap is made of a material having a mass density greater than 0.9 g/cc. Element 9: wherein the cap is made of a material selected from the group consisting of a high-density polymer, a metal, and any combination thereof. Element 10: wherein the medical device comprises an in vivo analyte sensor control device having a housing that houses the radiation sensitive component, the internal sterilization assembly further comprising a barrier shield positioned within the housing to block the radiation from propagating within the housing toward the radiation sensitive component. Element 11: further comprising a spring-loaded button at least partially received within the sensor applicator and engageable with a top of the medical device, wherein the collimator is defined through the button. Element 12: further comprising a sealed interface at the intersection of the button and the medical device. Element 13: wherein at least one of the button and the sensor applicator is made of a material selected from the group consisting of a high-density polymer, a metal, and any combination thereof. Element 14: wherein the sensor applicator includes a spring-loaded sheath and the medical device is housed within a pocket at least partially defined by the sheath. Element 15: wherein the collimator is defined through the sensor applicator.

By way of non-limiting example, exemplary combinations applicable to A, B, and C include: Element 3 with Element 4; Element 3 with Element 5; Element 3 with Element 6; Element 3 with Element 7; Element 8 with Element 9; Element 11 with Element 12; Element 11 with Element 13; and Element 14 with Element 15.

One-Piece Bio-Sensor Design with Sensor Preservation Vial

Figure 26A:
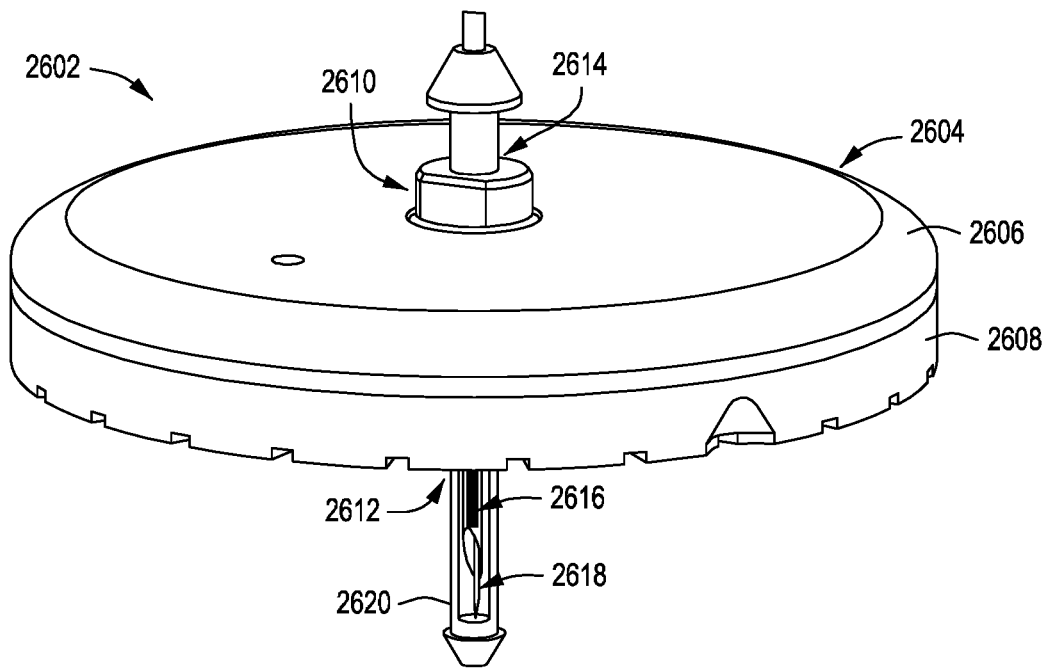
FIGS. 26A and 26B are isometric and side views, respectively, of an example sensor control device.
Figure 26B:
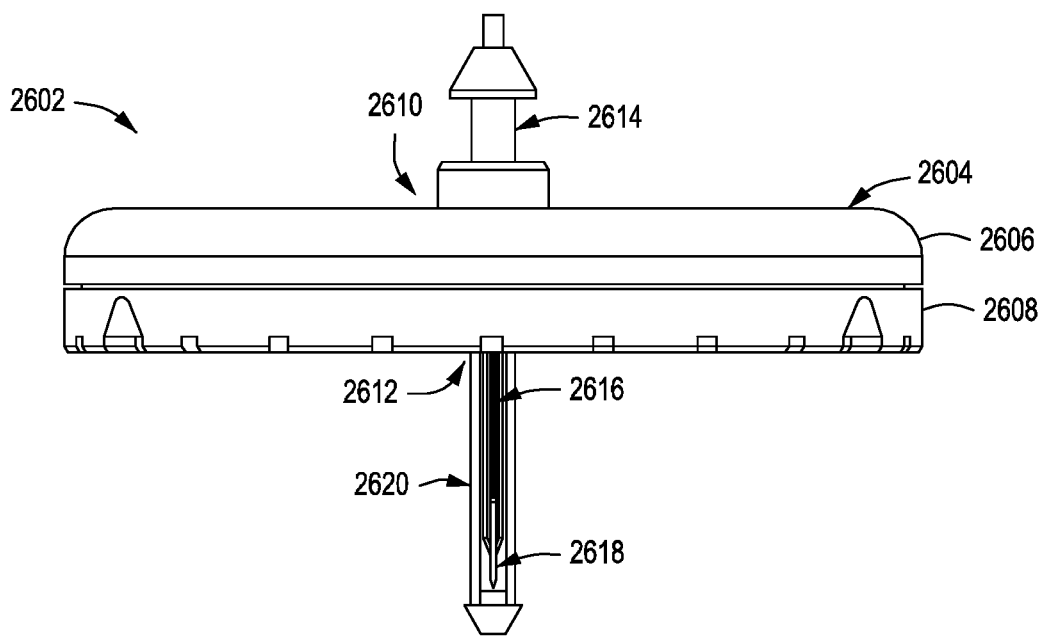

FIGS. 26A and 26B are isometric and side views, respectively, of an example sensor control device 2602, according to one or more embodiments of the present disclosure. The sensor control device 2602 (alternately referred to as a "puck") may be similar in some respects to the sensor control device 104 of FIG. 1 and therefore may be best understood with reference thereto. The sensor control device 2602 may replace the sensor control device 104 of FIG. 1 and, therefore, may be used in conjunction with the sensor applicator 102 (FIG. 1), which delivers the sensor control device 2602 to a target monitoring location on a user's skin.

The sensor control device 2602, however, may be incorporated into a one-piece system architecture in contrast to the sensor control device 104 of FIG. 1. Unlike the two-piece architecture, for example, a user is not required to open multiple packages and finally assemble the sensor control device 2602. Rather, upon receipt by the user, the sensor control device 2602 is already fully assembled and properly positioned within the sensor applicator 102 (FIG. 1). To use the sensor control device 2602, the user need only open one barrier (e.g., the applicator cap 210 of FIG. 2B) before promptly delivering the sensor control device 2602 to the target monitoring location.

As illustrated, the sensor control device 2602 includes an electronics housing 2604 that is generally disc-shaped and may have a circular cross-section. In other embodiments, however, the electronics housing 2604 may exhibit other cross-sectional shapes, such as ovoid or polygonal, without departing from the scope of the disclosure. The electronics housing 2604 may be configured to house or otherwise contain various electrical components used to operate the sensor control device 2602.

The electronics housing 2604 may include a shell 2606 and a mount 2608 that is matable with the shell 2606. The shell 2606 may be secured to the mount 2608 via a variety of ways, such as a snap fit engagement, an interference fit, sonic welding, or one or more mechanical fasteners (e.g., screws). In some cases, the shell 2606 may be secured to the mount 2608 such that a sealed interface therebetween is generated. In such embodiments, a gasket or other type of seal material may be positioned at or near the outer diameter (periphery) of the shell 2606 and the mount 2608, and securing the two components together may compress the gasket and thereby generate a sealed interface. In other embodiments, an adhesive may be applied to the outer diameter (periphery) of one or both of the shell 2606 and the mount 2608. The adhesive secures the shell 2606 to the mount 2608 and provides structural integrity, but may also seal the interface between the two components and thereby isolate the interior of the electronics housing 2604 from outside contamination. If the sensor control device 2602 is assembled in a controlled environment, there may be no need to terminally sterilize the internal electrical components. Rather, the adhesive coupling may provide a sufficient sterile barrier for the assembled electronics housing 2604.

The sensor control device 2602 may further include a plug assembly 2610 that may be coupled to the electronics housing 2604. The plug assembly 2610 may be similar in some respects to the plug assembly 207 of FIG. 2A. For example, the plug assembly 2610 may include a sensor module 2612 (partially visible) interconnectable with a sharp module 2614 (partially visible). The sensor module 2612 may be configured to carry and otherwise include a sensor 2616 (partially visible), and the sharp module 2614 may be configured to carry and otherwise include a sharp 2618 (partially visible) used to help deliver the sensor 2616 transcutaneously under a user's skin during application of the sensor control device 2602. As illustrated, corresponding portions of the sensor 2616 and the sharp 2618 extend from the electronics housing 2604 and, more particularly, from the bottom of the mount 2608. The exposed portion of the sensor 2616 may be received within a hollow or recessed portion of the sharp 2618. The remaining portion of the sensor 2616 is positioned within the interior of the electronics housing 2604.

As discussed in more detail below, the sensor control device 2602 may further include a sensor preservation vial 2620 that provides a preservation barrier surrounding and protecting the exposed portions of the sensor 2616 and the sharp 2618 from gaseous chemical sterilization.

Figure 27A:
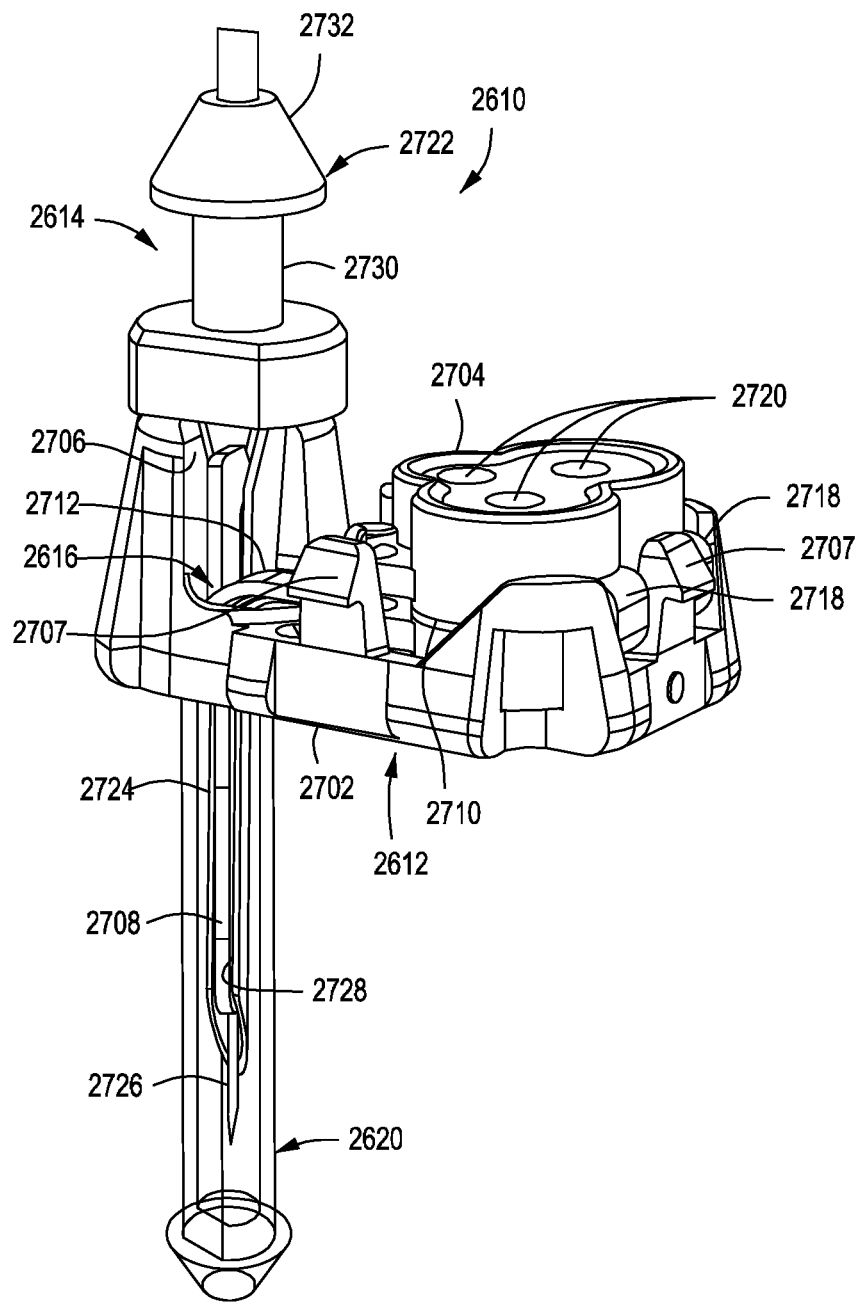
FIGS. 27A and 27B are isometric and exploded views, respectively, of the plug assembly of FIGS. 26A-26B.
Figure 27B:
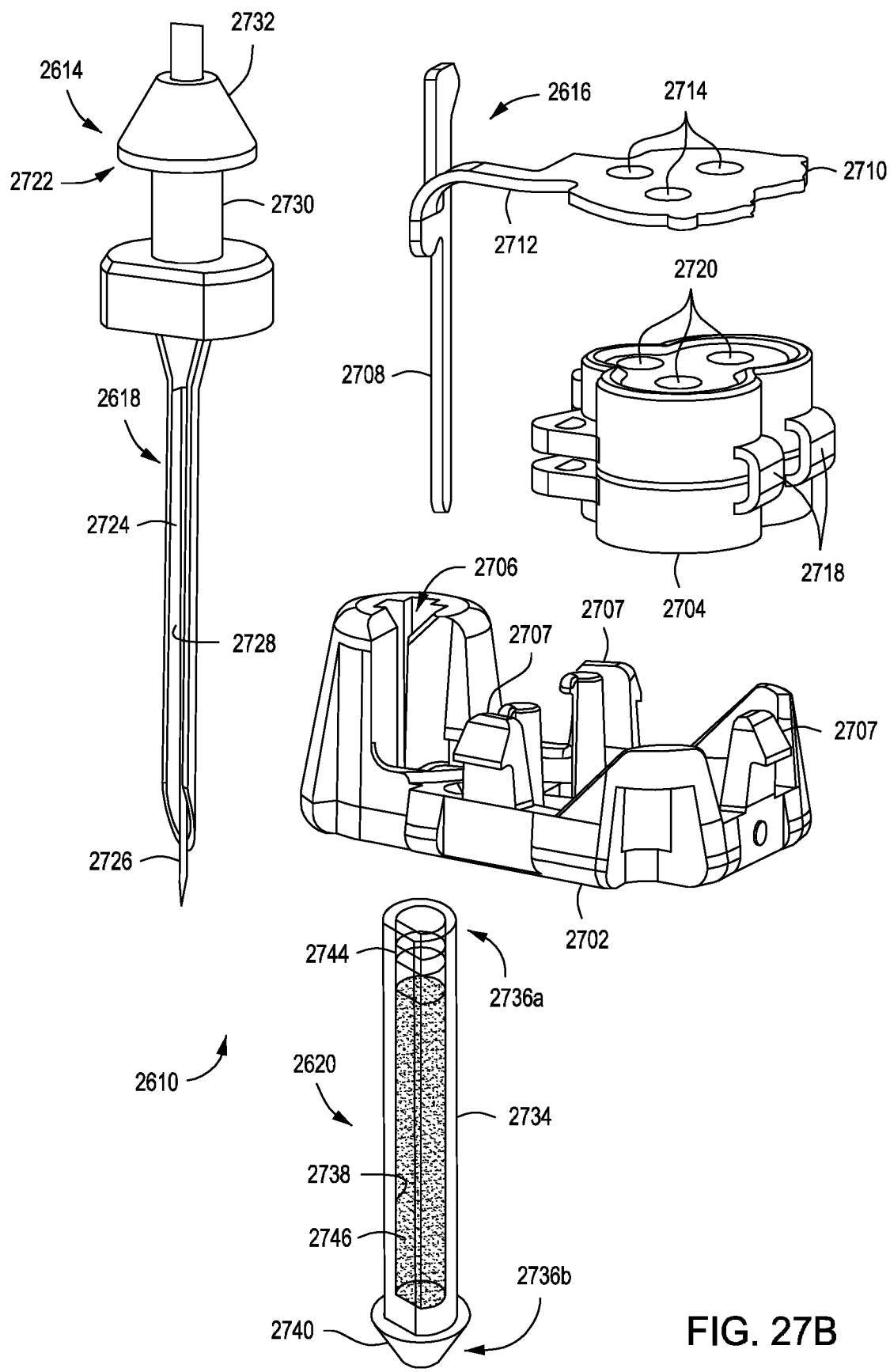

FIGS. 27A and 27B are isometric and exploded views, respectively, of the plug assembly 2610, according to one or more embodiments. The sensor module 2612 may include the sensor 2616, a plug 2702, and a connector 2704. The plug 2702 may be designed to receive and support both the sensor 2616 and the connector 2704. As illustrated, a channel 2706 may be defined through the plug 2702 to receive a portion of the sensor 2616. Moreover, the plug 2702 may provide one or more deflectable arms 2707 configured to snap into corresponding features provided on the bottom of the electronics housing 2604 (FIGS. 26A-26B).

The sensor 2616 includes a tail 2708, a flag 2710, and a neck 2712 that interconnects the tail 2708 and the flag 2710. The tail 2708 may be configured to extend at least partially through the channel 2706 and extend distally from the plug 2702. The tail 2708 includes an enzyme or other chemistry or biologic and, in some embodiments, a membrane may cover the chemistry. In use, the tail 2708 is transcutaneously received beneath a user's skin, and the chemistry included thereon helps facilitate analyte monitoring in the presence of bodily fluids.

The flag 2710 may comprise a generally planar surface having one or more sensor contacts 2714 (three shown in FIG. 27B) arranged thereon. The sensor contact(s) 2714 may be configured to align with a corresponding number of compliant carbon impregnated polymer modules (tops of which shown at 2720) encapsulated within the connector 2704.

The connector 2704 includes one or more hinges 2718 that enables the connector 2704 to move between open and closed states. The connector 2704 is depicted in FIGS. 27A-27B in the closed state, but can pivot to the open state to receive the flag 2710 and the compliant carbon impregnated polymer module(s) therein. The compliant carbon impregnated polymer module(s) provide electrical contacts 2720 (three shown) configured to provide conductive communication between the sensor 2616 and corresponding circuitry contacts provided within the electrical housing 2604 (FIGS. 26A-26B). The connector 2704 can be made of silicone rubber and may serve as a moisture barrier for the sensor 2616 when assembled in a compressed state and after application to a user's skin.

The sharp module 2614 includes the sharp 2618 and a sharp hub 2722 that carries the sharp 2618. The sharp 2618 includes an elongate shaft 2724 and a sharp tip 2726 at the distal end of the shaft 2724. The shaft 2724 may be configured to extend through the channel 2706 and extend distally from the plug 2702. Moreover, the shaft 2724 may include a hollow or recessed portion 2728 that at least partially circumscribes the tail 2708 of the sensor 2616. The sharp tip 2726 may be configured to penetrate the skin while carrying the tail 2708 to put the active chemistry present on the tail 2708 into contact with bodily fluids.

The sharp hub 2722 may include a hub small cylinder 2730 and a hub snap pawl 2732, each of which may be configured to help couple the plug assembly 2610 (and the entire sensor control device 2602) to the sensor applicator 102 (FIG. 1).

With specific reference to FIG. 27B, the preservation vial 2620 may comprise a generally cylindrical and elongate body 2734 having a first end 2736a and a second end 2736b opposite the first end 2736a. The first end 2736a may be open to provide access into an inner chamber 2738 defined within the body 2734. In contrast, the second end 2736b may be closed and may provide or otherwise define an enlarged head 2740. The enlarged head 2740 exhibits an outer diameter that is greater than the outer diameter of the remaining portions of the body 2734. In other embodiments, however, the enlarged head 2740 may be positioned at an intermediate location between the first and second ends 2736a,b.

Figure 27C:
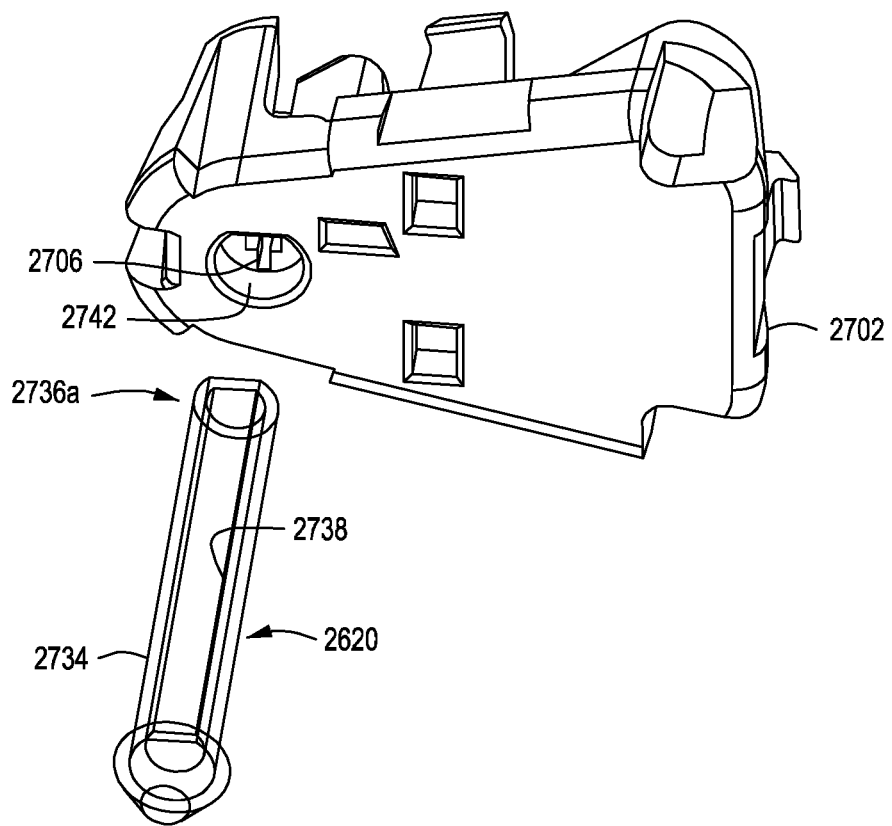
FIG. 27C is an exploded isometric bottom view of the plug and the preservation vial.

FIG. 27C is an exploded isometric bottom view of the plug 2702 and the preservation vial 2620. As illustrated, the plug 2702 may define an aperture 2742 configured to receive the preservation vial 2620 and, more particularly, the first end 2736a of the body 2734. The channel 2706 may terminate at the aperture 2742 such that components extending out of and distally from the channel 2706 will be received into the inner chamber 2738 when the preservation vial 2620 is coupled to the plug 2702.

The preservation vial 2620 may be removably coupled to the plug 2702 at the aperture 2742. In some embodiments, for example, the preservation vial 2620 may be received into the aperture 2742 via an interference or friction fit. In other embodiments, the preservation vial 2620 may be secured within the aperture 2742 with a frangible member (e.g., a shear ring) or substance that may be broken with minimal separation force. In such embodiments, for example, the preservation vial 2620 may be secured within the aperture 2742 with a tag (spot) of glue, a dab of wax, or the preservation vial 2620 may include an easily peeled off glue. As described below, the preservation vial 2620 may be separated from the plug 2702 prior to delivering the sensor control device 2602 (FIGS. 26A-26B) to the target monitoring location on the user's skin.

Referring again to FIGS. 27A and 27B, the inner chamber 2738 may be sized and otherwise configured to receive the tail 2708, a distal section of the shaft 2724, and the sharp tip 2726, collectively referred to as the "distal portions of the sensor 2616 and the sharp 2618." The inner chamber 2738 may be sealed or otherwise isolated to prevent substances that might adversely interact with the chemistry of the sensor 2616 from migrating into the inner chamber 2738.

More specifically, the inner chamber 2728 may be sealed to protect or isolate the distal portions of the sensor 2616 and the sharp 2618 during a gaseous chemical sterilization process since gases used during gaseous chemical sterilization can adversely affect the enzymes (and other sensor components, such as membrane coatings that regulate analyte influx) provided on the tail 2708.

In some embodiments, a seal 2744 (FIG. 27B) may provide a sealed barrier between the inner chamber 2738 and the exterior environment. In at least one embodiment, the seal 2744 may be arranged within the inner chamber 2738, but could alternatively be positioned external to the body 2734, without departing from the scope of the disclosure. The distal portions of the sensor 2616 and the sharp 2618 may penetrate the seal 2744 and extend into the inner chamber 2738, but the seal 2744 may maintain a sealed interface about the distal portions of the sensor 2616 and the sharp 2618 to prevent migration of contaminants into the inner chamber 2738. The seal 2744 may be made of, for example, a pliable elastomer or a wax.

In other embodiments (or in addition to the seal 2744), a sensor preservation fluid 2746 (FIG. 27B) may be present within the inner chamber 2738 and the distal portions of the sensor 2616 and the sharp 2618 may be immersed in or otherwise encapsulated by the preservation fluid 2746. The preservation fluid 2746 may generate a sealed interface that prevents sterilization gases from interacting with the enzymes provided on the tail 2708.

The plug assembly 2610 may be subjected to radiation sterilization to properly sterilize the sensor 2616 and the sharp 2618. Suitable radiation sterilization processes include, but are not limited to, electron beam (e-beam) irradiation, gamma ray irradiation, X-ray irradiation, or any combination thereof. In some embodiments, the plug assembly 2610 may be subjected to radiation sterilization prior to coupling the preservation vial 2620 to the plug 2702. In other embodiments, however, the plug assembly 2610 may sterilized after coupling the preservation vial 2620 to the plug 2702. In such embodiments, the body 2734 of the preservation vial 2620 and the preservation fluid 2746 may comprise materials and/or substances that permit the propagation of radiation therethrough to facilitate radiation sterilization of the distal portions of the sensor 2616 and the sharp 2618.

Suitable materials for the body 2734 include, but are not limited to, a non-magnetic metal (e.g., aluminum, copper, gold, silver, etc.), a thermoplastic, ceramic, rubber (e.g., ebonite), a composite material (e.g., fiberglass, carbon fiber reinforced polymer, etc.), an epoxy, or any combination thereof. In some embodiments, the material for the body 2734 may be transparent or translucent, but can otherwise be opaque, without departing from the scope of the disclosure.

The preservation fluid 2746 may comprise any inert and biocompatible fluid (i.e., liquid, gas, gel, wax, or any combination thereof) capable of encapsulating the distal portions of the sensor 2616 and the sharp 2618. In some embodiments, the preservation fluid 2746 may also permit the propagation of radiation therethrough. The preservation fluid 2746 may comprise a fluid that is insoluble with the chemicals involved in gaseous chemical sterilization. Suitable examples of the preservation fluid 2746 include, but are not limited to, silicone oil, mineral oil, a gel (e.g., petroleum jelly), a wax, fresh water, salt water, a synthetic fluid, glycerol, sorbitan esters, or any combination thereof. As will be appreciated, gels and fluids that are more viscous may be preferred so that the preservation fluid 2746 does not flow easily.

In some embodiments, the preservation fluid 2746 may include an anti-inflammatory agent, such as nitric oxide or another known anti-inflammatory agent. The anti-inflammatory agent may prove advantageous in minimizing local inflammatory response caused by penetration of the sharp 2618 and the sensor 2616 into the skin of the user. It has been observed that inflammation can affect the accuracy of glucose readings, and by including the anti-inflammatory agent the healing process may be accelerated, which may result in obtaining accurate readings more quickly.

Figure 28A:
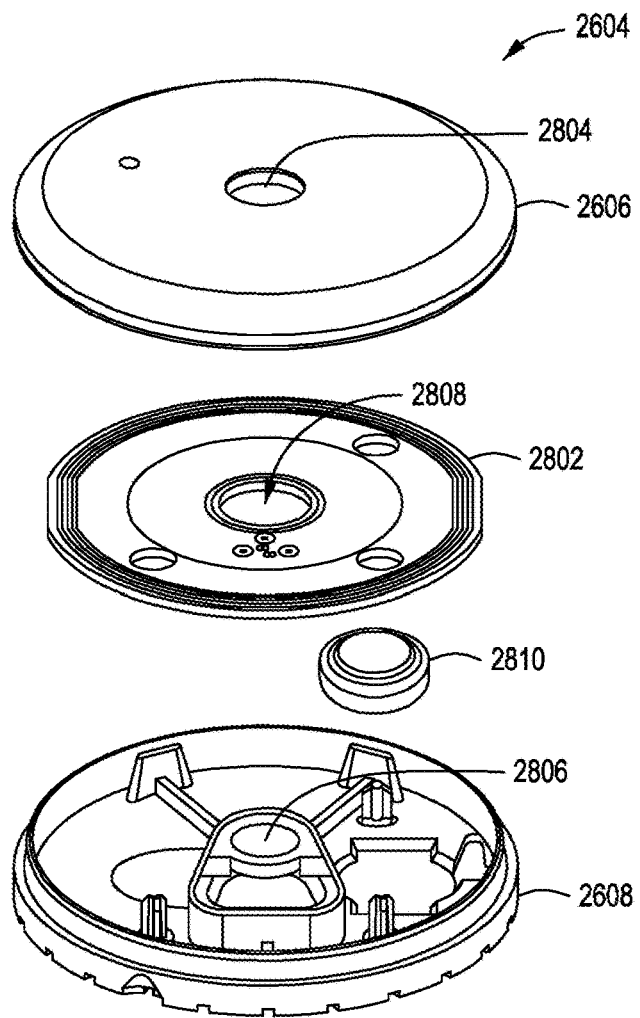
FIGS. 28A and 28B are exploded and bottom isometric views, respectively, of the electronics housing of FIGS. 26A-26B.
Figure 28B:
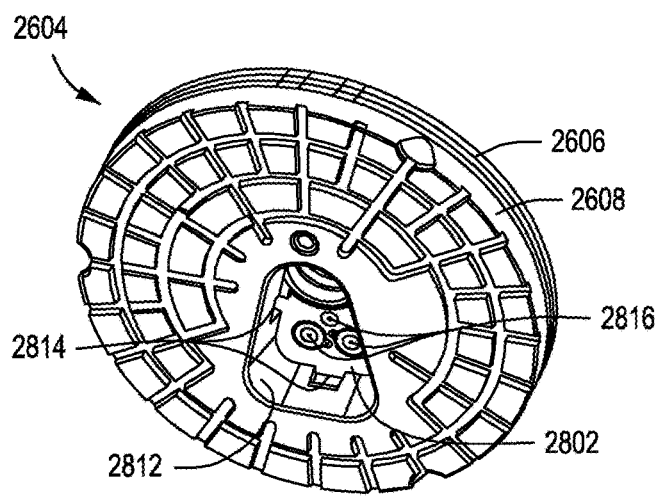

FIGS. 28A and 28B are exploded and bottom isometric views, respectively, of the electronics housing 2604, according to one or more embodiments. The shell 2606 and the mount 2608 operate as opposing clamshell halves that enclose or otherwise substantially encapsulate the various electronic components of the sensor control device 2602 (FIGS. 26A-26B).

A printed circuit board (PCB) 2802 may be positioned within the electronics housing 2604. A plurality of electronic modules (not shown) may be mounted to the PCB 2802 including, but not limited to, a data processing unit, resistors, transistors, capacitors, inductors, diodes, and switches. The data processing unit may comprise, for example, an application specific integrated circuit (ASIC) configured to implement one or more functions or routines associated with operation of the sensor control device 2602. More specifically, the data processing unit may be configured to perform data processing functions, where such functions may include but are not limited to, filtering and encoding of data signals, each of which corresponds to a sampled analyte level of the user. The data processing unit may also include or otherwise communicate with an antenna for communicating with the reader device 106 (FIG. 1).

As illustrated, the shell 2606, the mount 2608, and the PCB 2802 each define corresponding central apertures 2804, 2806, and 2808, respectively. When the electronics housing 2604 is assembled, the central apertures 2804, 2806, 2808 coaxially align to receive the plug assembly 2610 (FIGS. 27A-27B) therethrough. A battery 2810 may also be housed within the electronics housing 2604 and configured to power the sensor control device 2602.

In FIG. 28B, a plug receptacle 2812 may be defined in the bottom of the mount 2808 and provide a location where the plug assembly 2610 (FIGS. 27A-27B) may be received and coupled to the electronics housing 2604, and thereby fully assemble the sensor control device 2602 (FIG. 26A-3B). The profile of the plug 2702 (FIGS. 27A-27C) may match or be shaped in complementary fashion to the plug receptacle 2812, and the plug receptacle 2812 may provide one or more snap ledges 2814 (two shown) configured to interface with and receive the deflectable arms 2707 (FIGS. 27A-27B) of the plug 2702. The plug assembly 2610 is coupled to the electronics housing 2604 by advancing the plug 2702 into the plug receptacle 2812 and allowing the deflectable arms 2707 to lock into the corresponding snap ledges 2814. When the plug assembly 2610 (FIGS. 27A-27B) is properly coupled to the electronics housing 2604, one or more circuitry contacts 2816 (three shown) defined on the underside of the PCB 2802 may make conductive communication with the electrical contacts 2720 (FIGS. 27A-27B) of the connector 2704 (FIGS. 27A-27B).

Figure 29B:
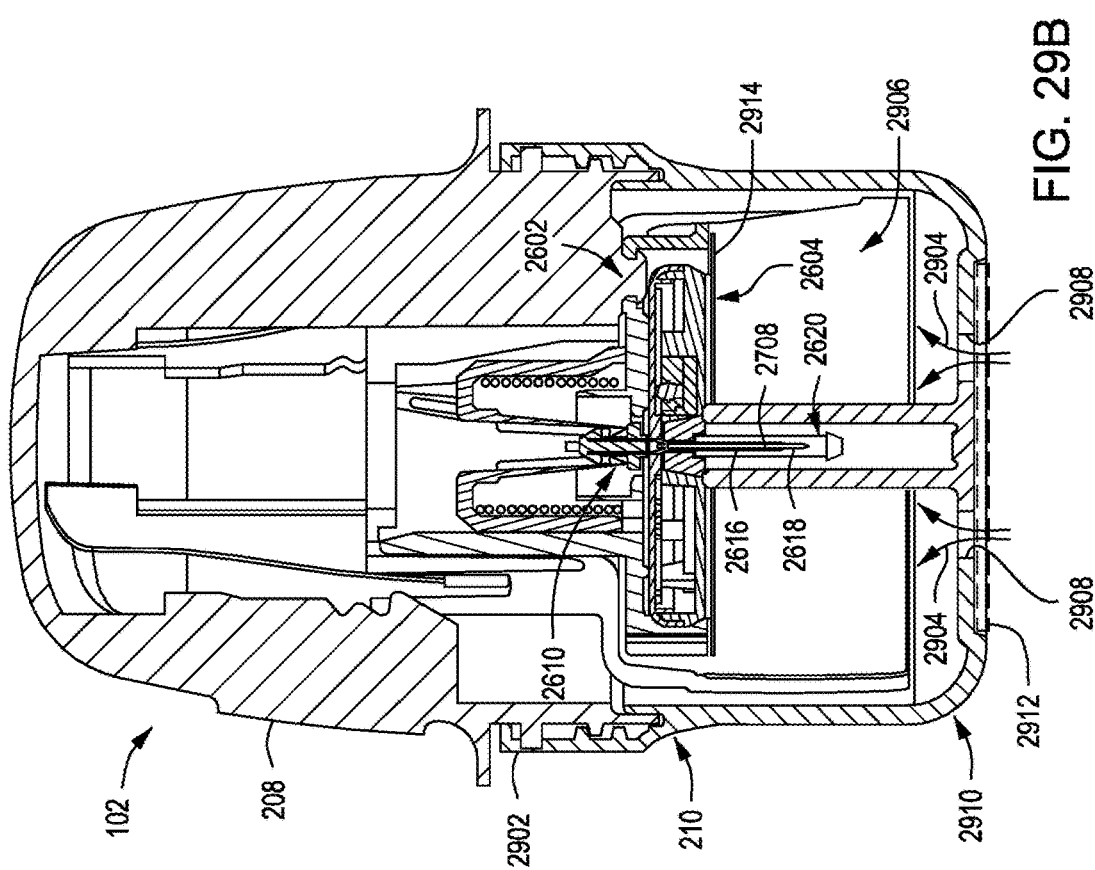
FIGS. 29A and 29B are side and cross-sectional side views, respectively, of the sensor applicator of FIG. 1 with the cap of FIG. 2B coupled thereto.
Figure 29A:
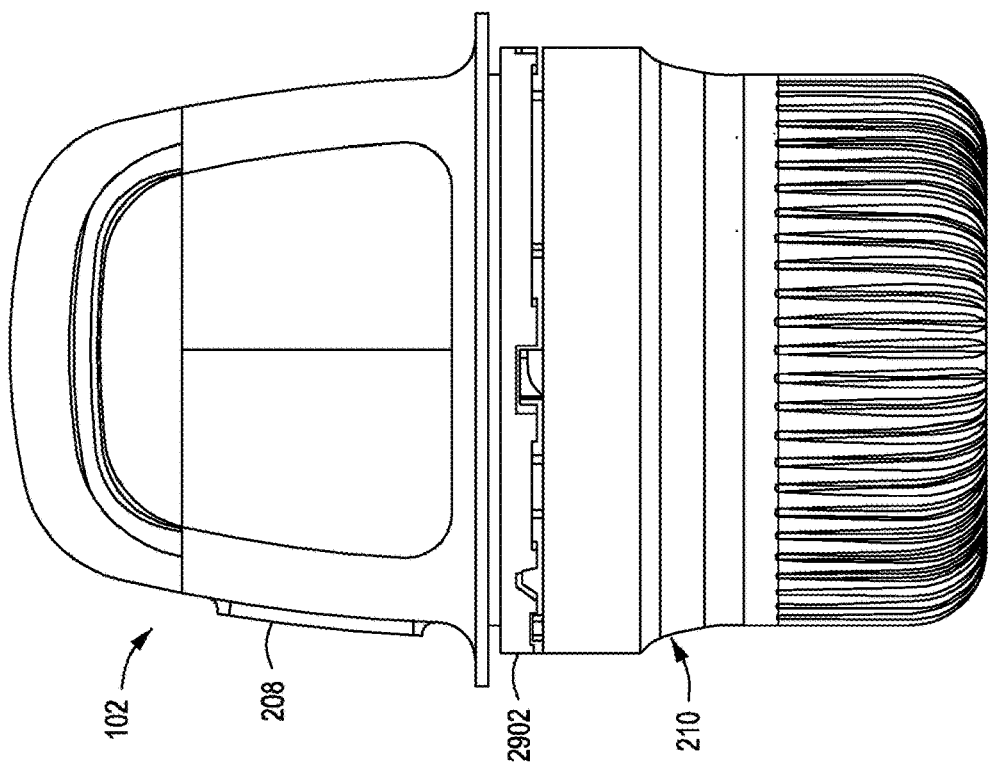

FIGS. 29A and 29B are side and cross-sectional side views, respectively, of an example embodiment of the sensor applicator 102 with the applicator cap 210 coupled thereto. More specifically, FIGS. 29A-29B depict how the sensor applicator 102 might be shipped to and received by a user. According to the present disclosure, and as seen in FIG.

29B, the sensor control device 2602 is already assembled and installed within the sensor applicator 102 prior to being delivered to the user.

As indicated above, prior to coupling the plug assembly 2610 to the electronics housing 2604, the plug assembly 2610 may be subjected to radiation sterilization to sterilize the distal portions of the sensor 2616 and the sharp 2618. Once properly sterilized, the plug assembly 2610 may then be coupled to the electronics housing 2604, as generally described above, and thereby form the fully assembled sensor control device 2602. The sensor control device 2602 may then be loaded into the sensor applicator 102, and the applicator cap 210 may be coupled to the sensor applicator 102. The applicator cap 210 may be threaded to the housing 208 and include a tamper ring 2902. Upon rotating (e.g., unscrewing) the applicator cap 210 relative to the housing 208, the tamper ring 2902 may shear and thereby free the applicator cap 210 from the sensor applicator 102.

According to the present disclosure, while loaded in the sensor applicator 102, the sensor control device 2602 may be subjected to gaseous chemical sterilization 2904 configured to sterilize the electronics housing 2604 and any other exposed portions of the sensor control device 2602. To accomplish this, a chemical may be injected into a sterilization chamber 2906 cooperatively defined by the sensor applicator 102 and the interconnected cap 210. In some applications, the chemical may be injected into the sterilization chamber 2906 via one or more vents 2908 defined in the applicator cap 210 at its proximal end 2910. Example chemicals that may be used for the gaseous chemical sterilization 2904 include, but are not limited to, ethylene oxide, vaporized hydrogen peroxide, and nitrogen oxide (e.g., nitrous oxide, nitrogen dioxide, etc.).

Since the distal portions of the sensor 2616 and the sharp 2618 are sealed within the preservation vial 2620, the chemicals used during the gaseous chemical sterilization process do not interact with the enzymes, chemistry or biologics provided on the tail 2708.

Once a desired sterility assurance level has been achieved within the sterilization chamber 2906, the gaseous solution is removed and the sterilization chamber 2906 is aerated. Aeration may be achieved by a series of vacuums and subsequently circulating nitrogen gas or filtered air through the sterilization chamber 2906. Once the sterilization chamber 2906 is properly aerated, the vents 2908 may be occluded with a seal 2912 (shown in dashed lines).

In some embodiments, the seal 2912 may comprise two or more layers of different materials. The first layer may be made of a synthetic material (e.g., a flash-spun high-density polyethylene fiber), such as Tyvek® available from DuPont®. Tyvek® is highly durable and puncture resistant and allows the permeation of vapors. The Tyvek® layer can be applied before the gaseous chemical sterilization process, and following the gaseous chemical sterilization process, a foil or other vapor and moisture resistant material layer may be sealed (e.g., heat sealed) over the Tyvek® layer to prevent the ingress of contaminants and moisture into the sterilization chamber 2906. In other embodiments, the seal 2912 may comprise only a single protective layer applied to the applicator cap 210. In such embodiments, the single layer is gas permeable for the sterilization process, but is also capable of protection against moisture and other harmful elements once the sterilization process is complete.

With the seal 2912 in place, the applicator cap 210 provides a barrier against outside contamination, and thereby maintains a sterile environment for the assembled sensor control device 2602 until the user removes (un-threads) the applicator cap 210. The applicator cap 210 may also create a dust-free environment during shipping and storage that prevents an adhesive patch 2914 used to secure the sensor control device 2602 to the user's skin from becoming dirty.

Figure 30:
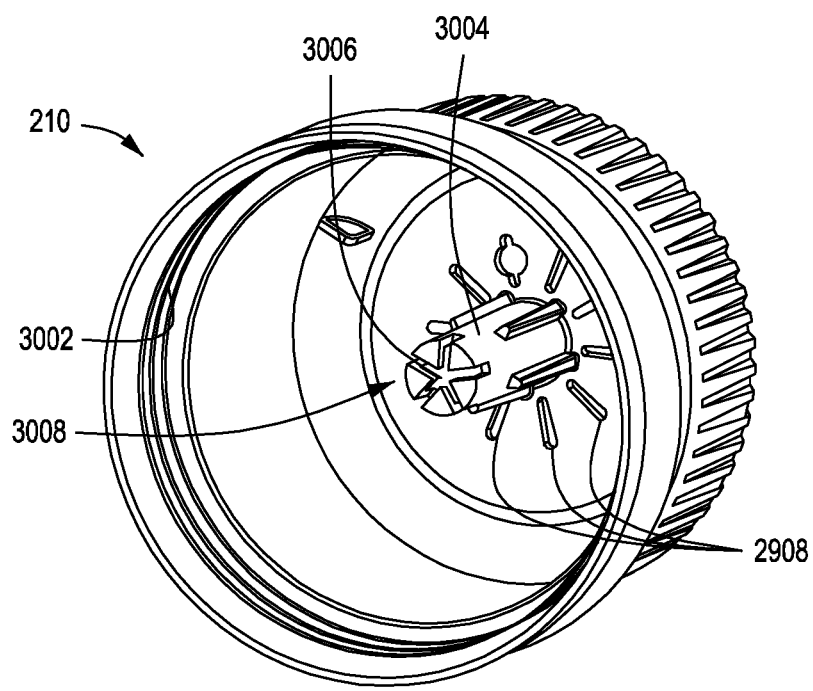
FIG. 30 is a perspective view of an example embodiment of the cap of FIGS. 29A-29B.

FIG. 30 is a perspective view of an example embodiment of the applicator cap 210, according to the present disclosure. As illustrated, the applicator cap 210 has a generally circular cross-section and defines a series of threads 7302 used to couple the applicator cap 210 to the sensor applicator 102 (FIGS. 29A and 29B). The vents 2908 are also visible in the bottom of the applicator cap 210.

The applicator cap 210 may further provide and otherwise define a cap post 3004 centrally located within the interior of the applicator cap 210 and extending proximally from the bottom thereof. The cap post 3004 may be configured to help support the sensor control device 2602 while contained within the sensor applicator 102 (FIGS. 29A-29B). Moreover, the cap post 3004 may define an opening 3006 configured to receive the preservation vial 2620 as the applicator cap 210 is coupled to the sensor applicator 102.

In some embodiments, the opening 3006 to the cap post 3004 may include one or more compliant features 3008 that are expandable or flexible to enable the preservation vial 2620 to pass therethrough. In some embodiments, for example, the compliant feature(s) 3008 may comprise a collet-type device that includes a plurality of compliant fingers configured to flex radially outward to receive the preservation vial 2620. In other embodiments, however, the compliant feature(s) 3008 may comprise an elastomer or another type of compliant material configured to expand radially to receive the preservation vial 2620.

Figure 31:
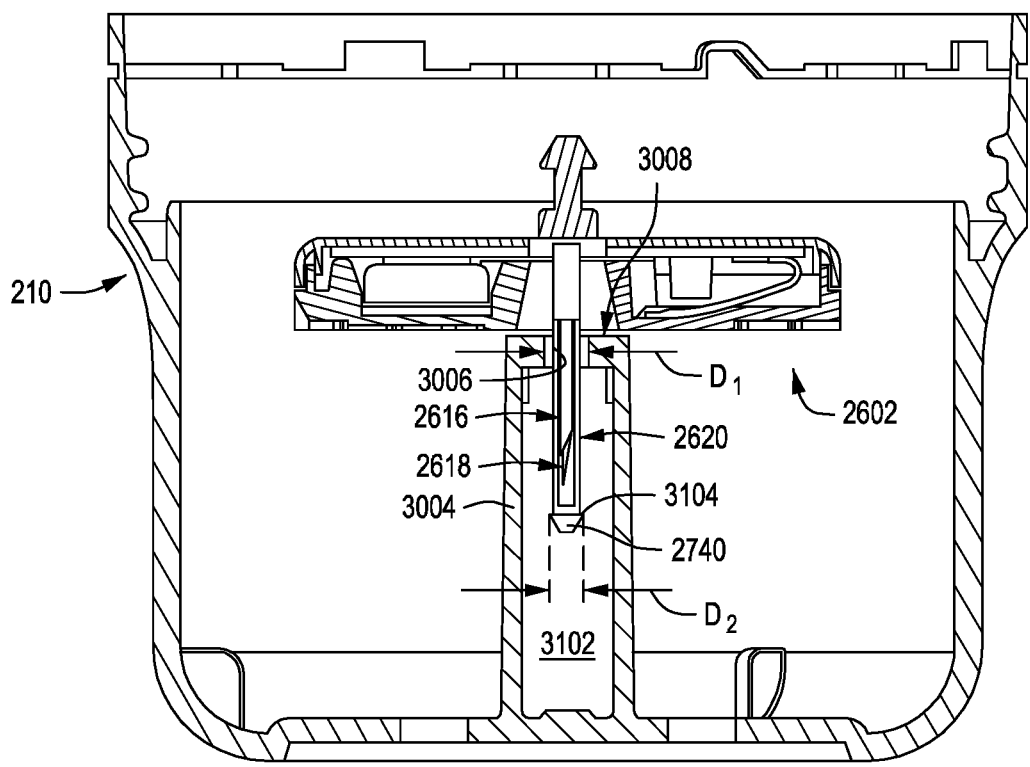
FIG. 31 is a cross-sectional side view of the sensor control device positioned within the cap.

FIG. 31 is a cross-sectional side view of the sensor control device 2602 positioned within the applicator cap 210, according to one or more embodiments. As illustrated, the cap post 3004 defines a post chamber 3102 configured to receive the preservation vial 2620. The opening 3006 to the cap post 3004 provides access into the post chamber 3102 and exhibits a first diameter $D_1$. In contrast, the enlarged head 2740 of the preservation vial 2620 exhibits a second diameter $D_2$ that is larger than the first diameter $D_1$ and greater than the outer diameter of the remaining portions of the preservation vial 2620. Accordingly, as the preservation vial 2620 is extended into the post chamber 3102, the compliant feature(s) 3008 of the opening 3006 may flex (expand) radially outward to receive the enlarged head 2740.

In some embodiments, the enlarged head 2740 may provide or otherwise define an angled outer surface that helps bias the compliant feature(s) 3008 radially outward. The enlarged head 2740, however, may also define an upper shoulder 3104 that prevents the preservation vial 2620 from reversing out of the post chamber 3102. More specifically, the shoulder 3104 may comprise a sharp surface at the second diameter $D_2$ that will engage but not urge the compliant feature(s) 3008 to flex radially outward in the reverse direction.

Once the enlarged head 2740 bypasses the opening 3006, the compliant feature(s) 3008 flex back to (or towards) their natural state. In some embodiments, the compliant feature(s) 3008 may engage the outer surface of the preservation vial 2620, but may nonetheless allow the applicator cap 210 to rotate relative to the preservation vial 2620. Accordingly, when a user removes the applicator cap 210 by rotating the applicator cap 210 relative to the sensor applicator 102 (FIGS. 29A-29B), the preservation vial 2620 may remain stationary relative to the cap post 3004.

Upon removing the applicator cap 210 from the sensor applicator 102, and thereby also separating the sensor control device 2602 from the applicator cap 210, the shoulder 3104 defined on the enlarged head 2740 will engage the compliant feature(s) 3008 at the opening 3006. Because the diameter of the shoulder 3104 is greater than the diameter of the opening 3006, the shoulder 3104 will bind against the compliant feature(s) 3008 and thereby separate the preservation vial 2620 from the sensor control device 2602, which exposes the distal portions of the sensor 2616 and the sharp 2618. Accordingly, the compliant feature(s) 3008 may prevent the enlarged head 2740 from exiting the post chamber 3102 via the opening 3006 upon separating the applicator cap 210 from the sensor applicator 102 and the sensor control device 2602. The separated preservation vial 2620 will fall into and remain within the post chamber 3102.

In some embodiments, instead of the opening 3006 including the compliant feature(s) 3008, as generally described above, the opening 3006 may alternatively be threaded. In such embodiments, a small portion near the distal end of the preservation vial 2620 may also be threaded and configured to threadably engage the threads of the opening 3006. The preservation vial 2620 may be received within the post chamber 3102 via threaded rotation. Upon removing the applicator cap 210 from the sensor applicator 102, however, the opposing threads on the opening 3006 and the preservation vial 2620 bind and the preservation vial 2620 may be separated from the sensor control device 2602.

Accordingly, there are several advantages to incorporating the sensor control device 2602 into an analyte monitoring system (e.g., the analyte monitoring system 100 of FIG. 1). Since the sensor control device 2602 is finally assembled in a controlled environment, tolerances can be reduced or eliminated altogether, which allows the sensor control device 2602 to be thin and small. Moreover, since the sensor control device 2602 is finally assembled in a controlled environment, a thorough pre-test of the sensor control device 2602 can be undertaken at the factory, thus fully testing the sensor unit prior to packaging for final delivery.

Embodiments disclosed herein include:

L. A sensor control device that includes an electronics housing, a plug assembly matable with the electronics housing and including a sensor module that has a sensor and a sharp module that has a sharp, and a preservation vial coupled to the plug assembly and defining an inner chamber, wherein distal portions of the sensor and the sharp are receivable within the inner chamber and isolated within the inner chamber from gaseous chemical sterilization.

M. An analyte monitoring system that includes a sensor applicator, a sensor control device positioned within the sensor applicator and including an electronics housing, a plug assembly coupled to the electronics housing and including a sensor module that has a sensor and a sharp module that has a sharp, and a preservation vial coupled to the plug assembly and defining an inner chamber. The analyte monitoring system further including a cap coupled to the sensor applicator to provide a barrier that seals the sensor control device within the sensor applicator, wherein distal portions of the sensor and the sharp are received within the inner chamber and isolated within the inner chamber from gaseous chemical sterilization.

N. A method of preparing an analyte monitoring system including loading a sensor control device into a sensor applicator, the sensor control device including an electronics housing, a plug assembly matable with the electronics housing and including a sensor module that has a sensor and a sharp module that has a sharp, and a preservation vial coupled to the plug assembly and defining an inner chamber. The method further including securing a cap to the sensor applicator and thereby providing a barrier that seals the sensor control device within the sensor applicator, sterilizing the sensor control device with gaseous chemical sterilization while the sensor control device is positioned within the sensor applicator, and isolating distal portions of the sensor and the sharp received within the inner chamber from the gaseous chemical sterilization.

Each of embodiments L, M, and N may have one or more of the following additional elements in any combination: Element 1: wherein the sensor module further includes a plug and the preservation vial is removably coupled to the plug. Element 2: wherein the preservation vial provides an enlarged head and a diameter of the enlarged head is greater than a diameter of remaining portions of the preservation vial. Element 3: further comprising a seal that provides a sealed barrier between the inner chamber and exterior to the inner chamber, wherein the distal portions of the sensor and the sharp penetrate the seal and extend into the inner chamber. Element 4: further comprising a preservation fluid within the inner chamber that isolates the distal portions of the sensor and the sharp from the gaseous chemical sterilization. Element 5: wherein the distal portions of the sensor and the sharp are at least partially immersed in the preservation fluid. Element 6: wherein the preservation fluid comprises an inert and biocompatible fluid selected from the group consisting of silicone oil, mineral oil, a gel, a wax, fresh water, salt water, a synthetic fluid, glycerol, sorbitan esters, and any combination thereof. Element 7: wherein the preservation fluid includes an anti-inflammatory agent.

Element 8: wherein the cap provides a cap post that defines a post chamber and an opening that receives an enlarged head of the preservation vial into the post chamber. Element 9: wherein the opening includes one or more compliant features that flex radially outward to receive the enlarged head. Element 10: wherein the one or more compliant features comprise a plurality of compliant fingers. Element 11: wherein the one or more compliant features prevent the enlarged head from exiting the post chamber through the opening upon separating the cap from the sensor applicator and the sensor control device. Element 12: wherein the cap is rotatable relative to the preservation vial when the preservation vial is received within the post chamber. Element 13: further comprising a preservation fluid within the inner chamber that isolates the distal portions of the sensor and the sharp from the gaseous chemical sterilization.

Element 14: wherein loading the sensor control device into a sensor applicator is preceded by assembling the plug assembly, coupling the preservation vial to the plug assembly such that the distal portions of the sensor and the sharp are received within the inner chamber, and coupling the plug assembly to an electronics housing and thereby providing the sensor control device. Element 15: wherein coupling the preservation vial to the plug assembly is preceded by sterilizing the plug assembly with radiation sterilization. Element 16: wherein isolating the distal portions of the sensor and the sharp from the gaseous chemical sterilization comprises at least partially immersing the distal portions of the sensor and the sharp within a preservation fluid present within the inner chamber. Element 17: wherein the cap provides a cap post that defines a post chamber having one or more compliant features arranged at an opening to the post chamber, and wherein securing the cap to the sensor applicator comprises receiving an enlarged head of the preservation vial into the post chamber via the opening, and flexing the one or more compliant features radially outward to receive the enlarged head.

By way of non-limiting example, exemplary combinations applicable to L, M, and N include: Element 4 with Element 5; Element 4 with Element 6; Element 4 with Element 7; Element 8 with Element 9; Element 9 with Element 10; Element 9 with Element 17; Element 8 with Element 12; Element 8 with Element 13; and Element 14 with Element 15.

Isolating One-Piece Sensor Design with Focused E-Beam Sterilization

Figure 32A:
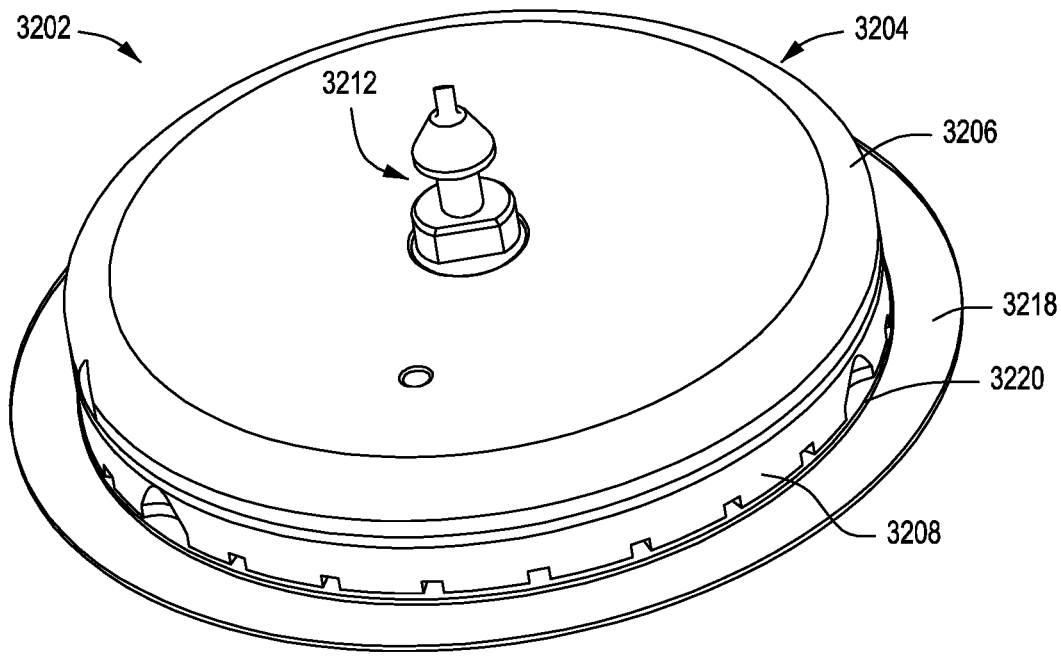
FIGS. 32A and 32B are isometric and side views, respectively, of an example sensor control device.
Figure 32B:
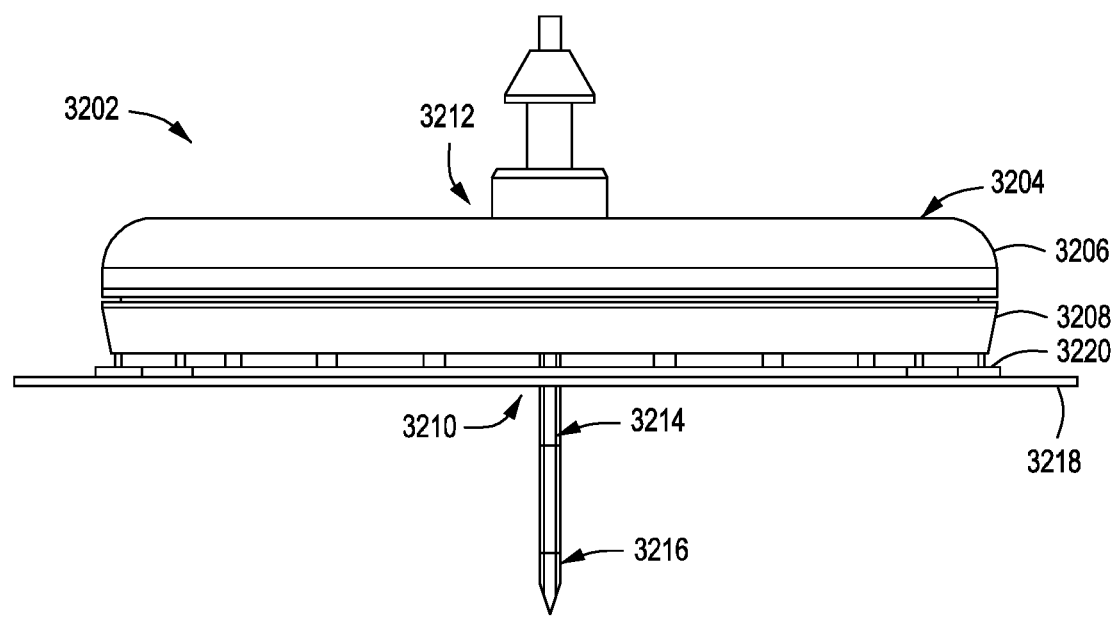

FIGS. 32A and 32B are isometric and side views, respectively, of an example sensor control device 3202, according to one or more embodiments of the present disclosure. The sensor control device 3202 (alternately referred to as a "puck") may be similar in some respects to the sensor control device 104 of FIG. 1 and therefore may be best understood with reference thereto. In some applications, the sensor control device 3202 may replace the sensor control device 104 of FIG. 1 and, therefore, may be used in conjunction with the sensor applicator 102 (FIG. 1), which delivers the sensor control device 3202 to a target monitoring location on a user's skin.

The sensor control device 3202, however, may be incorporated into a one-piece system architecture in contrast to the sensor control device 104 of FIG. 1. Unlike the two-piece architecture, for example, a user is not required to open multiple packages and finally assemble the sensor control device 3202 before use. Rather, upon receipt by the user, the sensor control device 3202 is already fully assembled and properly positioned within the sensor applicator 102 (FIG. 1). To use the sensor control device 3202, the user need only open one barrier (e.g., removing the applicator cap 210 of FIG. 2B) before promptly delivering the sensor control device 3202 to the target monitoring location.

As illustrated, the sensor control device 3202 includes an electronics housing 3204 that is generally disc-shaped and may have a circular cross-section. In other embodiments, however, the electronics housing 3204 may exhibit other cross-sectional shapes, such as ovoid or polygonal, without departing from the scope of the disclosure. The electronics housing 3204 may be configured to house or otherwise contain various electrical components used to operate the sensor control device 3202.

The electronics housing 3204 may include a shell 3206 and a mount 3208 that is matable with the shell 3206. The shell 3206 may be secured to the mount 3208 via a variety of ways, such as a snap fit engagement, an interference fit, sonic (or ultrasonic) welding, using one or more mechanical fasteners (e.g., screws), or any combination thereof. In some embodiments, the interface between the shell 3206 and the mount 3208 may be sealed. In such embodiments, a gasket or other type of seal material may be positioned or applied at or near the outer diameter (periphery) of the shell 3206 and the mount 3208. Securing the shell 3206 to the mount 3208 may compress the seal material and thereby generate a sealed interface. In at least one embodiment, an adhesive may be applied to the outer diameter (periphery) of one or both of the shell 3206 and the mount 3208, and the adhesive may not only secure the shell 3206 to the mount 3208 but may also seal the interface.

In embodiments where a sealed interface is created between the shell 3206 and the mount 3208, the interior of the electronics housing 3204 may be effectively isolated from outside contamination between the two components. In such embodiments, if the sensor control device 3202 is assembled in a controlled and sterile environment, there may be no need to sterilize the internal electrical components (e.g., via gaseous chemical sterilization). Rather, the sealed engagement may provide a sufficient sterile barrier for the assembled electronics housing 3204.

The sensor control device 3202 may further include a sensor module 3210 (partially visible in FIG. 32B) and a sharp module 3212 (partially visible). The sensor and sharp modules 3210, 3212 may be interconnectable and coupled to the electronics housing 3204. The sensor module 3210 may be configured to carry and otherwise include a sensor 3214 (FIG. 32B), and the sharp module 3212 may be configured to carry and otherwise include a sharp 3216 (FIG. 32B) used to help deliver the sensor 3214 transcutaneously under a user's skin during application of the sensor control device 3202.

As illustrated in FIG. 32B, corresponding portions of the sensor 3214 and the sharp 3216 extend from the electronics housing 3204 and, more particularly, from the bottom of the mount 3208. The exposed portion of the sensor 3214 may be received within a hollow or recessed portion of the sharp 3216. The remaining portion(s) of the sensor 3214 is/are positioned within the interior of the electronics housing 3204.

An adhesive patch 3218 may be positioned on and otherwise attached to the underside of the mount 3208. Similar to the adhesive patch 108 of FIG. 1, the adhesive patch 3218 may be configured to secure and maintain the sensor control device 3202 in position on the user's skin during operation. In some embodiments, a transfer adhesive 3220 may interpose the adhesive patch 3218 and the bottom of the mount 3208. The transfer adhesive 3220 may help facilitate the assembly process of the sensor control device 3202.

Figure 33A:
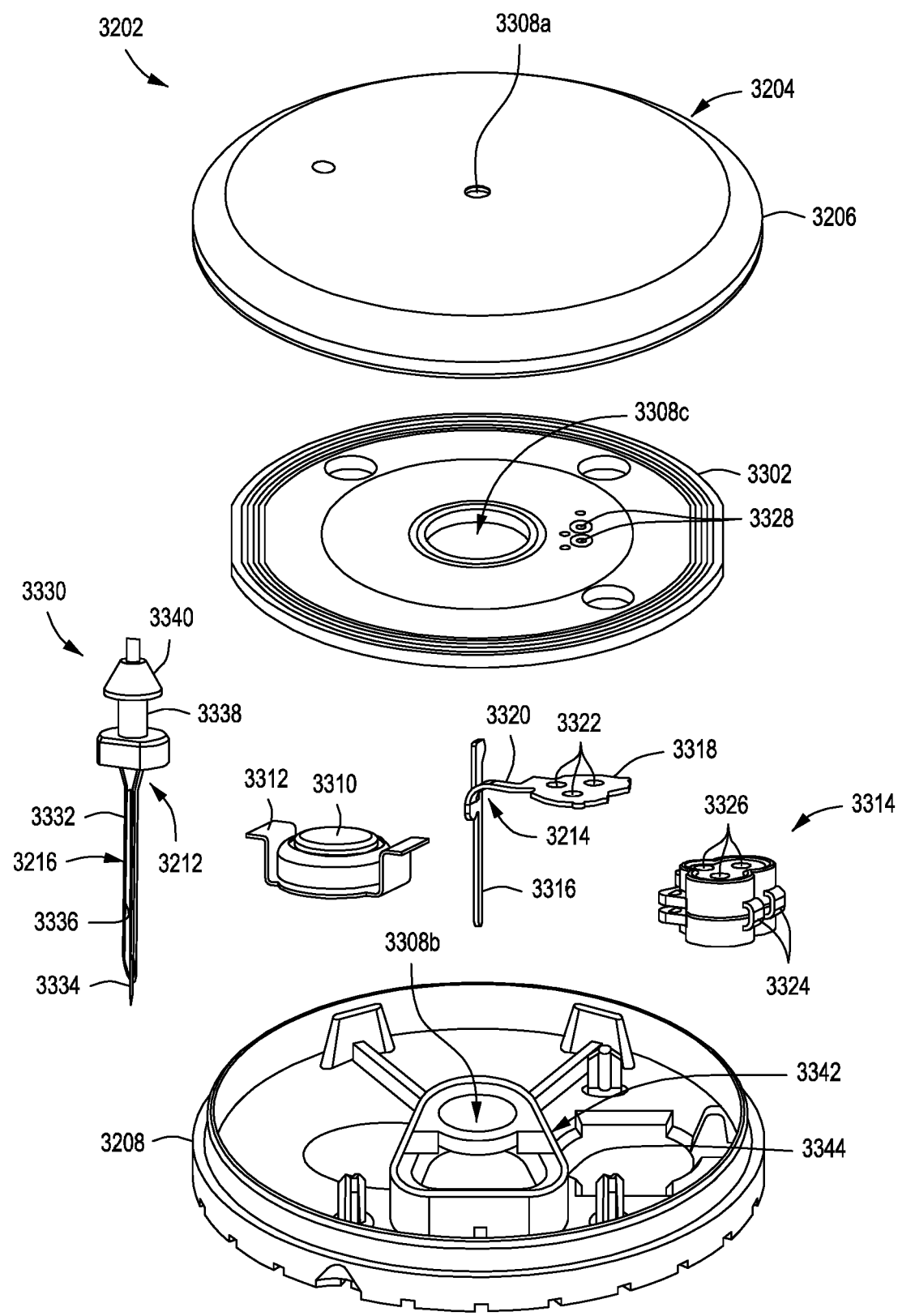
FIGS. 33A and 33B are exploded perspective top and bottom views, respectively, of the sensor control device of FIGS. 32A-32B.
Figure 33B:
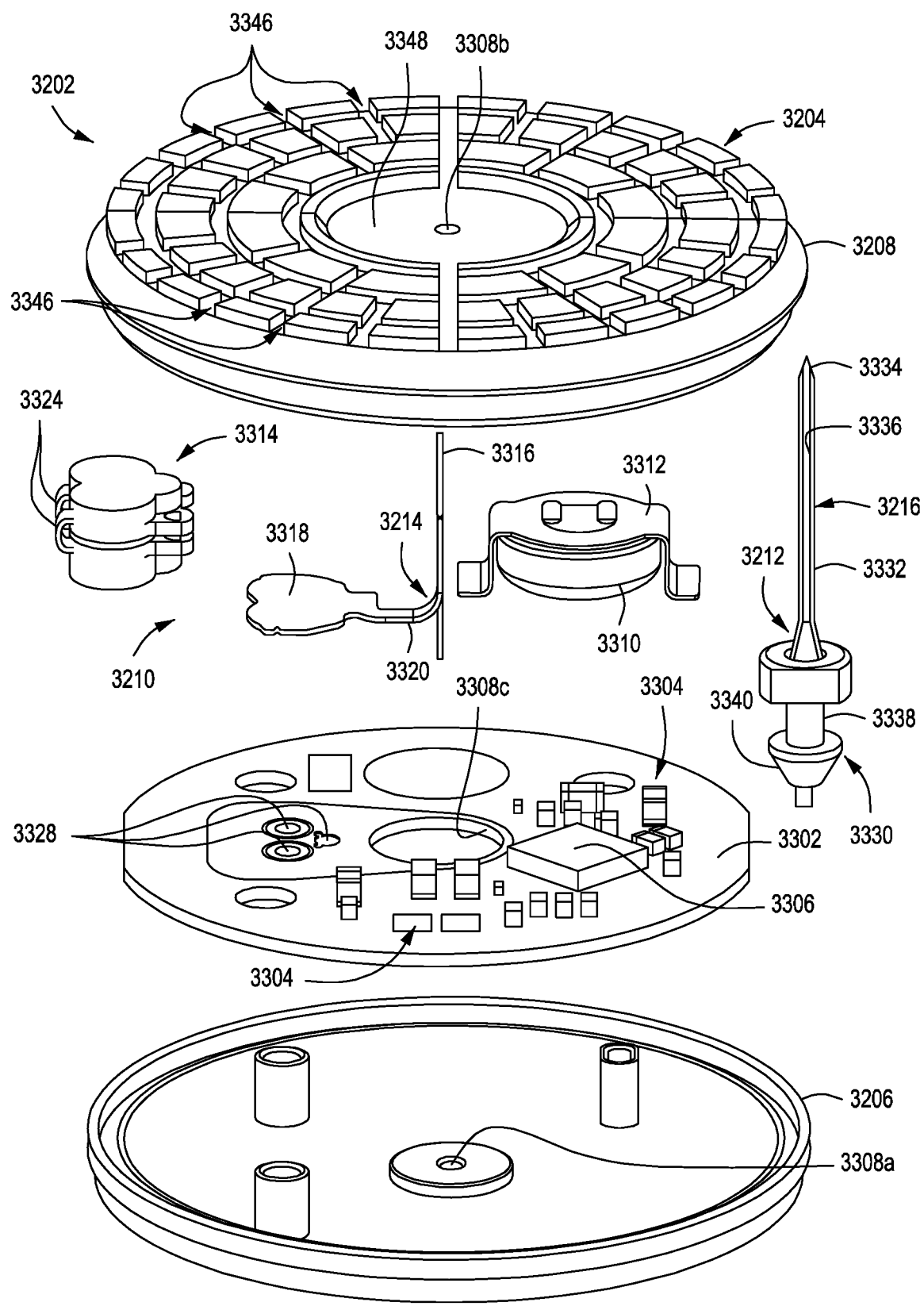

FIGS. 33A and 33B are exploded perspective top and bottom views, respectively, of the sensor control device 3202, according to one or more embodiments. As illustrated, the shell 3206 and the mount 3208 of the electronics housing 3204 operate as opposing clamshell halves that enclose or otherwise substantially encapsulate the various electronic components of the sensor control device 3202.

A printed circuit board (PCB) 3302 may be positioned within the electronics housing 3204. As shown in FIG. 33B, a plurality of electronic modules 3304 may be mounted to the underside of the PCB 3302. Example electronic modules 3304 include, but are not limited to, resistors, transistors, capacitors, inductors, diodes, and switches. A data processing unit 3306 (FIG. 33B) may also be mounted to the PCB 3302 and may comprise, for example, an application specific integrated circuit (ASIC) configured to implement one or more functions or routines associated with operation of the sensor control device 3202. More specifically, the data processing unit 3306 may be configured to perform data processing functions, such as filtering and encoding of data signals, each of which corresponds to a sampled analyte level of the user. The data processing unit 3306 may also include or otherwise communicate with an antenna for communicating with the reader device 106 (FIG. 1).

As illustrated, the shell 3206, the mount 3208, and the PCB 3302 each define corresponding central apertures 3308a, 3308b, 3308c, respectively. When the sensor control device 3202 is assembled, the central apertures 3308a-c coaxially align to receive portions of the sensor and sharp modules 3210, 3212 therethrough.

A battery 3310 and a corresponding battery mount 3312 may also be housed within the electronics housing 3204. The battery 3310 may be configured to power the sensor control device 3202.

The sensor module 3210 may include the sensor 3214 and a connector 3314. The sensor 3214 includes a tail 3316, a flag 3318, and a neck 3320 that interconnects the tail 3316 and the flag 3318. The tail 3316 may be configured to extend through the central aperture 3308b defined in the mount 3208 and extend distally from the underside thereof. The tail 3316 includes an enzyme or other chemistry or biologic and, in some embodiments, a membrane may cover the chemistry. In use, the tail 3316 is transcutaneously received beneath a user's skin, and the chemistry included thereon helps facilitate analyte monitoring in the presence of bodily fluids.

The flag 3318 may comprise a generally planar surface having one or more sensor contacts 3322 (three shown in FIG. 33A) disposed thereon. The flag 3318 may be configured to be received within the connector 3314 where the sensor contact(s) 3322 align with a corresponding number of compliant carbon impregnated polymer modules (not shown) encapsulated within the connector 3314.

The connector 3314 includes one or more hinges 3324 that enables the connector 3314 to pivot between open and closed states. The connector 3314 is depicted in FIGS. 33A-33B in the closed state, but can transition to the open state to receive the flag 3318 and the compliant carbon impregnated polymer module(s) therein. The compliant carbon impregnated polymer module(s) provide electrical contacts 3326 (three shown in FIG. 33A) configured to provide conductive communication between the sensor 3214 and corresponding circuitry contacts 3328 provided on the PCB 3302. When the sensor module 3210 is properly coupled to the electronics housing 3204, the circuitry contacts 3328 make conductive communication with the electrical contacts 3326 of the connector 3314. The connector 3314 can be made of silicone rubber and may serve as a moisture barrier for the sensor 3214.

The sharp module 3212 includes the sharp 3216 and a sharp hub 3330 that carries the sharp 3216. The sharp 3216 includes an elongate shaft 3332 and a sharp tip 3334 at the distal end of the shaft 3332. The shaft 3332 may be configured to extend through each of the coaxially aligned central apertures 3308a-c and extend distally from the bottom of the mount 3208. Moreover, the shaft 3332 may include a hollow or recessed portion 3336 that at least partially circumscribes the tail 3316 of the sensor 3214. The sharp tip 3334 may be configured to penetrate the skin while carrying the tail 3316 to put the active chemistry of the tail 3316 into contact with bodily fluids.

The sharp hub 3330 may include a hub small cylinder 3338 and a hub snap pawl 3340, each of which may be configured to help couple the sensor control device 3202 to the sensor applicator 102 (FIG. 1).

Referring specifically to FIG. 33A, in some embodiments the sensor module 3210 may be at least partially received within a sensor mount pocket 3342 included within the electronics housing 3204. In some embodiments, the sensor mount pocket 3342 may comprise a separate structure, but may alternatively form an integral part or extension of the mount 3208. The sensor mount pocket 3342 may be shaped and otherwise configured to receive and seat the sensor 3214 and the connector 3314. As illustrated, the sensor mount pocket 3342 defines an outer periphery 3344 that generally circumscribes the region where the sensor 3214 and the connector 3314 are to be received. In at least one embodiment, the outer periphery 3344 may be sealed to the underside of the PCB 3302 when the electronics housing 3204 is fully assembled. In such embodiments, a gasket (e.g., an O-ring or the like), an adhesive, or another type of seal material may be applied (arranged) at the outer periphery 3344 and may operate to seal the interface between the sensor mount pocket 3342 and the PCB 3302.

Sealing the interface between the sensor mount pocket 3342 and the underside of the PCB 3302 may help create or define a sealed zone or region within the electronics housing 3204. The sealed region may prove advantageous in helping to isolate (protect) the tail 3316 of the sensor 3214 from potentially harmful sterilization gases used during gaseous chemical sterilization.

Referring specifically to FIG. 33B, a plurality of channels or grooves 3346 may be provided or otherwise defined on the bottom of the mount 3208. As illustrated, the grooves 3346 may form a plurality of concentric rings in combination with a plurality of radially extending channels. The adhesive patch 3218 (FIGS. 32A-32B) may be attached to the underside of the mount 3208, and, in some embodiments, the transfer adhesive 3220 (FIGS. 32A-32B) may interpose the adhesive patch 3218 and the bottom of the mount 3208. The grooves 3346 may prove advantageous in promoting the egress of moisture away from the center of the electronics housing 3204 beneath the adhesive patch 3218.

In some embodiments, a cap post seal interface 3348 may be defined on the bottom of the mount 3208 at the center of the mount 3208. As illustrated, the cap post seal interface 3348 may comprise a substantially flat portion of the bottom of the mount 3208. The second central aperture 3308b is defined at the center of the cap post seal interface 3348 and the grooves 3346 may circumscribe the cap post seal interface 3348. The cap post seal interface 3348 may provide a sealing surface that may help isolate (protect) the tail 3316 of the sensor 3214 from potentially harmful sterilization gases used during gaseous chemical sterilization.

Figure 34B:
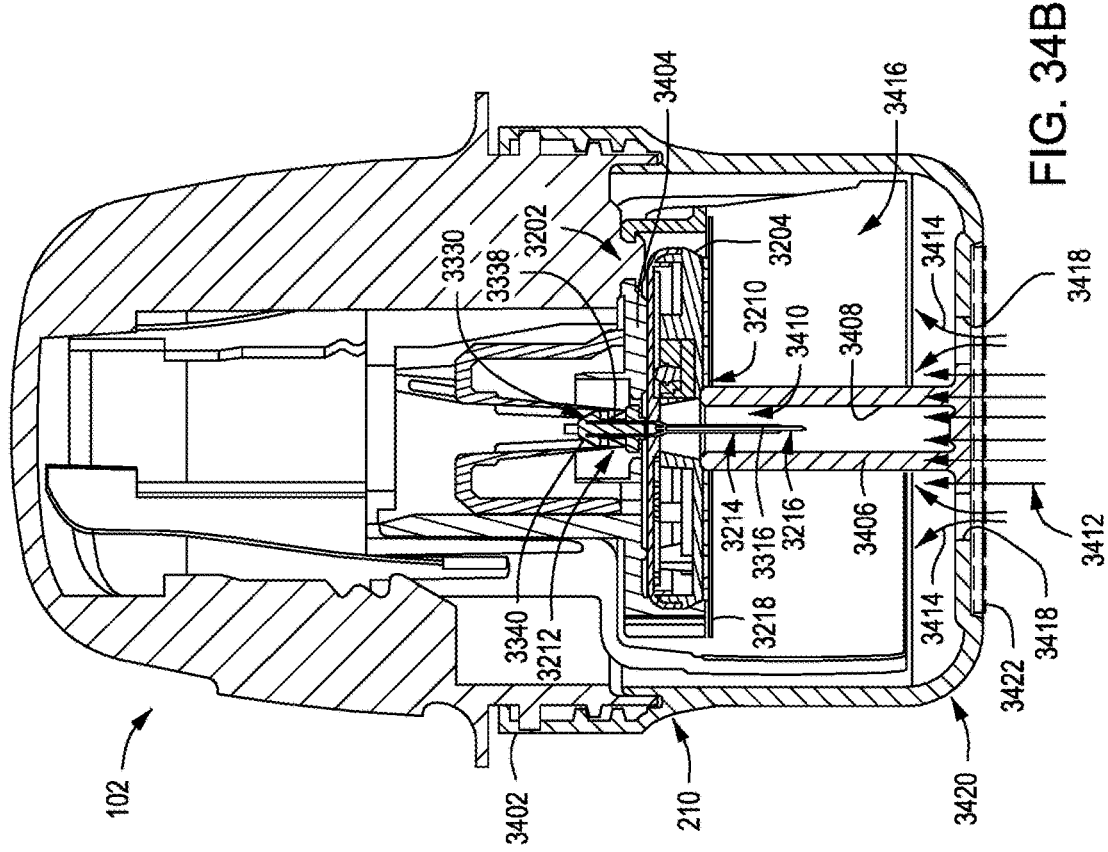
FIGS. 34A and 34B are side and cross-sectional side views, respectively, of the sensor applicator of FIG. 1 with the cap of FIG. 2B coupled thereto.
Figure 34A:
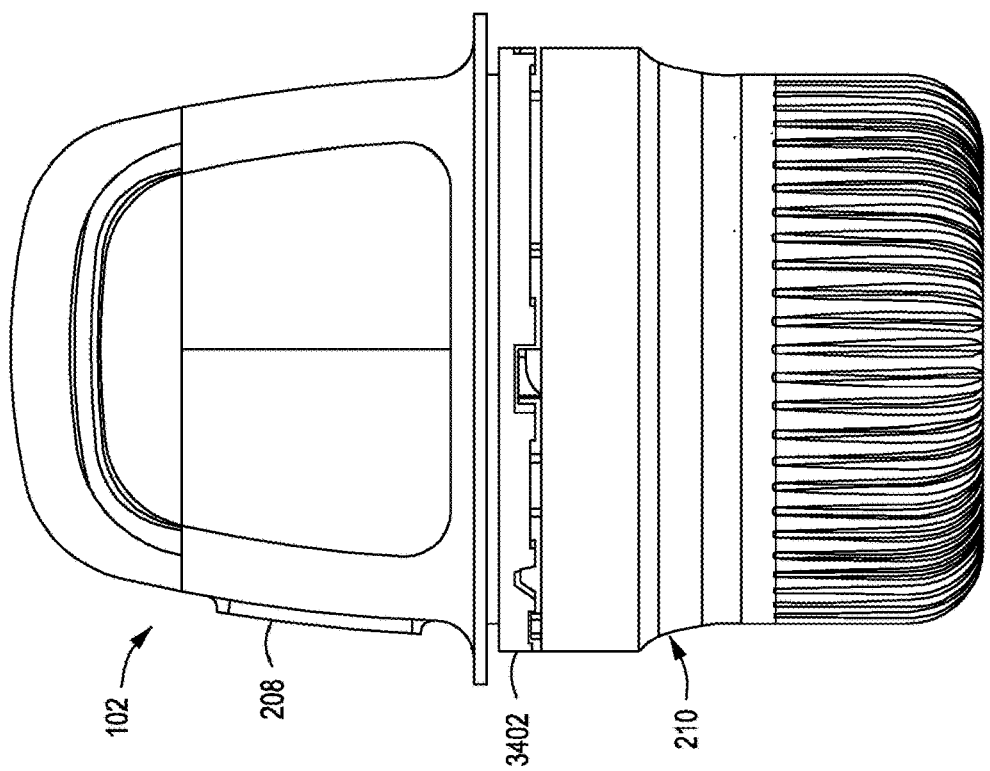

FIGS. 34A and 34B are side and cross-sectional side views, respectively, of the sensor applicator 102 with the applicator cap 210 coupled thereto. More specifically, FIGS. 34A-34B depict how the sensor applicator 102 might be shipped to and received by a user. According to the present disclosure, and as seen in FIG. 34B, the sensor control device 3202 is already assembled and installed within the sensor applicator 102 prior to being delivered to the user. The applicator cap 210 may be threaded to the housing 208 and include a tamper ring 3402. Upon rotating (e.g., unscrewing) the applicator cap 210 relative to the housing 208, the tamper ring 3402 may shear and thereby free the applicator cap 210 from the sensor applicator 102. Following which, the user may deliver the sensor control device 3202 to the target monitoring location, as generally described above with reference to FIGS. 2E-2G.

With specific reference to FIG. 34B, the sensor control device 3202 may be loaded into the sensor applicator 102 by mating the sharp hub 3330 with a sensor carrier 3404 included within the sensor applicator 102. More specifically, the hub small cylinder 3338 and the hub snap pawl 3340 may be received by corresponding mating features of the sensor carrier 3404.

Once the sensor control device 3202 is mated with the sensor carrier 3404, the applicator cap 210 may then be secured to the sensor applicator 102. As illustrated, the applicator cap 210 may provide and otherwise define a cap post 3406 centrally located within the interior of the applicator cap 210 and extending proximally from the bottom thereof. The cap post 3406 may be configured to help support the sensor control device 3202 while contained within the sensor applicator 102. Moreover, the cap post 3406 may define a post chamber 3408 configured to receive the sensor 3214 and the sharp 3216 as extending from the bottom of the electronics housing 3204. When the sensor control device 3202 is loaded into the sensor applicator 102, the sensor 3214 and the sharp 3216 may be arranged within a sealed region 3410 at least partially defined by the post chamber 3408 and configured to isolate the sensor 3214 and the sharp 3216 during gaseous chemical sterilization.

In some embodiments, prior to assembling and loading the sensor control device 3202 into the sensor applicator 102, the sensor and sharp modules 3210, 3212 may be subjected to radiation sterilization to sterilize the distal portions of the sensor 3214 and the sharp 3216. Once properly sterilized, the sensor and sharp modules 3210, 3212 may then be coupled to the electronics housing 3204 and the fully assembled sensor control device 3202 may then be loaded into the sensor applicator 102 as described above.

In other embodiments, however, the fully assembled sensor control device 3202 may first be loaded into the sensor applicator 102 and the sensor and sharp modules 3210, 3212 may then be subjected to radiation sterilization 3412 while positioned within the sensor applicator 102. The radiation sterilization 3412 may comprise, for example, e-beam irradiation, but other methods of sterilization may alternatively be used including, but not limited to, gamma ray irradiation, X-ray irradiation, or any combination thereof.

In some embodiments, as illustrated, the sensor control device 3202 may be subjected to "focused" radiation sterilization 3412, where the radiation (e.g., beams, waves, etc.) from the radiation sterilization 3412 is applied and otherwise directed only toward the sensor and sharp modules 3210, 3212 (e.g., the sensor 3214 and the sharp 3216). In such embodiments, the electrical components 3304 (FIG. 33B) coupled to the PCB 3302 (FIGS. 33A-33B), including the data processing unit 3306 (FIG. 33B), may be positioned out of the range of the propagating radiation and, therefore, will not be affected by the radiation. The electrical components 3304 and the data processing unit 3306, for example, may be positioned on the PCB 3302 near its outer periphery so as not to fall within the range (span) of the focused radiation sterilization 3412. In other embodiments, this may be accomplished by shielding the sensitive electrical components 3304 with proper electromagnetic shields.

According to the present disclosure, while loaded in the sensor applicator 102, the sensor control device 3202 may be subjected to gaseous chemical sterilization 3414 to sterilize the electronics housing 3204 and any other exposed portions of the sensor control device 3202. To accomplish this, a chemical may be injected into a sterilization chamber 3416 cooperatively defined by the sensor applicator 102 and the interconnected cap 210. In some applications, the chemical may be injected via one or more vents 3418 defined in the applicator cap 210 at its proximal end 3420. Example chemicals that may be used for the gaseous chemical sterilization 3414 include, but are not limited to, ethylene oxide, vaporized hydrogen peroxide, and nitrogen oxide (e.g., nitrous oxide, nitrogen dioxide, etc.).

Since the sensor 3214 and the sharp 3216 are sealed within the sealed region 3410, the chemicals used during the gaseous chemical sterilization process do not interact with the enzymes, chemistry or biologics provided on the tail 3316.

Once a desired sterility assurance level has been achieved within the sterilization chamber 3416, the gaseous solution is removed and the sterilization chamber 3416 is aerated. Aeration may be achieved by a series of vacuums and subsequently circulating nitrogen gas or filtered air through the sterilization chamber 3416. Once the sterilization chamber 3416 is properly aerated, the vents 3418 may be occluded with a seal 3422 (shown in dashed lines) applied to the proximal end 3420 of the applicator cap 210.

In some embodiments, the seal 3422 may comprise two or more layers of different materials. The first layer may be made of a synthetic material (e.g., a flash-spun high-density polyethylene fiber), such as Tyvek® available from DuPont®. Tyvek® is highly durable and puncture resistant and allows the permeation of vapors. The Tyvek® layer can be applied before the gaseous chemical sterilization 3414, and following the gaseous chemical sterilization 3414, a foil or other vapor and moisture resistant material layer may be sealed (e.g., heat sealed) over the Tyvek® layer to prevent the ingress of contaminants and moisture into the sterilization chamber 3416. In other embodiments, the seal 3422 may comprise only a single protective layer applied to the applicator cap 210. In such embodiments, the single layer is gas permeable for the sterilization process, but is also capable of protection against moisture and other harmful elements once the sterilization process is complete.

With the seal 3422 in place, the applicator cap 210 provides a barrier against outside contamination, and thereby maintains a sterile environment for the assembled sensor control device 3202 until the user removes (unthreads) the applicator cap 210. The applicator cap 210 may also create a dust-free environment during shipping and storage that prevents the adhesive patch 3218 used to secure the sensor control device 3202 to the user's skin from becoming dirty.

Figure 35:
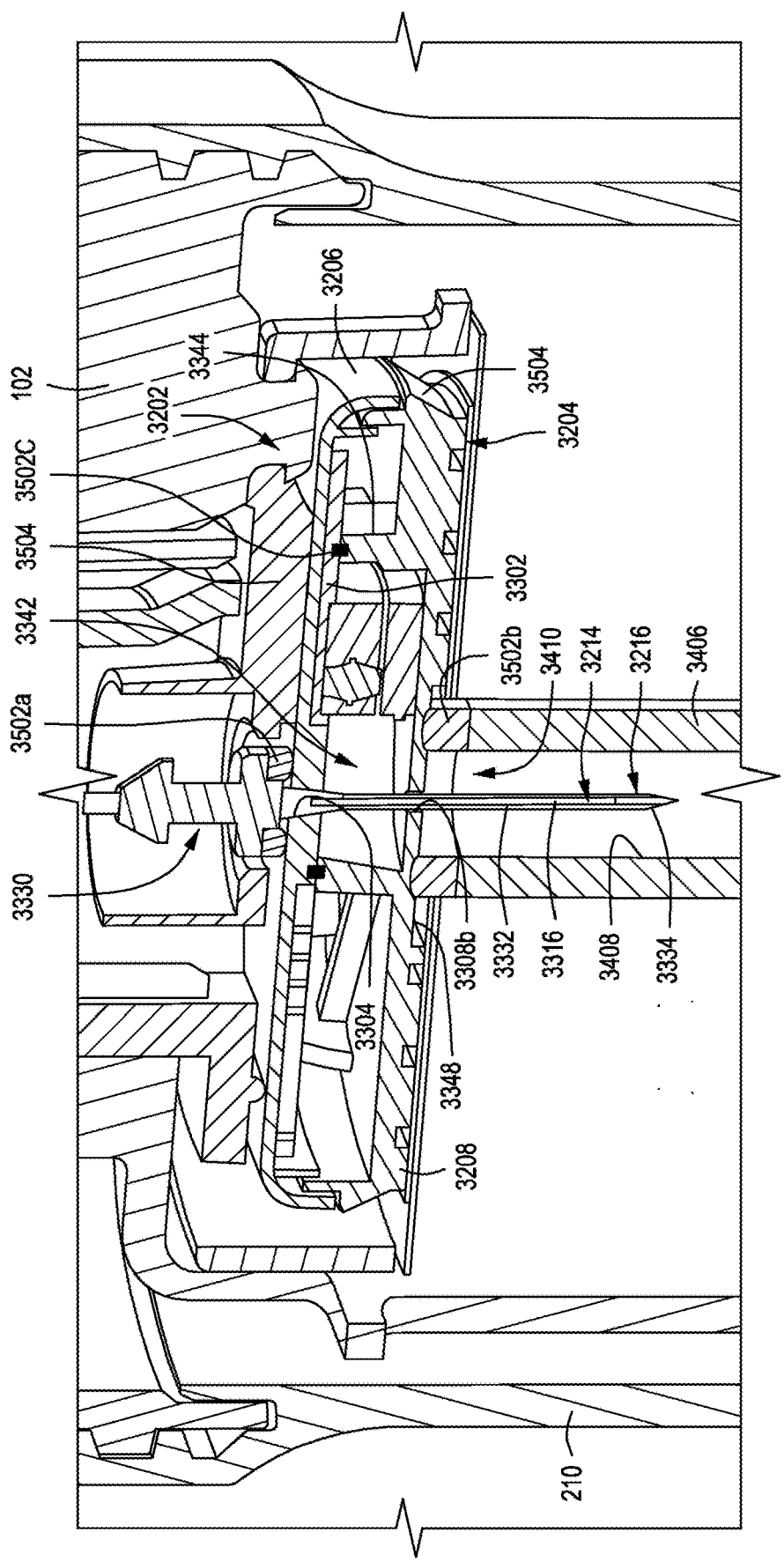
FIG. 35 is an enlarged cross-sectional side view of the sensor control device mounted within the sensor applicator.

FIG. 35 is an enlarged cross-sectional side view of the sensor control device 3202 mounted within the sensor applicator 102 with the applicator cap 210 secured thereto, according to one or more embodiments. As indicated above, portions of the sensor 3214 and the sharp 3216 may be arranged within the sealed region 3410 and thereby protected from substances that might adversely interact with the chemistry of the sensor 3214. More specifically, the gases used during the gaseous chemical sterilization 3414 (FIG. 34B) can adversely affect the enzymes provided on the tail 3316 of the sensor 3214, and the sealed region 3410 protects the tail 3316 from the ingress of such chemicals.

As illustrated, the sealed region 3410 may include (encompass) select portions of the interior of the electronics housing 3204 and the post chamber 3408 of the cap post 3406. In one or more embodiments, the sealed region 3410 may be defined and otherwise formed by at least a first seal 3502a, a second seal 3502b, and a third seal 3502c. The first seal 3502a may be arranged to seal the interface between the sharp hub 3330 and the shell 3206. Moreover, the first seal 3502a may circumscribe the first central aperture 3308a defined in the shell 3206 such that fluids (e.g., gaseous chemicals) are prevented from migrating into the interior of the electronics housing 3204 via the first central aperture 3308a.

In some embodiments, the first seal 3502a may form part of the sharp hub 3330. For example, the first seal 3502a may be overmolded onto the sharp hub 3330. In other embodiments, the first seal 3502a may be overmolded onto the top surface of the shell 3206. In yet other embodiments, the first seal 3502a may comprise a separate structure, such as an O-ring or the like, that interposes the sharp hub 3330 and the top surface of the shell 3206, without departing from the scope of the disclosure.

The second seal 3502b may be arranged to seal the interface between the cap post 3406 and the bottom of the mount 3208, and the second seal 3502b may circumscribe the second central aperture 3308b defined in the mount 3208. Consequently, the second seal 3502b may prevent fluids (e.g., gaseous chemicals) from migrating into the post chamber 3408 of the cap post 3406 and also from migrating into the interior of the electronics housing 3204 via the second central aperture 3308*b*.

In some embodiments, the second seal 3502*b* may form part of the cap post 3406. For example, the second seal 3502*b* may be overmolded onto the top of the cap post 3406. In other embodiments, the second seal 3502*b* may be overmolded onto the cap post seal interface 3348 at the bottom of the mount 3208. In yet other embodiments, the second seal 3502*b* may comprise a separate structure, such as an O-ring or the like, that interposes the cap post 3406 and the bottom of the mount 3208, without departing from the scope of the disclosure.

Upon loading the sensor control device 3202 into the sensor applicator 102 and securing the applicator cap 210 to the sensor applicator 102, the first and second seals 3502*a,b* become compressed and generate corresponding sealed interfaces. The first and second seals 3502*a,b* may be made of a variety of materials capable of generating a sealed interface between opposing structures. Suitable materials include, but are not limited to, silicone, a thermoplastic elastomer (TPE), polytetrafluoroethylene (Teflon®), rubber, an elastomer, or any combination thereof.

The third seal 3502*c* may be arranged to seal an interface between the sensor mount pocket 3342 and the PCB 3302 and, more particularly, between the outer periphery 3344 of the sensor mount pocket 3342 and the underside of the PCB 3302. The third seal 3502*c* may comprise a gasket (e.g., an O-ring or the like), an adhesive, or another type of seal material applied (arranged) at the outer periphery 3344. In operation, the third seal 3502*c* may prevent fluids (e.g., gaseous chemicals, liquids, etc.) from migrating into the interior of the sensor mount pocket 3342 and, therefore, into the post chamber 3408 to adversely react with the enzymes on the tail 3316.

The applicator cap 210 may be secured to the sensor applicator 102 by threading the applicator cap 210 to the sensor applicator 102 via relative rotation. As the applicator cap 210 rotates relative to the sensor applicator 102, the cap post 3406 advances until the second seal 3502*b* engages the cap post seal interface 3348 at the bottom of the mount 3208. Upon engaging the cap post seal interface 3348, the second seal 3502*b* may frictionally engage the mount 3208 and thereby urge corresponding rotation of the entire electronics housing 3204 in the same angular direction.

In prior art sensor control devices, such as the sensor control device 104 of FIG. 1, conical carrier grip features are commonly defined on the exterior of the electronics housing and configured to mate with corresponding conical features provided on radially biased arms of the sensor mount pocket 3342. Mating engagement between these corresponding conical features helps prevent the electronics housing from rotating within the sensor applicator 102.

In contrast, the electronics housing 3204 of the presently disclosed sensor control device 3202 provides or otherwise defines an angled and otherwise continuously smooth exterior surface 3504 about its outer diameter (periphery). In some embodiments, as illustrated, the smooth exterior surface 3504 may be provided on the mount 3208, but may alternatively be provided on the shell 3206, without departing from the scope of the disclosure. One or more radially biased arms of the sensor mount pocket 3342 may be positioned to engage the exterior surface 3504 to help center the sensor control device 3202 within the sensor applicator 102. As the electronics housing 3204 is urged to rotate through frictional engagement between the second seal 3502*b* and the bottom of the mount 3208, the exterior surface 3504 slidingly engages the radially biased arms, which do not inhibit rotation thereof.

Figure 36:
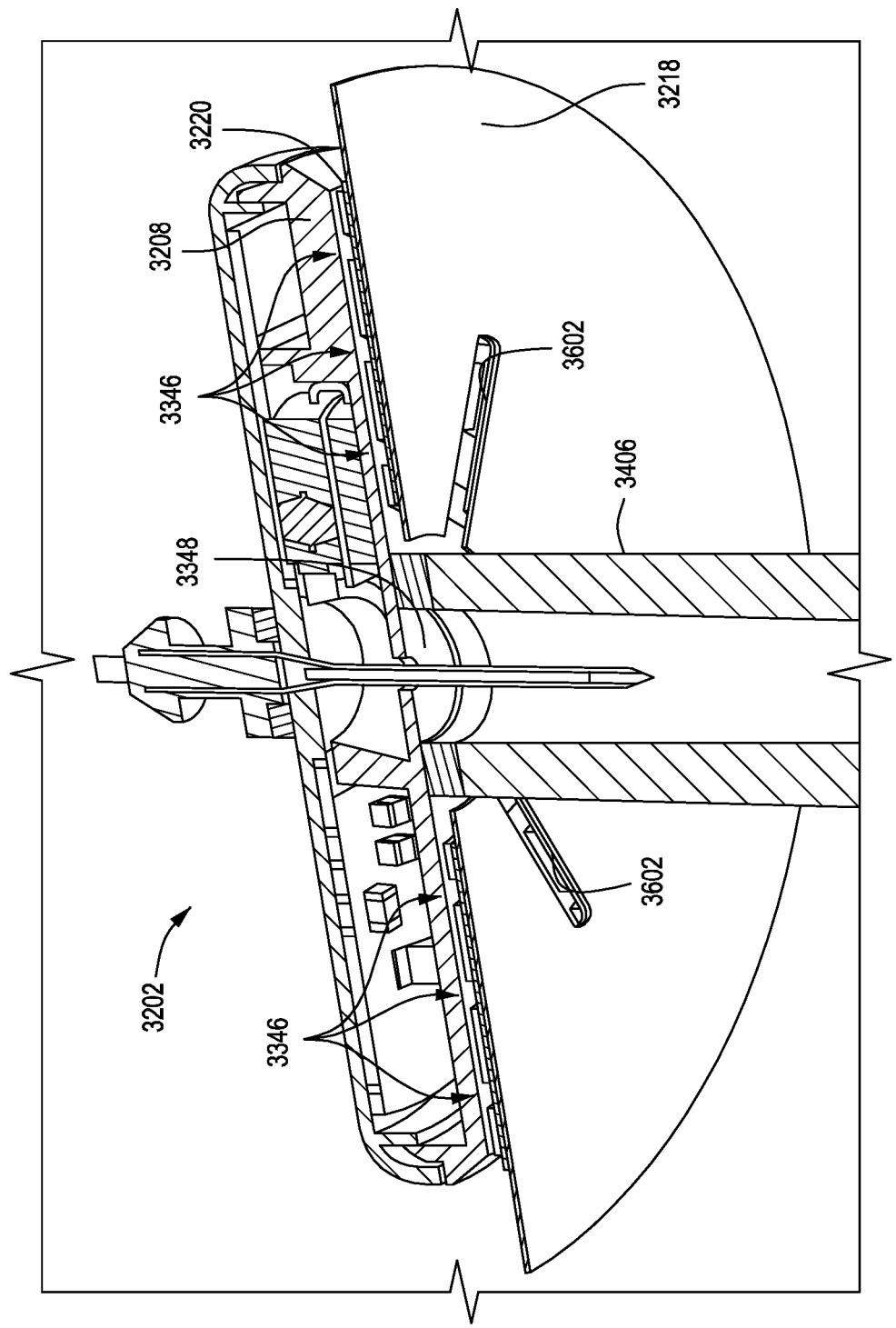
FIG. 36 is an enlarged cross-sectional bottom view of the sensor control device mounted atop the cap post.

FIG. 36 is an enlarged cross-sectional bottom view of the sensor control device 3202 positioned atop the cap post 3406, according to one or more embodiments. As illustrated, the adhesive patch 3218 is positioned on the underside of the mount 3208 and the transfer adhesive 3220 interposes the adhesive patch 3218 and the mount 3208.

The adhesive patch 3218 may occlude or otherwise cover most of the grooves 3346 defined on the bottom of the mount 3208. Moreover, as illustrated, the adhesive patch 3218 may extend a short distance into the cap post seal interface 3348. To enable the grooves 3346 to properly direct moisture away from the center of the electronics housing 3204 and from the cap post seal interface 3348, the adhesive patch 3218 (and the transfer adhesive 3220, if included) may provide or otherwise define one or more channels 3602 aligned with and otherwise arranged to fluidly communicate with the grooves 3346. In the illustrated embodiment, the channels 3602 extend radially outward from the center of the electronics housing 3204, but may alternatively be defined in other configurations and nonetheless interconnect with the grooves 3346 to facilitate fluid communication therebetween.

In operation, as moisture builds up around the center of the electronics housing 3204 and at the cap post seal interface 3348, the moisture is able to flow into the grooves 3346 via the channels 3602. Once in the grooves 3346, the moisture is able to flow radially outward beneath the adhesive patch 3218 and toward the outer periphery of the sensor control device 3202.

Embodiments disclosed herein include:

O. An analyte monitoring system that includes a sensor applicator, a sensor control device positioned within the sensor applicator and including an electronics housing having a shell and a mount matable with the shell, a printed circuit board positioned within the electronics housing, a sensor extending from a bottom of the mount, a sharp hub positioned adjacent a top of the shell, and a sharp carried by the sharp hub and extending through the electronics housing and from the bottom of the mount. The analyte monitoring system further including a cap coupled to the sensor applicator and providing a cap post that defines a post chamber that receives the sensor and the sharp extending from the bottom of the mount, and a sealed region encompassing the post chamber and a portion of an interior of the electronics housing, wherein the sealed region is defined by a first seal that seals an interface between the sharp hub and the shell, a second seal that seals an interface between the cap post and the bottom of the mount, and a third seal that seals an interface between the mount and the printed circuit board, and wherein portions of the sensor and the sharp reside within the sealed region and are thereby isolated from gaseous chemical sterilization.

P. A method of preparing an analyte monitoring system including loading a sensor control device into a sensor applicator, the sensor control device including an electronics housing having a shell and a mount matable with the shell, a printed circuit board positioned within the electronics housing, a sensor module having a sensor extending from a bottom of the mount, and a sharp module having a sharp hub and a sharp carried by the sharp hub, wherein the sharp extends through the electronics housing and from the bottom of the mount. The method further including securing a cap to the sensor applicator, wherein the cap provides a cap post that defines a post chamber that receives the sensor and the sharp extending from the bottom of the mount, creating a sealed region as the cap is secured to the sensor applicator, the sealed region encompassing the post chamber and a portion of an interior of the electronics housing, wherein portions of the sensor and the sharp reside within the sealed region, sterilizing the sensor control device with gaseous chemical sterilization while the sensor control device is positioned within the sensor applicator, and isolating the portions of the sensor and the sharp residing within the sealed region from the gaseous chemical sterilization.

Each of embodiments O and P may have one or more of the following additional elements in any combination: Element 1: wherein the first seal circumscribes a central aperture defined in the shell and prevents fluids from migrating into the portion of the interior of the electronics housing via the central aperture. Element 2: wherein the second seal circumscribes a central aperture defined in the mount and prevents fluids from migrating into the portion of the interior of the electronics housing via the central aperture and further prevents the fluids from migrating into the post chamber. Element 3: wherein the first seal is overmolded onto the sharp hub. Element 4: wherein the first seal interposes the sharp hub and a top surface of the shell. Element 5: wherein the second seal is overmolded onto the cap post. Element 6: wherein the second seal interposes the cap post and a bottom surface of the mount. Element 7: wherein the first and second seals are made of a material selected from the group consisting of silicone, a thermoplastic elastomer, polytetrafluoroethylene, and any combination thereof. Element 8: wherein the mount provides a sensor mount pocket that at least partially receives a sensor module within the electronics housing, and wherein the third seal is positioned at an outer periphery of the sensor mount pocket. Element 9: wherein the third seal comprises one of a gasket and an adhesive. Element 10: further comprising a plurality of grooves defined on the bottom of the mount, and a cap post seal interface defined on the bottom of the mount at a center of the mount, wherein the second seal seals against the cap post seal interface. Element 11: further comprising an adhesive patch coupled to the bottom of the mount and extending radially into the cap post seal interface, and one or more channels defined in the adhesive patch and interconnecting with the plurality of grooves to facilitate fluid communication between the cap post seal interface and the plurality of grooves. Element 12: wherein the electronics housing defines an angled and smooth exterior surface that allows the sensor control device to rotate unobstructed relative to the sensor applicator as the cap is coupled to the sensor applicator.

Element 13: wherein creating the sealed region as the cap is secured to the sensor applicator comprises sealing an interface between the sharp hub and the shell with a first seal, sealing an interface between the cap post and the bottom of the mount with a second seal, and sealing an interface between the mount and the printed circuit board with a third seal. Element 14: wherein loading the sensor control device into a sensor applicator is preceded by sterilizing the sensor and the sharp with radiation sterilization, and assembling the sensor and sharp modules to the electronics housing. Element 15: wherein sterilizing the sensor control device with the gaseous chemical sterilization is preceded by sterilizing the sensor and the sharp with radiation sterilization while the sensor control device is positioned within the sensor applicator. Element 16: wherein the radiation sterilization is at least one of focused radiation sterilization and low-energy radiation sterilization. Element 17: wherein the electronics housing defines an angled and smooth exterior surface, the method further comprising allowing the sensor control device to rotate relative to the sensor applicator as the cap is secured to the sensor applicator.

By way of non-limiting example, exemplary combinations applicable to O and P include: Element 1 with Element 2; Element 1 with Element 3; Element 1 with Element 4; Element 1 with Element 5; Element 1 with Element 6; Element 1 with Element 7; Element 1 with Element 8; Element 3 with Element 4; Element 3 with Element 5; Element 3 with Element 6; Element 10 with Element 11; and Element 15 with Element 16.

Figure 37A:
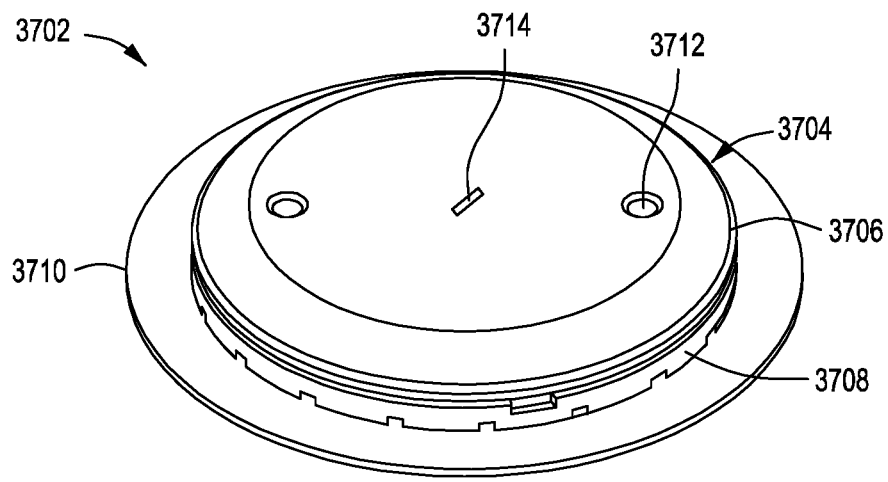
FIGS. 37A-37C are isometric, side, and bottom views, respectively, of an example sensor control device.
Figure 37B:
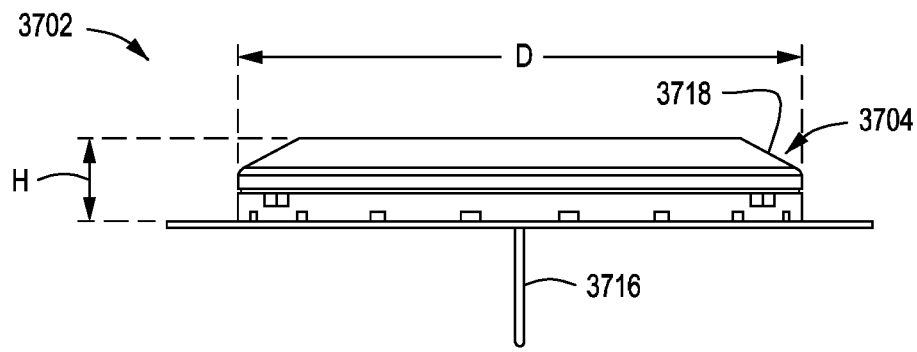
Figure 37C:
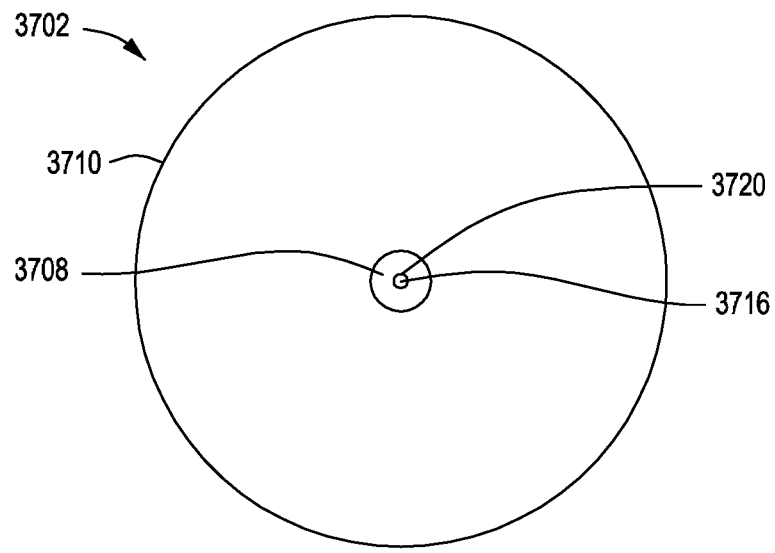

One-Piece Puck Architecture with ASIC Shields, Use of Low and Medium Energy Radiation Sterilization, and Magnetic Deflection FIGS. 37A-37C are isometric, side, and bottom views, respectively, of an example sensor control device 3702, according to one or more embodiments of the present disclosure. The sensor control device 3702 (alternately referred to as an on-body patch or unit) may be similar in some respects to the sensor control device 104 of FIG. 1 and therefore may be best understood with reference thereto. The sensor control device 3702 may replace the sensor control device 104 of FIG. 1 and, therefore, may be used in conjunction with the sensor applicator 102 (FIG. 1), which delivers the sensor control device 3702 to a target monitoring location on a user's skin. However, in contrast to the sensor control device 104 of FIG. 1, various structural advantages and improvements allow the sensor control device 3702 to be incorporated into a one-piece system architecture.

Unlike the sensor control device 104 of FIG. 1, for example, a user is not required to open multiple packages and finally assemble the sensor control device 3702 prior to delivery to the target monitoring location. Rather, upon receipt by the user, the sensor control device 3702 may already be assembled and properly positioned within the sensor applicator 102. To use the sensor control device 3702, the user need only break one barrier (e.g., the applicator cap 210 of FIG. 2B) before promptly delivering the sensor control device 3702 to the target monitoring location.

Referring first to FIG. 37A, the sensor control device 3702 comprises an electronics housing 3704 that is generally disc-shaped and may have a generally circular cross-section. In other embodiments, however, the electronics housing 3704 may exhibit other cross-sectional shapes, such as ovoid or polygonal, without departing from the scope of the disclosure. The electronics housing 3704 may include a shell 3706 and a mount 3708 that is matable with the shell 3706. An adhesive patch 3710 may be positioned on and otherwise attached to the underside of the mount 3708. Similar to the adhesive patch 108 of FIG. 1, the adhesive patch 3710 may be configured to secure and maintain the sensor control device 3702 in position on the user's skin during operation.

In some embodiments, the shell 3706 may define a reference feature 3712. As illustrated, the reference feature 3712 may comprise a depression or blind pocket defined in the shell 3706 and extending a short distance into the interior of the electronics housing 3704. The reference feature 3712 may operate as a "datum c" feature configured to help facilitate control of the sensor control device 3702 in at least one degree of freedom during factory assembly. In contrast, prior sensor control devices (e.g., the sensor control device 104 of FIG. 1) typically include a tab extending radially from the side of the shell. The tab is used as an in-process clocking datum, but must be removed at the end of fabrication, and followed by an inspection of the shell where the tab once existed, which adds complexity to the prior fabrication process.

The shell 3706 may also define a central aperture 3714 sized to receive a sharp (not shown) that is extendable through the center of the electronics housing 3704.

FIG. 37B depicts a portion of a sensor 3716 extending from the electronics housing 3704. The remaining portion(s) of the sensor 3716 is/are positioned within the interior of the electronics housing 3704. Similar to the sensor 110 of FIG. 1, the exposed portion of the sensor 3716 is configured to be transcutaneously positioned under the user's skin during use. The exposed portion of the sensor 3716 can include an enzyme or other chemistry or biologic and, in some embodiments, a membrane may cover the chemistry.

The sensor control device 3702 provides structural improvements that result in a height H and a diameter D that may be less than prior sensor control devices (e.g., the sensor control device 104 of FIG. 1). In at least one embodiment, for example, the height H may be about 1 mm or more less than the height of prior sensor control devices, and the diameter D may be about 2 mm or more less than the diameter of prior sensor control devices.

Moreover, the structural improvements of the sensor control device 3702 allows the shell 3706 to provide or otherwise define a chamfered or angled outer periphery 3718. In contrast, prior sensor control devices commonly require a rounded or outwardly arcuate outer periphery to accommodate internal components. The reduced height H, the reduced diameter D, and the angled outer periphery 3718 may each prove advantageous in providing a sensor control device 3702 that is thinner, smaller, and less prone to being prematurely detached by catching on sharp corners or the like while attached to the user's skin.

FIG. 37C depicts a central aperture 3720 defined in the underside of the mount 3708. The central aperture 3720 may be sized to receive a combination sharp (not shown) and sensor 3716, where the sensor 3716 is received within a hollow or recessed portion of the sharp. When the electronics housing 3704 is assembled, the central aperture 3720 coaxially aligns with the central aperture 3714 (FIG. 37A) of the shell 3706 (FIG. 37A) and the sharp penetrates the electronics housing by extending simultaneously through each central aperture 3714, 3720.

Figure 38A:
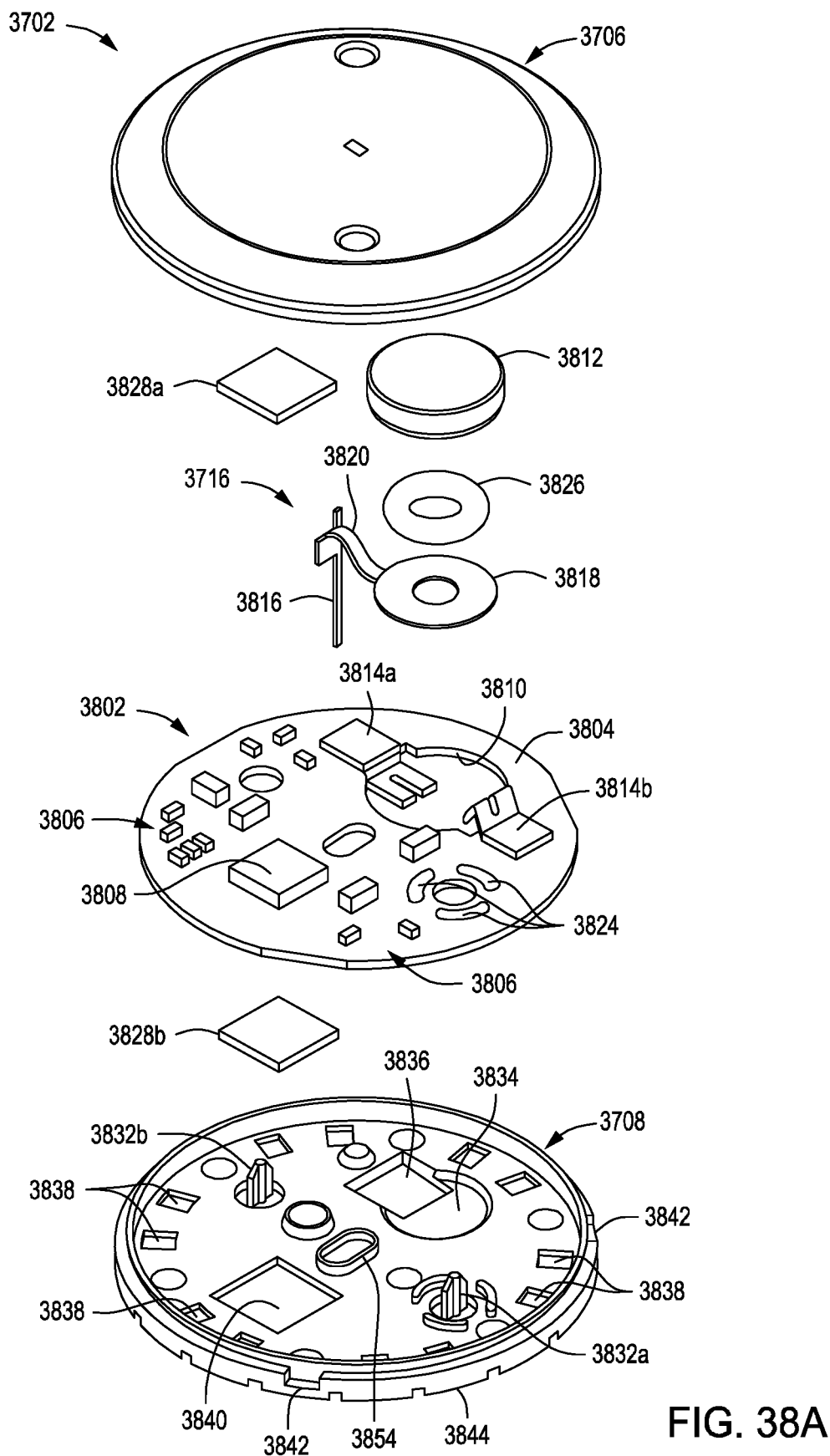
FIGS. 38A and 38B are isometric exploded top and bottom views, respectively, of the sensor control device of FIGS. 37A-37C.
Figure 38B:
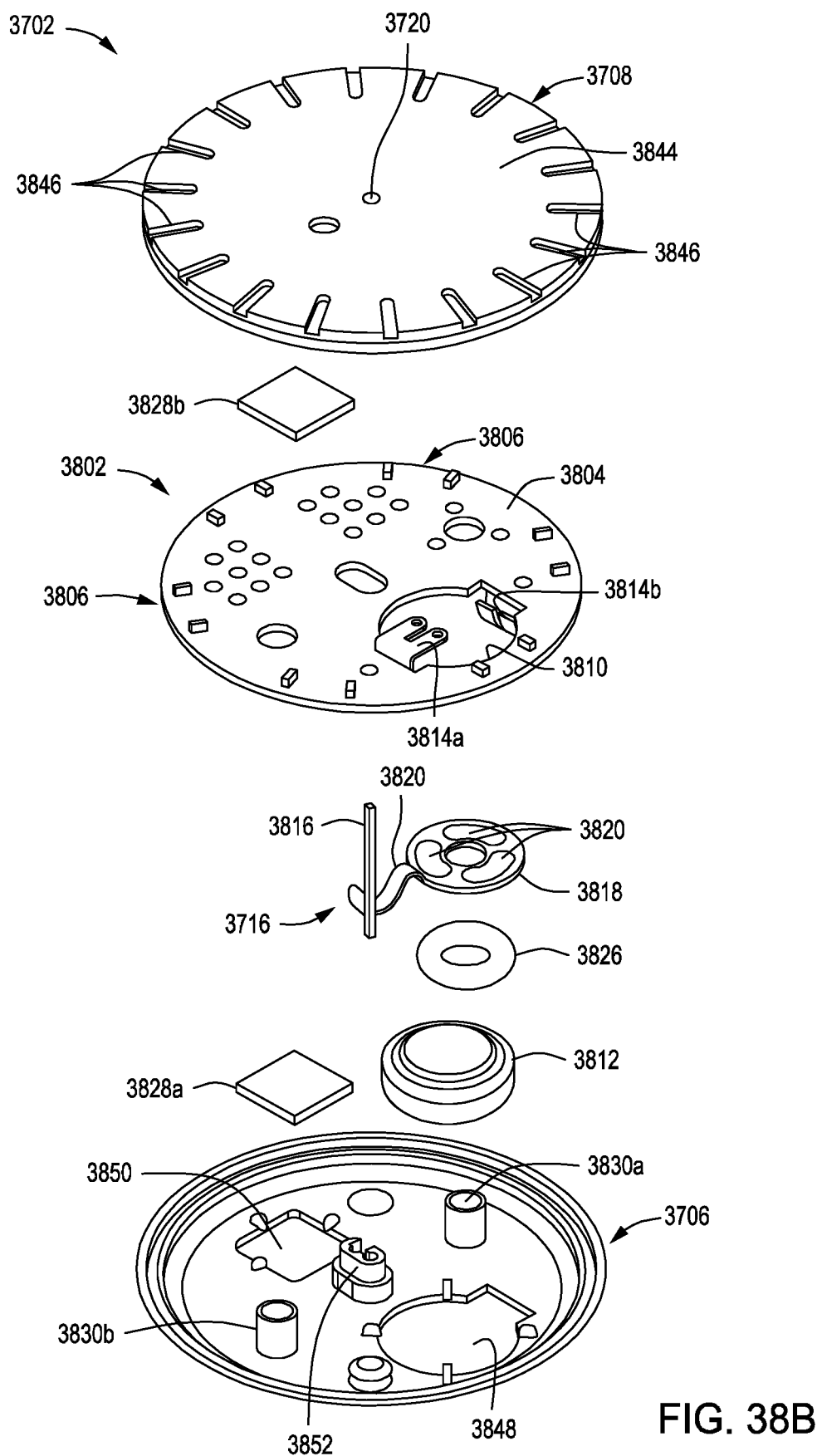

FIGS. 38A and 38B are exploded top and bottom views, respectively, of the sensor control device 3702, according to one or more embodiments. The shell 3706 and the mount 3708 operate as opposing clamshell halves that enclose or otherwise substantially encapsulate the various electronic components of the sensor control device 3702. As illustrated, the sensor control device 3702 may include a printed circuit board assembly (PCBA) 3802 that includes a printed circuit board (PCB) 3804 having a plurality of electronic modules 3806 coupled thereto. Example electronic modules 3806 include, but are not limited to, resistors, transistors, capacitors, inductors, diodes, and switches. Prior sensor control devices commonly stack PCB components on only one side of the PCB. In contrast, the PCB components 3806 in the sensor control device 3702 can be dispersed about the surface area of both sides (i.e., top and bottom surfaces) of the PCB 3804.

Besides the electronic modules 3806, the PCBA 3802 may also include a data processing unit 3808 mounted to the PCB 3804. The data processing unit 3808 may comprise, for example, an application specific integrated circuit (ASIC) configured to implement one or more functions or routines associated with operation of the sensor control device 3702. More specifically, the data processing unit 3808 may be configured to perform data processing functions, where such functions may include but are not limited to, filtering and encoding of data signals, each of which corresponds to a sampled analyte level of the user. The data processing unit 3808 may also include or otherwise communicate with an antenna for communicating with the reader device 106 (FIG. 1).

A battery aperture 3810 may be defined in the PCB 3804 and sized to receive and seat a battery 3812 configured to power the sensor control device 3702. An axial battery contact 3814*a* and a radial battery contact 3814*b* may be coupled to the PCB 3804 and extend into the battery aperture 3810 to facilitate transmission of electrical power from the battery 3812 to the PCB 3804. As their names suggest, the axial battery contact 3814*a* may be configured to provide an axial contact for the battery 3812, while the radial battery contact 3814*b* may provide a radial contact for the battery 3812. Locating the battery 3812 within the battery aperture 3810 with the battery contacts 3814*a,b* helps reduce the height H (FIG. 37B) of the sensor control device 3702, which allows the PCB 3804 to be located centrally and its components to be dispersed on both sides (i.e., top and bottom surfaces). This also helps facilitate the chamfer 3718 (FIG. 37B) provided on the electronics housing 3704.

The sensor 3716 may be centrally located relative to the PCB 3804 and include a tail 3816, a flag 3818, and a neck 3820 that interconnects the tail 3816 and the flag 3818. The tail 3816 may be configured to extend through the central aperture 3720 of the mount 3708 to be transcutaneously received beneath a user's skin. Moreover, the tail 3816 may have an enzyme or other chemistry included thereon to help facilitate analyte monitoring.

The flag 3818 may include a generally planar surface having one or more sensor contacts 3822 (three shown in FIG. 38B) arranged thereon. The sensor contact(s) 3822 may be configured to align with and engage a corresponding one or more circuitry contacts 3824 (three shown in FIG. 38A) provided on the PCB 3804. In some embodiments, the sensor contact(s) 3822 may comprise a carbon impregnated polymer printed or otherwise digitally applied to the flag 3818. Prior sensor control devices typically include a connector made of silicone rubber that encapsulates one or more compliant carbon impregnated polymer modules that serve as electrical conductive contacts between the sensor and the PCB. In contrast, the presently disclosed sensor contacts(s) 3822 provide a direct connection between the sensor 3716 and the PCB 3804 connection, which eliminates the need for the prior art connector and advantageously reduces the height H (FIG. 37B). Moreover, eliminating the compliant carbon impregnated polymer modules eliminates a significant circuit resistance and therefor improves circuit conductivity.

The sensor control device 3702 may further include a compliant member 3826, which may be arranged to interpose the flag 3818 and the inner surface of the shell 3706. More specifically, when the shell 3706 and the mount 3708 are assembled to one another, the compliant member 3826 may be configured to provide a passive biasing load against the flag 3818 that forces the sensor contact(s) 3822 into continuous engagement with the corresponding circuitry contact(s) 3824. In the illustrated embodiment, the compliant member 3826 is an elastomeric O-ring, but could alternatively comprise any other type of biasing device or mechanism, such as a compression spring or the like, without departing from the scope of the disclosure.

The sensor control device 3702 may further include one or more electromagnetic shields, shown as a first shield 3828a and a second shield 3828b. The shields 3828a,b may be arranged between the shell 3706 and the mount 3708; i.e., within the electronics housing 3704 (FIGS. 37A-37B). In the illustrated embodiment, the first shield 3828a is arranged above the PCB 3804 such that it faces the top surface of the PCB 3804, and the second shield 3828b is arranged below the PCB 3804 such that it faces the bottom surface of the PCB 3804.

The shields 3828a,b may be configured to protect sensitive electronic components from radiation while the sensor control device 3702 is subjected to radiation sterilization. More specifically, at least one of the shields 3828a,b may be positioned to interpose the data processing unit 3808 and a radiation source, such as an e-beam electron accelerator. In some embodiments, for example, at least one of the shields 3828a,b may be positioned adjacent to and otherwise aligned with the data processing unit 3808 and the radiation source to block or mitigate radiation absorbed dose that might otherwise damage the sensitive electronic circuitry of the data processing unit 3808.

In the illustrated embodiment, the data processing unit 3808 interposes the first and second shields 3828a,b such that the first and second shields 3828a,b essentially bookend the data processing unit 3808 in the axial direction. In at least one embodiment, however, only one of the shields 3828a,b may be necessary to properly protect the data processing unit 3808 during radiation sterilization. For example, if the sensor control device 3702 is subjected to radiation sterilization directed toward the bottom of the mount 3708, only the second shield 3828b may be needed to interpose the data processing unit 3808 and the radiation source, and the first shield 3828a may be omitted. Alternatively, if the sensor control device 3702 is subjected to radiation sterilization directed toward the top of the shell 3706, only the first shield 3828a may be needed to interpose the data processing unit 3808 and the radiation source, and the second shield 3828b may be omitted. In other embodiments, however, both shields 3828a,b may be employed, without departing from the scope of the disclosure.

The shields 3828a,b may be made of any material capable of attenuating (or substantially attenuating) the transmission of radiation. Suitable materials for the shields 3828a,b include, but are not limited to, lead, tungsten, iron-based metals (e.g., stainless steel), copper, tantalum, tungsten, osmium, aluminum, carbon, or any combination thereof. Suitable metals for the shields 3828a,b may be corrosion-resistant, austenitic, and any non-magnetic metal with a density ranging between about 2 grams per cubic centimeter (g/cc) and about 23 g/cc. The shields 3828a,b may be fabricated via a variety of manufacturing techniques including, but not limited to, stamping, casting, injection molding, sintering, two-shot molding, or any combination thereof.

In other embodiments, however, the shields 3828a,b may comprise a metal-filled thermoplastic polymer such as, but not limited to, polyamide, polycarbonate, or polystyrene. In such embodiments, the shields 3828a,b may be fabricated by mixing the shielding material in an adhesive matrix and dispensing the combination onto shaped components or otherwise directly onto the data processing unit 3808. Moreover, in such embodiments, the shields 3828a,b may comprise an enclosure that encapsulates (or substantially encapsulates) the data processing unit 3808. In such embodiments, the shields 3828a,b may comprise a metal-filled thermoplastic polymer, as mentioned above, or may alternatively be made of any of the materials mentioned herein that are capable of attenuating (or substantially attenuating) the transmission of radiation.

The shell 3706 may provide or otherwise define a first clocking receptacle 3830a (FIG. 38B) and a second clocking receptacle 3830b (FIG. 38B), and the mount 3708 may provide or otherwise define a first clocking post 3832a (FIG. 38A) and a second clocking post 3832b (FIG. 38A). Mating the first and second clocking receptacles 3830a,b with the first and second clocking posts 3832a,b, respectively, will properly align the shell 3706 to the mount 3708.

Referring specifically to FIG. 38A, the inner surface of the mount 3708 may provide or otherwise define a plurality of pockets or depressions configured to accommodate various component parts of the sensor control device 3702 when the shell 3706 is mated to the mount 3708. For example, the inner surface of the mount 3708 may define a battery locator 3834 configured to accommodate a portion of the battery 3812 when the sensor control device 3702 is assembled. An adjacent contact pocket 3836 may be configured to accommodate a portion of the axial contact 3814a.

Moreover, a plurality of module pockets 3838 may be defined in the inner surface of the mount 3708 to accommodate the various electronic modules 3806 arranged on the bottom of the PCB 3804. Furthermore, a shield locator 3840 may be defined in the inner surface of the mount 3708 to accommodate at least a portion of the second shield 3828b when the sensor control device 3702 is assembled. The battery locator 3834, the contact pocket 3836, the module pockets 3838, and the shield locator 3840 all extend a short distance into the inner surface of the mount 3708 and, as a result, the overall height H (FIG. 37B) of the sensor control device 3702 may be reduced as compared to prior sensor control devices. The module pockets 3838 may also help minimize the diameter of the PCB 3804 by allowing PCB components to be arranged on both sides (i.e., top and bottom surfaces).

Still referring to FIG. 38A, the mount 3708 may further include a plurality of carrier grip features 3842 (two shown) defined about the outer periphery of the mount 3708. The carrier grip features 3842 are axially offset from the bottom 3844 of the mount 3708, where a transfer adhesive (not shown) may be applied during assembly. In contrast to prior sensor control devices, which commonly include conical carrier grip features that intersect with the bottom of the mount, the presently disclosed carrier grip features 3842 are offset from the plane (i.e., the bottom 3844) where the transfer adhesive is applied. This may prove advantageous in helping ensure that the delivery system does not inadvertently stick to the transfer adhesive during assembly. Moreover, the presently disclosed carrier grip features 3842 eliminate the need for a scalloped transfer adhesive, which simplifies the manufacture of the transfer adhesive and eliminates the need to accurately clock the transfer adhesive relative to the mount 3708. This also increases the bond area and, therefore, the bond strength.

Referring to FIG. 38B, the bottom 3844 of the mount 3708 may provide or otherwise define a plurality of grooves 3846, which may be defined at or near the outer periphery of the mount 3708 and equidistantly spaced from each other. A transfer adhesive (not shown) may be coupled to the bottom 3844 and the grooves 3846 may be configured to help convey (transfer) moisture away from the sensor control device 3702 and toward the periphery of the mount 3708 during use. In some embodiments, the spacing of the grooves 3846 may interpose the module pockets 3838 (FIG. 38A) defined on the opposing side (inner surface) of the mount 3708. As will be appreciated, alternating the position of the grooves 3846 and the module pockets 3838 ensures that the opposing features on either side of the mount 3708 do not extend into each other. This may help maximize usage of the material for the mount 3708 and thereby help maintain a minimal height H (FIG. 37B) of the sensor control device 3702. The module pockets 3838 may also significantly reduce mold sink, and improve the flatness of the bottom 3844 that the transfer adhesive bonds to.

Still referring to FIG. 38B, the inner surface of the shell 3706 may also provide or otherwise define a plurality of pockets or depressions configured to accommodate various component parts of the sensor control device 3702 when the shell 3706 is mated to the mount 3708. For example, the inner surface of the shell 3706 may define an opposing battery locator 3848 arrangeable opposite the battery locator 3834 (FIG. 38A) of the mount 3708 and configured to accommodate a portion of the battery 3812 when the sensor control device 3702 is assembled. Moreover, a shield locator 3850 may be defined in the inner surface of the shell 3706 to accommodate at least a portion of the first shield 3828a when the sensor control device 3702 is assembled. The opposing battery locator 3848 and the shield locator 3850 extend a short distance into the inner surface of the shell 3706, which helps reduce the overall height H (FIG. 37B) of the sensor control device 3702.

A sharp and sensor locator 3852 may also be provided by or otherwise defined on the inner surface of the shell 3706. The sharp and sensor locator 3852 may be configured to receive both the sharp (not shown) and a portion of the sensor 3716. Moreover, the sharp and sensor locator 3852 may be configured to align and/or mate with a corresponding sharp and sensor locator 2054 (FIG. 38A) provided on the inner surface of the mount 3708.

Figure 39A:
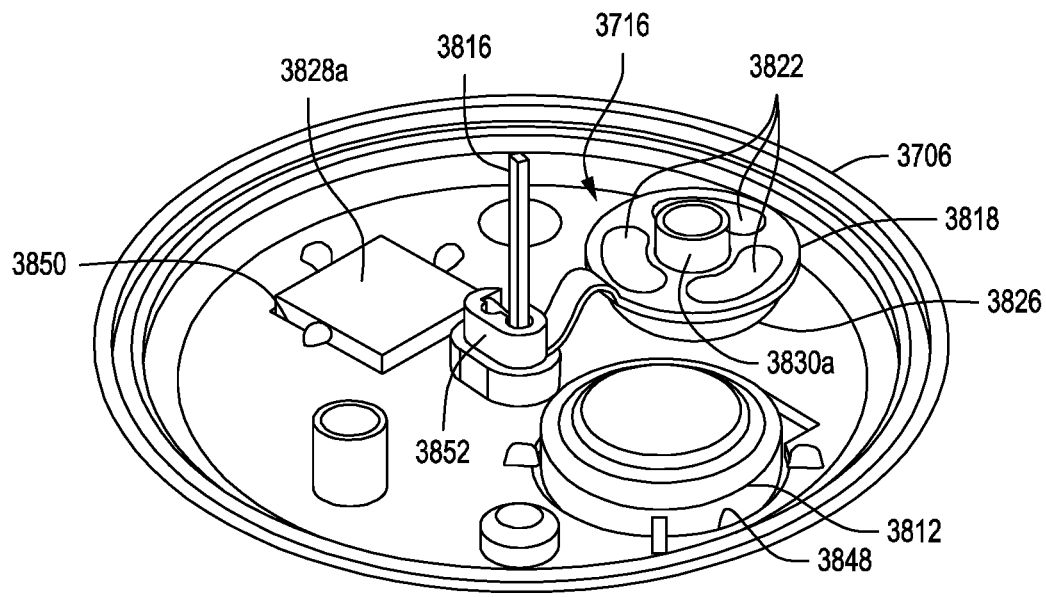
FIGS. 39A-39D show example assembly of the sensor control device of FIGS. 37A-37C.

FIGS. 39A-39D show progressive example assembly of the sensor control device 3702, according to one or more embodiments. In FIG. 39A, the battery 3812 has been loaded into the opposing battery locator 3848 and the first shield 3828a has been loaded into the shield locator 3850 defined in the inner surface of the shell 3706. The compliant member 3826 and the flag 3818 of the sensor 3716 may each be mounted to the first clocking receptacle 3830a. The tail 3816 of the sensor 3716 may be inserted into the sharp and the sensor locator 3852.

Figure 39B:
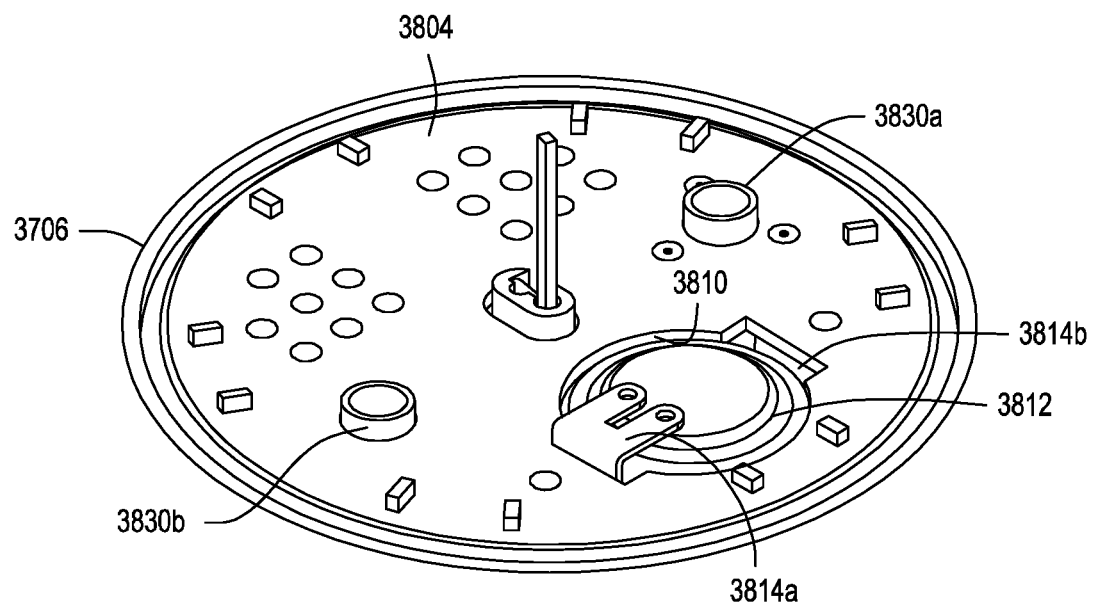

In FIG. 39B, the PCB 3804 may be loaded into the shell 3706 to align the battery aperture 3810 with the battery 3812 and the axial and radial battery contacts 3814a,b facilitate electrical communication.

Figure 39C:
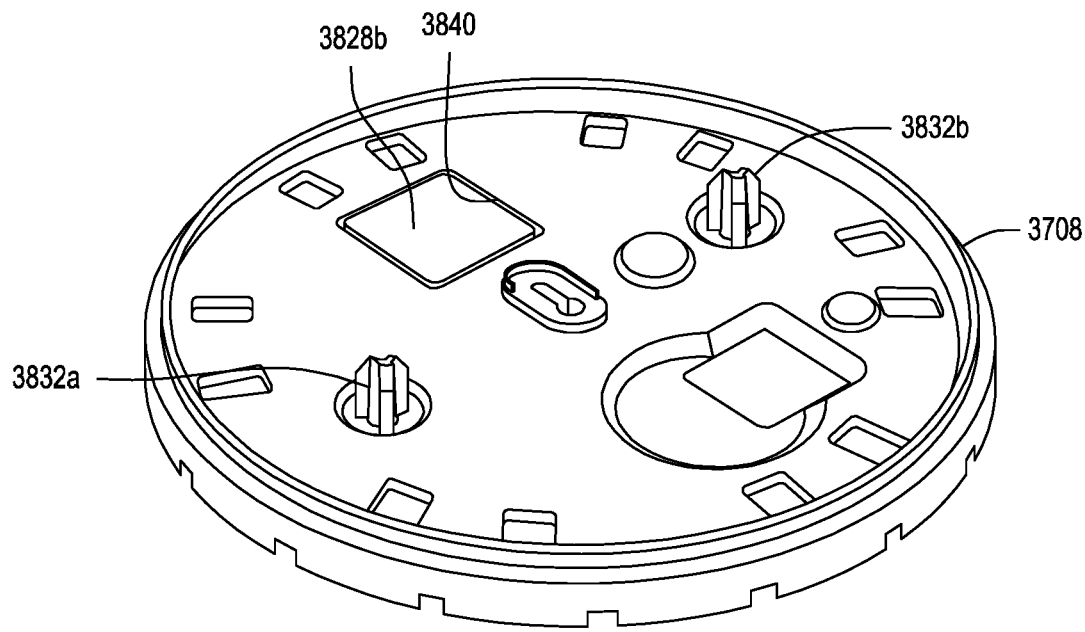

In FIG. 39C, the second shield 3828b has been loaded into the shield locator 3840 defined in the inner surface of the mount 3708. The mount 3708 is now ready to be coupled to the shell 3706 (FIGS. 39A and 39B). To accomplish this, the first and second clocking receptacles 3830a,b (FIG. 39B) of the shell 3706 may be coaxially aligned with the first and second clocking posts 3832a,b of the mount 3708, respectively. An adhesive may be applied to one or both of the shell 3706 and the mount 3708 to secure the two components together. In one embodiment, for example, the adhesive may be applied around the outer diameter (periphery) of the shell 3706, and the shell 3706 may then be transferred to the mount 3708 and mated with the corresponding outer diameter (periphery) of the mount 3708. In other embodiments, the adhesive may be applied around the outer diameter (periphery) of the mount 3708 or the outer diameter (periphery) of both the shell 3706 and the mount 3708, without departing from the scope of the disclosure. In at least one embodiment, an adhesive may be used to secure the first and second clocking receptacles 3830a,b to the first and second clocking posts 3832a,b, respectively.

Figure 39D:
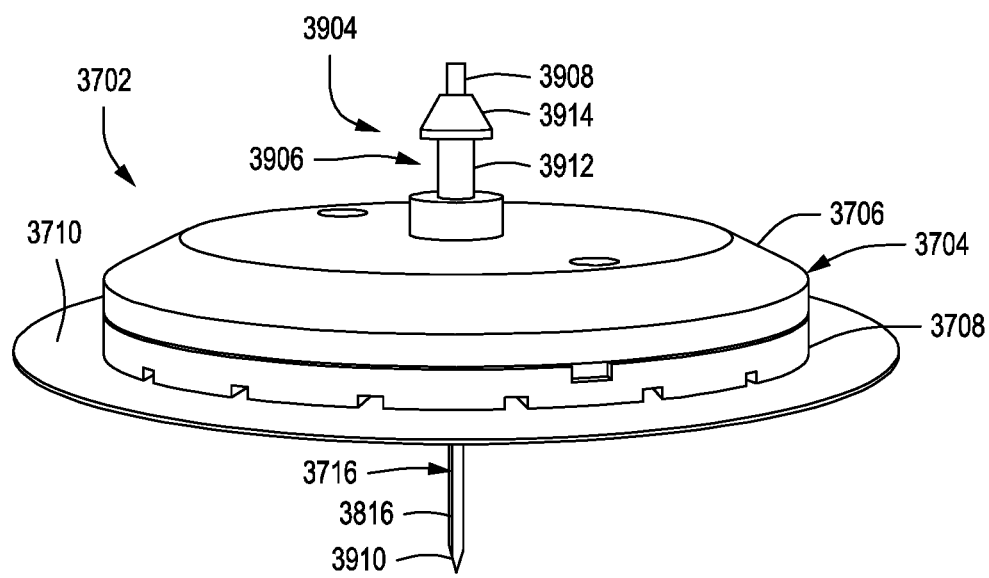

FIG. 39D shows the assembled sensor control device 3702, which may be tested to ensure the sensor 3716 and the corresponding electronics of the sensor control device 3702 function properly. The adhesive may not only secure the shell 3706 to the mount 3708 and provide structural integrity, but may also seal the interface between the two components and thereby isolate the interior of the electronics housing 3704 from outside contamination. Consequently, there may be no need to sterilize the internal electrical components of the sensor control device 3702 via gaseous chemical sterilization (e.g., ethylene oxide). Rather, the adhesive provides a sterile and moisture barrier to the interior of the assembled sensor control device 3702.

The adhesive patch 3710 may be applied to the bottom 3844 of the mount 3708. In some embodiments, the adhesive patch 3710 may have a removable release liner that is removed to enable the adhesive patch 3710 to be attached to the bottom 3844 of the mount 3708.

Either before or after securing the adhesive patch 3710, a sharp module 3904 may be coupled to the sensor control device 3702. As illustrated, the sharp module 3904 may include a sharp hub 3906 and a sharp 3908 carried by the sharp hub 3906 and extending through the electronics housing 3704. To couple the sharp module 3904 to the sensor control device 3702, a sharp tip 3910 of the sharp 3908 may be extended through the coaxially aligned central apertures 3714, 3720 (FIGS. 37A and 37C) of the shell 3706 and the mount 3708, respectively. As the sharp tip 3910 penetrates the sensor control device 3702, the tail 3816 may be received within a hollow or recessed portion of the sharp tip 3910. The sharp tip 3910 may be configured to penetrate the skin while carrying the tail 3816 to put the active chemistry present on the tail 3816 into contact with bodily fluids.

The sharp tip 3910 may be advanced through the sensor control device 3702 until the sharp hub 3906 engages the upper surface of the shell 3706. As illustrated, the sharp hub 3906 may include a hub small cylinder 3912 and a hub snap pawl 3914, each of which may be configured to help couple the sensor control device 3702 to a sensor applicator (e.g., the sensor applicator 102 of FIG. 1).

Figure 40B:
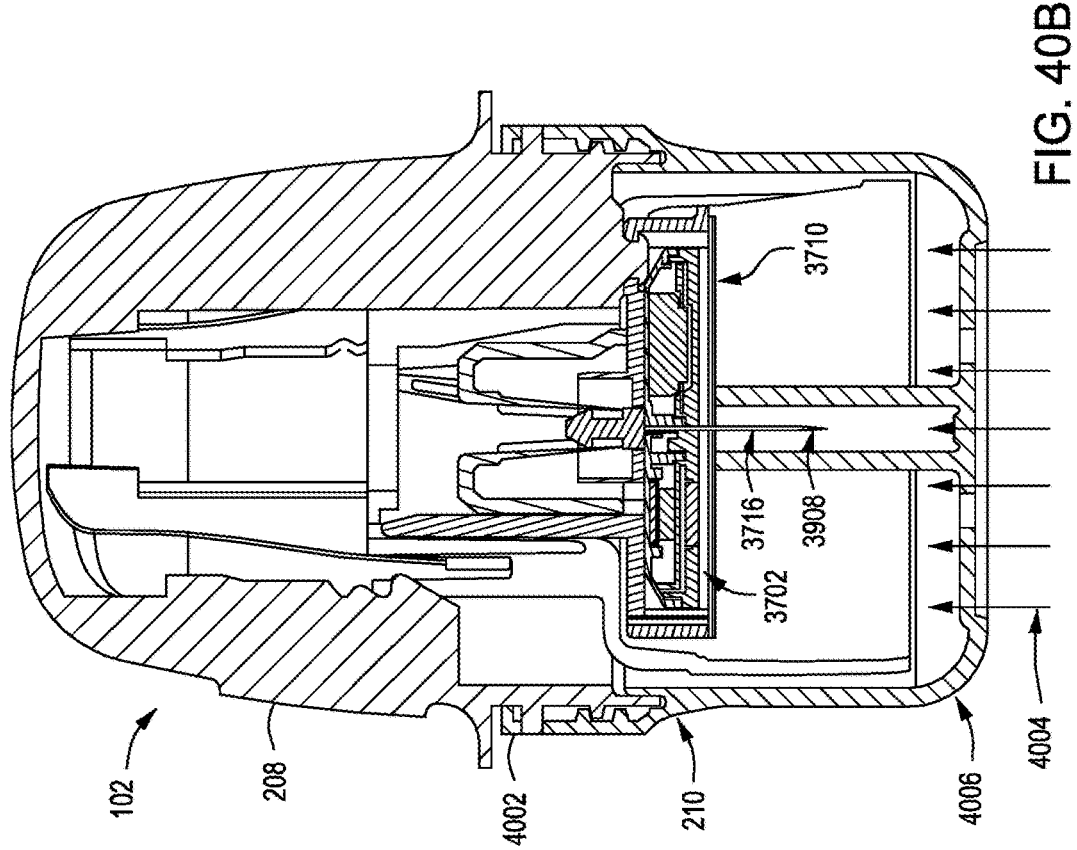
FIGS. 40A and 40B are side and cross-sectional side views, respectively, of a sensor applicator with the pre-assembled sensor control device of FIGS. 37A-37C arranged therein.
Figure 40A:
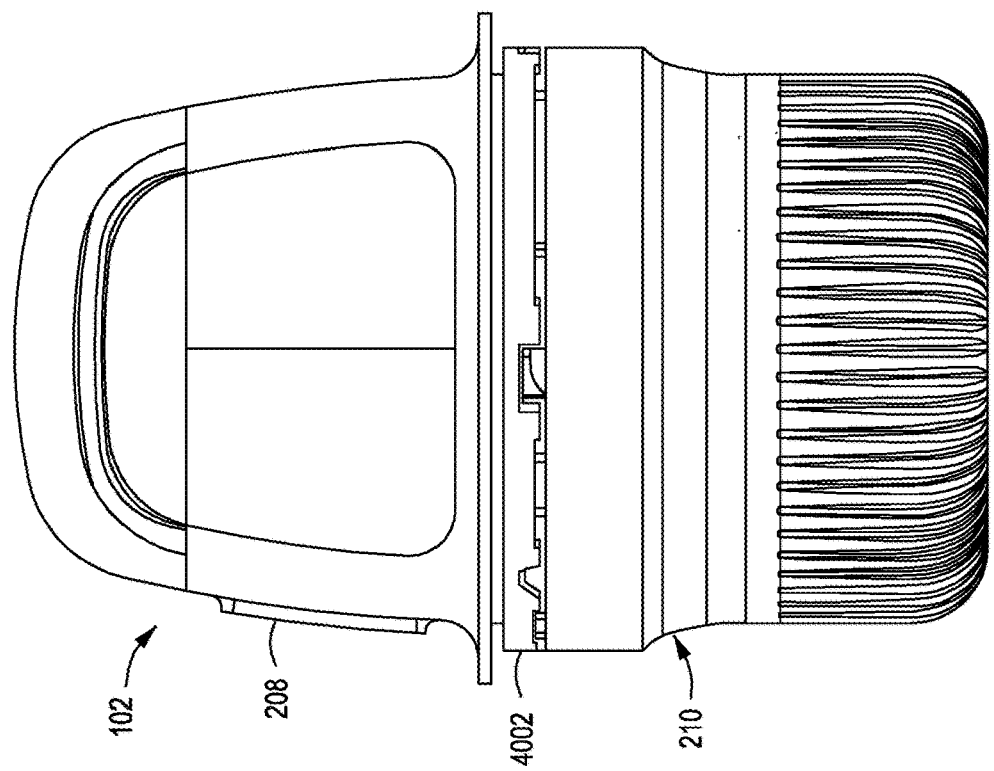

FIGS. 40A and 40B are side and cross-sectional side views, respectively, of the sensor applicator 102 sealed with the applicator cap 210. According to the present disclosure, and as seen in FIG. 40B, the sensor control device 3702 may already be assembled, as generally described above, and installed within the sensor applicator 102 prior to being delivered to a user. Accordingly, FIGS. 40A-40B depict how the sensor applicator 102 might be shipped to and received by the user.

The applicator cap 210 may be configured to provide a barrier against outside contamination, and thereby maintains a sterile environment for the assembled sensor control device 3702 positioned within the sensor applicator 102. The applicator cap 210 may also create a dust-free environment during shipping and storage that prevents the adhesive patch 3710 (FIG. 40B) from becoming dirty. The applicator cap 210 may be threaded to the housing 208 and include a tamper ring 4002. Upon rotating (e.g., unscrewing) the applicator cap 210 relative to the housing 208, the tamper ring 4002 may shear and thereby free the applicator cap 210 from the sensor applicator 102.

As shown in FIG. 40B, the sensor 3716 and the sharp 3908 are already incorporated into the assembled sensor control device 3702. Consequently, there is no need for a two-piece architecture system that requires the sensor tray 202 (FIG. 2) or a user to finally assemble the sensor control device 3702 as shown in and described with reference to FIGS. 2A-2D. Rather, according to the present disclosure, the sensor control device 3702 may be fully sterilized while loaded in the sensor applicator 102 prior to being packaged for shipment to a user.

More specifically, the sensor control device 3702 may be subjected to radiation sterilization 4004 while loaded (positioned) within the sensor applicator 102 to sterilize the sensor 3716 and the sharp 3908. The radiation sterilization 4004 may comprise, for example, e-beam irradiation, but other methods of sterilization may alternatively be used including, but not limited to, gamma ray irradiation, low energy X-ray irradiation, or any combination thereof.

In some embodiments, as illustrated, the radiation sterilization 4004 may be applied to the sensor control device 3702 through the applicator cap 210 and otherwise through a proximal end 4006 of the applicator cap 210. The applicator cap 210 may be made of any material that allows radiation to pass therethrough. In at least one embodiment, for example, cap 210 may be made of a thermoplastic. The radiation sterilization 4004 may propagate through the applicator cap 210 and impinge upon the sensor control device 3702 to inactivate or kill microorganisms or other contaminants that may be present on the sensor 3716 and the sharp 3908.

In some embodiments, the radiation sterilization 4004 may comprise electron beam (e-beam) irradiation. E-beam irradiation is a penetrating process that allows the sensor control device 3702 to be already mounted within the sensor applicator 102 before the irradiation process. By sterilizing the sensor control device 3702 after it has been packaged, the possibility of contamination during the time between sterilization and packaging is reduced.

Figure 41A:
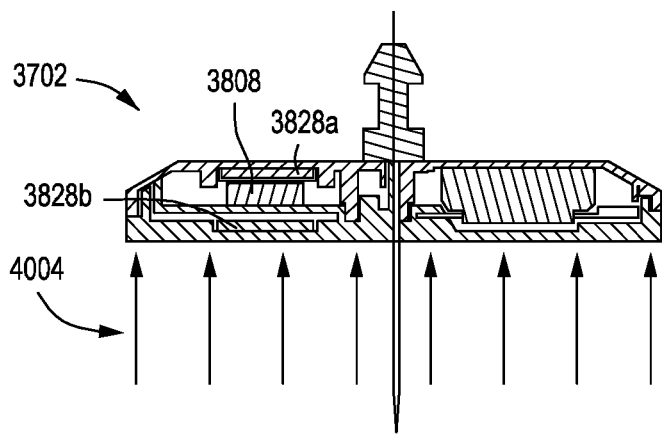
FIGS. 41A and 41B are enlarged cross-sectional views of the sensor control device during example radiation sterilization.
Figure 41B:
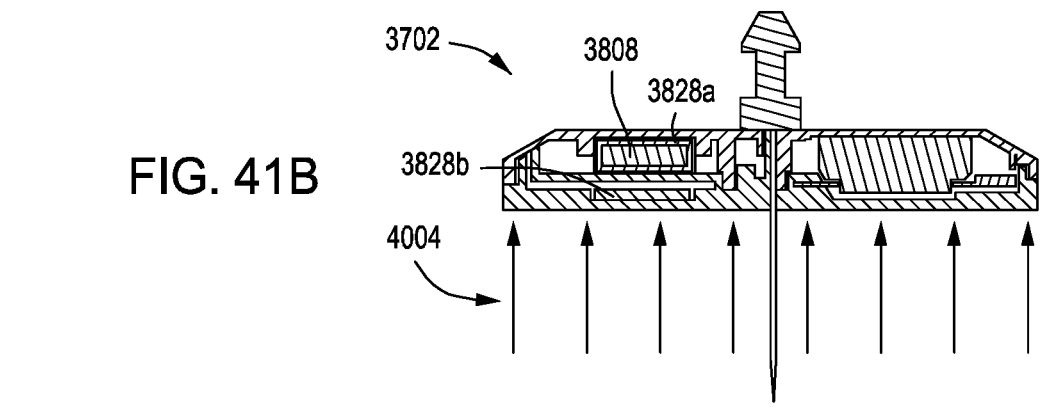

FIGS. 41A and 41B are enlarged cross-sectional views of the sensor control device 3702 during example radiation sterilization 4004, according to one or more embodiments of the present disclosure. In one aspect, one or more e-beam accelerators may be used to generate the radiation sterilization 4004 and, more particularly, to accelerate electrons into a concentrated highly charged electron stream. As materials pass through the stream of electrons, energy from the stream is absorbed and the absorption of this energy alters chemical and biological bonds. At certain levels of absorption, also known as the "absorbed dose," DNA chains and reproductive cells of microorganisms are destroyed, and thereby effectively sterilizing the target device or package. The irradiation dosage is important, as too low of a dosage may not result in complete sterilization, while too high of a dosage may result in adverse effects on the materials of the sensor control device 3702 and the packaging (the applicator cap 210 of FIG. 40B) being sterilized.

The electromagnetic shields 3828a,b included within the sensor control device 3702 may prove advantageous in shielding and otherwise protecting sensitive electronic components, such as the data processing unit 3808, while the sensor control device 3702 is subjected to the radiation sterilization 4004.

In FIG. 41A, one or both of the first and second shields 3828a,b may help shield the data processing unit 3808 from the absorbed dose of radiation from the radiation sterilization 4004. More specifically, the electromagnetic shields 3828a,b may be aligned with and otherwise positioned to block or otherwise mitigate radiation exposure that might otherwise damage the data processing unit 3808. In the illustrated embodiment, the radiation energy of the radiation sterilization 4004 propagates normal to the data processing unit 3808, and at least the second shield 3828b interposes the data processing unit 3808 and the source of the radiation sterilization 4004.

In FIG. 41B, the first shield 3828a covers and otherwise encapsulates the data processing unit 3808 and thereby helps shield the data processing unit 3808 from the absorbed dose of radiation from the radiation sterilization 4004. More specifically, by forming an enclosure around the data processing unit 3808, the first shield 3828a may be positioned to block or otherwise mitigate radiation exposure that might otherwise damage the data processing unit 3808. In such embodiments, the second shield 3828b may not be necessary.

The e-beam irradiation process of the radiation sterilization 4004 may include a continuous exposure or an intermittent exposure, and the e-beam accelerator may be of a continuous or a varying power, depending upon available machinery and determinations to achieve the desired internal and surface dosage limitations. The penetration power of e-beam irradiation correlates to the density of the underlying material being subjected to the radiation sterilization 4004 and the energy level of the e-beam accelerator. The larger and denser the material, the higher the energy the e-beam accelerator must output to achieve full penetration.

Figure 42:
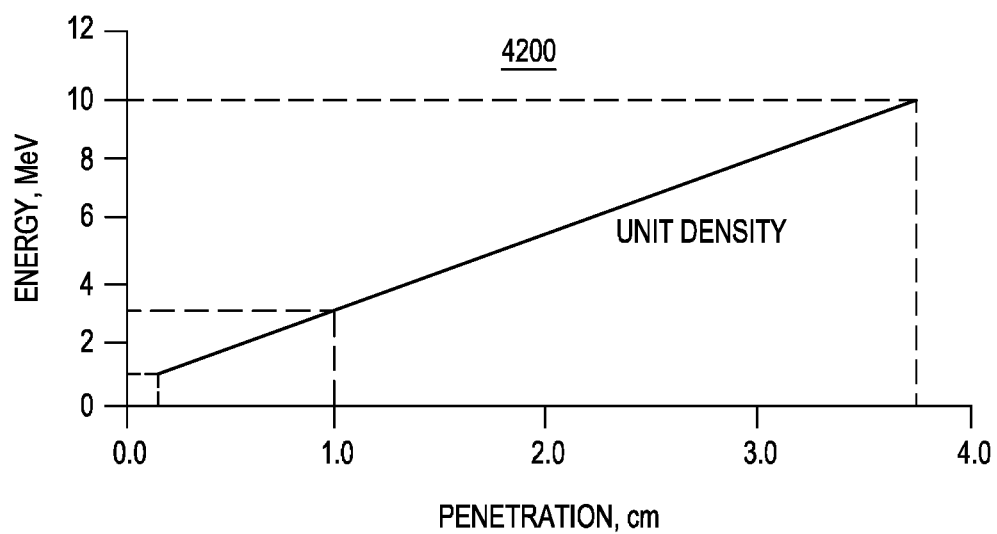
FIG. 42 is a plot that graphically depicts approximate penetration depth as a function of e-beam energy level for a one-sided e-beam sterilization (or irradiation) process.

FIG. 42 is a plot 4200 that graphically depicts an approximation of penetration depth as a function of the energy level of e-beam radiation sterilization for unit density materials such as water. As indicated by the plot 4200, the higher the energy level of the electrons of the e-beam radiation sterilization, the deeper the radiation will penetrate into a selected material. Most standard e-beam sterilization processes operate at a 10 mega electron-volt (MeV) energy level which, according to the plot 4200, will penetrate into a given material about 3.8 cm for a unit density material such as water (density=1 g/cc).

According to embodiments of the present disclosure, e-beam sterilization (e.g., the radiation sterilization 4004 of FIGS. 40B and 41A-41B) may be undertaken at lower energy levels and nonetheless achieve comparable or commensurate sterilization dose achieved at high energy levels (e.g., 10 MeV or more). In some embodiments, for example, radiation sterilization may be undertaken at an energy level ranging between about 0.5 MeV and about 3.0 MeV and can achieve an equivalent dose to irradiating at higher energy levels. In yet other embodiments, the radiation sterilization may be undertaken at an energy level as low as 0.1 MeV, without departing from the scope of the disclosure.

According to the plot 4200, dosing at an energy level ranging between about 0.5 MeV and about 3.0 MeV equates to a penetration depth ranging between about 0.2 cm and about 1.0 cm for a material with density of 1 g/cc. Accordingly, at lower energy levels, it may be possible to shield sensitive electronic components with high density materials and small thicknesses such that little or no radiation penetrates the shield.

In view of the foregoing, the material and configuration of the shields 3828a,b (FIGS. 41A-41B) may be selected and optimized (tuned) in view of low energy radiation sterilization to protect the data processing unit 3808 (FIGS. 41A-41B). The penetration depth for a given material may be determined for example in the range of 0.2 to 2.0 MeV, by Equation (1) below obtained from ISO/ASTM 51649: 2005 (E) "Standard Practice for Dosimetry in an Electron Beam Facility for Radiation Processing at Energies between 300 keV and 25 MeV."

$$Rp = \frac{(0.507E - 0.1243)}{\rho} \quad \text{Equation (1)}$$

where "E" is the energy level (MeV) of the e-beam accelerator and "p" is the density (g/cm³) of the given material. Equation 1 is derived from a Monte Carlo simulation for one-sided irradiation through polystyrene. As such, the computed penetration depth is an approximate value for polymeric and higher density materials. Based on the foregoing equation, Table 1 lists various materials that may be candidate materials for the shields 3828a,b, their respective densities in g/cc, and their calculated penetration depth Rp at energy levels E of 1 MeV, 2 MeV, and 5 MeV:

TABLE 1

| Element | Density (g/cc) | Penetration Depth (mm) | | |
|---|---|---|---|---|
| | | 1 MeV | 2 MeV | 5 MeV |
| Carbon | 2.3 | 1.69 | 3.94 | 10.67 |
| Aluminum | 2.7 | 1.42 | 3.30 | 8.93 |
| Iron | 7.9 | 0.49 | 1.13 | 3.06 |
| Stainless Steel | 8.1 | 0.47 | 1.10 | 2.99 |
| Copper | 8.9 | 0.43 | 1.00 | 2.71 |
| Lead | 11.4 | 0.34 | 0.78 | 2.12 |
| Tantalum | 16.7 | 0.23 | 0.53 | 1.45 |
| Tungsten | 19.4 | 0.20 | 0.46 | 1.25 |
| Osmium | 22.6 | 0.17 | 0.39 | 1.07 |

As indicated in Table 1, the higher the density of the material, the lower the penetration depth and, consequently, the thinner the material can be to adequately shield sensitive electronic components at lower energy levels. Moreover, the thinner the shield material, the thinner the product (e.g., the sensor control device 3702) can be.

According to one or more embodiments of the present disclosure, the shields 3828a,b that protect the data processing unit 3808 from radiation exposure may be any non-magnetic metal with a density of at least 2.0 g/cc. In other embodiments, the shields 3828a,b may be a non-magnetic metal with a density of at least 5.0 g/cc. According to Table 1, suitable materials for the shields 3828a,b can include, but are not limited to, iron, stainless steel, copper, lead, tantalum, tungsten, and osmium. Because of its low cost and availability, stainless steel may be a preferred material. In some embodiments, the material for the shields 3828a,b may be any non-magnetic metal with a density ranging between about 2.0 g/cc and about 23.0 g/cc. In other embodiments, the material for the shields 3828a,b may be a non-magnetic metal with a density ranging between about 5.0 g/cc and about 15.0 g/cc.

In other embodiments, the shields 3828a,b that protect the data processing unit 3808 from radiation exposure may be a metal-filled thermoplastic polymer where the shielding metal exhibits a density of at least 2.0 g/cc. In such embodiments, the metal-filled thermoplastic polymer may be, but not limited to, polyamide, polycarbonate, or polystyrene. In such embodiments, the shields 3828a,b may be fabricated by mixing the shielding material (metal) in an adhesive matrix and dispensing the combination onto shaped components or otherwise directly onto the data processing unit 3808. Moreover, in such embodiments, the shield(s) 3828a,b may comprise an enclosure that encapsulates (or substantially encapsulates) the data processing unit 3808.

Figure 43:
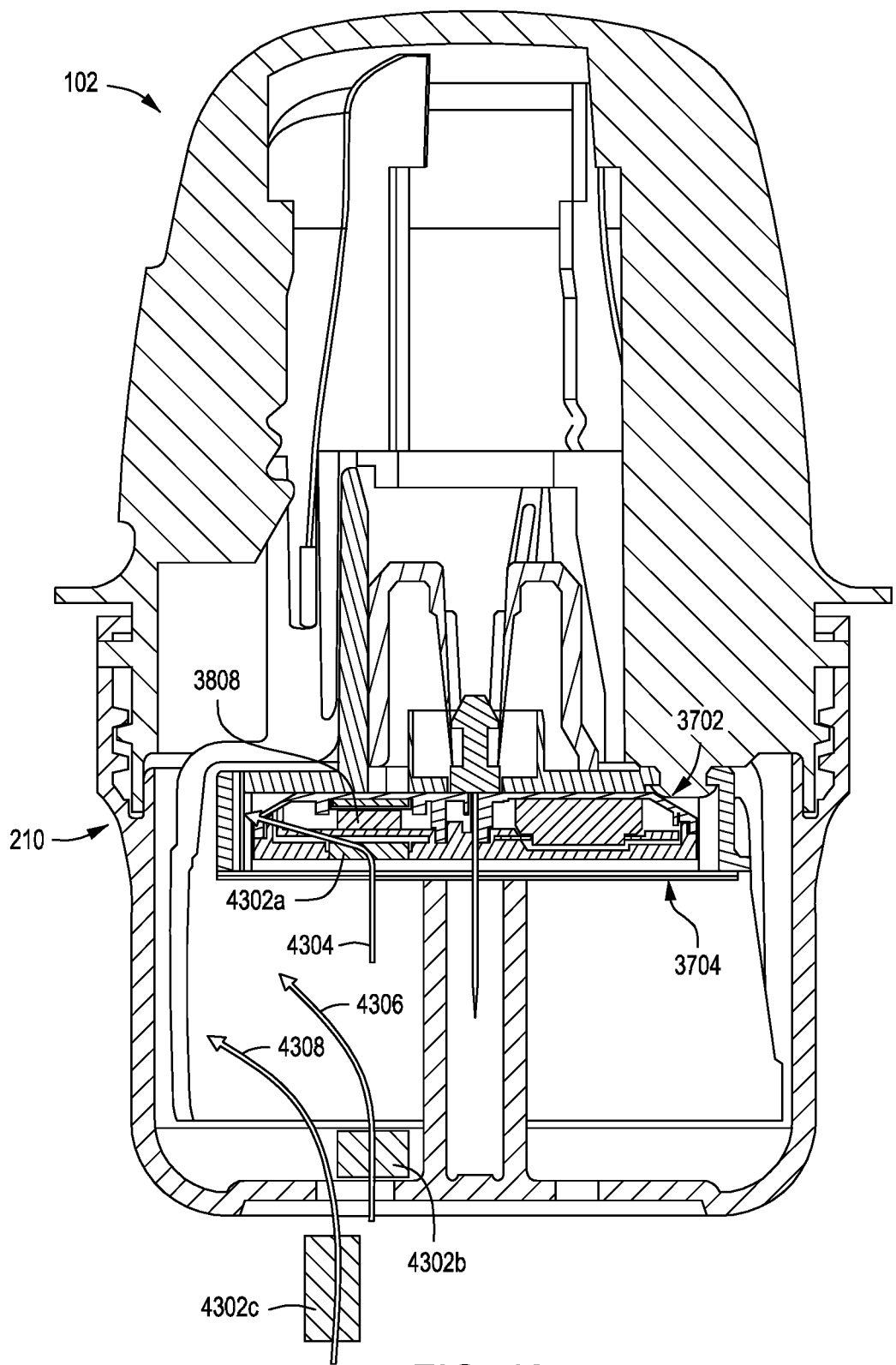
FIG. 43 is a cross-sectional side view of a sensor applicator with the pre-assembled sensor control device of FIGS. 37A-37C arranged therein, according to one or more additional embodiments.

FIG. 43 is a cross-sectional view of the sensor control device 3702 mounted within the sensor applicator 102 with the applicator cap 210 secured thereto, according to one or more additional embodiments. Similar to the embodiments of FIGS. 41A-41B, one or more shields may be used to protect sensitive electronic components of the sensor control device 3702. Unlike the embodiments of FIGS. 41A-41B, however, the shields of FIG. 43 are magnetic shields configured to divert propagating radiation from the radiation sterilization 4004 (FIGS. 40B and 41A-41B) away from or otherwise around the data processing unit 3808.

More specifically, it is possible to locally deflect an electron beam away from a component of interest, such as the data processing unit 3808, by generating a static magnetic field. Charged particles experience a force when travelling through a magnetic field, and the direction of this force is perpendicular to the direction of the field and the velocity of the charge. In equation form, a particle with mass m and charge q moving with velocity v in a magnetic field B experiences a force characterized by the following equation:

$$F = qv \times B \quad \text{Equation (2)}$$

This is a vector equation which indicates that the magnitude of the force F is:

$$F = (qvB)\sin\theta \quad \text{Equation (3)}$$

where θ is the angle between the velocity v and the magnetic field B, and the direction of the force is perpendicular to both the velocity v and the magnetic field B (in a sense given by the right hand rule). An electron (charge −e) injected into a uniform magnetic field B and moving perpendicular to the field B experiences a force:

$$F = -evB \quad \text{Equation (4)}$$

Now the force F remains perpendicular to the velocity v and the electron moves in a circular path of radius R. The radial (centripetal) acceleration is then:

$$a = -\frac{v^2}{R} \quad \text{Equation (5)}$$

Now apply Newton's second law of motion:

$$F = ma \quad \text{Equation (6)}$$

$$evB = m\frac{v^2}{R} \quad \text{Equation (7)}$$

Thus, the radius R of the electron's path is:

$$R = \frac{mv}{eB} \quad \text{Equation (8)}$$

Accordingly, an electron having a mass m with a charge e and traveling at a velocity v through a magnetic field B, perpendicular to the direction of the velocity v, will be deflected in a circle of radius R and at a tangent to this circle once outside the influence of the magnetic field B. The magnetic field may be placed (generated) anywhere along the path of the propagating radiation (e.g., the e-beam) before it can strike the component of interest (e.g., the data processing unit 3808).

In one embodiment, a first magnet 4302a may be arranged within the electronics housing 3704 adjacent the data processing unit 3808 to generate a static magnetic field. In the illustrated embodiment, the first magnet 4302a is arranged where the second shield 3828b of FIGS. 41A-41B was placed. In such embodiments, a propagating radiation beam 4304 (e.g., e-beam) may pass through the first magnet 4302a and the static magnetic field generated by the first magnet 4302a will cause the radiation beam 4304 to be diverted away from the data processing unit 3808.

In another embodiment, or in addition thereto, a second magnet 4302b may be arranged within the applicator cap 210 to generate a static magnetic field. In the illustrated embodiment, the second magnet 4302b is positioned to interpose the radiation source (e.g., an e-beam accelerator) and the data processing unit 3808. A propagating radiation beam 4306 (e.g., e-beam) may pass through the second magnet 4302b and the static magnetic field generated by the second magnet 4302b will cause the radiation beam 4306 to be diverted away from the data processing unit 3808.

In yet other embodiments, or in addition thereto, a third magnet 4302c may be arranged external to the applicator cap 210 and the sensor applicator 102 to generate a static magnetic field. In the illustrated embodiment, the third magnet 4302c is positioned outside of the applicator cap 210 and otherwise interposes the radiation source (e.g., an e-beam accelerator) and the data processing unit 3808. A propagating radiation beam 4308 (e.g., e-beam) may pass through the third magnet 4302c and the static magnetic field generated by the third magnet 4302c will cause the radiation beam 4308 to be diverted away from the data processing unit 3808.

As will be appreciated, precise alignment of the magnets 4302a-c relative to sensor control device 3702 would need to be taken into consideration and sufficient margin be applied to the location and field strength accordingly.

Embodiments disclosed herein include:

Q. A sensor control device that includes an electronics housing, a printed circuit board positioned within the electronics housing and having a data processing unit mounted thereto, a sensor extending from a bottom of the electronics housing, a sharp module removably coupled to the electronics housing and having a sharp that extends through the electronics housing and receives a portion of the sensor extending from the bottom of the electronics housing, and at least one shield positioned within the electronics housing to protect the data processing unit from radiation from a radiation sterilization process.

R. An analyte monitoring system that includes a sensor applicator, a sensor control device positioned within the sensor applicator and including an electronics housing, a printed circuit board positioned within the electronics housing and having a data processing unit mounted thereto, a sensor extending from a bottom of the electronics housing, a sharp module removably coupled to the electronics housing and having a sharp that extends through the electronics housing and receives a portion of the sensor extending from the bottom of the electronics housing, and at least one shield positioned within the electronics housing to protect the data processing unit from radiation from a radiation sterilization process. The analyte monitoring system further including a cap coupled to the sensor applicator to provide a barrier that seals the sensor control device within the sensor applicator.

S. A method of preparing an analyte monitoring system including loading a sensor control device into a sensor applicator, the sensor control device including an electronics housing, a printed circuit board positioned within the electronics housing and having a data processing unit mounted thereto, a sensor extending from a bottom of the electronics housing, a sharp module removably coupled to the electronics housing and having a sharp that extends through the electronics housing and receives a portion of the sensor extending from the bottom of the electronics housing, and at least one shield positioned within the electronics housing. The method further including securing a cap to the sensor applicator and thereby providing a barrier that seals the sensor control device within the sensor applicator, sterilizing the sensor and the sharp with radiation sterilization while the sensor control device is positioned within the sensor applicator, and shielding the data processing unit with the at least one shield from radiation from the radiation sterilization.

T. A sensor control device that includes an electronics housing having a shell matable with a mount, a printed circuit board positioned within the electronics housing and defining a battery aperture sized to receive a battery, an axial battery contact extending into the battery aperture to provide electrical communication, and a radial battery contact extending into the battery aperture to provide electrical communication.

Each of embodiments Q, R, S, and T may have one or more of the following additional elements in any combination: Element 1: further comprising a battery aperture defined in the printed circuit board, a battery received within the battery aperture, an axial battery contact coupled to the printed circuit board and extending into the battery aperture to facilitate electrical communication, and a radial battery contact coupled to the printed circuit board and extending into the battery aperture to facilitate electrical communication. Element 2: further comprising one or more sensor contacts arranged on a flag of the sensor, and one or more circuitry contacts provided on the printed circuit board and engageable with the one or more sensor contacts to facilitate direct connection between the sensor and the printed circuit board. Element 3: wherein the at least one shield interposes the data processing unit and a radiation source that facilitates radiation sterilization. Element 4: wherein the at least one shield comprises a first shield facing a bottom of the printed circuit board and a second shield facing a top of the printed circuit board, and wherein the data processing unit interposes the first and second shields. Element 5: wherein the at least one shield comprises an enclosure that encapsulates the data processing unit. Element 6: wherein the at least one shield is made of a non-magnetic metal that exhibits a density ranging between about 2 g/cc and about 23 g/cc. Element 7: wherein the at least one shield is made of thermoplastic polymer mixed with a non-magnetic metal having a density of at least 2.0 g/cc. Element 8: further comprising a plurality of electronic modules coupled to top and bottom surfaces of the printed circuit board. Element 9: wherein the electronics housing comprises a mount and the shell secured together and sealed with an adhesive. Element 10: wherein the at least one shield comprises a magnet arranged to divert the radiation away from the data processing unit.

Element 11: wherein the at least one shield interposes the data processing unit and a radiation source that facilitates radiation sterilization of the sensor and the sharp. Element 12: wherein the at least one shield is made with a non-magnetic metal having a density of at least 2.0 g/cc. Element 13: wherein the sensor control device is subjected to the radiation sterilization while positioned within the sensor applicator and at an energy level ranging between about 0.1 MeV and about 10.0 MeV. Element 14: wherein the at least one shield comprises a magnet arranged to divert the radiation away from the data processing unit.

Element 15: wherein the at least one shield interposes the data processing unit and a radiation source that facilitates the radiation sterilization, and wherein the at least one shield is made with a non-magnetic metal having a density of at least 2.0 g/cc, the method further comprising undertaking the radiation sterilization at an energy level ranging between about 0.1 MeV and about 10.0 MeV. Element 16: wherein the electronics housing comprises a shell matable with a mount, and wherein loading the sensor control device into the sensor applicator is preceded by sealing the shell to the mount with an adhesive and thereby generating a sterile barrier. Element 17: wherein the at least one shield comprises a magnet, and wherein shielding the data processing unit with the at least one shield comprises generating a static magnetic field with the magnet, and diverting the radiation away from the data processing unit with the static magnetic field.

Element 18: further comprising a plurality of electronic modules coupled to top and bottom surfaces of the printed circuit board. Element 19: wherein a plurality of module pockets are defined in an inner surface of the mount to accommodate the plurality of electronic modules. Element 20: wherein the mount and the shell are secured together and sealed with an adhesive. Element 21: wherein the shell defines a reference feature extending a short distance into an interior of the electronics housing. Element 22: further comprising an adhesive patch positioned on an underside of the mount. Element 23: wherein the shell defines an angled outer periphery. Element 24: further comprising a sensor partially arranged within the electronics housing and having a flag with one or more sensor contacts, and a compliant member arranged to interpose the flag and an inner surface of the shell and provide a passive biasing load against the flag to force the one or more sensor contacts into engagement with a corresponding one or more circuitry contacts provided on the printed circuit board. Element 25: wherein the compliant member comprises an elastomeric O-ring. Element 26: further comprising at least one shield positioned within the electronics housing, and a shield locator defined in an inner surface of the shell or the mount to accommodate at least a portion of the at least one shield. Element 27: wherein the at least one shield comprises a first shield and a second shield, and wherein the shield locator comprises a first shield locator defined in an inner surface of the shell to accommodate at least a portion of the first shield, and a second shield locator defined in an inner surface of the mount to accommodate at least a portion of the second shield. Element 28: further comprising one or more clocking receptacles defined on one of the mount or the shell, and one or more clocking posts defined on the other of the mount or the shell and sized to be received within the one or more clocking receptacles to properly align the shell to the mount. Element 29: wherein a battery locator is defined in an inner surface of at least one of the shell and the mount and sized to accommodate a portion of the battery. Element 30: wherein the inner surface of the at least one of the shell and the mount further defines a contact pocket adjacent the battery locator and sized to accommodate a portion of the axial contact. Element 31: further comprising a plurality of carrier grip features defined about an outer periphery of the mount and axially offset from a bottom of the mount.

By way of non-limiting example, exemplary combinations applicable to Q, R, S, and T include: Element 3 with Element 4; Element 12 with Element 13; Element 18 and Element 19; Element 20 and Element 21; Element 24 and Element 25; Element 26 and Element 27; and Element 28 and Element 30.

One-Piece Analyte Monitoring Systems with Sensor Cap

Referring briefly again to FIGS. 1 and 2A-2G, for the two-piece architecture system, the sensor tray 202 and the sensor applicator 102 are provided to the user as separate packages, thus requiring the user to open each package and finally assemble the system. In some applications, the discrete, sealed packages allow the sensor tray 202 and the sensor applicator 102 to be sterilized in separate sterilization processes unique to the contents of each package and otherwise incompatible with the contents of the other. More specifically, the sensor tray 202, which includes the plug assembly 207, including the sensor 110 and the sharp 220, may be sterilized using radiation sterilization, such as electron beam (or "e-beam") irradiation. Radiation sterilization, however, can damage the electrical components arranged within the electronics housing of the sensor control device 104. Consequently, if the sensor applicator 102, which contains the electronics housing of the sensor control device 104, needs to be sterilized, it may be sterilized via another method, such as gaseous chemical sterilization using, for example, ethylene oxide. Gaseous chemical sterilization, however, can damage the enzymes or other chemistry and biologics included on the sensor 110. Because of this sterilization incompatibility, the sensor tray 202 and the sensor applicator 102 are commonly sterilized in separate sterilization processes and subsequently packaged separately, which requires the user to finally assemble the components for use.

According to embodiments of the present disclosure, the sensor control device 104 may be modified to provide a one-piece architecture that may be subjected to sterilization techniques specifically designed for a one-piece architecture sensor control device. A one-piece architecture allows the sensor applicator 102 and the sensor control device 104 to be shipped to the user in a single, sealed package that does not require any final user assembly steps. Rather, the user need only open one package and subsequently deliver the sensor control device 104 to the target monitoring location. The one-piece system architecture described herein may prove advantageous in eliminating component parts, various fabrication process steps, and user assembly steps. As a result, packaging and waste are reduced, and the potential for user error or contamination to the system is mitigated.

Figure 44:
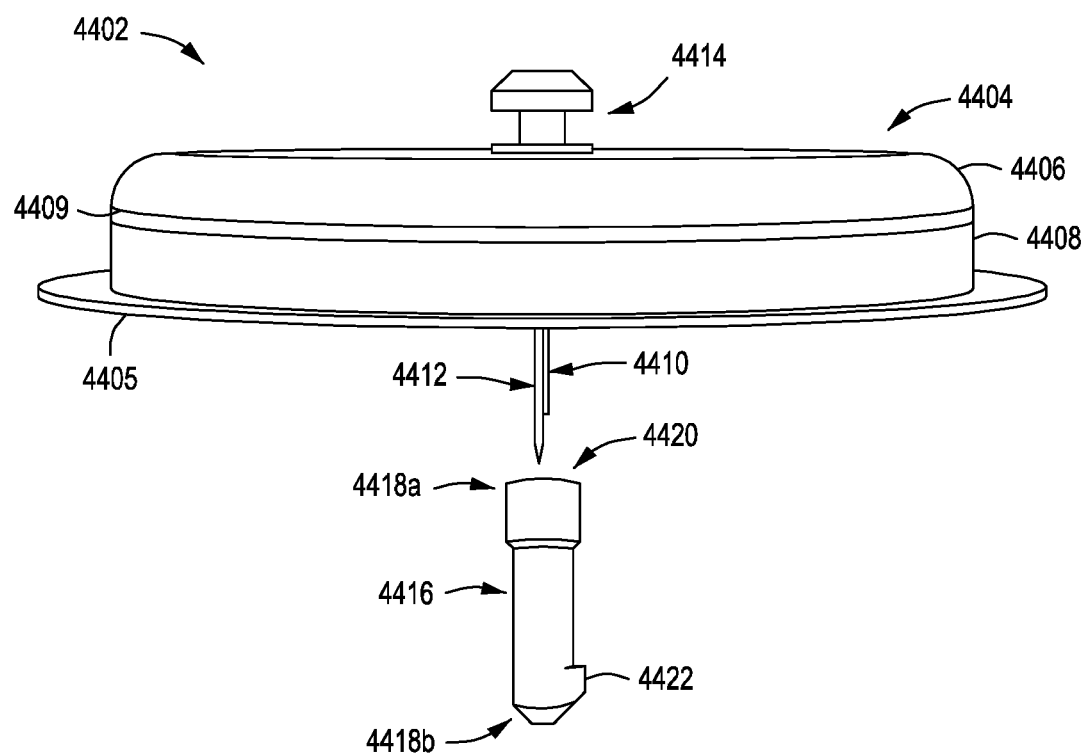
FIG. 44 is a side view of an example sensor control device.

FIG. 44 is a side view of an example sensor control device 4402, according to one or more embodiments of the present disclosure. The sensor control device 4402 may be similar in some respects to the sensor control device 104 of FIG. 1 and therefore may be best understood with reference thereto. Moreover, the sensor control device 4402 may replace the sensor control device 104 and, therefore, may be used in conjunction with the sensor applicator 102 of FIG. 1, which may deliver the sensor control device 4402 to a target monitoring location on a user's skin.

Unlike the sensor control device 104 of FIG. 1, however, the sensor control device 4402 may comprise a one-piece system architecture not requiring a user to open multiple packages and finally assemble the sensor control device 4402 prior to application. Rather, upon receipt by the user, the sensor control device 4402 may already be fully assembled and properly positioned within the sensor applicator 102 (FIG. 1). To use the sensor control device 4402, the user need only open one barrier (e.g., the applicator cap 210 of FIG. 2B) before promptly delivering the sensor control device 4402 to the target monitoring location for use.

As illustrated, the sensor control device 4402 includes an electronics housing 4404 that is generally disc-shaped and may have a circular cross-section. In other embodiments, however, the electronics housing 4404 may exhibit other cross-sectional shapes, such as ovoid or polygonal, without departing from the scope of the disclosure. The electronics housing 4404 may be configured to house or otherwise contain various electrical components used to operate the sensor control device 4402. In at least one embodiment, an adhesive patch 4405 may be arranged at the bottom of the electronics housing 4404. The adhesive patch 4405 may be similar to the adhesive patch 108 of FIG. 1, and may thus help adhere the sensor control device 4402 to the user's skin for use.

The electronics housing 4404 may include a shell 4406 and a mount 4408 that is matable with the shell 4406. The shell 4406 may be secured to the mount 4408 via a variety of ways, such as a snap fit engagement, an interference fit, sonic welding, one or more mechanical fasteners (e.g., screws), a gasket, an adhesive, or any combination thereof. In some cases, the shell 4406 may be secured to the mount 4408 such that a sealed interface therebetween is generated. In such embodiments, a seal member 4409, such as a gasket or an adhesive, may be positioned at or near the outer diameter (periphery) of the shell 4406 and the mount 4408, and securing the two components together may compress the seal member 4409 and thereby generate a sealed interface. The seal member 4409 secures the shell 4406 to the mount 4408 and provides structural integrity, but may also isolate the interior of the electronics housing 4404 from outside contamination. If the sensor control device 4402 is assembled in a controlled environment, there may be no need to terminally sterilize the internal electrical components. Rather, the sealed interface may provide a sufficient sterile barrier for the assembled electronics housing 4404.

The sensor control device 4402 may further include a sensor 4410 (partially visible) and a sharp 4412 (partially visible) used to help deliver the sensor 4410 transcutaneously under a user's skin during application of the sensor control device 4402. As illustrated, corresponding portions of the sensor 4410 and the sharp 4412 extend distally from the electronics housing 4404 and, more particularly, from the bottom of the mount 4408. The sharp 4412 may include a sharp hub 4414 configured to secure and carry the sharp 4412. To couple the sharp 4412 to the sensor control device 4402, the sharp 4412 may be advanced axially through the electronics housing 4404 until the sharp hub 4414 engages an upper portion of the shell 4406. As the sharp 4412 penetrates the electronics housing 4404, the exposed portion of the sensor 4410 may be received within a hollow or recessed (arcuate) portion of the sharp 4412. The remaining portion of the sensor 4410 is arranged within the interior of the electronics housing 4404.

The sensor control device 4402 may further include a sensor cap 4416, as shown exploded (detached). The sensor cap 4416 may be removably coupled to the sensor control device 4402 (e.g., the electronics housing 4404) at or near the bottom of the mount 4408. As illustrated, the sensor cap 4416 may comprise a generally cylindrical and elongate body having a first end 4418a and a second end 4418b opposite the first end 4418a. The first end 4418a may be open to provide access into an inner chamber 4420 defined within the body. In contrast, the second end 4418b may be closed and may provide or otherwise define an engagement feature 4422. As described herein, the engagement feature 4422 may be configured to help the sensor cap 4416 mate with the cap (e.g., the applicator cap 210 of FIG. 2B) of a sensor applicator (e.g., the sensor applicator 102 of FIGS. 1 and 2A-2G) such that the sensor cap 4416 is removed from the sensor control device 4402 upon removing the cap from the sensor applicator. While the engagement feature 4422 is shown at or near the second end 4418b of the sensor cap 4416, the engagement feature 4422 may alternatively be positioned at an intermediate location between the first and second ends 4418a,b.

As discussed in more detail below, the sensor cap 4416 may provide a sealed barrier surrounding and protecting the exposed portions of the sensor 4410 and the sharp 4412 from gaseous chemical sterilization. The sensor cap 4416 helps form a sealed sub-assembly that can first be sterilized using radiation sterilization, following which components of the sensor control device 4402 that are sensitive to radiation sterilization may be assembled to the sealed subassembly and then subjected to gaseous chemical sterilization.

Figure 45:
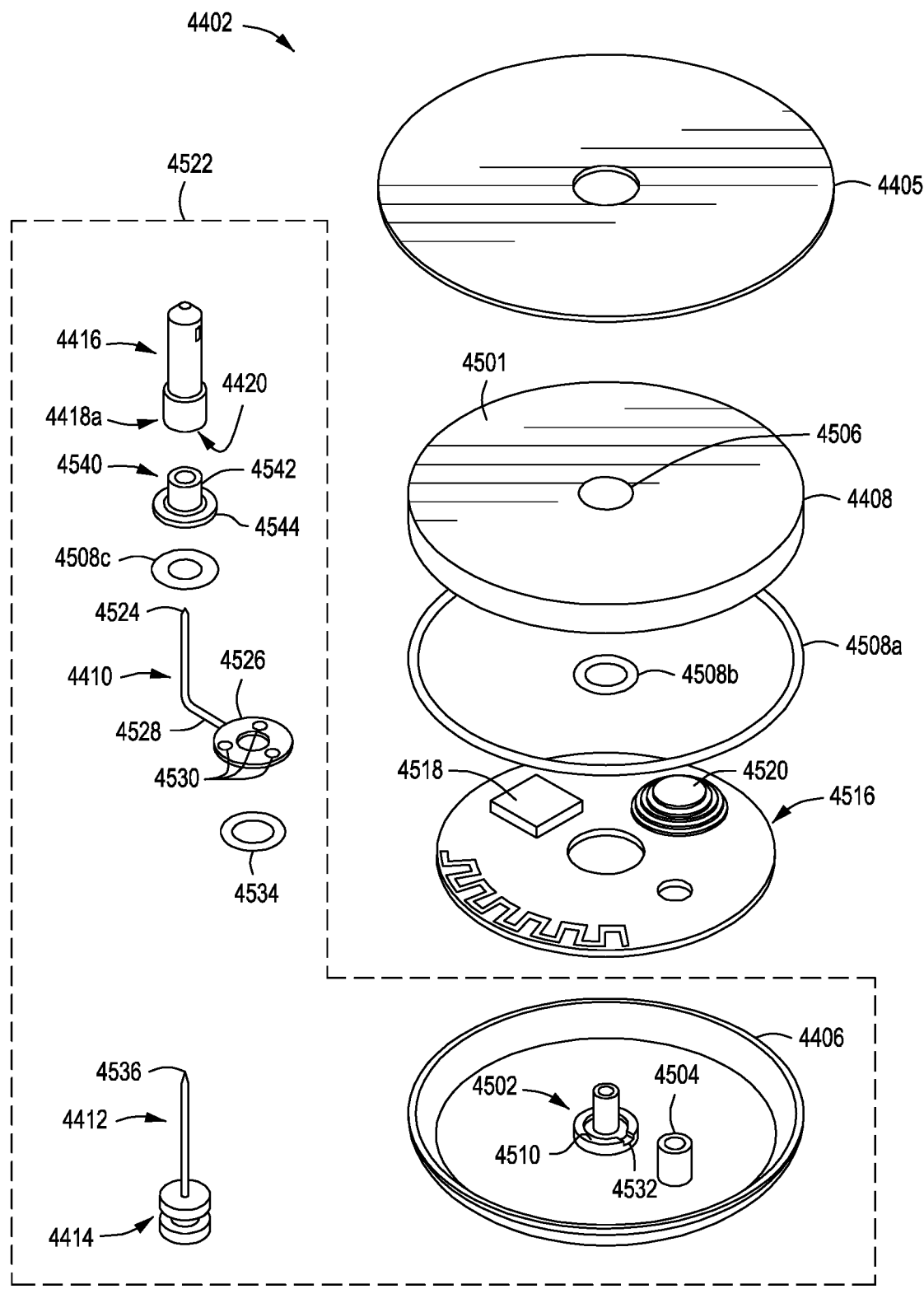
FIG. 45 is an exploded view of the sensor control device of FIG. 44.

FIG. 45 is an exploded view of the sensor control device 4402, according to one or more embodiments. The shell 4406 and the mount 4408 operate as opposing clamshell halves that enclose or otherwise substantially encapsulate the various electronic components of the sensor control device 4402. The adhesive patch 4405 may be applied to a bottom 4501 of the mount 4408.

As illustrated, the shell 4406 may provide or otherwise define a sharp and sensor locator 4502 and a clocking receptacle 4504. The sharp and sensor locator 4502 may be configured to receive portions of both the sharp 4412 and the sensor 4410. Moreover, the sharp and sensor locator 4502 may be configured to align with and be partially received within a central aperture 4506 defined in the mount 4408. Similarly, the clocking receptacle 4504 may be configured to align with and be received within a clocking post (not shown) defined on the inner surface of the mount 4408. Mating the sharp and sensor locator 4502 with the central aperture 4506, and simultaneously mating the clocking receptacle 4504 with the clocking post may help axially and rotationally align the shell 4406 with the mount 4408.

In some embodiments, a first seal member 4508a (i.e., the seal member 4409 of FIG. 44) may be applied to one or both of the shell 4406 and the mount 4408 to secure the two components together. As illustrated, the first seal member 4508a may be applied around the outer diameter (periphery) of the shell 4406, the mount 4408, or both. In another embodiment, or in addition thereto, a second seal member 4508b may be used to seal the interface between the sharp and sensor locator 4502 and the central aperture 4506. More specifically, the second seal member 4508b may be configured to provide a sealed interface at an annular ridge 4510 that circumscribes the sharp and sensor locator 4502. When the shell 4406 and the mount 4408 are mated, the annular ridge 4510 may juxtapose an opposing surface defined on the bottom of the mount 4408, and the seal member 4508b may facilitate a seal between the opposing structures. The seal members 4508a,b may comprise, for example, an adhesive or a gasket, and each may help secure the shell 4406 to the mount 4408 and seal the interface between the two components, and thereby isolate the interior of the electronics housing 4404 (FIG. 44) from outside contamination.

The sensor control device 4402 may include a printed circuit board (PCB) 4516 that may be arranged within the interior cavity formed by mating the shell 4406 and the mount 4408. A data processing unit 4518 and a battery 4520 may be mounted to or otherwise interact with the PCB 4516. The data processing unit 4518 may comprise, for example, an application specific integrated circuit (ASIC) configured to implement one or more functions or routines associated with operation of the sensor control device 4402. More specifically, the data processing unit 4518 may be configured to perform data processing functions, where such functions may include, but are not limited to, filtering and encoding of data signals, each of which corresponds to a sampled analyte level of the user. The data processing unit 4518 may also include or otherwise communicate with an antenna for communicating with the reader device 106 (FIG. 1).

The battery 4520 may provide power to the sensor control device 4402 and, more particularly, to the electronic components of the PCB 4516. While not shown in FIG. 45, other electronic modules or components may be mounted to the PCB 4516 and may include, but are not limited to, one or more resistors, transistors, capacitors, inductors, diodes, and switches.

The sensor control device 4402 may provide or otherwise include a sealed subassembly 4522 (outlined in dashed lines), which includes (among other component parts) the shell 4406, the sensor 4410, the sharp 4412, and the sensor cap 4416. As discussed in more detail below, the sealed subassembly 4522 may help isolate the sensor 4410 and the sharp 4412 within the inner chamber 4420 of the sensor cap 4416 during a gaseous chemical sterilization process, which might otherwise adversely affect the chemistry provided on the sensor 4410.

As illustrated, the sensor 4410 may include a tail 4524, a flag 4526, and a neck 4528 that interconnects the tail 4524 and the flag 4526. The tail 4524 may be configured to extend through the central aperture 4506 of the mount 4408 to be transcutaneously received beneath a user's skin. Moreover, the tail 4524 may have an enzyme or other chemistry included thereon to help facilitate analyte monitoring. The flag 4526 may include a generally planar surface having one or more sensor contacts 4530 (three shown) configured to align with and engage a corresponding one or more circuitry contacts (not shown) provided on the PCB 4516. In some embodiments, the sensor contacts 4530 may comprise a carbon impregnated polymer printed or otherwise digitally applied to the flag 4526.

In assembling the sealed subassembly, the flag 4526 may be received at the clocking receptacle 4504 and the tail 4524 may be received within the sharp and sensor locator 4502. In some embodiments, a groove 4532 may be defined in the annular ridge 4510 to receive and seat the neck 4528, and may allow the neck 4528 to be sealed below and on top and thereby isolate the enzymes and other chemistry included on the tail 4524.

The sensor control device 4402 may further include a compliant member 4534 receivable by the clocking receptacle 4504 and arranged to interpose the flag 4526 and the inner surface of the shell 4406. The compliant member 4534 may be configured to provide a passive biasing load against the flag 4526 that forces the sensor contacts 4530 into continuous engagement with the corresponding circuitry contacts on the PCB 4516. In the illustrated embodiment, the compliant member 4534 is an elastomeric O-ring, but could alternatively comprise any other type of biasing device or mechanism, such as a compression spring or the like. In other embodiments, however, the compliant member 4534 may form an integral part of the shell 4406, such as being an overmolded or co-molded portion of the shell 4406.

The sharp 4412 may include a sharp tip 4536 extendable through the coaxially aligned sharp and sensor locator 4502 and the central aperture 4506 of the shell 4406 and the mount 4408, respectively. In some embodiments, as the sharp tip 4536 extends through the sensor control device 4402, the tail 4524 of the sensor 4410 may be received within a hollow or recessed portion of the sharp tip 4536. The sharp tip 4536 may be configured to penetrate the skin while carrying the tail 4524 to put the active chemistry of the tail 4524 into contact with bodily fluids. The sharp tip 4536 may be advanced through the sensor control device 4402 until the sharp hub 4414 engages an upper surface of the shell 4406. In some embodiments, the sharp hub 4414 may form a sealed interface at the upper surface of the shell 4406.

In the illustrated embodiment, the sealed subassembly 4522 may further include a collar 4540 that provides or otherwise defines a column 4542 and an annular shoulder 4544 extending radially outward from the column 4542. In assembling the sealed subassembly 4522, at least a portion of the column 4542 may be received within the inner chamber 4420 of the sensor cap 4416 at the first end 4418*a*. The sensor cap 4416 may be removably coupled to the collar 4540 and separated from the collar 4540 prior to delivering the sensor control device 4402 to the target monitoring location on the user's skin. In some embodiments, the sensor cap 4416 may be removably coupled to the collar 4540 via an interference or friction fit. In other embodiments, the sensor cap 4416 may be threaded to the column 4542. In yet other embodiments, the sensor cap 4416 may be removably coupled to the collar 4540 with a frangible member (e.g., a shear ring) or substance that may be broken with minimal separation force (e.g., axial or rotational force). In such embodiments, for example, the sensor cap 4416 may be secured to the collar 4540 with a tag (spot) of glue or a dab of wax.

In some embodiments, a third seal member 4508*c* may interpose the annular shoulder 4544 and the annular ridge 4510 to form a sealed interface. In such embodiments, the third seal member 4508*c* may also extend (flow) into the groove 4532 defined in the annular ridge 4510 and thereby seal about the neck 4528 of the sensor 4410. Similar to the first and second seal members 4508*a,b*, the third seal member 4508*c* may comprise an adhesive or a gasket.

In some embodiments, however, the collar 4540 may be omitted from the sealed subassembly 4522 and the sensor cap 4416 may alternatively be removably coupled to the sharp and sensor locator 4502. In such embodiments, the sensor cap 4416 may be removably coupled to the sharp and sensor locator 4502 via an interference or friction fit, threading, with a frangible member or substance, or any combination thereof.

Figure 46A:
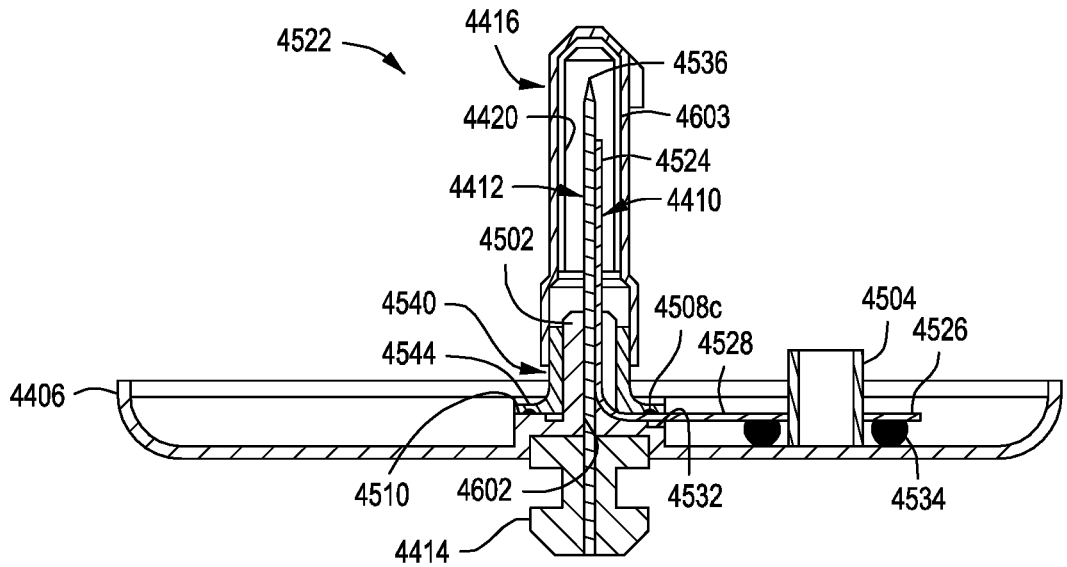
FIG. 46A is a cross-sectional side view of the assembled sealed subassembly of FIG. 45, according to one or more embodiments.

FIG. 46A is a cross-sectional side view of the assembled sealed subassembly 4522 of FIG. 45, according to one or more embodiments. To assemble the sealed subassembly 4522, the compliant member 4534 may first be received about the clocking receptacle 4504 and the flag 4526 of the sensor 4410 may subsequently be placed atop the compliant member 4534 and also about the clocking receptacle 4504. Alternatively, the compliant member 4534 may form part of the shell 4406 (e.g., co-molded, overmolded, etc.) at the clocking receptacle 4504, and the flag 4526 may be arranged thereon. The tail 4524 of the sensor 4410 may be received within the sharp and sensor locator 4502, and the neck 4528 may be seated within the groove 4532 defined in the annular ridge 4510.

The collar 4540 may then be extended over the sharp and sensor locator 4502 until the annular shoulder 4544 rests against the annular ridge 4510. In some embodiments, the third seal member 4508*c* may interpose the annular shoulder 4544 and the annular ridge 4510 to form a sealed interface, and the third seal member 4508*c* may also extend (flow) into the groove 4532 to form a seal about the neck 4528. The sensor cap 4416 may then be removably coupled to the collar 4540, as generally described above, such that portions of one or both of the collar 4540 and the sharp and sensor locator 4502 are received within the inner chamber 4420. In some embodiments, however, the collar 4540 may be omitted and the sensor cap 4416 may instead be received on the sharp and sensor locator 4502 and the third seal member 4508c may seal the interface(s) between the sensor cap 4416 and the sharp and sensor locator 4502.

Before or after assembling the sensor cap 4416, the sharp 4412 may be coupled to the sensor control device 4402 by extending the sharp tip 4536 through an aperture 4602 defined in the top of the shell 4406 and advancing the sharp 4412 through the sharp and sensor locator 4502 until the sharp hub 4414 engages a top surface of the shell 4406. In the illustrated embodiment, the top surface where the sharp hub 4414 engages the shell 4406 comprises a recessed portion of the shell 4406, but could alternatively comprise an upper surface that is level with adjacent portions of the shell 4406.

The inner chamber 4420 may be sized and otherwise configured to receive the tail 4524 and the sharp tip 4536. Moreover, the inner chamber 4420 may be sealed to isolate the sensor 4410 from substances that might adversely interact with the chemistry of the tail 4524. More specifically, the inner chamber 4420 may be sealed at the interface between the hub 4414 and the shell 4406, at the interface between the annular shoulder 4544 and the annular ridge 4510 (e.g., with the third seal member 4508c), and at the interface between the sensor cap 4416 and the collar 4540 (e.g., via an interference fit or the like). In some embodiments, a desiccant 4603 may be present within the inner chamber 4420 to maintain preferred humidity levels.

Once properly assembled, the sealed subassembly 4522 may be subjected to radiation sterilization to properly sterilize the sensor 4410 and the sharp 4412. Advantageously, this sterilization step may be undertaken apart from the other component parts of the sensor control device 4402 (FIG. 45) since radiation sterilization can damage sensitive electrical components associated with the PCB 4516 (FIG. 45), such as the data processing unit 4518 (FIG. 45).

Suitable radiation sterilization processes include, but are not limited to, electron beam (e-beam) irradiation, gamma ray irradiation, X-ray irradiation, or any combination thereof. In some embodiments, the sealed subassembly 4522 may be subjected to radiation sterilization prior to coupling the sensor cap 4416 to the collar 4540 (or the sharp and sensor locator 4502). In other embodiments, however, the sealed subassembly 4522 may be sterilized after coupling the sensor cap 4416 to the collar 4540 (or the sharp and sensor locator 4502). In such embodiments, the body of the sensor cap 4416 may comprise a material that permits propagation of radiation therethrough to facilitate radiation sterilization of the distal portions of the sensor 4410 and the sharp 4412. Suitable materials include, but are not limited to, a non-magnetic metal (e.g., aluminum, copper, gold, silver, etc.), a thermoplastic, ceramic, rubber (e.g., ebonite), a composite material (e.g., fiberglass, carbon fiber reinforced polymer, etc.), an epoxy, or any combination thereof. In some embodiments, the sensor cap 4416 may be transparent or translucent, but can otherwise be opaque, without departing from the scope of the disclosure.

Figure 46B:
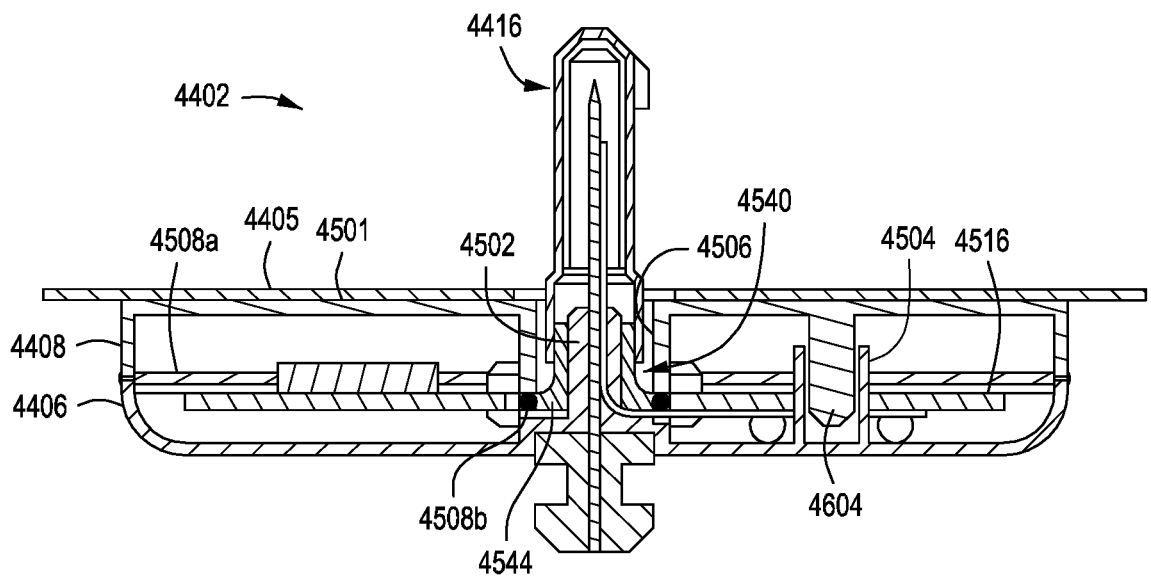
FIG. 46B is a cross-sectional side view of the fully assembled sensor control device of FIG. 44.

FIG. 46B is a cross-sectional side view of the fully assembled sensor control device 4402, according to one or more embodiments. Once assembled and properly sterilized, as discussed above, the sealed subassembly 4522 of FIG. 46A may be assembled to the remaining component parts of the sensor control device 4402. The PCB 4516 may be positioned within the shell 4406, and the mount 4408 may subsequently be secured to the shell 4406. To axially and rotationally align the shell 4406 with the mount 4408, the sensor cap 4416 may be aligned with and extended through the central aperture 4506 of the mount 4408. The sharp and sensor locator 4502 may then be received within the central aperture 4506, and the clocking receptacle 4504 may be mated with a clocking post 4604 defined by the mount 4408.

As discussed above, the first and second seal members 4508a,b may be used to secure the mount 4408 to the shell 4406 and also isolate the interior of the electronics housing 4404 from outside contamination. In the illustrated embodiment, the second seal member 4508b may interpose the annular shoulder 4544 of the collar 4540 and a portion of the mount 4408 and, more particularly, the central aperture 4506. The adhesive patch 4405 may then be applied to the bottom 4501 of the mount 4408.

Figure 47B:
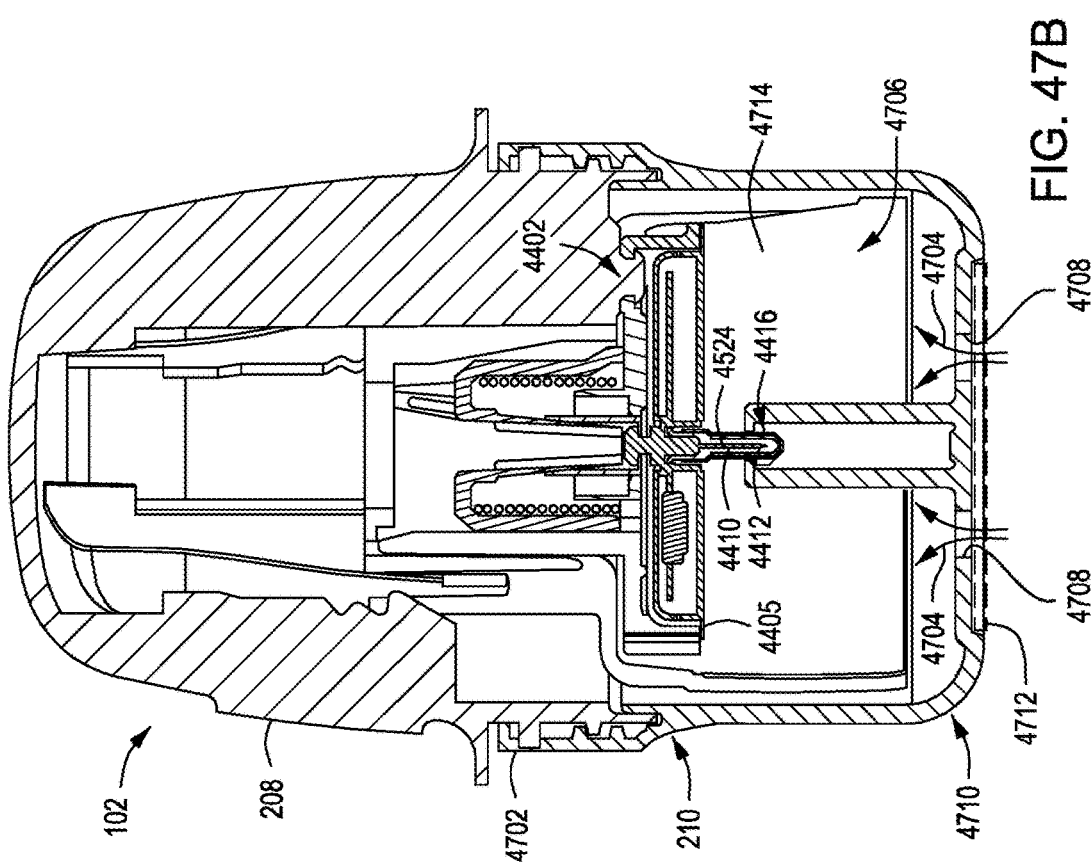
FIGS. 47A and 47B are side and cross-sectional side views, respectively, of an example embodiment of the sensor applicator of FIG. 1 with the cap of FIG. 2B coupled thereto.
Figure 47A:
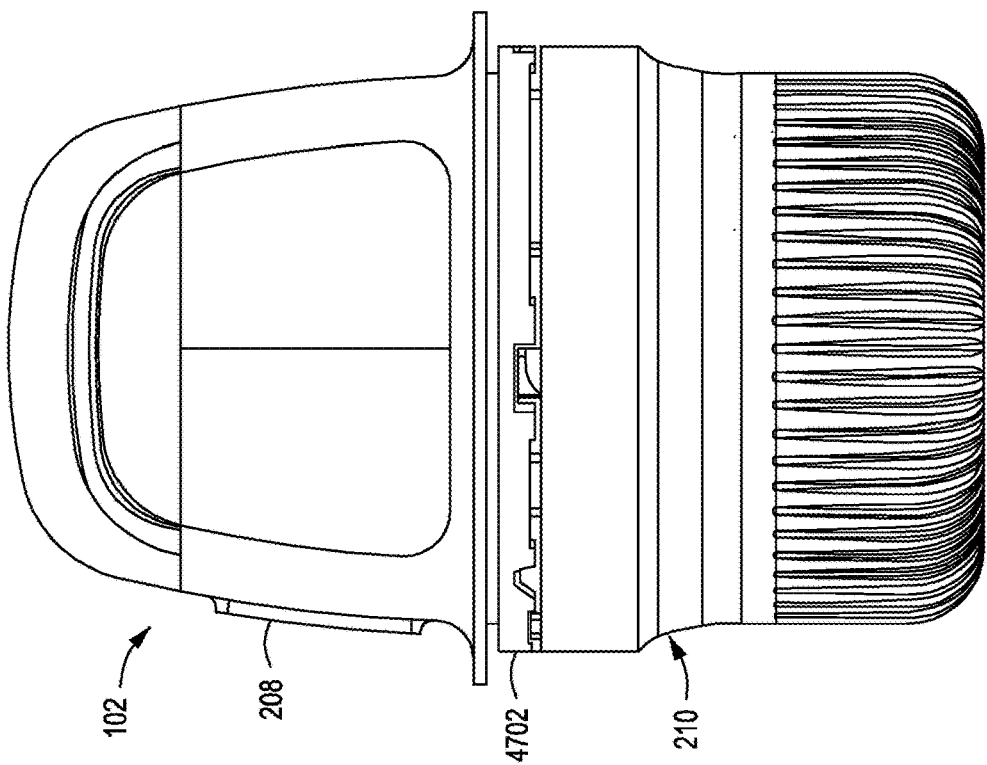

FIGS. 47A and 47B are side and cross-sectional side views, respectively, of an example embodiment of the sensor applicator 102 with the applicator cap 210 coupled thereto. More specifically, FIG. 47A depicts how the sensor applicator 102 might be shipped to and received by a user, and FIG. 47B depicts the sensor control device 4402 arranged within the sensor applicator 102. Accordingly, the fully assembled sensor control device 4402 may already be assembled and installed within the sensor applicator 102 prior to being delivered to the user, thus removing any additional assembly steps that a user would otherwise have to perform.

The fully assembled sensor control device 4402 may be loaded into the sensor applicator 102, and the applicator cap 210 may subsequently be coupled to the sensor applicator 102. In some embodiments, the applicator cap 210 may be threaded to the housing 208 and include a tamper ring 4702. Upon rotating (e.g., unscrewing) the applicator cap 210 relative to the housing 208, the tamper ring 4702 may shear and thereby free the applicator cap 210 from the sensor applicator 102.

According to the present disclosure, while loaded in the sensor applicator 102, the sensor control device 4402 may be subjected to gaseous chemical sterilization 4704 configured to sterilize the electronics housing 4404 and any other exposed portions of the sensor control device 4402. To accomplish this, a chemical may be injected into a sterilization chamber 4706 cooperatively defined by the sensor applicator 102 and the interconnected cap 210. In some applications, the chemical may be injected into the sterilization chamber 4706 via one or more vents 4708 defined in the applicator cap 210 at its proximal end 610. Example chemicals that may be used for the gaseous chemical sterilization 4704 include, but are not limited to, ethylene oxide, vaporized hydrogen peroxide, nitrogen oxide (e.g., nitrous oxide, nitrogen dioxide, etc.), and steam.

Since the distal portions of the sensor 4410 and the sharp 4412 are sealed within the sensor cap 4416, the chemicals used during the gaseous chemical sterilization process do not interact with the enzymes, chemistry, and biologics provided on the tail 4524 and other sensor components, such as membrane coatings that regulate analyte influx.

Once a desired sterility assurance level has been achieved within the sterilization chamber 4706, the gaseous solution may be removed and the sterilization chamber 4706 may be aerated. Aeration may be achieved by a series of vacuums and subsequently circulating a gas (e.g., nitrogen) or filtered air through the sterilization chamber 4706. Once the sterilization chamber 4706 is properly aerated, the vents 4708 may be occluded with a seal 4712 (shown in dashed lines).

In some embodiments, the seal 4712 may comprise two or more layers of different materials. The first layer may be made of a synthetic material (e.g., a flash-spun high-density polyethylene fiber), such as Tyvek® available from DuPont®. Tyvek® is highly durable and puncture resistant and allows the permeation of vapors. The Tyvek® layer can be applied before the gaseous chemical sterilization process, and following the gaseous chemical sterilization process, a foil or other vapor and moisture resistant material layer may be sealed (e.g., heat sealed) over the Tyvek® layer to prevent the ingress of contaminants and moisture into the sterilization chamber 4706. In other embodiments, the seal 4712 may comprise only a single protective layer applied to the applicator cap 210. In such embodiments, the single layer may be gas permeable for the sterilization process, but may also be capable of protection against moisture and other harmful elements once the sterilization process is complete.

With the seal 4712 in place, the applicator cap 210 provides a barrier against outside contamination, and thereby maintains a sterile environment for the assembled sensor control device 4402 until the user removes (unthreads) the applicator cap 210. The applicator cap 210 may also create a dust-free environment during shipping and storage that prevents the adhesive patch 4714 from becoming dirty.

Figure 48:
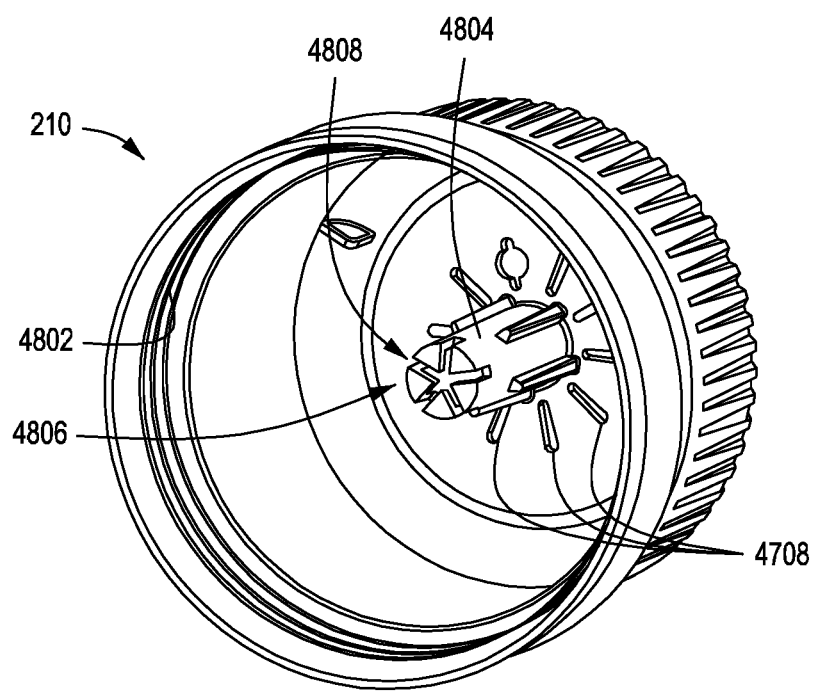
FIG. 48 is a perspective view of an example embodiment of the cap of FIGS. 47A-47B.

FIG. 48 is a perspective view of an example embodiment of the applicator cap 210, according to the present disclosure. As illustrated, the applicator cap 210 is generally circular and defines a series of threads 4802 used to couple the applicator cap 210 to the sensor applicator 102 (FIGS. 47A and 47B). The vents 4708 discussed above are also visible in the bottom of the applicator cap 210.

The applicator cap 210 may further provide and otherwise define a cap post 4804 centrally located within the interior of the applicator cap 210 and extending proximally from the bottom thereof. The cap post 4804 may be configured to receive the sensor cap 4416 (FIGS. 44, 45, 46A-46B) upon coupling the applicator cap 210 to the sensor applicator 102. More specifically, the cap post 4804 may define a receiver feature 4806 configured to interact with (e.g., receive) the engagement feature 4422 (FIG. 44) of the sensor cap 4416. Upon removing the applicator cap 210 from the sensor applicator 102, however, the receiver feature 4806 may retain the engagement feature 4422 and thereby prevent the sensor cap 4416 from separating from the cap post 4804. Consequently, removing the applicator cap 210 from the sensor applicator 102 will simultaneously detach the sensor cap 4416 from the sensor control device 4402 (FIG. 47B), and thereby expose the distal portions of the sensor 4410 (FIG. 47B) and the sharp 4412 (FIG. 47B).

As will be appreciated, many design variations of the engagement and receiver features 4422, 4806 may be employed, without departing from the scope of the disclosure. Any design may be used that allows the engagement feature 4422 to be received by the receiver feature 4806 upon coupling the applicator cap 210 to the sensor applicator 102, and subsequently prevent the sensor cap 4416 from separating from the cap post 4804 upon removing the applicator cap 210. In some embodiments, for example, the engagement and receiver features 4422, 4806 may comprise a threaded interface or a keyed mating profile that allows initial engagement but prevents subsequent disengagement.

In the illustrated embodiment, the receiver feature 4806 includes one or more compliant members 4808 that are expandable or flexible to receive the engagement feature 4422 (FIG. 44). The engagement feature 4422 may comprise, for example, an enlarged head or define one or more radial protrusions, and the compliant member(s) 4808 may comprise a collet-type device that includes a plurality of compliant fingers configured to flex radially outward to receive the enlarged head or radial protrusion(s). In other embodiments, however, the compliant member(s) 4808 may comprise an elastomer or another type of compliant material configured to expand radially to receive the enlarged head or radial protrusion(s).

Figure 49:
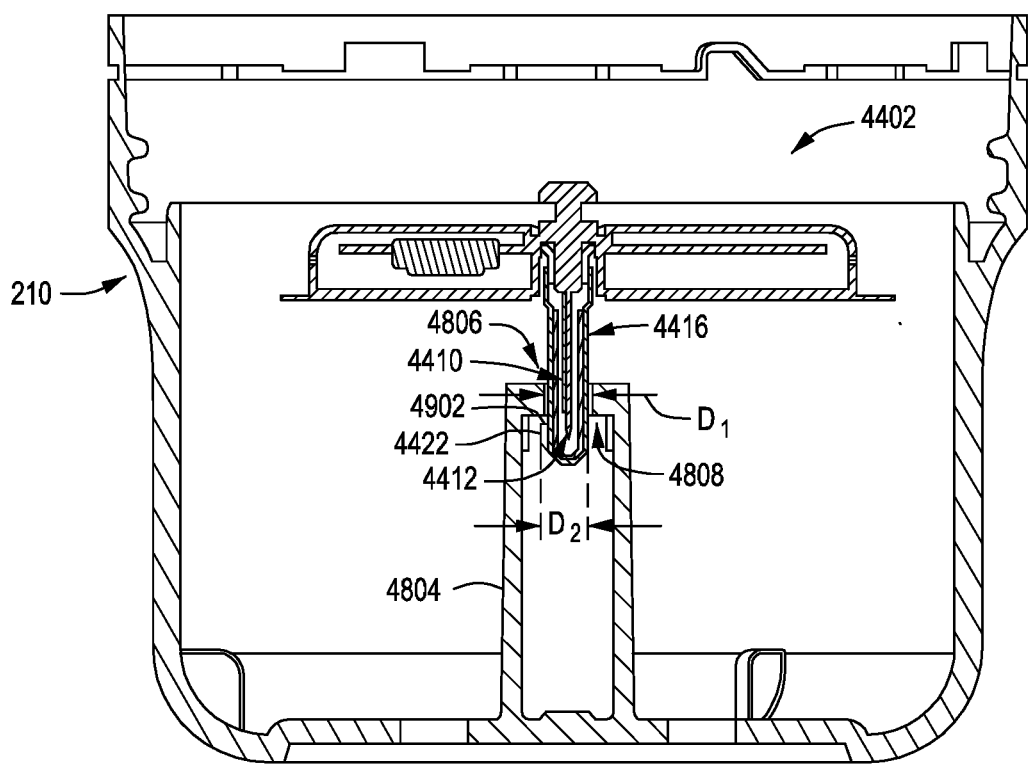
FIG. 49 is a cross-sectional side view of the sensor control device positioned within the cap of FIGS. 47A-47B.

FIG. 49 is a cross-sectional side view of the sensor control device 4402 positioned within the applicator cap 210, according to one or more embodiments. In the illustrated depiction, the remaining portions of the sensor applicator 102 (FIGS. 47A-47B) are omitted for simplicity. As illustrated, the opening to the receiver feature 4806 exhibits a first diameter $D_1$, while the engagement feature 4422 of the sensor cap 4416 exhibits a second diameter $D_2$ that is larger than the first diameter $D_1$ and greater than the outer diameter of the remaining portions of the sensor cap 4416. Accordingly, as the sensor cap 4416 is extended into the cap post 4804, the compliant member(s) 4808 may flex (expand) radially outward to receive the engagement feature 4422.

In some embodiments, the engagement feature 4422 may provide or otherwise define an angled outer surface that helps bias the compliant member(s) 4808 radially outward. The engagement feature 4422, however, may also define an upper shoulder 4902 that prevents the sensor cap 4416 from reversing out of the cap post 4804. More specifically, the shoulder 4902 may comprise a sharp surface at the second diameter $D_2$ that will engage but not urge the compliant member(s) 4808 to flex radially outward in the reverse direction.

Once the engagement feature 4422 bypasses the receiver feature 4806, the compliant member(s) 4808 flex back to (or towards) their natural state. Upon removing the applicator cap 210 from the sensor applicator 102 (FIGS. 47A-47B), the shoulder 4902 will engage and bind against the compliant member(s) 4808, thereby separating the sensor cap 4416 from the sensor control device 4402 and exposing the distal portions of the sensor 4410 and the sharp 4412.

In some embodiments, the receiver feature 4806 may alternatively be threaded and the engagement feature 4422 may also be threaded and configured to threadably engage the threads of the receiver feature 4806. The sensor cap 4416 may be received within the cap post 4804 via threaded rotation. Upon removing the applicator cap 210 from the sensor applicator 102, the opposing threads on the engagement and receiver features 4422, 4806 bind and the sensor cap 4416 may be separated from the sensor control device 4402.

Figure 50A:
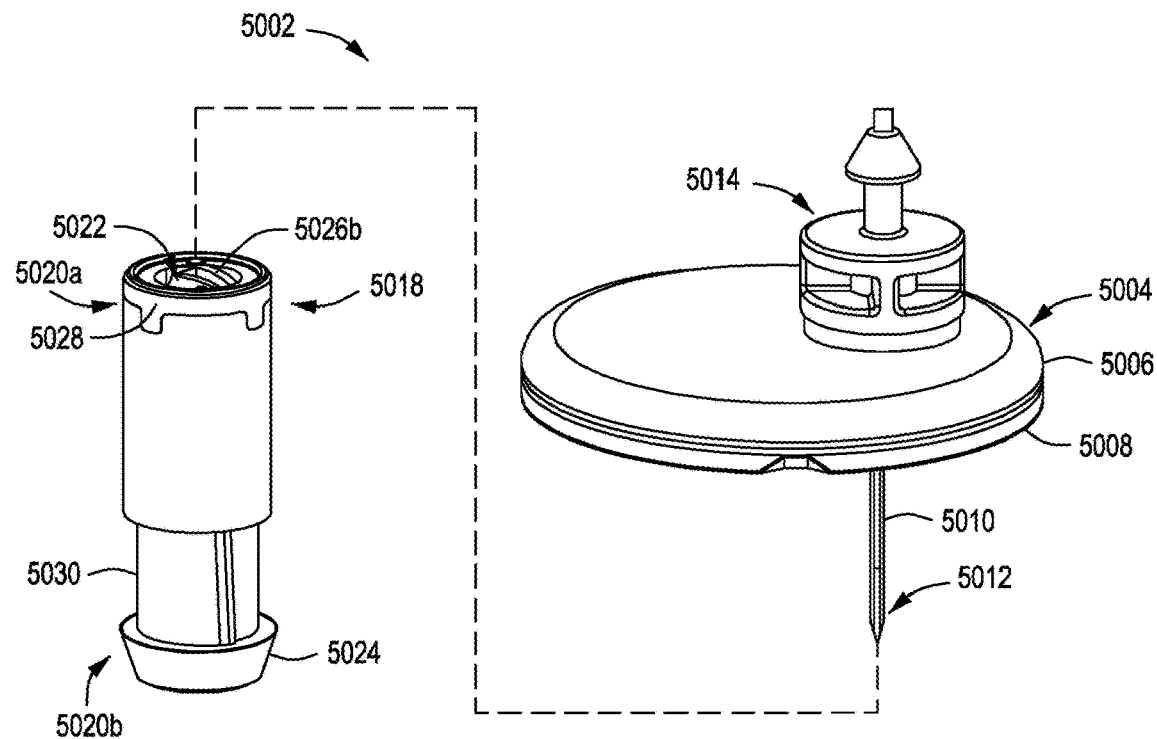
FIGS. 50A and 50B are isometric and side views, respectively, of another example sensor control device.
Figure 50B:
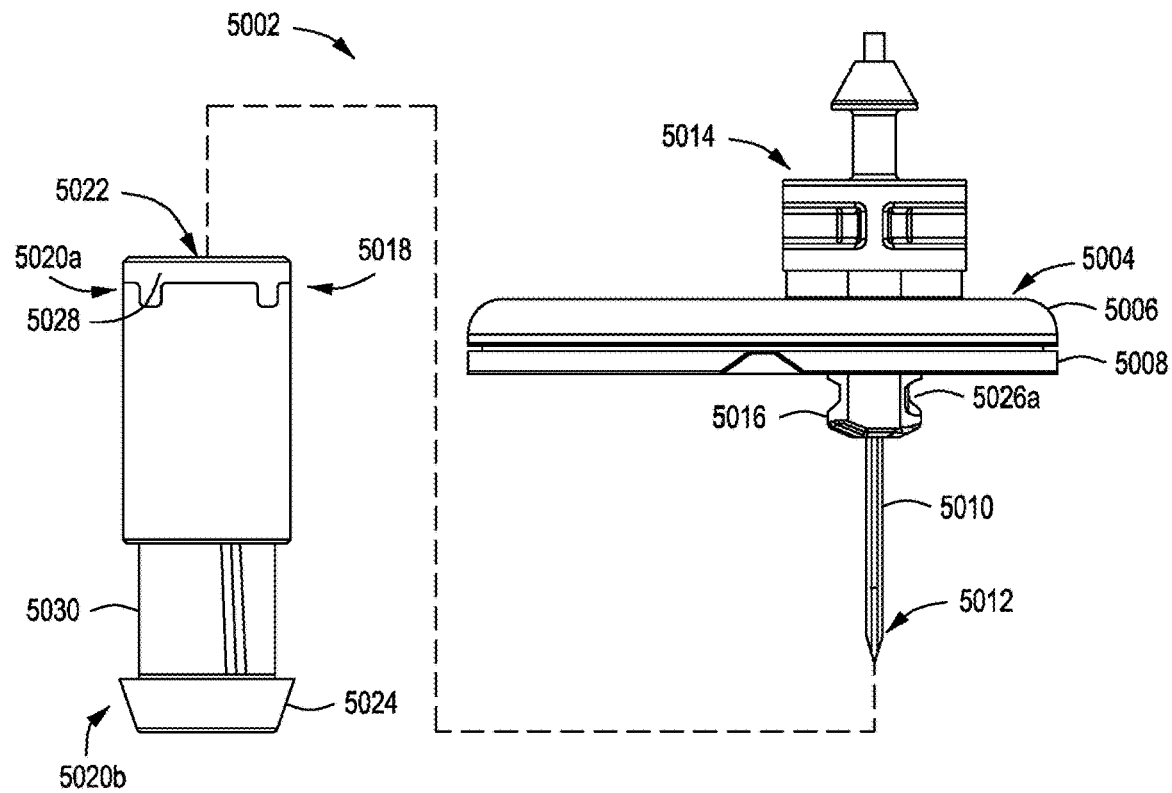

FIGS. 50A and 50B are isometric and side views, respectively, of another example sensor control device 5002, according to one or more embodiments of the present disclosure. The sensor control device 5002 may be similar in some respects to the sensor control device 4402 of FIG. 44 and therefore may be best understood with reference thereto. Moreover, the sensor control device 5002 may replace the sensor control device 104 of FIG. 1 and, therefore, may be used in conjunction with the sensor applicator 102 of FIG. 1, which may deliver the sensor control device 5002 to a target monitoring location on a user's skin. Similar to the sensor control device 4402 of FIG. 44, the sensor control device 5002 may comprise a one-piece architecture.

As illustrated, the sensor control device 5002 includes an electronics housing 5004 that includes a shell 5006 and a mount 5008 that is matable with the shell 5006. The shell 5006 may be secured to the mount 5008 via a variety of ways, such as a snap fit engagement, an interference fit, sonic welding, one or more mechanical fasteners (e.g., screws), a gasket, an adhesive, or any combination thereof.

In some cases, the shell 5006 may be secured to the mount 5008 such that a sealed interface is generated therebetween.

The sensor control device 5002 may further include a sensor 5010 (partially visible) and a sharp 5012 (partially visible), similar in function to the sensor 4410 and the sharp 4412 of FIG. 44. Corresponding portions of the sensor 5010 and the sharp 5012 extend distally from the bottom of the electronics housing 5004 (e.g., the mount 5008). The sharp 5012 may include a sharp hub 5014 configured to secure and carry the sharp 5012. As best seen in FIG. 50B, the sharp hub 5014 may include or otherwise define a mating member 5016. To couple the sharp 5012 to the sensor control device 5002, the sharp 5012 may be advanced axially through the electronics housing 5004 until the sharp hub 5014 engages an upper surface of the shell 5006 and the mating member 5016 extends distally from the bottom of the mount 5008. As the sharp 5012 penetrates the electronics housing 5004, the exposed portion of the sensor 5010 may be received within a hollow or recessed (arcuate) portion of the sharp 5012. The remaining portion of the sensor 5010 is arranged within the interior of the electronics housing 5004.

The sensor control device 5002 may further include a sensor cap 5018, shown exploded or detached from the electronics housing 5004 in FIGS. 50A-50B. Similar to the sensor cap 4416 of FIG. 44, the sensor cap 5018 may help provide a sealed barrier that surrounds and protects the exposed portions of the sensor 5010 and the sharp 5012 from gaseous chemical sterilization. As illustrated, the sensor cap 5018 may comprise a generally cylindrical body having a first end 5020a and a second end 5020b opposite the first end 5020a. The first end 5020a may be open to provide access into an inner chamber 5022 defined within the body. In contrast, the second end 5020b may be closed and may provide or otherwise define an engagement feature 5024. Similar to the engagement feature 4422 of FIG. 44, the engagement feature 5024 may help mate the sensor cap 5018 to the cap (e.g., the applicator cap 210 of FIG. 2B) of a sensor applicator (e.g., the sensor applicator 102 of FIGS. 1 and 2A-2G), and may help remove the sensor cap 5018 from the sensor control device 5002 upon removing the cap from the sensor applicator.

The sensor cap 5018 may be removably coupled to the electronics housing 5004 at or near the bottom of the mount 5008. More specifically, the sensor cap 5018 may be removably coupled to the mating member 5016, which extends distally from the bottom of the mount 5008. In at least one embodiment, for example, the mating member 5016 may define a set of external threads 5026a (FIG. 50B) matable with a set of internal threads 5026b (FIG. 50A) defined by the sensor cap 5018. In some embodiments, the external and internal threads 5026a,b may comprise a flat thread design (e.g., lack of helical curvature), which may prove advantageous in molding the parts. Alternatively, the external and internal threads 5026a,b may comprise a helical threaded engagement. Accordingly, the sensor cap 5018 may be threadably coupled to the sensor control device 5002 at the mating member 5016 of the sharp hub 5014. In other embodiments, the sensor cap 5018 may be removably coupled to the mating member 5016 via other types of engagements including, but not limited to, an interference or friction fit, or a frangible member or substance that may be broken with minimal separation force (e.g., axial or rotational force).

In some embodiments, the sensor cap 5018 may comprise a monolithic (singular) structure extending between the first and second ends 5020a,b. In other embodiments, however, the sensor cap 5018 may comprise two or more component parts. In the illustrated embodiment, for example, the sensor cap 5018 may include a seal ring 5028 positioned at the first end 5020a and a desiccant cap 5030 arranged at the second end 5020b. The seal ring 5028 may be configured to help seal the inner chamber 5022, as described in more detail below. In at least one embodiment, the seal ring 5028 may comprise an elastomeric O-ring. The desiccant cap 5030 may house or comprise a desiccant to help maintain preferred humidity levels within the inner chamber 5022. The desiccant cap 5030 may also define or otherwise provide the engagement feature 5024 of the sensor cap 5018.

FIGS. 51A and 51B are exploded isometric top and bottom views, respectively, of the sensor control device 5002, according to one or more embodiments. The shell 5006 and the mount 5008 operate as opposing clamshell halves that enclose or otherwise substantially encapsulate various electronic components of the sensor control device 5002. The electronic components housed within the electronics housing 5004 may be similar to the electronic components described with reference to FIG. 45 and, therefore, will not be described again. While not shown, the sensor control device 5002 may also include an adhesive patch that may be applied to the bottom 5102 (FIG. 51B) of the mount 5008, and may help adhere the sensor control device 5002 to the user's skin for use.

The sensor control device 5002 may provide or otherwise include a sealed subassembly that includes, among other component parts, the shell 5006, the sensor 5010, the sharp 5012, and the sensor cap 5018. Similar to the sealed subassembly 4522 of FIG. 45, the sealed subassembly of the sensor control device 5002 may help isolate the sensor 5010 and the sharp 5012 within the inner chamber 5022 (FIG. 51A) of the sensor cap 5018 during a gaseous chemical sterilization process, which might otherwise adversely affect the chemistry provided on the sensor 5010.

The sensor 5010 may include a tail 5104 that extends out an aperture 5106 (FIG. 51B) defined in the mount 5008 to be transcutaneously received beneath a user's skin. The tail 5104 may have an enzyme or other chemistry included thereon to help facilitate analyte monitoring. The sharp 5012 may include a sharp tip 5108 extendable through an aperture 5110 (FIG. 51A) defined by the shell 5006, and the aperture 5110 may be coaxially aligned with the aperture 5106 of the mount 5008. As the sharp tip 5108 penetrates the electronics housing 5004, the tail 5104 of the sensor 5010 may be received within a hollow or recessed portion of the sharp tip 5108. The sharp tip 5108 may be configured to penetrate the skin while carrying the tail 5104 to put the active chemistry of the tail 5104 into contact with bodily fluids.

The sharp tip 5108 may be advanced through the electronics housing 5004 until the sharp hub 5014 engages an upper surface of the shell 5006 and the mating member 5016 extends out the aperture 5106 in the bottom 5102 of the mount 5008. In some embodiments, a seal member (not shown), such as an O-ring or seal ring, may interpose the sharp hub 5014 and the upper surface of the shell 5006 to help seal the interface between the two components. In some embodiments, the seal member may comprise a separate component part, but may alternatively form an integral part of the shell 5006, such as being a co-molded or overmolded component part.

The sealed subassembly may further include a collar 5112 that is positioned within the electronics housing 5004 and extends at least partially into the aperture 5106. The collar 5112 may be a generally annular structure that defines or otherwise provides an annular ridge 5114 on its top surface. In some embodiments, as illustrated, a groove 5116 may be defined in the annular ridge 5114 and may be configured to accommodate or otherwise receive a portion of the sensor 5010 extending laterally within the electronics housing 5004.

In assembling the sealed subassembly, a bottom 5118 of the collar 5112 may be exposed at the aperture 5106 and may sealingly engage the first end 5020*a* of the sensor cap 5018 and, more particularly, the seal ring 5028. In contrast, the annular ridge 5114 at the top of the collar 5112 may sealingly engage an inner surface (not shown) of the shell 5006. In at least one embodiment, a seal member (not shown) may interpose the annular ridge 5114 and the inner surface of the shell 5006 to form a sealed interface. In such embodiments, the seal member may also extend (flow) into the groove 5116 defined in the annular ridge 5114 and thereby seal about the sensor 5010 extending laterally within the electronics housing 5004. The seal member may comprise, for example, an adhesive, a gasket, or an ultrasonic weld, and may help isolate the enzymes and other chemistry included on the tail 5104.

Figure 52:
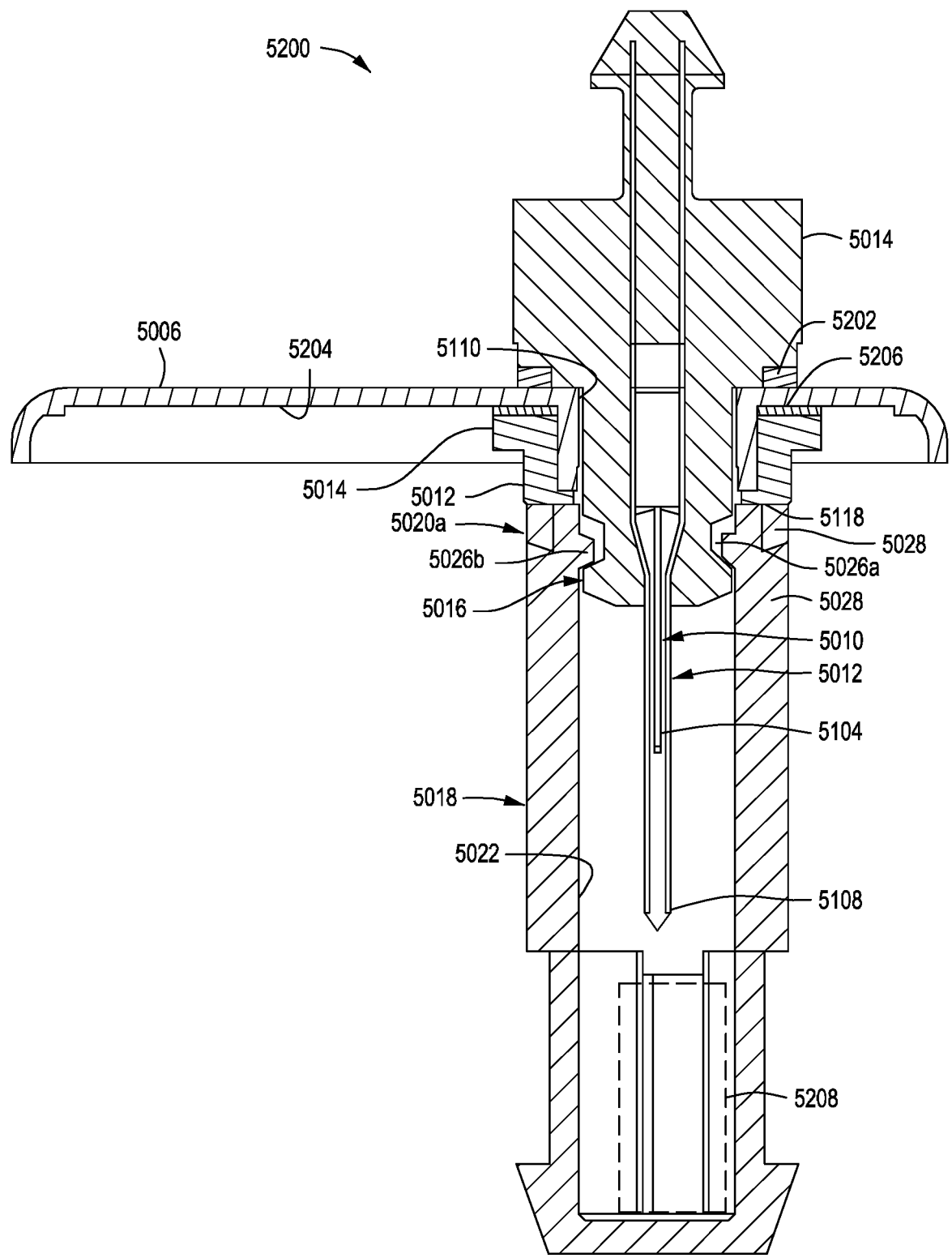
FIG. 52 is a cross-sectional side view of an assembled sealed subassembly, according to one or more embodiments.

FIG. 52 is a cross-sectional side view of an assembled sealed subassembly 5200, according to one or more embodiments. The sealed subassembly 5200 may form part of the sensor control device 5002 of FIGS. 50A-50B and 51A-51B and may include portions of the shell 5006, the sensor 5010, the sharp 5012, the sensor cap 5018, and the collar 5112. The sealed subassembly 5200 may be assembled in a variety of ways. In one assembly process, the sharp 5012 may be coupled to the sensor control device 5002 by extending the sharp tip 5108 through the aperture 5110 defined in the top of the shell 5006 and advancing the sharp 5012 through the shell 5006 until the sharp hub 5014 engages the top of the shell 5006 and the mating member 196 extends distally from the shell 5006. In some embodiments, as mentioned above, a seal member 5202 (e.g., an O-ring or seal ring) may interpose the sharp hub 5014 and the upper surface of the shell 5006 to help seal the interface between the two components.

The collar 5112 may then be received over (about) the mating member 5016 and advanced toward an inner surface 5204 of the shell 5006 to enable the annular ridge 5114 to engage the inner surface 5204. A seal member 5206 may interpose the annular ridge 5114 and the inner surface 5204 and thereby form a sealed interface. The seal member 5206 may also extend (flow) into the groove 5116 (FIGS. 51A-51B) defined in the annular ridge 5114 and thereby seal about the sensor 5010 extending laterally within the electronics housing 5004 (FIGS. 51A-51B). In other embodiments, however, the collar 5112 may first be sealed to the inner surface 5204 of the shell 5006, following which the sharp 5012 and the sharp hub 5014 may be extended through the aperture 5110, as described above.

The sensor cap 5018 may be removably coupled to the sensor control device 5002 by threadably mating the internal threads 5026*b* of the sensor cap 5018 with the external threads 5026*a* of the mating member 5016. Tightening (rotating) the mated engagement between the sensor cap 5018 and the mating member 5016 may urge the first end 5020*a* of the sensor cap 5018 into sealed engagement with the bottom 5118 of the collar 5112. Moreover, tightening the mated engagement between the sensor cap 5018 and the mating member 5016 may also enhance the sealed interface between the sharp hub 5014 and the top of the shell 5006, and between the annular ridge 5114 and the inner surface 5204 of the shell 5006.

The inner chamber 5022 may be sized and otherwise configured to receive the tail 5104 and the sharp tip 5108. Moreover, the inner chamber 5022 may be sealed to isolate the tail 5104 and the sharp tip 5108 from substances that might adversely interact with the chemistry of the tail 5104. In some embodiments, a desiccant 5208 (shown in dashed lines) may be present within the inner chamber 5022 to maintain proper humidity levels.

Once properly assembled, the sealed subassembly 5200 may be subjected to any of the radiation sterilization processes mentioned herein to properly sterilize the sensor 5010 and the sharp 5012. This sterilization step may be undertaken apart from the remaining portions of the sensor control device (FIGS. 50A-50B and 51A-51B) to prevent damage to sensitive electrical components. The sealed subassembly 5200 may be subjected to radiation sterilization prior to or after coupling the sensor cap 5018 to the sharp hub 5014. When sterilized after coupling the sensor cap 5018 to the sharp hub 5014, the sensor cap 5018 may be made of a material that permits the propagation of radiation therethrough. In some embodiments, the sensor cap 5018 may be transparent or translucent, but can otherwise be opaque, without departing from the scope of the disclosure.

Figure 53B:
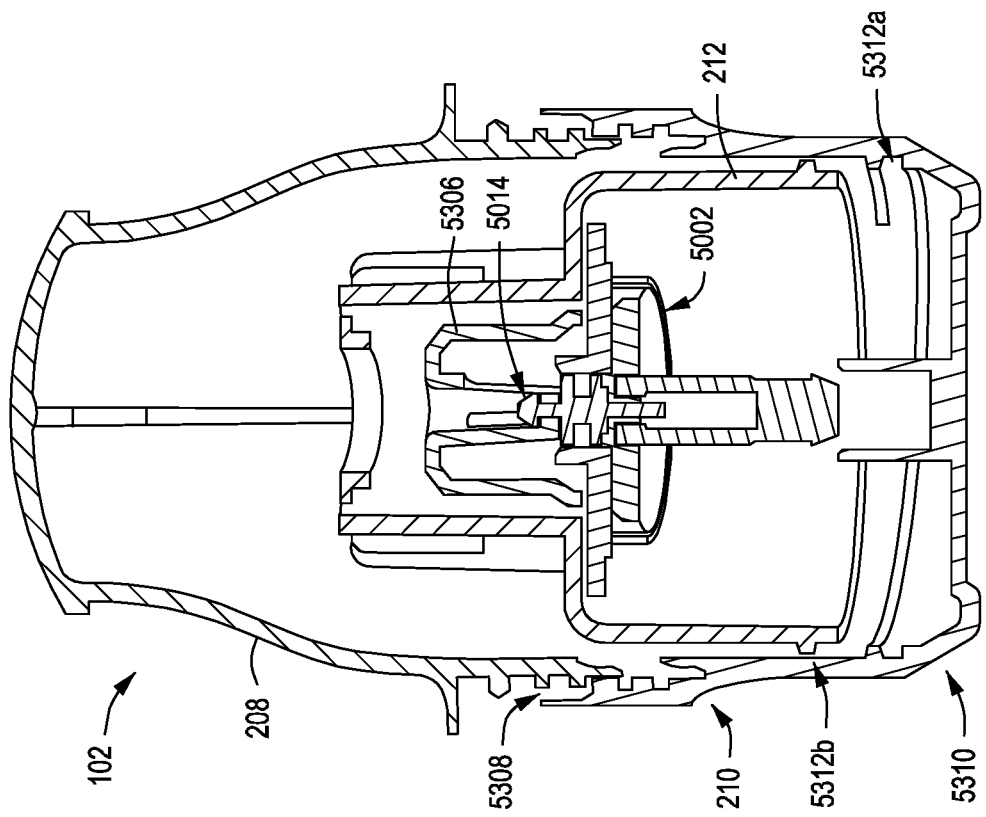
FIGS. 53A-53C are progressive cross-sectional side views showing assembly of the sensor applicator with the sensor control device of FIGS. 50A-50B.
Figure 53A:
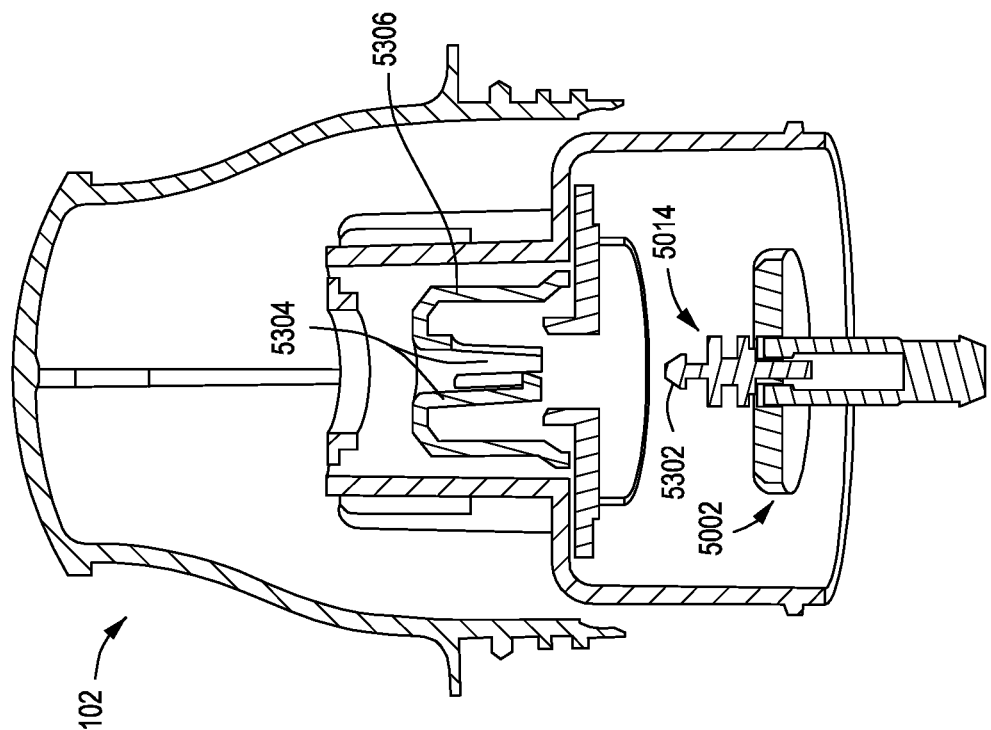
Figure 53C:
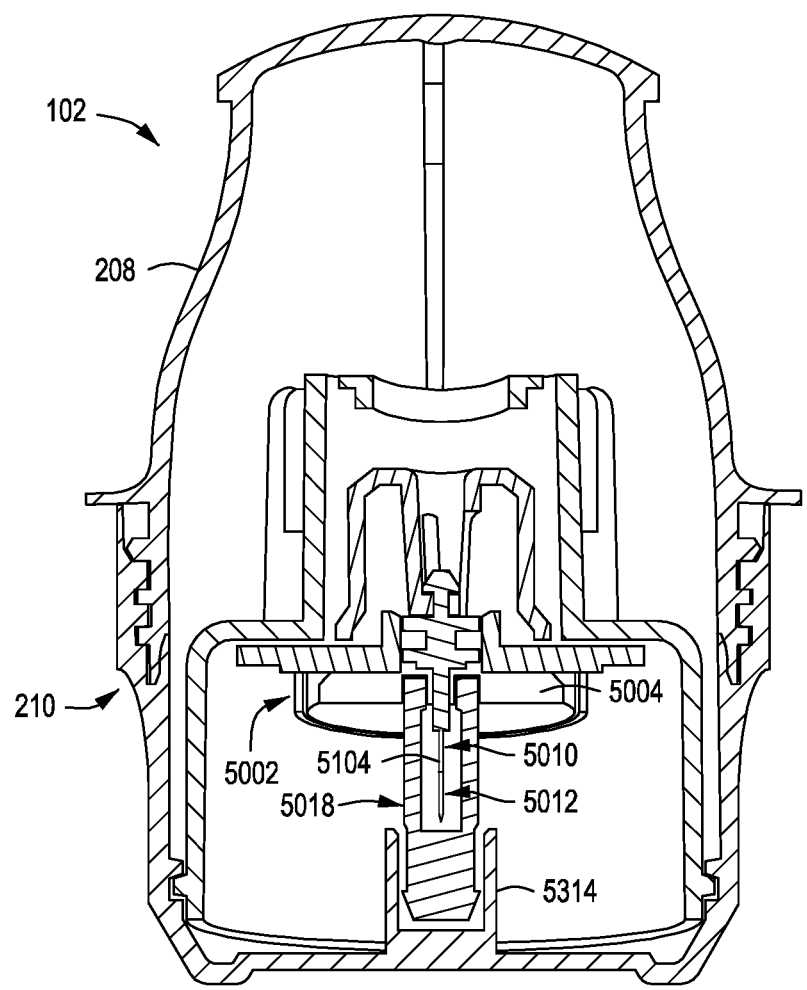

FIGS. 53A-53C are progressive cross-sectional side views showing assembly of the sensor applicator 102 with the sensor control device 5002, according to one or more embodiments. Once the sensor control device 5002 is fully assembled, it may then be loaded into the sensor applicator 102. With reference to FIG. 53A, the sharp hub 5014 may include or otherwise define a hub snap pawl 5302 configured to help couple the sensor control device 5002 to the sensor applicator 102. More specifically, the sensor control device 5002 may be advanced into the interior of the sensor applicator 102 and the hub snap pawl 5302 may be received by corresponding arms 5304 of a sharp carrier 5306 positioned within the sensor applicator 102.

In FIG. 53B, the sensor control device 5002 is shown received by the sharp carrier 5306 and, therefore, secured within the sensor applicator 102. Once the sensor control device 5002 is loaded into the sensor applicator 102, the applicator cap 210 may be coupled to the sensor applicator 102. In some embodiments, the applicator cap 210 and the housing 208 may have opposing, matable sets of threads 5308 that enable the applicator cap 210 to be screwed onto the housing 208 in a clockwise (or counter-clockwise) direction and thereby secure the applicator cap 210 to the sensor applicator 102.

As illustrated, the sheath 212 is also positioned within the sensor applicator 102, and the sensor applicator 102 may include a sheath locking mechanism 5310 configured to ensure that the sheath 212 does not prematurely collapse during a shock event. In the illustrated embodiment, the sheath locking mechanism 5310 may comprise a threaded engagement between the applicator cap 210 and the sheath 212. More specifically, one or more internal threads 5312*a* may be defined or otherwise provided on the inner surface of the applicator cap 210, and one or more external threads 5312*b* may be defined or otherwise provided on the sheath 212. The internal and external threads 5312*a,b* may be configured to threadably mate as the applicator cap 210 is threaded to the sensor applicator 102 at the threads 5308. The internal and external threads 5312*a,b* may have the same thread pitch as the threads 5308 that enable the applicator cap 210 to be screwed onto the housing 208.

In FIG. 53C, the applicator cap 210 is shown fully threaded (coupled) to the housing 208. As illustrated, the applicator cap 210 may further provide and otherwise define a cap post 5314 centrally located within the interior of the applicator cap 210 and extending proximally from the bottom thereof. The cap post 5314 may be configured to receive at least a portion of the sensor cap 5018 as the applicator cap 210 is screwed onto the housing 208.

With the sensor control device 5002 loaded within the sensor applicator 102 and the applicator cap 210 properly secured, the sensor control device 5002 may then be subjected to a gaseous chemical sterilization configured to sterilize the electronics housing 5004 and any other exposed portions of the sensor control device 5002. The gaseous chemical sterilization process may be similar to the gaseous chemical sterilization 4704 of FIG. 47B and, therefore, will not be described again in detail. Since the distal portions of the sensor 5010 and the sharp 5012 are sealed within the sensor cap 5018, the chemicals used during the gaseous chemical sterilization process are unable to interact with the enzymes, chemistry, and biologics provided on the tail 5104, and other sensor components, such as membrane coatings that regulate analyte influx.

Figure 54A:
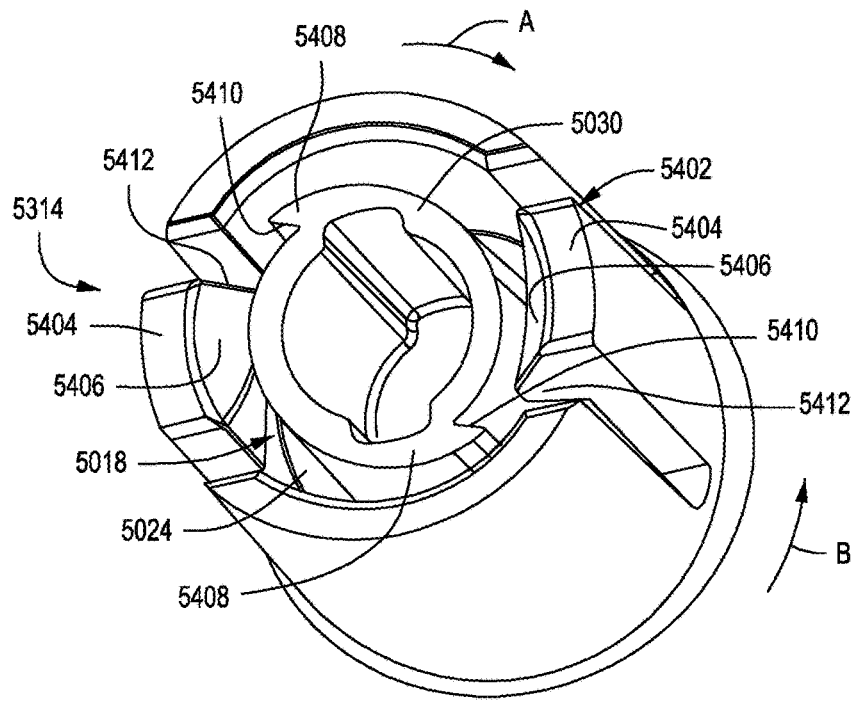
FIGS. 54A and 54B are perspective and top views, respectively, of the cap post of FIG. 53C, according to one or more additional embodiments.
Figure 54B:
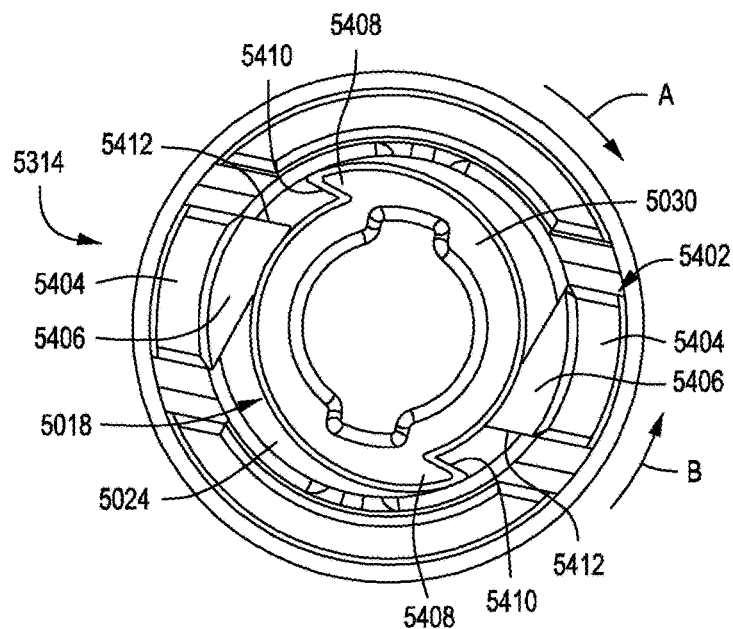

FIGS. 54A and 54B are perspective and top views, respectively, of the cap post 5314, according to one or more additional embodiments. In the illustrated depiction, a portion of the sensor cap 5018 is received within the cap post 5314 and, more specifically, the desiccant cap 5030 of the sensor cap 5018 is arranged within cap post 5314.

As illustrated, the cap post 5314 may define a receiver feature 5402 configured to receive the engagement feature 5024 of the sensor cap 5018 upon coupling (e.g., threading) the applicator cap 210 (FIG. 53C) to the sensor applicator 102 (FIGS. 53A-53C). Upon removing the applicator cap 210 from the sensor applicator 102, however, the receiver feature 5402 may prevent the engagement feature 914 from reversing direction and thus prevent the sensor cap 5018 from separating from the cap post 5314. Instead, removing the applicator cap 210 from the sensor applicator 102 will simultaneously detach the sensor cap 5018 from the sensor control device 5002 (FIGS. 50A-50B and 53A-53C), and thereby expose the distal portions of the sensor 5010 (FIGS. 53A-53C) and the sharp 5012 (FIGS. 53A-53C).

Many design variations of the receiver feature 5402 may be employed, without departing from the scope of the disclosure. In the illustrated embodiment, the receiver feature 5402 includes one or more compliant members 5404 (two shown) that are expandable or flexible to receive the engagement feature 5024 (FIGS. 50A-50B). The engagement feature 5024 may comprise, for example, an enlarged head and the compliant member(s) 5404 may comprise a collet-type device that includes a plurality of compliant fingers configured to flex radially outward to receive the enlarged head.

The compliant member(s) 5404 may further provide or otherwise define corresponding ramped surfaces 5406 configured to interact with one or more opposing camming surfaces 5408 provided on the outer wall of the engagement feature 5024. The configuration and alignment of the ramped surface(s) 5406 and the opposing camming surface(s) 5408 is such that the applicator cap 210 is able to rotate relative to the sensor cap 5018 in a first direction A (e.g., clockwise), but the cap post 5314 binds against the sensor cap 5018 when the applicator cap 210 is rotated in a second direction B (e.g., counter clockwise). More particularly, as the applicator cap 210 (and thus the cap post 5314) rotates in the first direction A, the camming surfaces 5408 engage the ramped surfaces 5406, which urge the compliant members 5404 to flex or otherwise deflect radially outward and results in a ratcheting effect. Rotating the applicator cap 210 (and thus the cap post 5314) in the second direction B, however, will drive angled surfaces 5410 of the camming surfaces 5408 into opposing angled surfaces 5412 of the ramped surfaces 5406, which results in the sensor cap 5018 binding against the compliant member(s) 5404.

Figure 55:
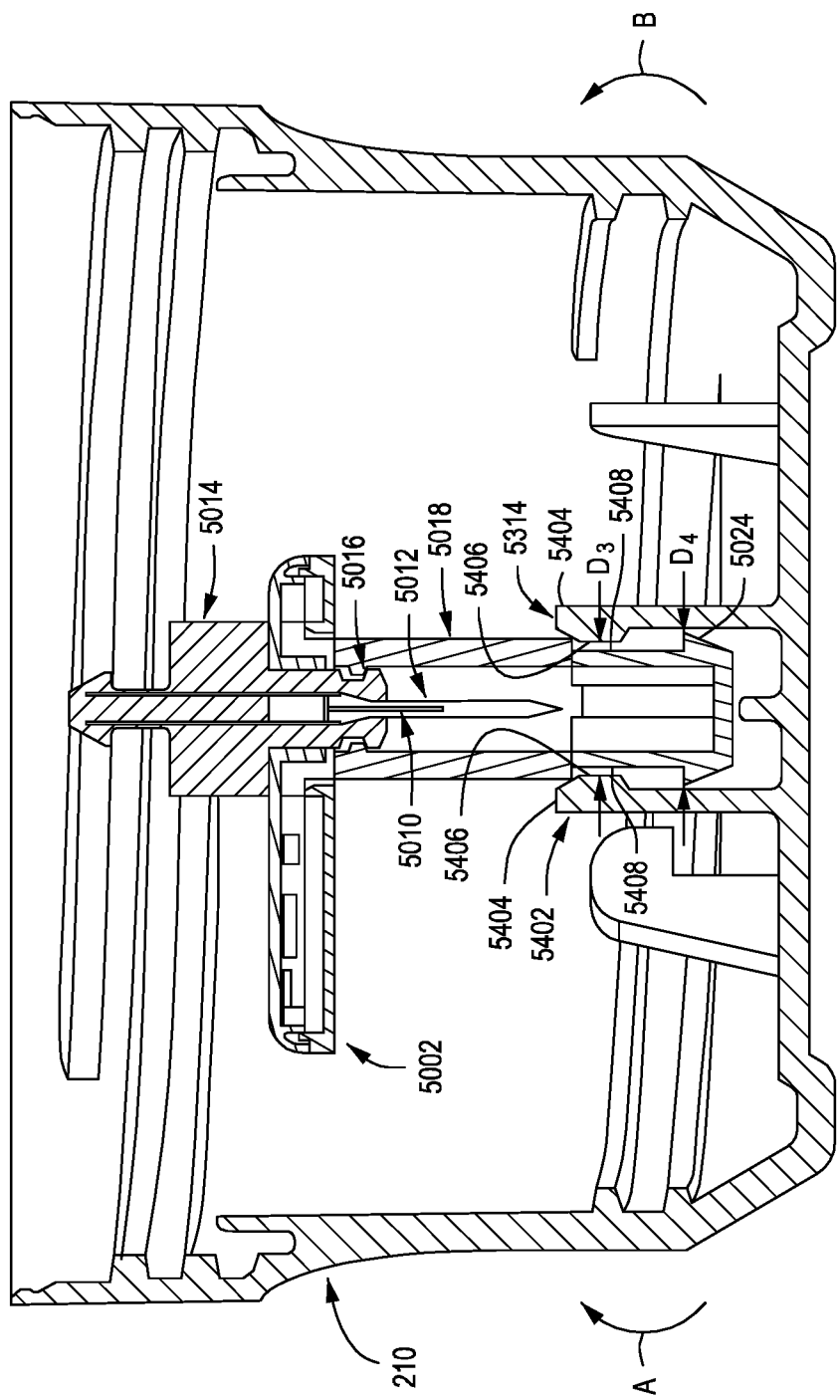
FIG. 55 is a cross-sectional side view of the sensor control device of FIGS. 50A-50B positioned within the cap of FIGS. 12B-12C.

FIG. 55 is a cross-sectional side view of the sensor control device 5002 positioned within the applicator cap 210, according to one or more embodiments. As illustrated, the opening to the receiver feature 5402 exhibits a first diameter $D_3$, while the engagement feature 5024 of the sensor cap 5018 exhibits a second diameter $D_4$ that is larger than the first diameter $D_3$ and greater than the outer diameter of the remaining portions of the sensor cap 5018. As the sensor cap 5018 is extended into the cap post 5314, the compliant member(s) 5404 of the receiver feature 5402 may flex (expand) radially outward to receive the engagement feature 5024. In some embodiments, as illustrated, the engagement feature 5024 may provide or otherwise define an angled outer surface that helps bias the compliant member(s) 5404 radially outward. Once the engagement feature 5024 bypasses the receiver feature 5402, the compliant member(s) 5404 are able to flex back to (or towards) their natural state and thus lock the sensor cap 5018 within the cap post 5314.

As the applicator cap 210 is threaded to (screwed onto) the housing 208 (FIGS. 53A-53C) in the first direction A, the cap post 5314 correspondingly rotates in the same direction and the sensor cap 5018 is progressively introduced into the cap post 5314. As the cap post 5314 rotates, the ramped surfaces 5406 of the compliant members 5404 ratchet against the opposing camming surfaces 5408 of the sensor cap 5018. This continues until the applicator cap 210 is fully threaded onto (screwed onto) the housing 208. In some embodiments, the ratcheting action may occur over two full revolutions of the applicator cap 210 before the applicator cap 210 reaches its final position.

To remove the applicator cap 210, the applicator cap 210 is rotated in the second direction B, which correspondingly rotates the cap post 5314 in the same direction and causes the camming surfaces 5408 (i.e., the angled surfaces 5410 of FIGS. 54A-54B) to bind against the ramped surfaces 5406 (i.e., the angled surfaces 5412 of FIGS. 54A-54B). Consequently, continued rotation of the applicator cap 210 in the second direction B causes the sensor cap 5018 to correspondingly rotate in the same direction and thereby unthread from the mating member 5016 to allow the sensor cap 5018 to detach from the sensor control device 5002. Detaching the sensor cap 5018 from the sensor control device 5002 exposes the distal portions of the sensor 5010 and the sharp 5012, and thus places the sensor control device 5002 in position for firing (use).

Figure 56B:
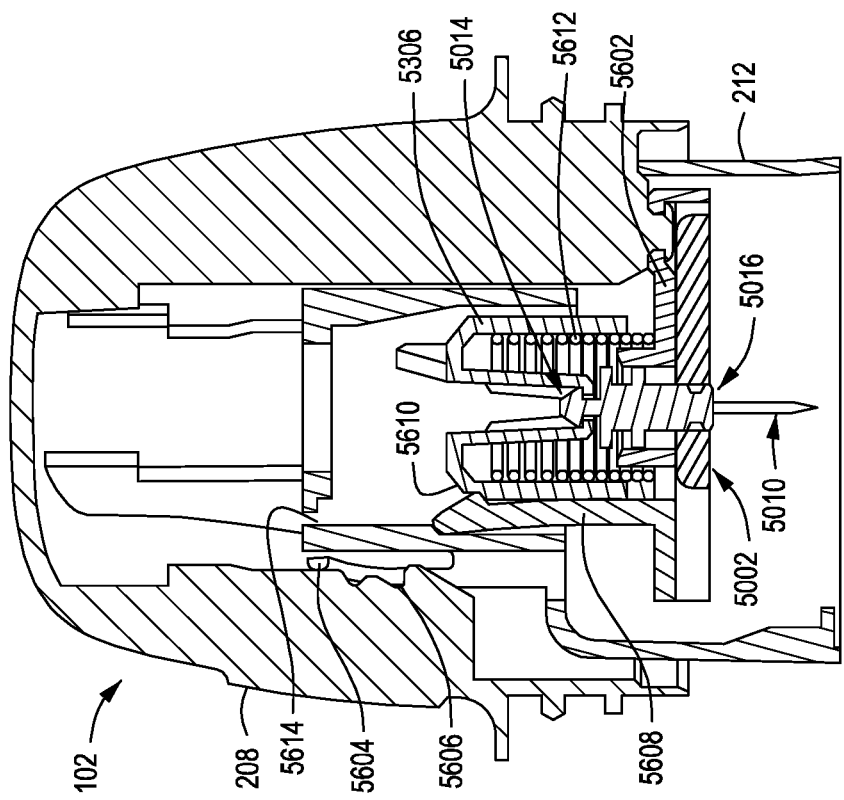
FIGS. 56A and 56B are cross-sectional side views of the sensor applicator ready to deploy the sensor control device to a target monitoring location.
Figure 56A:
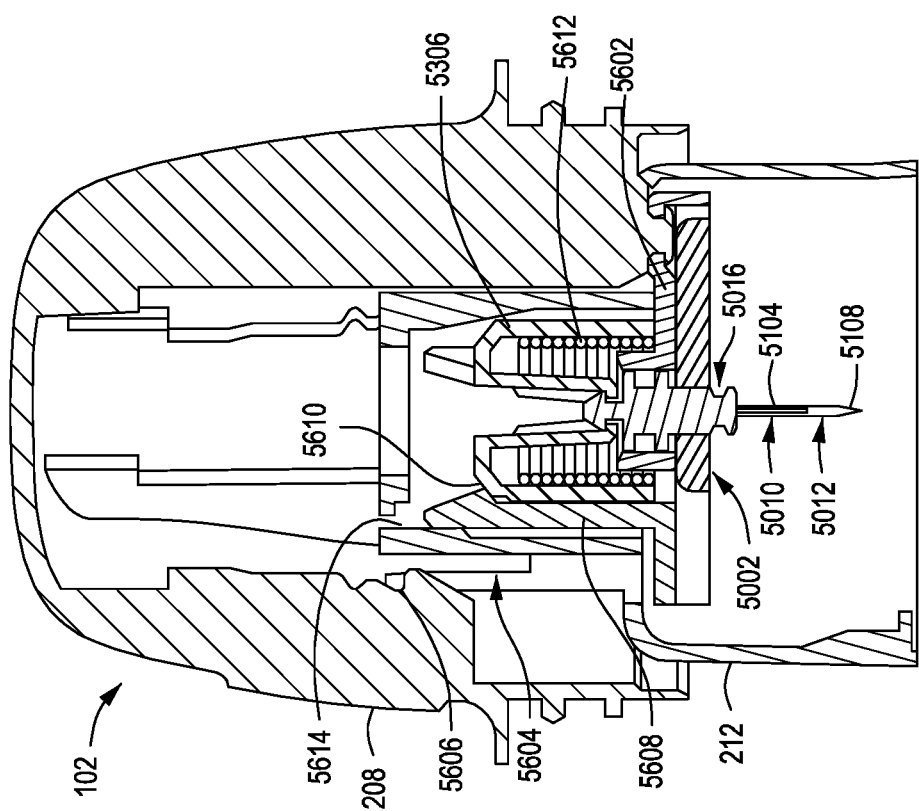

FIGS. 56A and 56B are cross-sectional side views of the sensor applicator 102 ready to deploy the sensor control device 5002 to a target monitoring location, according to one or more embodiments. More specifically, FIG. 56A depicts the sensor applicator 102 ready to deploy (fire) the sensor control device 5002, and FIG. 56B depicts the sensor applicator 102 in the process of deploying (firing) the sensor control device 5002. As illustrated, the applicator cap 210 (FIGS. 53A-53C and 55) has been removed, which correspondingly detaches (removes) the sensor cap 5018 (FIGS. 53A-53C and 55 and thereby exposes the tail 5104 of the sensor 5010 and the sharp tip 5108 of the sharp 5012, as described above. In conjunction with the sheath 212 and the sharp carrier 5306, the sensor applicator 102 also includes a sensor carrier 5602 (alternately referred to as a "puck" carrier) that helps position and secure the sensor control device 5002 within the sensor applicator 102.

Referring first to FIG. 56A, as illustrated, the sheath 212 includes one or more sheath arms 5604 (one shown) configured to interact with a corresponding one or more detents 5606 (one shown) defined within the interior of the housing 208. The detent(s) 5606 are alternately referred to as "firing" detent(s). When the sensor control device 5002 is initially installed in the sensor applicator 102, the sheath arms 5604 may be received within the detents 5606, which places the sensor applicator 102 in firing position. In the firing position, the mating member 5016 extends distally beyond the bottom of the sensor control device 5002. As discussed below, the process of firing the sensor applicator 102 causes the mating member 5016 to retract so that it does not contact the user's skin.

The sensor carrier 5602 may also include one or more carrier arms 5608 (one shown) configured to interact with a corresponding one or more grooves 5610 (one shown) defined on the sharp carrier 5306. A spring 5612 may be arranged within a cavity defined by the sharp carrier 5306 and may passively bias the sharp carrier 5306 upward within the housing 208. When the carrier arm(s) 5608 are properly received within the groove(s) 5610, however, the sharp carrier 5306 is maintained in position and prevented from moving upward. The carrier arm(s) 5608 interpose the sheath 212 and the sharp carrier 5306, and a radial shoulder 5614 defined on the sheath 212 may be sized to maintain the carrier arm(s) 5608 engaged within the groove(s) 5610 and thereby maintain the sharp carrier 5306 in position.

In FIG. 56B, the sensor applicator 102 is in the process of firing. As discussed herein with reference to FIGS. 2F-2G, this may be accomplished by advancing the sensor applicator 102 toward a target monitoring location until the sheath 212 engages the skin of the user. Continued pressure on the sensor applicator 102 against the skin may cause the sheath arm(s) 5604 to disengage from the corresponding detent(s) 5606, which allows the sheath 212 to collapse into the housing 208. As the sheath 212 starts to collapse, the radial shoulder 5614 eventually moves out of radial engagement with the carrier arm(s) 5608, which allows the carrier arm(s) 5608 to disengage from the groove(s) 5610. The passive spring force of the spring 5612 is then free to push upward on the sharp carrier 5306 and thereby force the carrier arm(s) 5608 out of engagement with the groove(s) 5610, which allows the sharp carrier 5306 to move slightly upward within the housing 208. In some embodiments, fewer coils may be incorporated into the design of the spring 5612 to increase the spring force necessary to overcome the engagement between carrier arm(s) 5608 and the groove(s) 5610. In at least one embodiment, one or both of the carrier arm(s) 5608 and the groove(s) 5610 may be angled to help ease disengagement.

As the sharp carrier 5306 moves upward within the housing 208, the sharp hub 5014 may correspondingly move in the same direction, which may cause partial retraction of the mating member 5016 such that it becomes flush, substantially flush, or sub-flush with the bottom of the sensor control device 5002. As will be appreciated, this ensures that the mating member 5016 does not come into contact with the user's skin, which might otherwise adversely impact sensor insertion, cause excessive pain, or prevent the adhesive patch (not shown) positioned on the bottom of the sensor control device 5002 from properly adhering to the skin.

Figure 57A:
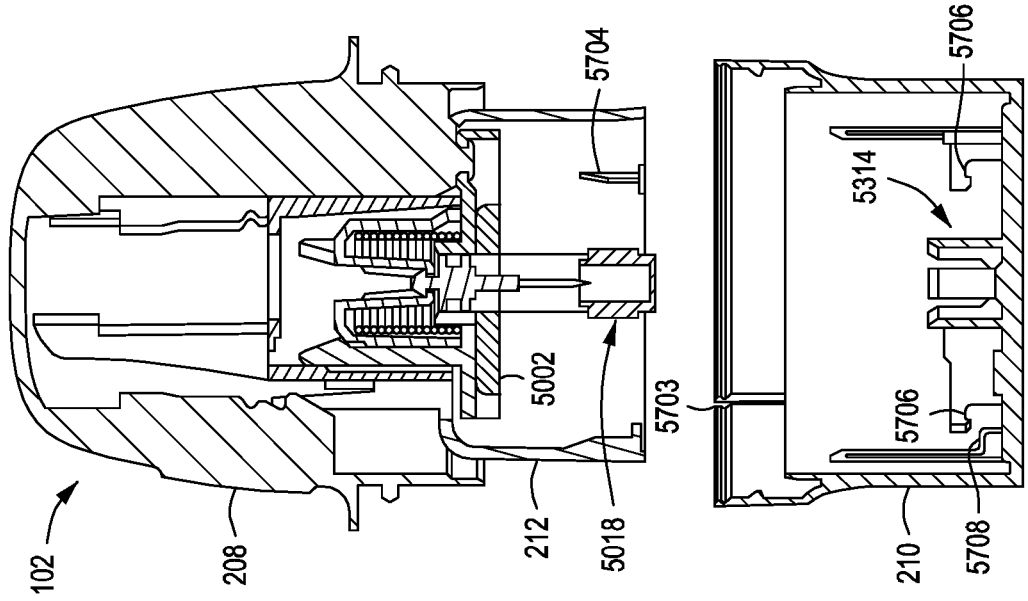
FIGS. 57A-57C are progressive cross-sectional side views showing assembly and disassembly of an example embodiment of the sensor applicator with the sensor control device of FIGS. 50A-50B.
Figure 57B:
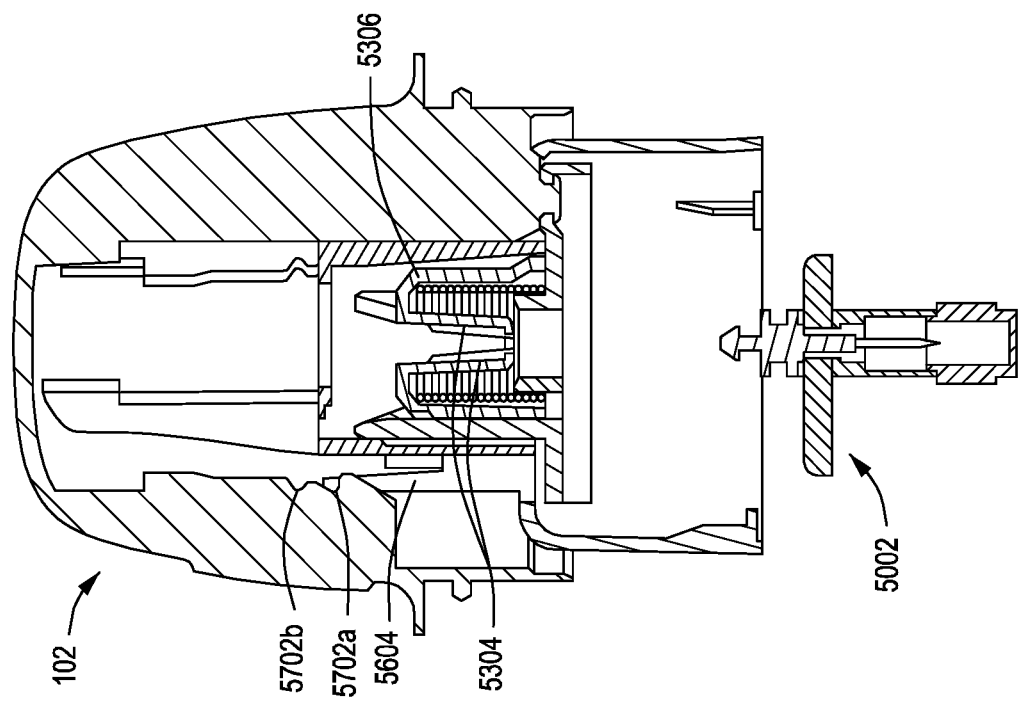
Figure 57C:
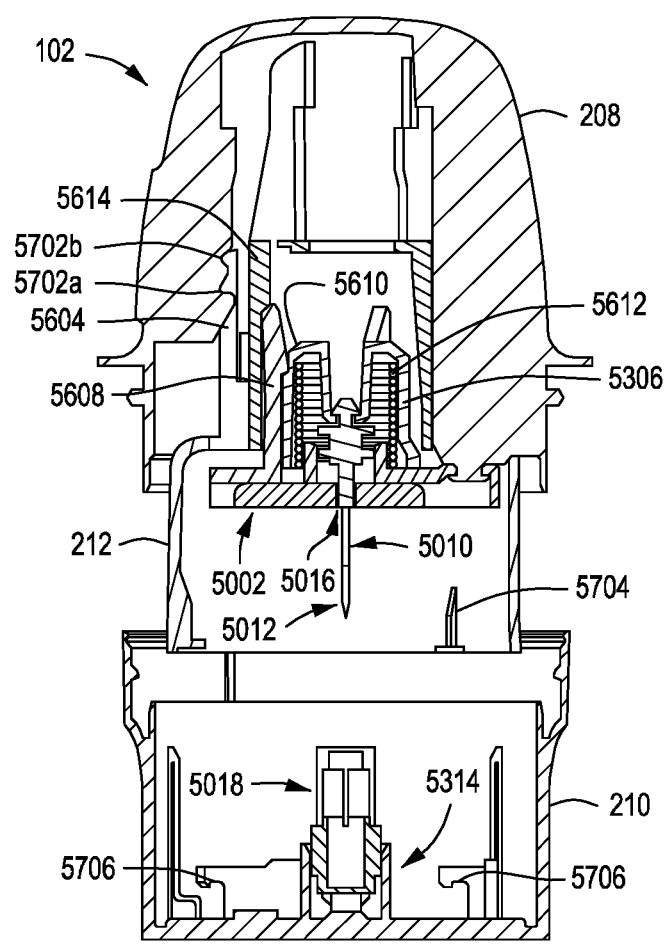

FIGS. 57A-57C are progressive cross-sectional side views showing assembly and disassembly of an alternative embodiment of the sensor applicator 102 with the sensor control device 5002, according to one or more additional embodiments. A fully assembled sensor control device 5002 may be loaded into the sensor applicator 102 by coupling the hub snap pawl 5302 into the arms 5304 of the sharp carrier 5306 positioned within the sensor applicator 102, as generally described above.

In the illustrated embodiment, the sheath arms 5604 of the sheath 212 may be configured to interact with a first detent 5702*a* and a second detent 5702*b* defined within the interior of the housing 208. The first detent 5702*a* may alternately be referred to a "locking" detent, and the second detent 5702*b* may alternately be referred to as a "firing" detent. When the sensor control device 5002 is initially installed in the sensor applicator 102, the sheath arms 5604 may be received within the first detent 5702*a*. As discussed below, the sheath 212 may be actuated to move the sheath arms 5604 to the second detent 5702*b*, which places the sensor applicator 102 in firing position.

In FIG. 57B, the applicator cap 210 is aligned with the housing 208 and advanced toward the housing 208 so that the sheath 212 is received within the applicator cap 210. Instead of rotating the applicator cap 210 relative to the housing 208, the threads of the applicator cap 210 may be snapped onto the corresponding threads of the housing 208 to couple the applicator cap 210 to the housing 208. Axial cuts or slots 5703 (one shown) defined in the applicator cap 210 may allow portions of the applicator cap 210 near its threading to flex outward to be snapped into engagement with the threading of the housing 208. As the applicator cap 210 is snapped to the housing 208, the sensor cap 5018 may correspondingly be snapped into the cap post 5314.

Similar to the embodiment of FIGS. 53A-53C, the sensor applicator 102 may include a sheath locking mechanism configured to ensure that the sheath 212 does not prematurely collapse during a shock event. In the illustrated embodiment, the sheath locking mechanism includes one or more ribs 5704 (one shown) defined near the base of the sheath 212 and configured to interact with one or more ribs 5706 (two shown) and a shoulder 5708 defined near the base of the applicator cap 210. The ribs 5704 may be configured to inter-lock between the ribs 5706 and the shoulder 5708 while attaching the applicator cap 210 to the housing 208. More specifically, once the applicator cap 210 is snapped onto the housing 208, the applicator cap 210 may be rotated (e.g., clockwise), which locates the ribs 5704 of the sheath 212 between the ribs 5706 and the shoulder 5708 of the applicator cap 210 and thereby "locks" the applicator cap 210 in place until the user reverse rotates the applicator cap 210 to remove the applicator cap 210 for use. Engagement of the ribs 5704 between the ribs 5706 and the shoulder 5708 of the applicator cap 210 may also prevent the sheath 212 from collapsing prematurely.

In FIG. 57C, the applicator cap 210 is removed from the housing 208. As with the embodiment of FIGS. 53A-53C, the applicator cap 210 can be removed by reverse rotating the applicator cap 210, which correspondingly rotates the cap post 5314 in the same direction and causes sensor cap 5018 to unthread from the mating member 5016, as generally described above. Moreover, detaching the sensor cap 5018 from the sensor control device 5002 exposes the distal portions of the sensor 5010 and the sharp 5012.

As the applicator cap 210 is unscrewed from the housing 208, the ribs 5704 defined on the sheath 212 may slidingly engage the tops of the ribs 5706 defined on the applicator cap 210. The tops of the ribs 5706 may provide corresponding ramped surfaces that result in an upward displacement of the sheath 212 as the applicator cap 210 is rotated, and moving the sheath 212 upward causes the sheath arms 5604 to flex out of engagement with the first detent 5702*a* to be received within the second detent 5702*b*. As the sheath 212 moves to the second detent 5702b, the radial shoulder 5614 moves out of radial engagement with the carrier arm(s) 5608, which allows the passive spring force of the spring 5612 to push upward on the sharp carrier 5306 and force the carrier arm(s) 5608 out of engagement with the groove(s) 5610. As the sharp carrier 5306 moves upward within the housing 208, the mating member 5016 may correspondingly retract until it becomes flush, substantially flush, or sub-flush with the bottom of the sensor control device 5002. At this point, the sensor applicator 102 in firing position. Accordingly, in this embodiment, removing the applicator cap 210 correspondingly causes the mating member 5016 to retract.

Figure 58A:
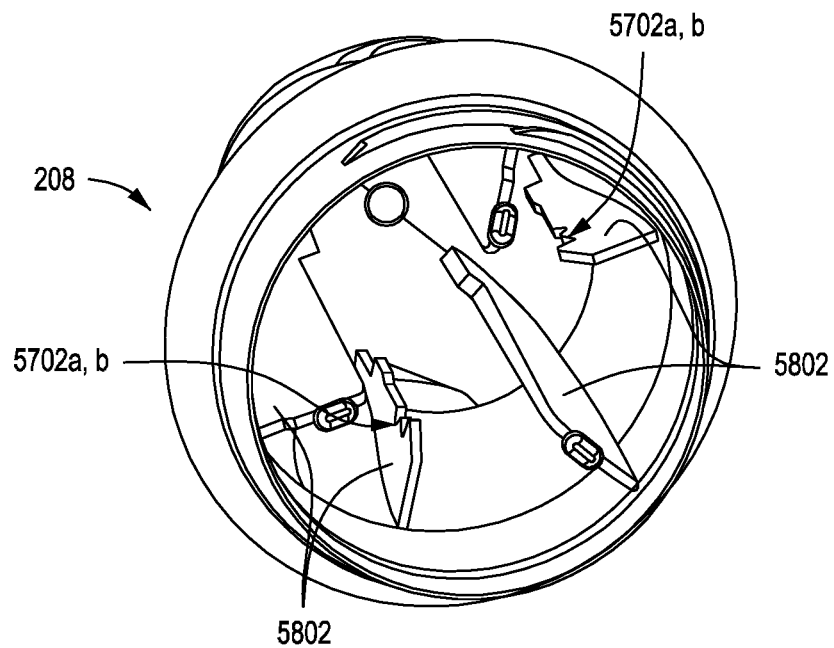
FIG. 58A is an isometric bottom view of the housing, according to one or more embodiments.

FIG. 58A is an isometric bottom view of the housing 208, according to one or more embodiments. As illustrated, one or more longitudinal ribs 5802 (four shown) may be defined within the interior of the housing 208. The ribs 5802 may be equidistantly or non-equidistantly spaced from each other and extend substantially parallel to centerline of the housing 208. The first and second detents 5702a,b may be defined on one or more of the longitudinal ribs 5802.

Figure 58B:
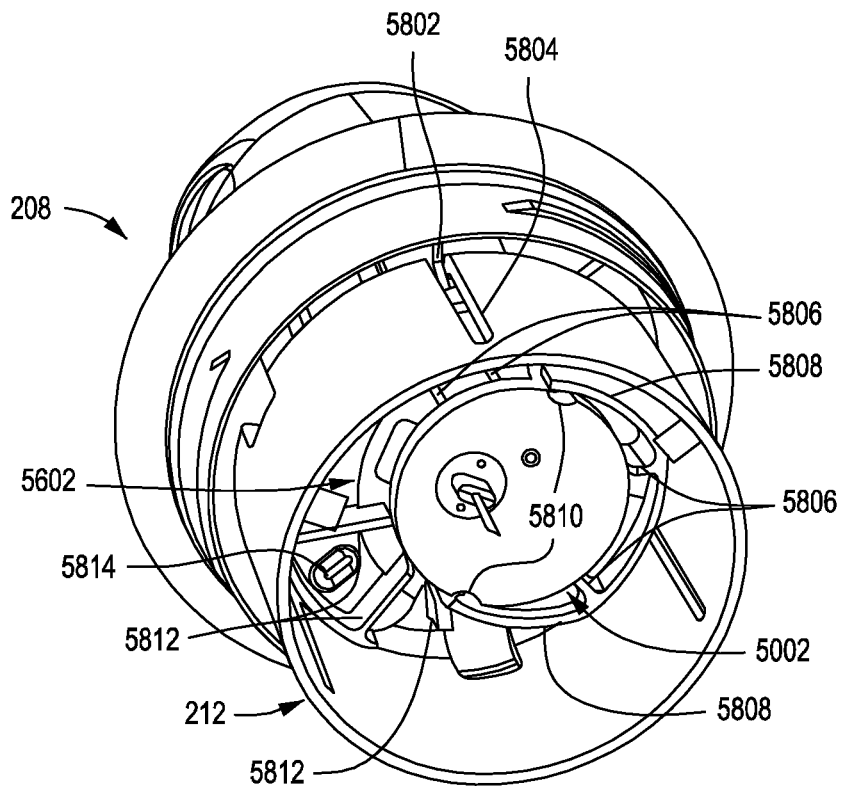
FIG. 58B is an isometric bottom view of the housing with the sheath and other components at least partially positioned therein.

FIG. 58B is an isometric bottom view of the housing 208 with the sheath 212 and other components at least partially positioned within the housing 208. As illustrated, the sheath 212 may provide or otherwise define one or more longitudinal slots 5804 configured to mate with the longitudinal ribs 5802 of the housing 208. As the sheath 212 collapses into the housing 208, as generally described above, the ribs 5802 may be received within the slots 5804 to help maintain the sheath 212 aligned with the housing during its movement. As will be appreciated, this may result in tighter circumferential and radial alignment within the same dimensional and tolerance restrictions of the housing 208.

In the illustrated embodiment, the sensor carrier 5602 may be configured to hold the sensor control device 5002 in place both axially (e.g., once the sensor cap 5018 is removed) and circumferentially. To accomplish this, the sensor carrier 5602 may include or otherwise define one or more support ribs 5806 and one or more flexible arms 5808. The support ribs 5806 extend radially inward to provide radial support to the sensor control device 5002. The flexible arms 5808 extend partially about the circumference of the sensor control device 5002 and the ends of the flexible arms 5808 may be received within corresponding grooves 5810 defined in the side of the sensor control device 5002. Accordingly, the flexible arms 5808 may be able to provide both axial and radial support to the sensor control device 5002. In at least one embodiment, the ends of the flexible arms 5808 may be biased into the grooves 5810 of the sensor control device 5002 and otherwise locked in place with corresponding sheath locking ribs 5812 provided by the sheath 212.

In some embodiments, the sensor carrier 5602 may be ultrasonically welded to the housing 208 at one or more points 5814. In other embodiments, however, the sensor carrier 5602 may alternatively be coupled to the housing 208 via a snap-fit engagement, without departing from the scope of the disclosure. This may help hold the sensor control device 5002 in place during transport and firing.

Figure 59:
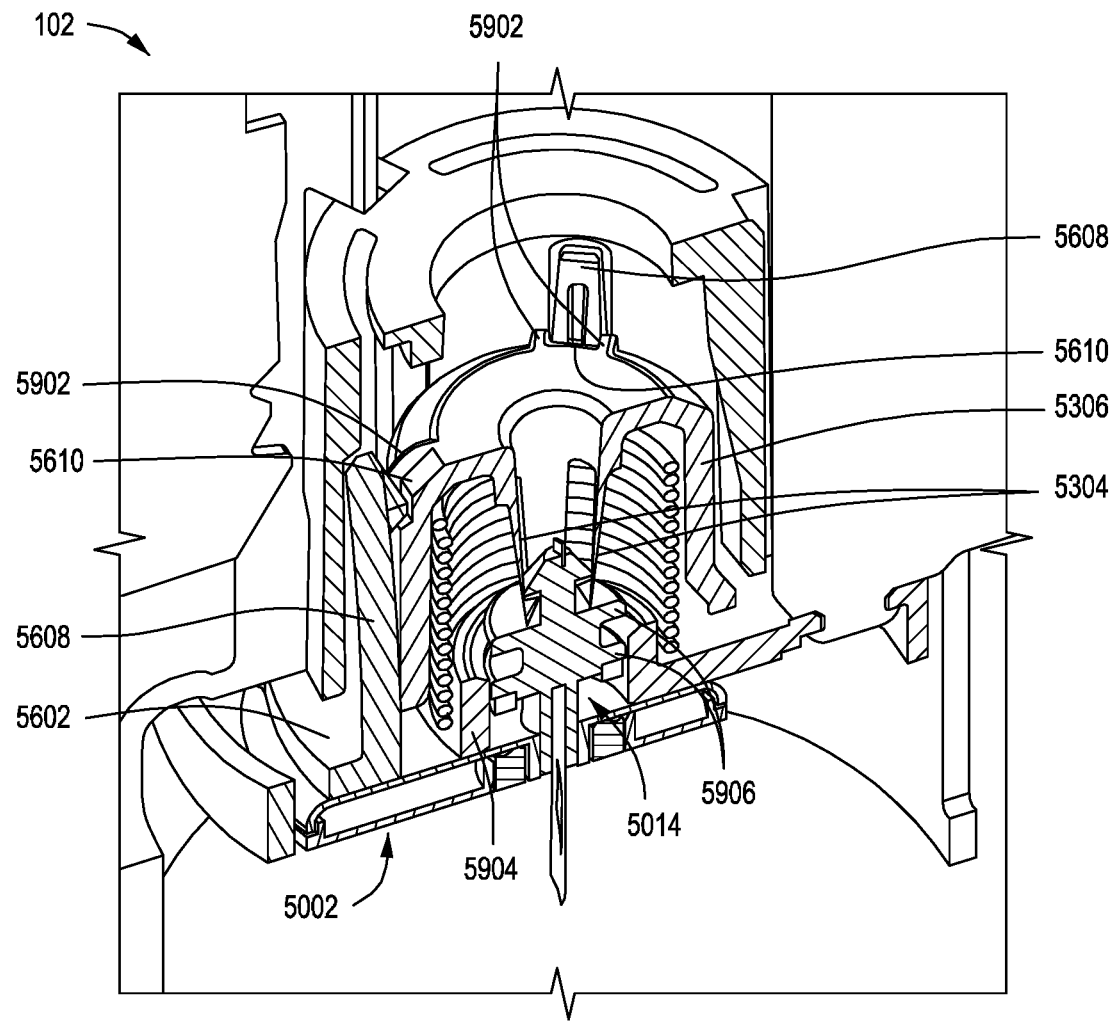
FIG. 59 is an enlarged cross-sectional side view of the sensor applicator with the sensor control device installed therein, according to one or more embodiments.

FIG. 59 is an enlarged cross-sectional side view of the sensor applicator 102 with the sensor control device 5002 installed therein, according to one or more embodiments. As discussed above, the sensor carrier 5602 may include one or more carrier arms 5608 (two shown) engageable with the sharp carrier 5306 at corresponding grooves 5610. In at least one embodiment, the grooves 5610 may be defined by pairs of protrusions 5902 defined on the sharp carrier 5306. Receiving the carrier arms 5608 within the grooves 5610 may help stabilize the sharp carrier 5306 from unwanted tilting during all stages of retraction (firing).

In the illustrated embodiment, the arms 5304 of the sharp carrier 5306 may be stiff enough to control, with greater refinement, radial and bi-axial motion of the sharp hub 5014. In some embodiments, for example, clearances between the sharp hub 5014 and the arms 5304 may be more restrictive in both axial directions as the relative control of the height of the sharp hub 5014 may be more critical to the design.

In the illustrated embodiment, the sensor carrier 5602 defines or otherwise provides a central boss 5904 sized to receive the sharp hub 5014. In some embodiments, as illustrated, the sharp hub 5014 may provide one or more radial ribs 5906 (two shown). In at least one embodiment, the inner diameter of the central boss 5904 helps provide radial and tilt support to the sharp hub 5014 during the life of sensor applicator 102 and through all phases of operation and assembly. Moreover, having multiple radial ribs 5906 increases the length-to-width ratio of the sharp hub 5014, which also improves support against tilting.

Figure 60A:
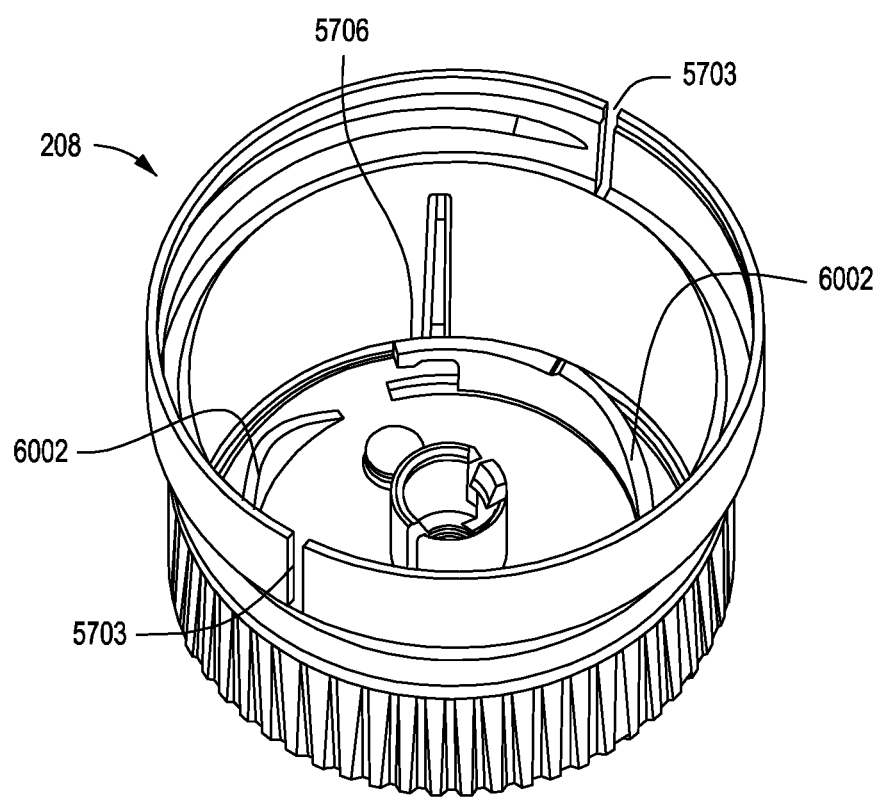
FIG. 60A is an isometric top view of the cap, according to one or more embodiments.

FIG. 60A is an isometric top view of the applicator cap 210, according to one or more embodiments. In the illustrated embodiment, two axial slots 5703 are depicted that separate upper portions of the applicator cap 210 near its threading. As mentioned above, the slots 5703 may help the applicator cap 210 flex outward to be snapped into engagement with the housing 208 (FIG. 57B). In contrast, the applicator cap 210 may be twisted (unthreaded) off the housing 208 by an end user.

FIG. 60A also depicts the ribs 5706 (one visible) defined by the applicator cap 210. By interlocking with the ribs 5704 (FIG. 57C) defined on the sheath 212 (FIG. 57C), the ribs 5706 may help lock the sheath 212 in all directions to prevent premature collapse during a shock or drop event. The sheath 212 may be unlocked when the user unscrews the applicator cap 210 from the housing (FIG. 59C), as generally described above. As mentioned herein, the top of each rib 5706 may provide a corresponding ramped surface 6002, and as the applicator cap 210 is rotated to unthread from the housing 208, the ribs 5704 defined on the sheath 212 may slidingly engage the ramped surfaces 6002, which results in the upward displacement of the sheath 212 into the housing 208.

In some embodiments, additional features may be provided within the interior of the applicator cap 210 to hold a desiccant component that maintains proper moisture levels through shelf life. Such additional features may be snaps, posts for press-fitting, heat-staking, ultrasonic welding, etc.

Figure 60B:
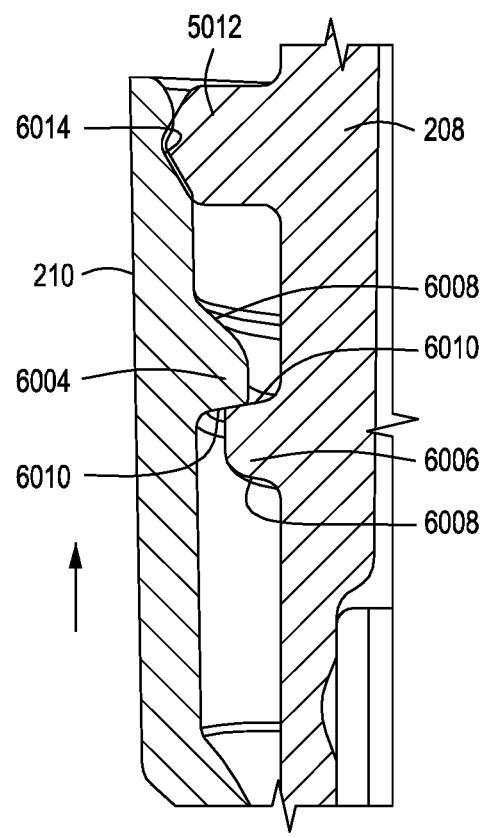
FIG. 60B is an enlarged cross-sectional view of the engagement between the cap and the housing, according to one or more embodiments.

FIG. 60B is an enlarged cross-sectional view of the engagement between the applicator cap 210 and the housing 208, according to one or more embodiments. As illustrated, the applicator cap 210 may define a set of inner threads 6004 and the housing 208 may define a set of outer threads 6006 engageable with the inner threads 6004. As mentioned herein, the applicator cap 210 may be snapped onto the housing 208, which may be accomplished by advancing the inner threads 6004 axially past the outer threads 6006 in the direction indicated by the arrow, which causes the applicator cap 210 to flex outward. To help ease this transition, as illustrated, corresponding surfaces 6008 of the inner and outer threads 6004, 6006 may be curved, angled, or chamfered. Corresponding flat surfaces 6010 may be provided on each thread 6004, 6006 and configured to matingly engage once the applicator cap 210 is properly snapped into place on the housing 208. The flat surfaces 6010 may slidingly engage one another as the user unthreads the applicator cap 210 from the housing 208.

The threaded engagement between the applicator cap 210 and the housing 208 results in a sealed engagement that protects the inner components against moisture, dust, etc. In some embodiments, the housing 208 may define or otherwise provide a stabilizing feature 6012 configured to be received within a corresponding groove 1914 defined on the applicator cap 210. The stabilizing feature 6012 may help stabilize and stiffen the applicator cap 210 once the applicator cap 210 is snapped onto the housing 208. This may prove advantageous in providing additional drop robustness to the sensor applicator 102. This may also help increase the removal torque of the applicator cap 210.

Figure 61A:
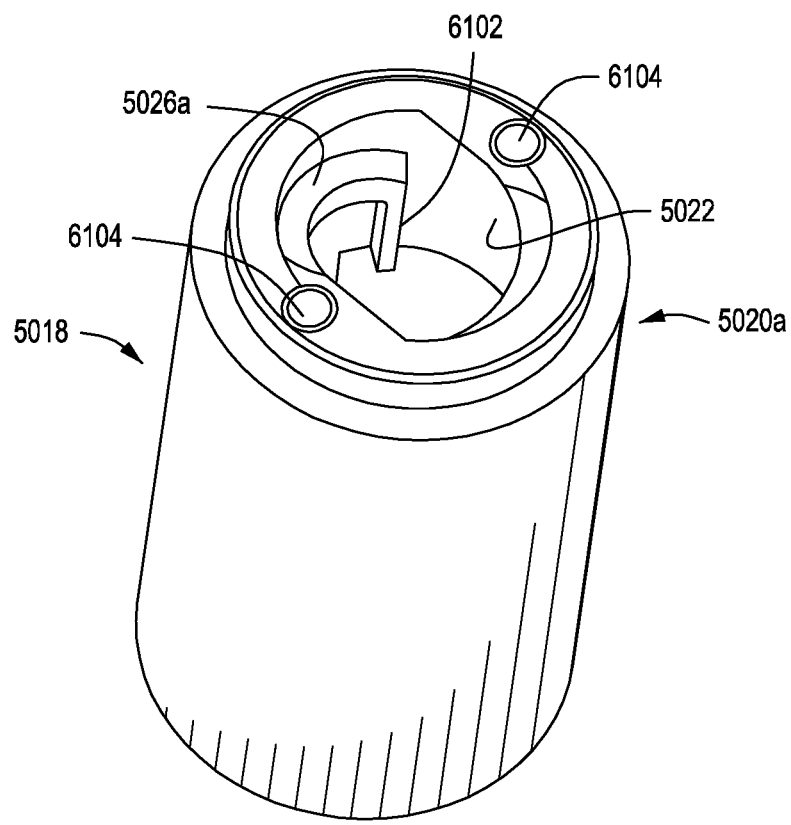
FIGS. 61A and 61B are isometric views of the sensor cap and the collar, respectively, according to one or more embodiments.
Figure 61B:
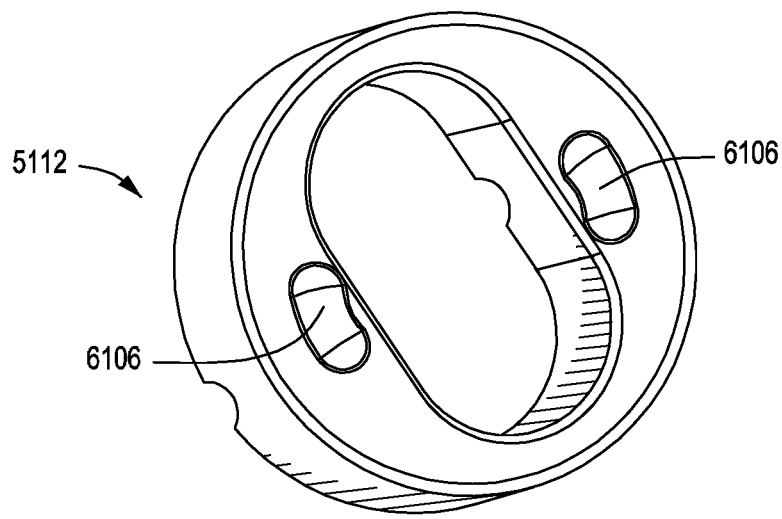

FIGS. 61A and 61B are isometric views of the sensor cap 5018 and the collar 5112, respectively, according to one or more embodiments. Referring to FIG. 61A, in some embodiments, the sensor cap 5018 may comprise an injection molded part. This may prove advantageous in molding the internal threads 5026a defined within the inner chamber 5022, as opposed to installing a threaded core or threading the inner chamber 5022. In some embodiments, one or more stop ribs 6102 (on visible) may be defined within the inner chamber 5022 to prevent over travel relative to mating member 5016 of the sharp hub 5014 (FIGS. 50A-50B).

Referring to both FIGS. 61A and 61B, in some embodiments, one or more protrusions 6104 (two shown) may be defined on the first end 5020a of the sensor cap 5018 and configured to mate with one or more corresponding indentations 6106 (two shown) defined on the collar 5112. In other embodiments, however, the protrusions 6104 may instead be defined on the collar 5112 and the indentations 6106 may be defined on the sensor cap 5018, without departing from the scope of the disclosure.

The matable protrusions 6104 and indentations 6106 may prove advantageous in rotationally locking the sensor cap 5018 to prevent unintended unscrewing of the sensor cap 5018 from the collar 5112 (and thus the sensor control device 5002) during the life of the sensor applicator 102 and through all phases of operation/assembly. In some embodiments, as illustrated, the indentations 6106 may be formed or otherwise defined in the general shape of a kidney bean. This may prove advantageous in allowing for some over-rotation of the sensor cap 5018 relative to the collar 5112. Alternatively, the same benefit may be achieved via a flat end threaded engagement between the two parts.

Embodiments disclosed herein include:

U. A sensor control device that includes an electronics housing, a sensor arranged within the electronics housing and having a tail extending from a bottom of the electronics housing, a sharp extending through the electronics housing and having a sharp tip extending from the bottom of the electronics housing, and a sensor cap removably coupled at the bottom of the electronics housing and defining a sealed inner chamber that receives the tail and the sharp.

V. An analyte monitoring system that includes a sensor applicator, a sensor control device positioned within the sensor applicator and including an electronics housing, a sensor arranged within the electronics housing and having a tail extending from a bottom of the electronics housing, a sharp extending through the electronics housing and having a sharp tip extending from the bottom of the electronics housing, and a sensor cap removably coupled at the bottom of the electronics housing and defining an engagement feature and a sealed inner chamber that receives the tail and the sharp. The analyte monitoring system may further include a cap coupled to the sensor applicator and providing a cap post defining a receiver feature that receives the engagement feature upon coupling the cap to the sensor applicator, wherein removing the cap from the sensor applicator detaches the sensor cap from the electronics housing and thereby exposes the tail and the sharp tip.

W. A method of preparing an analyte monitoring system that includes loading a sensor control device into a sensor applicator, the sensor control device including an electronics housing, a sensor arranged within the electronics housing and having a tail extending from a bottom of the electronics housing, a sharp extending through the electronics housing and having a sharp tip extending from the bottom of the electronics housing, and a sensor cap removably coupled at the bottom of the electronics housing and defining a sealed inner chamber that receives the tail and the sharp. The method further including securing a cap to the sensor applicator, sterilizing the sensor control device with gaseous chemical sterilization while the sensor control device is positioned within the sensor applicator, and isolating the tail and the sharp tip within the inner chamber from the gaseous chemical sterilization.

Each of embodiments U, V, and W may have one or more of the following additional elements in any combination: Element 1: wherein the sensor cap comprises a cylindrical body having a first end that is open to access the inner chamber, and a second end opposite the first end and providing an engagement feature engageable with a cap of a sensor applicator, wherein removing the cap from the sensor applicator correspondingly removes the sensor cap from the electronics housing and thereby exposes the tail and the sharp tip. Element 2: wherein the electronics housing includes a shell matable with a mount, the sensor control device further comprising a sharp and sensor locator defined on an inner surface of the shell, and a collar received about the sharp and sensor locator, wherein the sensor cap is removably coupled to the collar. Element 3: wherein the sensor cap is removably coupled to the collar by one or more of an interference fit, a threaded engagement, a frangible member, and a frangible substance. Element 4: wherein an annular ridge circumscribes the sharp and sensor locator and the collar provides a column and an annular shoulder extending radially outward from the column, and wherein a seal member interposes the annular shoulder and the annular ridge to form a sealed interface. Element 5: wherein the annular ridge defines a groove and a portion of the sensor is seated within the groove, and wherein the seal member extends into the groove to seal about the portion of the sensor. Element 6: wherein the seal member is a first seal member, the sensor control device further comprising a second seal member interposing the annular shoulder and a portion of the mount to form a sealed interface. Element 7: wherein the electronics housing includes a shell matable with a mount, the sensor control device further comprising a sharp hub that carries the sharp and is engageable with a top surface of the shell, and a mating member defined by the sharp hub and extending from the bottom of the electronics housing, wherein the sensor cap is removably coupled to the mating member. Element 8: further comprising a collar at least partially receivable within an aperture defined in the mount and sealingly engaging the sensor cap and an inner surface of the shell. Element 9: wherein a seal member interposes the collar and the inner surface of the shell to form a sealed interface. Element 10: wherein the collar defines a groove and a portion of the sensor is seated within the groove, and wherein the seal member extends into the groove to seal about the portion of the sensor.

Element 11: wherein the receiver feature comprises one or more compliant members that flex to receive the engagement feature, and wherein the one or more compliant members prevent the engagement feature from exiting the cap post upon removing the cap from the sensor applicator. Element 12: further comprising a ramped surface defined on at least one of the one or more compliant members, and one or more camming surfaces provided by the engagement feature and engageable with the ramped surface, wherein the ramped surface and the one or more camming surfaces allow the cap and the cap post to rotate relative to the sensor cap in a first direction, but prevent the cap and the cap post from rotating relative to the sensor cap in a second direction opposite the first direction. Element 13: wherein the electronics housing includes a shell matable with a mount, the sensor control device further comprising a sharp hub that carries the sharp and is engageable with a top surface of the shell, and a mating member defined by the sharp hub and extending from the bottom of the electronics housing, wherein the sensor cap is removably coupled to the mating member and rotating the cap in the second direction detaches the sensor cap from the mating member. Element 14: wherein the electronics housing includes a shell matable with a mount and the sensor control device further includes a sharp and sensor locator defined on an inner surface of the shell, and a collar received about the sharp and sensor locator, wherein the sensor cap is removably coupled to the collar.

Element 15: wherein the cap provides a cap post defining a receiver feature and the sensor cap defines an engagement feature, the method further comprising receiving the engagement feature with the receiver feature as the cap is secured to the sensor applicator. Element 16: further comprising removing the cap from the sensor applicator, and engaging the engagement feature on the receiver feature as the cap is being removed and thereby detaching the sensor cap from the electronics housing and exposing the tail and the sharp tip. Element 17: wherein loading the sensor control device into a sensor applicator is preceded by sterilizing the tail and the sharp tip with radiation sterilization, and sealing the tail and the sharp tip within the inner chamber.

By way of non-limiting example, exemplary combinations applicable to U, V, and W include: Element 2 with Element 3; Element 2 with Element 4; Element 4 with Element 5; Element 4 with Element 6; Element 7 with Element 8; Element 8 with Element 9; Element 9 with Element 10; Element 11 with Element 12; and Element 15 with Element 16.

Sensor Applicator with Actuating Needle Shroud

Referring again briefly to FIG. 1, the sensor control device 104 is often included with the sensor applicator 104 in what is known as a "two-piece" architecture that requires final assembly by a user before the sensor 110 can be properly delivered to the target monitoring location. In such applications, the sensor 110 and the associated electrical components included in the sensor control device 104 are provided to the user in multiple (two) packages, and the user must open the packaging and follow instructions to manually assemble the components before delivering the sensor 110 to the target monitoring location with the sensor applicator 6302. More recently, however, advanced designs of sensor control devices and associated sensor applicators have resulted in a one-piece architecture that allows the system to be shipped to the user in a single, sealed package that does not require any final user assembly steps. Rather, the user need only open one package, remove an applicator cap, and subsequently deliver the sensor control device to the target monitoring location.

Notwithstanding these advances, conventional sensor applicators commonly include a shroud that surrounds the entire outer periphery of the sensor control device. To deploy the sensor control device, the shroud is forced against the skin and retracts into the sensor applicator, which causes the combination introducer and sensor to be delivered transcutaneously under the user's skin. Having the shroud positioned away from the insertion site near the introducer leaves the skin at the insertion site in a generally soft and uncompressed state. It can be difficult to insert a sensor in uncompressed soft tissue due to the skin depression that occurs as the introducer tip enters the skin, commonly referred to as skin "tenting". Embodiments of the present disclosure include sensor applicators that incorporate a needle shroud to apply pressure to the skin at or near the insertion site.

Figure 62:
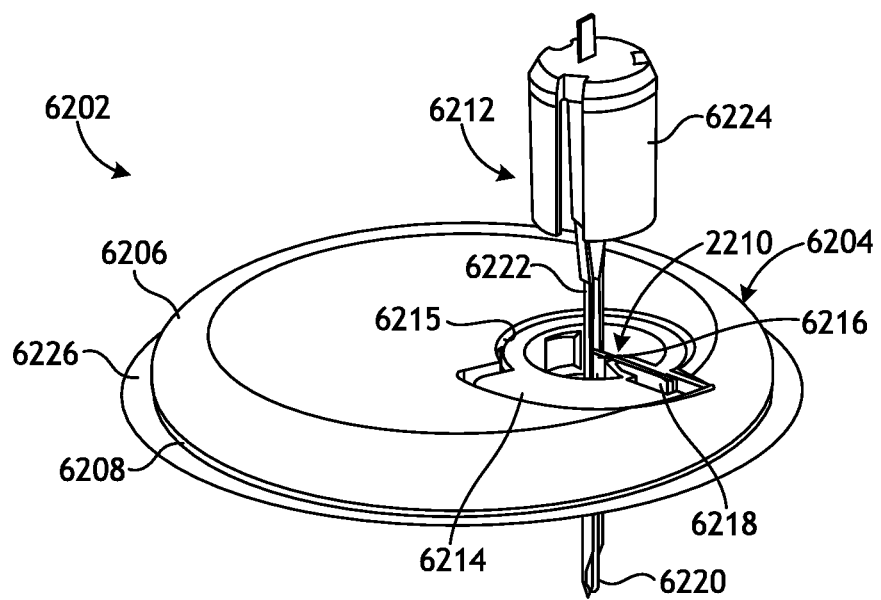
FIG. 62 is an isometric top view of an example sensor control device, according to one or more embodiments of the present disclosure.

FIG. 62 is an isometric top view of an example sensor control device 6202, according to one or more embodiments of the present disclosure. The sensor control device 6202 may be the same as or similar to the sensor control device 104 of FIG. 1 and, therefore, may be designed to be delivered to a target monitoring location on a user's skin through operation of a sensor applicator (not shown). As illustrated, the sensor control device 6202 includes an electronics housing 6204 that is generally disc-shaped and may have a circular cross-section. In other embodiments, however, the electronics housing 6204 may exhibit other cross-sectional shapes, such as oval, ovoid (e.g., pill- or egg-shaped), a squircle, polygonal, or any combination thereof, without departing from the scope of the disclosure. The electronics housing 6204 may house or otherwise contain various electronic components used to operate the sensor control device 6202. For example, a printed circuit board (PCB) may be positioned within the electronics housing and may have thereto one or more of a battery, a data processing unit, and various resistors, transistors, capacitors, inductors, diodes, and switches.

The electronics housing 6204 may include a shell 6206 and a mount 6208 that is matable with the shell 6206. The shell 6206 may be secured to the mount 6208 via a variety of ways, such as a snap fit engagement, an interference fit, sonic welding, one or more mechanical fasteners (e.g., screws), or any combination thereof. In some cases, the shell 6206 may be secured to the mount 6208 such that a sealed interface is generated therebetween. In such embodiments, a gasket or other type of seal material may be positioned at or near the outer diameter (periphery) of the shell 6206 and the mount 6208, and securing the two components together may compress the gasket and thereby generate a sealed interface. In other embodiments, an adhesive may be applied to the outer diameter (periphery) of one or both of the shell 6206 and the mount 6208. The adhesive secures the shell 6206 to the mount 6208 and provides structural integrity, but may also seal the interface between the two components and thereby isolate the interior of the electronics housing 6204 from outside contamination.

In the illustrated embodiment, the sensor control device 6202 also includes a sensor module 6210 interconnectable with a sharp module 6212. The sensor module 6210 may be coupled to the electronics housing 6204 with a collar 6214, and the collar 6214 may be mounted to the electronics housing 6204 within an aperture 6215 defined therethrough. The sensor module 6210 may include a sensor 6216 and a flexible connector 6218 used to help connect the sensor 6216 to the electronic components housed within the electronics housing 6204. A tail 6220 of the sensor 6216 may extend distally from the electronics housing 6204 and, more particularly, from the bottom of the mount 6208.

The sharp module 6212 may carry or otherwise include an introducer or sharp 6222 used to help deliver the sensor 6216 transcutaneously under a user's skin during deployment of the sensor control device 6202. In the illustrated embodiment, the sharp module 6212 includes a sharp hub 6224 that carries the sharp 6222. In one embodiment, the sharp hub 6224 may be overmolded onto the sharp 6222, but could alternatively be fabricated from plastic, metal, or another suitable material as a separate component, and bonded, welded, or mechanically attached to the sharp 6222. Similar to the tail 6220, the distal end of the sharp 6222 may extend distally from the electronics housing 6204 and, more particularly, from the bottom of the mount 6208. In at least one embodiment, the tail 6220 may be received within a hollow or recessed portion of the sharp 6222.

While the sensor control device 6202 is depicted as an eccentric assembly, with the sensor 6216 and the sharp 6222 extending distally at a location offset from a central axis of the electronics housing 6204, embodiments are contemplated herein where the sensor 6216 and the sharp 6222 are aligned with the central axis in a concentric design, without departing from the scope of the disclosure. Moreover, an adhesive patch 6226 may be positioned on and otherwise attached to the underside of the mount 6208. Similar to the adhesive patch 108 of FIG. 1, the adhesive patch 6226 may be configured to secure and maintain the sensor control device 6202 in position on the user's skin during operation.

Figure 63:
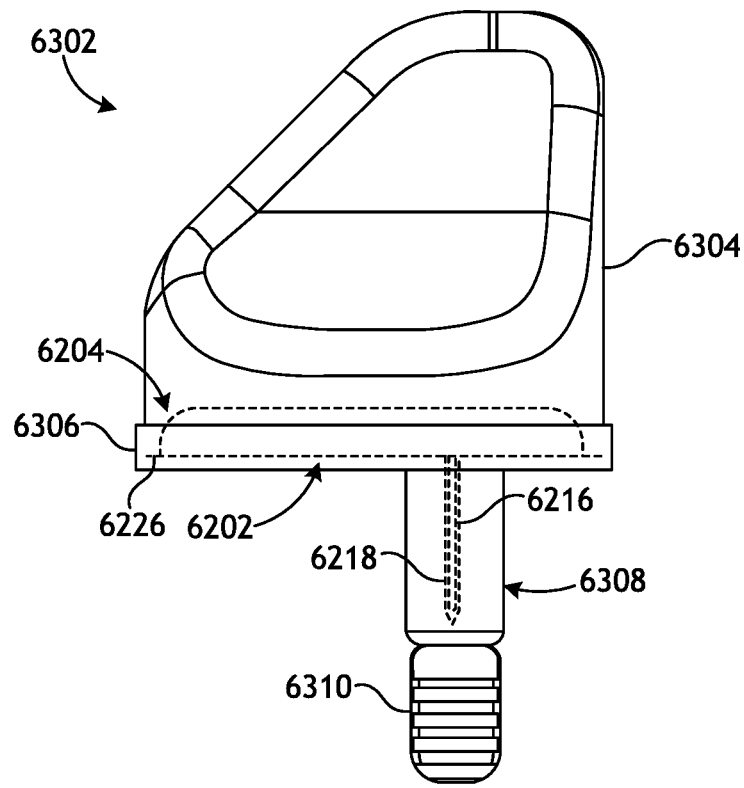
FIG. 63 is a schematic side view of an example sensor applicator, according to one or more embodiments of the present disclosure.

FIG. 63 is a schematic side view of an example sensor applicator 6302, according to one or more embodiments of the present disclosure. The sensor applicator 6302 may be similar in some respects to the sensor applicator 102 of FIG. 1 and, therefore, may be configured to house and facilitate deployment of a sensor control device, such as the sensor control device 6202 (shown in dashed lines). As illustrated, the sensor applicator 6302 may include a housing 6304 sized to receive the sensor control device 6202 therein. In some embodiments, an applicator cap 6306 may be removably coupled to the housing 6304. The applicator cap 6306 may be threaded to the housing 6304, for example, but could alternatively be coupled thereto via a snap fit engagement, an interference fit, or the like, without departing from the scope of the disclosure. The applicator cap 6306 may help protect and shield the adhesive patch 6226 from contaminants or damage prior to deploying the sensor control device 6202.

The sensor applicator 6302 may also include a sensor cap 6308 extending from the bottom of the sensor applicator 6302. The sensor cap 6308 may be configured to receive and protect the distal ends of the sensor 6216 and the sharp 6222 extending from the bottom of the electronics housing 6204. In some embodiments, the sensor cap 6308 may be coupled to or otherwise form an integral part or extension of the applicator cap 6306. In other embodiments, however, the applicator and sensor caps 6306, 6308 may constitute separate component parts that may be jointly or separately removable from the bottom of the housing 6304.

In some embodiments, the sensor cap 6308 may extend from the sensor control device 6202 and form part of a sterile barrier with the collar 6214 (FIG. 62) to protect the distal ends of the sensor 6216 and the sharp 6222. In such embodiments, the sensor cap 6308 may be removably coupled to the collar 6214, such as being threaded to the collar 6214 or coupled thereto using a bayonet coupling, an interference fit, a snap fit engagement, or any combination thereof. In other embodiments, the sensor cap 6308 may alternatively be removably coupled to another internal feature of the sensor applicator 6302, without departing from the scope of the disclosure.

In one or more embodiments, the sensor cap 6308 may include a gripping interface 6310 that provides a location for a user to grasp onto and remove the sensor cap 6308 from the sensor applicator 6302. The gripping interface 6310 may comprise, for example, a tab that can be grasped by the user with the thumb and forefinger. Once the applicator cap 6306 and the sensor cap 6308 are removed, a user may then use the sensor applicator 6302 to position the sensor control device 6202 (FIG. 62) at a target monitoring location on the user's body, as will be described below.

Figure 64A:
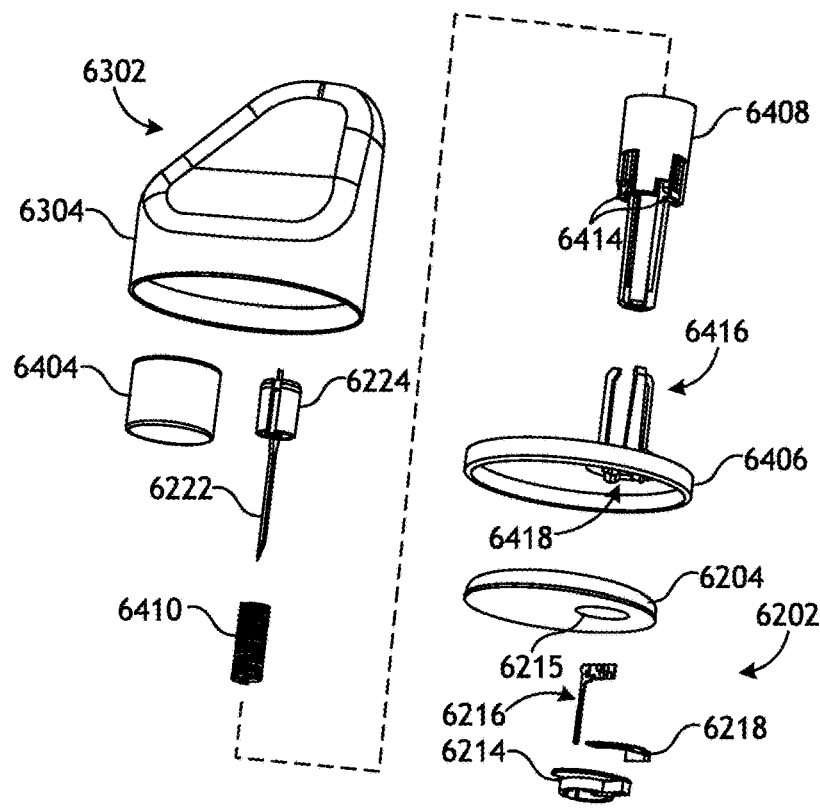
FIGS. 64A and 64B are exploded isometric views of the sensor applicator and the sensor control device of FIGS. 62 and 63.
Figure 64B:
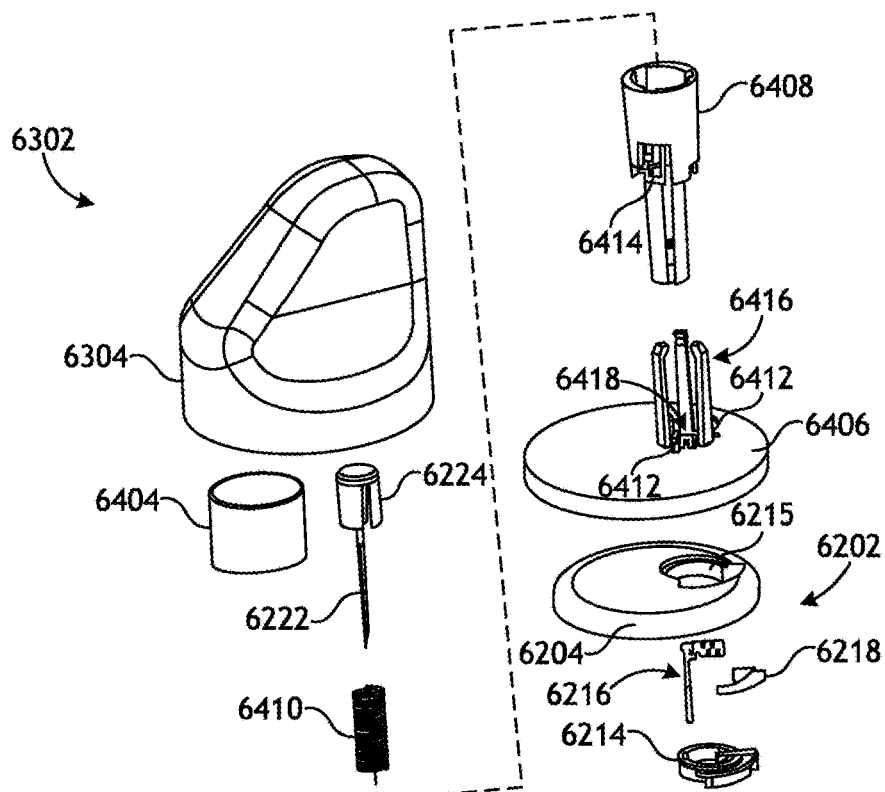

FIGS. 64A and 64B are exploded isometric views of the sensor applicator 6302 and the sensor control device 6202. The applicator cap 6306 and the sensor cap 6308 of FIG. 63 are not shown for simplicity. As illustrated, the collar 6214, the sensor 6216, and the flexible connector 6218 (collectively the sensor module 6210 of FIG. 62) may each be mounted to the electronics housing 6204 at or within the aperture 6215 defined in the electronics housing 6204.

The sensor applicator 6302 may include a desiccant 6404, a sensor retainer 6406, a needle shroud 6408, and a driver spring 6410. The desiccant 6404 may optionally contained within the housing 6304 to help maintain appropriate humidity levels. The housing 6304 may be matable with the sensor retainer 6406 (alternately referred to as a "puck retainer") to retain the needle shroud 6408, the driver spring 6410, the sharp hub 6224, and the sharp 6222 within the housing 6304. The sensor retainer 6406, the needle shroud 6408, the sharp hub 6224 with the sharp 6222, and the driver spring 6410 may all be operatively coupled to help facilitate deployment of the sensor control device 6202.

As described below, the needle shroud 6408 may be movable (actuatable) between an extended position and a retracted position to deploy the sensor control device 6202 from the sensor applicator 6302. As best seen in FIG. 64B, the sensor retainer 6406 may have one or more locking tabs 6412 engageable with a corresponding one or more locking members 6414 provided on the needle shroud 6408. Coupling the locking members 6414 to the locking tabs 6412 helps secure the needle shroud 6408 in the extended position, whereas disengaging the locking members 6414 from the locking tabs 6412 allows the needle shroud 6408 to move to the retracted position.

Those skilled in the art will readily appreciate that the locking tabs and members 6412, 6414 are merely one way to temporarily secure the needle shroud 6408 in the extended position. In other embodiments, for example, the locking tabs and members 6412, 6414 may be replaced with corresponding detents and mating grooves or other common types of removable or releasable couplings, without departing from the scope of the disclosure.

The sensor retainer 6406 may further include a plurality of upwardly extending fingers 6414 (three shown) configured to extend partially into the needle shroud 6408 to help retain the sharp hub 6224 until the needle shroud 6408 moves to the retracted position. Once the needle shroud 6408 reaches the retracted position, the fingers 6414 may be able to flex radially outward to release the needle shroud 6408, and the spring force of the driver spring 6410 may retract the sharp 6222 into the housing 6304.

The sensor retainer 6406 may define an aperture 6418 through which the lower portion of the needle shroud 6408 can extend. The lower end of the needle shroud 6408 extends through the aperture 6418 (and the aperture 6215 provided in the electronics housing 6204) when the needle shroud 6408 is in the extended position. Moving the needle shroud 6408 to the retracted position draws the lower end of the needle shroud 6408 upward through the aperture 6418 (and the aperture 6215 of the electronics housing 6204).

Figure 65A:
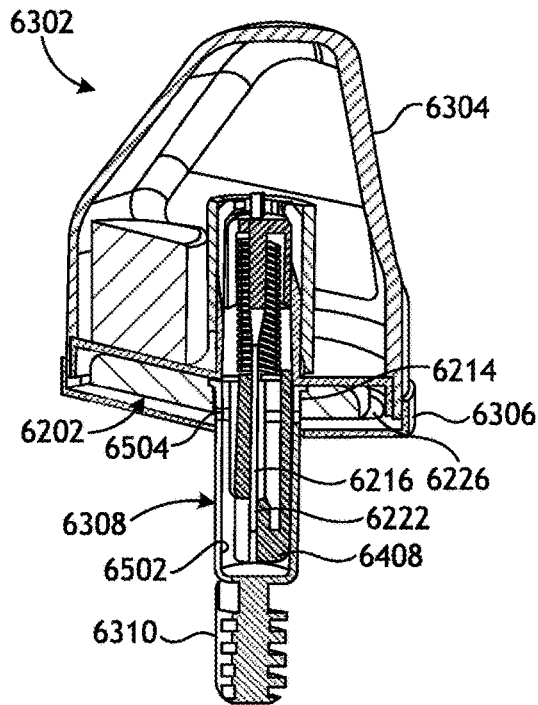
FIGS. 65A-65D are progressive cross-sectional side views of the sensor applicator of FIGS. 63 and 64A-64B depicting example deployment of a sensor control device, according to one or more embodiments.
Figure 65B:
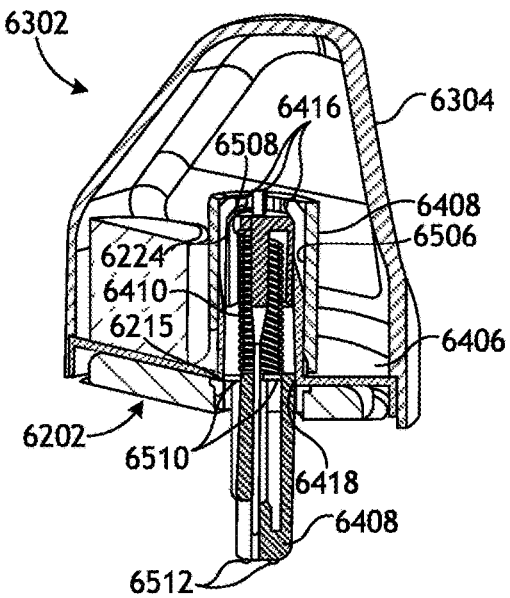
Figure 65C:
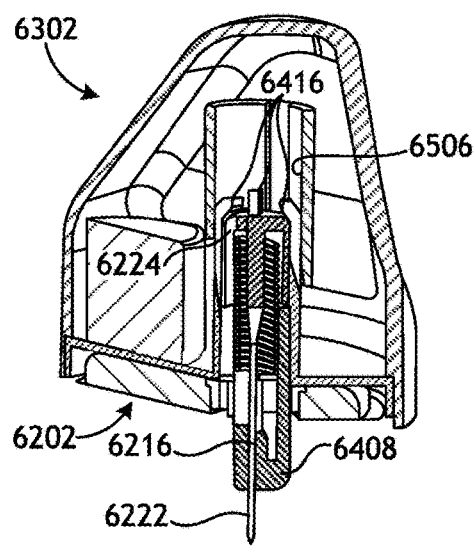
Figure 65D:
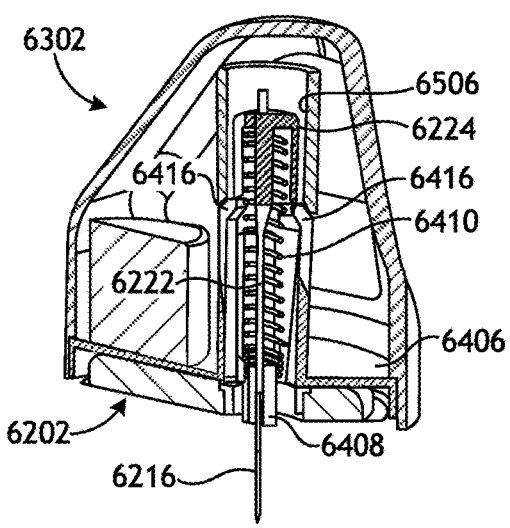

FIGS. 65A-65D are progressive cross-sectional side views of the sensor applicator 6302 depicting example deployment of the sensor control device 6202, according to one or more embodiments. User operation (actuation) of the sensor applicator 6302 can cause the needle shroud 6408 to move from the extended position, as shown in FIGS. 65A and 65B, to the retracted position, as shown in FIG. 65D. Once the needle shroud 6408 reaches the retracted position, the sensor control device 6202 may be able to be released (discharged) from the sensor retainer 6406, as described below.

Referring first to FIG. 65A, the applicator cap 6306 is removably coupled to the housing 6304. In some embodiments, the interface between the applicator cap 6306 and the housing 6304 may be sealed to help protect and shield the adhesive patch 6226 from contamination or damage prior to deploying the sensor control device 6202. The sensor cap 6308 is also depicted extending distally from the bottom of the sensor applicator 6302 and, more particularly, from the sensor control device 6202.

The sensor cap 6308 may define an interior 6502 sized to receive a lower portion of the needle shroud 6408 in the extended position. Moreover, distal ends of the sensor 6216 and the sharp 6222 may also extend into the interior 6502 of the sensor cap 6308 and the needle shroud 6408 may generally cover the distal ends of the sensor 6216 and the sharp 6222 when the needle shroud 6408 is in the extended position. In some embodiments, a seal 6504 may be positioned at an interface between the top of the sensor cap 6308 and the collar 6214 and thereby help form a sterile barrier for the sensor 6216 and the sharp 6222. In one embodiment, the seal 6504 may be co-molded or otherwise attached to the top of the sensor cap 6308. In other embodiments, however, the seal 6504 may be co-molded or attached to the collar 6214. In yet other embodiments, the seal 6504 may be a separate component part, such as an O-ring or the like placed between the top of the sensor cap 6308 and the collar 6214.

In one embodiment, as mentioned above, the sensor cap 6308 may be removably coupled to the collar 6214, such as through a bayonet coupling, an interference fit, a snap fit engagement, or any combination thereof. In other embodiments, however, the sensor cap 6308 may be removably coupled to the needle shroud 6408, without departing from the scope of the disclosure. Removably coupling the sensor cap 6308 to either the collar 6214 or the needle shroud 6408 may help maintain compression of the seal 6504. To remove the sensor cap 6308 from the sensor applicator 6302, a user may be able to grasp the gripping interface 6310 on the sensor cap 6308. As indicated above, in some embodiments, both the applicator and sensor caps 6306, 6308 may be removed simultaneously or separately.

In FIG. 65B, the applicator cap 6306 and the sensor cap 6308 have been removed from the sensor applicator 6302, thereby exposing the needle shroud 6408 and the bottom of the sensor control device 6202. With the needle shroud 6408 in the extended position, as illustrated, the upper portion of the needle shroud 6408 resides within the housing 6304, while the lower portion extends distally through the aperture 6418 defined in the sensor retainer 6406 and through the aperture 6215 defined through the sensor control device 6202. The upwardly extending fingers 6414 of the sensor retainer 6406 may extend into or otherwise be positioned within an inner chamber 6506 defined by the upper portion of the needle shroud 6408. Moreover, the sharp hub 6224 may be arranged within or between the fingers 6414, and the driver spring 6410 may be arranged to interpose and engage the sharp hub 6224 and the sensor retainer 6406.

More specifically, the top end of the driver spring 6410 may be received within a channel 6508 defined by the sharp hub 6224, and the bottom end of the driver spring 6410 may engage one or more projections 6510 defined by the sensor retainer 6406 and extending radially into the aperture 6418. Alternatively, the top end of the driver spring 6414 may engage an upper end of the sharp 6222, thus eliminating the need for an overmolded sharp hub 6224. The driver spring 6410 may be compressed between the sharp hub 6224 and the sensor retainer 6406 and prevented from releasing its spring force and expanding as long as the fingers 6414 are located within the inner chamber 6506. More particularly, the top of one or more of the fingers 6414 may extend radially inward and over the sharp hub 6224, thus preventing the sharp hub 6224 from moving upward until the fingers 6414 are no longer radially constrained by the inner chamber 6506. Moving the needle shroud 6408 to the retracted position, however, correspondingly places the fingers 6414 outside of the inner chamber 6506, which allows the driver spring 6410 force the sharp hub 6224 past the top of the fingers 6414, as described below.

With the needle shroud 6408 in the extended position, the locking tabs 6412 (FIG. 64B) of the sensor retainer 6406 may be engaged with the locking members 6414 (FIGS. 64A-64B) provided on the needle shroud 6408, which helps secure the needle shroud 6408 in the extended position. The locking members 6414 must be disengaged from the locking tabs 6412 to allow the needle shroud 6408 to move to the retracted position and thereby deploy the sensor control device 6202. This can be accomplished by the user positioning the sensor applicator 6302 at the target monitoring location and forcing the needle shroud 6408 against the skin, which places an axial load on the bottom end of the needle shroud 6408. The axial load will overcome the temporary engagement between the locking tabs 6412 and the locking members 6414, thus freeing the needle shroud 6408 and enabling the needle shroud 6408 to start its transition to the retracted position.

In some embodiments, disengaging the locking members 6414 from the locking tabs 6412 may result in a tactile response, thus providing the user with haptic feedback. More particularly, upon disengaging the locking members 6414 from the locking tabs 6412, a small vibration or tremor may result in the sensor applicator 6302, thus indicating to a user that the deployment process has begun. This haptic feedback may encourage the user to continue to apply pressure to the needle shroud 6408.

In some embodiments, one or more sensation features 6512 may be provided at the bottom end of the needle shroud 6408. The sensation features 6512 may contact the underlying skin to stimulate the nerve endings on the skin at that location and thereby help to mask the sensation of the sharp 6222 penetrating the skin. In some embodiments, the sensation features 6512 may comprise nubs or small projections defined on the end of the needle shroud 6408.

In FIG. 65C, the needle shroud 6408 has moved a short distance from the extended position and toward the retracted position, thus exposing the sensor 6216 and the sharp 6222 as they extend out of the lower end of the needle shroud 6408. More specifically, as the needle shroud 6408 is pressed against the skin, it compresses the skin, and moves relative to the sensor 6216 and the sharp 6222, which causes the sensor 6216 and the sharp 6222 to extend out of the needle shroud 6408 to penetrate the skin. One advantage of the needle shroud 6408 is its proximity to the insertion site of the sensor 6216 and the sharp 6222. More particularly, the needle shroud 6408 is able to provide local compression of the skin at the insertion site, which tightens the skin at the insertion site and thereby facilitates a more efficient insertion of the sensor 6216 and the sharp 6222.

Moving the needle shroud 6408 to the retracted position also moves the upper portion of the needle shroud 6408 relative to the fingers 6414 and the sharp hub 6224 arranged within the inner chamber 6506 of the needle shroud 6408. Friction between the fingers 6414 and the inner wall of the inner chamber 6506 provides a small amount of resistance while allowing motion of the housing towards the skin surface, which can be felt by the user during firing to help drive the sharp 6222 into the underlying skin by applying additional pressure to bypass the force bump.

In FIG. 65D, the needle shroud 6408 has moved to the retracted position, and the bottom end of the needle shroud 6408 may be flush with or inset into the bottom of the sensor control device 6202. Once the needle shroud 6408 has moved to the retracted position, the fingers 6414 of the sensor retainer 6406 may be positioned outside of the inner chamber 6506 and are therefore no longer radially constrained by the needle shroud 6408. Consequently, the spring force built up in the driver spring 6410 may release and force the sharp hub 6224 against the tops of the fingers 6414, which flexes the fingers 6414 radially outward and allows the sharp hub 6224 to move upward relative to the fingers 6414. As the sharp hub 6224 moves upward, the sharp 6222 correspondingly retracts out of the underlying skin and into the sensor applicator 6302, thus leaving only the sensor 6216 within the skin.

In some embodiments, the sensor applicator 6302 may provide haptic feedback to the user that provides an indication that the sensor deployment process is complete. More specifically, haptic or tactile feedback may be provided to the user when the needle shroud 6408 has moved to the retracted position and the sharp 6222 has fully retracted. In such embodiments, release of the driver spring 6410 may provide some degree of haptic feedback. However, springs, detents, or other elements may alternatively (or in addition) be included to also signal functionality and a completed firing process. In some applications, the forces generated by the experience may be tailored to be similar to taking a common retractable pen and pushing the thumb actuated "thruster" end against the skin.

Figure 66:
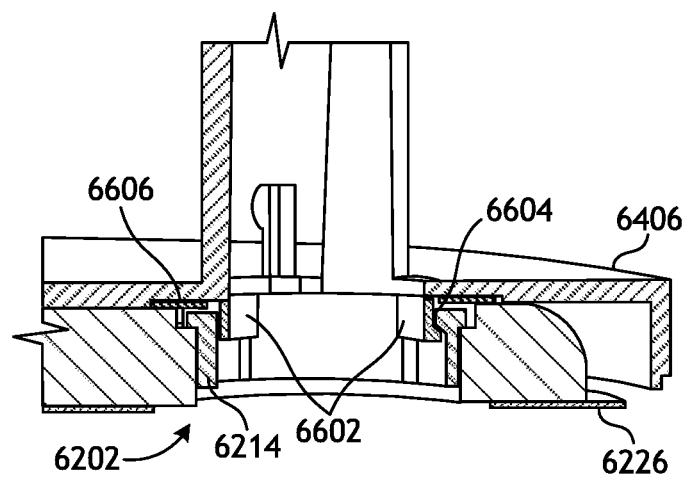
FIG. 66 is an enlarged cross-sectional side view of an engagement between the sensor retainer and the sensor control device of FIGS. 65A-65D, according to one or more embodiments.

FIG. 66 is an enlarged cross-sectional side view of an engagement between the sensor retainer 6406 and the sensor control device 6202, according to one or more embodiments. In some embodiments, the collar 6214 may be removably coupled to the sensor retainer 6406, which correspondingly retains the sensor control device 6202 to the sensor retainer 6406. In the illustrated embodiment, the sensor retainer 6406 may provide or otherwise define one or more first retention features 6602 operable to mate with one or more corresponding second retention features 6604 defined on the collar 6214. In the illustrated embodiment, the first and second retention features 6602, 6604 comprise tabs and corresponding lips or grooves that receive the tabs. However, the first and second retention features 6602, 6604 may comprise any type of removable coupling or engagement that temporarily couples the sensor control device 6202 to the sensor retainer 6406.

The sensor control device 6302 may be released from the sensor retainer 6406 by disengaging the first and second retention features 6602, 6604. This may be accomplished by attaching (sticking) the adhesive layer 6226 against the skin. The first and second retention features 6602, 6604 may be designed so that when the sensor control device 6202 is adhesively attached to the skin with the adhesive layer 6226, the engagement between the first and second retention features 6602, 6604 may be broken by retracting the sensor applicator 6302 away from the sensor control device 6202. This allows the sensor control device 6202 to separate from the sensor applicator 6302 and remain on the body.

In some embodiments, a seal 6606 may seal an interface between the top of the sensor control device 6202 and the bottom of the sensor retainer 6406, and thereby help form a sterile barrier for the sensor 6216 and the sharp 6222. In one embodiment, the seal 6606 may be co-molded or otherwise attached to the top of the sensor control device 6202 or the collar 6214. In other embodiments, however, the seal 6606 may be co-molded or attached to the bottom of the sensor retainer 6406. In yet other embodiments, the seal 6606 may be a separate component part, such as an O-ring or the like.

Figure 67:
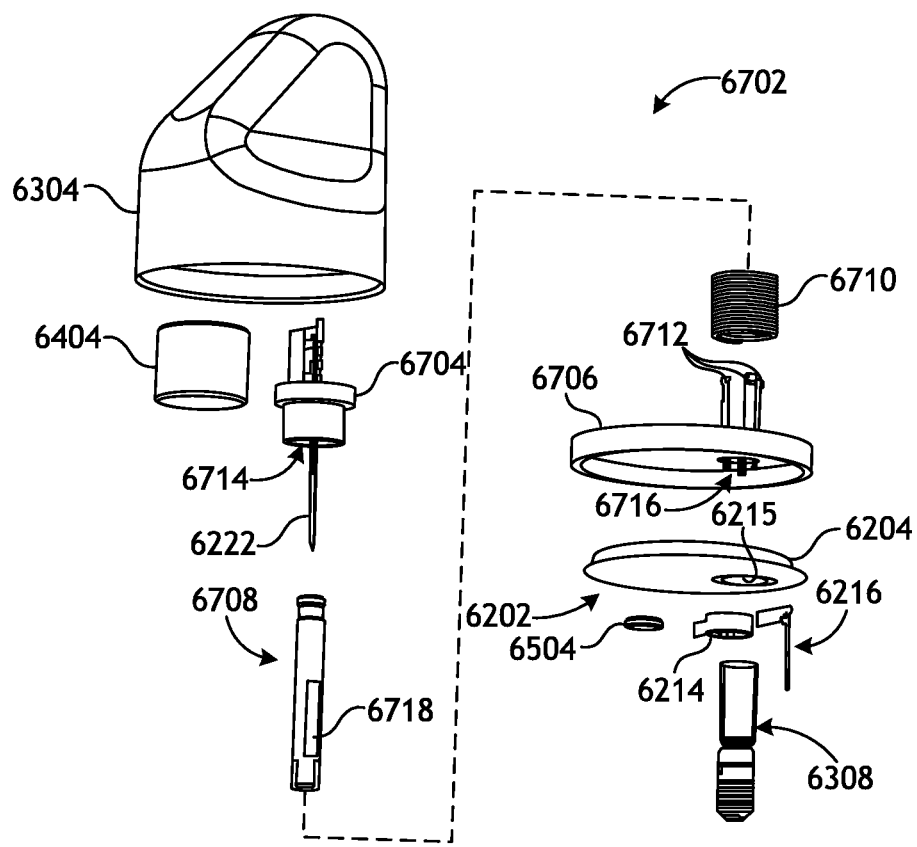
FIG. 67 is an exploded isometric view of another sensor applicator with the sensor control device of FIG. 62, according to one or more additional embodiments.

FIG. 67 is an exploded isometric view of another sensor applicator 6702 with the sensor control device 6202, according to one or more additional embodiments. The sensor applicator 6702 may be similar in some respects to the sensor applicator 6302 of FIGS. 63 and 64A-64B and may thus be best understood with reference thereto, where like numerals will correspond to like components not described again in detail. Similar to the sensor applicator 6302, for example, the sensor applicator 6702 may include the housing 6304 that may be sized to accommodate the desiccant 6404 and the sensor control device 6202 therein. The collar 6214 and the sensor 6216 of the sensor control device 6202 may each be mounted to the electronics housing 6204 at or within the aperture 6215 defined in the electronics housing 6204, as generally described above. Moreover, the sensor applicator 6702 may also include the sensor cap 6308 used to help form a sterile barrier with the collar 6214 and thereby protect the distal ends of the sensor 6216 and the sharp 6222. As described above, the seal 6504 may help form the sterile barrier by sealing the interface between the top of the sensor cap 6308 and the collar 6214 (or another portion of the sensor control device 6202).

A sharp hub 6704 carries the sharp 6222 and may be overmolded onto the sharp 6222, but could alternatively be fabricated from plastic, metal, or another suitable material as a separate component, and bonded, welded, or mechanically attached to the sharp 6222. The sensor applicator 6702 may also include a sensor retainer 6706, a needle shroud 6708, and a driver spring 6710. The sensor retainer 6706 (alternately referred to as a "puck retainer") may be matable with the housing 6304 to help retain the needle shroud 6708, the driver spring 6710, and the sharp hub 6704 generally within or connected to the housing 6304. More specifically, the sensor retainer 6706, the needle shroud 6708, the sharp hub 6704, and the driver spring 6710 may all be operatively coupled to help facilitate deployment of the sensor control device 6202.

In the illustrated embodiment, the driver spring 6710 may be sized to be arranged about the sharp hub 6704, and the sensor retainer 6706 may provide a plurality of upwardly extending fingers 6712 (three shown) configured to extend into an inner chamber 6714 defined by the sharp hub 6704. The sharp 6222 and the needle shroud 6708 may be extendable through the inner chamber 6714, and further extendable through an aperture 6716 defined in the sensor retainer 6706 and the aperture 6215 provided in the electronics housing 6204. The needle shroud 6708 may be movable (actuatable)

between an extended position and a retracted position to deploy the sensor control device 6202 from the sensor applicator 6702.

As described in more detail below, when the needle shroud 6708 is in the extended position, the fingers 6712 may be radially constrained between an outer surface of the needle shroud 6708 and an inner wall of the sharp hub 6704 within the inner chamber 6714, thus preventing the sharp hub 6704 (and the sharp 6222) from moving. Once the needle shroud 6708 moves to the extended position, however, the fingers 6712 may become aligned with one or more reliefs 6718 defined on the needle shroud 6708, which allow the fingers 6712 to flex radially inward and release the sharp hub 6704. In some embodiments, the driver spring 6710 may provide a spring force that urges the sharp hub 6704 upward and simultaneously flexes the fingers 6712 radially inward, which allows the sharp hub 6704 to move upward and retract the sharp 6222 into the housing 6304.

Figure 68A:
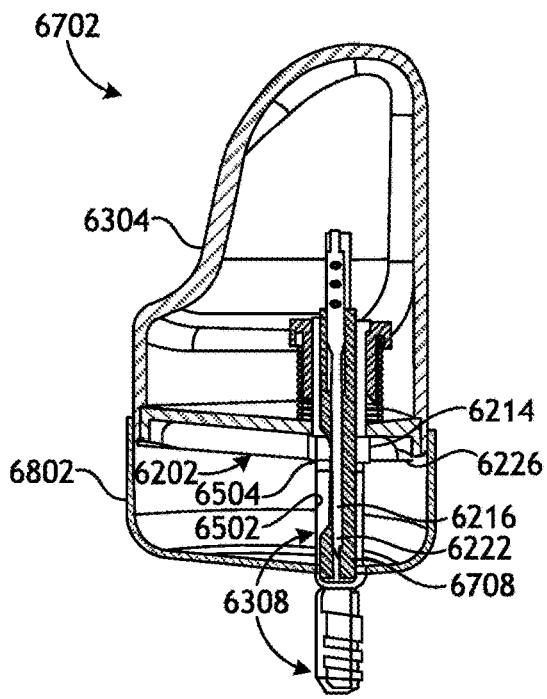
FIGS. 68A-68D are progressive cross-sectional side views of the sensor applicator of FIG. 67 depicting example deployment of the sensor control device, according to one or more embodiments.
Figure 68B:
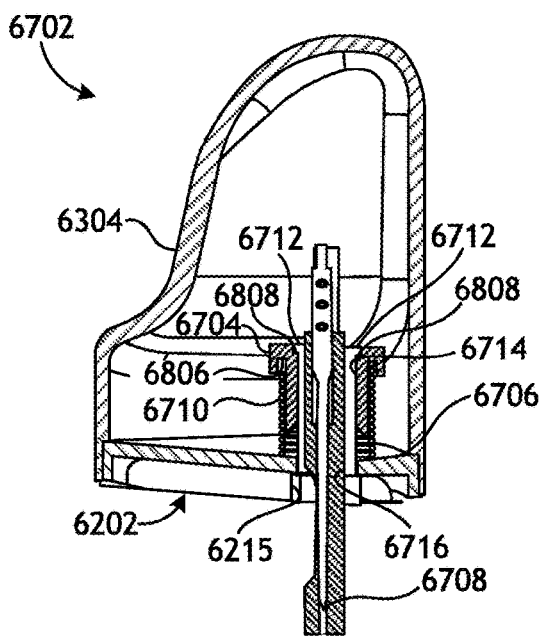
Figure 68C:
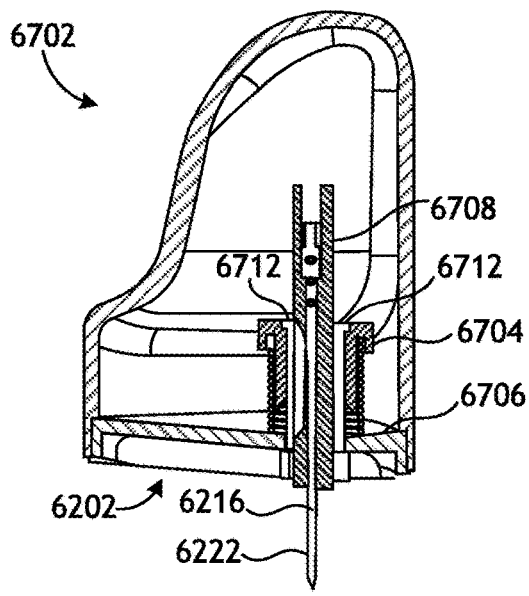
Figure 68D:
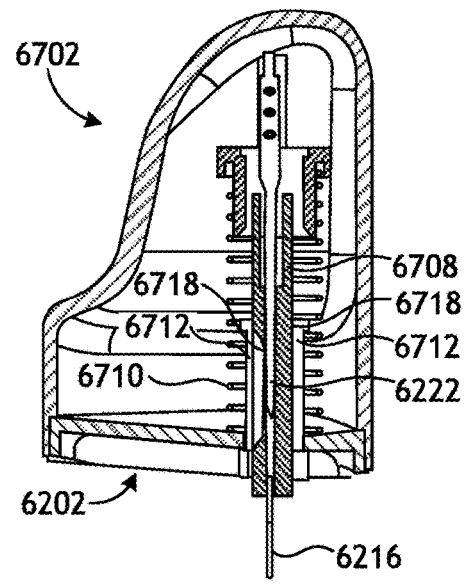

FIGS. 68A-68D are progressive cross-sectional side views of the sensor applicator 6702 depicting example deployment of the sensor control device 6202, according to one or more embodiments. User operation (actuation) of the sensor applicator 6702 can cause the needle shroud 6708 to move from the extended position, as shown in FIGS. 68A and 68B, to the retracted position, as shown in FIG. 68D. Once the needle shroud 6708 reaches the retracted position, the sensor control device 6202 may be able to be released (discharged) from the sensor retainer 6706.

Referring first to FIG. 68A, an applicator cap 6802 may be removably coupled to the housing 6304 and may be similar in some respects to the applicator cap 6306 of FIG. 63. In some embodiments, the interface between the applicator cap 6802 and the housing 6304 may be sealed to help protect and shield the adhesive patch 6226 from contamination or damage prior to deploying the sensor control device 6202. The sensor cap 6308 is also depicted extending distally from the bottom of the sensor applicator 6702 and, more particularly, from the sensor control device 6202. The interior 6502 of the sensor cap 6308 may accommodate the distal ends of the sensor 6216 and the sharp 6222 and the lower portion of the needle shroud 6708 in the extended position. Moreover, the seal 6504 may interpose the top of the sensor cap 6308 and the collar 6214 to help form a sterile barrier for the sensor 6216 and the sharp 6222.

In FIG. 68B, the applicator cap 6802 and the sensor cap 6308 have been removed from the sensor applicator 6702, thereby exposing the needle shroud 6708 and the bottom of the sensor control device 6202. With the needle shroud 6708 in the extended position, as illustrated, the upper portion of the needle shroud 6708 resides within the housing 6304, while the lower portion extends distally through the aperture 6716 defined in the sensor retainer 6706 and through the aperture 6215 defined through the sensor control device 6202. Moreover, the upper portion of the needle shroud 6708 extends into and through the inner chamber 6714 defined within the sharp hub 6704. The upwardly extending fingers 6712 of the sensor retainer 6706 extend into the inner chamber 6714 and interpose the needle shroud 6708 and the inner wall of the inner chamber 6714.

As indicated above, the driver spring 6710 may be positioned about an exterior portion of the sharp hub 6704 and may extend between the sharp hub 6704 and the sensor retainer 6706. More specifically, the top end of the driver spring 6710 may be received within a channel 6806 defined by the sharp hub 6704, and the bottom end of the driver spring 6710 may engage the sensor retainer 6706, such as a top surface of the sensor retainer 6706. The driver spring 6710 is compressed between the sharp hub 6704 and the sensor retainer 6706 when the needle shroud 6708 in the extended position. The driver spring 6710 is prevented from releasing its spring force and expanding as long as the fingers 6712 are radially constrained between the outer surface of the needle shroud 6708 and the inner wall of the inner chamber 6714. More particularly, the tops of the fingers 6712 may extend radially outward and received within a groove or notch 6808 defined on the sharp hub 6704. When the tops of the fingers 6712 are received within the notch(es) 6808, the sharp hub 6704 may be prevented from moving upward.

Figure 69A:
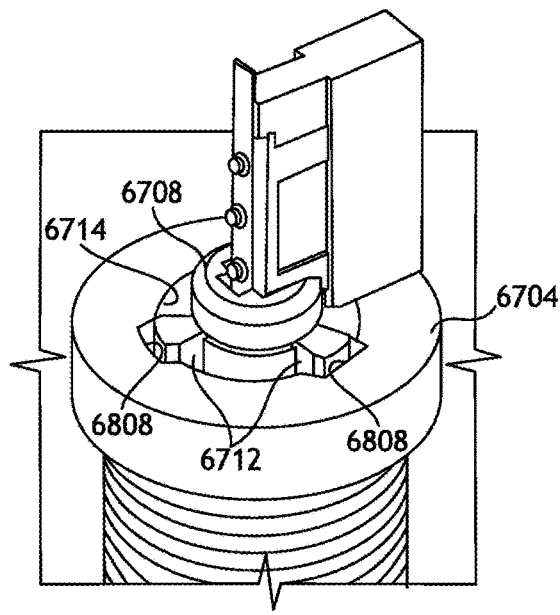
FIG. 69A is an enlarged schematic view of the sharp hub and the fingers of the sensor retainer.

Referring briefly to FIG. 69A, depicted is an enlarged schematic view of the sharp hub 6704 and the fingers 6712 of the sensor retainer 6706 of FIG. 67. As illustrated, the tops of each finger 6712 may extend or protrude radially outward to be received within corresponding notches 6808 defined at an upper end of the sharp hub 6704. The fingers 6712 extend within the inner chamber 6714 and interpose the outer radial surface of the needle shroud 6708 and the inner wall of the inner chamber 6714. The sharp hub 6704 is prevented from moving upward as long as the tops of the fingers 6712 are constrained into engagement with the notches 6808.

Figure 69B:
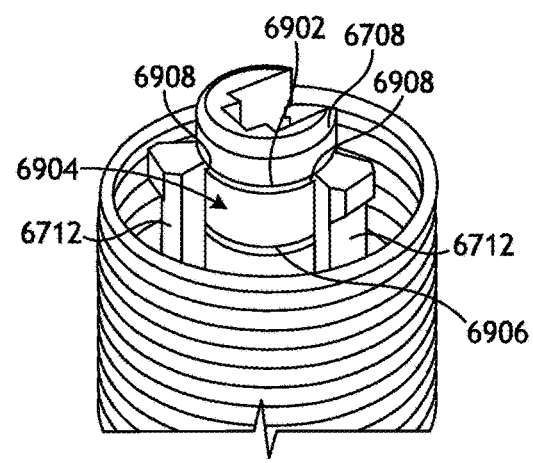
FIGS. 69B and 69C are enlarged schematic views of the fingers interacting with the upper portion of the needle shroud.
Figure 69C:
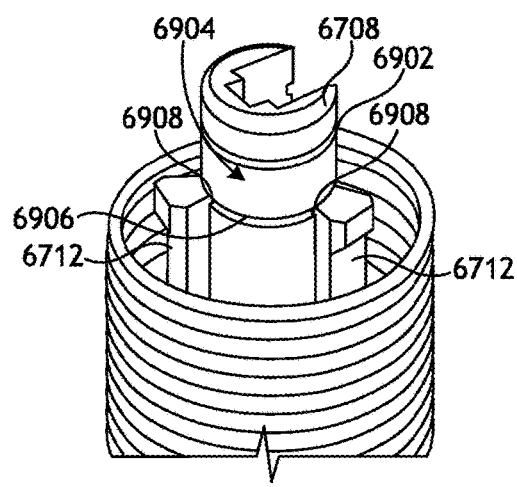

Referring briefly to FIGS. 69B and 69C, depicted are enlarged schematic views of the fingers 6712 interacting with the upper portion of the needle shroud 6708. In some embodiments, as illustrated, the upper portion (end) of the needle shroud 6708 may define a groove 6902 and a detent profile 6904 that terminates in a force bump 6906. In such embodiments, the upper ends of the fingers 6712 may provide or otherwise define inwardly extending (protruding) lips or features 6908 configured to interact with the groove 6902, the detent profile 6904, and the force bump 6906. With the needle shroud 6708 in the extended position, the features 6908 provided on the fingers 6712 may be engaged with and otherwise received by the groove 6902 provided on the needle shroud 6708, which helps axially maintain the needle shroud 6708 in the extended position.

The features 6908 must be disengaged from the groove 6902 to allow the needle shroud 6708 to move to the retracted position and thereby deploy the sensor control device 6202. This can be accomplished by the user positioning the sensor applicator 6702 (FIG. 68B) at the target monitoring location and forcing the bottom of the needle shroud 6708 against the skin, which places an axial load on the needle shroud 6708. The axial load will overcome the temporary engagement between the groove 6902 and the features 6908, thus freeing the needle shroud 6708 and enabling the needle shroud 6708 to start its upward transition to the retracted position.

As shown in FIG. 69C, the features 6908 have been disengaged from the groove 6902, and the features 6908 may slide along the detent profile 6904 as the needle shroud 6708 moves upward relative to the fingers 6712. When the features 6908 locate the force bump 6906, the user may apply additional pressure to overcome and otherwise bypass the force bump 6906. In some embodiments, disengaging the features 6908 from the groove 6902 or bypassing the force bump 6906 may result in a tactile response that may be felt by the user, thus providing the user with haptic feedback. More particularly, upon disengaging the features 6908 from the groove 6902 (or bypassing the force bump 6906), a small vibration or tremor may propagate through the sensor applicator 6702 (FIG. 68B), thus indicating to a user that the deployment process has begun. This haptic feedback may encourage the user to continue to apply pressure to the needle shroud 6708.

Referring again to FIGS. 68A-68D and, more particularly, to FIG. 68C, the needle shroud 6708 has moved from the extended position and toward the retracted position, thus exposing the sensor 6216 and the sharp 6222 as they extend out the lower end of the needle shroud 6708. More specifically, as the user presses the needle shroud 6708 against the skin, the needle shroud 6708 moves relative to the sensor 6216 and the sharp 6222, which causes the sensor 6216 and the sharp 6222 to extend out of the bottom of the needle shroud 6708 to penetrate the skin. One advantage of the needle shroud 6708 is its proximity to the insertion site of the sensor 6216 and the sharp 6222. More particularly, the needle shroud 6708 is able to provide local compression of the skin at the insertion site near the sharp 6222, which tightens the skin at the insertion site and thereby facilitates a more efficient insertion of the sharp 6222 and the sensor 6216.

Moving the needle shroud 6708 to the retracted position also moves the upper portion of the needle shroud 6708 relative to the fingers 6712 of the sensor retainer 6706 arranged within the inner chamber 6714 of the sharp hub 6704. Friction between the fingers 6712 and the outer surface of the needle shroud 6708 provides a small amount of resistance, which may be felt by the user during firing to help drive the sharp 6222 into the underlying skin without user hesitation.

In FIG. 68D, the needle shroud 6708 has moved to the retracted position, which aligns the fingers 6712 with the reliefs 6718 defined in the sidewall of the needle shroud 6708. Aligning the fingers 6712 with the reliefs 6718 allows the fingers 6712 to flex radially inward into the reliefs 6718 as the driver spring 6710 release and forces the sharp hub 6704 against the tops of the fingers 6712. Once the fingers 6712 enter the reliefs 6718, the sharp hub 6704 may be released and the spring force of the driver spring 6710 may move the sharp hub 6704 upward relative to the fingers 6712, which correspondingly retracts the sharp 6222 into the sensor applicator 6702, thus leaving only the sensor 6216 within the skin.

In some embodiments, the sensor applicator 6702 may provide haptic feedback to the user that provides an indication that the sensor deployment process is complete. More specifically, haptic or tactile feedback may be provided to the user when the needle shroud 6708 moves to the retracted position and the sharp 6222 has fully retracted. In such embodiments, release of the driver spring 6710 may provide some degree of haptic feedback that propagates through the sensor applicator 6702 to be felt by the user. However, springs, detents, or other elements may alternatively (or in addition) be included to also signal functionality and a completed firing process. In some applications, the forces generated by the experience may be tailored to be similar to taking a common retractable pen and pushing the thumb actuated "thruster" end against the skin.

Figure 70A:
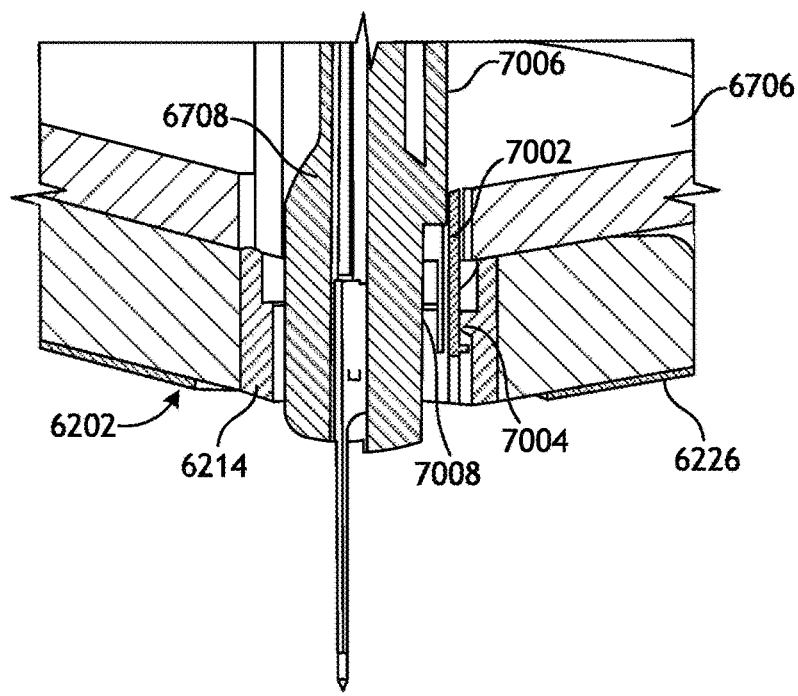
FIGS. 70A and 70B are enlarged cross-sectional side views of example engagement between the sensor retainer and the sensor control device, according to one or more embodiments.
Figure 70B:
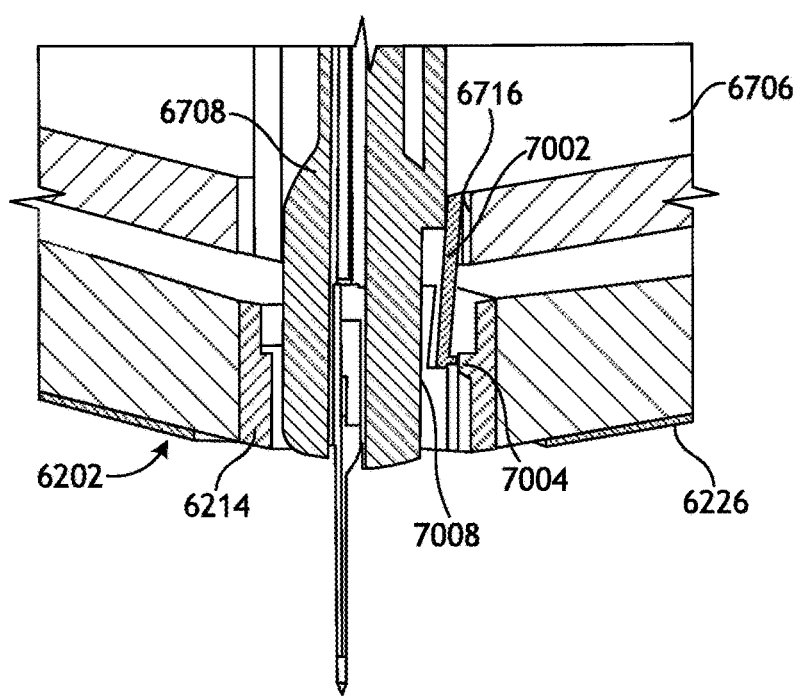

FIGS. 70A and 70B are enlarged cross-sectional side views of example engagement between the sensor retainer 6706 and the sensor control device 6202, according to one or more embodiments. In some embodiments, the collar 6214 may be removably coupled to the sensor retainer 6706, which correspondingly removably couples the sensor control device 6202 to the sensor retainer 6706. In the illustrated embodiment, the sensor retainer 6706 may provide or otherwise define one or more first retention features 7002 operable to mate with one or more corresponding second retention features 7004 defined on the collar 6214. In the illustrated embodiment, the first retention features 7002 comprise tabs that extend downwardly through the aperture 6716 of the sensor retainer 6706, and the second retention features 7004 comprise corresponding lips or grooves that receive the tabs. However, the first and second retention features 7002, 7004 may comprise any type of removable coupling or engagement that temporarily couples the sensor control device 6202 to the sensor retainer 6706.

As the needle shroud 6708 moves upward toward the retracted position, the first retention features 7002 may be radially constrained between an outer surface 7006 of the needle shroud 6708 and the collar 6214, which prevents the first retention features 7002 from disengaging from the second retention features 7004. Once the needle shroud 6708 reaches the retracted position, however, the first retention features 7002 may axially align with corresponding relief pockets 7008 defined in the sidewall of the needle shroud 6708. Once the first retention features 7002 axially align with the relief pockets 7008, the first retention features 7002 may be able to flex radially inward into the relief pockets 7008, which allows the sensor control device 6302 to be released from the sensor retainer 6706, as is shown in FIG. 70B. Flexing the first retention features 7002 radially inward may disengage the first and second retention features 7002, 7004, thus allowing the sensor control device to release from the sensor retainer 6706.

In some embodiments, the first and second retention features 7002, 7004 may be disengaged by attaching (sticking) the adhesive layer 6226 against the skin and pulling back on the sensor applicator 6702 (FIGS. 68A-68D). More specifically, the first and second retention features 7002, 7004 may be designed so that when the sensor control device 6202 is adhesively attached to the skin with the adhesive layer 6226, the engagement between the first and second retention features 7002, 7004 may be broken by retracting the sensor applicator 6702 away from the placed sensor control device 6202. This allows the sensor control device 6202 to separate from the sensor applicator 6702 and remain on the body.

Figure 71B:
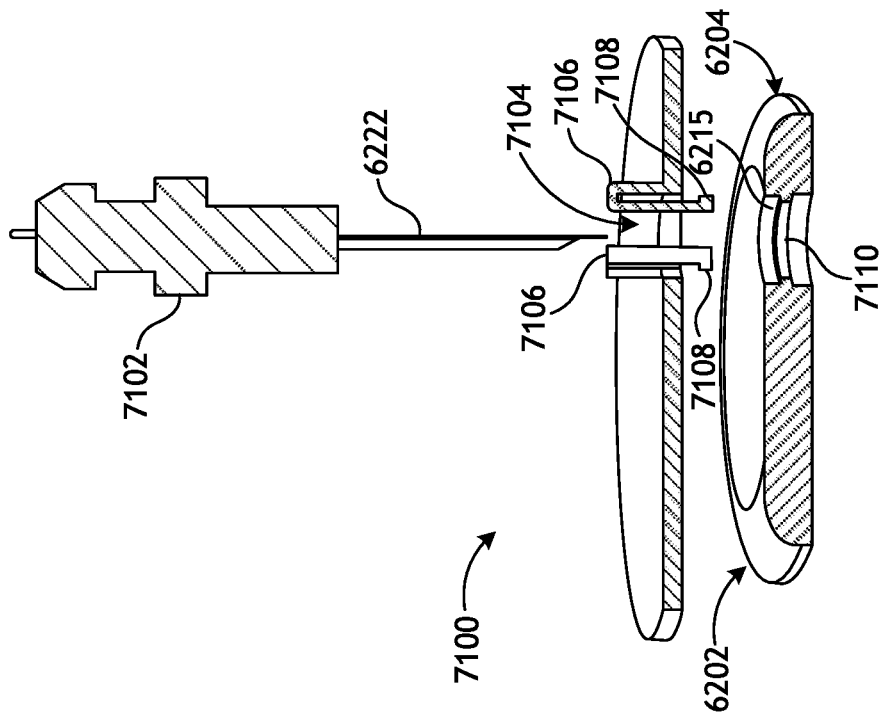
FIGS. 71A and 71B are isometric and cross-sectional side views, respectively, of an example sensor retainer, according to one or more embodiments of the present disclosure.
Figure 71A:
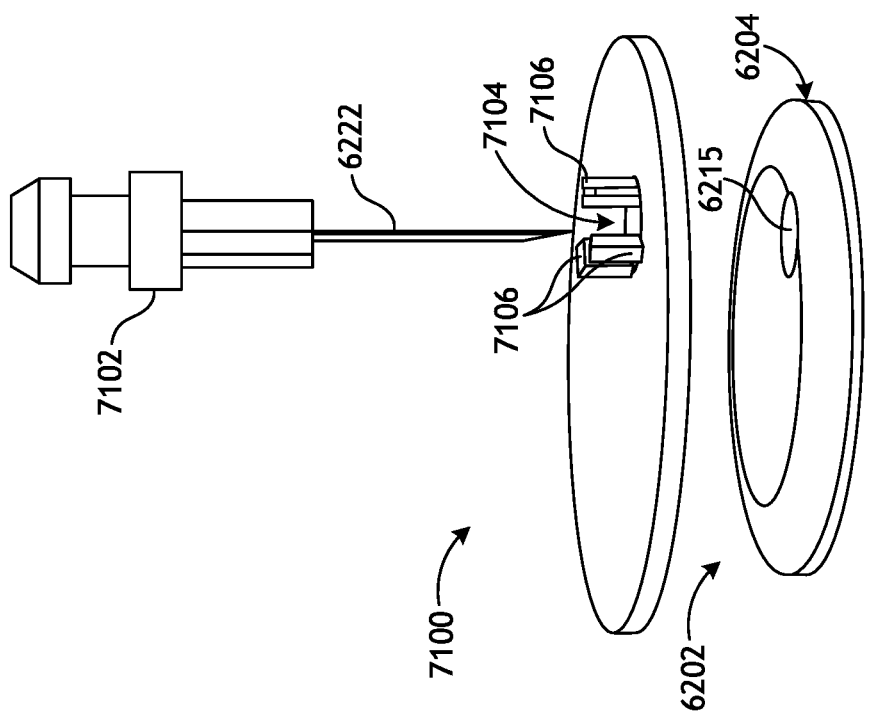

FIGS. 71A and 71B are isometric and cross-sectional side views, respectively, of an example sensor retainer 7100, according to one or more embodiments. The sensor retainer 7100 may be similar in some respects to the sensor retainers 6406, 6706 of FIGS. 64A-64B and 67, respectively, and therefore may be best understood with reference thereto. Similar to the sensor retainers 6406, 6706, for example, the sensor retainer 7100 may be configured to retain the sensor control device 6202 prior to deployment within a sensor applicator, such as any of the sensor applicators 102, 6302, 6702 of FIGS. 1, 63, 67, respectively, described herein.

In contrast to the sensor retainers 6406, 6706 of FIGS. 64A-64B and 67, however, the sensor retainer 7100 may interact with a sharp hub 7102 that carries the sharp 6222 to releasably couple the sensor control device 6202 to the sensor retainer 7100. As illustrated, the sensor retainer 7100 may define an aperture 7104 through which a lower portion of the sharp hub 7102 (and the sharp 6222) may extend. The aperture 7104 may align with the aperture 6215 defined in the electronics housing 6204 of the sensor control device 6202, and the lower portion of the sharp hub 7102 may also extend into the aperture 6215 when the sensor control device 6202 is removably (releasably) coupled to the sensor retainer 7100.

As illustrated, the sensor retainer 7100 may define or otherwise provide one or more arms 7106 that extend downwardly into the aperture 7104 and past the bottom of the sensor retainer 7100. As best seen in FIG. 71B, each arm 7106 may provide or otherwise define one or more first retention features 7108 operable to mate with one or more corresponding second retention features 7110 defined on or otherwise provided by the sensor control device 6202. In some embodiments, the second retention features 7110 may be provided by the collar 6214 (FIGS. 62 and 67) positioned within the aperture 6215, but could alternatively be provided on another part of the sensor control device 6202, without departing from the scope of the disclosure.

In the illustrated embodiment, the first retention features 7108 may be provided at the bottom end of the arms 7106 and may comprise tabs or protrusions that extend (project) radially outward. The second retention feature 7110 may comprise a lip or annular shoulder extending radially inward at the aperture 6215 to receive and otherwise mate with the first retention features 7108. Those skilled in the art will readily appreciate, however, that the first and second retention features 7108, 7110 may comprise any type of removable coupling or engagement that temporarily couples the sensor control device 6202 to the sensor retainer 6706, without departing from the scope of the disclosure.

Figure 72A:
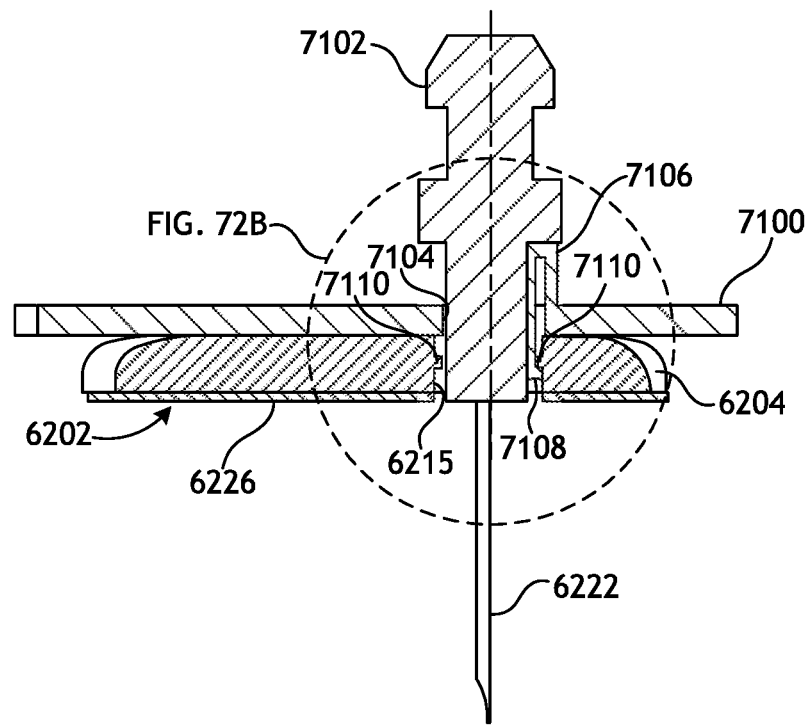
FIGS. 72A and 72B are enlarged cross-sectional side views of the sensor retainer of FIGS. 71A-71B retaining the sensor control device, according to one or more embodiments.
Figure 72B:
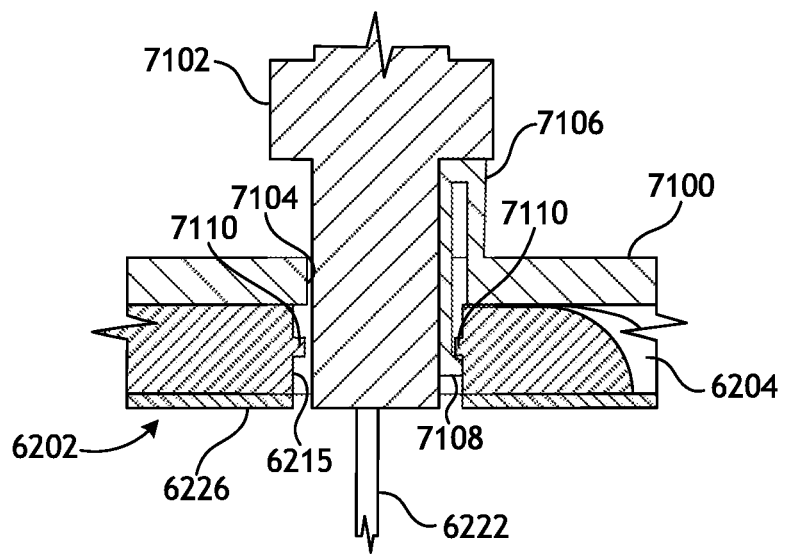

FIGS. 72A and 72B are enlarged cross-sectional side views of the sensor retainer 7100 retaining the sensor control device 6202. As illustrated, the lower portion of the sharp hub 7102 is received within the aperture 7104 of the sensor retainer 7100 and also extends at least partially through the aperture 6215 of the sensor control device 6202. The sharp hub 7102 is shown in FIGS. 72A-72B in an extended position, and may be movable to a retracted position where the sharp hub 7102 moves out of axial alignment with the apertures 6215, 7104. Moving the sharp hub 7102 to the retracted position may be accomplished through user intervention in firing the sensor applicator that houses the sensor control device 6202. Once the sensor applicator is fired, a spring or other biasing device (not shown) operatively coupled to the sharp hub 7102 may cause the sharp hub 7102 to quickly move upwardly relative to the sensor retainer 7100.

With the sharp hub 7102 in the extended position, as depicted, the first retention features 7108 may be engaged with or otherwise mated to the second retention feature 7110. Moreover, when the sharp hub 7102 is in the extended position, the arms 7106 may be radially constrained between the sidewall of the sharp hub 7102 and the second retention feature 7110, which prevents the first retention features 7108 from disengaging from the second retention features 7110. Once the sharp hub 7102 moves to the retracted position, however, the arms 7106 will no longer be backed by the sidewall of the sharp hub 7102, thus enabling the arms 7106 to flex radially inward to disengage the first and second retention features 7108, 7110 and thereby release the sensor control device 6302.

In some embodiments, the arms 7106 may flex radially inward to disengage the first and second retention features 7108, 7110 by attaching (sticking) the adhesive layer 6226 against the skin and pulling back on the sensor applicator that carries the sensor control device 6202. More specifically, the first and second retention features 7108, 7110 may be designed so that when the sensor control device 6202 is adhesively attached to the skin with the adhesive layer 6226, the engagement between the first and second retention features 7108, 7110 may be broken by retracting the sensor applicator away from the placed sensor control device 6202. This allows the sensor control device 6202 to separate from the sensor applicator and remain on the body.

Electronics housings of prior sensor control devices are commonly manufactured of rigid plastic materials, and are retained within a sensor applicator by sensor retainers that have a plurality of flexible arms. Such electronics housings often define a plurality of semi-hemispherical notches or grooves on the outer periphery of the electronics housing that are sized to receive the ends of the flexible arms. According to embodiments of the present disclosure, however, the electronics housing 6204 of the sensor control device 6202 may be constructed of flexible or soft materials, such as a soft encapsulant, a foam, or small injection molded components. With flexible or soft materials, it can be a challenge to define features on the exterior of the electronics housing that can be used to retain the sensor control device 6202 to the sensor retainer 7100 during shipment and during the insertion process.

Accordingly, the sensor retainer 7100 includes the arms 7106 that help grasp and retain the sensor control device at the matable first and second retention features 7108, 7110. The arms 7106 are flexible and capable of deflecting away from the second retention feature 7110 when the sensor control device 6202 is pulled from the sensor applicator by adhesive attachment to the skin. Prior to insertion, however, the arms 7106 are prevented from deflecting and releasing the sensor control device 6202 by the presence of the sharp hub 7102 extended within (through) the apertures 6215, 7104. The sensor retainer 7100 may retain the sensor control device 6202 due to the arms 7106 not being able to deflect radially inwards. During the firing (insertion) process, however, and when the sharp 6222 and the sharp hub 7102 are retracted from the skin, the arms 7106 are no longer back supported and will be deflected as the sensor control device 6202 is pulled from the sensor applicator.

In addition to providing a method to retain the sensor control device 6202 in the sensor applicator, the features of the sensor retainer 7100 enable a more compact applicator design by replacing the flexible arms of conventional sensor retainers. By relocating the flexible retention arms to the apertures 6215, 7104, the overall size of the sensor applicator may be reduced.

Figure 73B:
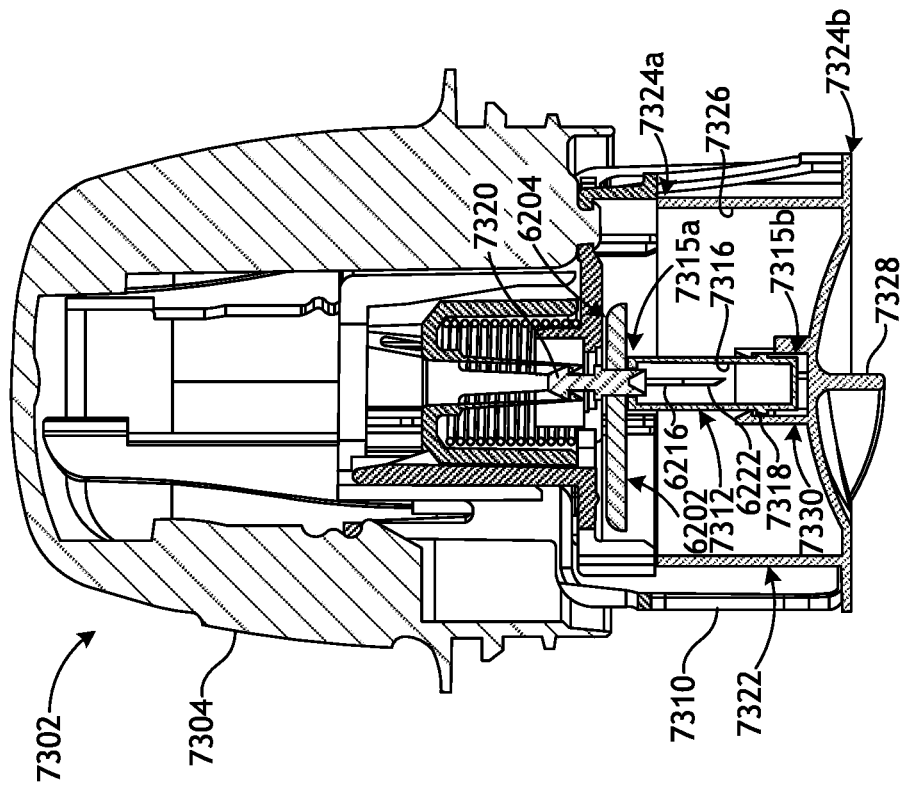
FIGS. 73A and 73B are side and cross-sectional side views, respectively, of an example sensor applicator, according to one or more embodiments.
Figure 73A:
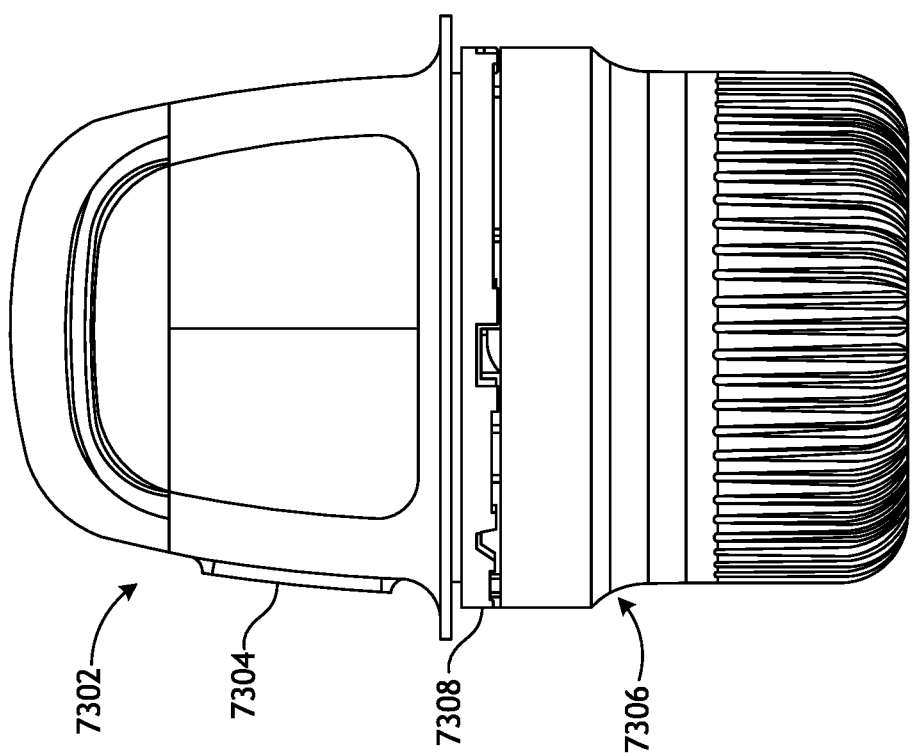

FIGS. 73A and 73B are side and cross-sectional side views, respectively, of an example sensor applicator 7302, according to one or more embodiments. The sensor applicator 7302 may be similar in some respects to the sensor applicator 102 of FIG. 1 and, therefore, may be designed to deliver (fire) a sensor control device, such as the sensor control device 6202. FIG. 73A depicts how the sensor applicator 7302 might be shipped to and received by a user, and FIG. 73B depicts the sensor control device 6202 arranged within the interior of the sensor applicator 7302.

As shown in FIG. 73A, the sensor applicator 7302 includes a housing 7304 and an applicator cap 7306 removably coupled to the housing 7304. In some embodiments, the applicator cap 7306 may be threaded to the housing 7304 and include a tamper ring 7308. Upon rotating (e.g., unscrewing) the applicator cap 7306 relative to the housing 7304, the tamper ring 7308 may shear and thereby free the applicator cap 7306 from the sensor applicator 7302.

In FIG. 73B, the applicator cap 7306 has been removed from the housing 7304, thus exposing a sheath 7310 that generally surrounds the sensor control device 6202. During firing of the sensor applicator 7302, the sheath 7310 may be actuated (e.g. pushed or forced into the housing 7304), which causes the sensor control device 6202 to be discharged from the sensor applicator 7302.

In the illustrated embodiment, the sensor control device 6202 may include a sensor cap 7314 removably coupled to the sensor control device 6202 at or near the bottom of the electronics housing 6204. The sensor cap 7314 may help provide or facilitate a sealed or sterile barrier surrounding and protecting the exposed portions of the sensor 6216 and the sharp 6222. As illustrated, the sensor cap 7314 may comprise a generally cylindrical and elongate body having a first end 7315a and a second end 7315b opposite the first end 7315a. The first end 7315a may be open to provide access into an inner chamber 7316 defined within the body, and the second end 7315b may be closed and may provide or otherwise define one or more engagement features 7318.

In some embodiments, the sensor cap 7314 may be removably coupled to the sensor control device 6202 by being coupled to a sharp hub 7320 that carries the sharp 6222 and extends through the electronics housing 6204. In such embodiments, the sharp hub 7320 may extend past the bottom of the electronics housing 6204 to provide a location where the sensor cap 7314 might engage the sharp hub 7320. Consequently, at least a portion of the sharp hub 7320 may be extend into the inner chamber 7316 of the sensor cap 7314. Prior to delivering the sensor control device 6202 to the target monitoring location on the user's skin, the sensor cap 7314 may be separated from the sharp hub 7320. In some embodiments, the sensor cap 7314 may be removably coupled to the sharp hub 7320 via an interference or friction fit. In other embodiments, the sensor cap 7314 may be threaded to the sharp hub 7320. In yet other embodiments, the sensor cap 7314 may be removably coupled to the sharp hub 7320 with a frangible member (e.g., a shear ring) or substance that may be broken with minimal separation force (e.g., axial or rotational force). In such embodiments, for example, the sensor cap 7314 may be secured to the sharp hub 7320 with a tag (spot) of glue or a dab of wax.

In some embodiments, however, the sharp hub 7320 may not extend past the bottom of the electronics housing 6204. In such embodiments, the sensor cap 7314 may alternatively be removably coupled to another portion of the sensor control device 6202, such as the collar 6214 (FIGS. 62 and 67) or the mount 6208 (FIG. 62). In such embodiments, the sensor cap 7314 may be removably coupled to the collar 6214 or the mount 6208 (or both) via an interference or friction fit, threading, with a frangible member or substance, or any combination thereof.

The inner chamber 7316 may be sized and otherwise configured to receive the distal ends of the sensor 6216 and the sharp 6222. Moreover, the inner chamber 7316 may be sealed to isolate the sensor 6216 from substances that might adversely interact with the chemistry of the sensor 6216. More specifically, the inner chamber 7316 may be sealed at the interface between the first end 7315a of the sensor cap 7312 and the location where it is removably coupled to the sensor control device 6202. In some embodiments, a desiccant may be present within the inner chamber 7316 to help maintain preferred humidity levels.

As illustrated, the sensor applicator 7302 may further include an internal applicator cover 7322 that may extend at least partially into the sheath 7310. The internal applicator cover 7322 may comprise a generally cylindrical body having a first end 7324a and a second end 7324b opposite the first end 7324a. A sidewall of the internal applicator cover 7322 may extend between the first and second ends 7324a,b and into the interior of the sheath 7310 when the internal applicator cover 7322 is coupled to the sensor applicator 7302. The internal applicator cover 7322 may be open at the first end 7324a to provide access to a cover interior 7326. The second end 7324b may be closed and may provide or otherwise define a gripping interface 7328.

In some embodiments, the internal applicator cover 7322 may be removably coupled to the sheath 7310, such as via an interference fit or a threaded engagement. In other embodiments, the applicator cap 7306 (FIG. 73A) may be used to help retain the internal applicator cover 7322 within the sensor applicator 7302 while applicator cap 7306 is coupled (threaded) to the housing 7304. In yet other embodiments, the internal applicator cover 7322 may be coupled to the sensor cap 7312. More particularly, the internal applicator cover 7322 may provide or otherwise define receiving features 7330 within the cover interior 7326 at or near the second end 7324b. The receiving features 7330 may be configured to receive the second end 7315b of the sensor cap 7312 and, more particularly, mate with the engagement features 7318 of the sensor cap 7312.

The internal applicator cover 7322 may be removed from the sensor applicator 7302 by a user grasping the gripping interface 7328 and rotating and/or pulling on the internal applicator cover 7322 relative to the shroud 7310 and out of engagement with the sensor applicator 7302. As described below, as the internal applicator cover 7322 is removed, engagement between the receiving features 7330 and the engagement features 7318 causes the sensor cap 7312 to also be removed from the sensor control device 6202, thus exposing the sensor 6216 and the sharp 6222 and readying the sensor control device 6202 for firing.

Figure 74A:
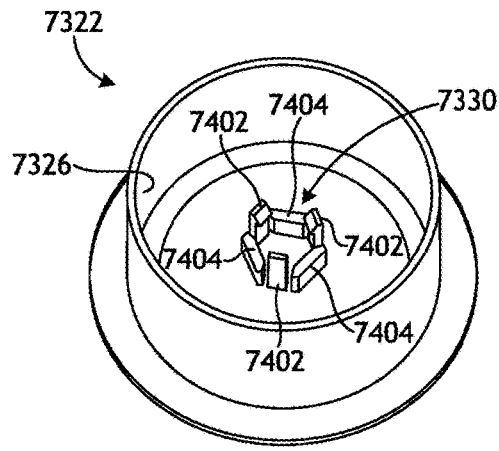
FIGS. 74A and 74B are isometric top and bottom views, respectively, of the internal applicator cover of FIG. 73B.
Figure 74B:
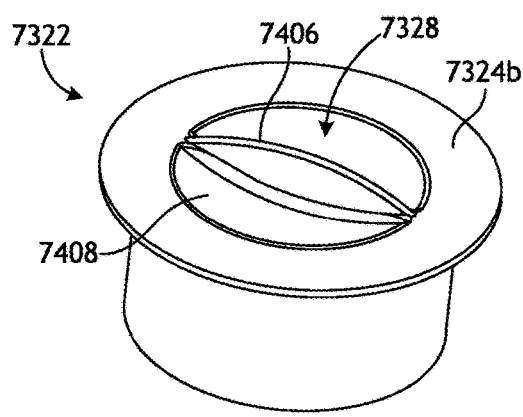

FIGS. 74A and 74B are isometric top and bottom views, respectively, of the internal applicator cover 7322. As depicted, the receiving features 7330 may be provided within the cover interior 7326 at or near the bottom of the internal applicator cover 7322. As indicated above, the receiving features 7330 may be designed to receive the lower end 7315b (FIG. 73B) of the sensor cap 7312 (FIG. 73B) and mate with the engagement features 7318 (FIG. 73B). As will be appreciated, many design variations of the engagement features 7318 and the receiving features 7330 may be employed, without departing from the scope of the disclosure. Any design may be used that allows the engagement features 7318 to be received by the receiving features 7330, and subsequently prevent the sensor cap 7312 from separating from the receiving features 7330 upon removing the internal applicator cover 7322.

In some embodiments, for example, the engagement and receiving features 7318, 7330 may comprise a threaded interface or a keyed mating profile that allows initial engagement but prevents subsequent disengagement. In the illustrated embodiment, the receiving features 7330 include one or more compliant members 7402 that are expandable or flexible to receive the engagement features 7318. The receiving features 7330 may also include two or more planar members 7404 configured to receive the lower end 7315b (FIG. 73B) of the sensor cap 7312 (FIG. 73B) and prevent the sensor cap 7312 from rotating relative to the internal applicator cover 7322.

In FIG. 74B, the gripping interface 7328 may comprise an upright flange 7406 extending across a depression 7408 formed into the second end 7324b. A user may be able to grip the internal applicator cover 7322 with the thumb and forefinger at the upright flange 7406, and apply a rotational or axial load to the internal applicator cover 7322 via the gripping interface 7328.

Figure 75:
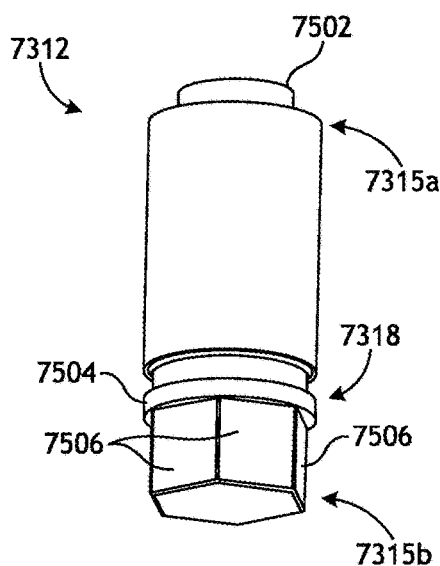
FIG. 75 is an isometric view of an example embodiment of the sensor cap of FIG. 73B, according to one or more embodiments.

FIG. 75 is an isometric view of an example embodiment of the sensor cap 7312, according to one or more embodiments. In some embodiments, as illustrated, the first end 7315a of the sensor cap 7312 may provide or define a reduced-diameter portion 7502 that may help facilitate removable coupling engagement to the sensor control device 6202 (FIG. 73B).

At the second end 7315b, the engagement features 7318 may comprise, for example, an enlarged head or annular ring 7504 that can interact with the compliant members 7402

(FIG. 74A) of the internal applicator cover 7322 (FIG. 74A). The annular ring 7504 may alternatively comprise one or more radial protrusions. In some embodiments, the engagement features 7318 may also provide or otherwise define two or more planar surfaces 7506 configured to interact with the planar members 7404 (FIG. 74A) of the internal applicator cover 7322. In at least one embodiment, the planar surfaces 7506 may provide a hexagonal shape to the second end 7315b and may mate with the planar members 7404.

Figure 76:
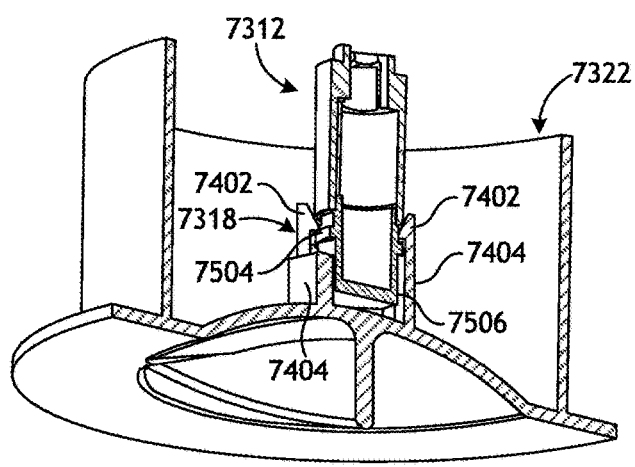
FIG. 76 is an isometric, cross-sectional side view of the sensor cap of FIG. 75 received by the internal applicator cover of FIGS. 74A-74B, according to one or more embodiments.

FIG. 76 is an isometric, cross-sectional side view of the sensor cap 7312 received by the internal applicator cover 7322, according to one or more embodiments. As illustrated, the engagement features 7318 are received within the receiving features 7330 of the internal applicator cover 7322. More particularly, the annular ring 7504 is received by the compliant members 7402, and the compliant members 7402 may comprise, for example, a collet-type device that includes a plurality of compliant fingers configured to flex radially outward to receive the annular ring 7504. In other embodiments, however, the compliant members 7402 may comprise an elastomer or another type of compliant material configured to expand radially to receive the annular ring 7504. Accordingly, as the sensor cap 7312 is extended into the receiving features 7330, the compliant members 7402 may flex (expand) radially outward to receive the engagement features 7318. Once the annular ring 7504 bypasses the compliant members 7402, the compliant members 7402 flex back to their natural state and thereby prevent the sensor cap 7312 from disengaging from the internal applicator cover 7322.

Mating the engagement features 7318 to the receiving features 7330 may also include mating the planar surfaces 7502 of the sensor cap 7312 with the planar members 7404 of the internal applicator cover 7322. The opposing planar members and surfaces 7404, 7502 may bind the sensor cap 7312 rotationally such that the sensor cap 7312 is unable to rotate relative to the internal applicator cover 7322.

Figure 77:
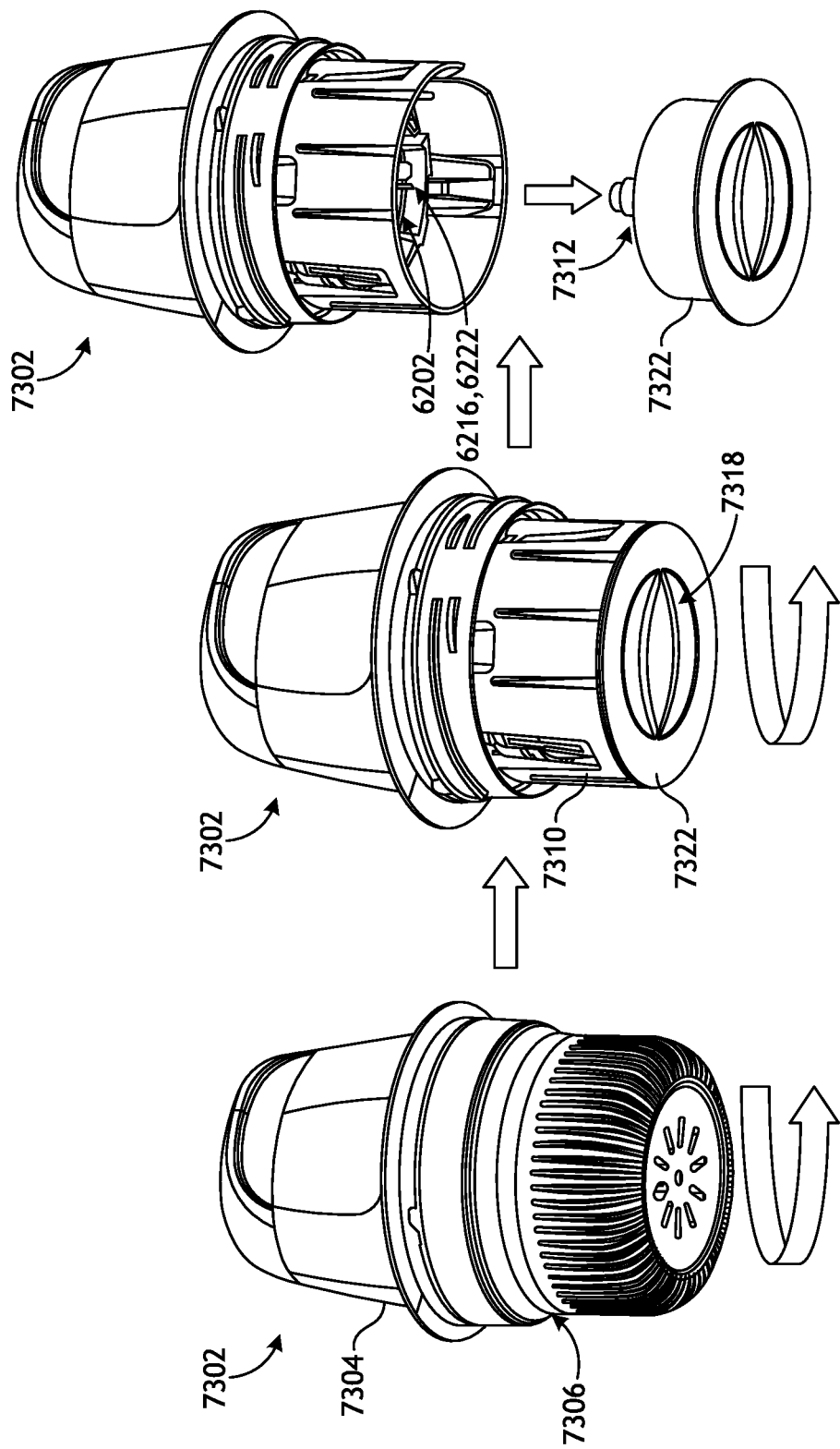
FIG. 77 shows progressive removal of the applicator cap of FIG. 73A and the internal applicator cover of FIGS. 74A-74B from the sensor applicator of FIGS. 73A-73B, according to one or more embodiments.

FIG. 77 shows progressive removal of the applicator cap 7306 and the internal applicator cover 7322 from the sensor applicator 7302, according to one or more embodiments. Moving from left to right in FIG. 77, the applicator cap 7306 may be removed by unscrewing it from the housing 7304. Removing the applicator cap 7306 exposes the sheath 7310 and the bottom of the internal applicator cover 7322. At this point, the sensor cap 7312 remains removably coupled to the sensor control device 6202 within the sensor applicator 7302. Consequently, the sterile barrier facilitated by the sensor cap 7312 is not broken by removal of the applicator cap 7306, and the sensor 6216 and the sharp 6222 remain protected. This feature may prove advantageous in the event the user changes his/her mind about firing the sensor applicator 7302 (i.e., deploying the sensor control device 6202) after removing the applicator cap 7306. In the event of a decision change, the sensor 6216 and the sharp 6222 remain protected within the sensor cap 7312, which is coupled to the internal applicator cover 7322.

To be able to properly fire the sensor applicator 7302 and thereby deploy the sensor control device 6202, the internal applicator cover 7322 must first be removed. As mentioned above, this can be done by the user gripping the internal applicator cover 7322 at the gripping interface 7328. The user may then apply a rotational or axial load to the internal applicator cover 7322 via the gripping interface 7328 to remove the internal applicator cover 7322. Upon removing the internal applicator cover 7322 from the sensor applicator 7302, the receiving features 7330 (FIG. 74A) of the internal applicator cover 7322 may retain the engagement features 7318 of the sensor cap 7312 and thereby prevent the sensor cap 7312 from separating from the receiving features 7330. Instead, removing the internal applicator cover 7322 from the sensor applicator 7302 will simultaneously detach the sensor cap 7312 from the sensor control device 6202, and thereby expose the distal portions of the sensor 6216 and the sharp 6222.

Figure 78:
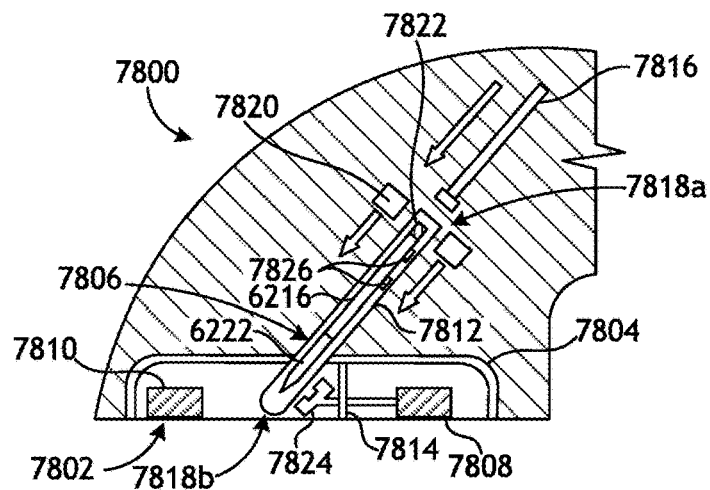
FIG. 78 is a schematic diagram of an example sensor applicator, according to one or more additional embodiments of the present disclosure.

FIG. 78 is a schematic diagram of an example sensor applicator 7800, according to one or more additional embodiments of the present disclosure. Similar to the other sensor applicators described herein, the sensor applicator 7800 may be configured to house and subsequently deploy a sensor control device 7802, which may be similar in some respects to any of the sensor control devices described herein. Alternatively, the sensor control device 7802 may comprise a type of medical device, a health care product, or a system that might require terminal sterilization of specific component parts. Example medical devices or health care products that may incorporate the principles of the present disclosure include, but are not limited to, ingestible products, cardiac rhythm management (CRM) devices, underskin sensing devices, externally mounted medical devices, or any combination thereof.

In the illustrated embodiment, the sensor control device 7802 includes a housing 7804, a part 7806 requiring sterilization, one or more radiation sensitive components 7808, and a battery 7810 that provides power to the sensor control device 7802. In the illustrated embodiment, the radiation sensitive component 7808 may comprise one or more electronic modules such as, but not limited to, a data processing unit (e.g., an application specific integrated circuit or ASIC), a resistor, a transistor, a capacitor, an inductor, a diode, and a switch.

In some embodiments, the part 7806 may comprise the sensor 6216 and the sharp 6222 described herein. As illustrated, the part 7806 may extend at an angle relative to the housing 7804, but could alternatively extend perpendicular to the housing 7804. In the illustrated embodiment, the part 7806 is arranged within a sterile chamber 7812 to protect the sensor 6216 and the sharp 6222 from external contamination. In some embodiments, the sterile chamber 7812 may have a desiccant arranged therein to help promote preferred humidity conditions.

The sensor 6216 and the sharp 6222 may be sterilized prior to being assembled in the sensor applicator 7800, or alternatively while assembled in the sensor applicator 7800. In at least one embodiment, the sensor 6216 and the sharp 6222 may be subjected to radiation sterilization to properly sterilize the part 7806 for use. Suitable radiation sterilization processes include, but are not limited to, electron beam (e-beam) irradiation, gamma ray irradiation, X-ray irradiation, or any combination thereof.

In some embodiments, the sensor control device 7802 may include a barrier shield 7814 positioned within the housing 7804 to help block radiation (e.g., electrons) from propagating within the housing 7804 toward the radiation sensitive components 7808. The barrier shield 7814 may be made of a material that reduces or eliminates radiation from penetrating therethrough and thereby damaging the radiation sensitive components 7808 within the housing 7804. The barrier shield 7814 may be made of a material having a density sufficient to absorb the dose of the beam energy being delivered.

In some embodiments, the sterile chamber 7812 may be comprise a cap that encapsulates the sensor 6216 and the sharp 6222 to provide a sealed barrier that protects exposed portions of the part 7806 until the part 7806 is placed in use.

In such embodiments, the sterile chamber 7812 may be removable or detachable to expose the sensor 6216 and the sharp 6222, as described below. Moreover, in such embodiments, the cap may be made of a material that permits propagation of radiation therethrough to facilitate radiation sterilization of the part 7806. Suitable materials for the sterile chamber 7812 include, but are not limited to, a non-magnetic metal (e.g., aluminum, copper, gold, silver, etc.), a thermoplastic, a ceramic, rubber (e.g., ebonite), a composite material (e.g., fiberglass, carbon fiber reinforced polymer, etc.), an epoxy, or any combination thereof. In some embodiments, the sterile chamber 7812 may be transparent or translucent, but can otherwise be opaque, without departing from the scope of the disclosure.

In other embodiments, the sterile chamber 7812 may comprise a chamber or compartment defined within one or both of the sensor applicator 7800 and the sensor control device 7802. In such embodiments, the sterile chamber 7812 may include a microbial barrier positioned at one or both ends of the sterile chamber 7812. More specifically, the sterile chamber 7812 may provide or include an upper microbial barrier 7818*a* and a lower microbial barrier 7818*b* opposite the upper microbial barrier 7818*a*. The upper and lower microbial barriers 7818*a,b* may help seal the sterile chamber 7812 and thereby isolate the sensor 6216 and the sharp 6222 from external contamination. The microbial barriers 7818*a,b* may be made of a radiation permeable material, such as a synthetic material (e.g., a flash-spun high-density polyethylene fiber). One example synthetic material comprises TYVEK®, available from DuPont®. In other embodiments, however, the microbial barriers 7818*a,b* may comprise, but are not limited to, tape, paper, film, foil, or any combination thereof.

In some embodiments, the part 7806 may be deployable and otherwise movable relative to the sensor applicator 7800. In such embodiments, the sensor 6216 and the sharp 6222 may be advanced distally out of the sterile chamber 7812 and past the bottom of the electronics housing 7804 to allow the sensor 6216 and the sharp 6222 to be transcutaneously received beneath a user's skin. Distally advancing the part 7806 may be accomplished via a variety of mechanical or electromechancial means. In some embodiments, for example, the sensor applicator 7800 may include a plunger 7816 configured to advance distally to push the sensor 6216 and the sharp 6222 out of the sterile chamber 7812. In such embodiments, the plunger 7816 may also be configured to attach to the sharp 6222 and subsequently retract the sharp 6222 while leaving the sensor 6216 extended. During operation, the plunger 7816 may penetrate the upper microbial barrier 7818*a* and force the sensor 6216 and the sharp 6222 distally through the lower microbial barrier 7818*b*.

In other embodiments, the part 7806 may be advanced distally out of the sterile chamber 7812 using a magnetic coupling. More specifically, the sensor applicator 7800 may include a driver magnet 7820 movable within the sensor applicator 7800 and magnetically coupled to a driven magnet 7822 disposed on the part 7806, such as on an upper end of the sharp 6222. The driver magnet 7820 may be configured to advance distally and simultaneously push the sensor 6216 and the sharp 6222 out of the sterile chamber 7812 as magnetically coupled to the driven magnet 7822. Once the sensor 6216 is properly placed, the driver magnet 7820 may be retracted proximally and simultaneously retract the sharp 6222 in the same direction while leaving the sensor 6216 extended. During operation, the driver magnet 7820 may cause the sensor 6216 and the sharp 6222 to penetrate distally through the lower microbial barrier 7818*b*.

In embodiments where the sterile chamber 7812 comprises a cap, the plunger 7816 may also be operable to discharge or push the cap out of the sensor applicator 7800. In such embodiments, a user may commence the firing process by priming the sensor applicator 7800, which may cause the cap to be discharged from the sensor applicator 7800. Further actuation of the sensor applicator 7800 by the user may cause the sensor 6216 and the sharp 6222 to be fully extended for subcutaneous implantation. In other embodiments, the cap may be removed either autonomously (e.g., it falls off or breaks away during firing) or the user may manually remove it by hand.

In some embodiments, the sensor applicator 7800 may further include an electrical connector 7824 in electrical communication with the electronics of the sensor control device 7802, such as the radiation sensitive components 7808. In at least one embodiment, the electrical connector 7824 may comprise one or more elastic pins made of a conductive polymer (e.g., a carbon impregnated polymer) and configured to facilitate electrical communication between the sensor 6216 and the radiation sensitive component 7808. In such embodiments, the sensor 6216 may include one or more connectors 7826 alignable with the electrical connector 7824 when the part 7806 is advanced distally, as described above. Moreover, in embodiments where the sterile chamber 7812 comprises a cap, the electrical connector 7824 may be flexible to allow the cap to pass by the electrical connector 7824 until the connectors 7826 align with the electrical connector 7824.

Figure 79:
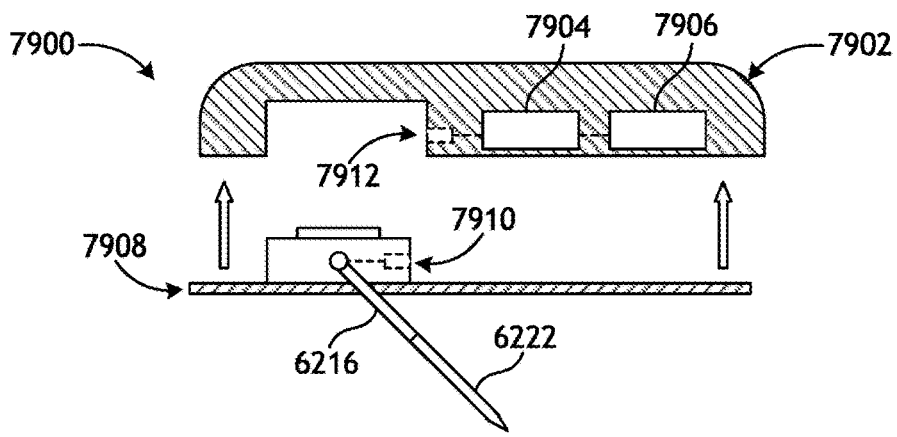
FIG. 79 is an exploded view of an example sensor control device, according to one or more additional embodiments.

FIG. 79 is an exploded view of an example sensor control device 7900, according to one or more additional embodiments. The sensor control device 7900 may be similar in some respects to any of the sensor control devices described herein. For example, the sensor control device 7900 may include a housing 7902 that contains or otherwise houses a battery 7904 that powers the sensor control device 7900 and one or more radiation sensitive components 7906. The radiation sensitive component 7906 may be similar to the radiation sensitive component 7808 of FIG. 78, and therefore will not be described again. In some embodiments, the housing 7902 may be made of a flexible or deformable material.

The sensor control device 7900 may further include a sensor module 7908 that may be coupled to the housing 7902 to form the assembled sensor control device 7900. As illustrated, the sensor module 7908 may include the sensor 6216 and the sharp 6222 extending distally therefrom. In the illustrated embodiment, the sensor 6216 and the sharp 6222 extend at an angle relative to the housing 7902, but could alternatively extend perpendicular to the housing 7902.

The sensor module 7908 may be sterilized separate from the housing 7902 to prevent damage to the radiation sensitive components 7906. Following sterilization, the sensor module 7908 may be paired or coupled to the housing 7902 via a variety of permanent or removable attachment means. In some embodiments, for example, the sensor module 7908 may be coupled to the housing 7902 via a snap-fit engagement, an interference fit, or using one or more mechanical fasteners. In other embodiments, however, the sensor module 7908 may be coupled to the housing 7902 using an adhesive, sonic welding, or laser welding. Pairing the sensor module 7908 to the housing 7902 may be done during manufacturing or may be accomplished by a user prior to deploying the sensor control device.

Coupling the sensor module 7908 to the housing 7902 may also facilitate communication between the sensor 6216 and the radiation sensitive components 7906. More particularly, in some embodiments, the sensor module 7908 may include one or more sensor contacts 7910 alignable with one or more electrical connectors 1912 provided on the housing 7902 when the sensor module 7908 is coupled to the housing 7902. The sensor contacts 7910 and the electrical connectors 1912 may comprise one or more elastic pins made of a conductive polymer (e.g., a carbon impregnated polymer) and configured to facilitate electrical communication between the sensor 6216 and the radiation sensitive component 7906.

Figure 80:
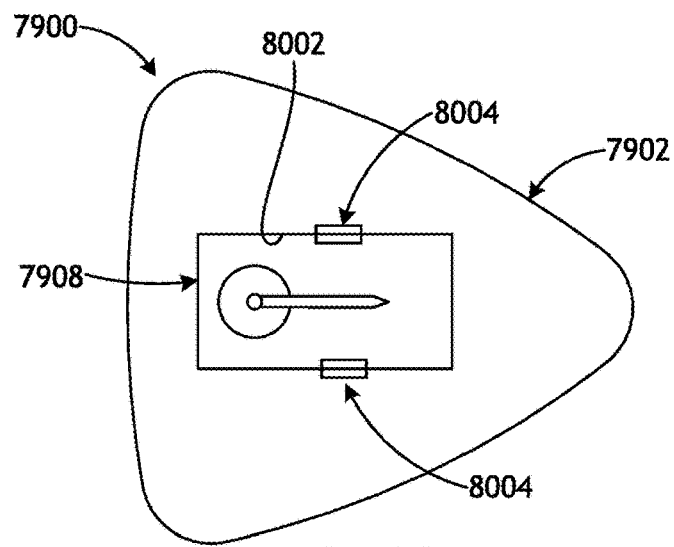
FIG. 80 is a bottom view of one embodiment of the sensor control device of FIG. 79.

FIG. 80 is a bottom view of one embodiment of the sensor control device 7900 of FIG. 79. As illustrated, the housing 7902 exhibits a generally polygonal cross-sectional shape and, more particularly, a triangular shape with rounded corners. In other embodiments, however, the housing 7902 may exhibit other cross-sectional shapes including, but not limited to, circular, oval, ovoid, or other polygonal shapes (e.g., square, rectangular, pentagonal, etc.), without departing from the scope of the disclosure.

In the illustrated embodiment, the sensor module 7908 may be coupled to the housing 7902 via a snap-in or snap-fit engagement. More specifically, the housing 7902 may define a cavity 8002 sized to receive the sensor module 7908, and one or both of the housing 7902 and the sensor module 7908 may define or otherwise provide tabs 8004 configured to matingly engage when the sensor module 7908 is received within the cavity 8002. The tabs 8004 may mate to secure the sensor module 7908 within the cavity 8002. As will be appreciated, the tabs 8004 may be replaced with any other type of device or mechanism that facilitates a snap-in or snap-fit engagement, without departing from the scope of the disclosure. As indicated above, coupling the sensor module 7908 to the housing 7902 may be done during manufacturing or may be accomplished by a user prior to deploying the sensor control device.

Embodiments disclosed herein include:

X. A sensor applicator that includes a housing and a sensor retainer arranged within the housing, a sensor control device removably coupled to the sensor retainer and including an electronics housing, a sensor arranged within the electronics housing and extending from a bottom of the electronics housing, and a sharp hub that carries a sharp extending through the electronics housing and from the bottom of the electronics housing. The sensor application further includes a needle shroud extendable through the sensor retainer and the electronics housing and movable between an extended position, where the needle shroud extends past the bottom of the electronics housing and covers distal ends of the sensor and the sharp, and a retracted position, where the needle shroud retracts into the housing and thereby exposes the distal ends of the sensor and the sharp.

Y. A method of deploying a sensor control device from a sensor applicator that includes positioning the sensor applicator adjacent a target monitoring location, the sensor applicator including a housing and a sensor retainer arranged within the housing, wherein the sensor control device is removably coupled to the sensor retainer and includes an electronics housing, a sensor arranged within the electronics housing and extending from a bottom of the electronics housing, and a sharp hub that carries a sharp extending through the electronics housing and from the bottom of the electronics housing. The method further includes aligning a needle shroud with the target monitoring location, the needle shroud extending through the sensor retainer and the electronics housing, engaging the needle shroud against the target monitoring location to move the needle shroud from an extended position, where the needle shroud extends past the bottom of the electronics housing and covers distal ends of the sensor and the sharp, and pushing on the sensor applicator to move the needle shroud to a retracted position, where the needle shroud retracts into the housing and exposes the distal ends of the sensor and the sharp to transcutaneously receive the sensor at the target monitoring location.

Each of embodiments X and Y may have one or more of the following additional elements in any combination: Element 1: further comprising a sensor cap defining an inner chamber that receives the distal ends of the tail and the sharp and forms a sterile barrier that protects the distal ends of the sensor and the sharp. Element 2: further comprising an applicator cap removably coupled to the housing, wherein the applicator cap and the sensor cap are simultaneously removable from the housing. Element 3: wherein the sensor cap extends from the sensor control device. Element 4: wherein the sensor control device further includes a collar coupled to the electronics housing, and wherein the sensor cap is removably coupled to the collar. Element 5: wherein the sensor cap provides a gripping interface for a user to grasp onto and remove the sensor cap from the sensor applicator. Element 6: wherein the needle shroud is received within the sensor cap when the needle shroud is in the extended position. Element 7: further comprising one or more first retention features provided on the sensor retainer, one or more second retention features provided on the sensor control device and matable with the one or more first features, wherein disengaging the one or more second retention features from the one or more first features deploys the sensor control device for use. Element 8: wherein the sensor retainer provides a plurality of upwardly extending fingers engageable with the sharp hub to prevent the sharp hub from moving relative to the sensor retainer when the needle shroud is in the extended position. Element 9: wherein the plurality of fingers are extendable into an upper portion of the needle shroud and interpose the sharp hub and an inner wall of the upper portion of the needle shroud when the needle shroud is in the extended position. Element 10: further comprising a driver spring compressed between the sharp hub and the sensor retainer when the needle shroud is in the extended position, wherein moving the needle shroud to the retracted positon allows the driver spring to expand and move the sharp hub to retract the sharp into the housing. Element 11: wherein the plurality of fingers are extendable into the sharp hub and interpose the needle shroud and an inner wall of the sharp hub when the needle shroud is in the extended position. Element 12: further comprising a driver spring compressed between the sharp hub and the sensor retainer when the needle shroud is in the extended position, wherein moving the needle shroud to the retracted positon allows the driver spring to expand and move the sharp hub to retract the sharp into the housing. Element 13: wherein the needle shroud defines a groove at an upper end and the plurality of fingers provide inwardly extending features engageable with the groove to help maintain the needle shroud in the extended position. Element 14: wherein the sensor retainer includes one or more locking tabs matable with one or more locking members provided on the needle shroud to secure the needle shroud in the extended position.

Element 15: further comprising forming a sterile barrier with a sensor cap that receives the distal ends of the tail and the sharp, wherein the needle shroud is received within the sensor cap when the needle shroud is in the extended position, and removing the sensor cap prior to engaging the needle shroud against the target monitoring location. Element 16: wherein one or more first retention features provided on the sensor retainer are matable with one or more second retention features provided on the sensor control device to couple the sensor control device to the sensor retainer, the method further comprising adhesively attaching the sensor control device to the target monitoring location, and pulling the sensor applicator away from the target monitoring location to disengage the one or more second retention features from the one or more first retention features and thereby detach the sensor control device from the sensor retainer. Element 17: wherein the sensor retainer provides a plurality of upwardly extending fingers engageable with the sharp hub, the method further comprising preventing the sharp hub from moving relative to the sensor retainer with the plurality of fingers when the needle shroud is in the extended position. Element 18: wherein the plurality of fingers are extendable into an upper portion of the needle shroud and interpose the sharp hub and an inner wall of the upper portion of the needle shroud when the needle shroud is in the extended position, the method further comprising moving the sharp hub to retract the sharp into the housing when the needle shroud moves to the retracted position with a driver spring extending between the sharp hub and the sensor retainer. Element 19: wherein the plurality of fingers are extendable into the sharp hub and interpose the needle shroud and an inner wall of the sharp hub when the needle shroud is in the extended position, the method further comprising moving the sharp hub to retract the sharp into the housing when the needle shroud moves to the retracted position with a driver spring extending between the sharp hub and the sensor retainer.

By way of non-limiting example, exemplary combinations applicable to X and Y include: Element 1 with Element 2; Element 1 with Element 3; Element 3 with Element 4; Element 1 with Element 5; Element 1 with Element 6; Element 8 with Element 9; Element 9 with Element 10; Element 8 with Element 11; Element 11 with Element 12; Element 11 with Element 13; Element 15 with Element 16; Element 17 with Element 19; and Element 17 with Element 19.

Localized Axial-Radial Sensor Seal for Analyte Monitoring

Referring briefly again to FIG. 1, the system 100 may comprise what is known as a "two-piece" architecture that requires final assembly by a user before the sensor 110 can be properly delivered to the target monitoring location. According to embodiments of the present disclosure, the sensor control device assembly of FIG. 1 may instead comprise a one-piece architecture that incorporates sterilization techniques specifically designed for a one-piece architecture. The one-piece architecture allows the sensor control device assembly to be shipped to the user in a single, sealed package that does not require any final user assembly steps. Rather, the user need only open one package and subsequently deliver the sensor control device to the target monitoring location. The one-piece system architecture described herein may prove advantageous in eliminating component parts, various fabrication process steps, and user assembly steps. As a result, packaging and waste are reduced, and the potential for user error or contamination to the system is mitigated.

Figure 81A:
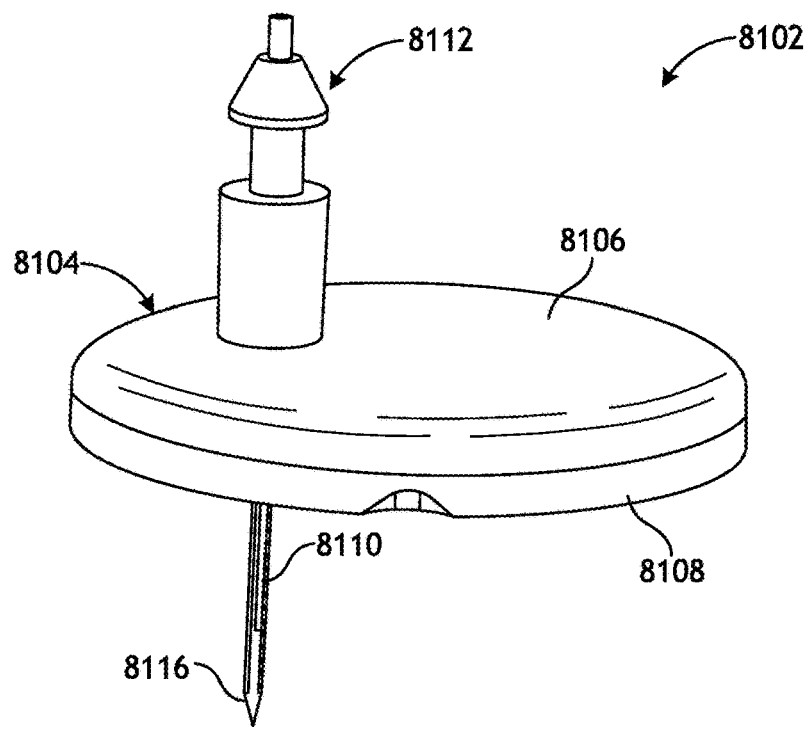
FIGS. 81A and 81B are isometric and side views, respectively, of a sensor control device in accordance with one or more embodiments of the present disclosure.
Figure 81B:
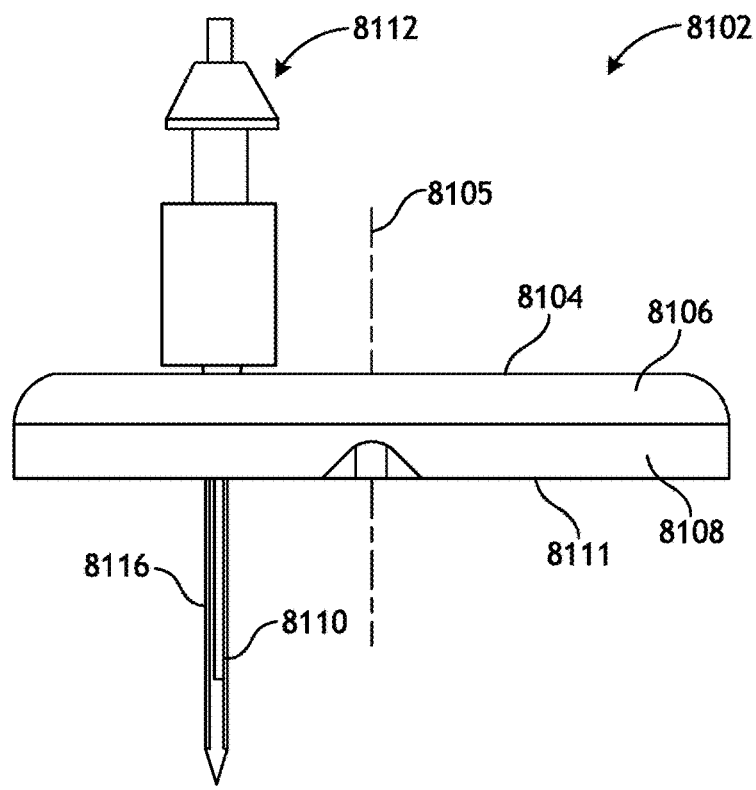

FIGS. 81A and 81B are isometric and side views, respectively, of an example sensor control device 8102. The sensor control device 8102 may be similar in some respects to the sensor control device 104 of FIG. 1 and therefore may be best understood with reference thereto. In some applications, the sensor control device 8102 may replace the sensor control device 104 of FIG. 1 and, therefore, may be used in conjunction with the analyte monitoring system 100 (FIG. 1) or the sensor applicator 102, which delivers the sensor control device 8102 to a target monitoring location on a user's skin.

The sensor control device 8102 includes an electronics housing 8104 that is generally disc-shaped and may have a circular cross-section. In other embodiments, however, the electronics housing 8104 may exhibit other cross-sectional shapes, such as ovoid or polygonal and may be non-symmetrical. The electronics housing 8104 may include a shell 8106 and a mount 8108 configured to engage or couple with the shell 8106. The shell 8106 may be secured to the mount 8108 via a variety of ways, such as a snap fit engagement, an interference fit, sonic (or ultrasonic) welding, using one or more mechanical fasteners (e.g., screws), or any combination thereof. In some embodiments, the interface between the shell 8106 and the mount 8108 may be sealed. In such embodiments, a gasket or other type of seal material may be positioned or applied at or near the outer diameter (periphery) of the shell 8106 and the mount 8108. Securing the shell 8106 to the mount 8108 may compress the seal material and thereby generate a sealed interface. In at least one embodiment, an adhesive may be applied to the outer diameter (periphery) of one or both of the shell 8106 and the mount 8108, and the adhesive may not only secure the shell 8106 to the mount 8108 but may also seal the interface.

In embodiments where a sealed interface is created between the shell 8106 and the mount 8108, the interior of the electronics housing 8104 may be effectively isolated from outside contamination between the two components. In such embodiments, if the sensor control device 8102 is assembled in a controlled and sterile environment, there may be no need to sterilize the internal electrical components (e.g., via gaseous chemical sterilization). Rather, the sealed engagement may provide a sufficient sterile barrier for the assembled electronics housing 8104.

The sensor control device 8102 may further include a sensor 8110, a sharp module 8112 engaged with the sensor 8110. The sensor 8110 and the sharp module 8112 may be interconnectable and may be coupled to the electronics housing 8104. The sharp module 8112 may be configured to carry and otherwise include a sharp 8116 used to help deliver the sensor 8110 transcutaneously under a user's skin during application of the sensor control device 8102.

As best seen in FIG. 81B, corresponding portions of the sensor 8110 and the sharp 8116 extend from the electronics housing 8104 and, more particularly, from the bottom of the mount 8108. The exposed portion of the sensor 8110 may be received within a hollow or recessed portion of the sharp 8116. The remaining portion(s) of the sensor 8110 is/are positioned within the interior of the electronics housing 8104.

Figure 82:
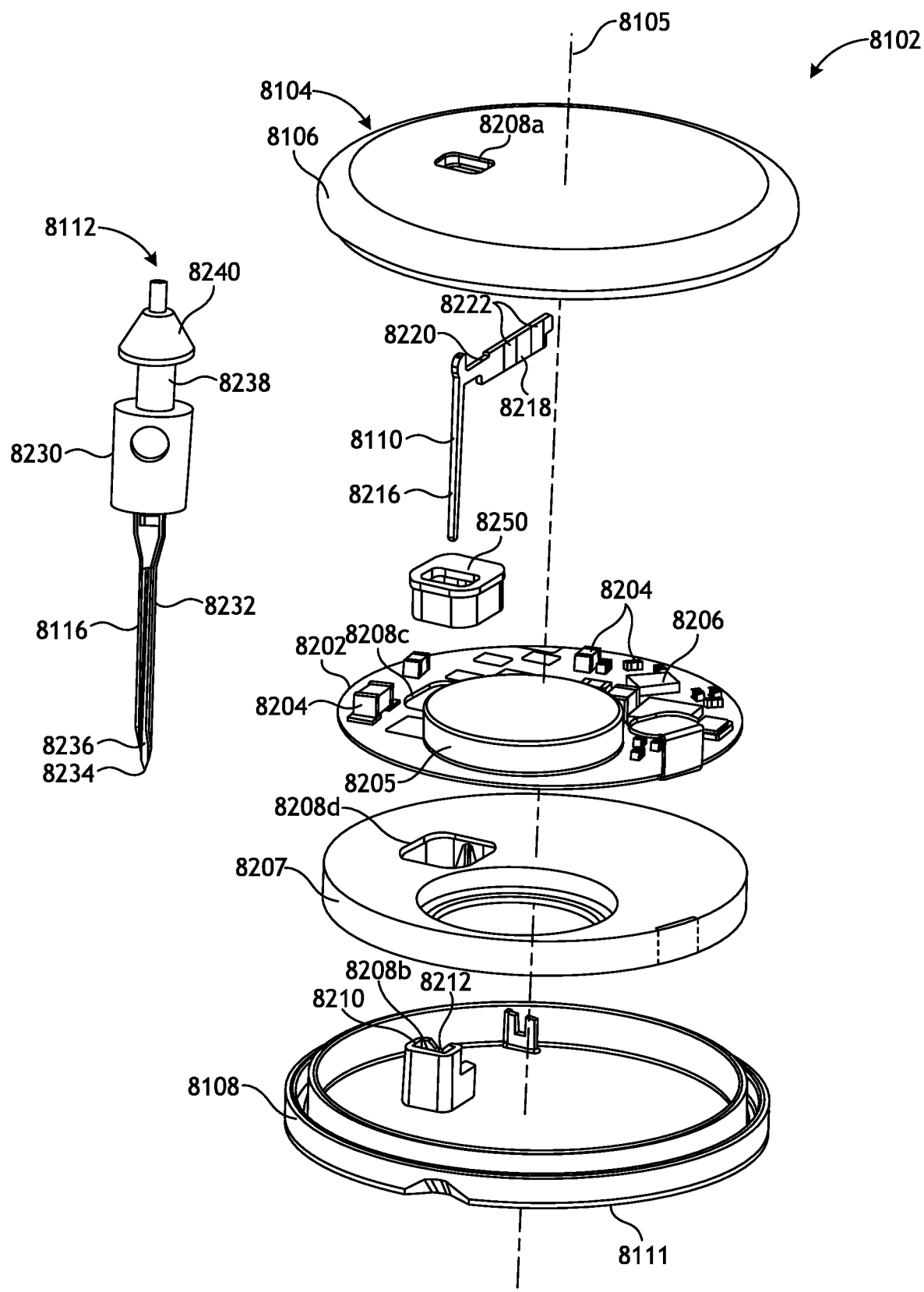
FIG. 82 is an exploded perspective top view of the sensor control device of FIG. 81A.

FIG. 82 is an exploded perspective top view of the sensor control device 8102, according to one or more embodiments. As illustrated, the shell 8106 and the mount 8108 of the electronics housing 8104 may operate as opposing clamshell halves that enclose or otherwise substantially encapsulate the various electronic components of the sensor control device 8102. Various electrical components may be positioned within the electronics housing 8104, including a printed circuit board (PCB) 8202 having a plurality of electronic modules 8204 and a battery 8205 mounted to the PCB 8202. The battery 8205 may be configured to power the sensor control device 8102. Example electronic modules 8204 include, but are not limited to, resistors, transistors, capacitors, inductors, diodes, integrated circuits, and switches. A data processing unit 8206 (FIG. 82) may also be mounted to the PCB 8202 and may comprise, for example, an application specific integrated circuit (ASIC) configured to implement one or more functions or routines associated with operation of the sensor control device 8102. More specifically, the data processing unit 8206 may be configured to perform data processing functions, such as filtering and encoding of data signals, each of which corresponds to a sampled analyte level of the user. The data processing unit 8206 may also include or otherwise communicate with an antenna for communicating with the reader device 106 (FIG. 1). As shown in FIG. 82, the PCB 8202 and various components mounted to it may be encapsulated or otherwise contained within an encapsulating material 8207.

As illustrated in FIG. 82, the shell 8106, the mount 8108, and the PCB 8202, and encapsulating material 8207 each define corresponding channels or apertures 8208*a*, 8208*b*, 8208*c*, 8208*d*, respectively. Due to their placement with respect to the outer surface of electronics housing 8104, aperture 8208*a* in the shell 8106 may be referred to as a top aperture, and aperture 8208*b* in the mount 8108 may be referred to as a bottom aperture. The mount 8108 further includes a channel 8210 that extends upward from aperture 8208*b* and a slot 8212 that extends through a side wall of channel 8210. When the sensor control device 8102 is assembled, the apertures 8208*a-c* align and the channel 8210 extends through apertures 8208*a*, 8208*c*, 8208*d* to receive portions of the sensor 8110 and the sharp module 8112 therethrough. The centers or central regions of apertures 8208*a*, 8208*b*, 8208*c*, 8208*d* and channel 8210 are arranged in an eccentric manner with respect to electronics housing 8104, being spaced apart from the sensor central axis 8105. The sharp 8110 and sensor 8110, which may extend through at least one of these apertures and channel 8210, are likewise spaced apart from the sensor central axis 8105 and are arranged in an eccentric manner.

The sensor control device 8102 may further include a housing support 8250 to be located in electronics housing 8104 in the vicinity of apertures 8208*a*, 8208*b*, 8208*c*, 8208*d* to provide support between shell 8106 and mount 8108. The illustrated embodiment, housing support 8250 for electronics housing 8104 is a collar 8250. The collar 8250 may exhibit a variety of shapes, such as cylindrical, tubular, annular, polygonal, or any combination thereof.

The sensor 8110 includes a tail 8216, a flag 8218, and a neck 8220 that interconnects the tail 8216 and the flag 8218. The central aperture 8208*b* and channel 8210 defined in the mount 8108 may be configured to receive the tail 8216, which may extend therethrough and extend distally from the underside thereof. The slot 8212 in the mount 8108 may be configured to receive the sensor neck 8220, allowing the flag 8218 to extend to or toward the PCB 8202. The tail 8216 includes an enzyme or other chemistry or biologic and, in some embodiments, a membrane may cover the chemistry. In use, the tail 8216 is transcutaneously received beneath a user's skin, and the chemistry included thereon helps facilitate analyte monitoring in the presence of bodily fluids.

The flag 8218 may comprise a generally planar surface having one or more sensor contacts 8222 (two shown in FIG. 82) disposed thereon. The flag 8218 or the contacts 8222 are configured to couple electrically to the PCB 8202 or modules on PCB 8202, which may include a corresponding number of contacts (not shown), such as contacts on compliant carbon impregnated polymer modules for example.

The sharp module 8112 includes the sharp 8116 and a sharp hub 8230 that carries the sharp 8116. The sharp 8116 includes an elongate shaft 8232 and a sharp tip 8234 at the distal end of the shaft 8232. The shaft 8232 may be configured to extend through each of the coaxially aligned central apertures 8208*a-c* and extend distally from the bottom of the mount 8108. Moreover, the shaft 8232 may include a hollow or recessed portion 8236 that at least partially circumscribes the tail 8216 of the sensor 8110. The sharp tip 8234 may be configured to penetrate the skin while carrying the tail 8216 to put the active chemistry of the tail 8216 into contact with bodily fluids.

The sharp hub 8230 may include a hub small cylinder 8238 and a hub snap pawl 8240, each of which may be configured to help couple the sensor control device 8102 to the sensor applicator 102 (FIG. 1).

An adhesive or adhesive patch (not shown), similar to the adhesive patch 108 of FIG. 1, may be positioned on and otherwise attached to the bottom 8111 of the mount 8108. As discussed above, the adhesive patch may be configured to secure and maintain the sensor control device 8102 in position on the user's skin during operation.

Figure 83:
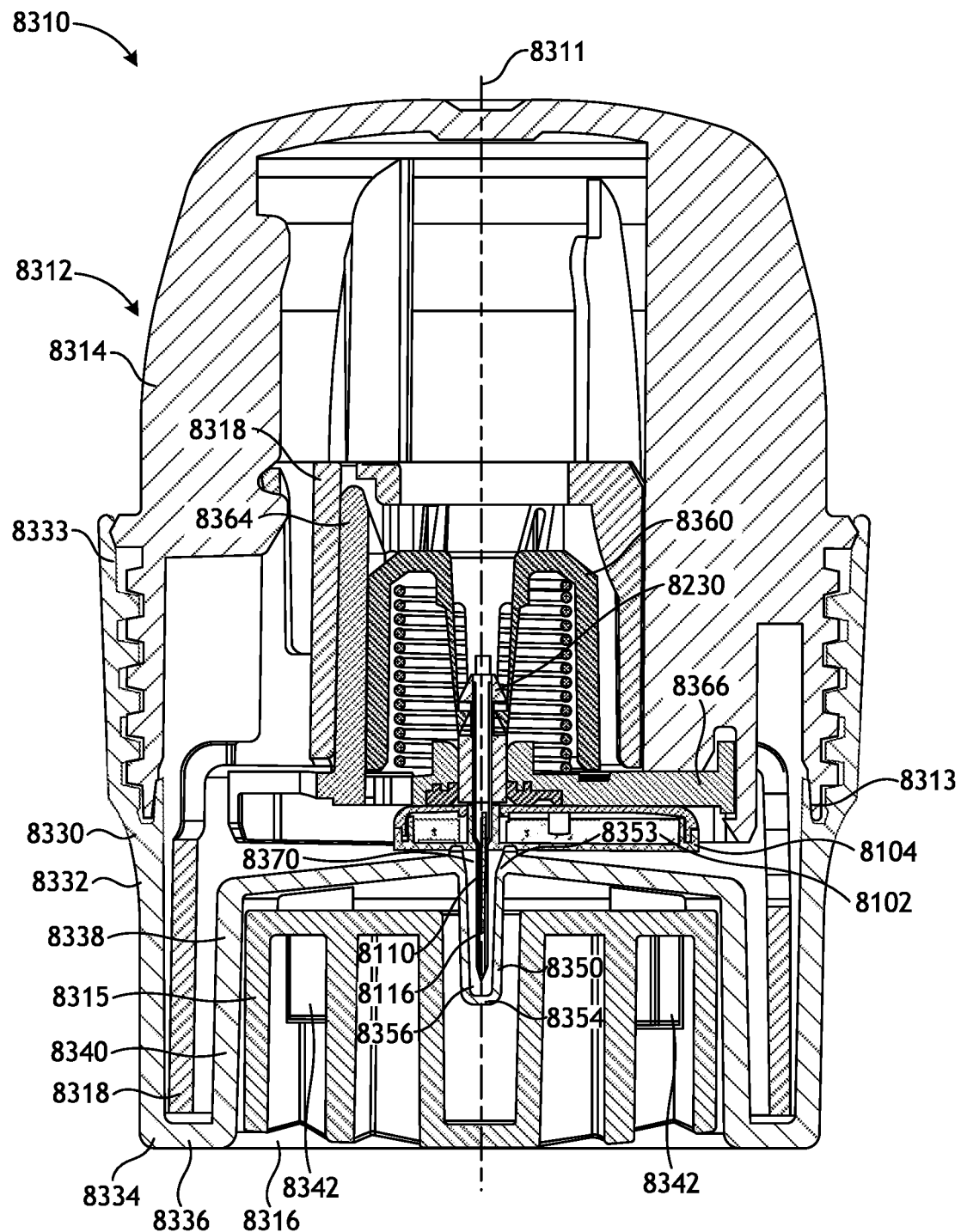
FIG. 83 is a cross-sectional side view in perspective of an example sensor control device assembly including a sensor control device of FIG. 81A mounted within the sensor applicator, the sensor control device being compatible with the analyte monitoring system of FIG. 1.

FIG. 83 is a cross-sectional side view of a sensor control device assembly 8310 having a central or longitudinal assembly axis 8311 and including a sensor applicator 8312 with a cap 8330 coupled thereto and the sensor control device 8102 installed inside. In some applications, the sensor control device assembly 8310 with its sensor control device 8102 and applicator 8312 may replace the sensor control device 104 and the applicator 102 of FIG. 1 and, therefore, may be used in conjunction with the analyte monitoring system 100 (FIG. 1).

The cap 8330 may be threaded to the sensor applicator 8312 and may include a tamper-evident ring or wrap (not shown) to evidence or inhibit premature unthreading. Moreover, the cap 8330 may define an undercut 8313 at the base of the threaded interface that provides additional stiffness in tilting at the interface between the cap 8330 and the housing 8314 and a detent force that may need to be overcome for the cap 8330 to unscrew. Upon rotating (e.g., unscrewing) the cap 8330 relative to sensor applicator 8312, the tamper ring or wrap may shear and thereby free the cap 8330 and desiccant 8315 from the sensor applicator 8312. Following which, the user may deliver the sensor control device 8102 to the target monitoring location.

The sensor applicator 8312 includes a housing 8314 that is disposed around and slidingly coupled to a sheath 8318 and is configured to move a prescribed axial distance relative to the sheath 8318. Sheath 8318 defines a bottom for sensor applicator 8312, the bottom that rests against a user's skin, for example, when sensor control device assembly 8310 is used to place a sensor control device 8102 on the user. Sensor applicator 8312 also includes a sharp carrier 8360 and a sensor carrier 8364 interposed between the sheath 8318 and sharp carrier 8360. Sensor carrier 8364 includes a radially extending platform 8366 located below sharp carrier 8360, which may rest on the platform 8366. Platform 8366 is coupled to housing 8314 to move when housing 8314 moves axially relative to sheath 8318.

The cap 8330 may include an outer shell 8332 that extends from a threaded first end 8333 to a bottom or second end 8334. A base 8336 may be located at the second end 8334, a support structure 8338 may extend from the base 8336 upward toward the first end 8333, and a post 8350 extending from the support structure 8338. Likewise, when installed, support structure 8338 may extend upward from the bottom of the sheath 8318 of the sensor applicator 8312. The support structure 8338 is located within the outer shell 8332 and includes an inner shell 8340 supported by a plurality of ribs 8342. Viewed from base 8336, inner shell

8340 is concave. The post 8350 is centrally located within the interior of the cap 8330 and may be aligned with assembly axis 8311. The post 8350 extends downward from a first end 8353 at the top of inner shell 8340 to a second end 8354 closer to cap base 8336. The post 8350 defines a post chamber 8356, which is open at first end 8353 and closed at second end 8354.

The support structure 8338 or the post 8350 may be configured to help support the sensor control device 8102 while contained within the sensor applicator 8312. Moreover, the post chamber 8356 is configured to receive the sensor 8110 and the sharp 8116 when extending from the bottom of the electronics housing 8104. When the sensor control device 8102 is loaded into the sensor applicator 8312, the sensor 8110 and the sharp 8116 may be arranged within a sealed region 8370 at least partially defined by the post chamber 8356 and configured to isolate the sensor 8110 and the sharp 8116 from various other regions in sensor control device assembly 8310, which may contain various fluids or contaminants at various times.

The cap 8330 provides a barrier against outside contamination, and thereby maintains a sterile environment for the sensor control device assembly 8310, including the sensor control device 8102 contained therein, until the user removes (unthreads) the cap 8330. The cap 8330 may also create a dust-free environment during shipping and storage.

A desiccant 8315 may be included in cap 8330, being located within the outer volume of the inner shell 8340, and a cover member or seal 8316, which in this example includes foil, may be applied to base 8336 to contain and seal the desiccant 8315 against the intrusion of moisture and other contamination, and may also provide evidence of tampering.

In some embodiments, the seal 8316 may comprise only a single protective layer applied to the cap 8330, such as foil. In some embodiments, the seal 8316 may comprise two or more layers of different materials. The first layer may be made of a synthetic material (e.g., a flash-spun high-density polyethylene fiber), such as Tyvek® available from DuPont®. Tyvek® is highly durable and puncture resistant and allows the permeation of vapors. The Tyvek® layer can be applied before a gaseous chemical sterilization is performed, and following the gaseous chemical sterilization, a foil or other vapor and moisture resistant material layer may be sealed (e.g., heat sealed) over the Tyvek® layer to prevent the ingress of contaminants and moisture.

Figure 84:
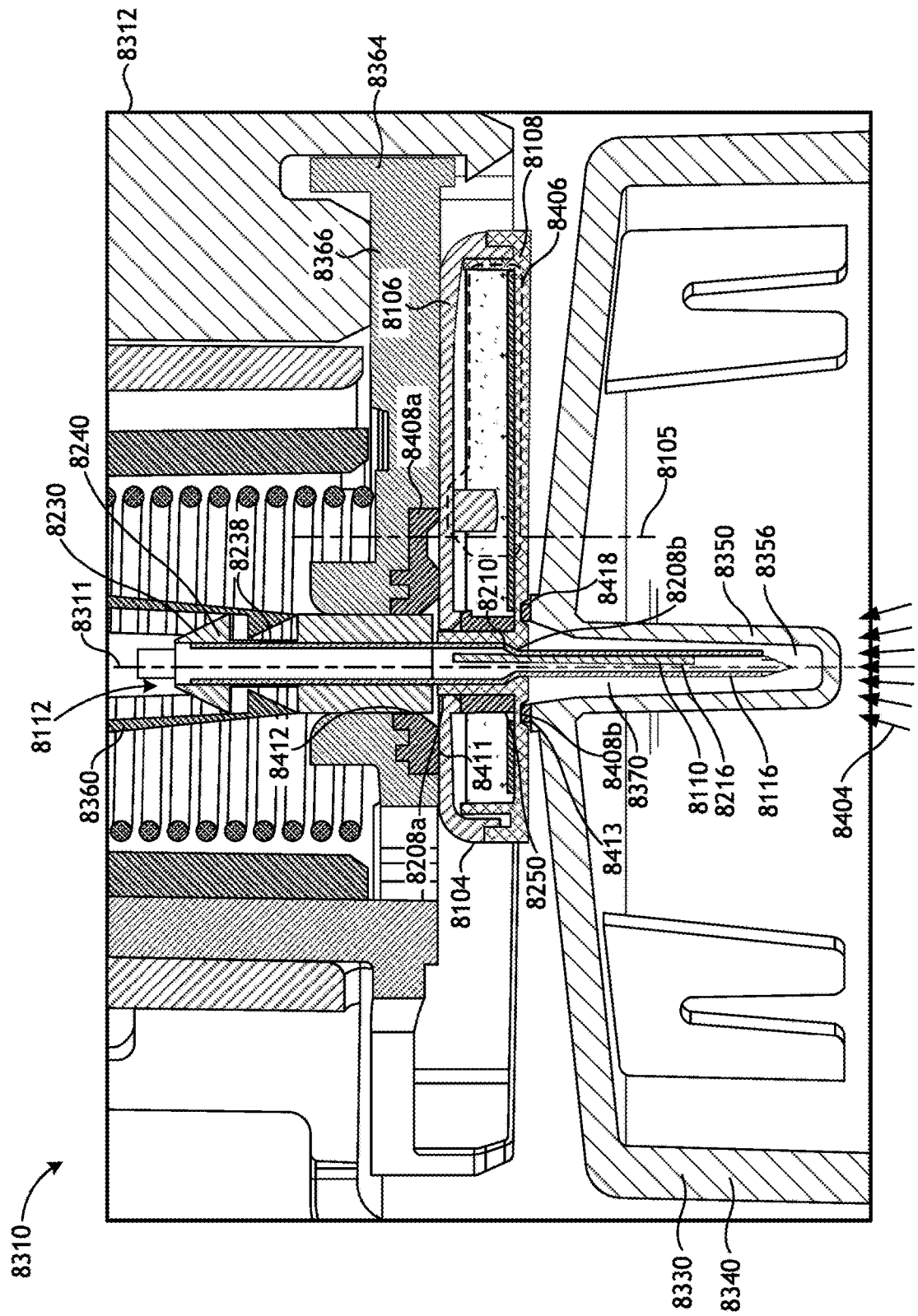
FIG. 84 is an enlarged cross-sectional side view of the sensor control device assembly of FIG. 83.

Referring now to FIG. 84, illustrated is an enlarged cross-sectional side view of the sensor control device assembly 8310 having sensor control device 8102 mounted within the sensor applicator 8312 and the cap 8330 secured thereto, according to one or more embodiments. The sensor control device 8102 may be loaded into the sensor applicator 8312 by mating the sharp hub 8230 with the sharp carrier 8360 and by mating the electronics housing 8104 of the sensor control device 8102 with the sensor carrier 8364 (alternately referred to as a "puck carrier"). More specifically, the hub small cylinder 8238 and the hub snap pawl 8240 of sharp hub 8230 may be received by corresponding mating features of the sharp carrier 8360.

After installation in sensor control device assembly 8310, the sensor control device 8102 may be subjected to "focused" radiation sterilization 8404, where the radiation is applied and otherwise directed toward the sensor 8110 and the sharp 8116. In such embodiments, some or all of the electrical components 8204 (FIG. 82), such as components group 8406 indicated with a dashed enclosure in FIG. 84, may be positioned out of the range (span) of the propagating radiation 8404 and, therefore, will not be affected by the radiation. For this purpose, apertures 8208a, 8208b, 8208c, 8208d, sensor 8110, and sharp module 8112 are spaced apart from the sensor central axis 8105 to increase the distance between these features that receive radiation 8404 and the components group 8406 of PCB 8202 that may contain various of the components 8204, 8206 that are to be protected from radiation 8404. For example, some or all of the electrical components 8204 and the data processing unit 8206, as examples, may be positioned on the PCB 8202 near its outer periphery so as not to fall within the range (span) of the focused radiation sterilization 8404. In other embodiments, this protection from radiation may be accomplished by shielding some or all of the electrical components 8204 and the data processing unit 8206, as examples, with proper electromagnetic shields.

As indicated above, portions of the sensor 8110 and the sharp 8116 may be arranged within the sealed region 8370 and thereby protected from substances that might adversely interact with the chemistry of the sensor 8110. More specifically, the sealed region 8370 protects the tail 8216. The sealed region 8370 may include (encompass) select portions of the interior of the electronics housing 8104 and the post chamber 8356 of the post 8350. In one or more embodiments, the sealed region 8370 may be defined and otherwise formed by at least a first seal 8408a and a second seal 8408b. Coupling the shell 8106 to the mount 8108 may create a sealed interface therebetween that may also participate in defining the extent of sealed region 8370.

The first seal 8408a may be arranged to seal an interface between the sharp hub 8230 and the shell 8106. In the present example, the first seal 8408a may be arranged to seal a first interface 8411 between the sensor carrier 8364 and the top of the electronics housing 8104, e.g., the shell 8106. The first seal 8408a may also be arranged to seal a second interface 8412 between the sensor carrier 8364 and sharp hub 8230 of the sharp module 8112. Moreover, at first interface 8411 the first seal 8408a may circumscribe the first central aperture 8208a defined in the shell 8106 such that contaminants are prevented from migrating in a radial direction (relative to sensor axis 8105) into the interior of the electronics housing 8104 via the first central aperture 8208a or channel 8210. At second interface 8412 the first seal 8408a may prevent fluid from migrating in an axial direction relative to assembly axis 8311 (or, alternatively, relative to sensor axis 8105) into the interior of the electronics housing 8104 via the first central aperture 8208a or channel 8210. Therefore, the first seal 8408a interposes the sensor carrier 8364 and the electronics housing 8104 and interposes sensor carrier 8364 and the sharp hub 1039 and is configured to provide axial and radial sealing. In this example, first seal 8408a is interposed between sensor applicator 8312 (e.g., the sensor carrier 8364) and sensor control device 8104 and is also interposed between sensor applicator 8312 and sharp module 8112.

In at least one embodiment, the first seal 8408a may be overmolded on to the sensor carrier 8364, thus forming a part of sensor carrier 8364. In other embodiments, however, the first seal 8408a may form part of the sharp hub 8230, such as by being overmolded onto the sharp hub 8230. In yet other embodiments, the first seal 8408a may be overmolded onto the top surface of the shell 8106. In even further embodiments, the first seal 8408a may comprise a separate structure, such as an O-ring or the like, that interposes the sharp hub 8230 and the top surface of the shell 8106, without departing from the scope of the disclosure.

The second seal 8408b may be arranged to seal an interface 8413 between the post 8350 and the bottom of the mount 8108, and the second seal 8408*b* may circumscribe the second central aperture 8208*b* defined in the mount 8108. The second seal 8408*b* may also circumscribe the post chamber 8356. Consequently, the second seal 8408*b* may prevent contaminants from migrating into the post chamber 8356 of the post 8350 and also from migrating into the interior of the electronics housing 8104 via the second central aperture 8208*b*. For clarity, interface 8413 may also be referred to as a third interface. At third interface 8413, the second seal 8408*b* may prevent fluid from migrating in the radial direction.

As illustrated in FIG. 84, the housing support 8250, which in this example is a collar 8250, may be located in electronics housing 8104 in the vicinity of apertures 8208*a*, 8208*b*, 8208*c*, 8208*d* and around collar 8250 of mount 8108 to provide support between shell 8106 and mount 8108 when an axial force is applied to engage seals 8408*a*, 8408*b* with electronics housing 8104. The collar 8250 extends between the top and bottom of the electronics housing 8104 (e.g. shell 8106 and mount 8108, respectively) and is positioned about the sensor 8110 to support the top of the electronics housing 8104 against flexing toward the bottom of the electronics housing and to support the bottom of the electronics housing against flexing toward the top of the electronics housing. Thus, collar 8250 is configured to provide a reaction force between top and bottom of the electronics housing 8104 when seals 8408*a*, 8408*b* engage electronics housing 8104. Some embodiments include a housing support 8250 that is formed or bonded as a portion of electronics housing 8104 and may be, as examples, an extension of shell 8106 or an extension of mount 8108.

Upon loading the sensor control device 8102 into the sensor applicator 8312 and securing the cap 8330 to the sensor applicator 8312, the first and second seals 8408*a,b* become compressed and generate corresponding sealed interfaces. The first and second seals 8408*a,b* may be made of a variety of materials capable of generating a sealed interface between opposing structures. Suitable materials include, but are not limited to, silicone, a thermoplastic elastomer (TPE), polytetrafluoroethylene (Teflon®), rubber, an elastomer, or any combination thereof.

The cap 8330 may be secured to the sensor applicator 8312 by threading the cap 8330 to the sensor applicator 8312 via relative rotation. As the cap 8330 rotates relative to the sensor applicator 8312, the post 8350 advances axially until post 8350 or the inner shell 8340 of cap 8330 engages the second seal 8408*b* on the sealable surface 8418 at the bottom of the mount 8108, creating a sealed interface 8413 therebetween. As the electronics housing 8104 of sensor control device 8102 is urged to rotate through frictional engagement between the second seal 8408*b* and post 8350 or the inner shell 8340 of cap 8330, sensor carrier 8364 inhibits rotation of the sensor control device 8102.

Figure 85:
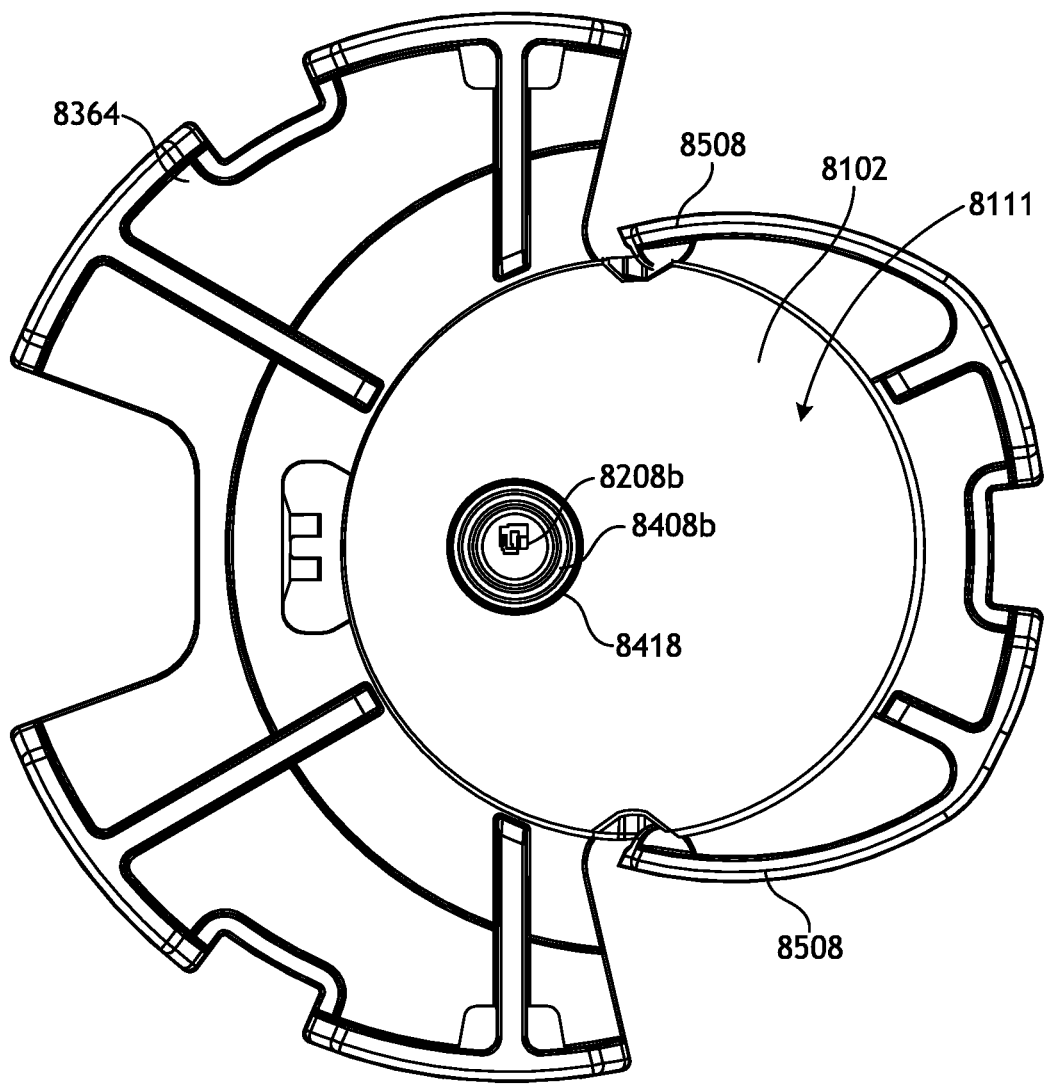
FIG. 85 is a bottom view of a few members of the sensor control device assembly of FIG. 83, the members including the sensor control device held in a sensor carrier of the sensor applicator.

FIG. 85 shows a bottom view of sensor control device 8102 and sensor carrier 8364. Sensor carrier 8364 includes a pair of arms 8506 that extend around sensor control device 8102. Arms 8506 may grasp notches formed in electronic housing 8106. As illustrated, a sealable surface 8418 that extends around second central aperture 8208*b* may be defined on the bottom of the mount 8108. The sealable surface 8418 may comprise a groove. The sealable surface 8418 may receive second seal 8408*b* to isolate (protect) the tail 8216 of the sensor 8110 from environmental contamination or from potentially harmful sterilization gases when gaseous chemical sterilization is used. In the illustrated embodiment, the second seal 8408*b* is overmolded onto the bottom of the mount 8108 within a groove of sealable surface 8418. Thus, second seal 8408*b* forms a part of the electronics housing 8104. In other embodiments, however, the second seal 8408*b* may form part of the post 8350 (FIG. 84). For example, the second seal 8408*b* may be overmolded onto the top of the post 8350. In yet other embodiments, the second seal 8408*b* may comprise a separate structure, such as an O-ring or the like, that interposes the post 8350 and the bottom of the mount 8108, without departing from the scope of the disclosure.

Figure 86:
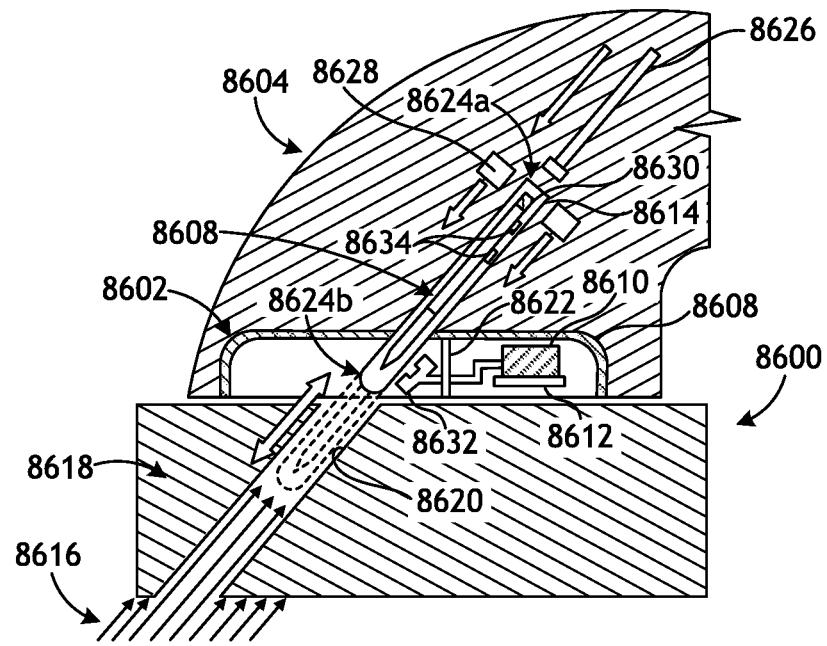
FIG. 86 is a schematic diagram of an example sterilization assembly, according to one or more embodiments of the present disclosure.

FIG. 86 is a schematic diagram of an example sterilization assembly 8600, according to one or more embodiments of the present disclosure. The sterilization assembly 8600 (hereafter the "assembly 8600") may be designed and otherwise configured to help sterilize a medical device 8602 that may be deployed for use from a sensor applicator 8604. The medical device 8602 may comprise, for example, a sensor control device similar in some respects to any of the sensor control devices described herein. In such embodiments, the sensor applicator 8604 may be similar in some respects to any of the sensor applicators described herein. Alternatively, the medical device 8602 may comprise other types of medical devices, health care products, or systems requiring terminal sterilization of specific component parts. Example medical devices or health care products that may incorporate the principles of the present disclosure include, but are not limited to, ingestible products, cardiac rhythm management (CRM) devices, under-skin sensing devices, externally mounted medical devices, or any combination thereof.

As illustrated, the medical device 8602 may include a housing 8606, a part 8608 requiring sterilization, and one or more radiation sensitive components 8610. In the illustrated embodiment, the radiation sensitive component 8610 may be mounted to a printed circuit board (PCB) 8612 positioned within the housing 8606 and may include one or more electronic modules such as, but not limited to, a data processing unit (e.g., an application specific integrated circuit or ASIC), a resistor, a transistor, a capacitor, an inductor, a diode, and a switch.

As illustrated, the part 8608 may extend at an angle relative to the housing 8606, but could alternatively extend perpendicular to the housing 8606. In some embodiments, the part 8608 may comprise a sensor (e.g., the sensor 8110 of FIGS. 81A-81B) and a sharp (e.g., the sharp 8116 of FIGS. 81A-81B) used to help implant the sensor beneath the skin of a user. In some embodiments, as illustrated, the part 8608 may be temporarily encapsulated within a sterile chamber 8614 that provides a sealed barrier to protect exposed portions of the part 8608 (e.g., the sensor and associated sharp) until the part 8608 is needed for use.

The medical device 8602 may be subjected to radiation sterilization 8616 to properly sterilize the part 8608 for use. Suitable radiation sterilization 8616 processes include, but are not limited to, electron beam (e-beam) irradiation, gamma ray irradiation, X-ray irradiation, or any combination thereof. As illustrated, the assembly 8600 may include a radiation shield 8618 positioned external to the medical device 8602 and configured to help sterilize the part 8608 while preventing (impeding) propagating radiation 8616 from disrupting or damaging the radiation sensitive components 8610. To accomplish this, the radiation shield 8618 may provide a collimator 8620 that generally comprises a hole or passageway extending at least partially through the body of the radiation shield 8618. The collimator 8620 provides a sterilization zone designed to direct (focus) the radiation 8616 toward the part 8608.

While the collimator 8610 focuses the radiation 8616 (e.g., beams, waves, energy, etc.) toward the part 8608, the remaining portions of the radiation shield 8618 may be made of a material that reduces or eliminates the radiation 8616 from penetrating therethrough and thereby damaging the radiation sensitive components 8610 within the housing 8606. In other words, the radiation shield 8618 may be made of a material having a density sufficient to absorb the dose of the beam energy being delivered. In some embodiments, for example, the radiation shield 8618 may be made of any material that has a mass density greater than 0.9 grams per cubic centimeter (g/cc). In other embodiments, however, the mass density of a suitable material may be less than 0.9 g/cc, without departing from the scope of the disclosure. Suitable materials for the radiation shield 8618 include, but are not limited to, a high-density polymer, (e.g., polyethylene, polypropylene, polystyrene, polytetrafluoroethylene, etc.), a metal (e.g., lead, stainless steel, aluminum, etc.), any combination thereof, or any material having a mass density greater than 0.9 g/cc.

The collimator 8620 can exhibit any suitable cross-sectional shape necessary to focus the radiation on the part 8608 for sterilization. In the illustrated embodiment, for example, the collimator 8620 has a circular cross-section with parallel sides. In other embodiments, however, the collimator 8620 may have a polygonal cross-sectional shape, such as cubic or rectangular (e.g., including parallelogram), without departing from the scope of the disclosure.

In some embodiments, the assembly 8600 may further include a barrier shield 8622 positioned within the housing 8606. The barrier shield 8622 may be configured to help block radiation 8616 (e.g., electrons) from propagating within the housing 8606 toward the radiation sensitive components 8610. The barrier shield 8622 may be made of any of the materials mentioned above for the radiation shield 8618. In the illustrated embodiment, the barrier shield 8622 is positioned vertically within the housing 8606, but may alternatively be positioned at any other angular configuration suitable for protecting the radiation sensitive components 8610.

In some embodiments, the sterile chamber 8614 may comprise a cap that encapsulates the part 8608 to provide a sealed barrier that protects exposed portions of the part 8608 until the part 8608 is placed in use. In such embodiments, the sterile chamber 8614 may be removable or detachable to expose the part 8608, as described below. Moreover, in such embodiments, the cap may be made of a material that allows radiation to propagate therethrough to allow sterilization of the part 8608. Suitable materials for the sterile chamber 8614 include, but are not limited to, a non-magnetic metal (e.g., aluminum, copper, gold, silver, etc.), a thermoplastic, ceramic, rubber (e.g., ebonite), a composite material (e.g., fiberglass, carbon fiber reinforced polymer, etc.), an epoxy, or any combination thereof. In some embodiments, the sterile chamber 8614 may be transparent or translucent, but can otherwise be opaque, without departing from the scope of the disclosure.

In other embodiments, the sterile chamber 8614 may comprise a chamber or compartment defined within one or both of the sensor applicator 8604 and the sensor control device 8602. In such embodiments, the sterile chamber 8614 may include a microbial barrier positioned at one or both ends of the sterile chamber 8614. More specifically, the sterile chamber 8614 may provide or include an upper microbial barrier 8624a and a lower microbial barrier 8624b opposite the upper microbial barrier 8624a. The upper and lower microbial barriers 8624a,b may help seal the sterile chamber 8614 to thereby isolate the part 8608 from external contamination. The microbial barriers 8624a,b may be made of a radiation permeable material, such as a synthetic material (e.g., a flash-spun high-density polyethylene fiber). One example synthetic material comprises TYVEK®, available from DuPont®. In other embodiments, however, the microbial barriers 8624a,b may comprise, but are not limited to, tape, paper, film, foil, or any combination thereof.

In embodiments where the sterile chamber 8614 comprises a cap, the sterile chamber 8614 may be movable distally to help facilitate the sterilization process. More specifically, the sterile chamber 8614 may be movable at least partially into the sterilization zone formed by the collimator 8620. Once positioned within the sterilization zone, the part 8608 may be subjected to the radiation 8616 to sterilize the part 8608 for use. Once sterilization is done, the sterile chamber 8614 may be retracted proximally in preparation for firing the sensor control device 8602. Distally advancing the sterile chamber 8614 may be accomplished via a variety of mechanical or electromechancial means. In some embodiments, for example, the sensor applicator 8604 may include a plunger 8626 configured to advance distally to push the sterile chamber 8614 distally, and subsequently retract the sterile chamber 8614 once the sterilization process is complete.

The part 8608 itself may also be deployable and otherwise movable relative to the sensor applicator 8604. More particularly, the part 8608 may be advanced distally past the bottom of the electronics housing 8606 to allow the part 8608 to be transcutaneously received beneath a user's skin. In some embodiments, the plunger 8626 may be used to push the part 8608 out of the sterile chamber 8614. In such embodiments, the plunger 8626 may also be configured to attach to a portion of the part 8608 (e.g., the sharp) and subsequently retract that portion of the part 8608 while leaving another portion of the part 8608 (e.g., the sensor) extended. Moreover, in such embodiments, the plunger 8626 may be configured to penetrate the upper microbial barrier 8624a and force the part 8608 distally through the lower microbial barrier 8624b.

In other embodiments, the part 8608 may be advanced distally out of the sterile chamber 8614 using a magnetic coupling. More specifically, the sensor applicator 8604 may include a driver magnet 8628 movable within the sensor applicator 8604 and magnetically coupled to a driven magnet 8630 disposed on the part 8608, such as on an upper end of the sharp. The driver magnet 8628 may be configured to advance distally and simultaneously push the part 8608 out of the sterile chamber 8614 as magnetically coupled to the driven magnet 8630. In such embodiments, actuation of the magnetic coupling may force the part 8608 distally through the lower microbial barrier 8624b. Once the sensor is properly placed, the driver magnet 8628 may be retracted proximally and simultaneously retract the sharp in the same direction while leaving the sensor extended.

In embodiments where the sterile chamber 8614 comprises a cap, the plunger 8626 may also be operable to discharge or push the cap out of the sensor applicator 8604 to enable the part 8608 to be properly received by the user. In such embodiments, a user may commence the firing process by priming the sensor applicator 8604, which may cause the cap to be discharged or ejected from the sensor applicator 8604. Further actuation of the sensor applicator 8604 by the user may cause the part 8608 to be fully extended for subcutaneous implantation. In other embodiments, however, the cap may be removed either autonomously (e.g., it falls off or breaks away) or the user may manually remove it by hand.

In some embodiments, the sensor applicator 8604 may further include an electrical connector 8632 in electrical communication with the electronics of the sensor control device 8602, such as the radiation sensitive component 8610. In at least one embodiment, the electrical connector 8632 may comprise one or more elastic pins made of a conductive polymer (e.g., a carbon impregnated polymer) and configured to facilitate electrical communication between the sensor and the radiation sensitive component 8610. In such embodiments, the sensor may include one or more connectors 8634 alignable with the electrical connector 8632 when the part 8608 is advanced distally, as described above. Moreover, in embodiments where the sterile chamber 8614 comprises a cap, the electrical connector 8632 may be flexible to allow the cap to pass by the electrical connector 8632 until the connectors 8634 align with the electrical connector 8632.

Figure 87:
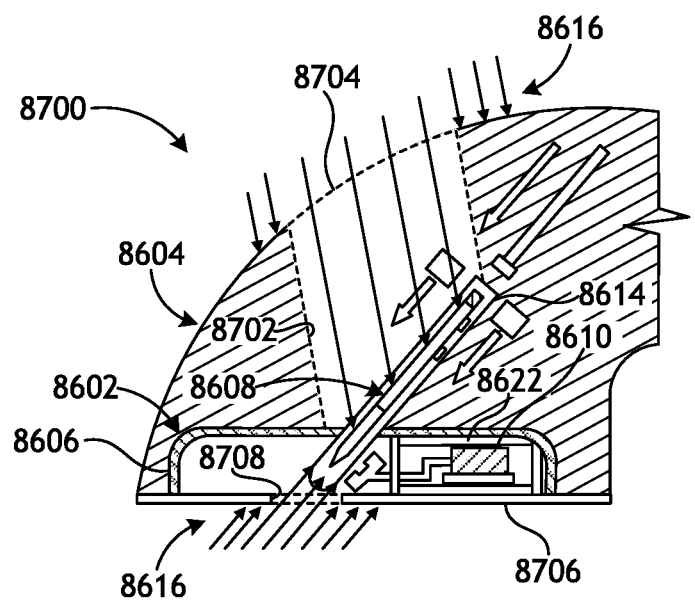
FIG. 87 is a schematic diagram of another example sterilization assembly, according to one or more embodiments of the present disclosure.

FIG. 87 is a schematic diagram of another example sterilization assembly 8700, according to one or more embodiments of the present disclosure. The sterilization assembly 8700 (hereafter the "assembly 8700") may be similar in some respects to the assembly 8600 of FIG. 86 and therefore may be best understood with reference thereto, where like numerals will represent like components not described again in detail. Similar to the assembly 8600, for example, the medical device 8602 may be arranged for deployment within the sensor applicator 8604, and the part 8608 requiring sterilization may be temporarily encapsulated within the sterile chamber 8614. Unlike the assembly 8600, however, the part 8608 may be subjected to the radiation sterilization 8616 through the body of the sensor applicator 8604.

More specifically, the radiation sterilization 8616 may be directed to the top of the sensor applicator 8604, which defines a collimator 8702 that allows the radiation 8616 to impinge upon and sterilize the part 8608. As illustrated, the collimator 8702 generally comprises a hole or passageway extending through the body of the sensor applicator 8604. The collimator 8702 focuses (guides) the radiation 8616 toward the part 8608 and can exhibit any suitable cross-sectional shape necessary to focus the radiation 8616 on the part 8608 for sterilization. In the illustrated embodiment, for example, the collimator 8702 has a circular cross-section with parallel sides, but may alternatively exhibit a polygonal cross-sectional shape, such as cubic or rectangular (e.g., including parallelogram), without departing from the scope of the disclosure.

The sensor applicator 8604 may also act as a radiation shield that helps prevent (impede) propagating radiation 8616 from disrupting or damaging the radiation sensitive components 8610, except through the collimator 8702. To accomplish this, the sensor applicator 8604 may be made of a material similar to the material of the radiation shield 8618 of FIG. 86. In at least one embodiment, however, the radiation sterilization 8616 may be emitted from a device or machine configured to focus and/or aim the radiation 8616 directly into the collimator 8702, and thereby mitigating radiation 8616 exposure to adjacent portions of the sensor applicator 8604.

In some embodiments, a seal 8704 may be arranged at the opening to the collimator 8702 at the top of the sensor applicator 8604. The seal 8704 may comprise a radiation permeable, microbial barrier, similar to the microbial barriers 8624a,b of FIG. 86. The seal 8704 may seal off the collimator 8702, while simultaneously allowing the radiation 8616 to pass therethrough to sterilize the part 8608.

In at least one embodiment, the position of the radiation sensitive components 8610 may be moved away from the line of fire of the radiation 8616. In other embodiments, the barrier shield 8622 may extend about at least two sides of the radiation sensitive components 8610 to ensure sufficient blockage of the radiation 8616. In at least one embodiment, however, the barrier shield 8622 may fully encapsulate the radiation sensitive components 8610.

In one embodiment, the radiation sterilization 8616 may be directed toward the part 8608 from the bottom of the sensor control device 8602 and the bottom of the sensor applicator 8604. In such embodiments, a shield 8706 may be positioned at the bottom of one or both of the sensor control device 8602 and the bottom of the sensor applicator 8604. The shield 8706 may be made of any of the materials mentioned above for the radiation shield 8618 of FIG. 86. Consequently, the shield 8706 may be configured to help block the radiation 8616 (e.g., electrons) from propagating toward the radiation sensitive components 8610. The shield 8706, however, may define or otherwise provide an aperture 8708 aligned with the part 8608 to allow the radiation 8616 to impinge upon the part 8608 for proper sterilization.

In at least one embodiment, the shield 8706 may form part of the sensor control device 8602 and may be deployed simultaneously with the sensor control device 8602 from the sensor applicator 8604. In some embodiments, the shield 8706 may be removable from the sensor control device 8602 and otherwise only used during the sterilization process. In other embodiments, the shield 8706 may be arranged within the housing 8606 and otherwise form an integral part thereof, without departing from the scope of the disclosure.

Figure 88A:
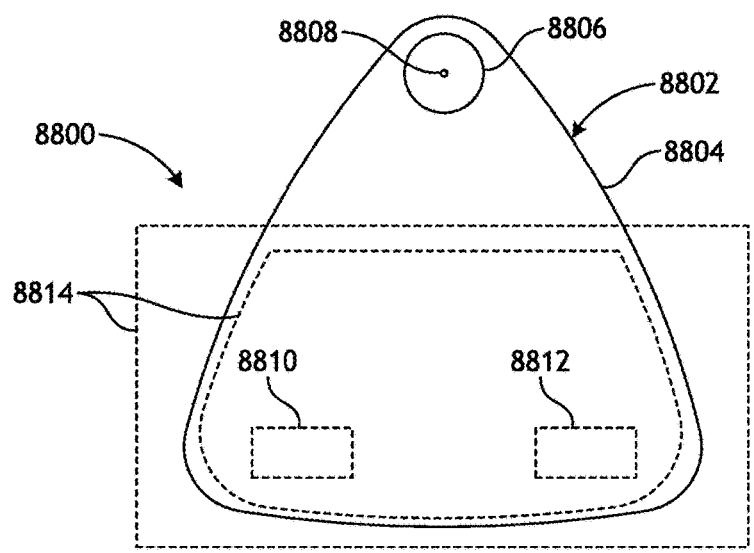
FIG. 88A is a schematic bottom view of another example sterilization assembly, according to one or more embodiments of the present disclosure.

FIG. 88A is a schematic bottom view of another example sterilization assembly 8800, according to one or more embodiments of the present disclosure. The sterilization assembly 8800 (hereafter the "assembly 8800") may be used to sterilize a medical device 8802, which may comprise a sensor control device or any of the other types of medical devices mentioned herein. In the illustrated embodiment, the medical device 8802 comprises a sensor control device having a housing 8804 that defines an aperture 8806 through which a part 8808 requiring sterilization may extend. In the view of FIG. 88A, the part 8808 extends through the aperture 8806 and out of the page. Moreover, the part 8808 may comprise one or both of a sensor and a sharp, as generally described herein. The medical device 8802 may also include a battery 8810 and a radiation sensitive component 8812 arranged within the housing 8804. The battery 8810 may power the medical device 8802 and the radiation sensitive component 8812 may be similar to the radiation sensitive component 8610 of FIGS. 86 and 87.

As illustrated, the housing 8804 may exhibit a generally polygonal cross-sectional shape. More specifically, the housing 8804 is generally triangular with rounded corners. The position of the radiation sensitive component 8812 relative to the part 8808 is effectively as far away as possible within the confines of the housing 8804. As will be appreciated, this may help reduce the chances of the radiation sensitive component 8812 being damaged during a radiation sterilization process to sterilize the part 8808.

The assembly 8800 may also include a shield 8814 (shown in dashed lines), which may be made of the materials mentioned above for the radiation shield 8618 of FIG. 86. Consequently, the shield 8814 may be configured to help protect the radiation sensitive component 8812 from damaging radiation during a sterilization process. In one embodiment, the shield 8814 may be arranged external to the housing 8804 and otherwise arranged to interpose the radiation sensitive component 8812 and the propagating electrons from the radiation treatment. In other embodiments, however, the shield 8814 may be arranged within the housing 8804 and otherwise form part of the medical device 8802, without departing from the scope of the disclosure.

Figure 88B:
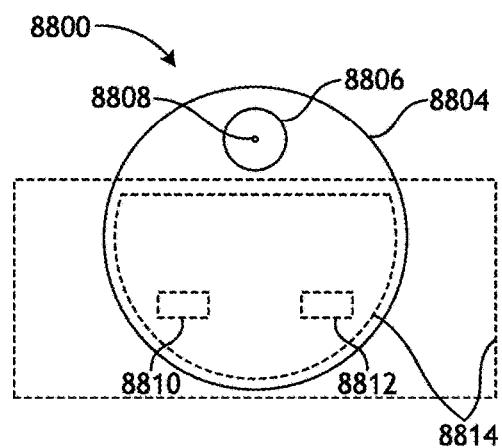
FIGS. 88B and 88C are schematic bottom views of alternative embodiments of the sterilization assembly of FIG. 88A, according to one or more additional embodiments of the present disclosure.
Figure 88C:
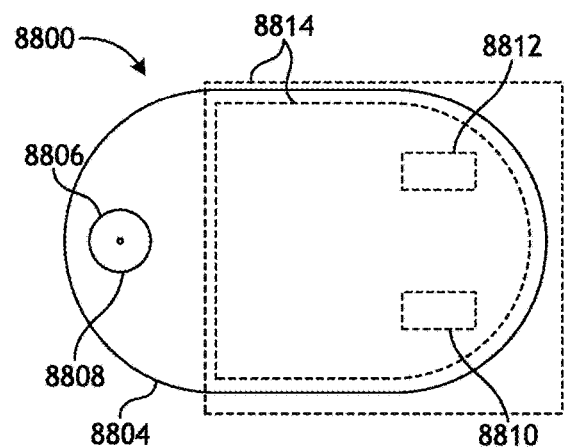

FIGS. 88B and 88C are schematic bottom views of alternative embodiments of the sterilization assembly 8800 of FIG. 88A, according to one or more additional embodiments of the present disclosure. In FIG. 88B, the housing 8804 exhibits a generally circular shape, and in FIG. 88C, the housing 8804 exhibits a generally oval or ovoid shape. As will be appreciated, the housing 8804 may alternatively exhibit other cross-sectional shapes, including additional polygonal shapes (e.g., square, rectangular, pentagonal, etc.), without departing from the scope of the disclosure.

In FIGS. 88B and 88C, the part 8808 extends through the aperture 8806 and out of the page. Moreover, the battery 8810 and the radiation sensitive component 8812 may be arranged within the housing 8804 and the radiation sensitive component 8812 may be positioned relative to the part 8808 as far away as possible within the confines of the housing 8804. Again, this may help reduce the chances of the radiation sensitive component 8812 being damaged during a radiation sterilization process to sterilize the part 8808. The shield 8814 (shown in dashed lines) may again be included and configured to help protect the radiation sensitive component 8812 from damaging radiation during a sterilization process. As illustrated, the shield 8814 may be arranged external to the housing 8804, or alternatively within the housing 8804 and otherwise form part of the medical device 8802, without departing from the scope of the disclosure.

Figure 89:
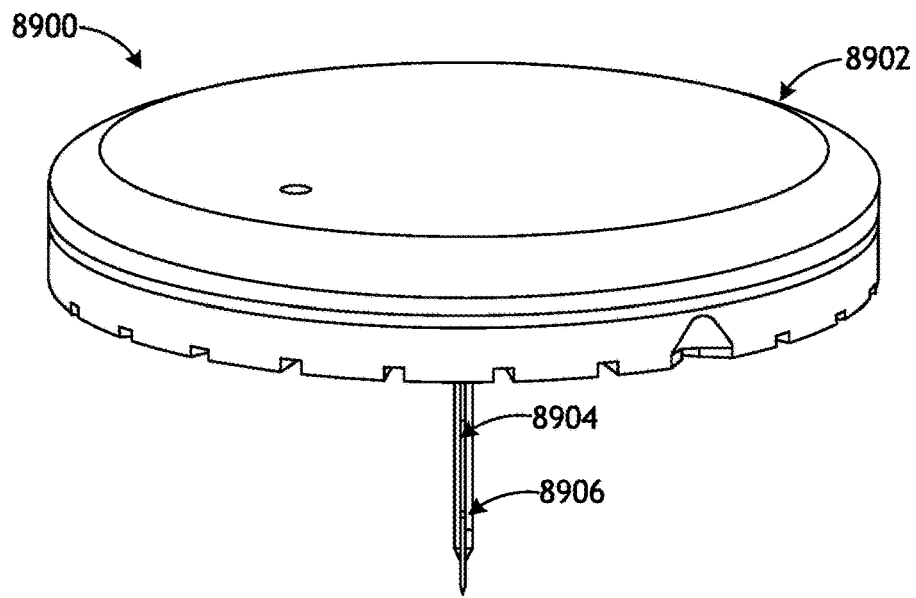
FIG. 89 is an isometric schematic view of an example sensor control device, according to one or more embodiments.

FIG. 89 is an isometric schematic view of an example sensor control device 8900, according to one or more embodiments. The sensor control device 8900 may be similar in some respects to the sensor control devices described herein and, therefore, may be used as an on-body monitoring device used to monitor blood glucose levels. As illustrated, the sensor control device 8900 includes a housing 8902 that may contain and otherwise housing electronics used to operate the sensor control device 8900. In the illustrated embodiment, the housing 8902 is generally disc-shaped and with a circular cross-section, but could alternatively exhibit other cross-sectional shapes, such as ovoid or polygonal and may be non-symmetrical. While not shown, an adhesive patch may be attached to the bottom of the housing 8902 to help attach the sensor control device 8900 to the skin of a user at a target monitoring location.

The sensor control device 8900 may further include a sensor 8904 and a sharp 8906 extending distally from the bottom of the housing 8902. The sensor 8904 and the sharp 8906 may be similar in some respects to the sensor 8110 and the sharp 8116 of FIGS. 81A-81B. Accordingly, in some embodiments, the sharp 8906 may be used to help deliver the sensor 8904 transcutaneously under a user's skin during application of the sensor control device 8900. The exposed portion of the sensor 8904 may be received within a hollow or recessed portion of the sharp 8906, and the remaining portion(s) of the sensor 8904 is/are positioned within the interior of the electronics housing 8902.

In some embodiments, the sharp 8906 may be made of a dermal-dissolving material. In such embodiments, the sharp 8906 may be used to help introduce the sensor 8904 into the user's skin, but may dissolve after a predetermined time period upon exposure to chemicals and/or substances commonly found in the human body. Consequently, in such embodiments, there is no need to retract the sharp 8906. Rather, the sharp 8906 may remain embedded within the user's dermal layer until it safely dissolves. A dermal-dissolving sharp 8906 may also make sterilization applications much easier, since low-energy surface sterilization may only be needed.

In other embodiments, the sharp 8906 may be omitted from the sensor control device 8900. In such embodiments, the sensor 8904 may be made of materials that are rigid enough to allow the sensor 8904 to be transcutaneously received beneath a user's skin for monitoring without the assistance of the sharp 8906. Accordingly, the sensor 8906 may operate as both a sensor and a sharp or introducer. Such embodiments may prove advantageous in eliminating the mechanisms and assemblies typically required to retract the sharp 8906.

As will be appreciated, any of the embodiments mentioned herein may incorporate a dermal dissolving sharp or introducer, or may alternatively include a sharp that operates as both a sensor and a sharp, without departing from the scope of the disclosure.

Figure 90:
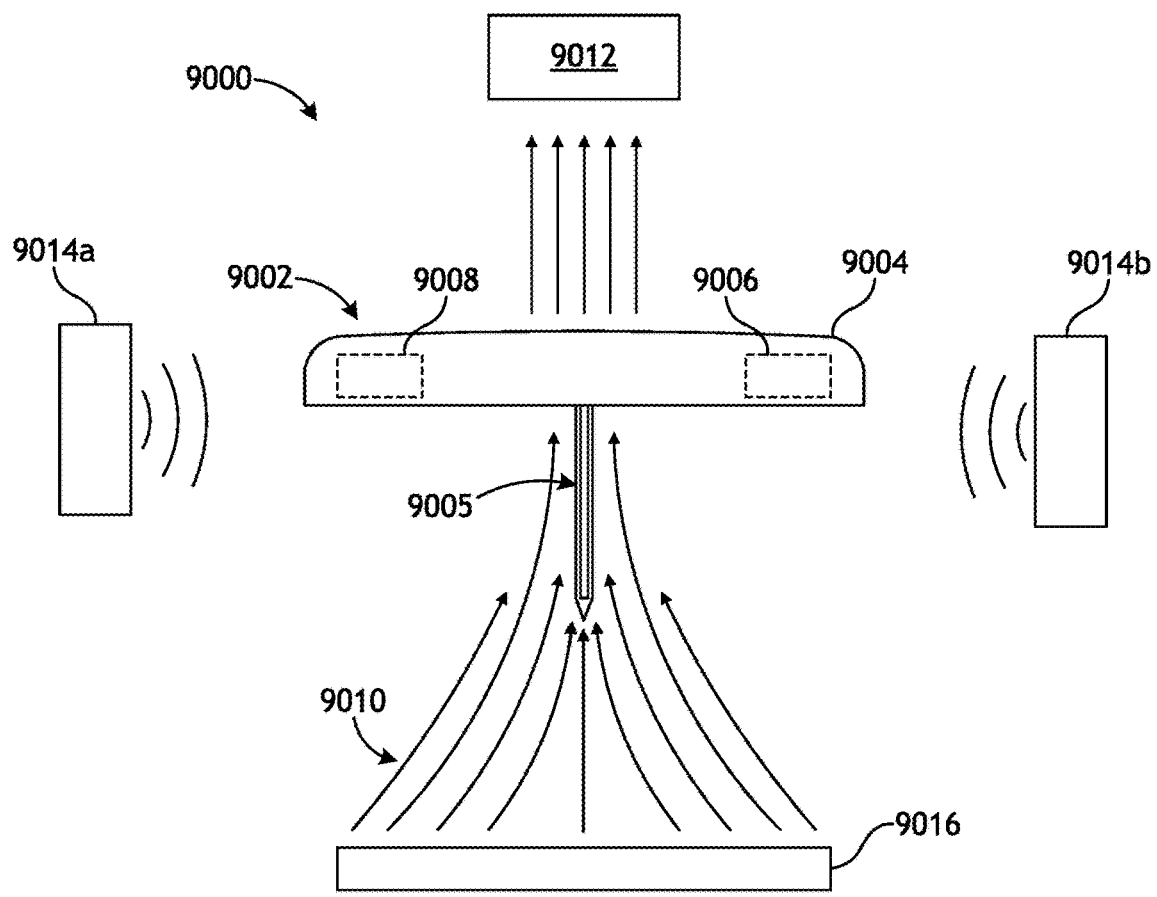
FIG. 90 is a schematic diagram of another example sterilization assembly, according to one or more embodiments.

FIG. 90 is a schematic diagram of another example sterilization assembly 9000, according to one or more embodiments. Similar to the other sterilization assemblies described herein, the sterilization assembly 9000 (hereafter the "assembly 9000") may be used to help sterilize a medical device, such as a sensor control device 9002. The sensor control device 9002 may be similar in some respects to some or all of the sensor control devices described herein. For example, the sensor control device 9002 includes a housing 9004 that may contain and otherwise house the electronics used to operate the sensor control device 9002. The sensor control device 9002 may further include a part 9005 requiring sterilization, one or more radiation sensitive components 9006, and a battery 9008 that powers the sensor control device 9002. The radiation sensitive component 9006 may be arranged within the housing 9004 and may include one or more electronic modules such as, but not limited to, a data processing unit (e.g., an application specific integrated circuit or ASIC), a resistor, a transistor, a capacitor, an inductor, a diode, and a switch.

As illustrated, the part 9005 may extend perpendicularly from the bottom of the housing 9004, but could alternatively extend at an angle relative to the housing 9004. Moreover, while the part 9005 extends generally concentric with a centerline of the housing 9004, the part 9005 could alternatively extend from the housing 9004 at a location eccentric to the centerline, without departing from the scope of the disclosure. In some embodiments, the part 9005 may comprise a sensor (e.g., the sensor 8110 of FIGS. 81A-81B) and a sharp (e.g., the sharp 8116 of FIGS. 81A-81B) used to help implant the sensor beneath the skin of a user.

The medical device 8602 may be subjected to radiation sterilization 9010 to properly sterilize the part 9005 for use. Suitable radiation sterilization 9010 processes include, but are not limited to, electron beam (e-beam) irradiation, gamma ray irradiation, X-ray irradiation, or any combination thereof. To help guide and otherwise focus the radiation 9010 toward the part 9005 and simultaneously away from the radiation sensitive component 9006, the assembly 9000 may include or otherwise employ one or more magnets configured to direct the electrons of the radiation 9010 in a predetermined sterilization path.

More particularly, as illustrated, the assembly 9000 may include a central magnet 9012 and opposing lateral magnets 9014*a* and 9014*b*. The central magnet 9012 may be arranged opposite a radiation source 9016 such that the part 9005 to be sterilized interposes the central magnet 9012 and the radiation source 9016. The central magnet 9012 may be tuned and otherwise configured to draw the electrons of the radiation 9010 toward the central magnet 9012, which generally urges the radiation 9010 toward the center of the sensor control device 9002 and otherwise to where the part 9005 is located. In addition, the lateral magnets 9014*a,b* may be arranged on opposite sides of the sensor control device 9002 and tuned or otherwise configured to generate a magnetic field that pushes the electrons of the radiation 9010 toward the center of the sensor control device 9002 or otherwise to where the part 9005 is located. Accordingly, the central and lateral magnets 9012, 9014*a,b* may cooperatively urge the radiation 9010 away from the radiation sensitive components 9006 and instead toward the part 9005 to sterilize the part 9005.

Embodiments disclosed herein include:

Z. A sensor control device assembly that includes a sensor applicator, a sensor control device positioned within the sensor applicator and including an electronics housing, a sensor extending from a bottom of the electronics housing, a sharp hub positioned adjacent a top of the electronics housing, and a sharp carried by the sharp hub and extending through the electronics housing and from the bottom of the electronics housing, a cap removably coupled to the sensor applicator and providing a support structure that defines a post chamber that receives the sensor and the sharp extending from the bottom of the electronics housing, a first seal that provides a radial seal against the sharp hub and an axial seal against the top of the electronics housing, and a second seal that seals an interface between the post and the bottom of the electronics housing.

AA. A method including positioning a sensor control device within a sensor applicator, the sensor control device including an electronics housing, a sensor extending from a bottom of the electronics housing, a sharp hub positioned adjacent a top of the electronics housing, and a sharp carried by the sharp hub and extending through the electronics housing and from the bottom of the electronics housing, removably coupling a cap to the sensor applicator, the cap providing a support structure that defines a post chamber that receives the sensor and the sharp extending from the bottom of the electronics housing, providing a radial seal against the sharp hub with a first seal, providing an axial seal against the top of the electronics housing with the first seal, and sealing an interface between the post and the bottom of the electronics housing with a second seal.

BB. A sensor control device assembly includes a sensor applicator, a sensor control device positioned within the sensor applicator and including an electronics housing having a top and a bottom, a sensor coupled to the electronics housing, and a sharp module engageable with the electronics housing and having a sharp. The sensor control device assembly further includes a post having a first end positioned proximal the bottom of the electronics housing, a second end opposite the first end, and a post chamber extending between the first and second ends, wherein distal portions of the sensor and the sharp are receivable within the post chamber, a first seal interposing the sensor applicator and the electronics housing to seal an interface therebetween and interposing the sensor applicator and the sharp module to seal an interface therebetween, and a second seal interposing the first end of the post and the bottom of the electronics housing.

Each of embodiments Z, AA, and BB may have one or more of the following additional elements in any combination: Element 1: further comprising a sensor carrier arranged within the sensor applicator to secure the sensor control device, wherein the first seal is overmolded onto the sensor carrier. Element 2: wherein the cap comprises a first end threaded to the sensor applicator, and a second end opposite the first end, and wherein the support structure extends from the second end into the sensor applicator and toward the sensor control device. Element 3: wherein the first seal circumscribes a top aperture defined in the electronics housing and prevents contaminants from migrating into an interior of the electronics housing via the top aperture. Element 4: wherein the second seal circumscribes a bottom aperture defined on the bottom of the electronics housing and prevents contaminants from migrating into an interior of the electronics housing via the bottom aperture and into the post chamber. Element 5: wherein the sensor control device includes a housing support positioned within the electronics housing and extending between the top and bottom of the electronics housing and positioned about the sensor to support the top of the electronics housing against flexing toward the bottom of the electronics housing and to support the bottom of the electronics housing against flexing toward the top of the electronics housing. Element 7: wherein the sensor and the sharp are positioned eccentric from a central axis of the electronics housing. Element 8: wherein the first seal is overmolded onto the top of the electronics housing.

Element 9: further creating a sealed region as the cap is coupled to the sensor applicator, the sealed region encompassing the post chamber and a portion of an interior of the electronics housing, wherein portions of the sensor and the sharp reside within the sealed region. Element 10: further comprising sterilizing the sensor and the sharp with radiation sterilization while positioned within the sensor applicator. Element 11: wherein the radiation sterilization is at least one of focused radiation sterilization and low-energy radiation sterilization. Element 12: wherein the first seal is over overmolded onto a sensor carrier arranged within the sensor applicator to secure the sensor control device. Element 13: wherein removably coupling the cap to the sensor applicator comprises advancing the support structure into the sensor applicator and thereby causing the second seal to seal the interface between the post and the bottom of the electronics housing. Element 14: wherein the sensor control device includes a housing support positioned within the electronics housing and extending between the top and bottom of the electronics housing, the method further comprising supporting the top of the electronics housing against flexing toward the bottom of the electronics housing with the housing support, and supporting the bottom of the electronics housing against flexing toward the top of the electronics housing with the housing support. Element 15: further comprising preventing contaminants from migrating into an interior of the electronics housing via a top aperture defined in the electronics housing with the first seal. Element 16: further comprising preventing contaminants from migrating into the post chamber and an interior of the electronics housing via a bottom aperture defined on the bottom of the electronics housing with the second seal.

Element 17: further comprising a sensor carrier positioned within the sensor applicator to secure the sensor control device, wherein the first seal seals a first interface between the sensor carrier and the electronics housing and a second interface between the sensor carrier and the sharp module. Element 18: further comprising a cap removably coupled to the sensor applicator and providing a support structure that extends from the bottom of the sensor applicator toward the sensor control device, wherein the post extends from the support structure.

By way of non-limiting example, exemplary combinations applicable to Z, AA, and BB include: Element 10 with Element 11; and Element 13 with Element 14.

Seal Arrangement for Analyte Monitoring Systems

Figure 91A:
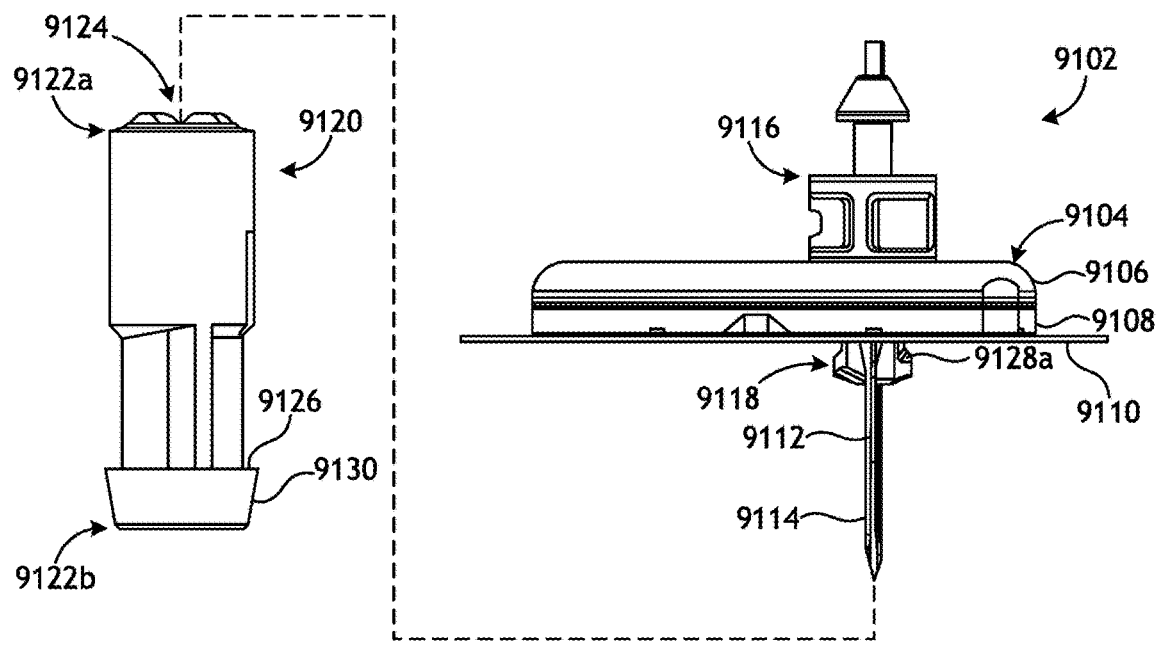
FIGS. 91A and 91B are side and isometric views, respectively, of an example sensor control device, according to one or more embodiments of the present disclosure.
Figure 91B:
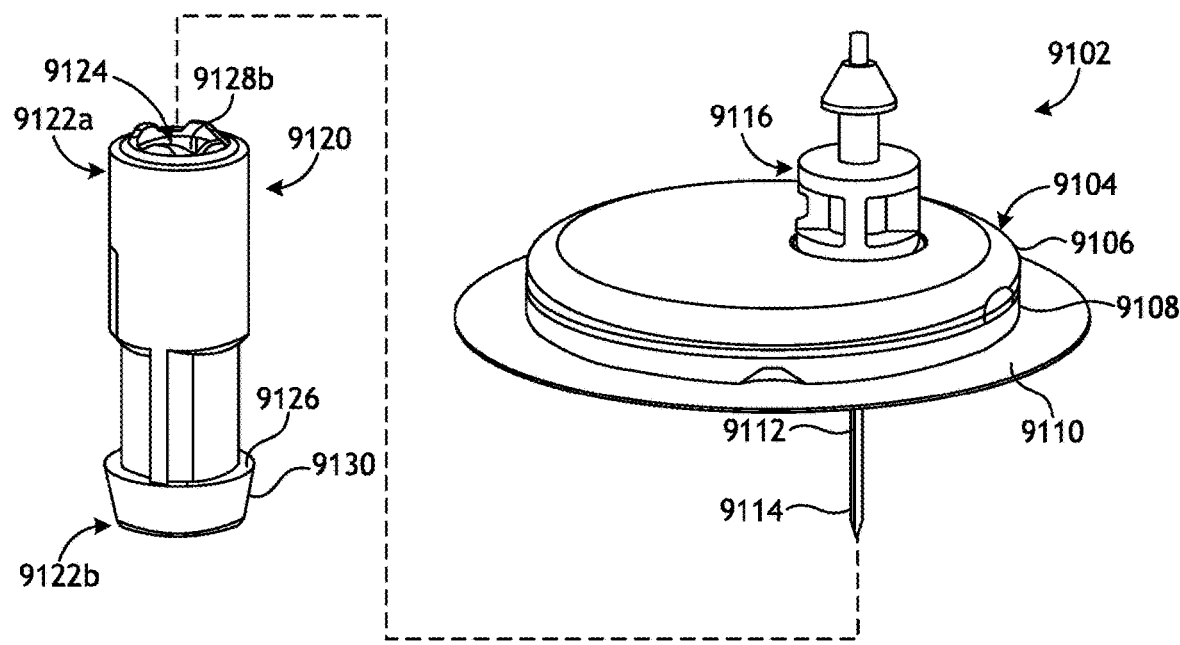

FIGS. 91A and 91B are side and isometric views, respectively, of an example sensor control device 9102, according to one or more embodiments of the present disclosure. The sensor control device 9102 may be similar in some respects to the sensor control device 104 of FIG. 1 and therefore may be best understood with reference thereto. Moreover, the sensor control device 9102 may replace the sensor control device 104 of FIG. 1 and, therefore, may be used in conjunction with the sensor applicator 102 of FIG. 1, which may deliver the sensor control device 9102 to a target monitoring location on a user's skin.

As illustrated, the sensor control device 9102 includes an electronics housing 9104, which may be generally disc-shaped and have a circular cross-section. In other embodiments, however, the electronics housing 9104 may exhibit other cross-sectional shapes, such as ovoid, oval, or polygonal, without departing from the scope of the disclosure. The electronics housing 9104 includes a shell 9106 and a mount 9108 that is matable with the shell 9106. The shell 9106 may be secured to the mount 9108 via a variety of ways, such as a snap fit engagement, an interference fit, sonic welding, laser welding, one or more mechanical fasteners (e.g., screws), a gasket, an adhesive, or any combination thereof. In some cases, the shell 9106 may be secured to the mount 9108 such that a sealed interface is generated therebetween. An adhesive patch 9110 may be positioned on and otherwise attached to the underside of the mount 9108. Similar to the adhesive patch 108 of FIG. 1, the adhesive patch 9110 may be configured to secure and maintain the sensor control device 9102 in position on the user's skin during operation.

The sensor control device 9102 may further include a sensor 9112 and a sharp 9114 used to help deliver the sensor 9112 transcutaneously under a user's skin during application of the sensor control device 9102. Corresponding portions of the sensor 9112 and the sharp 9114 extend distally from the bottom of the electronics housing 9104 (e.g., the mount 9108). A sharp hub 9116 may be overmolded onto the sharp 9114 and configured to secure and carry the sharp 9114. As best seen in FIG. 91A, the sharp hub 9116 may include or otherwise define a mating member 9118. In assembling the sharp 9114 to the sensor control device 9102, the sharp 9114 may be advanced axially through the electronics housing 9104 until the sharp hub 9116 engages an upper surface of the electronics housing 9104 or an internal component thereof and the mating member 9118 extends distally from the bottom of the mount 9108. As described herein below, in at least one embodiment, the sharp hub 9116 may sealingly engage an upper portion of a seal overmolded onto the mount 9108. As the sharp 9114 penetrates the electronics housing 9104, the exposed portion of the sensor 9112 may be received within a hollow or recessed (arcuate) portion of the sharp 9114. The remaining portion of the sensor 9112 is arranged within the interior of the electronics housing 9104.

The sensor control device 9102 may further include a sensor cap 9120, shown detached from the electronics housing 9104 in FIGS. 91A-91B. The sensor cap 9120 may help provide a sealed barrier that surrounds and protects exposed portions of the sensor 9112 and the sharp 9114. As illustrated, the sensor cap 9120 may comprise a generally cylindrical body having a first end 9122a and a second end 9122b opposite the first end 9122a. The first end 9122a may be open to provide access into an inner chamber 9124 defined within the body. In contrast, the second end 9122b may be closed and may provide or otherwise define an engagement feature 9126. As described in more detail below, the engagement feature 9126 may help mate the sensor cap 9120 to an applicator cap of a sensor applicator (e.g., the sensor applicator 102 of FIG. 1), and may help remove the sensor cap 9120 from the sensor control device 9102 upon removing the sensor cap from the sensor applicator.

The sensor cap 9120 may be removably coupled to the electronics housing 9104 at or near the bottom of the mount 9108. More specifically, the sensor cap 9120 may be removably coupled to the mating member 9118, which extends distally from the bottom of the mount 9108. In at least one embodiment, for example, the mating member 9118 may define a set of external threads 9128a (FIG. 91A) matable with a set of internal threads 9128b (FIG. 91B) defined within the inner chamber 9124 of the sensor cap 9120. In some embodiments, the external and internal threads 9128a,b may comprise a flat thread design (e.g., lack of helical curvature), but may alternatively comprise a helical threaded engagement. Accordingly, in at least one embodiment, the sensor cap 9120 may be threadably coupled to the sensor control device 9102 at the mating member 9118 of the sharp hub 9116. In other embodiments, the sensor cap 9120 may be removably coupled to the mating member 9118 via other types of engagements including, but not limited to, an interference or friction fit, or a frangible member or substance (e.g., wax, an adhesive, etc.) that may be broken with minimal separation force (e.g., axial or rotational force).

In some embodiments, the sensor cap 9120 may comprise a monolithic (singular) structure extending between the first and second ends 9122a,b. In other embodiments, however, the sensor cap 9120 may comprise two or more component parts. In the illustrated embodiment, for example, the body of the sensor cap 9120 may include a desiccant cap 9130 arranged at the second end 9122b. The desiccant cap 9130 may house or comprise a desiccant to help maintain preferred humidity levels within the inner chamber 9124. Moreover, the desiccant cap 9130 may also define or otherwise provide the engagement feature 9126 of the sensor cap 9120. In at least one embodiment, the desiccant cap 9130 may comprise an elastomeric plug inserted into the bottom end of the sensor cap 9120.

Figure 92A:
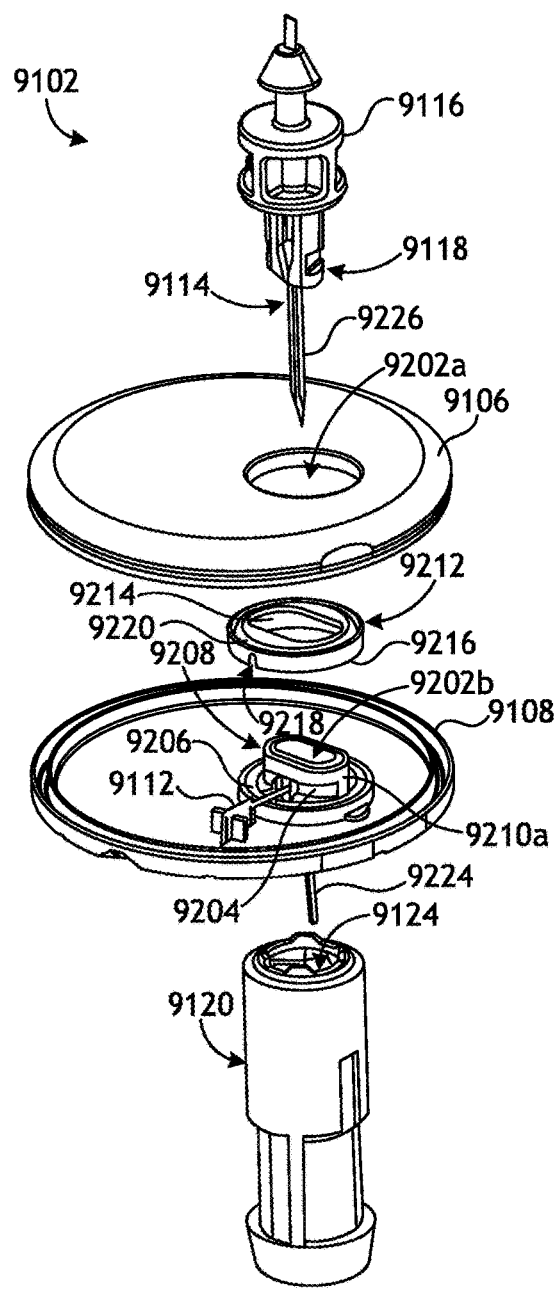
FIGS. 92A and 92B are exploded, isometric top and bottom views, respectively, of the sensor control device of FIG. 2, according to one or more embodiments.
Figure 92B:
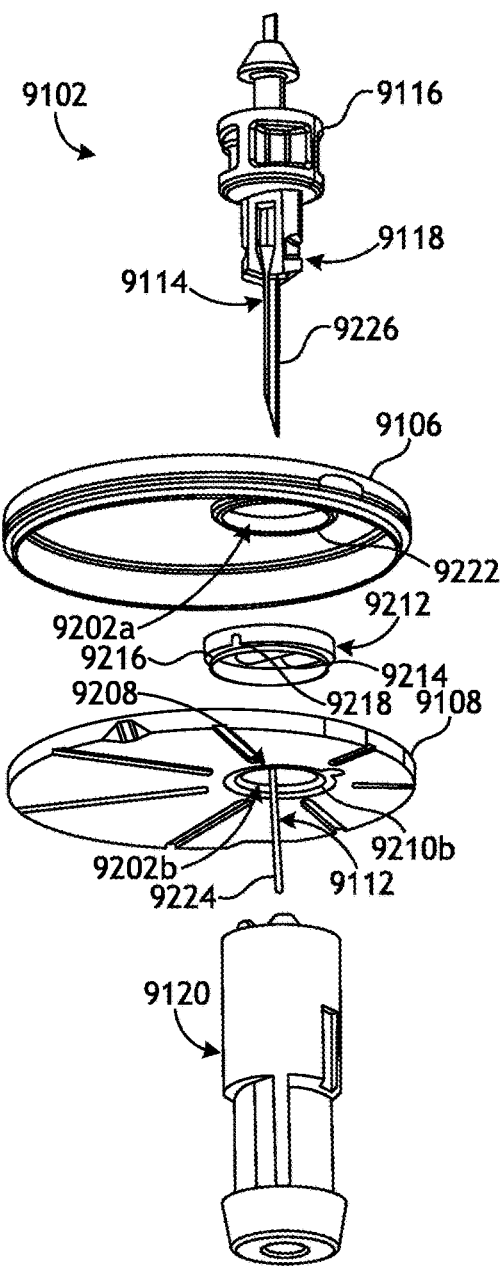

FIGS. 92A and 92B are exploded, isometric top and bottom views, respectively, of the sensor control device 9102, according to one or more embodiments. The shell 9106 and the mount 9108 operate as opposing clamshell halves that enclose or otherwise substantially encapsulate various electronic components (not shown) of the sensor control device 9102. Example electronic components that may be arranged between the shell 9106 and the mount 9108 include, but are not limited to, a battery, resistors, transistors, capacitors, inductors, diodes, and switches.

The shell 9106 may define a first aperture 9202a and the mount 9108 may define a second aperture 9202b, and the apertures 9202a,b may align when the shell 9106 is properly mounted to the mount 9108. As best seen in FIG. 92A, the mount 9108 may provide or otherwise define a pedestal 9204 that protrudes from the inner surface of the mount 9108 at the second aperture 9202b. The pedestal 9204 may define at least a portion of the second aperture 9202b. Moreover, a channel 9206 may be defined on the inner surface of the mount 9108 and may circumscribe the pedestal 9202. In the illustrated embodiment, the channel 9206 is circular in shape, but could alternatively be another shape, such as oval, ovoid, or polygonal.

The mount 9108 may comprise a molded part made of a rigid material, such as plastic or metal. In some embodiments, a seal 9208 may be overmolded onto the mount 9108 and may be made of an elastomer, rubber, a-polymer, or another pliable material suitable for facilitating a sealed interface. In embodiments where the mount 9108 is made of a plastic, the mount 9108 may be molded in a first "shot" of injection molding, and the seal 9208 may be overmolded onto the mount 9108 in a second "shot" of injection molding. Accordingly, the mount 9108 may be referred to or otherwise characterized as a "two-shot mount."

In the illustrated embodiment, the seal 9208 may be overmolded onto the mount 9108 at the pedestal 9204 and also on the bottom of the mount 9108. More specifically, the seal 9208 may define or otherwise provide a first seal element 9210*a* overmolded onto the pedestal 9204, and a second seal element 9210*b* (FIG. 92B) interconnected to (with) the first seal element 9210*a* and overmolded onto the mount 9108 at the bottom of the mount 9108. In some embodiments, one or both of the seal elements 9210*a,b* may help form corresponding portions (sections) of the second aperture 9202*b*. While the seal 9208 is described herein as being overmolded onto the mount 9108, it is also contemplated herein that one or both of the seal elements 9210*a,b* may comprise an elastomeric component part independent of the mount 9208, such as an O-ring or a gasket.

The sensor control device 9102 may further include a collar 9212, which may be a generally annular structure that defines a central aperture 9214. The central aperture 9214 may be sized to receive the first seal element 9210*a* and may align with both the first and second apertures 9202*a,b* when the sensor control device 9102 is properly assembled. The shape of the central aperture 9214 may generally match the shape of the second aperture 9202*b* and the first seal element 9210*a*.

In some embodiments, the collar 9212 may define or otherwise provide an annular lip 9216 on its bottom surface. The annular lip 9216 may be sized and otherwise configured to mate with or be received into the channel 9206 defined on the inner surface of the mount 9108. In some embodiments, a groove 9218 may be defined on the annular lip 9216 and may be configured to accommodate or otherwise receive a portion of the sensor 9112 extending laterally within the mount 9108. In some embodiments, the collar 9212 may further define or otherwise provide a collar channel 9220 (FIG. 92A) on its upper surface sized to receive and otherwise mate with an annular ridge 9222 (FIG. 92B) defined on the inner surface of the shell 9106 when the sensor control device 9102 is properly assembled.

The sensor 9112 may include a tail 9224 that extends through the second aperture 9202*b* defined in the mount 9108 to be transcutaneously received beneath a user's skin. The tail 9224 may have an enzyme or other chemistry included thereon to help facilitate analyte monitoring. The sharp 9114 may include a sharp tip 9226 extendable through the first aperture 9202*a* defined by the shell 9106. As the sharp tip 9226 penetrates the electronics housing 9104, the tail 9224 of the sensor 9112 may be received within a hollow or recessed portion of the sharp tip 9226. The sharp tip 9226 may be configured to penetrate the skin while carrying the tail 9224 to put the active chemistry of the tail 9224 into contact with bodily fluids.

The sensor control device 9102 may provide a sealed subassembly that includes, among other component parts, portions of the shell 9106, the sensor 9112, the sharp 9114, the seal 9208, the collar 9212, and the sensor cap 9120. The sealed subassembly may help isolate the sensor 9112 and the sharp 9114 within the inner chamber 9124 (FIG. 92A) of the sensor cap 9120. In assembling the sealed subassembly, the sharp tip 9226 is advanced through the electronics housing 9104 until the sharp hub 9116 engages the seal 9208 and, more particularly, the first seal element 9210*a*. The mating member 9118 provided at the bottom of the sharp hub 9116 may extend out the second aperture 9202*b* in the bottom of the mount 9108, and the sensor cap 9120 may be coupled to the sharp hub 9116 at the mating member 9118. Coupling the sensor cap 9120 to the sharp hub 9116 at the mating member 9118 may urge the first end 9122*a* of the sensor cap 9120 into sealed engagement with the seal 9208 and, more particularly, into sealed engagement with the second seal element 9210*b* on the bottom of the mount 9108. In some embodiments, as the sensor cap 9120 is coupled to the sharp hub 9116, a portion of the first end 9122*a* of the sensor cap 9120 may bottom out (engage) against the bottom of the mount 9108, and the sealed engagement between the sensor hub 9116 and the first seal element 9210*a* may be able to assume any tolerance variation between features.

Figure 93:
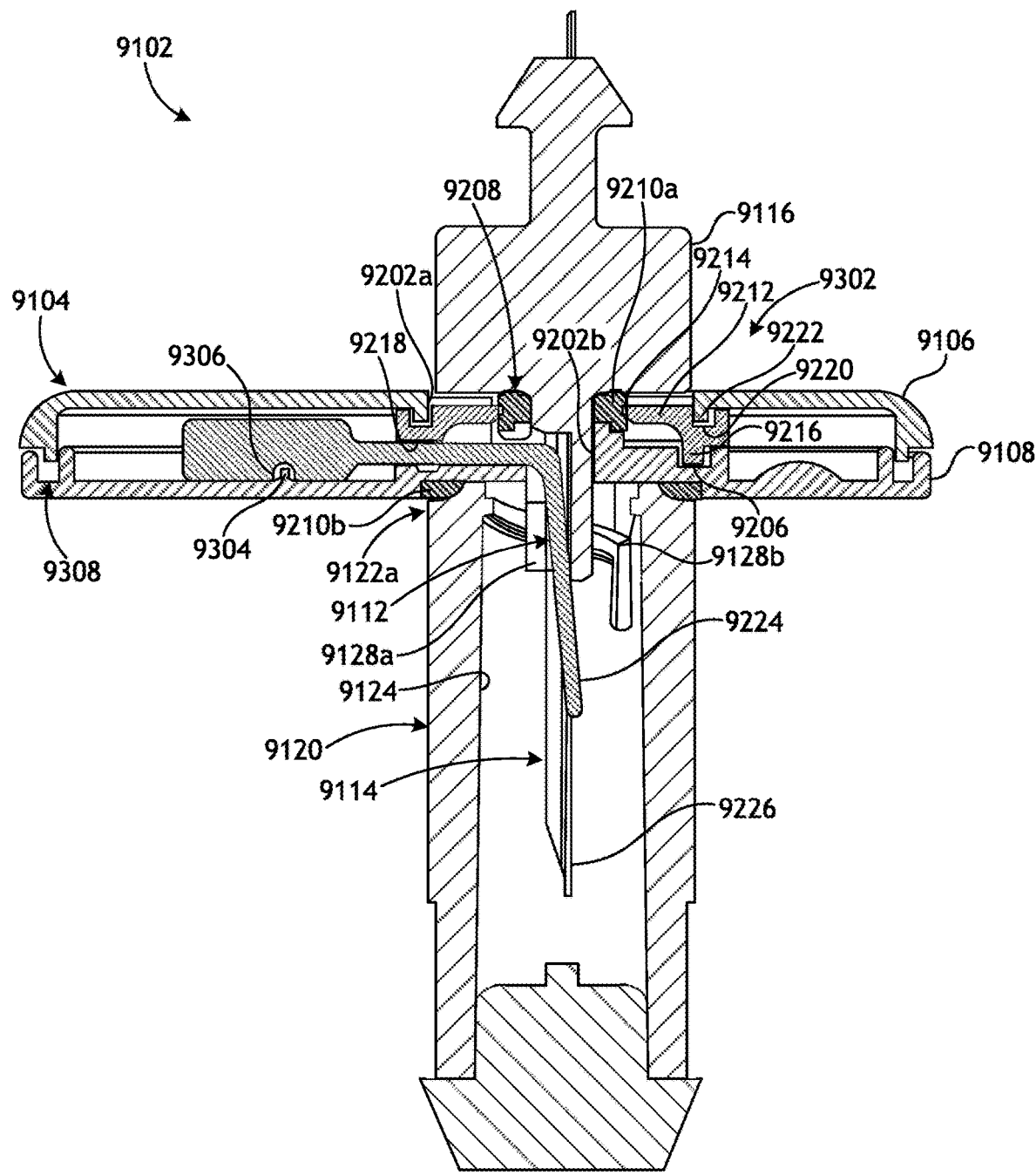
FIG. 93 is a cross-sectional side view of the sensor control device of FIGS. 91A-91B and 92A-92B, according to one or more embodiments.

FIG. 93 is a cross-sectional side view of the sensor control device 9102, according to one or more embodiments. As indicated above, the sensor control device 9102 may include or otherwise incorporate a sealed subassembly 9302, which may be useful in isolating the sensor 9112 and the sharp 9114 within the inner chamber 9124 of the sensor cap 9120. To assemble the sealed subassembly 9302, the sensor 9112 may be located within the mount 9108 such that the tail 9224 extends through the second aperture 9202*b* at the bottom of the mount 9108. In at least one embodiment, a locating feature 9304 may be defined on the inner surface of the mount 9108, and the sensor 9112 may define a groove 9306 that is matable with the locating feature 9304 to properly locate the sensor 9112 within the mount 9108.

Once the sensor 9112 is properly located, the collar 9212 may be installed on the mount 9108. More specifically, the collar 9212 may be positioned such that the first seal element 9210*a* of the seal 9208 is received within the central aperture 9214 defined by the collar 9212 and the first seal element 9210*a* generates a radial seal against the collar 9212 at the central aperture 9214. Moreover, the annular lip 9216 defined on the collar 9212 may be received within the channel 9206 defined on the mount 9108, and the groove 9218 defined through the annular lip 9216 may be aligned to receive the portion of the sensor 9112 that traverses the channel 9206 laterally within the mount 9108. In some embodiments, an adhesive may be injected into the channel 9206 to secure the collar 9212 to the mount 9108. The adhesive may also facilitate a sealed interface between the two components and generate a seal around the sensor 9112 at the groove 9218, which may isolate the tail 9224 from the interior of the electronics housing 9104.

The shell 9106 may then be mated with or otherwise coupled to the mount 9108. In some embodiments, as illustrated, the shell 9106 may mate with the mount 9108 via a tongue-and-groove engagement 9308 at the outer periphery of the electronics housing 9104. An adhesive may be injected (applied) into the groove portion of the engagement 9308 to secure the shell 9106 to the mount 9108, and also to create a sealed engagement interface. Mating the shell 9106 to the mount 9108 may also cause the annular ridge 9222 defined on the inner surface of the shell 9106 to be received within the collar channel 9220 defined on the upper surface of the collar 9212. In some embodiments, an adhesive may be injected into the collar channel 9220 to secure the shell 9106 to the collar 9212, and also to facilitate a sealed interface between the two components at that location.

When the shell 9106 mates with the mount 9108, the first seal element 9210a may extend at least partially through (into) the first aperture 9202a defined in the shell 9106.

The sharp 9114 may then be coupled to the sensor control device 9102 by extending the sharp tip 9226 through the aligned first and second apertures 9202a,b defined in the shell 9106 and the mount 9108, respectively. The sharp 9114 may be advanced until the sharp hub 9116 engages the seal 9208 and, more particularly, engages the first seal element 9210a. The mating member 9118 may extend (protrude) out the second aperture 9202b at the bottom of the mount 9108 when the sharp hub 9116 engages the first seal element 9210a.

The sensor cap 9120 may then be removably coupled to the sensor control device 9102 by threadably mating the internal threads 9128b of the sensor cap 9120 with the external threads 9128a of the mating member 9118. The inner chamber 9124 may be sized and otherwise configured to receive the tail 9224 and the sharp tip 9226 extending from the bottom of the mount 9108. Moreover, the inner chamber 9124 may be sealed to isolate the tail 9224 and the sharp tip 9226 from substances that might adversely interact with the chemistry of the tail 9224. In some embodiments, a desiccant (not shown) may be present within the inner chamber 9124 to maintain proper humidity levels.

Tightening (rotating) the mated engagement between the sensor cap 9120 and the mating member 9118 may urge the first end 9122a of the sensor cap 9120 into sealed engagement with the second seal element 9210b in an axial direction (e.g., along the centerline of the apertures 9202a,b), and may further enhance the sealed interface between the sharp hub 9116 and the first seal element 9210a in the axial direction. Moreover, tightening the mated engagement between the sensor cap 9120 and the mating member 9118 may compress the first seal element 9210a, which may result in an enhanced radial sealed engagement between the first seal element 9210a and the collar 9212 at the central aperture 9214. Accordingly, in at least one embodiment, the first seal element 9210a may help facilitate axial and radial sealed engagements.

As mentioned above, the first and second seal elements 9210a,b may be overmolded onto the mount 9108 and may be physically linked or otherwise interconnected. Consequently, a single injection molding shot may flow through the second aperture 9202b of the mount 9108 to create both ends of the seal 9208. This may prove advantageous in being able to generate multiple sealed interfaces with only a single injection molded shot. An additional advantage of a two-shot molded design, as opposed to using separate elastomeric components (e.g., O-rings, gaskets, etc.), is that the interface between the first and second shots is a reliable bond rather than a mechanical seal. Hence, the effective number of mechanical sealing barriers is effectively cut in half. Moreover, a two-shot component with a single elastomeric shot also has implications to minimizing the number of two-shot components needed to achieve all the necessary sterile barriers.

Once properly assembled, the sealed subassembly 9302 may be subjected to a radiation sterilization process to sterilize the sensor 9112 and the sharp 9114. The sealed subassembly 9302 may be subjected to the radiation sterilization prior to or after coupling the sensor cap 9120 to the sharp hub 9116. When sterilized after coupling the sensor cap 9120 to the sharp hub 9116, the sensor cap 9120 may be made of a material that permits the propagation of radiation therethrough. In some embodiments, the sensor cap 9120 may be transparent or translucent, but can otherwise be opaque, without departing from the scope of the disclosure.

Figure 93A:
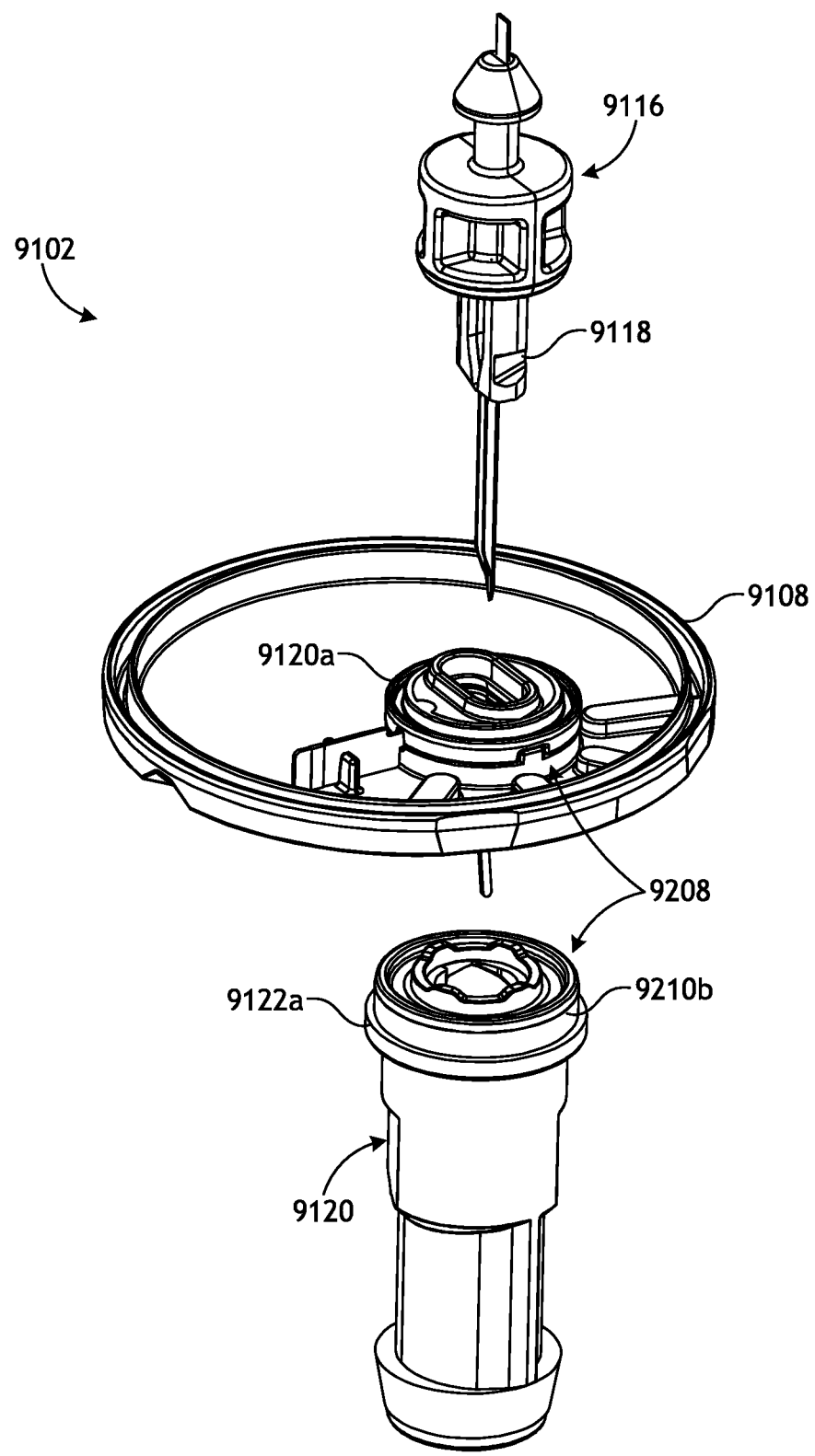
FIG. 93A is an exploded isometric view of a portion of another embodiment of the sensor control device of FIGS. 91A-91B and 92A-92B.

FIG. 93A is an exploded isometric view of a portion of another embodiment of the sensor control device 9102 of FIGS. 91A-91B and 92A-92B. Embodiments included above describe the mount 9108 and the seal 9208 being manufactured via a two-shot injection molding process. In other embodiments, however, as briefly mentioned above, one or both of the seal elements 9210a,b of the seal 9208 may comprise an elastomeric component part independent of the mount 9208. In the illustrated embodiment, for example, the first seal element 9210a may be overmolded onto the collar 9212 and the second seal element 9210b may be overmolded onto the sensor cap 9120. Alternatively, the first and second seal elements 9210a,b may comprise a separate component part, such as a gasket or O-ring positioned on the collar 9212 and the sensor cap 9120, respectively. Tightening (rotating) the mated engagement between the sensor cap 9120 and the mating member 9118 may urge the second seal element 9210b into sealed engagement with the bottom of the mount 9108 in an axial direction, and may enhance a sealed interface between the sharp hub 9116 and the first seal element 9210a in the axial direction.

Figure 94A:
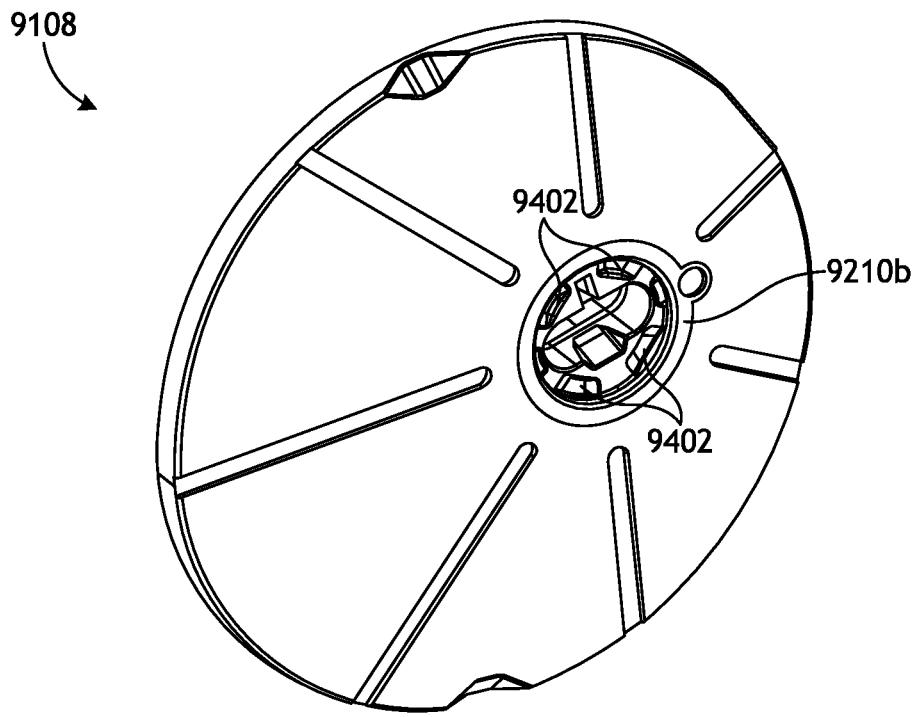
FIG. 94A is an isometric bottom view of the mount of FIGS. 91A-91B and 92A-92B.
Figure 94B:
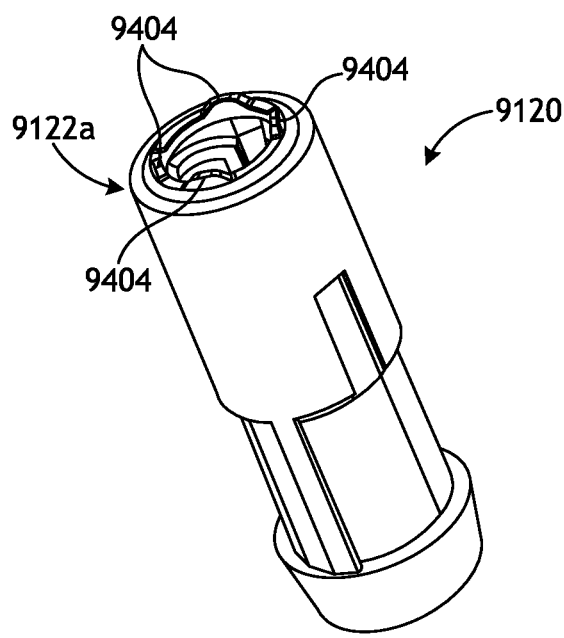
FIG. 94B is an isometric top view of the sensor cap of FIGS. 91A-91B and 92A-92B.

FIG. 94A is an isometric bottom view of the mount 9108, and FIG. 94B is an isometric top view of the sensor cap 9120, according to one or more embodiments. As shown in FIG. 94A, the mount 9108 may provide or otherwise define one or more indentations or pockets 9402 at or near the opening to the second aperture 9202b. As shown in FIG. 94B, the sensor cap 9120 may provide or otherwise define one or more projections 9404 at or near the first end 9122a of the sensor cap 9120. The projections 9404 may be received within the pockets 9402 when the sensor cap 9120 is coupled to the sharp hub 9116 (FIGS. 92A-92B and 93). More specifically, as described above, as the sensor cap 9120 is coupled to the mating member 9118 (FIGS. 92A-92B and 93) of the sensor hub 9116, the first end 9122a of the sensor cap 9120 is brought into sealed engagement with the second seal element 9210b. In this process, the projections 9404 may also be received within the pockets 9402, which may help prevent premature unthreading of the sensor cap 9120 from the sharp hub 9116.

Figure 95B:
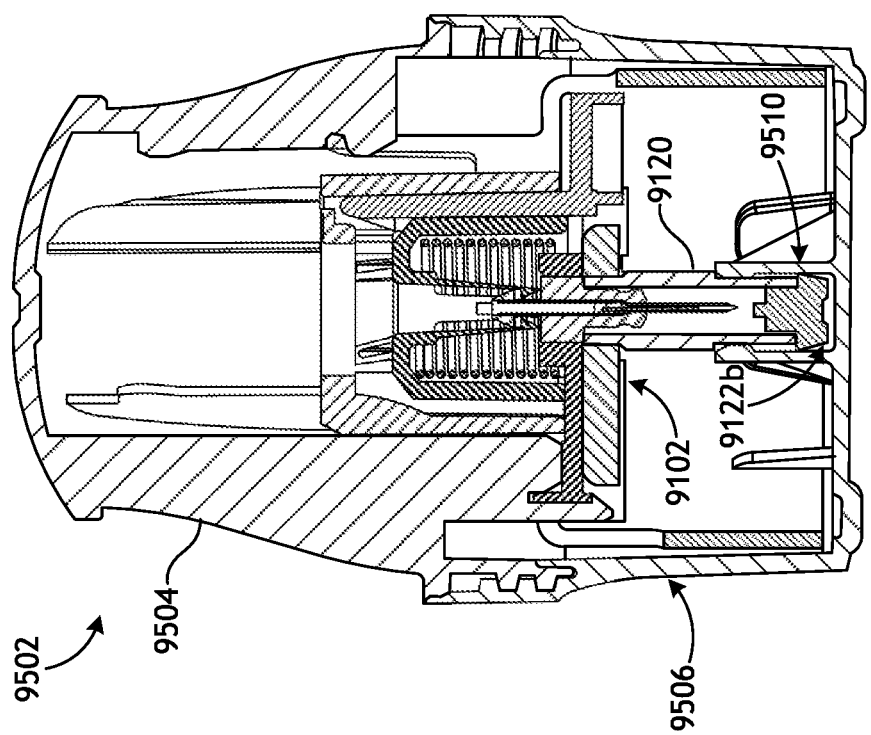
FIGS. 95A and 95B are side and cross-sectional side views, respectively, of an example sensor applicator, according to one or more embodiments.
Figure 95A:
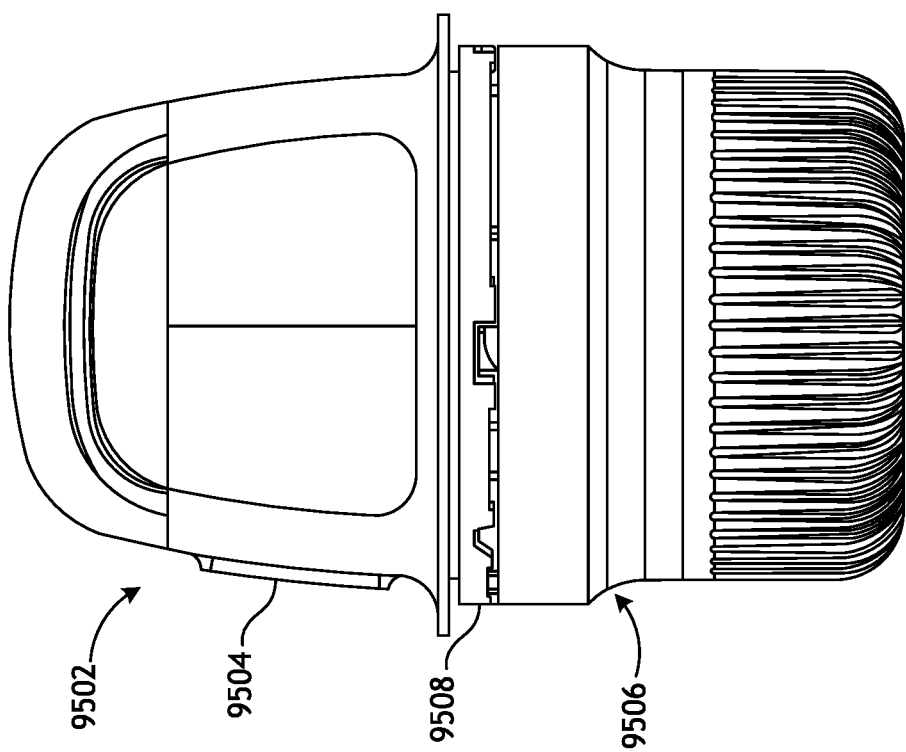

FIGS. 95A and 95B are side and cross-sectional side views, respectively, of an example sensor applicator 9502, according to one or more embodiments. The sensor applicator 9502 may be similar in some respects to the sensor applicator 102 of FIG. 1 and, therefore, may be designed to deliver (fire) a sensor control device, such as the sensor control device 9102. FIG. 95A depicts how the sensor applicator 9502 might be shipped to and received by a user, and FIG. 95B depicts the sensor control device 9102 arranged within the interior of the sensor applicator 9502.

As shown in FIG. 95A, the sensor applicator 9502 includes a housing 9504 and an applicator cap 9506 removably coupled to the housing 9504. In some embodiments, the applicator cap 9506 may be threaded to the housing 9504 and include a tamper ring 9508. Upon rotating (e.g., unscrewing) the applicator cap 9506 relative to the housing 9504, the tamper ring 9508 may shear and thereby free the applicator cap 9506 from the sensor applicator 9502.

In FIG. 95B, the sensor control device 9102 is positioned within the sensor applicator 9502. Once the sensor control device 9102 is fully assembled, it may then be loaded into the sensor applicator 9502 and the applicator cap 9506 may be coupled to the sensor applicator 9502. In some embodiments, the applicator cap 9506 and the housing 9504 may have opposing, matable sets of threads that enable the applicator cap 9506 to be screwed onto the housing 9504 in a clockwise (or counter-clockwise) direction and thereby secure the applicator cap 9506 to the sensor applicator 9502.

Securing the applicator cap 9506 to the housing 9504 may also cause the second end 9122*b* of the sensor cap 9120 to be received within a cap post 9510 located within the interior of the applicator cap 9506 and extending proximally from the bottom thereof. The cap post 9510 may be configured to receive at least a portion of the sensor cap 9120 as the applicator cap 9506 is coupled to the housing 9504.

Figure 96A:
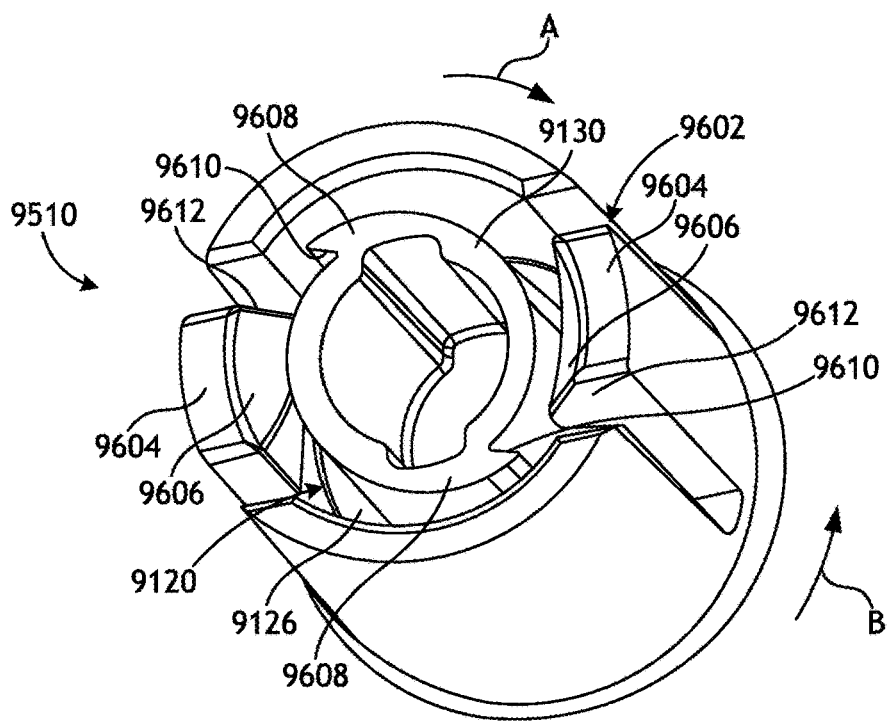
FIGS. 96A and 96B are perspective and top views, respectively, of the cap post of FIG. 95B, according to one or more embodiments.
Figure 96B:
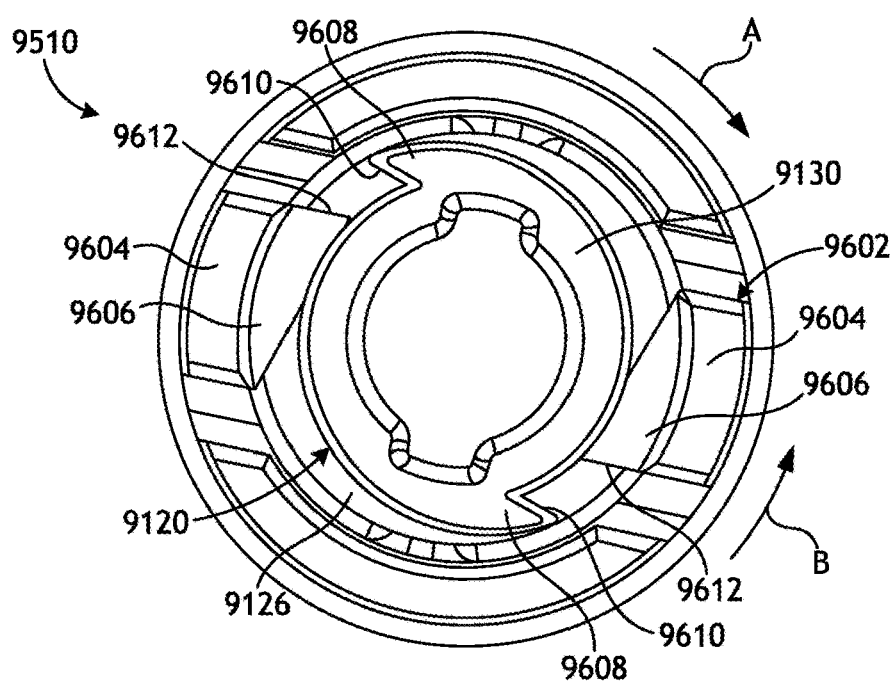

FIGS. 96A and 96B are perspective and top views, respectively, of the cap post 9510, according to one or more additional embodiments. In the illustrated depiction, a portion of the sensor cap 9120 is received within the cap post 9510 and, more specifically, the desiccant cap 9130 of the sensor cap 9120 is arranged within cap post 9510.

The cap post 9510 may define a receiver feature 9602 configured to receive the engagement feature 9126 of the sensor cap 9120 upon coupling (e.g., threading) the applicator cap 9506 (FIG. 95B) to the sensor applicator 9502 (FIGS. 95A-95B). Upon removing the applicator cap 9506 from the sensor applicator 9502, however, the receiver feature 9602 may prevent the engagement feature 9126 from reversing direction and thus prevent the sensor cap 9120 from separating from the cap post 9510. Instead, removing the applicator cap 9506 from the sensor applicator 9502 will simultaneously detach the sensor cap 9120 from the sensor control device 9102 (FIGS. 91A-91B and 92A-92B), and thereby expose the distal portions of the sensor 9112 (FIGS. 92A-92B) and the sharp 9114 (FIGS. 92A-92B).

Many design variations of the receiver feature 9602 may be employed, without departing from the scope of the disclosure. In the illustrated embodiment, the receiver feature 9602 includes one or more compliant members 9604 (two shown) that are expandable or flexible to receive the engagement feature 9126. The engagement feature 9126 may comprise, for example, an enlarged head and the compliant member(s) 9604 may comprise a collet-type device that includes a plurality of compliant fingers configured to flex radially outward to receive the enlarged head.

The compliant member(s) 9604 may further provide or otherwise define corresponding ramped surfaces 9606 configured to interact with one or more opposing camming surfaces 9608 provided on the outer wall of the engagement feature 9126. The configuration and alignment of the ramped surface(s) 9606 and the opposing camming surface(s) 9608 is such that the applicator cap 9506 is able to rotate relative to the sensor cap 9120 in a first direction A (e.g., clockwise), but the cap post 9510 binds against the sensor cap 9120 when the applicator cap 9506 is rotated in a second direction B (e.g., counter clockwise). More particularly, as the applicator cap 9506 (and thus the cap post 9510) rotates in the first direction A, the camming surfaces 9608 engage the ramped surfaces 9606, which urge the compliant members 9604 to flex or otherwise deflect radially outward and results in a ratcheting effect. Rotating the applicator cap 9506 (and thus the cap post 9510) in the second direction B, however, will drive angled surfaces 9610 of the camming surfaces 9608 into opposing angled surfaces 9612 of the ramped surfaces 9606, which results in the sensor cap 9120 binding against the compliant member(s) 9604.

Figure 97:
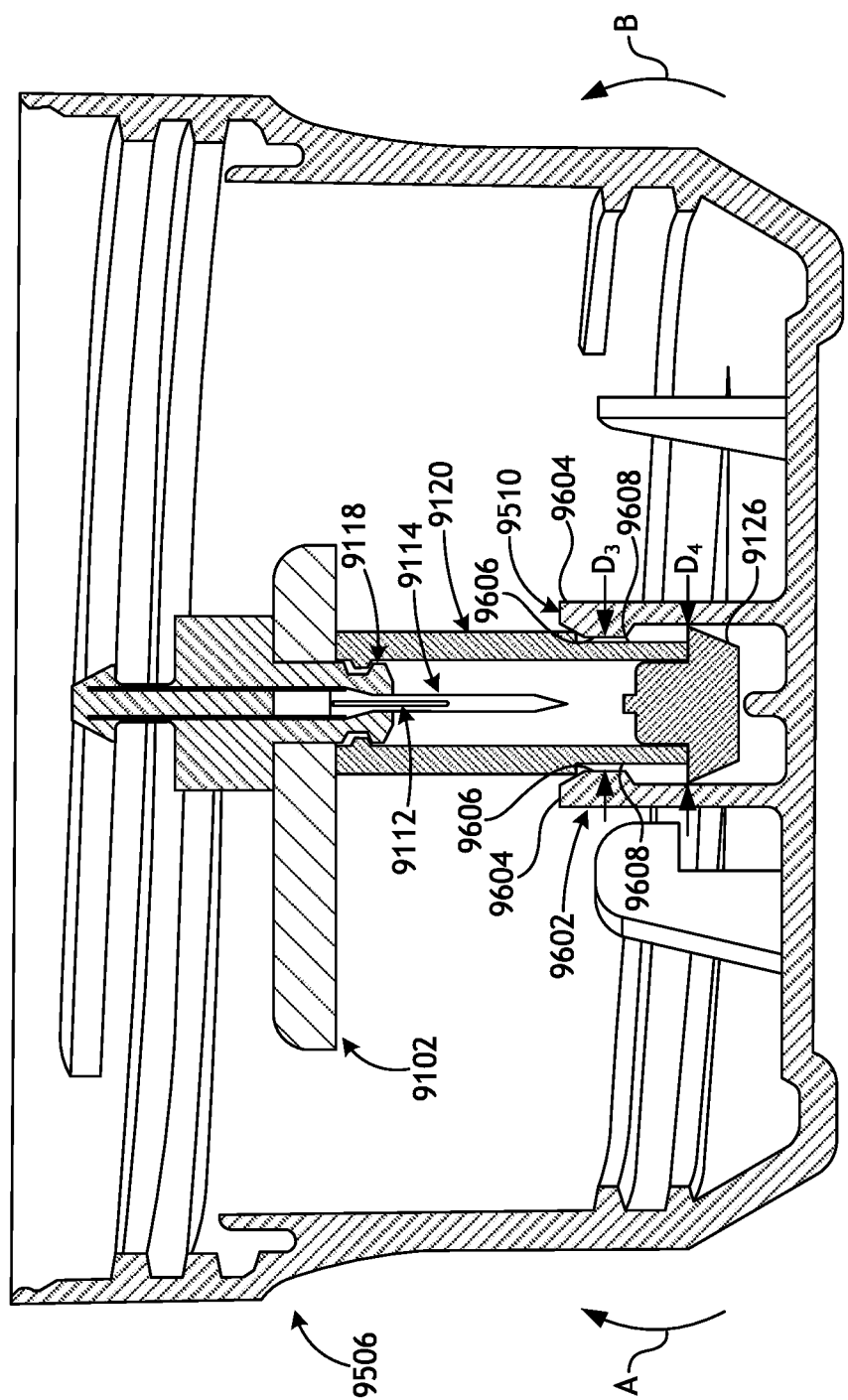
FIG. 97 is a cross-sectional side view of the sensor control device positioned within the applicator cap, according to one or more embodiments.

FIG. 97 is a cross-sectional side view of the sensor control device 9102 positioned within the applicator cap 9506, according to one or more embodiments. As illustrated, the opening to the receiver feature 9602 exhibits a first diameter $D_3$, while the engagement feature 9126 of the sensor cap 9120 exhibits a second diameter $D_4$ that is larger than the first diameter $D_3$ and greater than the outer diameter of the remaining portions of the sensor cap 9120. As the sensor cap 9120 is extended into the cap post 9510, the compliant member(s) 9604 of the receiver feature 9602 may flex (expand) radially outward to receive the engagement feature 9126. In some embodiments, as illustrated, the engagement feature 9126 may provide or otherwise define an angled outer surface that helps bias the compliant member(s) 9604 radially outward. Once the engagement feature 9126 bypasses the receiver feature 9602, the compliant member(s) 9604 are able to flex back to (or towards) their natural state and thus lock the sensor cap 9120 within the cap post 9510.

As the applicator cap 9506 is threaded to (screwed onto) the housing 9504 (FIGS. 95A-95B) in the first direction A, the cap post 9510 correspondingly rotates in the same direction and the sensor cap 9120 is progressively introduced into the cap post 9510. As the cap post 9510 rotates, the ramped surfaces 9606 of the compliant members 9604 ratchet against the opposing camming surfaces 9608 of the sensor cap 9120. This continues until the applicator cap 9506 is fully threaded onto (screwed onto) the housing 9504. In some embodiments, the ratcheting action may occur over two full revolutions of the applicator cap 9506 before the applicator cap 9506 reaches its final position.

To remove the applicator cap 9506, the applicator cap 9506 is rotated in the second direction B, which correspondingly rotates the cap post 9510 in the same direction and causes the camming surfaces 9608 (i.e., the angled surfaces 9610 of FIGS. 96A-96B) to bind against the ramped surfaces 9606 (i.e., the angled surfaces 9612 of FIGS. 96A-96B). Consequently, continued rotation of the applicator cap 9506 in the second direction B causes the sensor cap 9120 to correspondingly rotate in the same direction and thereby unthread from the mating member 9118 to allow the sensor cap 9120 to detach from the sensor control device 9102. Detaching the sensor cap 9120 from the sensor control device 9102 exposes the distal portions of the sensor 9112 and the sharp 9114, and thus places the sensor control device 9102 in position for firing (use).

Figure 98:
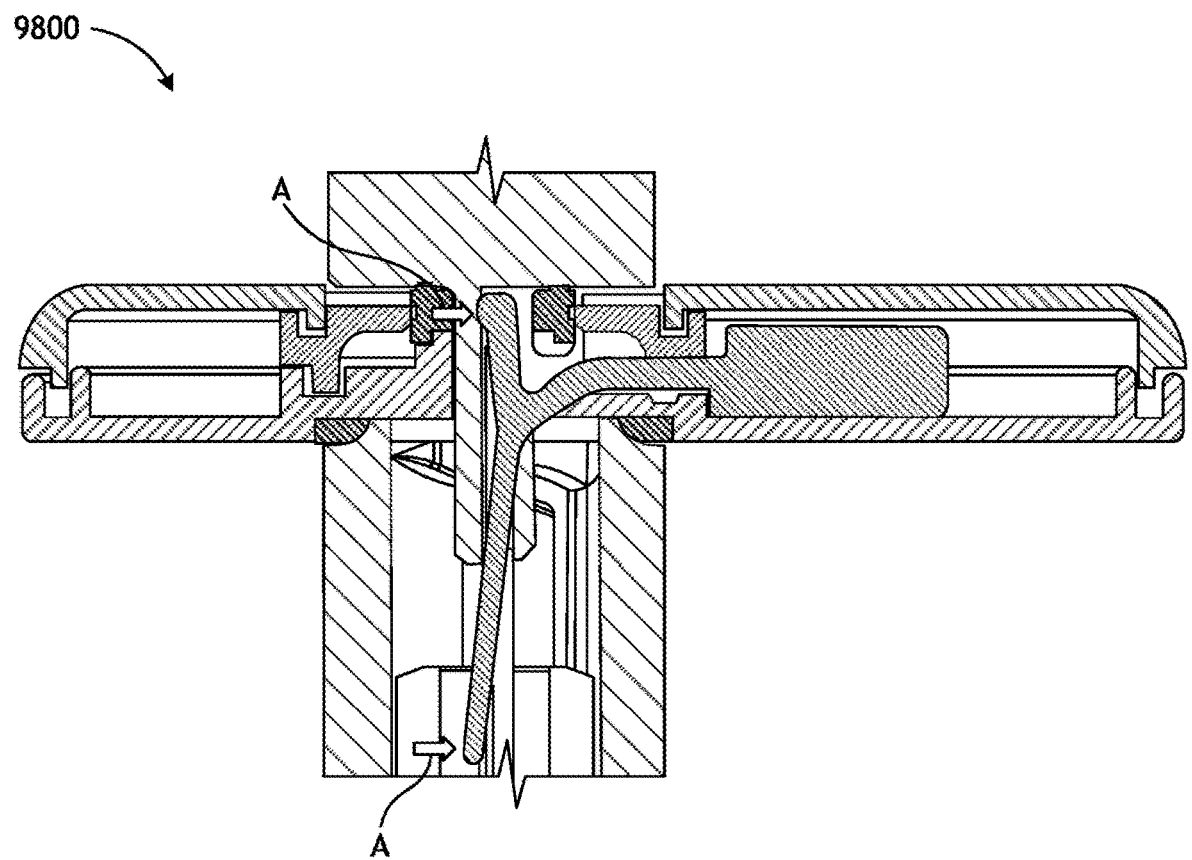
FIG. 98 is a cross-sectional view of a sensor control device showing example interaction between the sensor and the sharp.

FIG. 98 is a cross-sectional view of a sensor control device 9800 showing example interaction between the sensor and the sharp. After assembly of the sharp, the sensor should sit in a channel defined by the sharp. The sensor control device in FIG. 9 does not show the sensor deflected inwards and otherwise aligned fully with the sharp, but such may be the case upon full assembly as slight bias forces may be assumed by the sensor at the locations indicated by the two arrows A. Biasing the sensor against the sharp may be advantageous so that any relative motion between the sensor and the sharp during subcutaneous insertion does not expose the sensor tip (i.e., the tail) outside the sharp channel, which could potentially cause an insertion failure.

Embodiments disclosed herein include:

CC. A sensor control device that includes an electronics housing including a shell that defines a first aperture and a mount that defines a second aperture alignable with the first aperture when the shell is coupled to the mount, a seal overmolded onto the mount at the second aperture and comprising a first seal element overmolded onto a pedestal protruding from an inner surface of the mount, and a second seal element interconnected with the first seal element and overmolded onto a bottom of the mount, a sensor arranged within the electronics housing and having a tail extending through the second aperture and past the bottom of the mount, and a sharp that extends through the first and second apertures and past the bottom of the electronics housing.

DD. An assembly that includes a sensor applicator, a sensor control device positioned within the sensor applicator and including an electronics housing including a shell that defines a first aperture and a mount that defines a second aperture alignable with the first aperture when the shell is mated to the mount, a seal overmolded onto the mount at the second aperture and comprising a first seal element overmolded onto a pedestal protruding from an inner surface of the mount, and a second seal element interconnected with the first seal element and overmolded onto a bottom of the mount, a sensor arranged within the electronics housing and having a tail extending through the second aperture and past the bottom of the mount, and a sharp that extends through the first and second apertures and past the bottom of the electronics housing. The assembly further including a sensor cap removably coupled to the sensor control device at the bottom of the mount and defining a sealed inner chamber that receives the tail and the sharp, and an applicator cap coupled to the sensor applicator.

Each of embodiments CC and DD may have one or more of the following additional elements in any combination: Element 1: wherein the mount comprises a first injection molded part molded in a first shot, and the seal comprises a second injection molded part overmolded onto the first injection molded part in a second shot. Element 2: further comprising a sharp hub that carries the sharp and sealingly engages the first seal element, and a sensor cap removably coupled to the sharp hub at the bottom of the mount and sealingly engaging the second seal element, wherein the sensor cap defines an inner chamber that receives the tail and the sharp. Element 3: wherein the sharp hub provides a mating member that extends past the bottom of the mount and the sensor cap is removably coupled to the mating member. Element 4: further comprising one or more pockets defined on the bottom of the mount at the second aperture, and one or more projections defined on an end of the sensor cap and receivable within the one or more pockets when the sensor cap is coupled to the sharp hub. Element 5: further comprising a collar positioned within the electronics housing and defining a central aperture that receives and sealingly engages the first seal element in a radial direction. Element 6: further comprising a channel defined on the inner surface of the mount and circumscribing the pedestal, an annular lip defined on an underside of the collar and matable with the channel, and an adhesive provided in the channel to secure and seal the collar to the mount at the channel. Element 7: further comprising a groove defined through the annular lip to accommodate a portion of the sensor extending laterally within the mount, wherein the adhesive seals about the sensor at the groove. Element 8: further comprising a collar channel defined on an upper surface of the collar, an annular ridge defined on an inner surface of the shell and matable with the collar channel, and an adhesive provided in the collar channel to secure and seal the shell to the collar. Element 9: wherein one or both of the first and second seal elements define at least a portion of the second aperture. Element 10: wherein the first seal element extends at least partially through the first aperture when the shell is coupled to the mount.

Element 11: wherein the sensor control device further includes a sharp hub that carries the sharp and sealingly engages the first seal element, and wherein the sensor cap is removably coupled to the sharp hub at the bottom of the mount and sealingly engages the second seal element. Element 12: wherein the sensor control device further includes one or more pockets defined on the bottom of the mount at the second aperture, and one or more projections defined on an end of the sensor cap and receivable within the one or more pockets when the sensor cap is coupled to the sharp hub. Element 13: wherein the sensor control device further includes a collar positioned within the electronics housing and defining a central aperture that receives and sealingly engages the first seal element in a radial direction. Element 14: wherein the sensor control device further includes a channel defined on the inner surface of the mount and circumscribing the pedestal, an annular lip defined on an underside of the collar and matable with the channel, and an adhesive provided in the channel to secure and seal the collar to the mount at the channel. Element 15: wherein the sensor control device further includes a groove defined through the annular lip to accommodate a portion of the sensor extending laterally within the mount, and wherein the adhesive seals about the sensor at the groove. Element 16: wherein the sensor control device further includes a collar channel defined on an upper surface of the collar, an annular ridge defined on an inner surface of the shell and matable with the collar channel, and an adhesive provided in the collar channel to secure and seal the shell to the collar. Element 17: wherein one or both of the first and second seal elements define at least a portion of the second aperture. Element 18: wherein the first seal element extends at least partially through the first aperture.

By way of non-limiting example, exemplary combinations applicable to CC and DD include: Element 2 with Element 3; Element 2 with Element 4; Element 5 with Element 6; Element 6 with Element 7; Element 5 with Element 8; Element 11 with Element 12; Element 13 with Element 14; Element 14 with Element 15; and Element 13 with Element 16.

Axial-Radial Thermal Cycle Resistant Cap Seal

Figure 99:
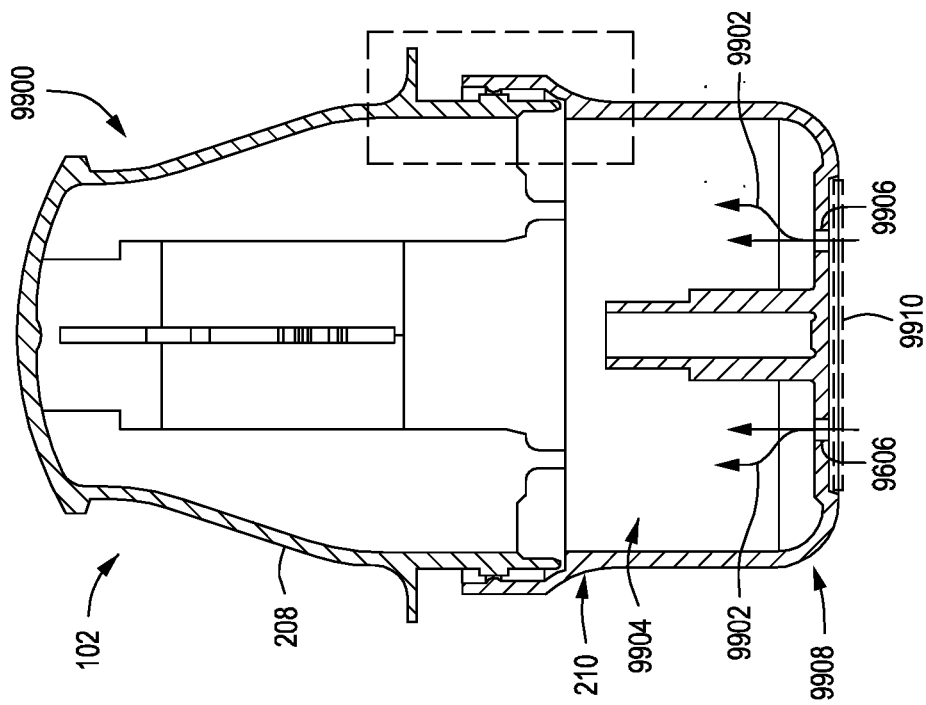
FIG. 99 is a cross-sectional side view of an example analyte monitoring system enclosure used to house at least a portion of a sensor control device.

FIG. 99 is a cross-sectional side view of an example analyte monitoring system enclosure 9900 used to house at least a portion of the sensor control device 104 of FIG. 1, according to one or more embodiments. As illustrated, the analyte monitoring system enclosure 9900 includes the sensor applicator 102 and the applicator cap 210 matable with the sensor applicator 102. The applicator cap 210 provides a barrier that protects the internal contents of the sensor applicator 102. In some embodiments, the applicator cap 210 may be secured to the housing 208 by a threaded engagement and, upon rotating (e.g., unscrewing) the applicator cap 210 relative to the housing 208, the applicator cap 210 can be freed from the sensor applicator 102. In other embodiments, however, the applicator cap 210 may be secured to the housing 208 via an interference or shrink fit engagement.

As described herein below, the coupled engagement between the sensor applicator 102 and the applicator cap 210 may prove vital in properly sterilizing the components positioned within the sensor applicator 102 and maintaining a sterile environment as sealed with the applicator cap 210. The embodiments described herein below may be applicable to analyte monitoring systems that incorporate a two-piece or a one-piece architecture. More particularly, in embodiments employing a two-piece architecture, the electronics housing (not shown) that retains the electrical components for the sensor control device 104 (FIG. 1) may be positioned within the sensor applicator 102 and the applicator cap 210 maintains the sterile environment. In contrast, in embodiments employing a one-piece architecture, the sensor applicator 102 may contain the fully assembled sensor control device 104 (not shown), and the applicator cap 210 maintains the sterile environment for the fully assembled sensor control device.

The components arranged within the sensor applicator 102 and sealed with the applicator cap 210 may be subjected to gaseous chemical sterilization 9902 configured to sterilize exposed portions of such components. To accomplish this, a chemical may be injected into a sterilization chamber 9904 cooperatively defined by the housing 208 and the interconnected cap 210. In some applications, the chemical may be injected into the sterilization chamber 9904 via one or more vents 9906 (two shown) defined in the applicator cap 210 at its proximal end 9908. Example chemicals that may be used for the gaseous chemical sterilization 9902 include, but are not limited to, ethylene oxide, vaporized hydrogen peroxide, and nitrogen oxide (e.g., nitrous oxide, nitrogen dioxide, etc.).

Once a desired sterility assurance level has been achieved within the sterilization chamber 9904, the gaseous solution may be evacuated via the vents 9906 and the sterilization chamber 9904 is aerated. Aeration may be achieved by a series of vacuums and subsequently circulating nitrogen gas or filtered air through the sterilization chamber 9904. Once the sterilization chamber 9904 is properly aerated, the vents 9906 may be occluded with a seal 9910 (shown in dashed lines).

In some embodiments, the seal 9910 may comprise two or more layers of different materials. The first layer may be made of a synthetic material (e.g., a flash-spun high-density polyethylene fiber), such as Tyvek® available from DuPont®. Tyvek® is highly durable and puncture resistant and allows the permeation of vapors. The Tyvek® layer can be applied before the gaseous chemical sterilization process, and following the gaseous chemical sterilization process, a foil or other vapor and moisture resistant material layer may be sealed (e.g., heat sealed) over the Tyvek® layer to prevent the ingress of contaminants and moisture into the sterilization chamber 9904. In other embodiments, the seal 9910 may comprise only a single protective layer applied to the applicator cap 210. In such embodiments, the single layer is gas permeable for the sterilization process, but is also capable of protection against moisture and other harmful elements once the sterilization process is complete.

With the seal 9910 in place, the applicator cap 210 provides a barrier against outside contamination, and thereby maintains a sterile environment for the components arranged within the sensor applicator 102 until the user removes (unthreads) the applicator cap 210 from the housing 208.

Figure 100B:
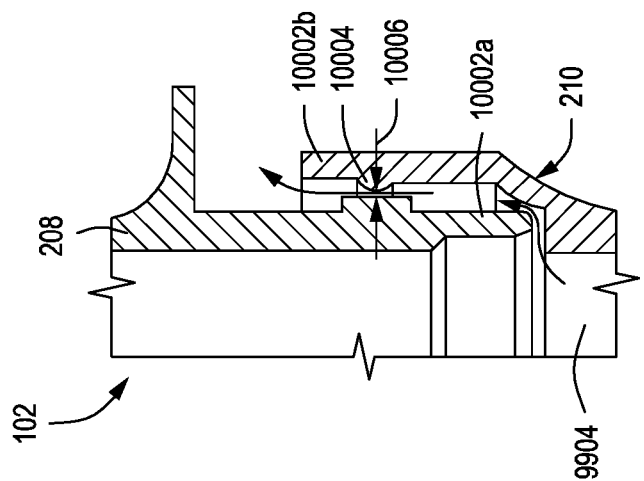
FIG. 100B is an enlarged cross-sectional side view of the interface between the sensor applicator and the cap as indicated by the dashed box of FIG. 99 during or after gaseous chemical sterilization.
Figure 100A:
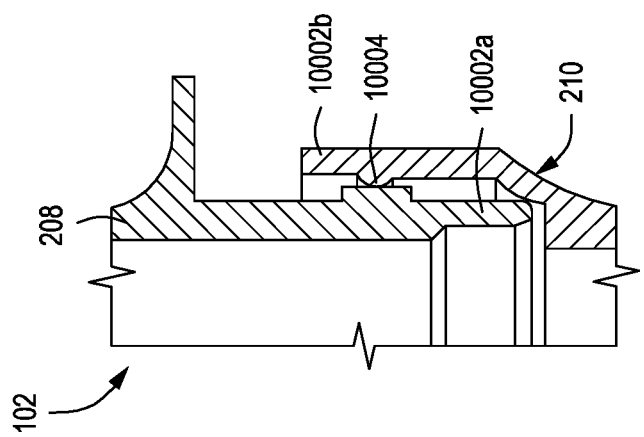
FIG. 100A is an enlarged cross-sectional side view of the interface between the sensor applicator and the cap as indicated by the dashed box of FIG. 99.

FIG. 100A is an enlarged cross-sectional side view of the interface between the sensor applicator 102 and the applicator cap 210, as indicated by the dashed box of FIG. 99. As illustrated the housing 208 provides a first axial extension 10002a and the applicator cap 210 provides a second axial extension 10002b matable with the first axial extension 10002a. In the illustrated embodiment, the diameter of the second axial extension 10002b of the applicator cap 210 is sized to receive the diameter of the first axial extension 10002a of the housing 208. In other embodiments, however, the reverse may be employed, where the diameter of the first axial extension 10002a may be sized to receive the diameter of the second axial extension 10002b, without departing from the scope of the disclosure.

In either scenario, a radial seal 10004 may be defined or otherwise provided at the interface between the first and second axial extensions 10002a,b and the radial seal 10004 may help prevent migration of fluids or contaminants across the interface in either axial direction. In the illustrated embodiment, the radial seal 10004 comprises a radial protrusion formed on the inner radial surface of the second axial extension 10002b. In other embodiments, however, the radial seal 10004 may alternatively be formed on the outer radial surface of the first axial extension 10002a, without departing from the scope of the disclosure. In embodiments where the second axial extension 10002b is received within the first axial extension 10002a, the radial seal 10004 may be formed on the inner radial surface of the first axial extension 10002a or alternatively on the outer radial surface of the second axial extension 10002b.

Gaseous chemical sterilization 9902 (FIG. 99) is commonly undertaken at elevated temperatures reaching 60° C. (140° F.) or more. At such elevated temperatures, the housing 208 and the applicator cap 210 may be subjected to thermal expansion that may affect the integrity of the radial seal 10004. The housing 208 and the applicator cap 210 may be made of dissimilar materials that have dissimilar coefficients of thermal expansion. In some embodiments, for example, the housing 208 may be made of polycarbonate and the applicator cap 210 may be made of polypropylene. Polypropylene exhibits a coefficient of thermal expansion of about 100-180 $10^{-6} K^{-1}$ and polycarbonate exhibits a coefficient of thermal expansion of about 66-70 $10^{-6} K^{-1}$. Since polypropylene has a thermal coefficient that is higher than polycarbonate, the applicator cap 210 will tend to expand at a greater rate than the polycarbonate housing 208 during gaseous chemical sterilization 9902. Moreover, the increased expansion of the applicator cap 210 can affect the seal integrity (capability) of the radial seal 10004.

FIG. 100B is an enlarged cross-sectional side view of the interface between the sensor applicator 102 and the applicator cap 210, as indicated by the dashed box of FIG. 99 during and/or after gaseous chemical sterilization. Since the applicator cap 210 exhibits a thermal coefficient greater than the thermal coefficient of the housing 208, the applicator cap 210 expands at a greater rate than the housing 208 upon being subjected to the elevated temperatures required for gaseous chemical sterilization 9902 (FIG. 99). Consequently, a gap 10006 may be created between the opposing radial surfaces of the first and second axial extensions 10002a,b as the radial seal 10004 separates from opposed radial engagement. As shown by the arrows, the gap 10006 may provide a flow path for the outflow of toxic gases used for gaseous chemical sterilization 9902.

Following gaseous chemical sterilization 9902, and as the temperature is lowered to ambient, the applicator cap 210 may radially contract and the gap 10006 may close, thereby sealing the interface at the radial seal 10004 once again. Such embodiments may prove advantageous in simplifying the design of the applicator cap 210. More specifically, and according to one or more embodiments of the present disclosure, the gaseous chemical sterilization 9902 process may be carried out entirely through the gap 10006 formed between the opposing radial surfaces of the first and second axial extensions 10002a,b. In such embodiments, the temperature of the housing 208 and the applicator cap 210 may be elevated until the gap 10006 is created. Once the gap 10006 is created, the gaseous chemicals (e.g., ethylene oxide) used during the gaseous chemical sterilization 9902 may be injected into the sterilization chamber 9904 through the gap 10006 and otherwise by bypassing the radial seal 10004. The sterilization chamber 9904 may be subsequently aerated by drawing out the gaseous chemicals through the gap 10006 and circulating another fluid, such as nitrogen, into and out of the sterilization chamber 9904 via the gap 10006.

In such embodiments, the vents 9906 (FIG. 99) defined in the applicator cap 210 and the seal 9910 (FIG. 99) attached to the bottom of the applicator cap 210 may be omitted and otherwise unnecessary. Accordingly, in such embodiments, the bottom of the applicator cap 210 may be solid. Moreover, in such embodiments, a desiccant may be positioned within the applicator cap 210 or the sterilization chamber 9904 to aid maintenance of a low humidity environment for biological components sensitive to moisture.

In other embodiments, however, the applicator cap 210 may undergo stress relaxation at the enlarged diameter during gaseous chemical sterilization 9902. This may occur in embodiments where the material of the applicator cap 210 exhibits a thermal coefficient greater than the material of the housing 208 and the gaseous chemical sterilization 9902 spans a long period of time (e.g., one hour, five hours, ten hours, fifteen hours, or more). As the temperature is lowered to ambient, the applicator cap 210 may remain substantially at the enlarged diameter and the gap 10006 may correspondingly remain, which jeopardizes the integrity of the radial seal 10004.

Stress relaxation of the applicator cap 210 may also occur in embodiments where the housing 208 is made of a material that has a higher thermal coefficient than the applicator cap 210. In such embodiments, the housing 208 will expand at a greater rate than the applicator cap 210 and thereby radially expand against the applicator cap 210. The gap 10006 will not be generated as the housing 208 continuously biases against the applicator cap 210 during thermal expansion. The material of the applicator cap 210, however, will undergo stress relaxation at an enlarged diameter, and upon cooling the system to ambient, the gap 10006 may be generated as the housing 208 radially contracts but the applicator cap 210 remains near the enlarged diameter. The resulting gap 10006 compromises the sealed interface at the radial seal 10004, and thereby prevents the applicator cap 210 from providing a barrier.

Figure 101:
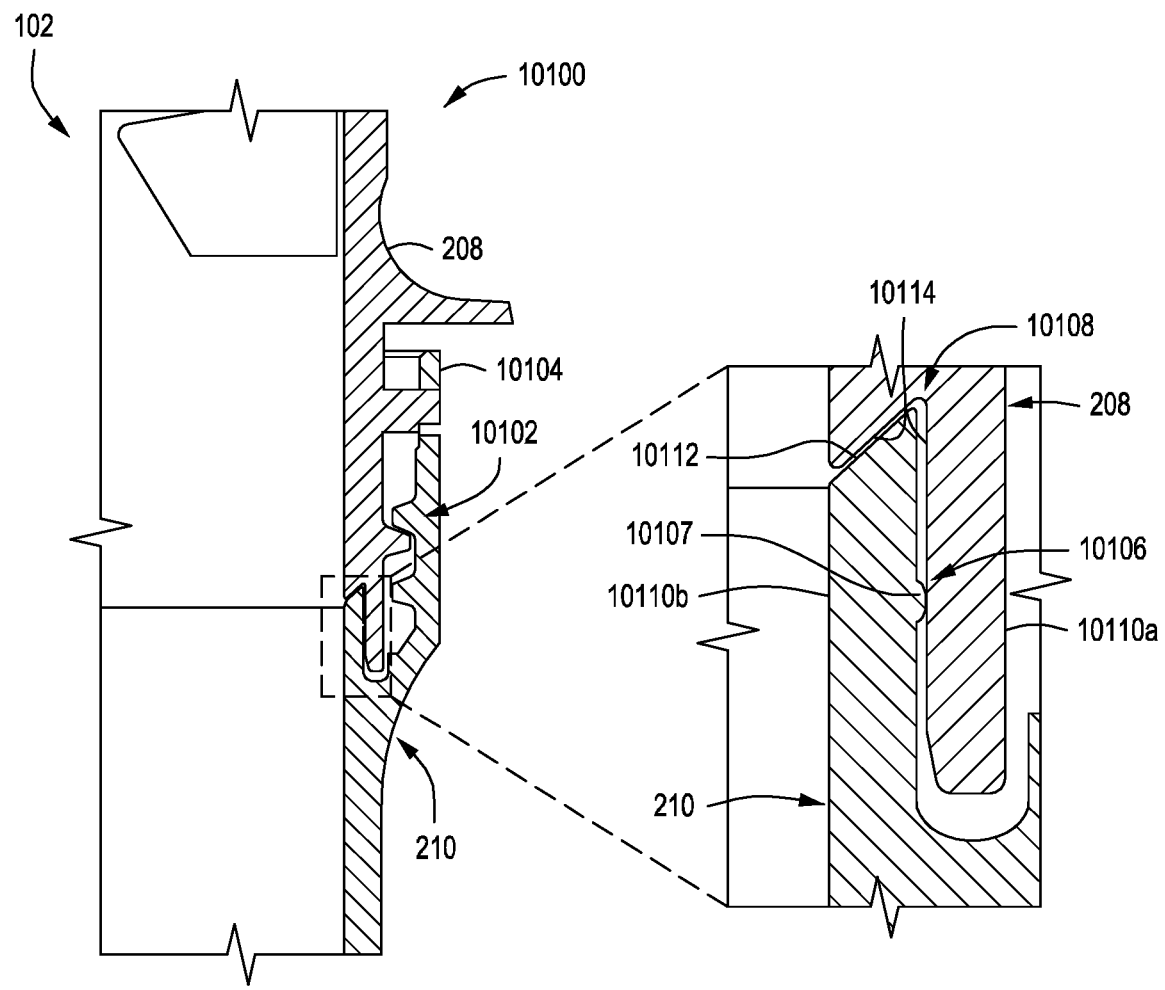
FIG. 101 is a cross-sectional side view of another example analyte monitoring system enclosure used to house at least a portion of the sensor control device of FIG. 1.

FIG. 101 is an enlarged cross-sectional side view of another example analyte monitoring system enclosure 10100 used to house at least a portion of the sensor control device 104 of FIG. 1, according to one or more embodiments. Similar to the analyte monitoring system enclosure 9900 of FIGS. 99 and 1007A-100B, the analyte monitoring system enclosure 10100 includes the sensor applicator 102 and the applicator cap 210 matable with the sensor applicator 102. In the illustrated embodiment, the applicator cap 210 is secured to the housing 208 by complimentary mating threads 10102, and may include a tamper ring 10104. Upon rotating (e.g., unscrewing) the applicator cap 210 relative to the housing 208, the tamper ring 10104 may shear and thereby free the applicator cap 210 from the sensor applicator 102.

As best seen in the enlarged view, the interface between the housing 208 and the applicator cap 210 may provide or otherwise define a radial seal 10106 and an axial-radial seal 10108. More specifically, the housing 208 may provide a first axial extension 10110a and the applicator cap 210 may provide a second axial extension 10110b extending in the opposite direction. In the illustrated embodiment, the diameter of the first axial extension 10110a may be sized to receive the smaller diameter second axial extension 10110b of the applicator cap 210. In other embodiments, however, the diameter of the second axial extension 10110b may be sized to receive a smaller diameter first axial extension 10110a of the housing 208, without departing from the scope of the disclosure.

In either scenario, the radial seal 10106 may be defined or otherwise provided at an interface between the first and second axial extensions 10110a,b and configured to help prevent the migration of fluids or contaminants across the interface in either axial direction. In the illustrated embodiment, the radial seal 10106 comprises a radial protrusion 10107 formed on the outer radial surface of the second axial extension 10110b, but the radial protrusion 10107 may alternatively be formed on the inner radial surface of the first axial extension 10110a, without departing from the scope of the disclosure. In embodiments where the first axial extension 10110a is received within the second axial extension 10110b, the radial seal 10106 may be formed on the outer radial surface of the first axial extension 10110a or alternatively on the inner radial surface of the second axial extension 10110b.

As its name suggests, the axial-radial seal 10108 may be configured to provide a sealed interface between the housing 208 and the applicator cap 210 in both axial and radial directions, and thereby prevent the migration of fluids or contaminants across the interface in both axial and radial directions. To accomplish this, the axial-radial seal 10108 may comprise a beveled or chamfered surface 10112 configured to mate with a fillet 10114, where the fillet 10114 comprises angularly offset surfaces angled to substantially mate with the angled profile of the chamfered surface 10112 in both axial and radial directions. In the illustrated embodiment, the chamfered surface 10112 is defined on the end of the second axial extension 10110b and the fillet 10114 is defined by the first axial extension 10110a. In other embodiments, however, the chamfered surface 10112 may alternatively be defined on the end of the first axial extension 10110a and the fillet 10114 may be defined by the second axial extension 10110b, without departing from the scope of the disclosure.

The radial seal 10106 and the axial-radial seal 10108 may be configured to cooperatively help maintain fluid tight interfaces between the housing 208 and the applicator cap 210. During gaseous chemical sterilization 9902 (FIG. 99), however, and since the housing 208 and the applicator cap 210 may be made of dissimilar materials having dissimilar coefficients of thermal expansion, the elevated temperatures may result in loss of a fluid tight seal at the radial seal 10106. Nonetheless, the axial-radial seal 10108 may be designed and otherwise configured to maintain a fluid tight interface between the housing 208 and the applicator cap 210 while withstanding the elevated temperatures of gaseous chemical sterilization 9902. Regardless of the materials of either of the housing 208 or the applicator cap 210, and regardless of the respective coefficients of thermal expansion, the axial-radial seal 10108 may prove advantageous in maintaining a fluid tight interface. In some embodiments, the applicator cap 210 may provide a sterile barrier.

Figure 102:
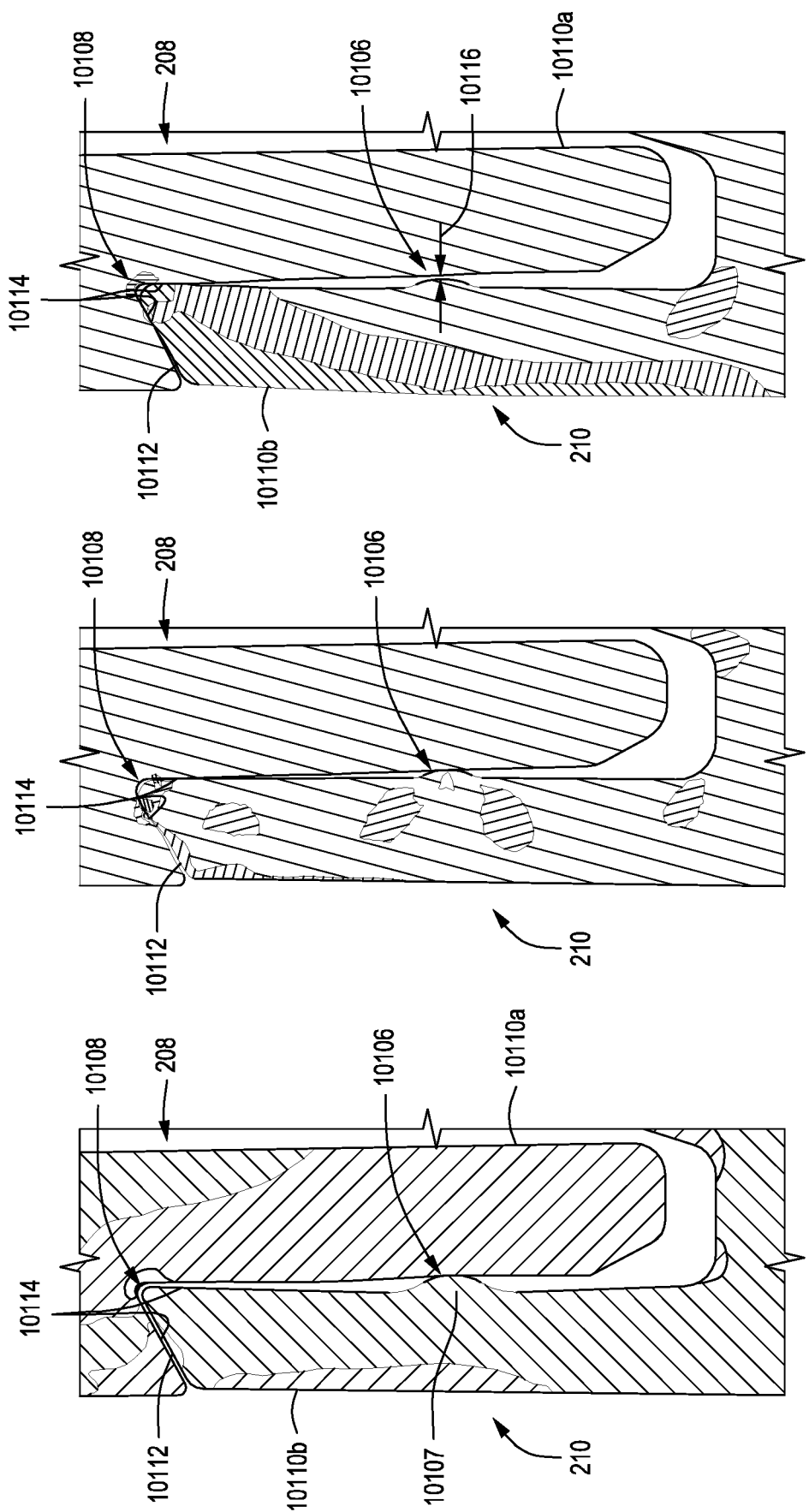
FIGS. 102A-102C provide finite element analysis results corresponding to the interface between the housing and the cap during example gaseous chemical sterilization.

FIGS. 102A-102C depict finite element analysis (FEA) results corresponding to the interface between the housing 208 and the applicator cap 210 during example gaseous chemical sterilization, according to one or more embodiments. FIG. 102A depicts FEA analysis results as the applicator cap 210 is secured to the housing 208, such as by screwing the applicator cap 210 onto the housing 208 via the threads 10102 (FIG. 101). As illustrated, a radial preload may be generated at the radial seal 10106 as the radial protrusion 10107 provided on the second axial extension 10110b is urged into radial contact with the inner radial surface of the first axial extension 10110a. Moreover, a combination axial and radial preload may be generated at the axial-radial seal 10108 as the chamfered surface 10112 is urged into both axial and radial engagement with the fillet 10114.

FIG. 102B depicts FEA analysis results during an increase in temperature resulting from gaseous chemical sterilization. The temperature increase results in differential expansion between the materials of the housing 208 and cap 210. Depending on the materials chosen, the applicator cap 210 may expand radially more or less than the housing 208. During this temperature increase and the radial expansion of the housing 208 and the applicator cap 210, the axial-radial seal 10108 remains intact as the chamfered surface 10112 is wedged into both axial and radial engagement with the fillet 10114. Hence, the expansion of the fillet 10114 may dictate the final position of the axial-radial seal 10108 at elevated temperature. Depending upon whether the housing 208 material has a higher coefficient of thermal expansion than the applicator cap 210 material, or vice-versa, this result may or may not apply to the radial seal 10106.

The elevated temperatures during gaseous chemical sterilization are typically maintained for long periods of time. During this time, stress relaxation may occur in all the stressed zones of the applicator cap 210 and insignificant residual stress is expected at the end of the temperature cycle. This implies that most of the preload (and hence sealing) is lost at elevated temperature.

FIG. 102C depicts FEA analysis results after decreasing the temperature following gaseous chemical sterilization. In embodiments where the applicator cap 210 is made of a material having a higher coefficient of thermal expansion than the housing 208, the radial seal 10106 is likely lost upon decreasing the temperature to ambient due to stress relaxation at the elevated temperature. As a result, separation of the first and second axial extensions 10110a,b occurs and a gap 2816 is formed between the two surfaces after cooling. In contrast, in embodiments where the housing 208 is made of a material having a higher coefficient of thermal expansion than the applicator cap 210, the radial seal 10106 may be re-activated following cooling. In either scenario, however, the axial-radial seal 10108 may remain intact throughout the temperature cycle as the chamfered surface 10112 is continuously wedged into both axial and radial engagement with the fillet 10114. Accordingly, the axial-radial seal 10108 may prove advantageous in maintaining sealed engagement between the housing 208 and the applicator cap 210 regardless of the materials used.

Embodiments disclosed herein include:

EE. An analyte monitoring system enclosure including a sensor applicator including a housing that provides a first axial extension, a cap matable with the housing and providing a second axial extension, and an axial-radial seal that seals an interface between the housing and the cap in both axial and radial directions, wherein the axial-radial seal includes a fillet defined by one of the first and second axial extensions, and a chamfered surface matable with the fillet and defined on an end of the other of the first and second axial extensions.

FF. A method of sterilizing contents within an analyte monitoring system enclosure including injecting a chemical gas into the analyte monitoring system enclosure, the analyte monitoring system enclosure comprising a sensor applicator including a housing that provides a first axial extension, and a cap matable with the housing and providing a second axial extension. The method further including sealing an interface between the housing and the cap in both axial and radial directions with an axial-radial seal, wherein the axial-radial seal includes a fillet defined by one of the first and second axial extensions, and a chamfered surface matable with the fillet and defined on an end of the other of the first and second axial extensions, increasing and decreasing a temperature of the analyte monitoring system enclosure, and maintaining the axial-radial seal as the temperature is increased and decreased.

GG. A method of sterilizing contents within an analyte monitoring system enclosure including providing the analyte monitoring system enclosure, the analyte monitoring system enclosure comprising a sensor applicator including a housing that provides a first axial extension, and a cap matable with the housing and providing a second axial extension. The method further including increasing a temperature of the analyte monitoring system enclosure until a gap forms between the first and second axial extensions, injecting a chemical gas into the analyte monitoring system enclosure through the gap, evacuating the chemical gas from the analyte monitoring system enclosure through the gap, and decreasing the temperature of the analyte monitoring system and sealing an interface between the first and second axial extensions with a radial seal.

Each of embodiments EE, FF, and GG may have one or more of the following additional elements in any combination: Element 1: wherein the housing and the cap are made of dissimilar materials having dissimilar coefficients of thermal expansion. Element 2: wherein the fillet comprises angularly offset surfaces angled to mate with an angled profile of the chamfered surface in both the axial and radial directions. Element 3: further comprising a radial seal provided between the first and second axial extensions. Element 4: wherein the radial seal comprises a radial protrusion formed on an inner or outer surface of one of the first and second axial extensions. Element 5: wherein the first axial extension is received within the second axial extension and the radial protrusion is formed on the outer surface of the first axial extension or the inner surface of the second axial extension. Element 6: wherein the second axial extension is received within the first axial extension and the radial protrusion is formed on the inner surface of the first axial extension or the outer surface of the second axial extension. Element 7: wherein the cap is secured to the housing via a threaded engagement.

Element 8: wherein maintaining the axial-radial seal comprises wedging the chamfered surface into one or both of axial and radial engagement with the fillet as the temperature is increased and decreased. Element 9: wherein the housing and the cap are made of dissimilar materials having dissimilar coefficients of thermal expansion. Element 10: further comprising radially sealing an interface between the housing and the cap with a radial seal. Element 11: wherein the radial seal comprises a radial protrusion formed on an inner radial surface or an outer radial surface of one of the first and second axial extensions, and wherein radially sealing the interface comprises urging the radial protrusion into engagement with an opposing surface of the other of the first and second axial extensions. Element 12: wherein the cap is secured to the housing via a threaded engagement.

Element 13: wherein the housing and the cap are made of dissimilar materials having dissimilar coefficients of thermal expansion. Element 14: wherein the radial seal comprises a radial protrusion formed on an inner radial surface or an outer radial surface of one of the first and second axial extensions, and wherein radially sealing the interface comprises urging the radial protrusion into engagement with an opposing surface of the other of the first and second axial extensions. Element 15: wherein the bottom of the cap is solid without vents formed therein. Element 16: further maintaining a low humidity environment within the cap with a desiccant.

By way of non-limiting example, exemplary combinations applicable to EE, FF, and GG include: Element 3 with Element 4; Element 4 with Element 5; Element 4 with Element 6; and Element 10 with Element 11.

Conversion Process for Sensor Control Devices

Referring again briefly to FIG. 1, the sensor control device 104 is often included with the sensor applicator 104 in what is known as a "two-piece" architecture that requires final assembly by a user before the sensor 110 can be properly delivered to the target monitoring location. More specifically, the sensor 110 and the associated electrical components included in the sensor control device 104 are provided to the user in multiple (two) packages, and the user must open the packaging and follow instructions to manually assemble the components before delivering the sensor 110 to the target monitoring location with the sensor applicator 102. More recently, advanced designs of sensor control devices and sensor applicators have resulted in a one-piece architecture that allows the system to be shipped to the user in a single, sealed package that does not require any final user assembly steps. Rather, the user need only open one package and subsequently deliver the sensor control device to the target monitoring location. Notwithstanding these advancements, however, sensor control devices are still frequently made of hard plastic materials that contain several component parts.

According to the present disclosure, sensor control devices (e.g., the sensor control device 104) may alternatively be manufactured through a converting process that incorporate large rolls of process material that are progressively modified to form or otherwise assemble flexible sensor control devices in step-wise fashion. The converting processes described herein may use pressure sensitive adhesives (PSAs) or tapes, thermoformed films, die-cut or layered components, and other materials that readily lend themselves to roll-to-roll or other high volume manufacturing processes. These high-volume manufacturing processes have the potential to greatly decrease the cost of manufacturing sensor control devices and increase the rate of assembly.

Figure 103:
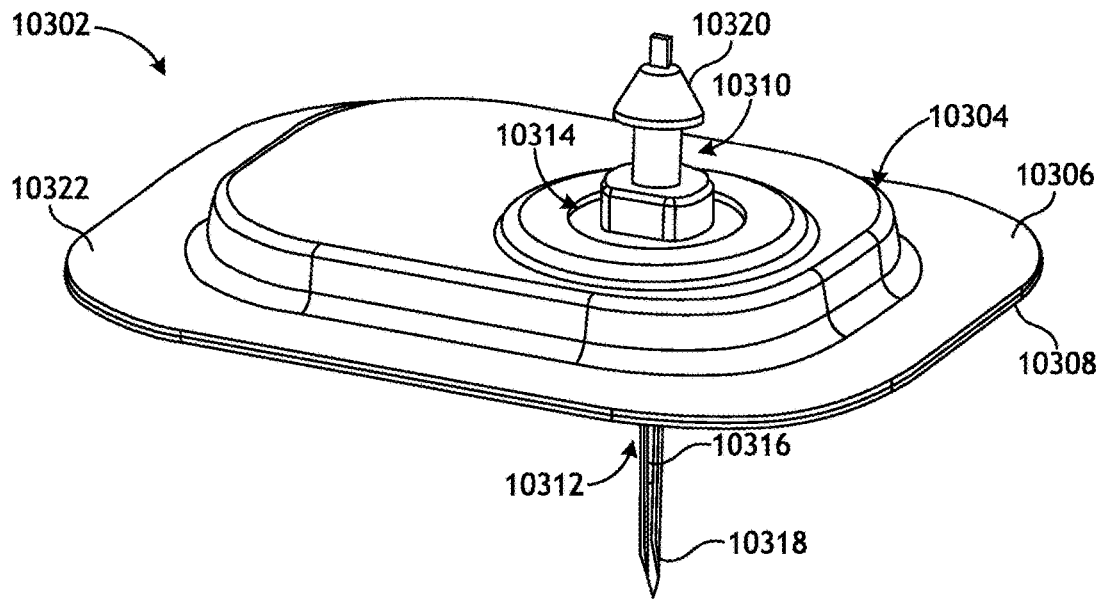
FIG. 103 is an isometric view of an example sensor control device.

FIG. 103 is an isometric view of an example sensor control device 10302, according to one or more embodiments of the present disclosure. The sensor control device 10302 may be the same as or similar to the sensor control device 104 of FIG. 1 and, therefore, may be used in conjunction with the sensor applicator 102 (FIG. 1), which delivers the sensor control device 10302 to a target monitoring location on a user's skin.

As illustrated, the sensor control device 10302 includes an electronics housing 10304 that is generally planar in shape and can exhibit a variety of cross-sectional shapes. In the illustrated embodiment, the electronics housing 10304 is rectangular with rounded corners, but could exhibit other cross-sectional shapes, such as circular, oval, ovoid (e.g., pill- or egg-shaped), a squircle, another polygonal shape (e.g., square, pentagonal, etc.), or any combination thereof, without departing from the scope of the disclosure. The electronics housing 10304 may be configured to house or otherwise contain various electronic components used to operate the sensor control device 10302.

The electronics housing 10304 may include an upper cover 10306 and a lower cover 10308 that is matable with the upper cover 10306. In some embodiments, the upper and lower covers 10306, 10308 may comprise a film, a foil, a foam, a laminated material (e.g., a laminated metal or foil), a coextruded material, a cast film, a comolded material, or any combination thereof. Accordingly, the upper and lower covers 10306, 10308 may be made of a variety of semi-rigid or flexible materials including, but not limited to, a plastic or thermoplastic, a metal, a composite material (e.g., fiberglass, etc.), or any combination thereof. Moreover, the upper and lower covers 10306, 10308 may be formed via a variety of manufacturing processes including, but not limited to, thermoforming, vacuum forming, injection molding, die-cutting, stamping, compression molding, transfer molding, or any combination thereof.

The upper cover 10306 may be secured to the lower cover 10308 via a variety of mating techniques, such as sonic welding, ultrasonic welding, laser welding, heat sealing, an adhesive substrate (e.g., a pressure sensitive adhesive or tape), or any combination thereof. In some cases, the upper cover 10306 may be secured to the lower cover 10308 such that a sealed interface is generated therebetween. The sealed interface may provide structural integrity, but may also isolate the interior of the electronics housing 10304 from outside contamination. In the illustrated embodiment, securing the upper cover 10306 to the lower cover 10308 may result in the formation of a flange 10322 extending about the periphery of the electronics housing 10304. In other embodiments, however, the upper and lower covers 10306, 10308 may be secured without forming the flange 10322.

In the illustrated embodiment, the sensor control device 10302 may optionally include a plug assembly 10310 that may be coupled to the electronics housing 10304. The plug assembly 10310 may include a sensor module 10312 (partially visible) interconnectable with a sharp module 10314 (partially visible). The sensor module 10312 may be configured to carry and otherwise include a sensor 10316 (partially visible), and the sharp module 10314 may be configured to carry and otherwise include an introducer or sharp 10318 (partially visible) used to help deliver the sensor 10316 transcutaneously under a user's skin during application of the sensor control device 10302. In the illustrated embodiment, the sharp module 10314 includes a sharp hub 10320 that carries the sharp 10318.

As illustrated, corresponding portions of the sensor 10316 and the sharp 10318 extend distally from the electronics housing 10304 and, more particularly, from the bottom of the lower cover 10308. In at least one embodiment, the exposed portion of the sensor 10316 (alternately referred to as the "tail") may be received within a hollow or recessed portion of the sharp 10318. The remaining portions of the sensor 10316 are positioned within the interior of the electronics housing 10304.

Figure 104A:
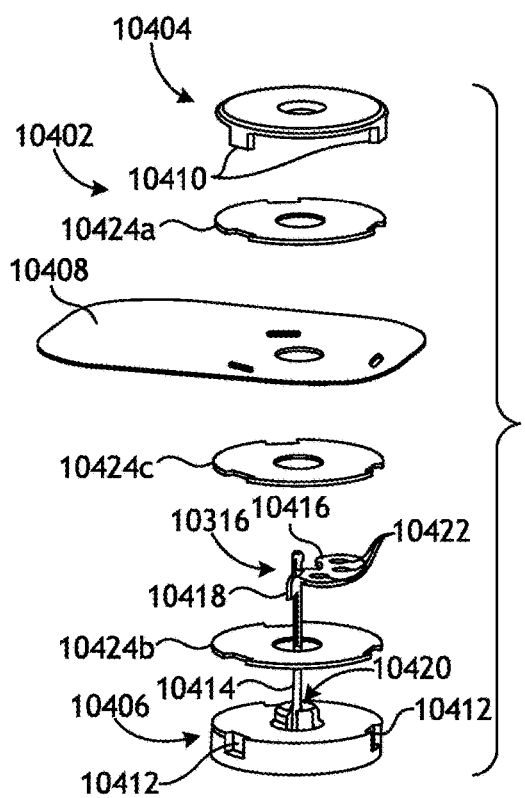
FIGS. 104A and 104B are exploded, isometric views of the sensor control device of FIG. 103, according to one or more embodiments.
Figure 104B:
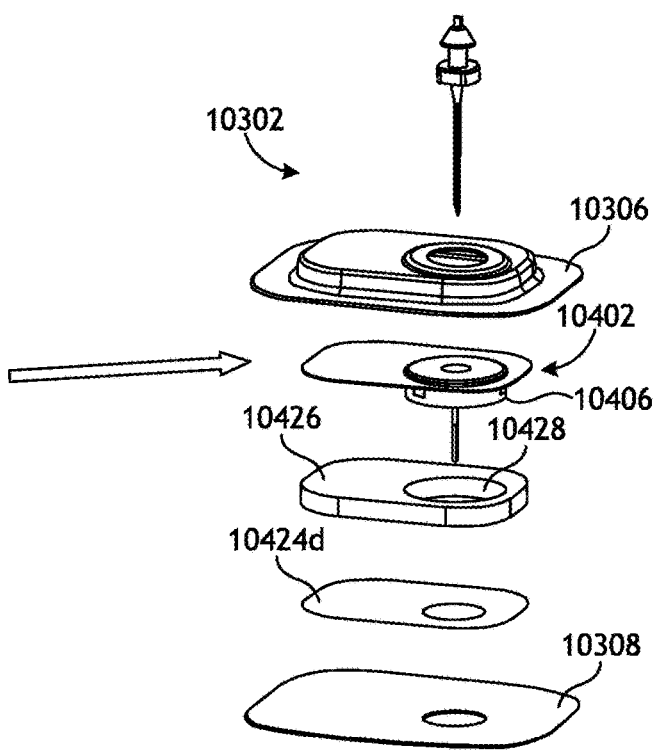

FIGS. 104A and 104B are exploded, isometric views of the sensor control device 10302 of FIG. 103, according to one or more embodiments. More specifically, FIG. 104A is an exploded, isometric view of a sensor electronics module 10402 included in the sensor control device 10302, and FIG. 104B is an exploded, isometric view of the sensor control device 10302 with the sensor electronics module 10402.

Referring first to FIG. 104A, the sensor electronics module 10402 may include a cap 10404, a sensor holder 10406, the sensor 10316, and a printed circuit board (PCB) 10408. The cap 10404 and the sensor holder 10406 may be made of injection molded plastic, for example, and may be configured to secure the sensor 10316 within the sensor electronics module 10402. To accomplish this, the cap 10404 and the sensor holder 10406 may be engageable and matable. In the illustrated embodiment, for example, the cap 10404 includes or defines one or more castellations or projections 10410 sized to be received within or mate with one or more corresponding grooves or pockets 10412 defined on the sensor holder 10406. Mating the projections 10410 with the pockets 10412 may help secure the sensor 10316 within the sensor electronics module 10402 and may also clamp down on the PCB 10408 and the other component parts of the sensor electronics module 10402, thus resulting in a solid structural component. In other embodiments, however, the projections 10410 may alternatively be provided on the sensor holder 10406, and the cap 10404 may instead define the pockets 10412, without departing from the scope of the disclosure.

As illustrated, the sensor 10316 includes a tail 10314, a flag 10416, and a neck 10418 that interconnects the tail 10314 and the flag 10416. The tail 10314 may be configured to extend at least partially through a channel 10420 defined in the sensor holder 10406 and extend distally from the sensor electronics module 10402. The tail 10314 includes an enzyme or other chemistry or biologic and, in some embodiments, a membrane may cover the chemistry. In use, the tail 10314 is transcutaneously received beneath a user's skin, and the chemistry included thereon helps facilitate analyte monitoring in the presence of bodily fluids. The flag 10416 may comprise a generally planar surface having one or more sensor contacts 10422 (three shown) arranged thereon. The sensor contacts 10422 may be configured to align with a corresponding number of circuitry contacts (not shown) included on the PCB 10408 that provide conductive communication between the sensor 10316 and the electronic components provided on the PCB 10408.

In some embodiments, the PCB 10408 may be flexible, and may be sized to be positioned within the electronics housing 10304 (FIG. 103). A plurality of electronic modules (not shown) may be mounted to the PCB 10408 including, but not limited to, a data processing unit, resistors, transistors, capacitors, inductors, diodes, and switches. The data processing unit may comprise, for example, an application specific integrated circuit (ASIC) configured to implement one or more functions or routines associated with operation of the sensor control device 10302 (FIGS. 103 and 104B). More specifically, the data processing unit may be configured to perform data processing functions, where such functions may include but are not limited to, filtering and encoding of data signals, each of which corresponds to a sampled analyte level of the user. The data processing unit may also include or otherwise communicate with an antenna for communicating with the reader device 106 (FIG. 1). One or more batteries (not shown) may also be mounted to the PCB 10408 and used to power the sensor control device 10302.

The sensor electronics module 10402 may further include one or more adhesive substrates, shown as a first adhesive substrate 10424a, a second adhesive substrate 10424b, and a third adhesive substrate 10424c. In some embodiments, each adhesive substrate 10424a-c may comprise a pressure-adhesive tape that forms a bond when pressure is applied. The first adhesive substrate 10424a may interpose the cap 10404 and the PCB 10408 and may operate to secure the cap 10404 to the PCB 10408. The second adhesive substrate 10424b may interpose the sensor holder 10406 and the sensor 10316 (i.e., the flag 10416) and may operate to secure the sensor 10316 to the sensor holder 10406.

The third adhesive substrate 10424c may interpose the sensor 10316 (i.e., the flag 10416) and the flexible PCB 10408 to couple the sensor 10316 to the PCB 10408. In some embodiments, the third adhesive substrate 10424c may also comprise a Z-axis anisotropic (or conductive) pressure-adhesive tape. In such embodiments, the third adhesive substrate 10424c may also facilitate electrical communication between the sensor contacts 10422 provided on the flag 10416 and the corresponding circuitry contacts included on the PCB 10408. Coupling the cap 10404 and the sensor holder 10406 may help maintain sufficient pressure on the third adhesive substrate 10424c to ensure reliable electrical connection between the sensor 10316 and the PCB 10408. Each of the adhesive substrates 320a-c may also seal against liquid and moisture, thus helping to mitigate the chances of shorting the sensor 10316 and the PCB 10408.

Referring now to FIG. 104B, the sensor electronics module 10402 may be sized to be received between the upper and lower covers 10306, 10308. In the illustrated embodiment, the upper cover 10306 provides or otherwise defines a cavity that may receive the sensor electronics module 10402. In other embodiments, however, the lower cover 10308, or both the upper and lower covers 10306, 10308, could alternatively define the cavity, without departing from the scope of the disclosure.

The sensor control device 10302 may also include a filler 10426 that may be arranged between the upper and lower covers 10306, 10308. In some embodiments, the filler 10426 may comprise foam made of a low-density polyethylene, polyolefin, or polyurethane. Moreover, the filler 10426 may be die cut and/or molded to mate with the sensor electronics module 10402. As illustrated, for instance, the filler 10426 may define an aperture 328 sized to receive a portion of the sensor electronics module 10402 and, more particularly, the sensor holder 10406. In some embodiments, the filler 10426 may operate similar to a potting material by taking up space within the electronics housing 10304 (FIG. 103) that would otherwise be occupied by air. Moreover, the material of the filler 10426 may expand less than air at elevated altitudes, such as would be experienced during shipping. The filler 10426 may also help to stabilize the electrical components of the PCB 10408 (FIG. 104B) and mitigate vibration.

The sensor control device 10302 may further include a fourth adhesive substrate 10424d, which may also comprise a pressure-adhesive tape that forms a bond when pressure is applied. The fourth adhesive substrate 10424b may interpose the lower cover 10308 and the filler 10426, and may operate to secure the filler 10426 to the lower cover 10308. The adhesive substrates 10424a-d may each be die-cut, thermoformed, or stamped pieces of material.

Figure 105:
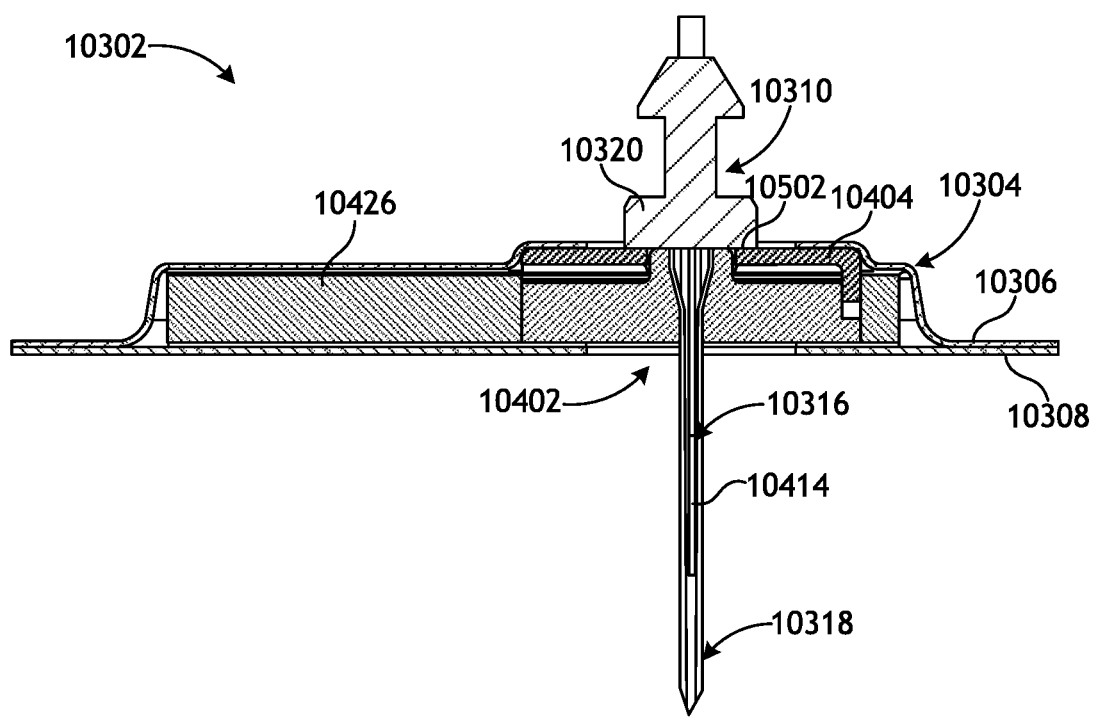
FIG. 105 is a cross-sectional side view of the assembled sensor control device of FIGS. 104A-104B, according to one or more embodiments.

FIG. 105 is a cross-sectional side view of the assembled sensor control device 10302, according to one or more embodiments. Securing the upper and lower covers 10306, 10308 to one another, as described above, secures the sensor electronics module 10402 and the filler 10426 within the electronics housing 10304. Once the upper and lower covers 10306, 10308 are secured, the plug assembly 10310 may be received by the sensor control device 10302 by extending the sharp 10318 through the electronics housing 10304 until the sharp hub 10320 engages a top surface 10502 of the sensor control device 10302, such as a top surface of the cap 10404. As the sharp 10318 extends through the electronics housing 10304, the sensor 10316 (e.g., the tail 10314) may be received within a hollow or recessed portion of the sharp 10318.

As described in more detail below, the sensor control device 10302 may be manufactured via a converting process, where some parts of the sensor control device 10302 are assembled or otherwise formed in a step-wise fashion from large rolls of material. As a result, the sensor control device 10302 may be entirely made at a factory, thus eliminating user assembly. Moreover, whereas current sensor control devices commonly use glues, potting, or casting and encapsulating compounds to seal and enclose (encapsulate) the sensor 10316 and the PCB 10408, fabricating the sensor control device 10302 using the presently disclosed converting processes eliminates the need for glues or "wet chemistry," thus making the fabrication process not dependent on curing methods or time.

Figure 106:
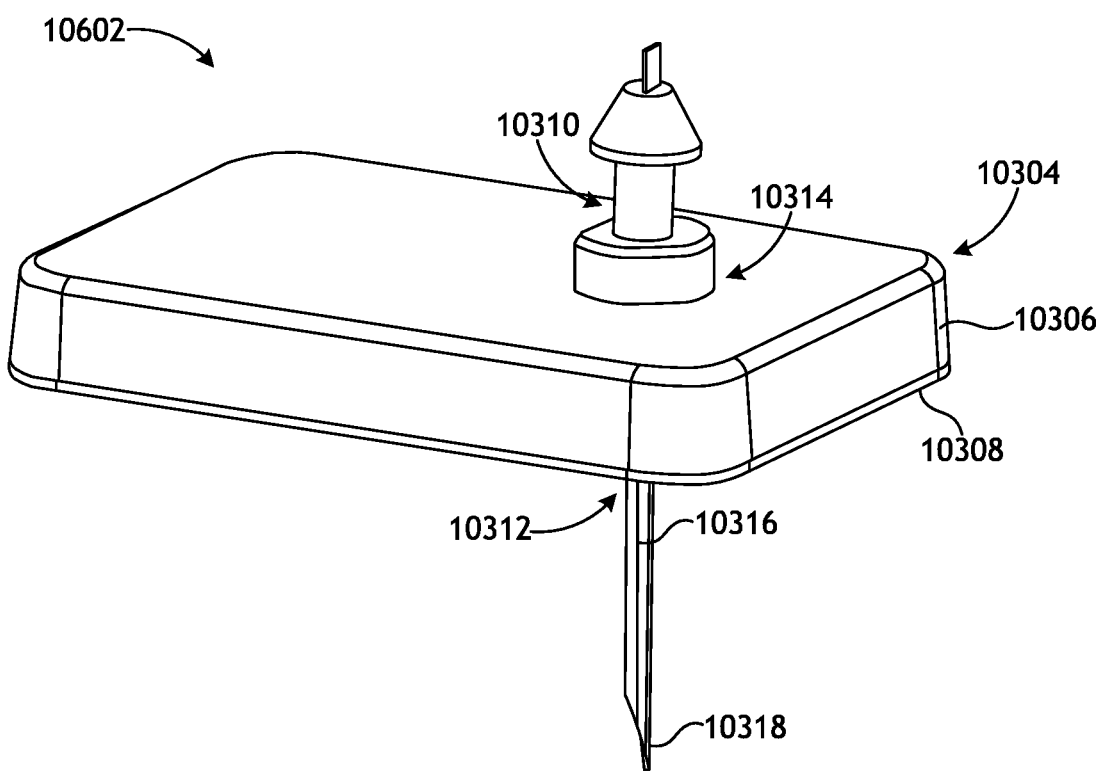
FIG. 106 is an isometric view of another example sensor control device.

FIG. 106 is an isometric view of another example sensor control device 10602, according to one or more embodiments of the present disclosure. The sensor control device 10602 may be the same as or similar to the sensor control device 104 of FIG. 1 and, therefore, may be used in conjunction with the sensor applicator 102 (FIG. 1), which delivers the sensor control device 10602 to a target monitoring location on a user's skin. Moreover, the sensor control device 10602 may be similar in some respects to the sensor control device 10302 of FIGS. 103, 104A-104B and 105 and therefore may be best understood with reference thereto, where like numerals will represent like components not described again in detail.

Similar to the sensor control device 10302 of FIGS. 103, 104A-104B and 105, the sensor control device 10602 includes the electronics housing 10304 made of the upper and lower covers 10306, 10308. The sensor control device 10602 may further include the plug assembly 10310, the sensor module 10312 with the sensor 10316, and the sharp module 10314 with the sharp 10318. Corresponding portions of the sensor 10316 and the sharp 10318 extend distally from the electronics housing 10304 and, more particularly, from the bottom of the lower cover 10308. Unlike the sensor control device 10302, however, one or both of the upper and lower covers 10306, 10308 may be made of a rigid material such as, but not limited to, a plastic, a metal, a composite material, a ceramic, or any combination thereof. Alternatively, one or both of the upper and lower covers 10306, 10308 can be made of a semi rigid or flexible materials, such as an elastomer.

Figure 107A:
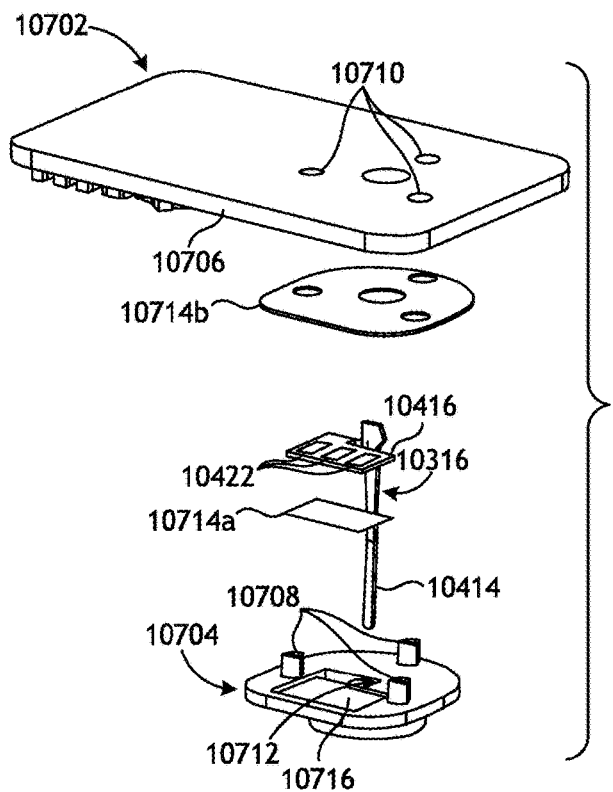
FIGS. 107A and 107B are exploded, isometric views of the sensor control device of FIG. 106, according to one or more embodiments.
Figure 107B:
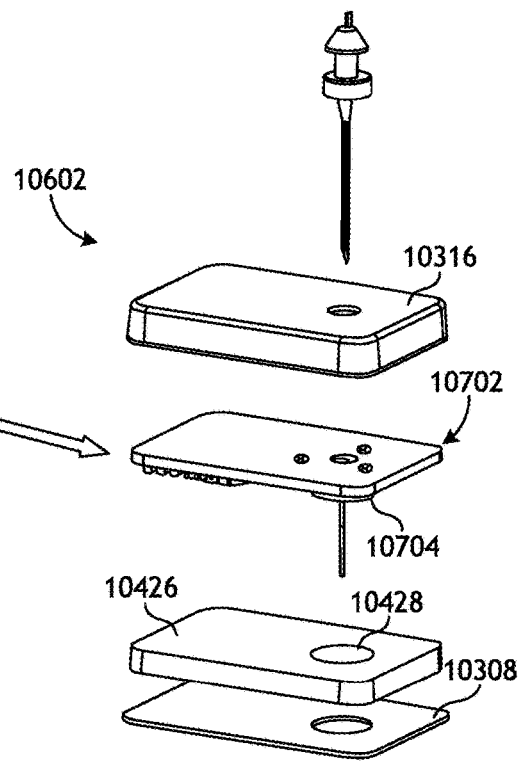

FIGS. 107A and 107B are exploded, isometric views of the sensor control device 10602 of FIG. 106, according to one or more embodiments. More specifically, FIG. 107A is an exploded, isometric view of a sensor electronics module 10702 included in the sensor control device 10602, and FIG. 107B is an exploded, isometric view of the sensor control device 10602 with the sensor electronics module 10702.

Referring first to FIG. 107A, the sensor electronics module 10702 includes a sensor holder 10704, the sensor 10316, and a printed circuit board (PCB) 10706, which may be similar in some respects to the PCB 10408 of FIG. 104A. The sensor holder 10704 may be made of injection molded plastic, for example, and may be configured to secure the sensor 10316 to the sensor electronics module 10702. To accomplish this, the sensor holder 10704 may be engageable and matable with the PCB 10706. In the illustrated embodiment, for example, the sensor holder 10704 includes or defines one or more projections 107608 (three shown) sized to be received within or mate with one or more corresponding holes 10710 (three shown) defined on the PCB 10706. Mating the projections 107608 with the holes 10710 may secure the sensor 10316 to the sensor electronics module 10702, thus resulting in a solid structural component. In other embodiments, however, the projections 107608 may alternatively be provided on the PCB 10706, and the sensor holder 10704 may instead define the holes 10710, without departing from the scope of the disclosure.

The tail 10314 of the sensor 10316 may be configured to extend through a channel 10712 defined in the sensor holder 10704 and extend distally from the sensor electronics module 10702. The sensor contacts 10422 of the flag 10416 may be configured to align with a corresponding number of circuitry contacts (not shown) included on the PCB 10706 that provide conductive communication between the sensor 10316 and corresponding electronic components provided on the PCB 10706.

The sensor electronics module 10702 may further include one or more adhesive substrates, shown as a first adhesive substrate 10714a and a second adhesive substrate 10714b. Similar to the adhesive substrates 10424a-d of FIGS. 104A-104B, each adhesive substrate 10714a,b may comprise a pressure-adhesive tape that forms a bond when pressure is applied, and may each be die-cut, thermoformed, or stamped pieces of material. The first adhesive substrate 10714a may interpose the sensor holder 10704 and the sensor 10316 (i.e., the flag 10416) and may operate to secure the sensor 10316 to the sensor holder 10704. In some embodiments, the sensor holder 10704 may define a depression 10716 sized to receive one or both of the first adhesive substrate 10714a and the flag 10416.

The second adhesive substrate 10714b may be configured to help attach the sensor 10316 and the sensor holder 10704 to the PCB 10706. Moreover, the second adhesive substrate 10714b may comprise a Z-axis anisotropic (or conductive) pressure-adhesive tape and may therefore also facilitate electrical communication between the sensor contacts 10422 provided on the flag 10416 with the corresponding circuitry contacts included on the PCB 10706. Coupling the sensor holder 10704 to the PCB 10706 may help maintain sufficient pressure on the second adhesive substrate 10714b to ensure reliable electrical contact between the sensor 10316 and the PCB 10706. The adhesive substrates 10714a,b may also seal against liquid and moisture, thus helping to mitigate the chances of shorting the sensor 10316 and the PCB 10706.

Referring now to FIG. 107B, the sensor electronics module 10702 may be sized to be received between the upper and lower covers 10306, 10308. In the illustrated embodiment, the upper cover 10306 provides or otherwise defines a cavity that can receive the sensor electronics module 10702. In other embodiments, however, the lower cover 10308, or a combination of the upper and lower covers 10306, 10308, could alternatively define the cavity, without departing from the scope of the disclosure. The sensor control device 10602 may also include the filler 10426 arranged between the upper and lower covers 10306, 10308 and defining the aperture 10428 sized to receive a portion of the sensor electronics module 10702 and, more particularly, the sensor holder 10704.

Figure 108:
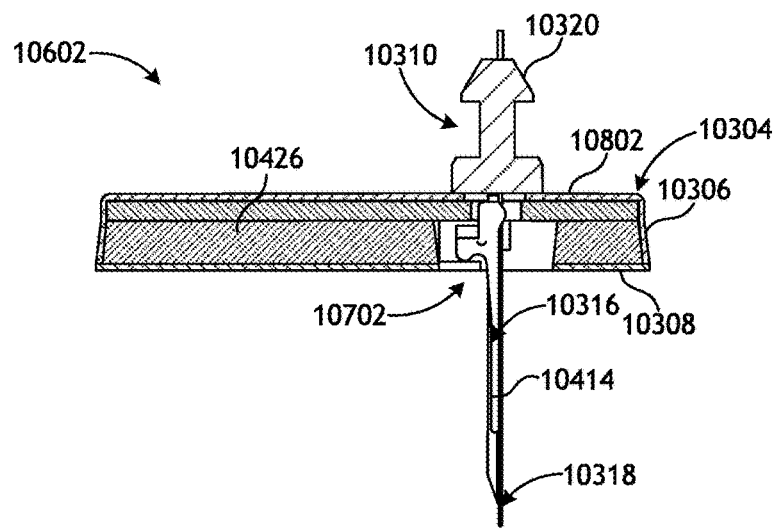
FIG. 108 is a cross-sectional side view of the assembled sensor control device of FIGS. 107A-107B, according to one or more embodiments.

FIG. 108 is a cross-sectional side view of the assembled sensor control device 10602, according to one or more embodiments. Securing the upper and lower covers 10306, 10308 to one another, as described herein, secures the sensor electronics module 10702 and the filler 10426 within the electronics housing 10304. Once the upper and lower covers 10306, 10308 are secured and otherwise sealed, the plug assembly 10310 may be received by the sensor control device 10602 by extending the sharp 10318 through the electronics housing 10304 until the sharp hub 10320 engages a top surface 10802 of the sensor control device 10602, such as a top surface of the upper cover 10306. As the sharp 10318 extends through the electronics housing 10304, the sensor 10316 (e.g., the tail 10314) may be received within a hollow or recessed portion of the sharp 10318.

Figure 109:
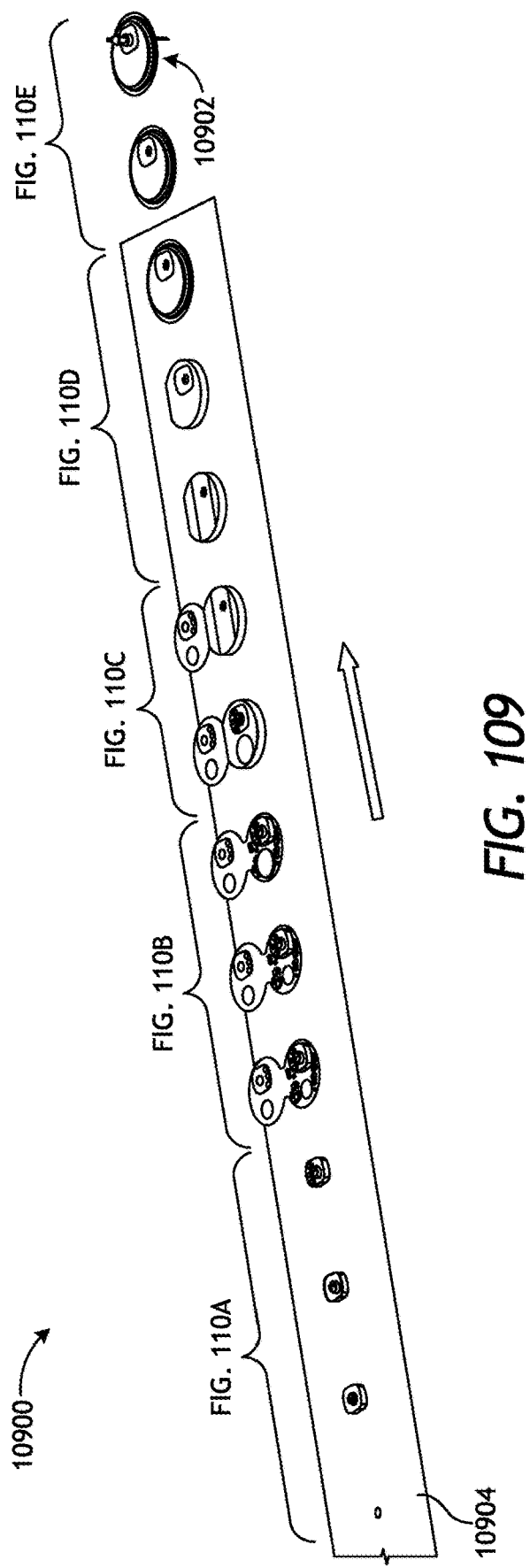
FIG. 109 is an isometric view of an example converting process for manufacturing a sensor control device in accordance with the principles of the present disclosure.

FIG. 109 is an isometric view of an example converting process 10900 for manufacturing a sensor control device 10902 in accordance with the principles of the present disclosure. More specifically, the converting process 10900 is depicted showing progressive, step-wise building of a web-based assembly that results in the fabrication of the sensor control device 10902. The sensor control device 10902 may be the same as or similar to any of the sensor control devices 104, 10302, 10602 described herein with reference to FIGS. 1, 103, and 106, respectively. Accordingly, any of the sensor control devices 104, 10302, 10602 may be fabricated using the presently described converting process 10900.

Whereas current sensor control devices are commonly made of hard plastics and require use assembly, the sensor control device 10902 made by the converting process 10900 may be made of flexible materials that do not require user assembly. Alternatively, rigid materials may instead be incorporated, without departing from the scope of the disclosure. The converting process 10900 may incorporate the use of one or more continuous rolls of process materials, such as a base substrate 10904 that may eventually form the lower cover 10308 (FIGS. 103 and 106) of the electronics housing 10304 (FIGS. 103 and 106). The base substrate 10904 may be continuously unrolled (unwound) from an adjacent roll (not shown) of material. This web-based process may include or exclude the incorporate of injection molded parts, such as for the upper or lower covers 10306, 10308. Consequently, fabrication of sensor control devices (e.g., the sensor control device 10902) using the converting process 10900 may proceed in a continuous process that progressively modifies and/or arranges the materials and component parts to form the sensor control devices 10902.

FIGS. 110A-110E are referenced in FIG. 109 and depict progressive fabrication of the sensor control device 10902, according to one or more embodiments. FIGS. 110A-110E will be described below to detail the various steps of the example converting process 10900.

Figure 110A:
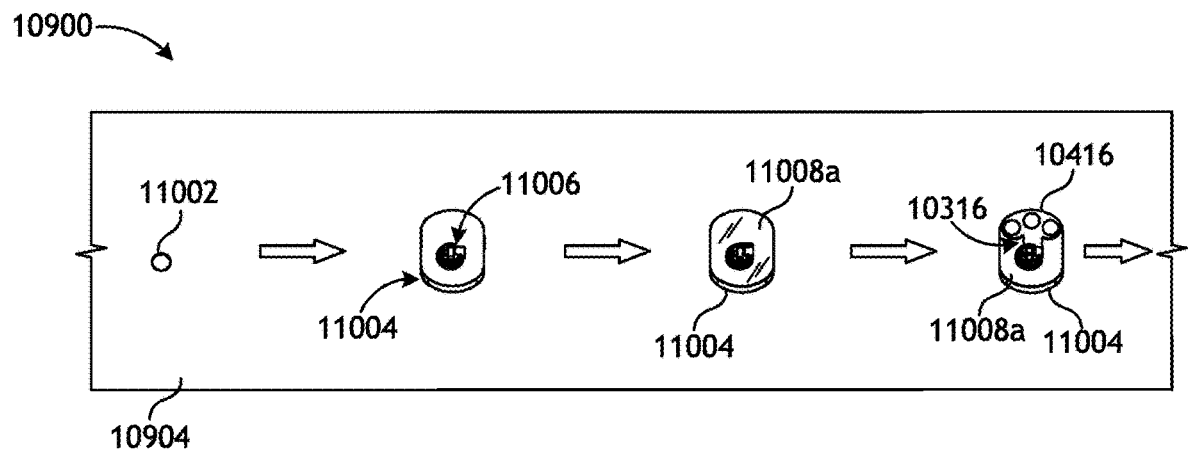
FIGS. 110A-110E depict progressive fabrication of the sensor control device of FIG. 109, according to one or more embodiments.

Referring first to FIG. 110A, in a first step of the process 10900, a hole 11002 may be punched or otherwise formed in the base substrate 10904, which may comprise a sheet of material that may eventually form the base or lower cover 10308 (FIGS. 103 and 106) of the sensor control device 10902 (FIG. 109). The base substrate 10904 may comprise a belt or thin film made of a variety of different materials including, but not limited to, a plastic, a metal, a composite material, or any combination thereof. In at least one embodiment, the base substrate 10904 may comprise a laminated aluminum foil having a polyester film on one side (e.g., the bottom side), and a polyolefin heat seal layer on the opposing side (e.g., the top side).

In a second step of the process 10900, a sensor holder 11004 may be coupled to the base substrate 10904. The sensor holder 11004 may be the same as or similar to either of the sensor holders 10406, 10704 of FIGS. 104A and 107A, respectively. Accordingly, the sensor holder 11004 may define a channel 11006 sized to receive the tail 10314 (FIGS. 104A and 107A) of the sensor 10316 (FIGS. 104A and 107A). In some embodiments, the sensor holder 11004 may be ultrasonically welded or heat-sealed to the base substrate 10904, thus resulting in a sealed and watertight engagement. In at least one embodiment, however, the base substrate 10904 may comprise or otherwise include an adhesive substrate on the top side to secure and seal the sensor holder in place.

In a third step of the process 10900, a first adhesive substrate 11008a may be attached to the top of the sensor holder 11004. The first adhesive substrate 11008a may be similar to any of the adhesive substrates 10424a-d (FIGS. 104A-104B), 10714a,b (FIGS. 107A-107B) described herein, and may thus comprise a pressure-adhesive tape that forms a bond when pressure is applied. In at least one embodiment, the first adhesive substrate 11008a may comprise double-sided polyolefin foam tape and may be pressure sensitive on both sides.

In a fourth step of the process 10900, the sensor 10316 may be secured to the sensor holder 11004 using the first adhesive substrate 11008a. More specifically, the tail 10314 (FIGS. 104A and 107A) may be extended through the channel 11006 and the flag 10416 may be bent generally orthogonal to the tail 10314 and coupled to the underlying first adhesive substrate 11008a.

Figure 110B:
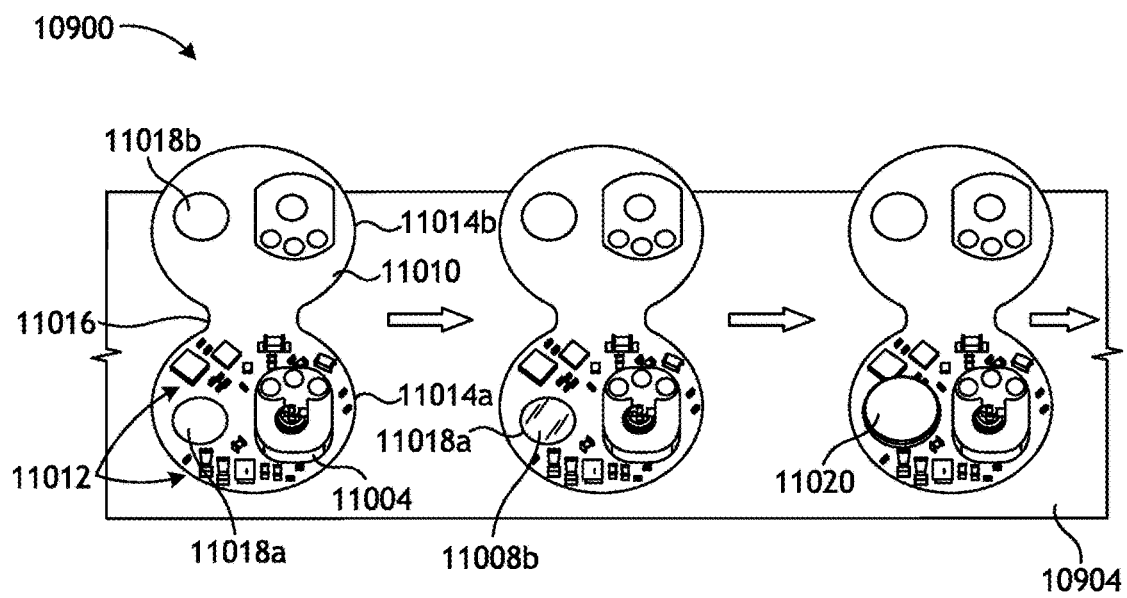

Referring now to FIG. 110B, in a fifth step of the process 10900, a printed circuit board (PCB) 11010 may be positioned on the base substrate 10904 and about the sensor holder 11004. The PCB 11010 may be similar in some respects to the PCB 10408 of FIGS. 104A and 107A, and may thus include a plurality of electronic modules 11012 mounted thereto. The electronic modules 11012 may include one or both of a Bluetooth antenna and a near field communication (NFC) antenna. As illustrated, the PCB 11010 may define two opposing lobes 11014a and 11014b interconnected by a neck portion 11016. Opposing battery contacts 11018a and 11018b may be provided on the opposing lobes 11014a,b to facilitate electrical communication with a battery 11020.

In a sixth step of the process 10900, a second adhesive substrate 11008b may be applied to the first battery contact 11018a in preparation for receiving the battery 11020 in an adjacent seventh step of the process 10900. The second adhesive substrate 11008b may comprise a pressure-adhesive tape used to couple the battery 11020 to the first battery contact 11018a. The second adhesive substrate 11008b, however, may also comprise a Z-axis anisotropic (or conductive) pressure-adhesive tape that also facilitates electrical communication (i.e., transfer of electrical power) between the battery 11020 and the first battery contact 11018a.

Figure 110C:
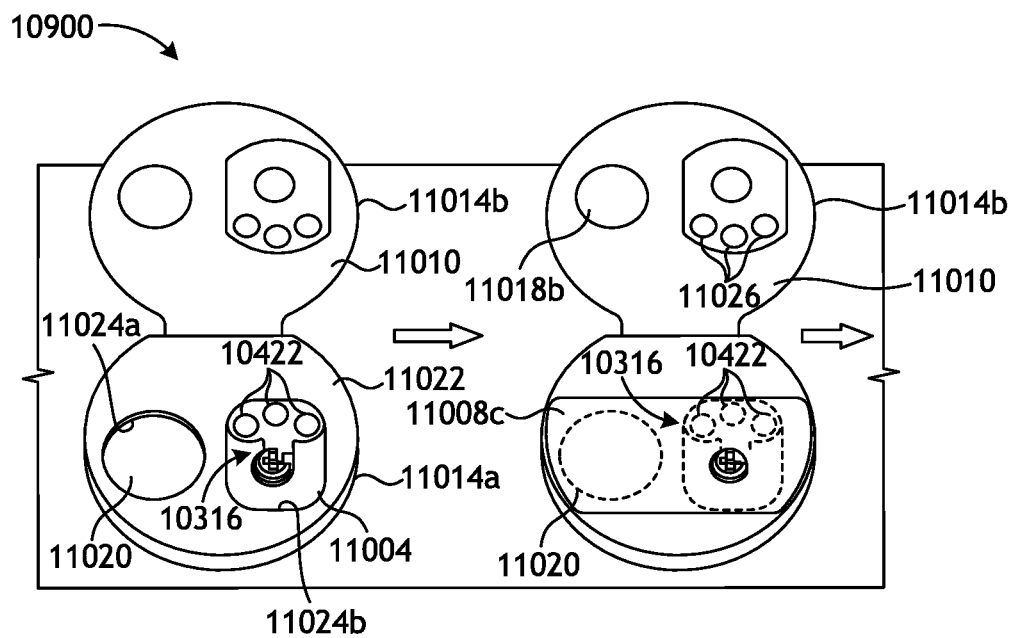

Referring now to FIG. 110C, in an eighth step of the process 10900, a filler 11022 may be positioned or arranged on the first lobe 11014a of the PCB 11010. The filler 11022 may be the same as or similar to the filler 10426 of FIG. 104B or 107B, and may thus comprise foam made of a low-density polyethylene or polyolefin. Moreover, the filler 11022 may be die cut and/or molded to fit around one or both of the battery 11020 and the sensor holder 11004. In the illustrated embodiment, the filler 11022 may define apertures 11024a and 11024b to receive the battery 11020 and/or the sensor holder 11004. The filler 11022 may also operate as a potting material that takes up space that would otherwise be occupied by air, and thus help to stabilize the electronic modules 11012 (FIG. 110B) of the PCB 11010 and mitigate damaging vibration.

In a ninth step of the process 10900, a third adhesive substrate 11008c may be applied to a top of the filler 11022 to help couple the second lobe 11014b of the PCB 11010 to the top of the filler 11022 in a subsequent step of the process 10900. The third adhesive substrate 11008c may comprise a pressure-adhesive tape, but may also comprise a Z-axis anisotropic (or conductive) pressure-adhesive tape that also facilitates electrical communication (i.e., transfer of electrical power) between the battery 11020 and the second battery contact 11018b. The third adhesive substrate 11008c may also facilitate electrical communication between the sensor contacts 10422 provided on the sensor 10316 and corresponding circuitry contacts 11026 (three shown) included on the PCB 11010.

Figure 110D:
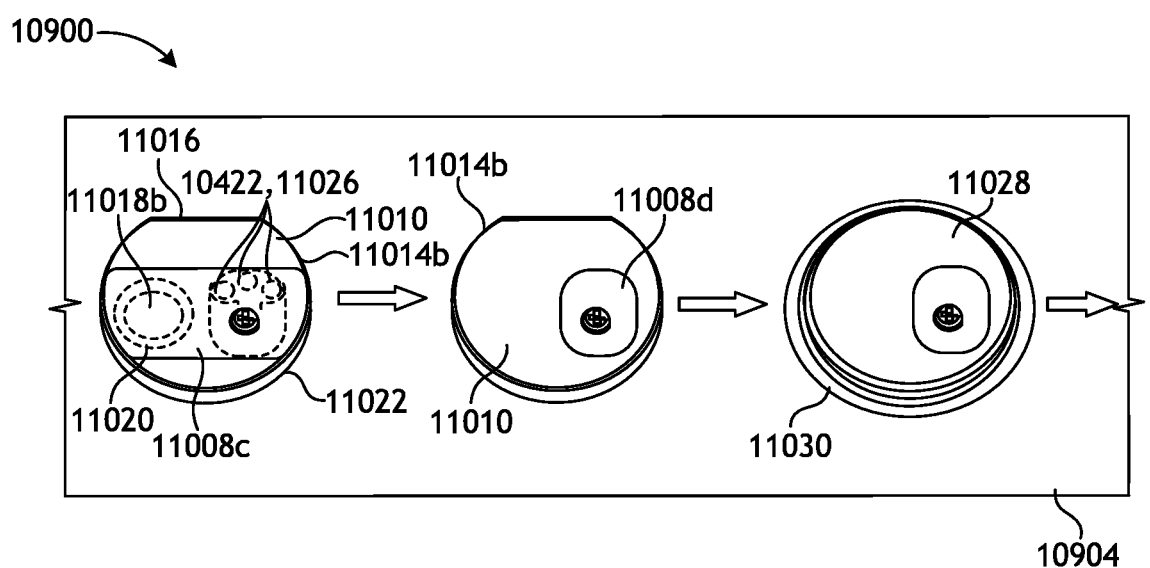

Referring now to FIG. 110D, in a tenth step of the process 10900, the second lobe 11014b of the PCB 11010 may be folded down at the neck 11016 to couple the PCB 11010 to the filler 11022. Coupling the PCB 11010 to the filler 11022 may also complete the conductive pathway via the third adhesive substrate 11008c between the battery 11020 and the second battery contact 11018b, and between the sensor contacts 10422 and the corresponding circuitry contacts 11026.

In an eleventh step of the process 10900, a fourth adhesive substrate 11008d may be applied to a portion of the top of the second lobe 11014b of the PCB 11010. The fourth adhesive substrate 11008d may also comprise a pressure-adhesive tape, and may be used to couple an upper cover 11028 to the PCB 11010, as provided in a twelfth step of the process 10900. The upper cover 11028 may be the same as or similar to the upper cover 10306 of FIGS. 103 and 106, and the fourth adhesive substrate 11008d may help secure the upper cover 10306 to the PCB 11010.

In some embodiments, the upper cover 11028 may be provided by another roll of material continuously provided to the web-based assembly in the process 10900. In some embodiments, the upper cover 11028 may be vacuum-formed, but could alternatively, be cold formed or injection molded, without departing from the scope of the disclosure. Accordingly, as indicated above, this web-based process 10900 may include or exclude injection molded parts, such as for the upper or lower covers 10306, 10308. In some embodiments, the upper cover 11028 may be formed or defined to provide a flange 11030 about its periphery, and the flange 11030 may provide a location to seal the upper cover 11028 to the base substrate 10904 (i.e., the "lower cover"). The upper cover 11028 may be secured to the base substrate 10904 via one or more of sonic welding, ultrasonic welding, laser welding, photonic flash soldering, heat sealing, an adhesive substrate (e.g., a pressure sensitive adhesive or tape), or any combination thereof. Alternatively, the fourth adhesive substrate 11008d may sufficiently couple the upper cover 11028 to the base substrate 10904, or an additional adhesive substrate (not shown) may be applied at the flange 11030 to secure the upper cover 11028 to the base substrate 10904, without departing from the scope of the disclosure.

Figure 110E:
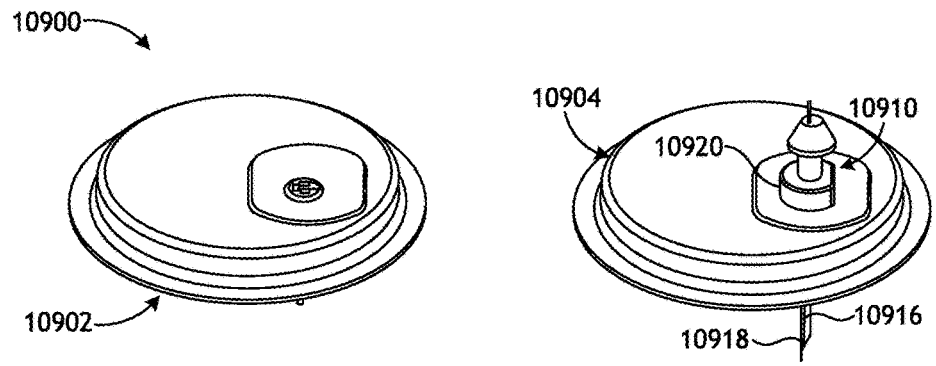

Referring now to FIG. 110E, in a thirteenth step of the process 10900, the outer diameter of the sensor control device 10902 may be trimmed to remove the excess portions of the base substrate 10904 (FIGS. 110A and 110D). In some embodiments, as illustrated, the sensor control device 10902 may have a substantially circular cross-section, but could alternatively comprise any other cross-sectional shape, such as polygonal, oval, ovoid (e.g., pill- or egg-shaped), a squircle, or any combination thereof, without departing from the scope of the disclosure.

In a fourteenth and final step of the process 10900, the plug assembly 10310 as described herein may be received by the sensor control device 10902 by extending the sharp 10318 through the sensor control device 10902 until the sharp hub 10320 engages a top surface of the sensor control device 10902. As the sharp 10318 extends through the sensor control device 10902, the sensor 10316 may be received within a hollow or recessed portion of the sharp 10318.

Figure 111A:
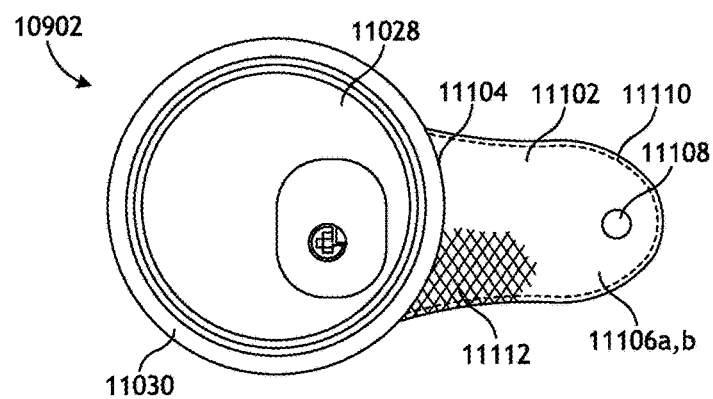

FIG. 111A is a top view of the sensor control device 10902 in preparation for pressure testing and/or vacuum sealing, according to one or more embodiments. In the illustrated embodiment, a web 11102 may form part of or otherwise extend from the sensor control device 10902 across a tab section 11104. The tab section 11104 may form part of the flange 11030 or may otherwise extend therefrom. The web 11102 may comprise two layers of film 11106a and 11106b. In some embodiments, for instance, the upper layer 11106a may be connected to or form part of the material that forms the upper cover 11028, as described above with reference to FIGS. 110D and 110E, and the lower layer 11106b may be connected to or form part of the base material 10904, as described above with reference to FIGS. 109, 110A and 110D.

An aperture 11108 may be defined through the upper layer 11106a (or the lower layer 11106b) to facilitate fluid communication between the two layers 11106a,b and the interior of the sensor control device 10902. A seal 11110 may be made about the periphery of the web 11102 to seal the upper and lower layers 11106a,b together. Moreover, the flange 11030 may be sealed about the periphery of the sensor control device 10902 except across the tab section 11104, thus facilitating fluid communication into and/or out of the sensor control device via the web 11102. In some embodiments, one or both of the upper and lower layers 11106a,b may provide or otherwise define a pattern or web of interconnected channels 11112 that help facilitate fluid communication between the aperture 11108 and the interior of the sensor control device 10902 via the tab section 11104.

By injecting air (or another fluid) into the sensor control device 10902 via the aperture 11108 and the web 11102, the sensor control device 10902 may be pressure tested to determine if the outer periphery (e.g., the flange 11030) or other portions of the sensor control device 10902 are properly sealed. This is often referred to as "pressure decay testing," and helps verify seal integrity of medical devices made of layers of film. Alternatively, air may be evacuated from the sensor control device 10902 via the aperture 11108 and the web 11102 to place the interior of the sensor control device 10902 under vacuum conditions. The channels 11112 may prove advantageous in helping to draw the vacuum without entirely collapsing the upper and lower layers 11106a,b.

Figure 111B:
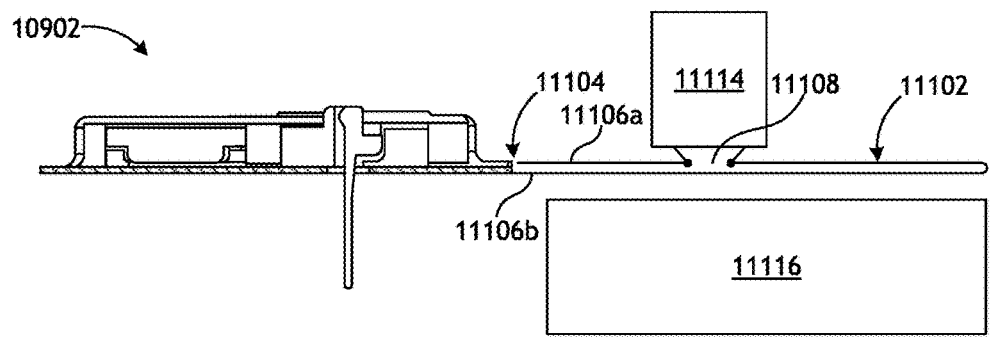

FIG. 111B is a cross-sectional side view of the sensor control device 10902 with a compressor 11114. The compressor 11114 may have proper fittings to fluidly couple to the web 11102 via the aperture 11108. In some embodiments, the compressor 11114 may be arranged on a back support 11116 to help support the pressure fitting at the aperture 11108.

To pressure test the sensor control device 10902 to determine if it meets pressure requirements, the compressor 11114 may inject air into the web 11102 via the aperture 11108, and the air may circulate to the interior of the sensor control device 10902 between the opposing layers 11106a,b and via the tab section 11104. This allows seal integrity testing to be performed during the manufacturing process of the sensor control device 10902. Once the seal integrity is verified, the periphery of the sensor control device 10902 at the tab section 11104 may be sealed and the web 11102 may be trimmed from the sensor control device 10902.

In some embodiments, after the sensor control device 10902 has been pressure tested, operation of the compressor 11114 may be reversed to pull a vacuum on the sensor control device 10902, as indicated above. Once the vacuum is drawn, the periphery of the sensor control device 10902 at the tab section 11104 may be sealed, thus leaving the sensor control device 10902 under vacuum conditions. As will be appreciated, vacuum conditions may prove advantageous since the sensor control device 10902 may be transported through high altitudes, where a non-vacuum sealed device would have a tendency to expand or "pillow" out. Moreover, the vacuum may be drawn during the manufacturing process, following which the web 11102 may be trimmed from the sensor control device 10902.

Figure 112:
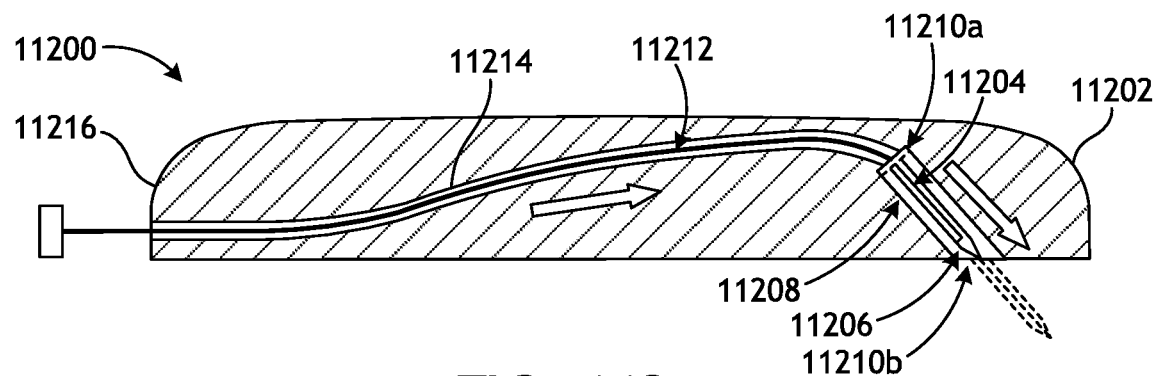

FIG. 112 is a partial cross-sectional side view of an example sensor control device 11200, according to one or more embodiments. The sensor control device 11200 may be similar in some respects to any of the sensor control devices described herein. As illustrated, the sensor control device 11200 may include a housing 11202 configured to house electronic modules or components used to operate the sensor control device. Example electronic modules include, but are not limited to a battery, a data processing unit (e.g., an application specific integrated circuit or ASIC), a resistor, a transistor, a capacitor, an inductor, a diode, and a switch.

The sensor control device 11200 may further include a sensor 11204 and a sharp 11206, which may be similar to any of the sensors and sharps described herein. Consequently, the sharp 11206 may be used to help transcutaneously implant the sensor 11204 beneath a user's skin for monitoring blood glucose levels. In the illustrated embodiment, the sensor 11204 and the sharp 11206 are arranged within a sterile chamber 11208 to protect the sensor 11204 and the sharp 11206 from external contamination. In some embodiments, the sterile chamber 11208 may have a desiccant arranged therein to help promote preferred humidity conditions.

In some embodiments, the sensor 11204 and the sharp 11206 may be sterilized while assembled within the sensor control device 11200. In at least one embodiment, the sensor 11204 and the sharp 11206 may be subjected to radiation sterilization to properly sterilize the sensor 11204 and the sharp 11206 for use. Suitable radiation sterilization processes include, but are not limited to, electron beam (e-beam) irradiation, gamma ray irradiation, X-ray irradiation, or any combination thereof.

In some embodiments, the sterile chamber 11208 may comprise a cap that provides a sealed barrier that protects exposed portions of the sensor 11204 and the sharp 11206 until placed in use. In such embodiments, the sterile chamber 11208 may be removable or detachable to expose the sensor 11204 and the sharp 11206, as described below. Moreover, in such embodiments, the cap may be made of a material that permits propagation of radiation therethrough to facilitate radiation sterilization of the sensor 11204 and the sharp 11206. Suitable materials for the sterile chamber 11208 include, but are not limited to, a non-magnetic metal (e.g., aluminum, copper, gold, silver, etc.), a thermoplastic, ceramic, rubber (e.g., ebonite), a composite material (e.g., fiberglass, carbon fiber reinforced polymer, etc.), an epoxy, or any combination thereof. In some embodiments, the sterile chamber 11208 may be transparent or translucent, but can otherwise be opaque, without departing from the scope of the disclosure.

In other embodiments, the sterile chamber 11208 may comprise a chamber or compartment defined within the sensor control device 11200. In such embodiments, the sterile chamber 11208 may include a microbial barrier positioned at one or both ends of the sterile chamber 11208. More specifically, the sterile chamber 11208 may provide or include an upper microbial barrier 11210a and a lower microbial barrier 11210b opposite the upper microbial barrier 11210a. The upper and lower microbial barriers 11210a,b may help seal the sterile chamber 11208 to thereby isolate the sensor 11204 and the sharp 11206 from external contamination. The microbial barriers 11210a,b may be made of a radiation permeable material, such as a synthetic material (e.g., a flash-spun high-density polyethylene fiber). One example synthetic material comprises TYVEK®, available from DuPont®. In other embodiments, however, the microbial barriers 11210a,b may comprise, but are not limited to, tape, paper, film, foil, or any combination thereof.

In some embodiments, the sensor 11204 and the sharp 11206 may be deployable and otherwise movable relative to the sensor control device 11200. In such embodiments, the sensor 11204 and the sharp 11206 may be advanced distally out of the sterile chamber 11208 and past the bottom of the housing 11202 to allow the sensor 11204 and the sharp 11206 to be transcutaneously received beneath a user's skin. Distally advancing the sensor 11204 and the sharp 11206 may be accomplished via a variety of mechanical or electromechancial means. In some embodiments, for example, the sensor control device 11200 may include a pusher 11212 configured to advance to push the sensor 11204 and the sharp 11206 out of the sterile chamber 11208. In such embodiments, the pusher 11212 may also be configured to attach to the sharp 11206 and subsequently retract the sharp 11206 while leaving the sensor 11204 extended. During operation, the pusher 11212 may penetrate the upper microbial barrier 11210a and force the sensor 11204 and the sharp 11206 distally through the lower microbial barrier 11210b.

As illustrated, the pusher 11212 may comprise a flexible shaft that extends within a curved pathway 11214 defined laterally through the housing 11202 and does not penetrate the top of the housing 11202. The pathway 11214 may terminate at or near an upper end of the sterile chamber 11208. In at least one embodiment, as illustrated, the pusher 11212 may extend out of the housing 11202 at a sidewall 11216 thereof. In such embodiments, actuation of the pusher 11212 may originate at the location of the sidewall 11216 to advance or retract the pusher 11212 within the pathway 11214 and thereby act on the sterile chamber 11208 and/or the sensor 11204, and the sharp 11206.

In embodiments where the sterile chamber 11208 comprises a cap, the pusher 11212 may be operable to discharge or push the cap out of the sensor control device 11200. In such embodiments, a user may commence the firing process by priming the sensor control device 11200, which may cause the cap to be discharged from the sensor control device 11200. Further actuation of the sensor control device 11200 by the user may cause the sensor 11204 and the sharp 11206 to be fully extended for subcutaneous implantation. In other embodiments, the cap may be removed either autonomously (e.g., it falls off or breaks away during firing) or the user may manually remove it by hand.

Figure 113:
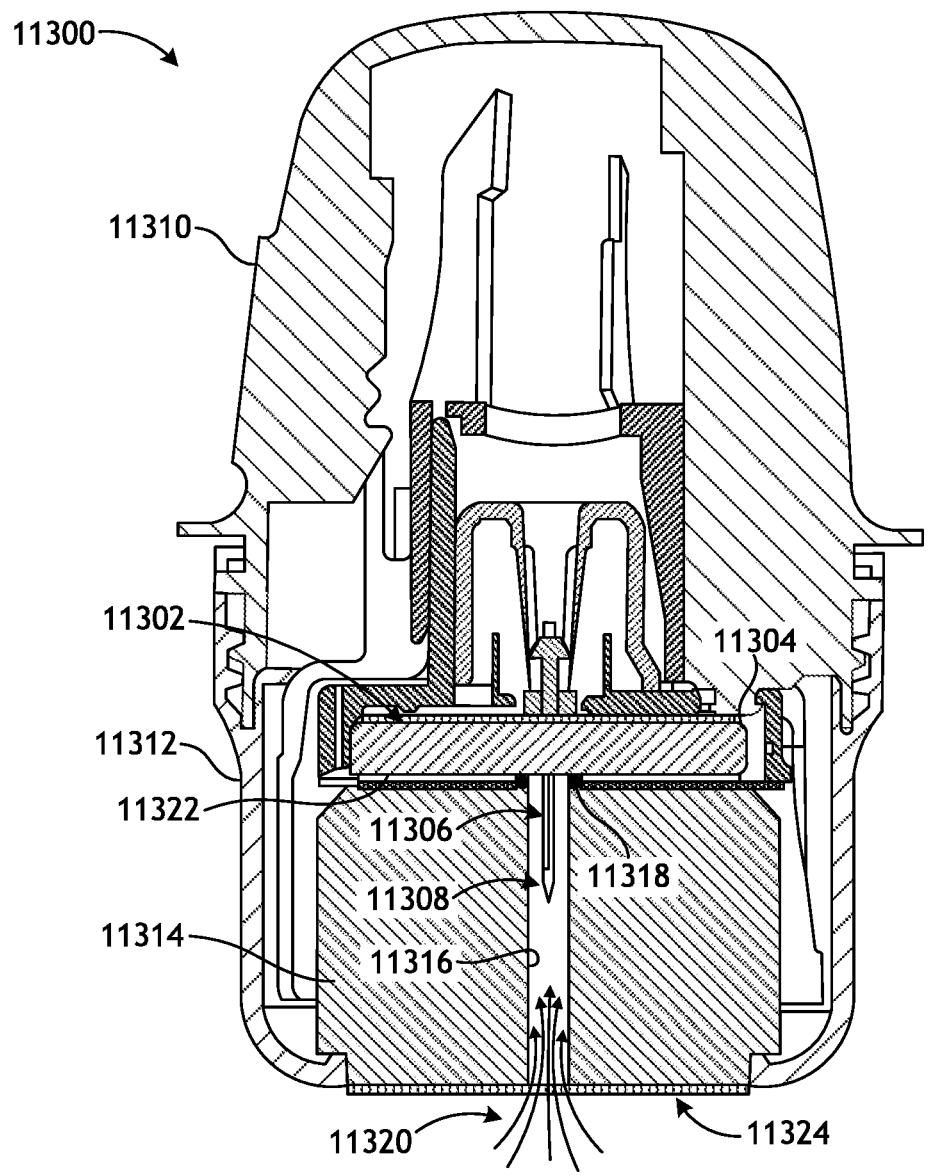

FIG. 113 is a cross-sectional side view of an example sensor applicator 11300, according to one or more embodiments. The sensor applicator 11300 may be similar in some respects to any of the sensor applicators described herein. Accordingly, the sensor applicator 11300 may be configured to house a sensor control device 11302 and may be operable to deploy the sensor control device 11302 to a target monitoring location. The sensor control device 11302 may be similar in some respects to any of the sensor control devices described herein. As illustrated, the sensor control device 11302 may include an electronics housing 11304 configured to house electronic modules or components used to operate the sensor control device 11302. The sensor control device 11302 may further include a sensor 11306 and a sharp 11308, which may be similar to any of the sensors and sharps described herein. Consequently, the sharp 11308 may be used to help transcutaneously implant the sensor 11306 beneath a user's skin for monitoring blood glucose levels.

In the illustrated embodiment, the sensor applicator includes a housing 11310 and an applicator cap 11312 removably coupled to the housing 11310. The applicator cap 11312 may be threaded to the housing 11310 and may be removed by rotating (e.g., unscrewing) the applicator cap 11312 relative to the housing 11310.

In the illustrated embodiment, the sensor applicator 11300 may include a filler 11314 arranged at least partially within the applicator cap 11312. In some embodiments, the filler 11314 may form an integral part or extension of the applicator cap 11312, such as being molded with or overmolded onto the applicator cap 11312. In other embodiments, the filler 11314 may comprise a separate structure fitted within or attached to the applicator cap 11312, without departing from the scope of the disclosure. In some embodiments, the filler 11314 may generally help support the sensor control device 11302 while contained within the sensor applicator 11302.

The filler 11314 may define or otherwise provide a sterilization zone 11316 configured to receive the sensor 11306 and the sharp 11308 as extending from the bottom of the electronics housing 11304. The sterilization zone 11316 may generally comprise a hole or passageway extending at least partially through the body of the filler 11314. When the sensor control device 11302 is loaded into the sensor applicator 11302 and the applicator cap 11312 is secured thereto, the sensor 11306 and the sharp 11308 may be positioned within the sterilization zone 11316 of the filler 11314, which may be sealed to isolate the sensor 11306 and the sharp 11308 from external contamination.

The applicator cap 11312 and the filler 11314 may each be made of a gas impermeable material, such as a plastic or polycarbonate. Moreover, a gasket 11318 may be located at an interface between the filler 11314 and the bottom of the electronics housing 11304 to generate a gas-tight seal. In some embodiments, the gasket 11318 may be overmolded onto the filler 11314 or alternatively onto the bottom of the electronics housing 11304. In other embodiments, however, the gasket 11318 may comprise a separate component part or seal, such as an O-ring or the like.

While the sensor control device 11302 is positioned within the sensor applicator 11302, the sensor 11306 and the sharp 11308 may be sterilized. According to the present embodiment, sterilizing the sensor 11306 and the sharp 11308 may be accomplished by introducing a sterilizing gas 11320 into the sterilization zone 11316. The sterilizing gas 11320 may comprise, for example, nitrogen dioxide ($NO_2$), which operates to sterilize the sensor 11306 and the sharp 11308 without adversely affecting the chemistry on the sensor 11306. Moreover, the gasket 11318 may prevent the sterilizing gas 11320 from migrating laterally out of the sterilization zone 11316 and impinging upon and damaging an adhesive layer 11322 attached to the bottom of the electronics housing 11304. Accordingly, the sterilization zone 11316 allows transmission of the sterilizing gas 11320 to impinge upon and sterilize the sensor 11306 and the sharp 11308, while the remaining portions of the filler 11314 and the gasket 11318 prevent (impede) the sterilizing gas 11320 from damaging the integrity of the adhesive layer 11322.

In some embodiments, a microbial barrier 11324 may be applied to the end of the filler 11314 and/or the applicator cap 11312 to seal off the sterilization zone 11316. In some embodiments, the microbial barrier 11324 may comprise two or more layers of different materials. The first layer may be made of a synthetic material (e.g., a flash-spun high-density polyethylene fiber), such as Tyvek® available from DuPont®. Tyvek® is highly durable and puncture resistant and allows the permeation of vapors and gases. The Tyvek® layer can be applied before or after application of the sterilizing gas 11320, and following the sterilizing process, a foil or other vapor and moisture resistant material layer may be sealed (e.g., heat sealed) over the Tyvek® layer to prevent the ingress of contaminants and moisture into the sterilization zone 11316. In other embodiments, the microbial barrier 11324 may comprise only a single protective layer applied to the end of the filler 11314. In such embodiments, the single layer is gas permeable for the sterilization process, but is also capable of protection against moisture and other harmful elements once the sterilization process is complete. Accordingly, the microbial barrier 11324 may operate as a moisture and contaminant layer, without departing from the scope of the disclosure.

It is noted that, while the sensor 11306 and the sharp 11308 extend from the bottom of the electronics housing 11304 and into the sterilization zone 11316 generally concentric with a centerline of the sensor applicator 11302 and the applicator cap 11312, it is contemplated herein to have an eccentric arrangement. More specifically, in at least one embodiment, the sensor 11306 and the sharp 11308 may extend from the bottom of the electronics housing 11304 eccentric to the centerline of the sensor applicator 11302 and the applicator cap 11312. In such embodiments, the filler 11314 may be re-designed and otherwise configured such that the sterilization zone 11316 is also eccentrically positioned to receive the sensor 11306 and the sharp 11308, without departing from the scope of the disclosure.

Embodiments disclosed herein include:

HH. A sensor control device that includes an electronics housing including an upper cover securable to a lower cover, a sensor electronics module positionable between the upper and lower covers and including a sensor holder defining a channel, a sensor including a tail extendable through the channel and a flag that includes one or more sensor contacts, a printed circuit board (PCB) having one or more circuitry contacts alignable with the one or more sensor contacts, a first adhesive substrate interposing the flag and the sensor holder to secure the sensor to the sensor holder, and a second adhesive substrate interposing the flag and the PCB to secure the sensor to the PCB and facilitate electrical communication between the one or more sensor contacts and the one or more circuitry contacts. The sensor control device further includes a sharp extendable through the electronics housing, wherein the sharp and the tail extend from a bottom of the electronics housing.

II. A converting process of fabricating a sensor control device that includes positioning a sensor holder defining a channel on a base substrate, extending a tail of a sensor through the channel and securing a flag of the sensor to the sensor holder with a first adhesive substrate applied to a top of the sensor holder, wherein the flag includes one or more sensor contacts, positioning a printed circuit board (PCB) on the base substrate and about the sensor holder, the PCB providing one or more circuitry contacts alignable with the one or more sensor contacts, attaching the PCB to the flag with a second adhesive substrate applied to a top of the flag, facilitating electrical communication between the one or more sensor contacts and the one or more circuitry contacts with the second adhesive substrate, positioning an upper cover over the PCB and securing the upper cover to the base substrate to form an electronics housing, trimming the base substrate about an outer periphery of the electronics housing, and extending a sharp through the electronics housing, wherein the sharp and the tail extend from a bottom of the electronics housing.

Each of embodiments HH and II may have one or more of the following additional elements in any combination: Element 1: further comprising a filler positionable between the upper and lower covers with the sensor electronics module. Element 2: further comprising a third adhesive substrate interposing the lower cover and the filler to secure the filler to the lower cover. Element 3: wherein the sensor electronics module further includes a cap matable with the sensor holder to help secure the sensor within the sensor electronics module. Element 4: wherein the sensor electronics module further includes a third adhesive substrate interposing the cap and the PCB to secure the cap to the PCB. Element 5: wherein the sensor holder is matable with the PCB. Element 6: wherein one or both of the upper and lower covers are made of a material selected from the group consisting of a film, a foil, a foam, a laminated material, and any combination thereof. Element 7: wherein one or both of the upper and lower covers are formed by a manufacturing process selected from the group consisting of thermoforming, vacuum forming, injection molding, die-cutting, stamping, compression molding, transfer molding, and any combination thereof. Element 8: wherein the upper cover is secured to the lower cover via at least one of sonic welding, ultrasonic welding, laser welding, heat sealing, an adhesive substrate, and any combination thereof.

Element 9: wherein the base substrate comprises a film of material disposed on a roll, and attaching the sensor holder to the base substrate is preceded by unrolling the base substrate from the roll, and forming a hole in the base substrate. Element 10: wherein positioning the sensor holder on the base substrate comprises securing the sensor holder to the base substrate using at least one of ultrasonic welding, heat sealing, an adhesive substrate, and any combination thereof. Element 11: wherein the PCB defines first and second lobes interconnected by a neck portion and the one or more circuitry contacts are provided on the second lobe, and wherein attaching the PCB to the flag comprises folding the second lobe onto the first lobe at the neck portion, and aligning the one or more circuitry contacts with the one or more sensor contacts. Element 12: wherein each lobe provides a battery contact, and the method further comprises applying a third adhesive substrate to the battery contact on the first lobe, attaching a battery to the third adhesive substrate, wherein the second adhesive substrate is further applied to a top of the battery, and folding the second lobe onto the first lobe to align the battery contact on the second lobe with the top of the battery, wherein the second and third adhesive substrates comprise Z-axis anisotropic pressure-adhesive tapes that facilitate electrical communication between the battery and the battery contacts. Element 13: further comprising positioning a filler on the PCB and about the sensor holder, and mitigating vibration and stabilizing electronic modules of the PCB with the filler. Element 14: further comprising applying a third adhesive substrate between the PCB and the upper cover to secure the upper cover to the PCB. Element 15: wherein positioning the upper cover over the PCB comprises forming the upper cover using a process selected from the group consisting of thermoforming, cold forming, vacuum forming, injection molding, die-cutting, stamping, and any combination thereof. Element 16: wherein securing the upper cover to the base substrate comprises sealing the upper cover to the base substrate using a process selected from the group consisting of sonic welding, ultrasonic welding, laser welding, heat sealing, using an adhesive substrate, and any combination thereof. Element 17: further comprising forming a web extending from the outer periphery of the electronics housing and across a tab section, the web providing upper and lower layers sealed at a periphery, facilitating fluid communication into an interior of the electronics housing via the web and an aperture defined in the upper layer, and pressure testing the electronics housing by injecting air into the electronics housing via the aperture and the web. Element 18: further comprising extracting air from the interior of the electronics housing via the web and the aperture, and sealing the outer periphery of the electronics housing under vacuum conditions.

By way of non-limiting example, exemplary combinations applicable to HH and II include: Element 1 with Element 2; Element 3 with Element 4; Element 11 with Element 12; and Element 17 with Element 18.

Example Embodiments of Sensor Module and Plug

Figure 114A:
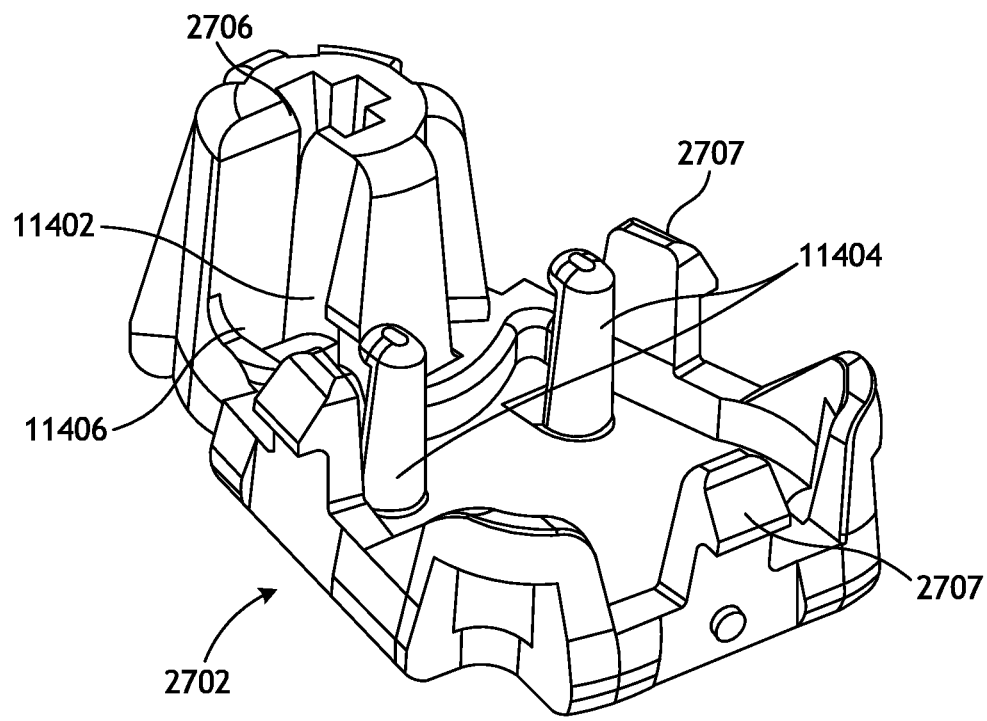
Figure 114B:
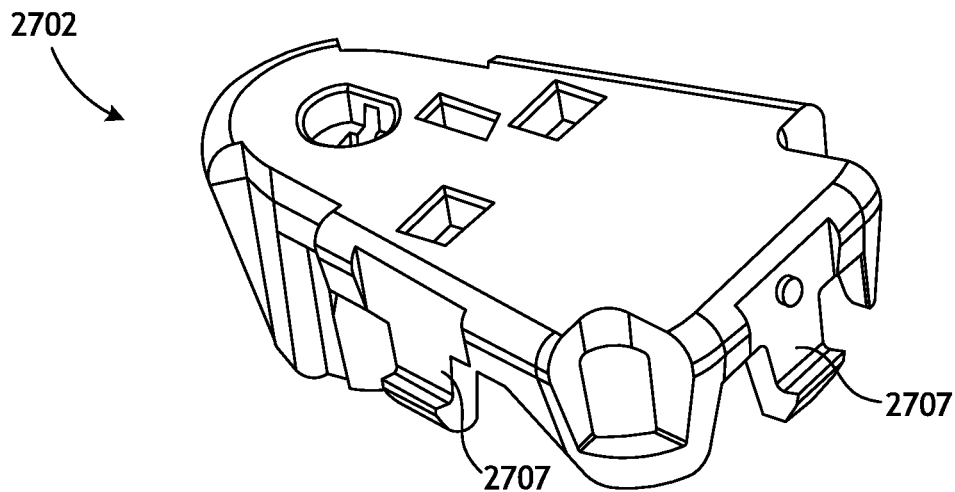

FIGS. 114A and 114B are top and bottom perspective views, respectively, of an example embodiment of the plug 2702 of FIGS. 27A-27B, according to one or more embodiments. As described above, the plug 2702 may be designed to hold the connector 2704 (FIGS. FIGS. 27A-27B and 115A-115B) and the sensor 2616 (FIGS. 27B and 116). The plug 2702 is capable of being securely coupled with the electronics housing 2604 (FIGS. 26A-26B), and the deflectable arms 2707 are configured to snap into corresponding features provided on the bottom of the electronics housing 2604. The sharp slot 2706 can provide a location for the sharp tip 2726 (FIG. 27B) to pass through and the sharp shaft 2724 (FIGS. 27A-27B) to temporarily reside. As illustrated, a sensor ledge 11402 can define a sensor position in a horizontal plane, prevent a sensor from lifting the connector 2704 off of connector posts 11404 and maintain the sensor 2616 parallel to a plane of connector seals. It can also define sensor bend geometry and minimum bend radius. It can limit sensor travel in a vertical direction and prevent a tower from protruding above an electronics housing surface and define a sensor tail length below a patch surface. A sensor wall 11406 can constrain the sensor 2616 and define a sensor bend geometry and minimum bend radius.

Figure 115A:
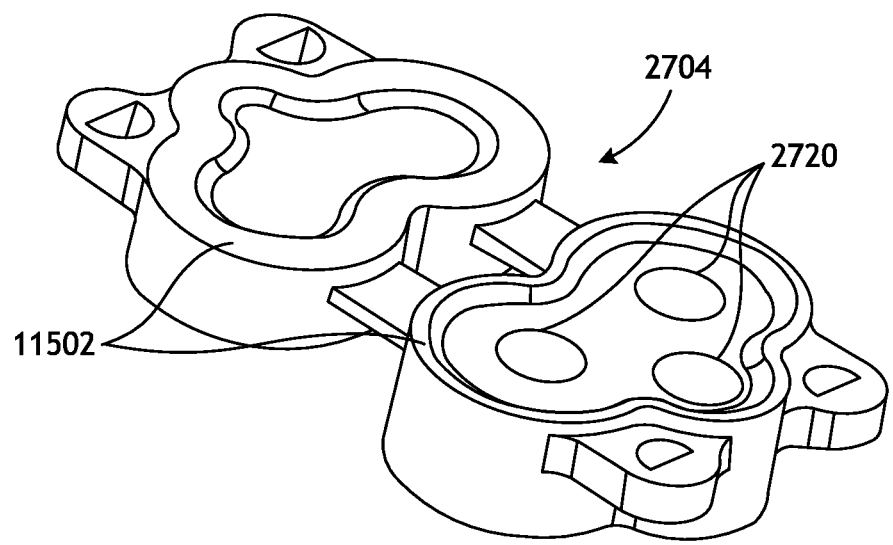
Figure 115B:
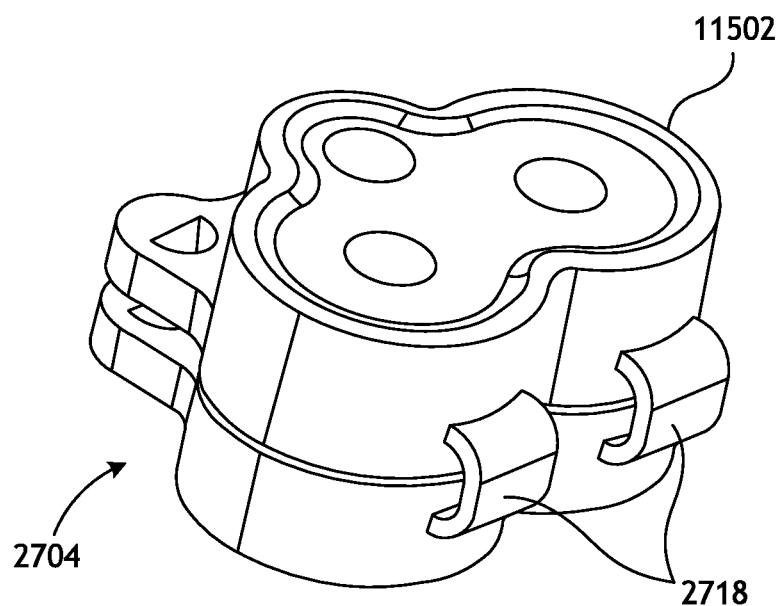
Figure 116:
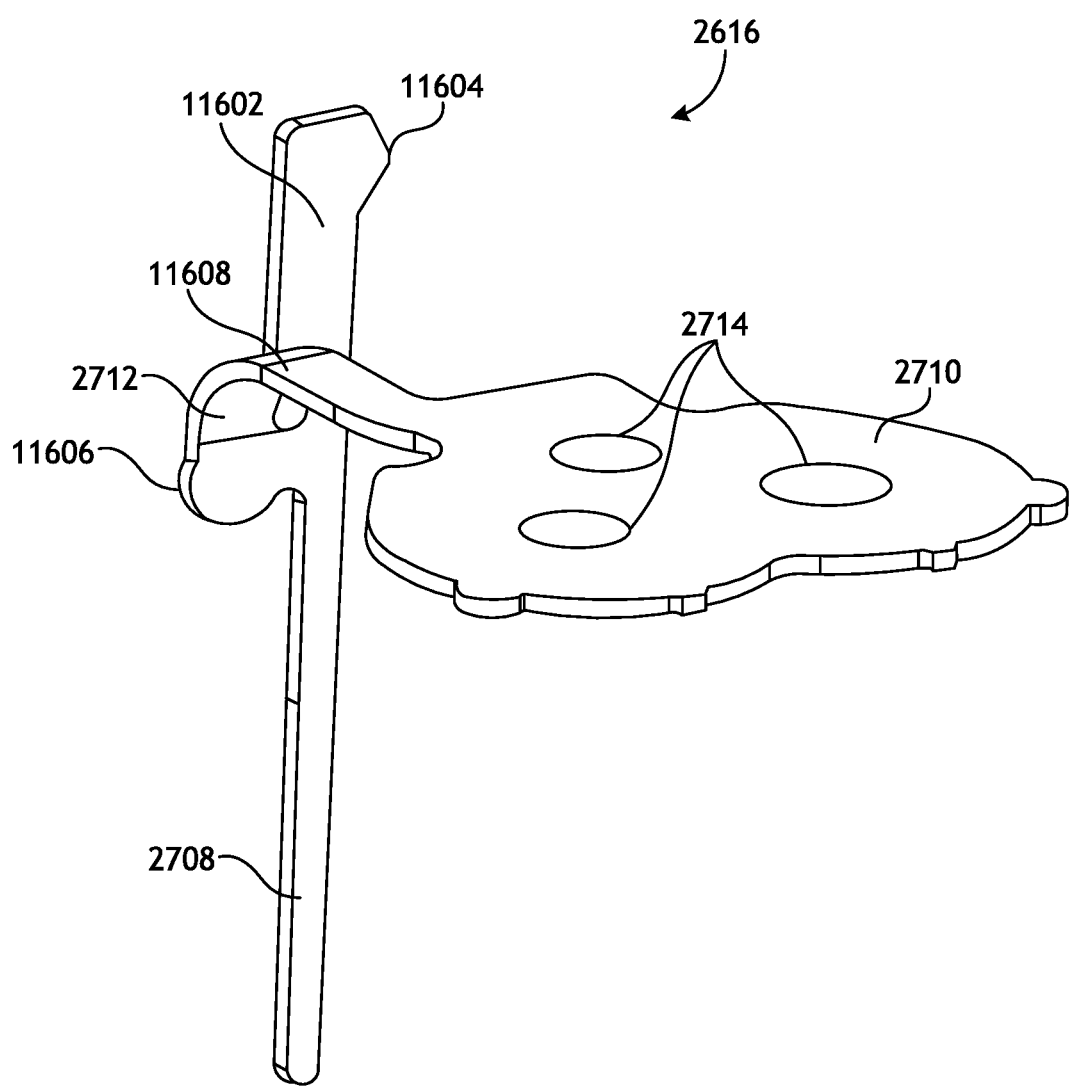

FIGS. 115A and 115B are perspective views depicting an example embodiment of the connector 2704 in open and closed states, respectively. The connector 2704 can be made of silicone rubber that encapsulates compliant carbon impregnated polymer modules that serve as the electrical conductive contacts 2720 between the sensor 2616 (FIGS. 27B and 116) and electrical circuitry contacts for the electronics within housing 2604. The connector 2704 can also serve as a moisture barrier for the sensor 2616 when assembled in a compressed state after transfer from a container to an applicator and after application to a user's skin. A plurality of seal surfaces 11502 can provide a watertight seal for electrical contacts and sensor contacts. The hinges 2718 connect two distal and proximal portions of the connector 2704.

FIG. 116 is a perspective view of an example embodiment of the sensor 2616. The neck 2712 can be a zone which allows folding of the sensor 2616, for example ninety degrees. A membrane on the tail 2708 can cover an active analyte sensing element of the sensor 2616. The tail 2708 can be the portion of the sensor 2616 that resides under a user's skin after insertion. The flag 2710 includes the contacts 2714 and also provides a sealing surface. A biasing tower 11602 can be a tab that biases the tail 2708 into the sharp slot 2706 (FIGS. 114A-114B). A bias fulcrum 11604 can be an offshoot of the biasing tower 11602 that contacts an inner surface of a needle to bias the tail 2708 into a slot defined by the sharp. A bias adjuster 11606 can reduce a localized bending of a tail connection and prevent sensor trace damage. The contacts 2714 can electrically couple the active portion of the sensor to the connector 2704, and a service loop 11608 can translate an electrical path from a vertical direction ninety degrees and engage with the sensor ledge 11402 (FIG. 114B).

Figure 117A:
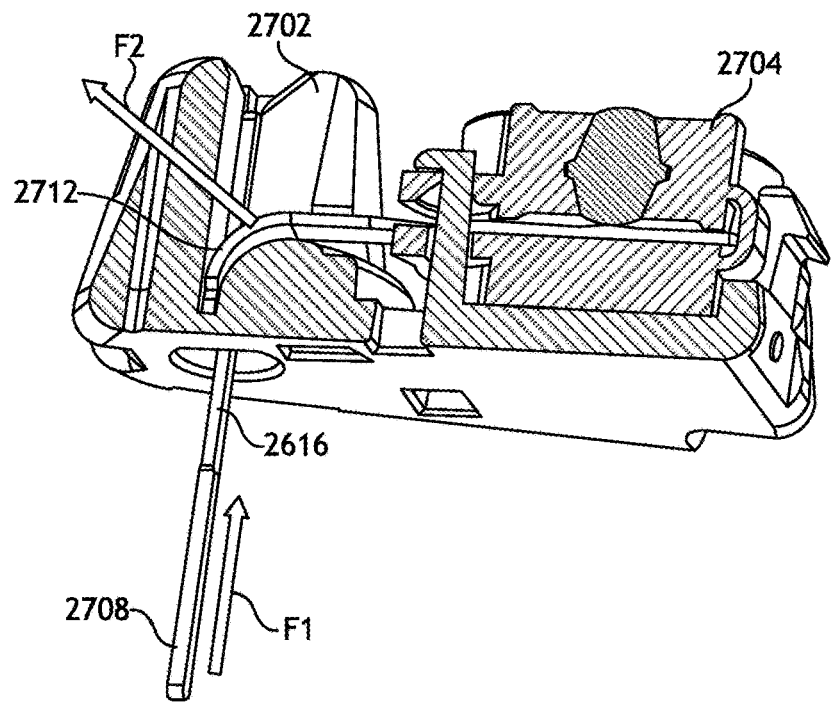
Figure 117B:
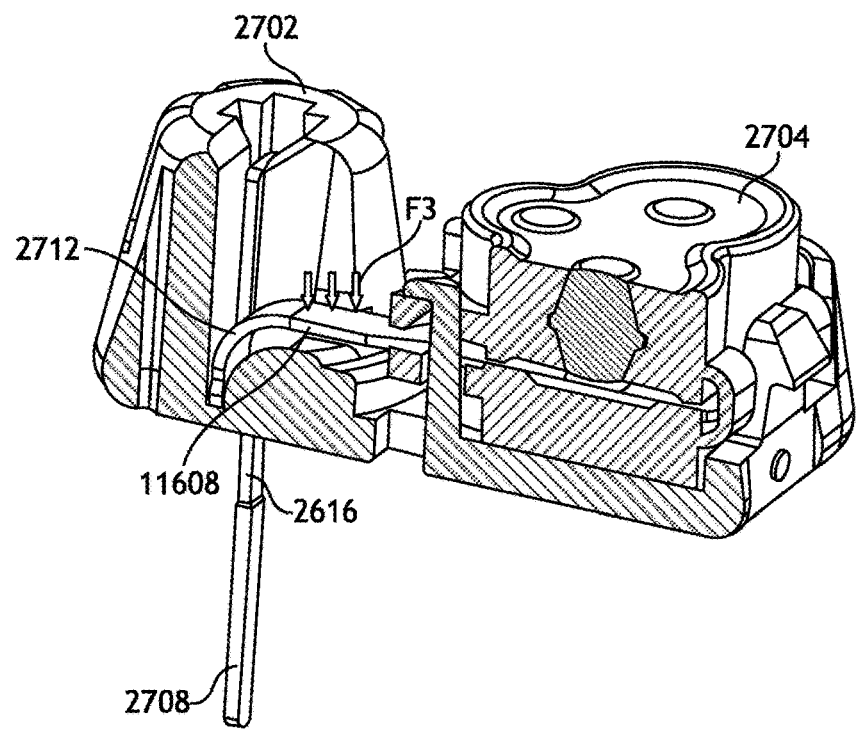

FIGS. 117A and 117B are bottom and top perspective views, respectively, depicting an example embodiment of a sensor module assembly comprising the sensor plug 2702, the connector 2704, and the sensor 2616. According to one aspect of the aforementioned embodiments, during or after insertion, the sensor 2616 can be subject to axial forces pushing up in a proximal direction against the sensor 2616 and into the sensor module, as shown by force F1 of FIG. 15A. According to some embodiments, this can result in an adverse force F2 being applied to neck 2712 of the sensor 2616 and, consequently, result in adverse forces F3 being translated to service loop 11608 of the sensor 2616. In some embodiments, for example, axial forces F1 can occur as a result of a sensor insertion mechanism in which the sensor is designed to push itself through the tissue, a sharp retraction mechanism during insertion, or due to a physiological reaction created by tissue surrounding sensor 2616 (e.g., after insertion).

Figure 118A:
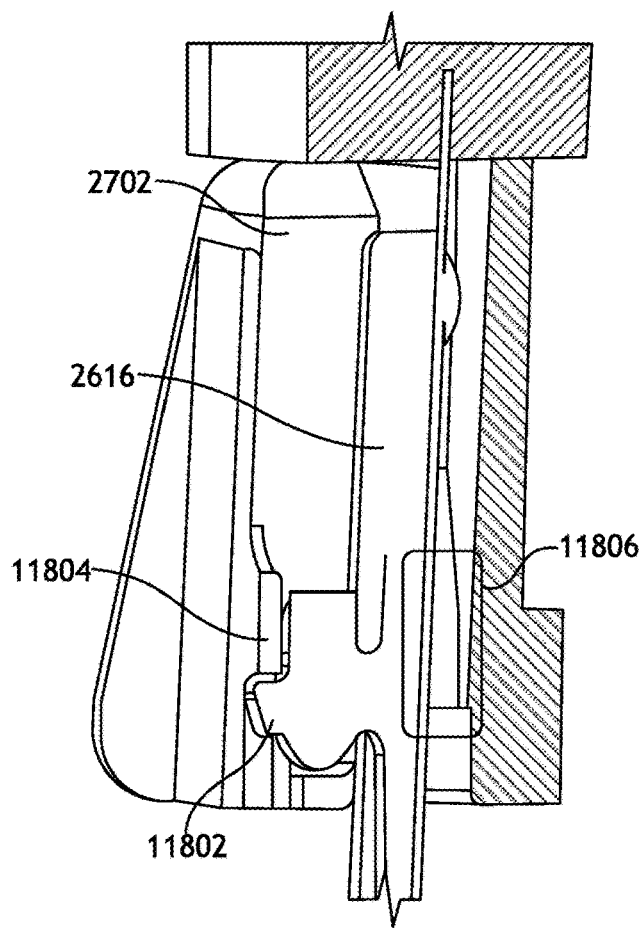
Figure 118B:
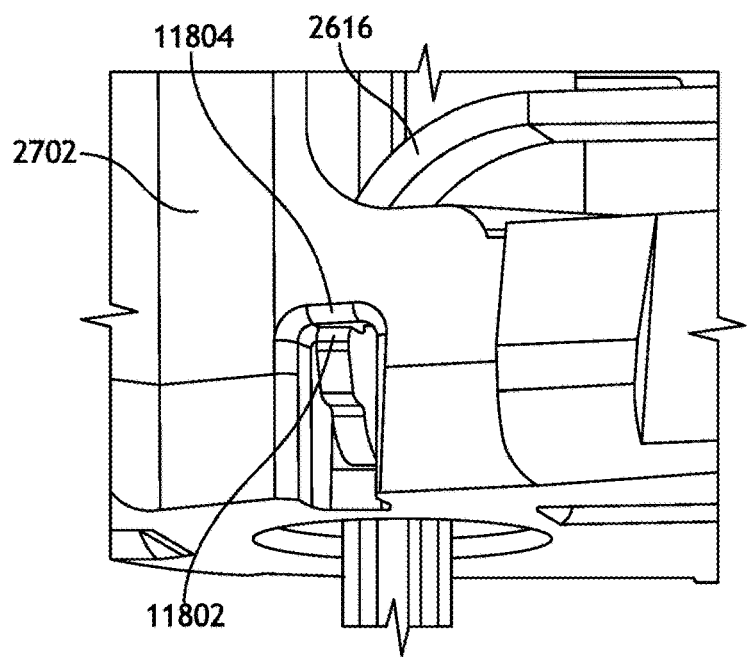

FIGS. 118A and 118B are close-up partial views of an example embodiment of the sensor plug 2702 having certain axial stiffening features. In a general sense, the embodiments described herein are directed to mitigating the effects of axial forces on the sensor 2616 as a result of insertion and/or retraction mechanisms, or from a physiological reaction to the sensor in the body. As illustrated, the sensor 2616 comprises a proximal portion having a hook feature 11802 configured to engage a catch feature 11804 of the plug 2702. In some embodiments, the plug 2702 can also include a clearance area 11806 to allow a distal portion of the sensor 2616 to swing backwards during assembly to allow for the assembly of the hook feature 11802 of the sensor 2616 over and into the catch feature 11804 of the plug 2702.

According to another aspect of the embodiments, the hook and catch features 11802, 11084 operate in the following manner. The sensor 2616 includes a proximal sensor portion, coupled to the plug 2702, as described above, and a distal sensor portion that is positioned beneath a skin surface in contact with a bodily fluid. The proximal sensor portion may include the hook feature 11802 adjacent to the catch feature 11804 of the plug 2702. During or after sensor insertion, one or more forces are exerted in a proximal direction along a longitudinal axis of the sensor 2616. In response to the one or more forces, the hook feature 11802 engages the catch feature 11804 to prevent displacement of the sensor 2616 in a proximal direction along the longitudinal axis.

According to another aspect of the disclosure, the sensor 2616 can be assembled with the plug 2702 in the following manner. The sensor 2616 is loaded into the plug 2702 by displacing the proximal sensor portion in a lateral direction to bring the hook feature 11802 in proximity to the catch feature 11804 of the plug 2702. More specifically, displacing the proximal sensor portion in a lateral direction causes the proximal sensor portion to move into the clearance area 11806 of the plug 2702.

Although FIGS. 118A and 118B depict the hook feature 11802 as a part of the sensor 2616, and the catch feature 11804 as a part of the plug 2702, those of skill in the art will appreciate that the hook feature 11802 can instead be a part of the plug 2702, and, likewise, the catch feature 11804 can instead be a part of the sensor 3106. Similarly, those of skill in the art will also recognize that other mechanisms (e.g., detent, latch, fastener, screw, etc.) implemented on the sensor 2616 and the plug 2702 to prevent axial displacement of sensor 2616 are possible and within the scope of the present disclosure.

Figure 119:
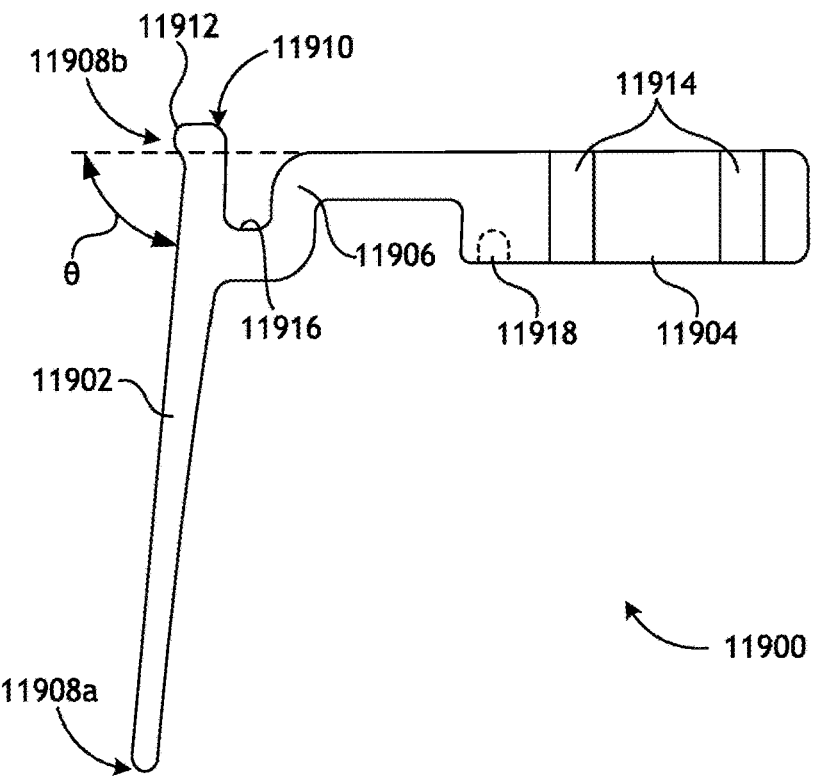

FIG. 119 is a side view of an example sensor 11900, according to one or more embodiments of the disclosure. The sensor 11900 may be similar in some respects to any of the sensors described herein and, therefore, may be used in an analyte monitoring system to detect specific analyte concentrations. As illustrated, the sensor 11900 includes a tail 11902, a flag 11904, and a neck 11906 that interconnects the tail 11902 and the flag 11904. The tail 11902 includes an enzyme or other chemistry or biologic and, in some embodiments, a membrane may cover the chemistry. In use, the tail 11902 is transcutaneously received beneath a user's skin, and the chemistry included thereon helps facilitate analyte monitoring in the presence of bodily fluids.

The tail 11902 may be received within a hollow or recessed portion (e.g., the recessed portion 2728 of FIG. 27B) of a sharp (not shown) to at least partially circumscribe the tail 11902 of the sensor 11900. As illustrated, the tail 11902 may extend at an angle Θ offset from horizontal. In some embodiments, the angle Θ may be about 85°. Accordingly, in contrast to other sensor tails, the tail 11902 may not extend perpendicularly from the flag 11904, but instead at an angle offset from perpendicular. This may prove advantageous in helping maintain the tail 11902 within the keep the recessed portion of the sharp.

The tail 11902 includes a first or bottom end 11908a and a second or top end 11908b opposite the top end 11908a. A tower 11910 may be provided at or near the top end 11908b and may extend vertically upward from the location where the neck 11906 interconnects the tail 11902 to the flag 11904. During operation, if the sharp moves laterally, the tower 11910 will help picot the tail 11902 toward the sharp and otherwise stay within the recessed portion (e.g., the recessed portion 2728 of FIG. 27B) of the sharp. Moreover, in some embodiments, the tower 11910 may provide or otherwise define a protrusion 11912 that extends laterally therefrom. When the sensor 11900 is mated with the sharp and the tail 11902 extends within the recessed portion of the sharp, the protrusion 11912 may engage the inner surface of the recessed portion. In operation, the protrusion 11912 may help keep the tail 11902 within the recessed portion.

The flag 11904 may comprise a generally planar surface having one or more sensor contacts 11914 arranged thereon. The sensor contact(s) 11914 may be configured to align with a corresponding number of compliant carbon impregnated polymer modules encapsulated within a connector.

In some embodiments, as illustrated, the neck 11906 may provide or otherwise define a dip or bend 11916 extending between the flag 11904 and the tail 11902. The bend 11916 may prove advantageous in adding flexibility to the sensor 11900 and helping prevent bending of the neck 11906.

In some embodiments, a notch 11918 (shown in dashed lines) may optionally be defined in the flag near the neck 11906. The notch 11918 may add flexibility and tolerance to the sensor 11900 as the sensor 11900 is mounted to the mount. More specifically, the notch 11918 may help take up interference forces that may occur as the sensor 11900 is mounted within the mount.

Figure 120A:
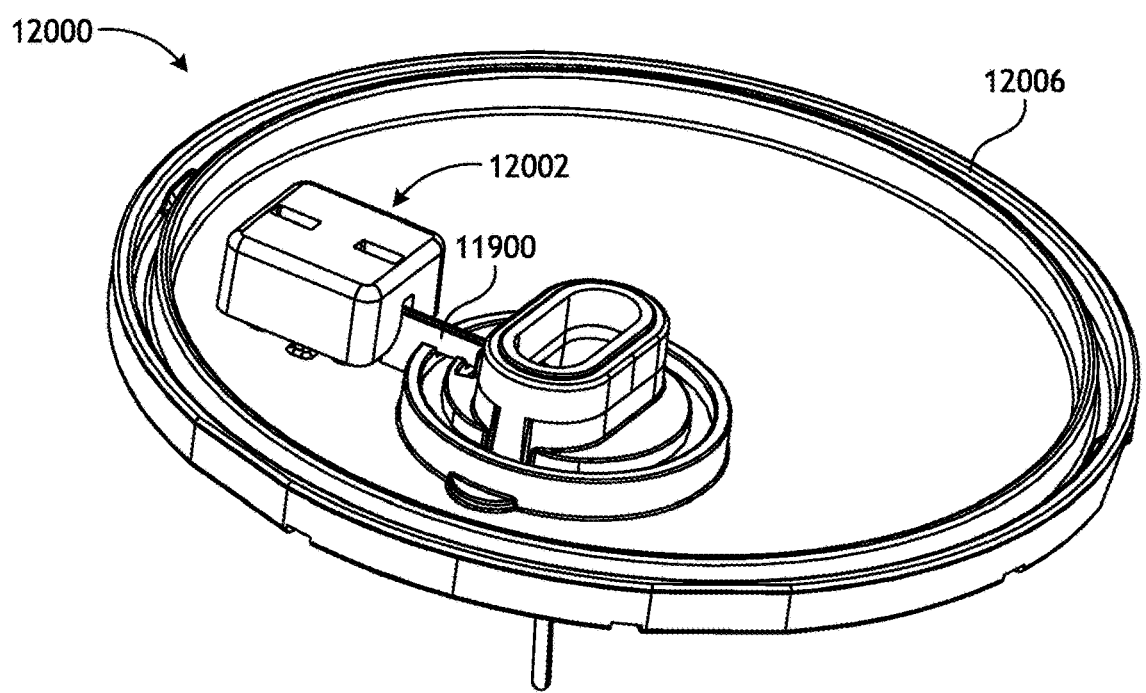
Figure 120B:
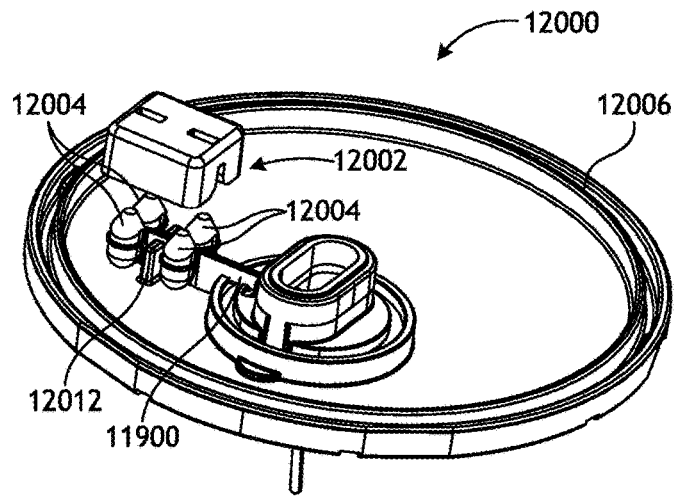
Figure 120C:
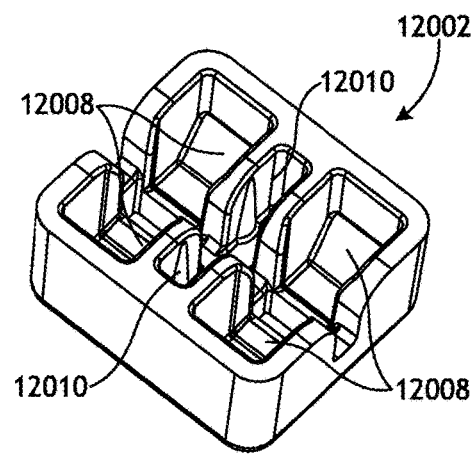

FIGS. 120A and 120B are isometric and partially exploded isometric views of an example connector assembly 12000, according to one or more embodiments. As illustrated, the connector assembly 12000 may include a connector 12002, and FIG. 120C is an isometric bottom view of the connector 12002. The connector 12002 may comprise an injection molded part used to help secure one or more compliant carbon impregnated polymer modules 12004 (four shown in FIG. 120B) to a mount 12006. More specifically, the connector 12002 may help secure the modules 12004 in place adjacent the sensor 11900 and in contact with the sensor contacts 11914 (FIG. 119) provided on the flag 11904 (FIG. 119). The modules 12004 may be made of a conductive material to provide conductive communication between the sensor 11900 and corresponding circuitry contacts (not shown) provided within the mount 12006.

As best seen in FIG. 120C, the connector 12002 may define pockets 12008 sized to receive the modules 12004. Moreover, in some embodiments, the connector 12002 may further define one or more depressions 12010 configured to mate with one or more corresponding flanges 12012 (FIG. 120B) on the mount 12006. Mating the depressions 12010 with the flanges 12012 may secure the connector 12002 to the mount 12006 via an interference fit or the like. In other embodiments, the connector 12002 may be secured to the mount 12006 using an adhesive or via sonic welding.

FIGS. 121A and 121B are isometric and partially exploded isometric views of another example connector assembly 12100, according to one or more embodiments. As illustrated, the connector assembly 12100 may include a connector 12102, and FIG. 121C is an isometric bottom view of the connector 12102. The connector 12102 may comprise an injection molded part used to help keep one or more compliant metal contacts 12104 (four shown in FIG. 121B) secured against the sensor 11900 on a mount 12106. More specifically, the connector 12102 may help secure the contacts 12104 in place adjacent the sensor 11900 and in contact with the sensor contacts 11914 (FIG. 119) provided on the flag 11904. The contacts 12104 may be made of a stamped conductive material that provides conductive communication between the sensor 11900 and corresponding circuitry contacts (not shown) provided within the mount 12106. In some embodiments, for example, the contacts 12104 may be soldered to a PCB (not shown) arranged within the mount 12106.

As best seen in FIG. 121C, the connector 12102 may define pockets 12108 sized to receive the contacts 12104. Moreover, in some embodiments, the connector 12102 may further define one or more depressions 12110 configured to mate with one or more corresponding flanges 12112 (FIG. 120B) on the mount 12006. Mating the depressions 12110 with the flanges 12112 may help secure the connector 12102 to the mount 12106 via an interference fit or the like. In other embodiments, the connector 12102 may be secured to the mount 12106 using an adhesive or via sonic welding.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, and right and the like are used in relation to the illustrative embodiments as they are depicted in the figures, the upward direction being toward the top of the corresponding figure and the downward direction being toward the bottom of the corresponding figure.

What is claimed is:

1. An assembly for delivery of a glucose sensor comprising:
    a sensor control device including:
        an electronics housing comprising:
            a shell having an upper surface with a first aperture defined therein,
            a mount mated to the shell and having a second aperture aligned with the first aperture;
            a seal overmolded onto the mount at the second aperture, the seal comprising a first seal element overmolded onto a pedestal protruding from an inner surface of the mount;
        a circuit board disposed within the electronics housing and comprising
            a plurality of electronics modules including a Bluetooth antenna;
        a glucose sensor coupled with the circuit board and configured to measure a glucose level; and
        an adhesive patch attached to the underside of the mount and configured to secure the sensor control device on a user's skin.

2. The assembly of claim 1, wherein the electronics housing further includes a plurality of carrier grip features along an outer periphery of the electronics housing.

3. The assembly of claim 1, further comprising an adhesive to secure the shell to the mount.

4. The assembly of claim 3, wherein the adhesive isolates an interior of the electronics housing from outside contamination.

5. The assembly of claim 1, wherein the seal further comprises a second seal element interconnected with the first seal element and overmolded onto an underside of the mount.

6. The assembly of claim 5, further comprising an applicator including:
a housing;
a sheath coupled to the housing to engage the user's skin at a target monitoring location;
a sharp carrier coupled to a sharp extending through the first aperture and the second aperture, the sharp configured to penetrate the user's skin to position a part of the glucose sensor in contact with interstitial fluid of the user;
a sensor carrier to hold the sensor control device within the applicator;
a spring biasing the sharp carrier to move upward within the housing; and
an applicator cap configured to be coupled to the housing to seal an interior of the applicator.

7. The assembly of claim 6, wherein the glucose sensor comprises:
a tail portion extending through the second aperture and configured to monitor the glucose level;
a flag portion having a planar surface including a plurality of electrical contacts configured to couple with the circuit board; and
a neck portion interconnecting the tail portion and the flag portion.

8. The assembly of claim 7, wherein the plurality of electrical contacts on the flag portion include a carbon impregnated polymer.

9. The assembly of claim 7, wherein the applicator further comprises:
a sharp hub carrying a sharp and sealingly engaging the first seal element; and
a sensor cap removably coupled to the sharp hub at the underside of the mount and sealingly engaging the second seal element,
wherein the sensor cap defines an inner chamber configured to receive the tail and the sharp.

10. The assembly of claim 9, wherein the sharp hub provides a mating member extending past the underside of the mount and the sensor cap is removably coupled to the mating member.

11. The assembly of claim 9, further comprising one or more pockets defined on a underside of the mount at the second aperture, and one or more projections defined on an end of the sensor cap and receivable within the one or more pockets when the sensor cap is coupled to the sharp hub.

12. The assembly of claim 6, wherein the sensor carrier includes one or more carrier arms engaged with the sharp carrier to maintain the sharp carrier in position, and wherein the spring is biasing the sharp carrier to move upward within the housing when the one or more carrier arms disengage from the sharp carrier.

13. The assembly of claim 6, wherein the sensor carrier includes one or more flexible arms configured to hold the sensor control device within the applicator.

14. The assembly of claim 6, wherein the applicator cap includes a seal on a proximal end.

15. The assembly of claim 14, wherein the seal occludes a plurality of vents on the proximal end of the applicator cap.

16. The assembly of claim 6, wherein the sheath is collapsible to allow the sensor control device to advance into engagement with the user's skin.

17. The assembly of claim 6, wherein the sharp carrier and the sharp are configured to be automatically retracted after the housing is advanced towards the target monitoring location.

18. The assembly of claim 6, wherein the sharp includes a hollow portion configured to receive at least a portion of the glucose sensor.

19. The assembly of claim 6, wherein the sharp includes a non-circular cross-section.

20. The assembly of claim 6, wherein the sharp is beveled.

21. The assembly of claim 5, wherein at least one of the first and second seal elements define at least a portion of the second aperture.

22. The assembly of claim 1, further comprising a collar positioned within the electronics housing and defining a central aperture configured to receive and sealingly engage the first seal element in a radial direction.

23. The assembly of claim 22, further comprising a channel defined on the inner surface of the mount and circumscribing the pedestal, an annular lip defined on an underside of the collar and matable with the channel, and an adhesive provided in the channel to secure and seal the collar to the mount at the channel.

24. The assembly of claim 23, further comprising a groove defined through the annular lip to accommodate a portion of the sensor extending laterally within the mount, wherein the adhesive seals about the sensor at the groove.

25. The assembly of claim 22, further comprising a collar channel defined on an upper surface of the collar, an annular ridge defined on an inner surface of the shell and matable with the collar channel, and an adhesive provided in the collar channel to secure and seal the shell to the collar.

26. The assembly of claim 1, wherein the first seal element extends at least partially through the first aperture when the shell is coupled to the mount.

* * * * *